(12) United States Patent
Regueiro-Ren et al.

(10) Patent No.: US 8,846,647 B2
(45) Date of Patent: Sep. 30, 2014

(54) C-17 AND C-3 MODIFIED TRITERPENOIDS WITH HIV MATURATION INHIBITORY ACTIVITY

(75) Inventors: Alicia Regueiro-Ren, Middletown, CT (US); Zheng Liu, Beacon Falls, CT (US); Jacob Swidorski, Southington, CT (US); Ny Sin, East Hampton, CT (US); Brian Lee Venables, Durham, CT (US); Sing-Yuen Sit, Meriden, CT (US); Yan Chen, Guilford, CT (US); Jie Chen, Madison, CT (US); Nicholas A. Meanwell, East Hampton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 317 days.

(21) Appl. No.: 13/359,727

(22) Filed: Jan. 27, 2012

(65) Prior Publication Data
US 2013/0035318 A1    Feb. 7, 2013

Related U.S. Application Data

(60) Provisional application No. 61/437,893, filed on Jan. 31, 2011.

(51) Int. Cl.
| | |
|---|---|
| *A61K 31/56* | (2006.01) |
| *A61K 31/58* | (2006.01) |
| *C07J 53/00* | (2006.01) |
| *C07J 63/00* | (2006.01) |

(52) U.S. Cl.
CPC .................................. *C07J 63/008* (2013.01)
USPC .............. 514/169; 514/176; 540/47; 552/510

(58) Field of Classification Search
CPC ..................................................... C07J 63/008
USPC ....................... 552/510; 540/47; 514/169, 176
See application file for complete search history.

(56) References Cited

U.S. PATENT DOCUMENTS

| | | | |
|---|---|---|---|
| 5,413,999 | A | 5/1995 | Vacca et al. |
| 5,679,828 | A | 10/1997 | Lee et al. |
| 7,354,924 | B2 | 4/2008 | Wang et al. |
| 7,365,221 | B2 | 4/2008 | Allaway et al. |
| 7,745,625 | B2 | 6/2010 | Ueda et al. |
| 2005/0239748 | A1 | 10/2005 | Power et al. |
| 2008/0207573 | A1 | 8/2008 | Yager et al. |

FOREIGN PATENT DOCUMENTS

| | | |
|---|---|---|
| WO | WO 98/51293 | 11/1998 |
| WO | WO 98/51294 | 11/1998 |
| WO | WO 2004/089357 | 10/2004 |
| WO | WO 2006/053255 | 5/2006 |
| WO | WO 2008/127364 | 10/2008 |
| WO | WO 2009/100532 | 8/2009 |
| WO | WO 2011/007230 | 1/2011 |

OTHER PUBLICATIONS

U.S. Appl. No. 61/537,099, filed Sep. 21, 2011, Liu et al.
U.S. Appl. No. 61/599,040, filed Feb. 15, 2012, Swidorski et al.
U.S. Appl. No. 13/151,706, filed Jun. 2, 2011, Regueiro-Ren et al.

(Continued)

*Primary Examiner* — Barbara P Badio
(74) *Attorney, Agent, or Firm* — John F. Levis

(57) ABSTRACT

Compounds having drug and bio-affecting properties, their pharmaceutical compositions and methods of use are set forth. In particular, C-17 and C-3 modified triterpenoids that possess unique antiviral activity are provided as HIV maturation inhibitors, as represented by compounds of Formulas I, II and III:

Formula I

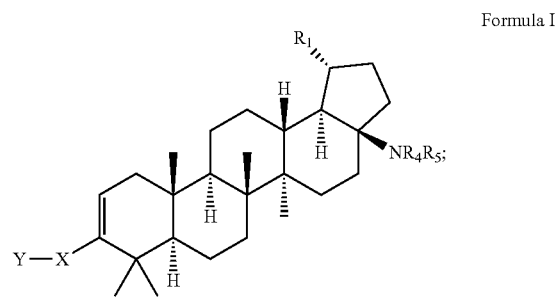

Formula II

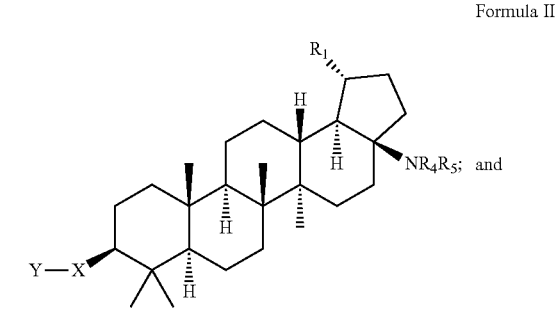

Formula III

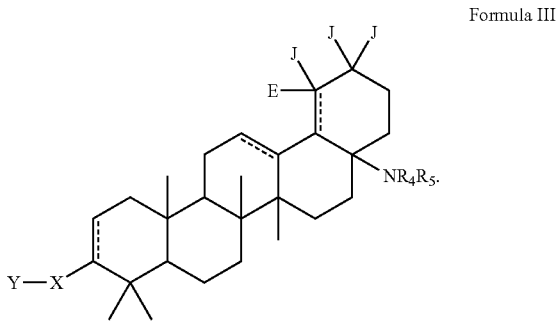

These compounds are useful for the treatment of HIV and AIDS.

16 Claims, No Drawings

(56) References Cited

OTHER PUBLICATIONS

U.S. Appl. No. 13/151,722, filed Jun. 2, 2011, Regueiro-Ren et al.
U.S. Appl. No. 13/359,680, filed Jan. 27, 2012, Regueiro-Ren et al.
Blair, W.S. et al., "HIV-1 entry—an expanding portal for drug discovery", Drug Discovery Today, vol. 5, No. 5, pp. 183-194 (2000).
Hotoda, H., "Small-molecule inhibitors of HIV-1 entry via chemokine receptors", Drugs of the Future, vol. 24, No. 12, pp. 1355-1362 (1999).
Kashiwada, Y. et al., "Betulinic Acid and Dihydrobetulinic Acid Derivatives as Potent Anti-HIV Agents", Journal of Medicinal Chemistry, vol. 39, No. 5, pp. 1016-1017 (1996).
Meanwell, N.A. et al., "Inhibitors of the entry of HIV into host cells", Current Opinion in Drug Discovery & Development, vol. 6, No. 4, pp. 451-461 (2003).
Pokrovskii, A.G. et al., "Synthesis of derivatives of plant triterpenes and study of their antiviral and immunostimulating activity", Khimiya y Interesakh Ustoichivogo Razvitiya, vol. 9, No. 3, pp. 485-491 (2001) (English abstract).
Sodroski, J.G., "HIV-1 Entry Inhibitors in the Side Pocket: Minireview", Cell, vol. 99, pp. 243-246 (1999).

C-17 AND C-3 MODIFIED TRITERPENOIDS WITH HIV MATURATION INHIBITORY ACTIVITY

CROSS REFERENCE TO RELATED APPLICATIONS

This patent application claims the benefit of U.S. provisional patent application No. 61/437,893 filed Jan. 31, 2011.

FIELD OF THE INVENTION

The present invention relates to novel compounds useful against HIV and, more particularly, to compounds derived from betulinic acid and other structurally-related compounds which are useful as HIV maturation inhibitors, and to pharmaceutical compositions containing same, as well as to methods for their preparation.

BACKGROUND OF THE INVENTION

HIV-1 (human immunodeficiency virus-1) infection remains a major medical problem, with an estimated 45-50 million people infected worldwide at the end of 2010. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC-EMTRIVA®), COMBIVIR® (contains -3TC plus AZT), TRIZIVIR® (contains abacavir, lamivudine, and zidovudine), EPZICOM® (contains abacavir and lamivudine), TRUVADA® (contains VIREAD® and EMTRIVA®); non-nucleoside reverse transcriptase inhibitors: nevirapine (or VIRAMUNE®), delavirdine (or RESCRIPTOR®) and efavirenz (or SUSTIVA®), ATRIPLA® (TRUVADA®+SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®) and cobicistat, and integrase inhibitors such as raltegravir (ISENTRESS®), and entry inhibitors such as enfuvirtide (T-20) (FUZEON®) and maraviroc (SELZENTRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. No. 7,354,924 and US 2005/0209246 are illustrative of HIV attachment inhibitors.

Another emerging class of compounds for the treatment of HIV are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the hydroxyl in the 3 carbon of betulin with succinic acid also produced a compound capable of inhibiting HIV-1 activity (Pokrovskii, A. G., et al., Gos. Nauchnyi Tsentr Virusol. Biotekhnol. "Vector" 9:485-491 (2001)).

Other references to the use of treating HIV infection with compounds derived from betulinic acid include US 2005/0239748 and US 2008/0207573, as well as WO2006/053255, WO2009/100532 and WO2011/007230.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) lup-20(29)-en-28-oic acid.

Reference is also made herein to the applications by Bristol-Myers Squibb entitled "MODIFIED C-3 BETULINIC ACID DERIVATIVES AS HIV MATURATION INHIBITORS" U.S. Ser. No. 13/151,706 filed on Jun. 2, 2011 and "C-28 AMIDES OF MODIFIED C-3 BETULINIC ACID DERIVATIVES AS HIV MATURATION INHIBITORS" U.S. Ser. No. 13/151,722, filed on Jun. 2, 2011. Reference is also made to the application entitled "C-28 AMINES OF C-3 MODIFIED BETULINIC ACID DERIVATIVES AS HIV MATURATION INHIBITORS" U.S. Ser. No. 61/437,870, filed on Jan. 31, 2011.

What is now needed in the art are new compounds which are useful as HIV maturation inhibitors, as well as new pharmaceutical compositions containing these compounds.

SUMMARY OF THE INVENTION

The present invention provides compounds of Formulas I, II, and III below, including pharmaceutically acceptable salts thereof, their pharmaceutical formulations, and their use in patients suffering from or susceptible to a virus such as HIV. The compounds of Formulas I-III are effective antiviral agents, particularly as inhibitors of HIV. They are useful for the treatment of HIV and AIDS.

One embodiment of the present invention is directed to a compound, including pharmaceutically acceptable salts thereof, which is selected from the group of:

a compound of formula I

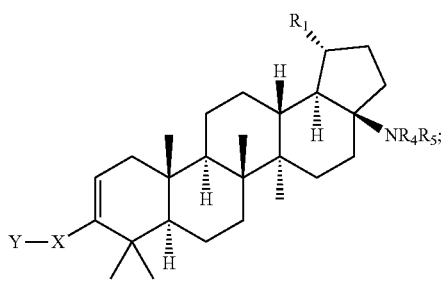

Formula I a compound of formula II

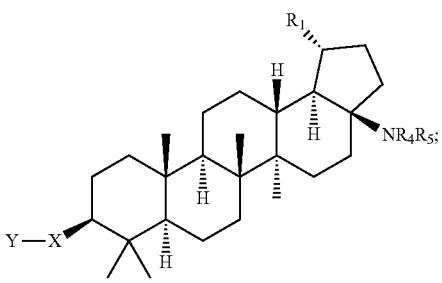

Formula II and
a compound of formula III

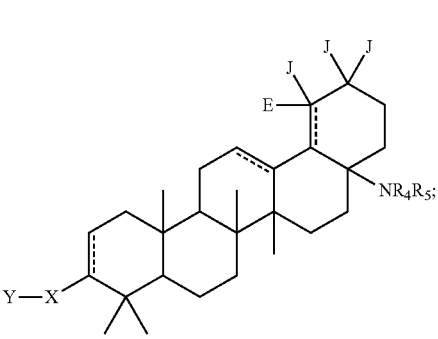

Formula III wherein $R_1$ is isopropenyl or isopropyl;
J and E are —H or —$CH_3$, and E is absent when the double bond is present;
X is a phenyl or heteroaryl ring substituted with A, wherein A is at least one member selected from the group of —H, -halo, -hydroxyl, —$C_{1-6}$ alkyl, —$C_{1-6}$ alkoxy, and —$COOR_2$;

$R_2$ is —H, —$C_{1-6}$ alkyl, -alkylsubstituted $C_{1-6}$ alkyl or -arylsubstituted $C_{1-6}$ alkyl;
Y is selected from the group of —$COOR_2$, —$C(O)NR_2SO_2R_3$, —$C(O)NHSO_2NR_2R_2$, —$NR_2SO_2R_2$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, and —CONHOH,
wherein n=1-6;
$R_3$ is —$C_{1-6}$ alkyl or -alkylsubstituted $C_{1-6}$ alkyl;
$R_4$ is selected from the group of —H, —$C_{1-6}$ alkyl, —$C_{1-6}$ alkyl-$C(OR_3)_2$—$C_{3-6}$ cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, —$SO_2NR_2R_2$,

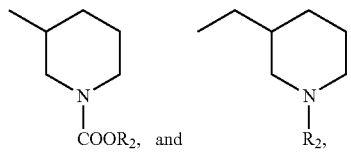

wherein $Q_1$ is selected from the group of heteroaryl, substituted heteroaryl, halogen, —$CF_3$, —$OR_2$, —$COOR_2$, —$NR_8R_9$, —$CONR_{10}R_{11}$ and —$SO_2R_2$;
$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-$NR_8R_9$, —$COR_{10}$, —$COR_6$, —$COCOR_6$, —$SO_2R_7$ and —$SO_2NR_2R_2$;
with the proviso that only one of $R_4$ or $R_5$ can be selected from the group of —$COR_6$, —$COCOR_6$, —$SO_2R_7$ and —$SO_2NR_2R_2$;
or $R_4$ and $R_5$ are taken together with the adjacent N to form

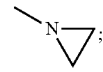

$R_6$ is selected from the group of —H, —$C_{1-6}$ alkyl, —$C_{1-6}$ alkyl-substitutedalkyl, —$C_{3-6}$ cycloalkyl, —$C_{3-6}$ substituted-cycloalkyl-$Q_2$, —$C_{1-6}$ alkyl-$Q_2$, —$C_{1-6}$ alkyl-substituted-alkyl-$Q_2$, —$C_{3-6}$ cycloalkyl-$Q_2$, aryl-$Q_2$, —$NR_{13}R_{14}$, and —$OR_{15}$;
wherein $Q_2$ is selected from the group of aryl, heteroaryl, substituted heteroaryl, —$OR_2$, —$COOR_2$, —$NR_8R_9$, $SO_2R_2$, —$CONHSO_2R_3$, and —$CONHSO_2NR_2R_2$;
$R_7$ is selected from the group of —$C_{1-6}$ alkyl, —$C_{1-6}$ substituted alkyl, —$C_{3-6}$ cycloalkyl, aryl, and heteroaryl;
$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$,
and $R_8$ and $R_9$ can also be independently selected from the group of

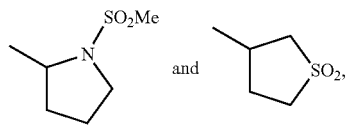

or $R_8$ and $R_9$ are taken together with the adjacent N to form a cycle selected from the group of:

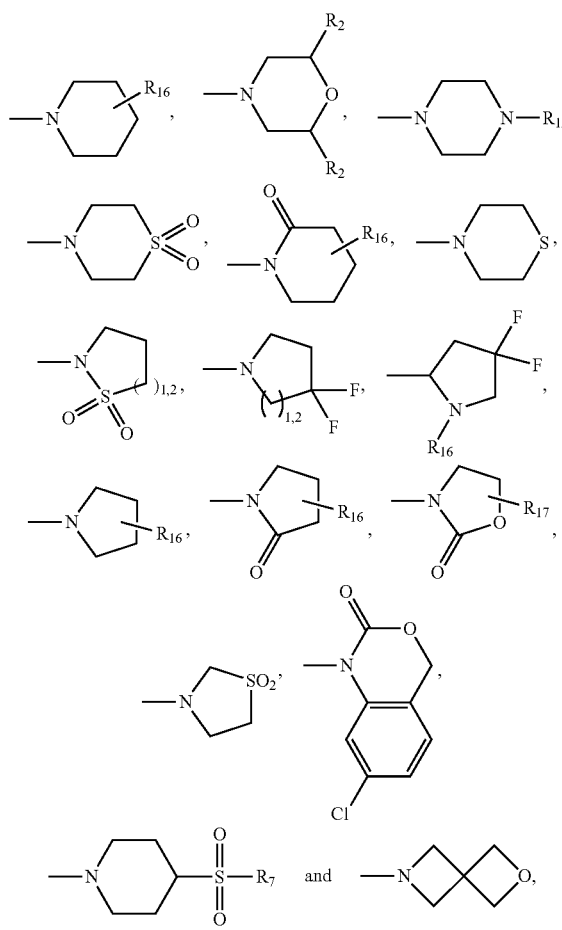

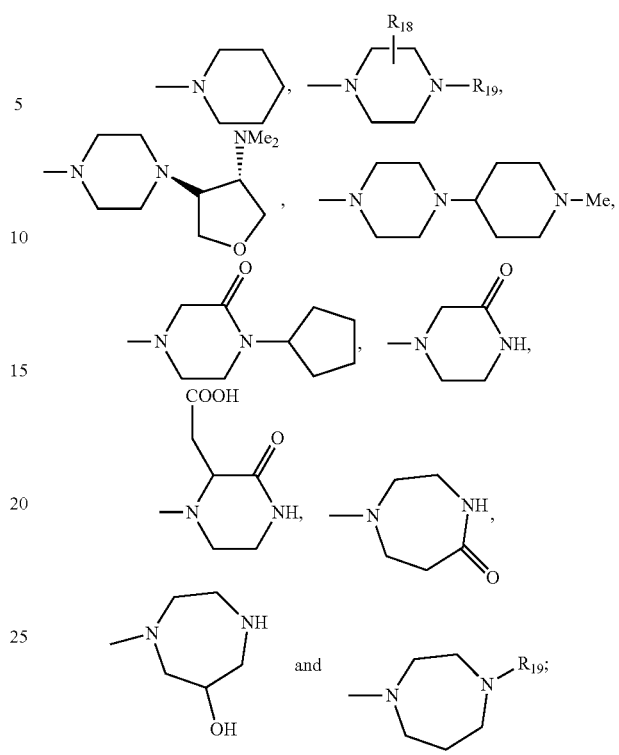

with the proviso that only one of $R_8$ or $R_9$ can be —COOR$_3$;
$R_{10}$ and $R_{11}$ are independently selected from the group of —H, —C$_{1-6}$ alkyl, —C$_{1-6}$ substituted alkyl and —C$_{3-6}$ cycloalkyl,
or $R_{10}$ and $R_{11}$ are taken together with the adjacent N to form a cycle such as

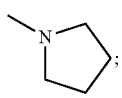

$R_{12}$ is selected from the group of —C$_{1-6}$ alkyl, —C$_{1-6}$ alkyl-OH; —C$_{1-6}$ alkyl, —C$_{1-6}$ substituted alkyl, —C$_{3-6}$ cycloalkyl, —COR$_7$, —COONR$_{22}$R$_{23}$, —SOR$_7$, and —SONR$_{24}$R$_{25}$;
$R_{13}$ and $R_{14}$ are independently selected from the group of —H, —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$ cycloalkyl-Q$_3$, C$_{1-6}$ substituted alkyl-Q$_3$ and

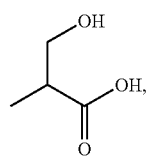

or $R_{13}$ and $R_{14}$ are taken together with the adjacent N to form a cycle selected from the group of:

$Q_3$ is selected from the group of heteroaryl, substituted heteroaryl, —NR$_2$OR$_{21}$, —CONR$_2$R$_2$, —COOR$_2$, —OR$_2$, and —SO$_2$R$_3$;
$R_{15}$ is selected from the group of —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$ cycloalkyl-Q$_3$ and —C$_{1-6}$ substituted alkyl-Q$_3$,
$R_{16}$ is selected from the group of —H, —C$_{1-6}$ alkyl, —NR$_2$R$_2$, and —COOR$_3$;
$R_{17}$ is selected from the group of —H, —C$_{1-6}$ alkyl, —COOR$_3$, and aryl;
$R_{18}$ is selected from the group of —COOR$_2$ and —C$_{1-6}$ alkyl-COOR$_2$;
$R_{19}$ is selected from the group of —H, —C$_{1-6}$ alkyl, —C$_{1-6}$ alkyl-Q$_4$, —COR$_3$, —COOR$_3$, wherein Q$_4$ is selected from the group of —NR$_2$R$_2$ and —OR$_2$;
$R_{20}$ and $R_{21}$ are independently selected from the group of —H, —C$_{1-6}$ alkyl, —C$_{1-6}$ substituted alkyl, —C$_{1-6}$ substituted alkyl-OR$_2$, and —COR$_3$,
or $R_{20}$ and $R_{21}$ are taken together with the adjacent N to form a cycle selected from the group of

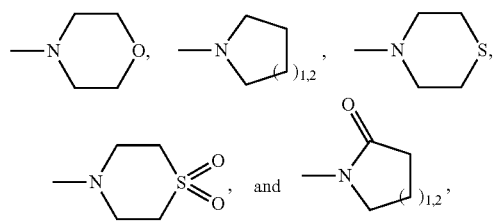

with the proviso that only one of $R_{20}$ or $R_{21}$ can be —COR$_3$,
$R_{22}$ and $R_{23}$ are independently selected from the group of H, —C$_{1-6}$ alkyl, —C$_{1-6}$ substituted alkyl, and —C$_{1-6}$ cycloalkyl,
or $R_{22}$ and $R_{23}$ are taken together with the adjacent N to form a cycle selected from the group of

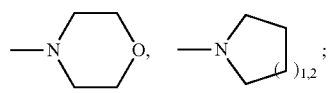

$R_{24}$ and $R_{25}$ are independently from the group of H, —$C_{1-6}$ alkyl, —$C_{1-6}$ substituted alkyl, —$C_{1-6}$ alkyl-$Q_5$, —$C_{1-6}$ cycloalkyl, aryl, substituted aryl, heteroaryl, and substituted heteroaryl, and $Q_5$ is selected from the group of halogen and $SO_2R_3$.

In a further embodiment, there is provided a method for treating mammals infected with a virus, especially wherein said virus is HIV, comprising administering to said mammal an antiviral effective amount of a compound which is selected from the group of compounds of Formulas I, II, III above, and one or more pharmaceutically acceptable carriers, excipients or diluents. Optionally, the compound of Formulas I, II, and/or III can be administered in combination with an antiviral effective amount of another—AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising an antiviral effective amount of a compound which is selected from the group of compounds of Formulas I, II, and III, and one or more pharmaceutically acceptable carriers, excipients, and diluents; and optionally in combination with an antiviral effective amount of another AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formulas I, II, and III herein.

Also provided herein are intermediate compounds useful in making the compounds of Formulas I, II, and III herein.

The present invention is directed to these, as well as other important ends, hereinafter described.

DETAILED DESCRIPTION OF THE EMBODIMENTS

Since the compounds of the present invention may possess asymmetric centers and therefore occur as mixtures of diastereomers and enantiomers, the present disclosure includes the individual diastereoisomeric and enantiomeric forms of the compounds of Formulas I, II and III in addition to the mixtures thereof.

Definitions

Unless otherwise specifically set forth elsewhere in the application, one or more of the following terms may be used herein, and shall have the following meanings:

"H" refers to hydrogen, including its isotopes, such as deuterium.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$-fluoroalkyl" refers to F-substituted $C_1$-$C_4$ alkyl wherein at least one H atom is substituted with F atom, and each H atom can be independently substituted by F atom;

"Halogen" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, amidino, guanidino, ureido, phosphonyl, amino and $-NR^xR^y$ with $R^x$ and $R^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a $Z_3CC(=O)$— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS(=O)_2$— groups with Z as defined above.

A "trihalomethanesulfonamido" group refers to a $Z_3CS(=O)_2NR^x$— group with Z as defined above and Rx being H or $(C_{1-6})$alkyl.

A "sulfinyl" group refers to a —S(=O)—R" group, with R" being $(C_{1-6})$alkyl.

A "sulfonyl" group refers to a —$S(=O)_2$R" group with R" being $(C_{1-6})$alkyl.

A "S-sulfonamido" group refers to a —$S(=O)_2NR^XR^Y$, with $R^X$ and $R^Y$ independently being H or $(C_{1-6})$alkyl.

A "N-Sulfonamido" group refers to a R"$S(=O)_2NR_X$— group, with $R_x$ being H or $(C_{1-6})$alkyl.

A "O-carbamyl" group refers to a —$OC(=O)NR^xR^y$ group, with $R^X$ and $R^Y$ independently being H or $(C_{1-6})$alkyl.

A "N-carbamyl" group refers to a $R^xOC(=O)NR^y$ group, with $R^x$ and $R^y$ independently being H or $(C_{1-6})$alkyl.

A "O-thiocarbamyl" group refers to a —$OC(=S)NR^xR^y$ group, with $R^x$ and $R^y$ independently being H or $(C_{1-6})$alkyl.

A "N-thiocarbamyl" group refers to a $R^xOC(=S)NR^y$— group, with $R^x$ and $R^y$ independently being H or $(C_{1-6})$alkyl.

An "amino" group refers to an —$NH_2$ group.

A "C-amido" group refers to a —$C(=O)NR^xR^y$ group, with $R^x$ and $R^y$ independently being H or $(C_{1-6})$alkyl.

A "C-thioamido" group refers to a —$C(=S)NR^xR^y$ group, with $R^x$ and $R^y$ independently being H or $(C_{1-6})$alkyl.

A "N-amido" group refers to a $R^xC(=O)NR^y$— group, with $R^x$ and $R^y$ independently being H or $(C_{1-6})$alkyl.

An "ureido" group refers to a —$NR^xC(=O)NR^yR^{y2}$ group, with $R^x$, $R^y$, and $R^{y2}$ independently being H or $(C_{1-6})$alkyl.

A "guanidino" group refers to a —$R^xNC(=N)NR^yR^{y2}$ group, with $R^x$, $R^y$, and $R^{y2}$ independently being H or $(C_{1-6})$alkyl.

A "amidino" group refers to a $R^xR^yNC(=N)$— group, with $R^x$ and $R^y$ independently being H or $(C_{1-6})$alkyl.

A "cyano" group refers to a —CN group.

A "silyl" group refers to a —$Si(R")_3$, with R" being $(C_{1-6})$ alkyl or phenyl.

A "phosphonyl" group refers to a $P(=O)(OR^x)_2$ with $R^x$ being $(C_{1-6})$alkyl.

A "hydrazino" group refers to a —$NR^xNR^yR^{y2}$ group, with $R^x$, $R^y$, and $R^{y2}$ independently being H or $(C_{1-6})$alkyl.

A "4, 5, or 6 membered ring cyclic N-lactam" group refers to

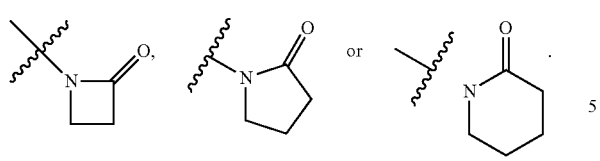

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates, half acid esters such as malonates, succinates or glutarates, and the like. In certain embodiments, amino acid esters may be especially preferred.

Examples of such prodrug esters include

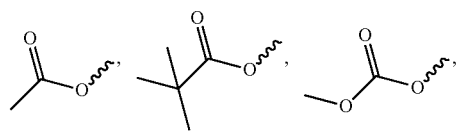

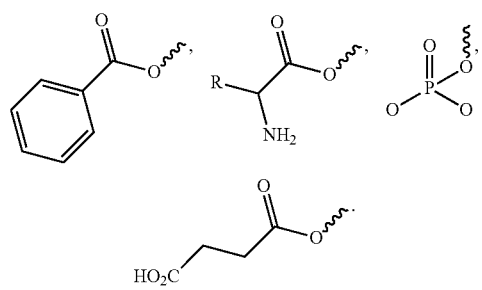

The term "prodrug ethers" include both phosphate acetals and O-glucosides. Representative examples of such prodrug ethers include

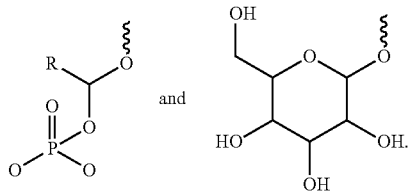

As set forth above, the invention is directed to a compound, including pharmaceutically acceptable salts thereof, which is selected from the group of:

a compound of formula I

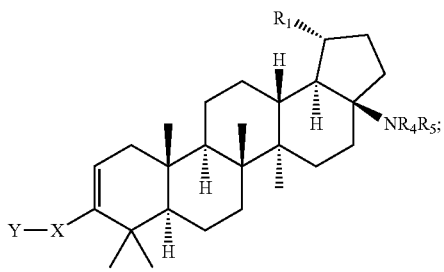

Formula I a compound of formula II

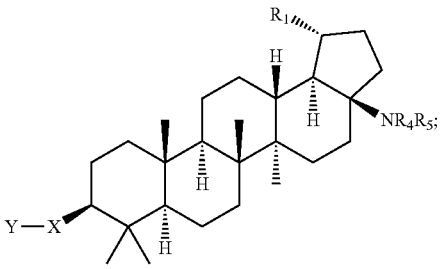

Formula II and
a compound of formula III

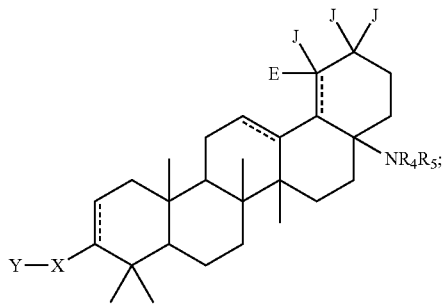

Formula III wherein $R_1$ is isopropenyl or isopropyl;
J and E are —H or —$CH_3$, and E is absent when the double bond is present;
X is a phenyl or heteroaryl ring substituted with A, wherein A is at least one member selected from the group of —H, -halo, -hydroxyl, —$C_{1-6}$ alkyl, —$C_{1-6}$ alkoxy, and —$COOR_2$;
$R_2$ is —H, —$C_{1-6}$ alkyl, -alkylsubstituted $C_{1-6}$ alkyl or -aryl-substituted $C_{1-6}$ alkyl;
Y is selected from the group of —$COOR_2$, —$C(O)NR_2SO_2R_3$, —$C(O)NHSO_2NR_2R_2$, —$NR_2SO_2R_2$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, and —CONHOH,
wherein n=1-6;
$R_3$ is —$C_{1-6}$ alkyl or -alkylsubstituted $C_{1-6}$ alkyl;
$R_4$ is selected from the group of —H, —$C_{1-6}$ alkyl, —$C_{1-6}$ alkyl-$C(OR_3)_2$—$C_{3-6}$ cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, —$SO_2NR_2R_2$,

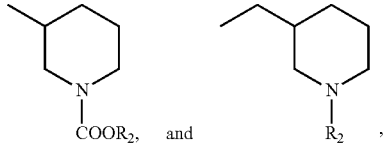

wherein $Q_1$ is selected from the group of heteroaryl, substituted heteroaryl, halogen, —$CF_3$, —$OR_2$, —$COOR_2$, —$NR_8R_9$, —$CONR_{10}R_{11}$ and —$SO_2R_7$;
$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-$NR_8R_9$, —$COR_{10}$, —$COR_6$, —$COCOR_6$, —$SO_2R_7$ and —$SO_2NR_2R_2$;
with the proviso that only one of $R_4$ or $R_5$ can be selected from the group of —$COR_6$, —$COCOR_6$, —$SO_2R_7$ and —$SO_2NR_2R_2$;
or $R_4$ and $R_5$ are taken together with the adjacent N to form

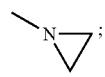

$R_6$ is selected from the group of —H, —$C_{1-6}$ alkyl, —$C_{1-6}$ alkyl-substitutedalkyl, —$C_{3-6}$ cycloalkyl, —$C_{3-6}$ substituted-cycloalkyl-$Q_2$, —$C_{1-6}$ alkyl-$Q_2$, —$C_{1-6}$ alkyl-substituted-alkyl-$Q_2$, —$C_{3-6}$ cycloalkyl-$Q_2$, aryl-$Q_2$, —$NR_{13}R_{14}$, and —$OR_{15}$;
wherein $Q_2$ is selected from the group of aryl, heteroaryl, substituted heteroaryl, —$OR_2$, —$COOR_2$, —$NR_8R_9$, $SO_2R_7$, —$CONHSO_2R_3$, and —$CONHSO_2NR_2R_2$;
$R_7$ is selected from the group of —$C_{1-6}$ alkyl, —$C_{1-6}$ substituted alkyl, —$C_{3-6}$ cycloalkyl, aryl, and heteroaryl;
$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$,
and $R_8$ and $R_9$ can also be independently selected from the group of

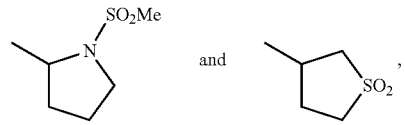

or $R_8$ and $R_9$ are taken together with the adjacent N to form a cycle selected from the group of:

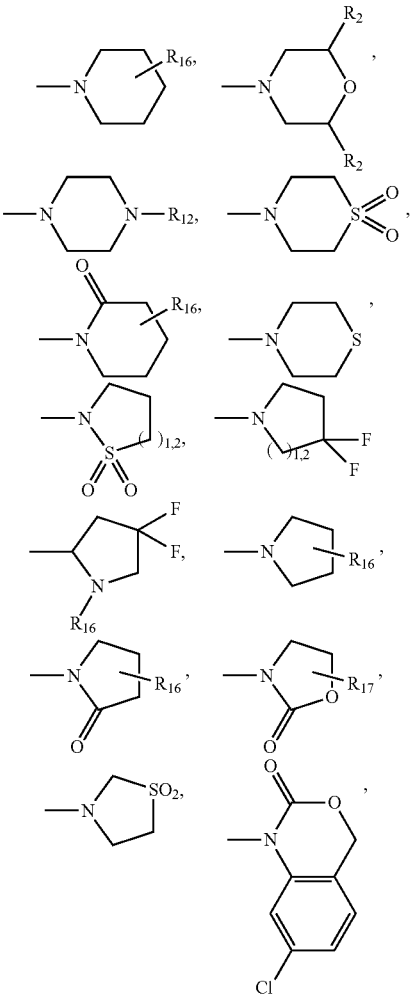

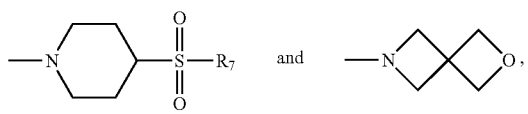 and with the proviso that only one of $R_8$ or $R_9$ can be —$COOR_3$;

$R_{10}$ and $R_{11}$ are independently selected from the group of —H, —$C_{1-6}$ alkyl, —$C_{1-6}$ substituted alkyl and —$C_{3-6}$ cycloalkyl, or $R_{10}$ and $R_{11}$ are taken together with the adjacent N to form a cycle such as

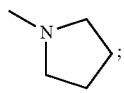

$R_{12}$ is selected from the group of —$C_{1-6}$ alkyl, —$C_{1-6}$ alkyl-OH, —$C_{1-6}$ alkyl, —$C_{1-6}$ substituted alkyl, —$C_{3-6}$ cycloalkyl, —$COR_7$, —$COONR_{22}R_{23}$, —$SOR_7$, and —$SONR_{24}R_{25}$;

$R_{13}$ and $R_{14}$ are independently selected from the group of —H, —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$, $C_{1-6}$ substituted alkyl-$Q_3$ and

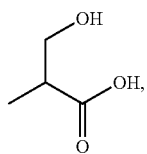

or $R_{13}$ and $R_{14}$ are taken together with the adjacent N to form a cycle selected from the group of:

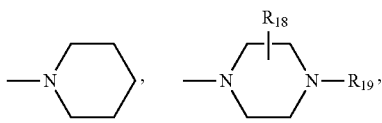

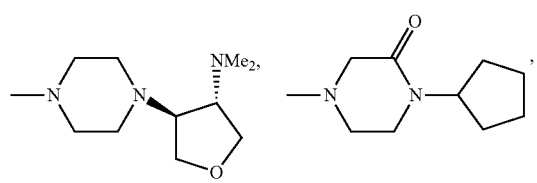

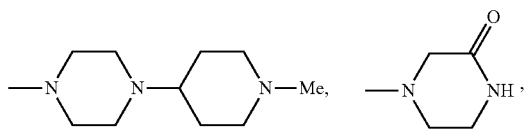

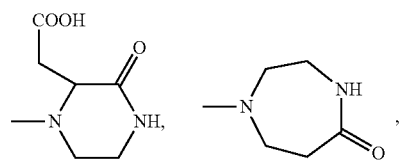

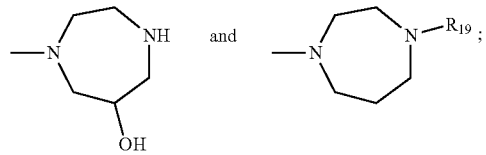

$Q_3$ is selected from the group of heteroaryl, substituted heteroaryl, —$NR_{20}R_{21}$, —$CONR_2R_2$, —$COOR_2$, —$OR_2$, and —$SO_2R_3$;

$R_{15}$ is selected from the group of —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$ and —$C_{1-6}$ substituted alkyl-$Q_3$, $R_{16}$ is selected from the group of —H, —$C_{1-6}$ alkyl, —$NR_2R_2$, and —$COOR_3$;

$R_{17}$ is selected from the group of —H, —$C_{1-6}$ alkyl, —$COOR_3$, and aryl;

$R_{18}$ is selected from the group of —$COOR_2$ and —$C_{1-6}$ alkyl-$COOR_2$;

$R_{19}$ is selected from the group of —H, —$C_{1-6}$ alkyl, —$C_{1-6}$ alkyl-$Q_4$, —$COR_3$, —$COOR_3$, wherein $Q_4$ is selected from the group of —$NR_2R_2$ and —$OR_2$;

$R_{20}$ and $R_{21}$ are independently selected from the group of —H, —$C_{1-6}$ alkyl, —$C_{1-6}$ substituted alkyl, —$C_{1-6}$ substituted alkyl-$OR_2$, and —$COR_3$, or $R_{20}$ and $R_{21}$ are taken together with the adjacent N to form a cycle selected from the group of

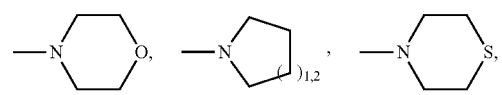

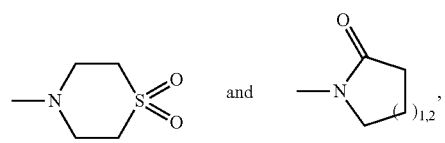

with the proviso that only one of $R_{20}$ or $R_{21}$ can be —$COR_3$, $R_{22}$ and $R_{23}$ are independently selected from the group of H, —$C_{1-6}$ alkyl, —$C_{1-6}$ substituted alkyl, and —$C_{1-6}$ cycloalkyl, or $R_{22}$ and $R_{23}$ are taken together with the adjacent N to form a cycle selected from the group of

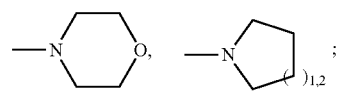

$R_{24}$ and $R_{25}$ are independently from the group of H, —$C_{1-6}$ alkyl, —$C_{1-6}$ substituted alkyl, —$C_{1-6}$ alkyl-$Q_5$, —$C_{1-6}$ cycloalkyl, aryl, substituted aryl, heteroaryl, and substituted heteroaryl, and $Q_5$ is selected from the group of halogen and $SO_2R_3$.

Even more preferred compounds include those wherein $R_1$ is isopropenyl.

More preferred compounds include those which are encompassed by Formula I. Of these, those wherein X is a phenyl ring are even more preferred. Even more preferred are compounds of Formula I wherein X is a phenyl ring and Y is in the para position.

Also preferred are compounds of Formula I wherein A is at least one member selected from the group of —H, —OH, -halo, —$C_{1-3}$ alkyl, and —$C_{1-3}$ alkoxy, wherein -halo is selected from the group of —Cl, —F and —Br, with —F being more preferred. It is even more preferred that A is —H.

Also preferred are compounds of Formula I wherein Y is —$COOR_2$, and more preferably —COOH.

Also preferred are compounds wherein $R_4$ is selected from the group of —H, —$C_{1-6}$ alkyl, —$C_{1-6}$ alkyl-$Q_1$, and —$COR_6$. Especially preferred are compounds wherein $R_4$ is —$C_{1-6}$ alkyl-$Q_1$ or —$COR_6$.

It is also preferred that $R_5$ is —H.

In addition, it is preferred that $Q_1$ is —$NR_8R_9$.

In another preferred embodiment there is provided a compound of Formula Ia below wherein X is a phenyl ring and Y is —COOH in the para position:

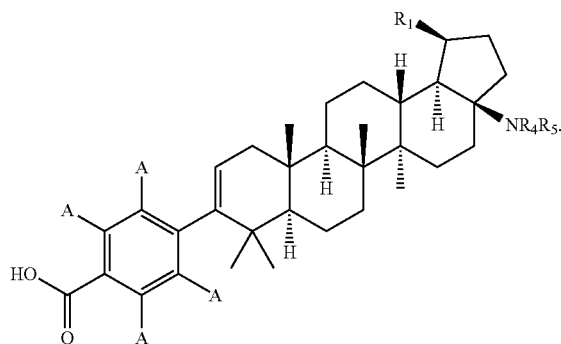

Formula Ia

In this embodiment, it is also preferred that A is at least one member selected from the group of —H, -halo, —OH, —$C_{1-3}$ alkyl and —$C_{1-3}$ alkoxy. It is particularly preferred that A is at least one member selected from the group of —H, -fluoro, -chloro, —OH, -methyl and -methoxy, with —H being even more preferred.

In addition, in a further embodiment of the invention compounds of Formula II are preferred, as are compounds of Formula III.

Other compounds, including pharmaceutically acceptable salts thereof, which are preferred as part of the invention include the following:

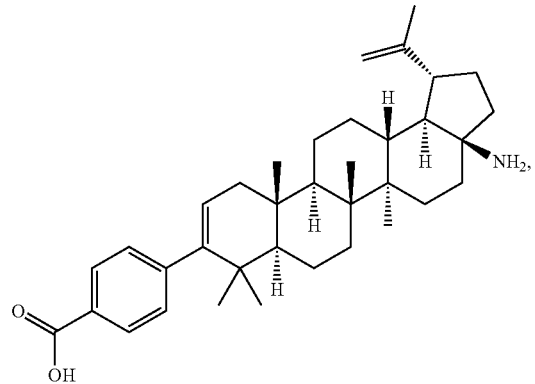

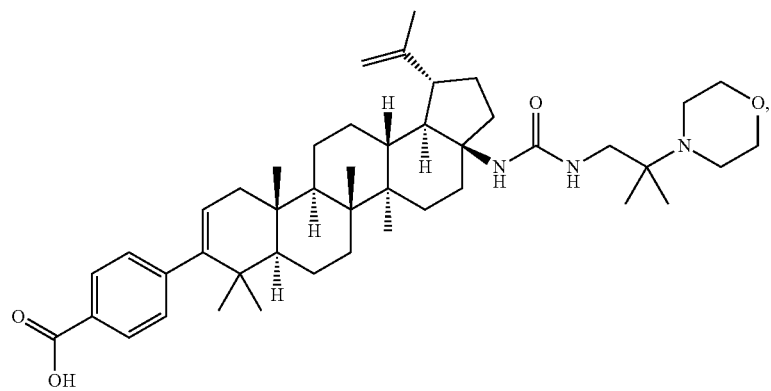

-continued
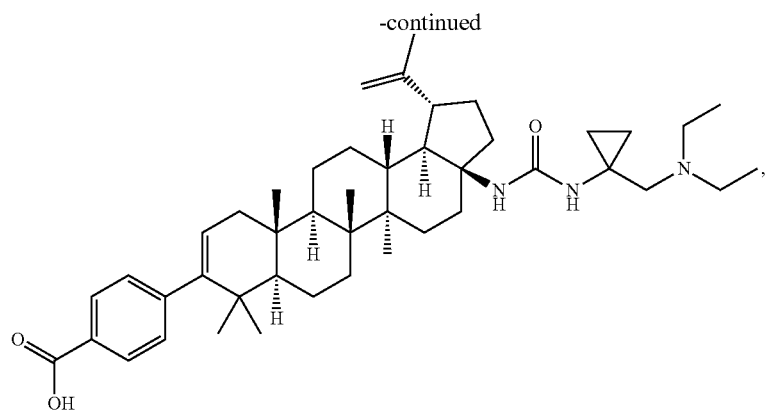
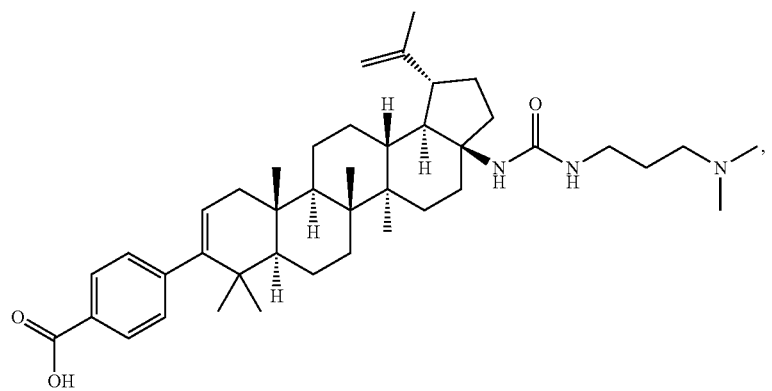
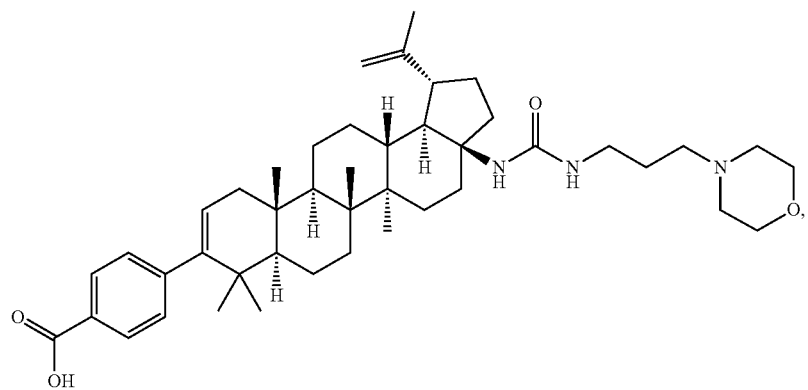
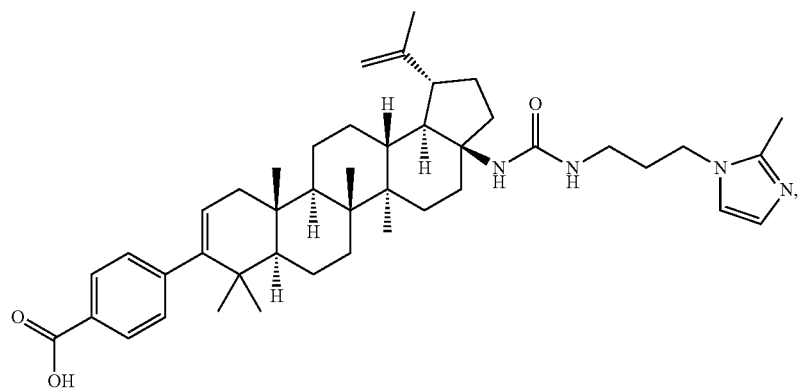

-continued
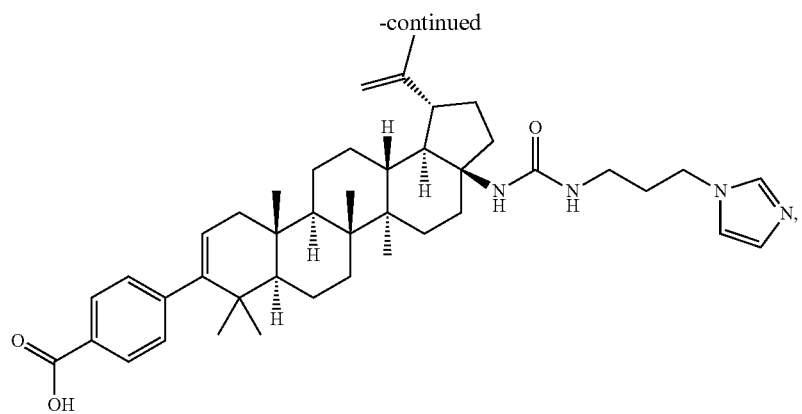
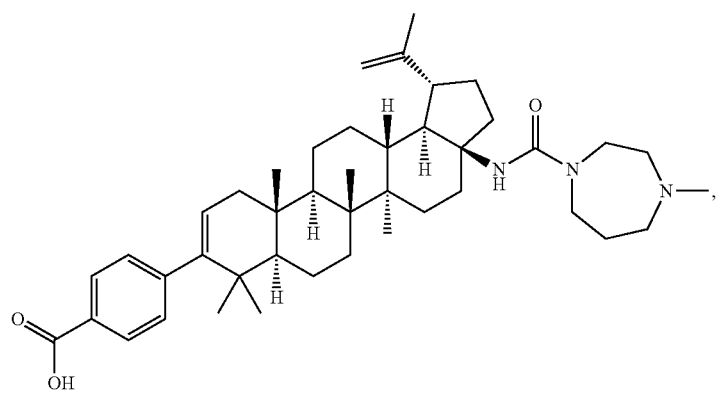
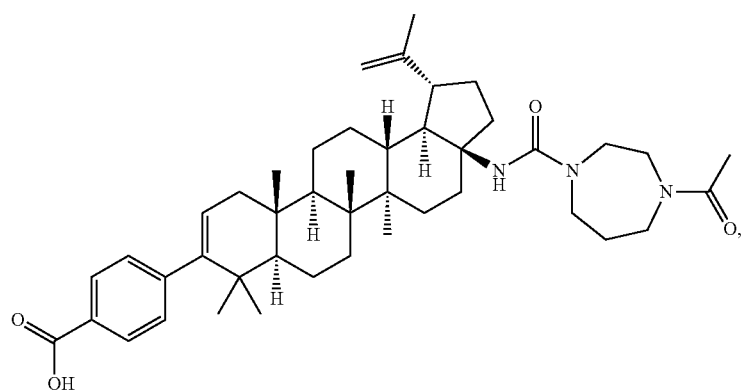
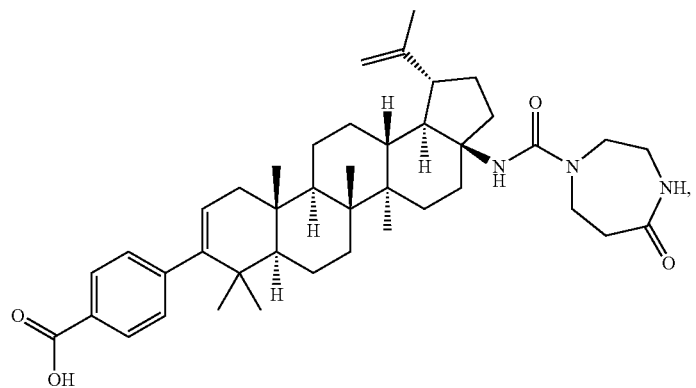

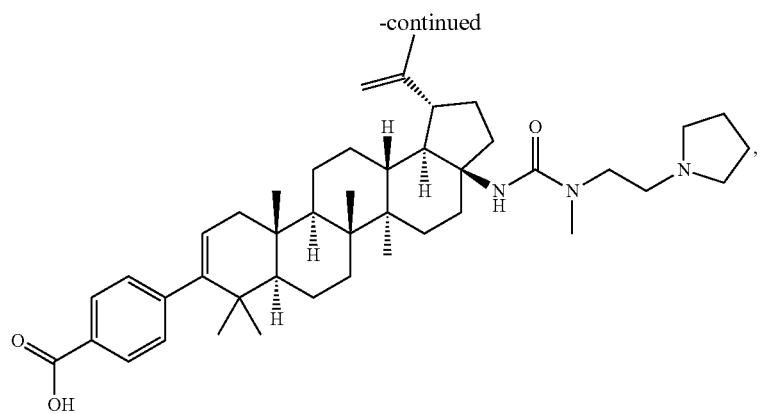
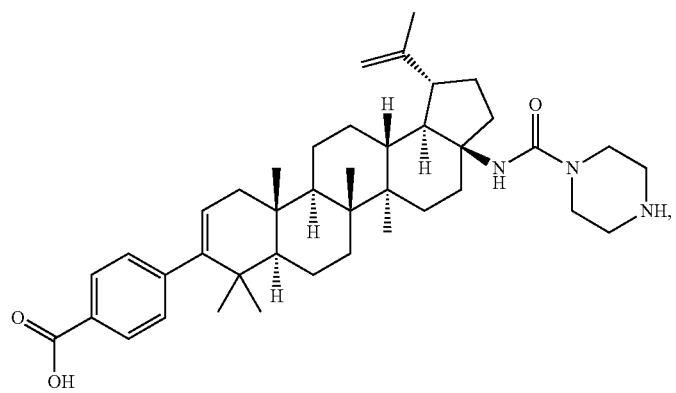
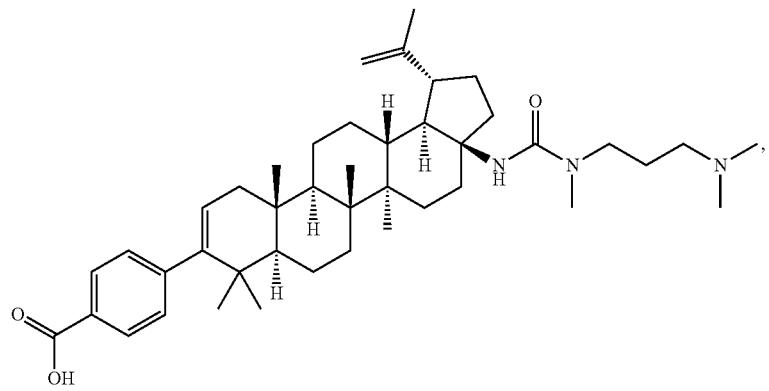
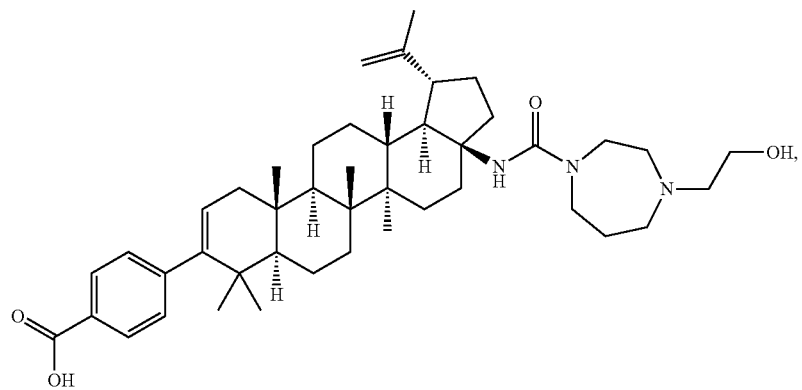

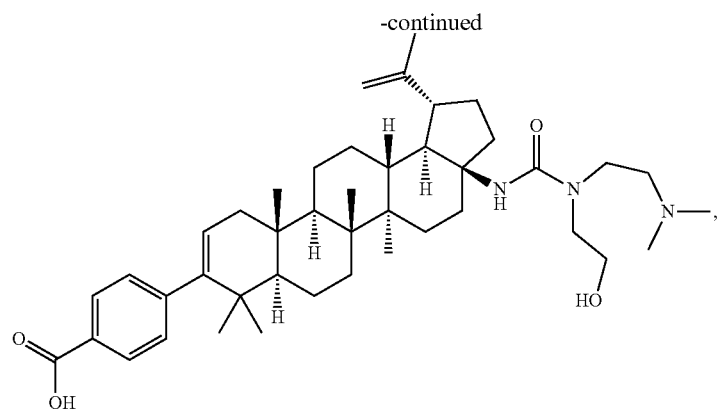
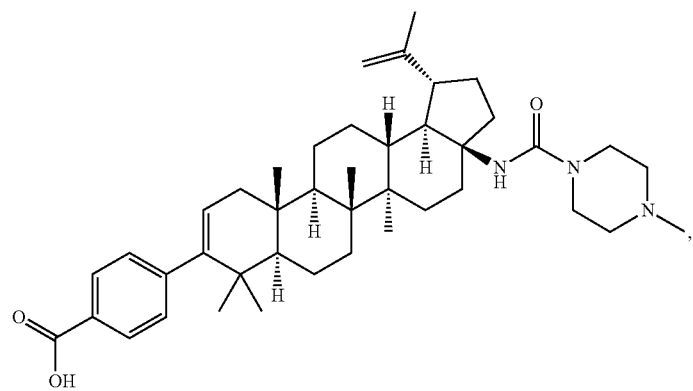
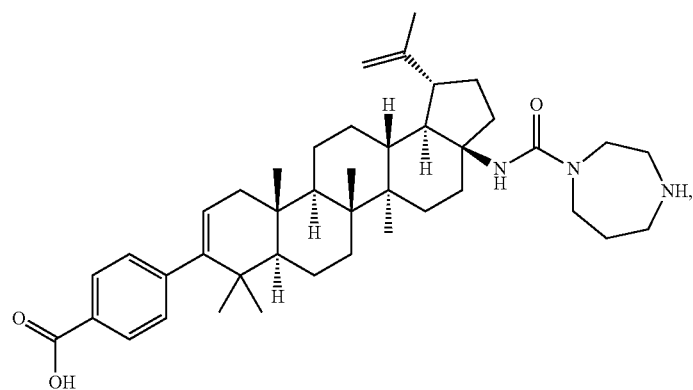
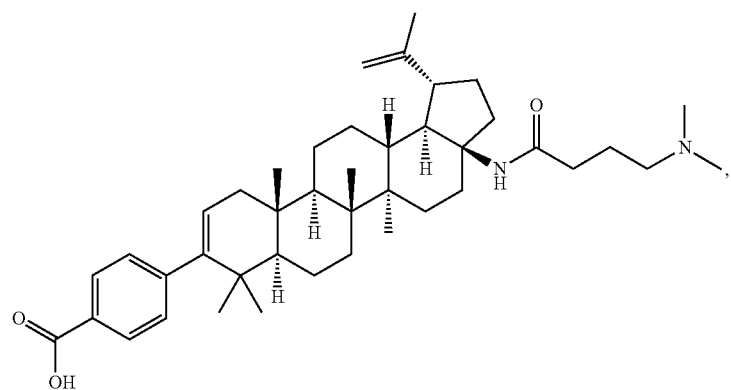

-continued
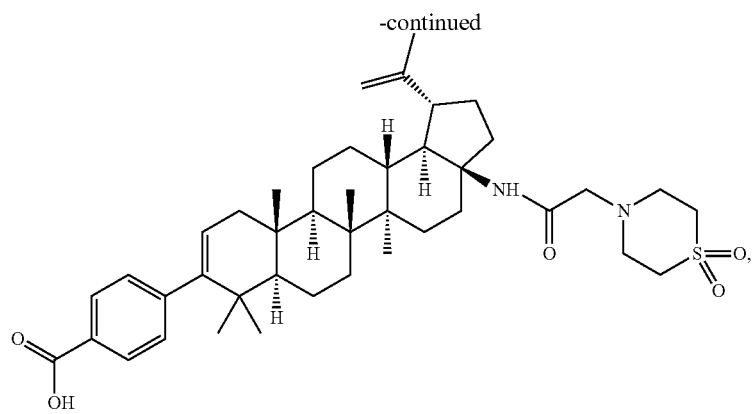
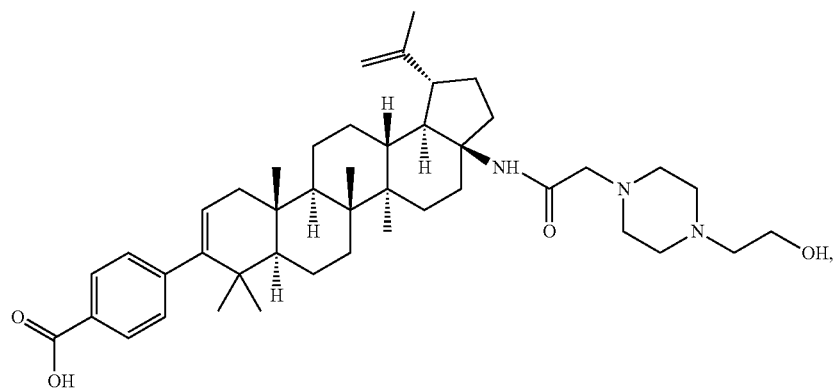
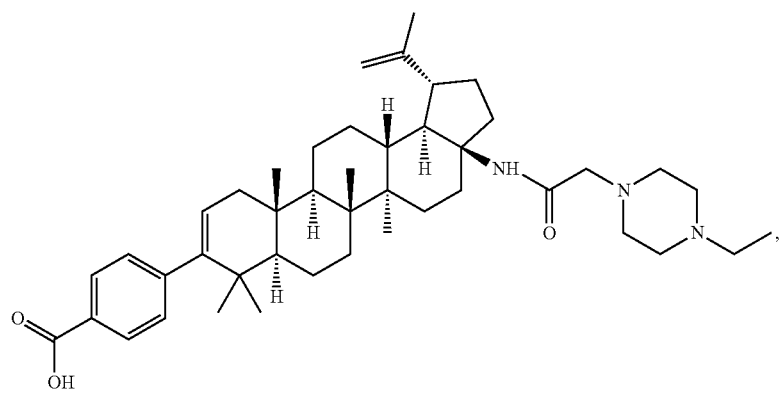
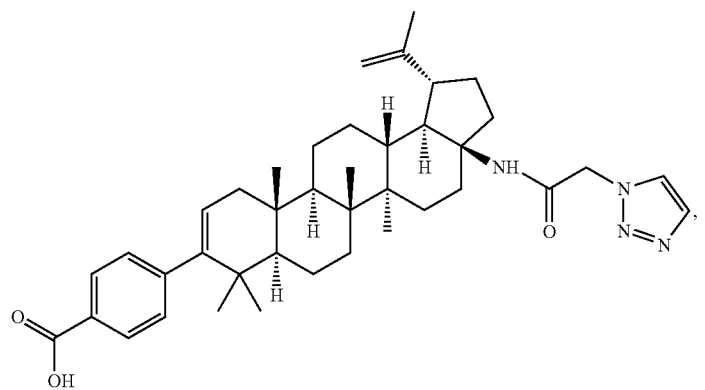

-continued
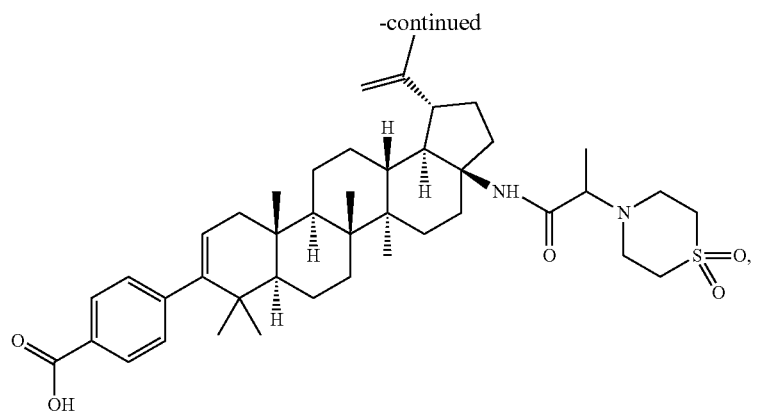
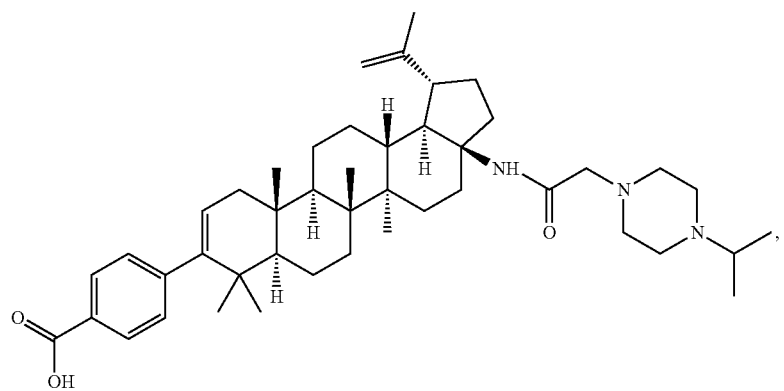
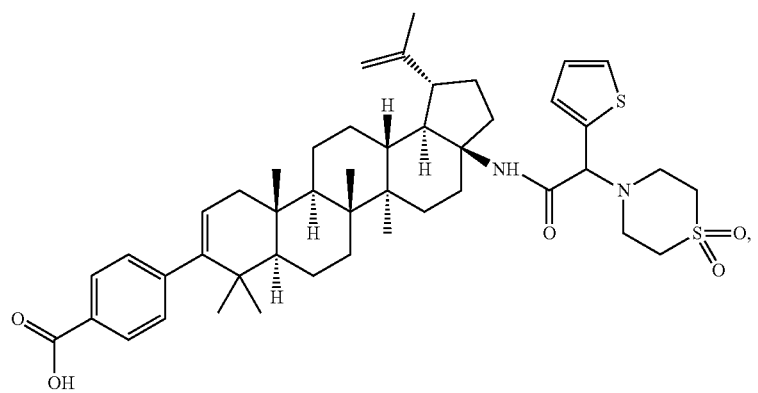
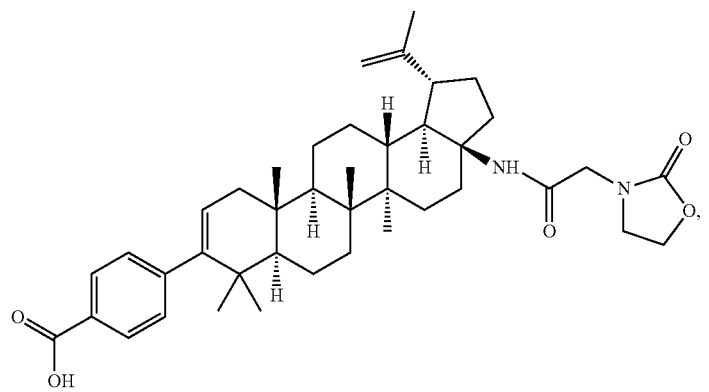

-continued
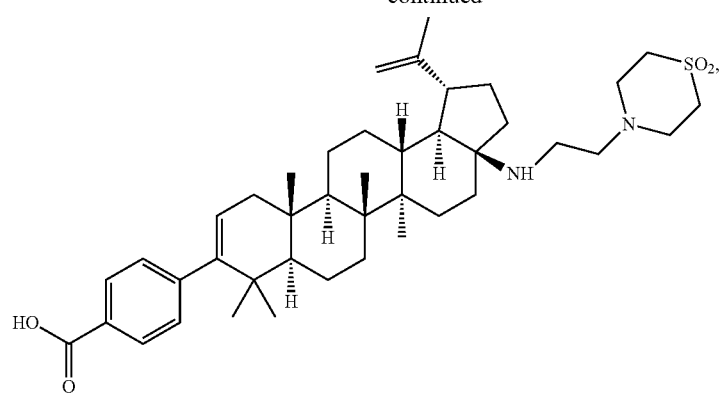
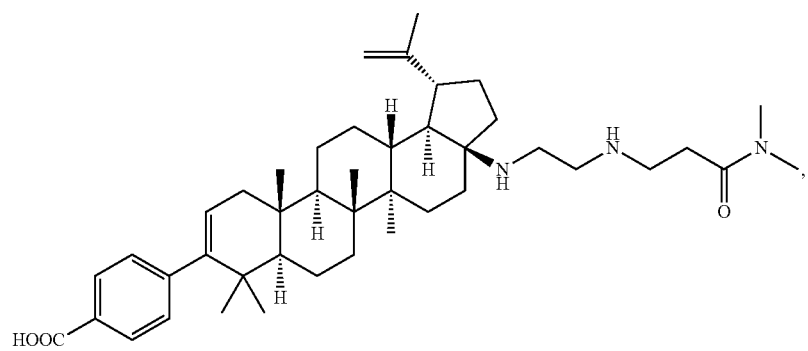
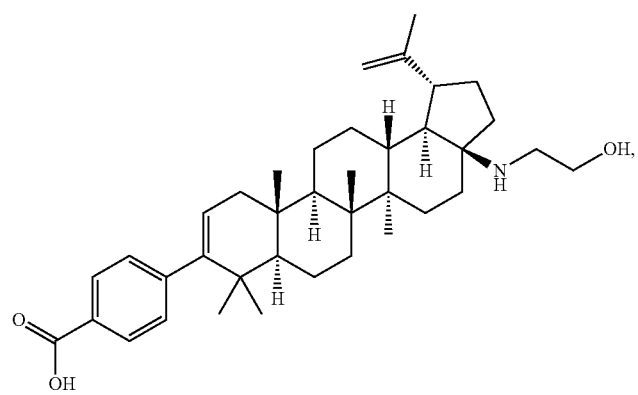
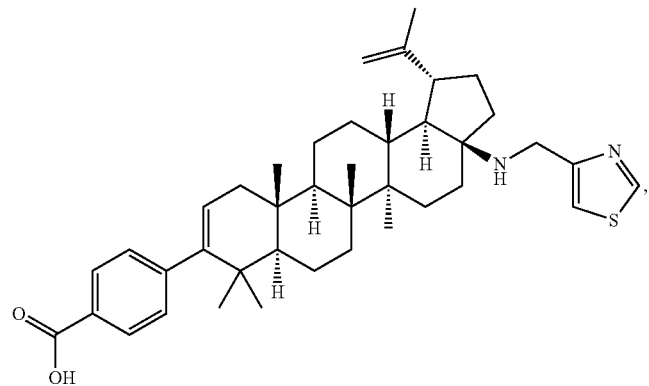

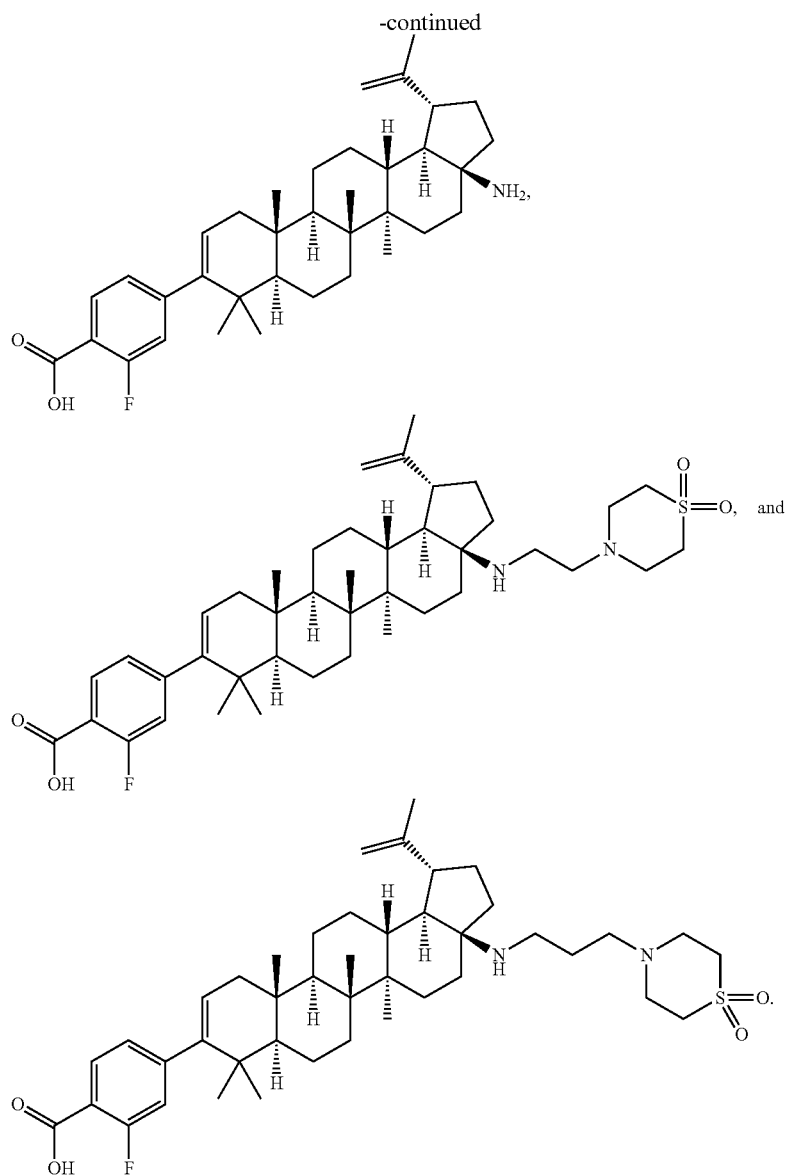
Also preferred are the following compounds, including pharmaceutically acceptable salts thereof:
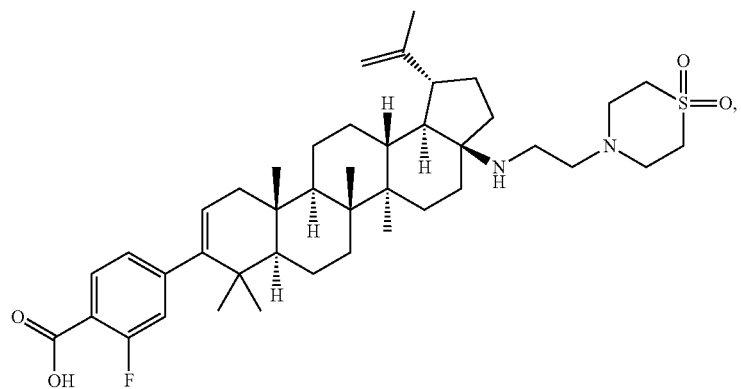

-continued
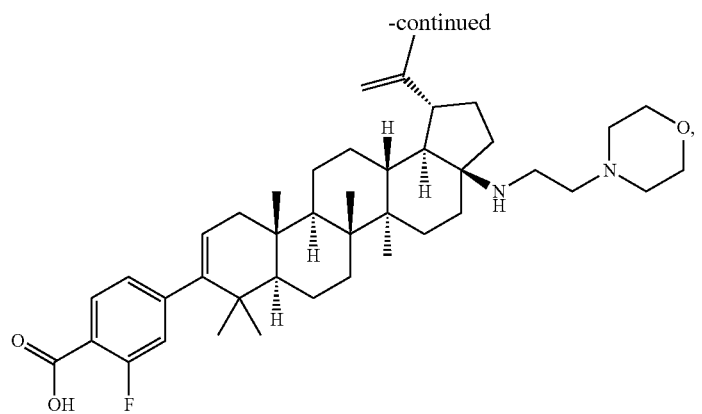
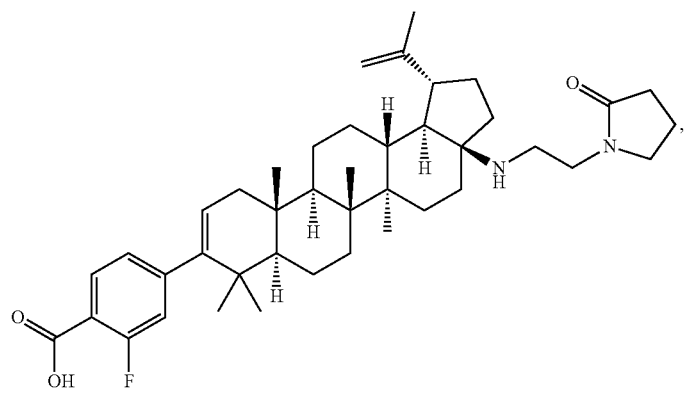
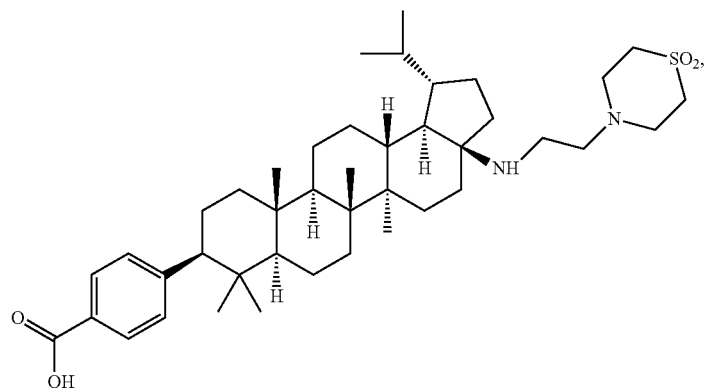
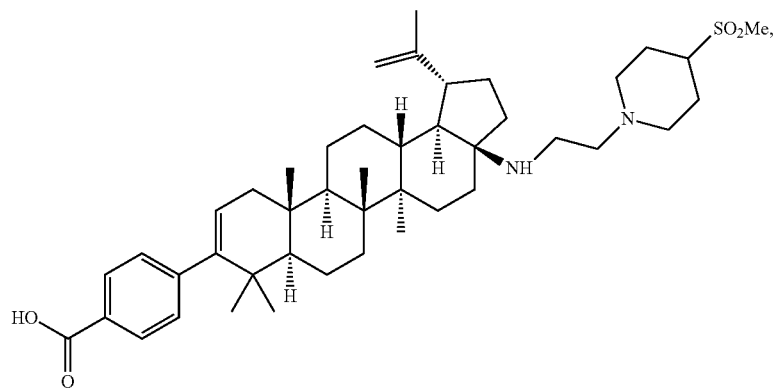

-continued
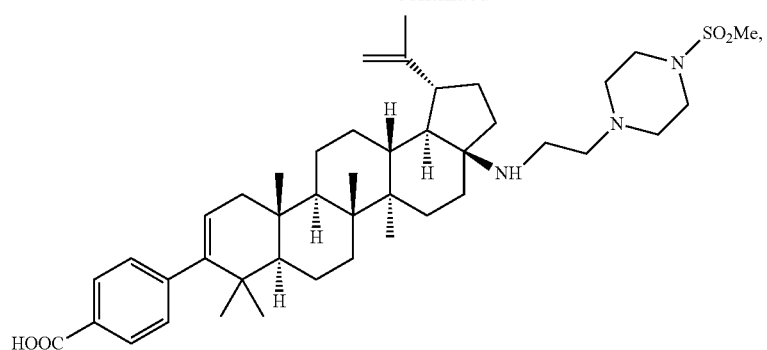
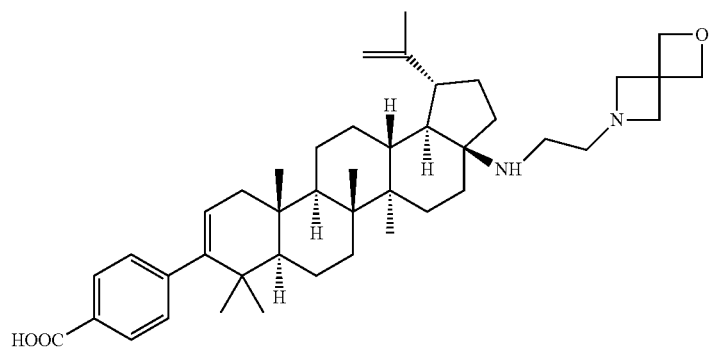
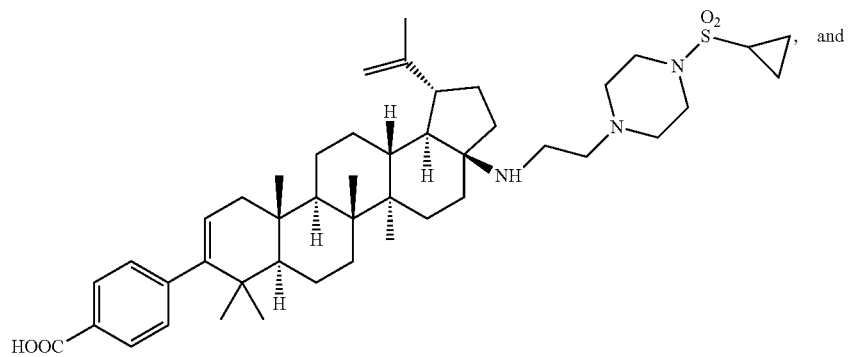
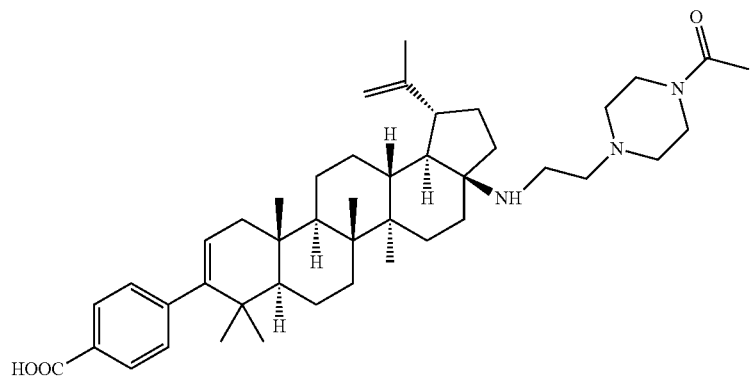

-continued

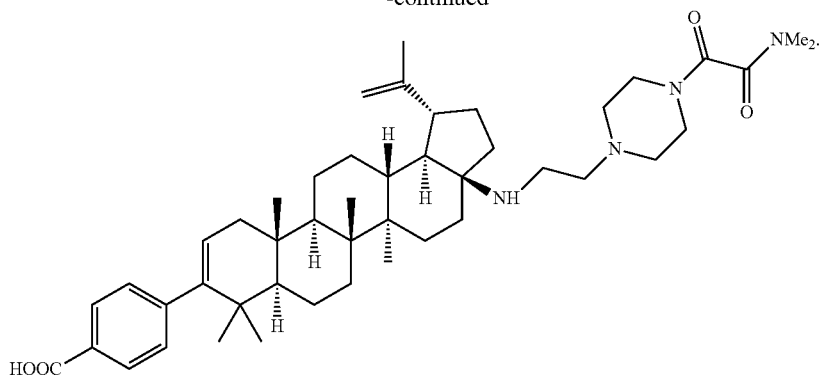

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formulas I, II, and/or III, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formulas I, II, and/or III herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

| ANTIVIRALS | | |
|---|---|---|
| Drug Name | Manufacturer | Indication |
| 097 | Hoechst/Bayer | HIV infection, AIDS, ARC (non-nucleoside reverse transcriptase |

ANTIVIRALS -continued

| Drug Name | Manufacturer | Indication |
|---|---|---|
| | | (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside |

ANTIVIRALS

| Drug Name | Manufacturer | Indication |
| --- | --- | --- |
| | | reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |

ANTIVIRALS

| Drug Name | Manufacturer | Indication |
|---|---|---|
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| Selzentry Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® 4'-ethynyl-d4T | Oncolys BioPharma BMS | HIV infection AIDs in development |
| CMX-157 Lipid conjugate of nucleotide tenofovir | Chimerix | HIV infection AIDs |
| GSK1349572 Integrase inhibitor | GSK | HIV infection AIDs |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |

| IMMUNOMODULATORS | | |
|---|---|---|
| Drug Name | Manufacturer | Indication |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldesleukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

| ANTI-INFECTIVES | | |
|---|---|---|
| Drug Name | Manufacturer | Indication |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*. Meanwell, Nicholas A.; Kadow, John F. Current Opinion in Drug Discovery & Development (2003), 6(4), 451-461. Specifically the compounds can be utilized in combination with attachment inhibitors, fusion inhibitors, and chemokine receptor antagonists aimed at either the CCR5 or CXCR4 coreceptor. HIV attachment inhibitors are also set forth in U.S. Pat. No. 7,354,924 and US 2005/0209246.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2 (R)-hydroxy-1-(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound of the present invention and other active agents may be administered separately or in conjunction. In addition, the administration of one element may be prior to, concurrent to, or subsequent to the administration of other agent(s).

GENERAL CHEMISTRY

Methods of Synthesis

The present invention comprises compounds of Formulas I, II, and III, their pharmaceutical formulations, and their use in patients suffering from or susceptible to HIV infection. The compounds of Formulas I, II, and III also include pharmaceutically acceptable salts thereof. General procedures to construct compounds of Formulas I, II, and III and intermediates useful for their synthesis are described in the following Schemes (after the Abbreviations).

Abbreviations

One or more of the following abbreviations, most of which are conventional abbreviations well known to those skilled in the art, may be used throughout the description of the disclosure and the examples:
Bz$_2$O=benzoic anhydride
TBTU=O-(benzotriazol-1-yl)-N,N,N',N'-tetramethyluronium tetrafluoroborate
HATU=2-(1H-7-azabenzotriazol-1-yl)-1,1,3,3-tetramethyluronium hexafluorophosphate methanaminium
DCE=dichloroethane
DCM=dichloromethane
CDI=carbonyl diimidazole
prep. HPLC=preparative high performance liquid chromatography
rt=room temperature
DIPEA=diisopropylethylamine
DMAP=4-dimethylaminopyridine
DMSO=dimethylsulfoxide
THF=tetrahydrofuran
KHMDS=potassium bis(trimethylsilyl)amide
min=minute(s)
h=hour(s)
sat.=saturated
TEA=triethylamine
EtOAc=ethyl acetate
TFA=trifluoroacetic acid
PCC=pyridinium chlorochromate
TLC=thin layer chromatography
Tf$_2$NPh=(trifluoromethylsulfonyl)methanesulfonamide
dioxane=1,4-dioxane
PG=protective group
atm=atmosphere(s)
mol=mole(s)
mmol=milimole(s)
mg=milligram(s)
µg=microgram(s)
µl=microliter(s)
µm=micrometer(s)
mm=millimeter(s)
HOAc=acetic acid
MeOH=methanol
DMF=N,N-dimethylformamide
TBAF=tetrabutylammonium fluoride
TBDMSCl=tert-butyldimethylsilyl chloride The terms "C-3" and "C-28" refer to certain positions of a triterpene core as numbered in accordance with IUPAC rules (positions depicted below with respect to an illustrative triterpene: betulin):

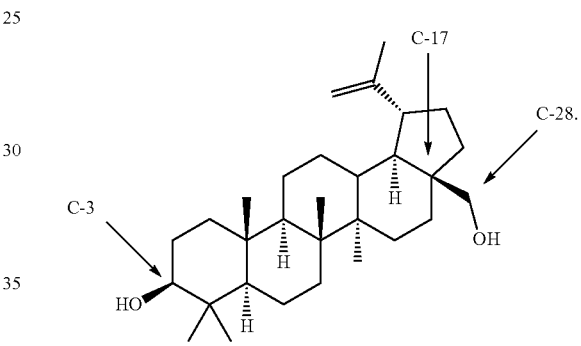

The same numbering is maintained when referring to the compound series in schemes and general descriptions of methods.

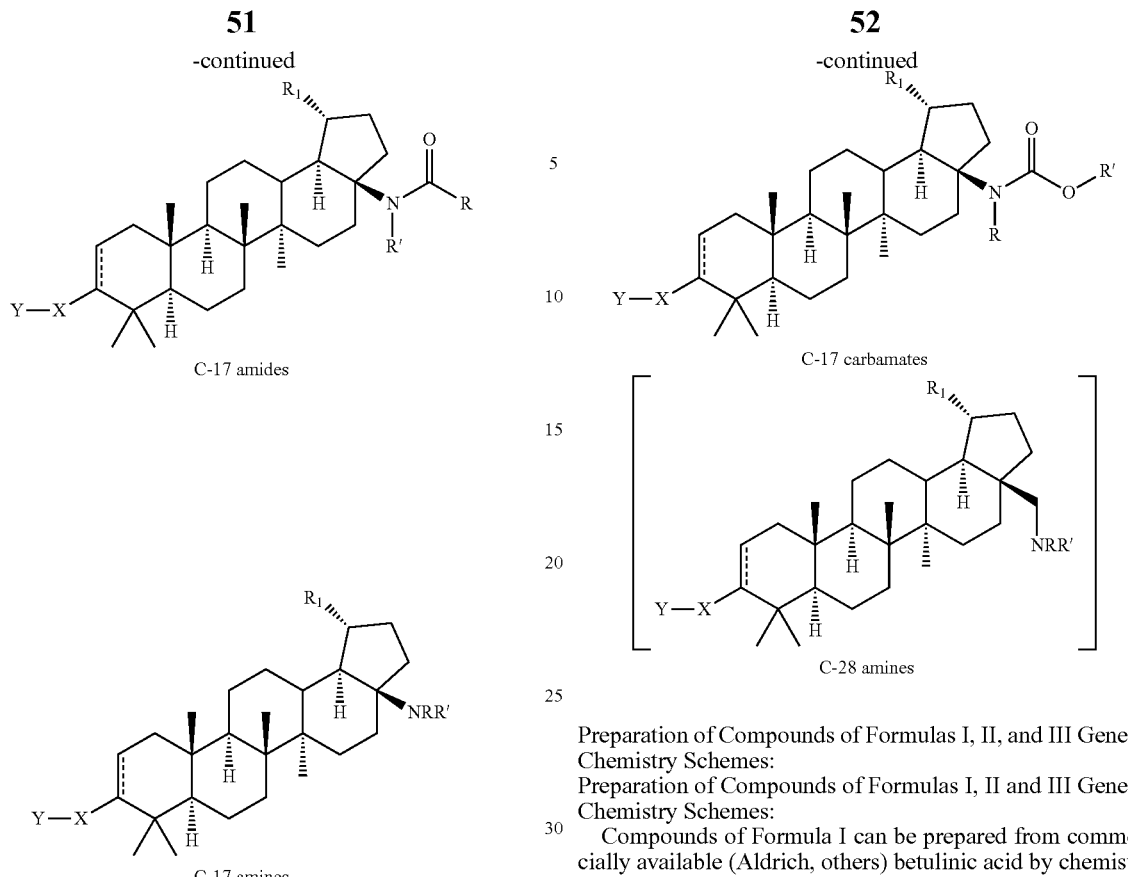

Preparation of Compounds of Formulas I, II, and III General Chemistry Schemes:

Preparation of Compounds of Formulas I, II and III General Chemistry Schemes:

Compounds of Formula I can be prepared from commercially available (Aldrich, others) betulinic acid by chemistry described in the following schemes. Compounds of Formula II and III are described thereafter.

General reaction schemes are set forth as follows:

Scheme 1

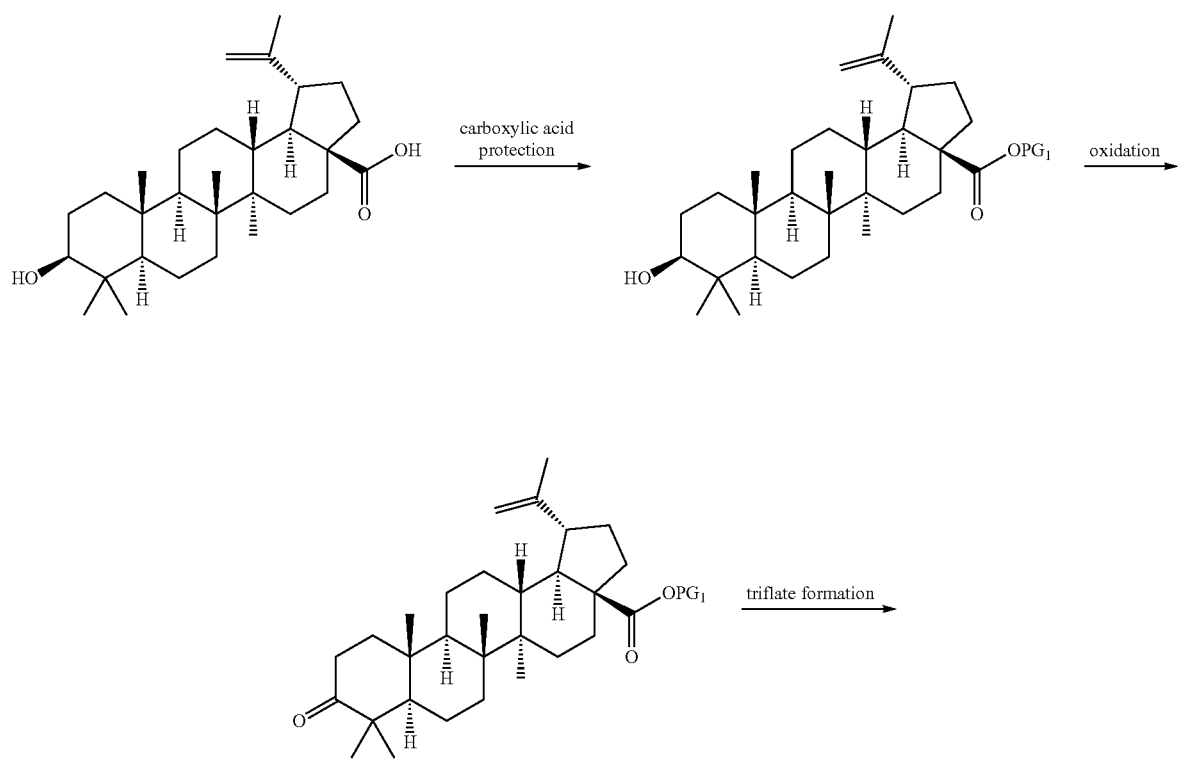

-continued
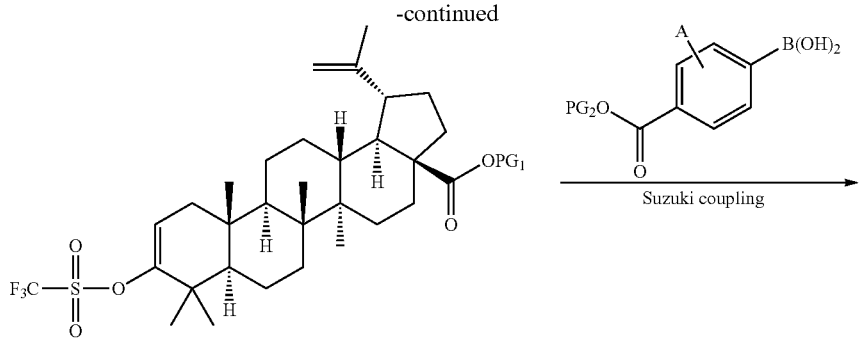
Suzuki coupling
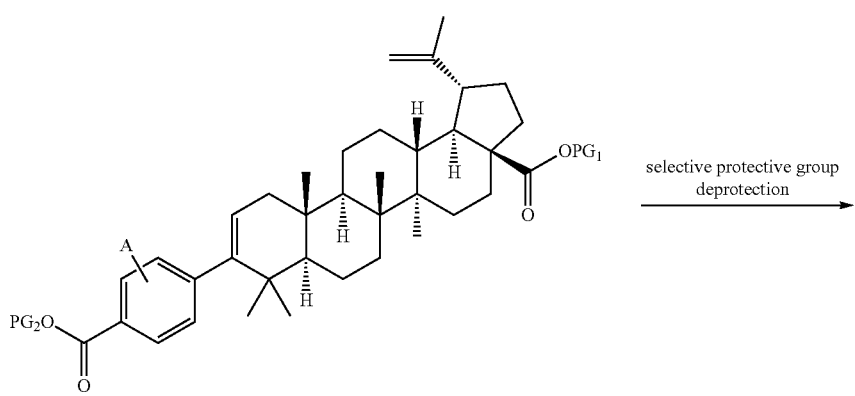
selective protective group deprotection
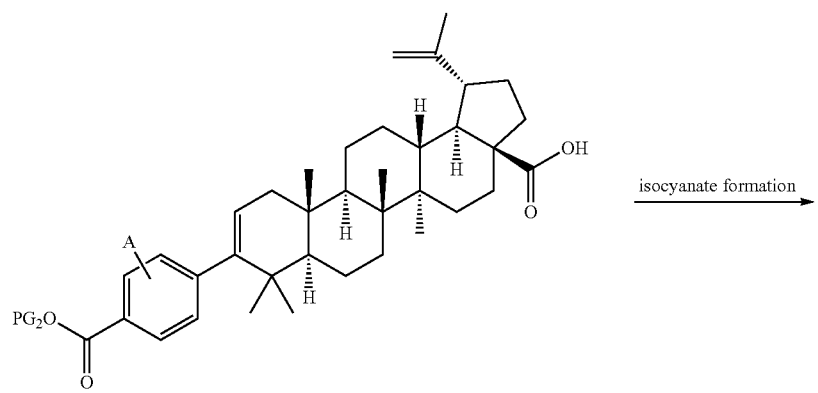
isocyanate formation
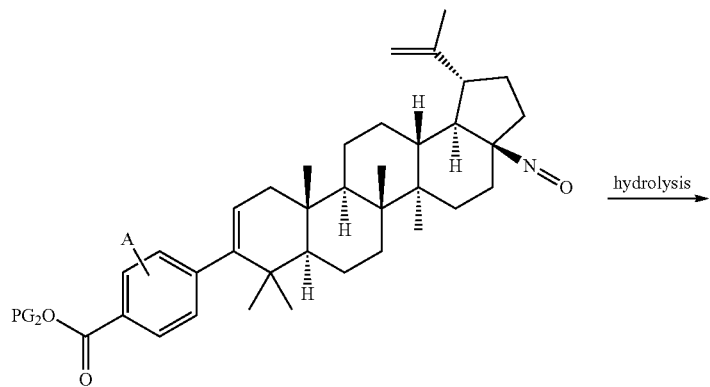
hydrolysis -continued

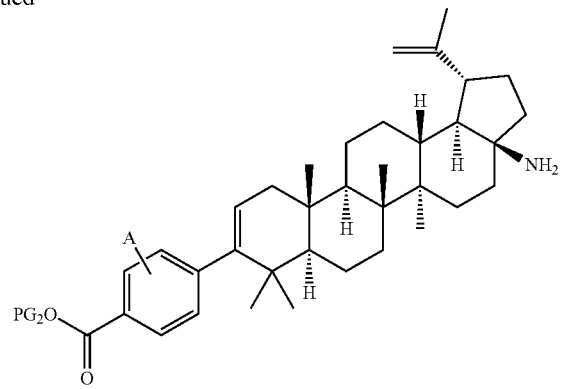

Scheme 1 describes the preparation of the key intermediate C-17 primary amine from betulinic acid. The carboxylic acid present in betulinic acid was protected with a suitable protective group. Standard oxidation (i.e. PCC, Dess-Martin) of the C-3 hydroxyl group produces the C-3 ketone which is then converted into the triflate using conditions know to those skilled in the art. Palladium-catalyzed cross coupling with a boronic acid derivative (Stille coupling using stannanes can also be used) afforded the corresponding C-3-modified betulinic acid derivatives. The C-28 carboxylic ester was then selectively deprotected and submitted to Curtius rearrangement conditions to afford the C-17 primary amine. This reaction can be carried out in one single step or stepwise via isolation of the isocyanate intermediate, as shown in Scheme 1.

Scheme 2

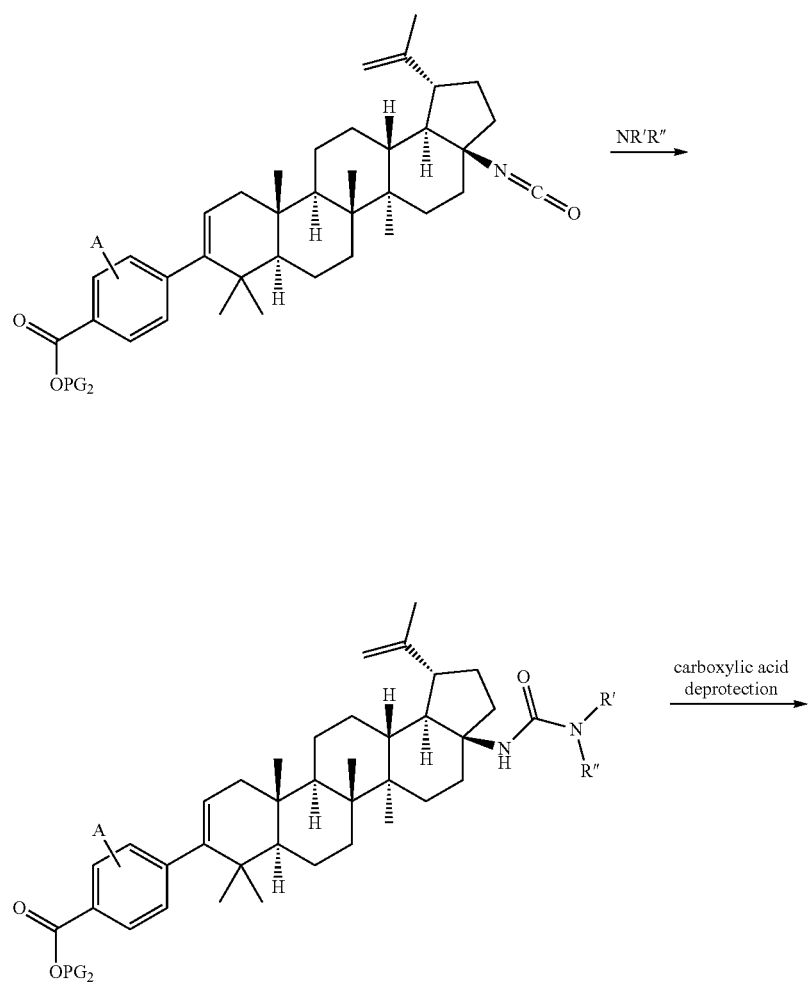

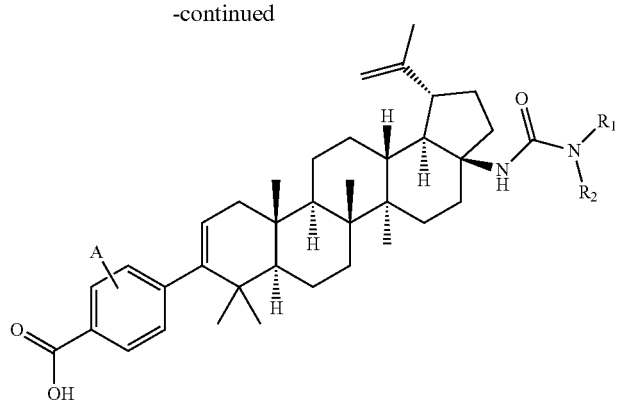
The isocyanate can be further modified to prepare ureas as shown in Scheme 2. Addition of an amine to a solution of the isocyanate in a solvent such as THF or dioxane in the presence of Hunig's base or TEA at room temperature or heating if necessary, affords the corresponding C-17 urea. Hydrolysis of the benzoic ester affords the benzoic acid derivative.
Scheme 3
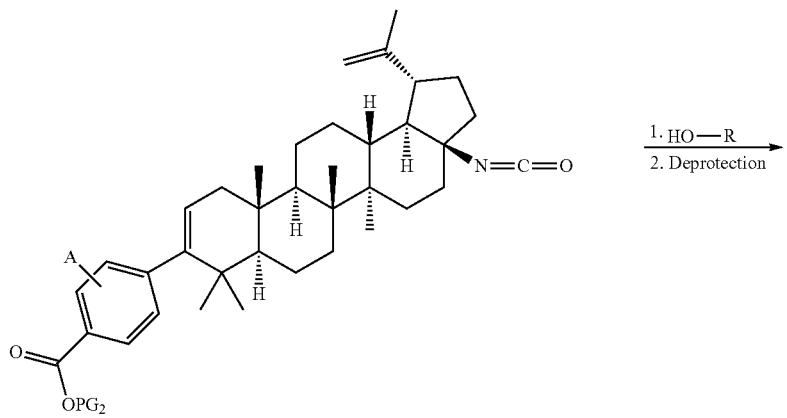
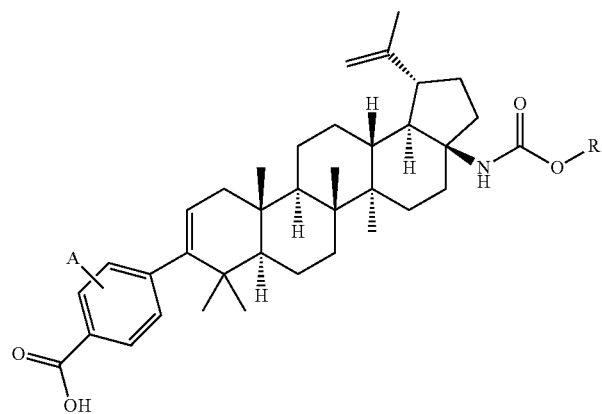

Similarly, carbamates can be prepared by adding an alcohol to the isocyanate in a solution of THF or dioxane in the presence of a base such as sodium hydride at room temperature or heating when necessary followed by hydrolysis of the carboxylic ester. The deprotection may also happen under the conditions of the first reaction, so no additional step may be needed.

The C-17 primary amine can be further modified using standard methods, known to those skill in the art. Some examples are shown in the following schemes.

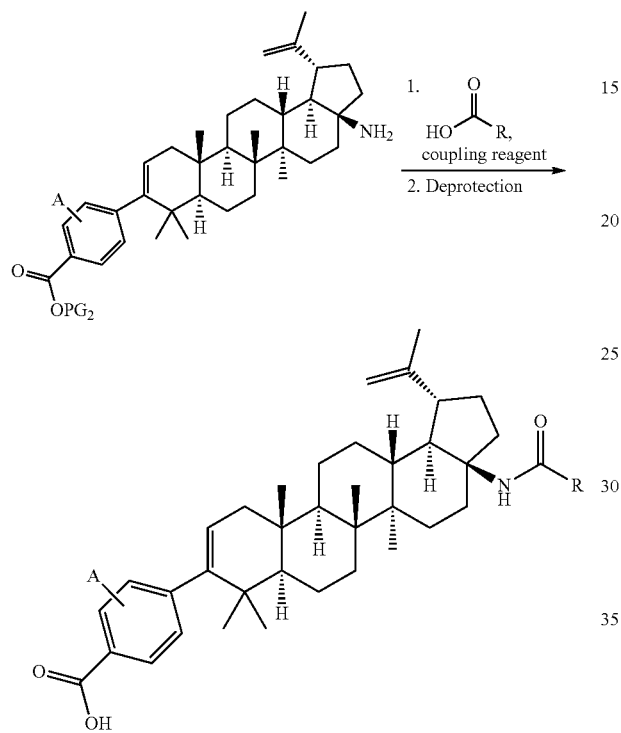

C-17 amides can be prepared by reacting a carboxylic acid with the C-17 primary amine in the presence of an adequate coupling reagent such as HATU, DCC, and others known to those skilled in the art, in the presence of a base such as Hunig's base, TEA, etc., in the appropriate solvent (DCM, THF, DMF, etc.). Hydrolysis of the carboxylic ester affords the benzoic acid. Alternatively, some amides can be prepared by treating the C-17 primary amine with the corresponding carboxylic acid chloride reagent instead of an acid. Similarly, sulfonamides can be prepared from the C-17 primary amine by using a sulfonyl chloride as the sulfonylating agent.

Scheme 5

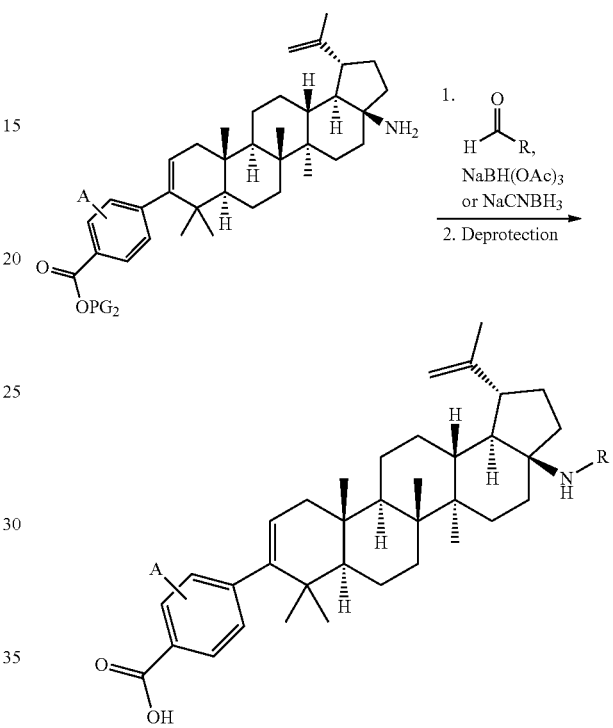

The C-17 primary amine can be treated with an aldehyde under reductive amination conditions (e.g. NaBH(OAc)$_3$) in the presence of AcOH/NaOAc or Ti(OPr)$_4$ in a solvent such as THF, 1,4-dioxane, DCE or DCM) to afford C-17 secondary amines Hydrolysis of the carboxylic ester renders the benzoic acid compound.

Scheme 6

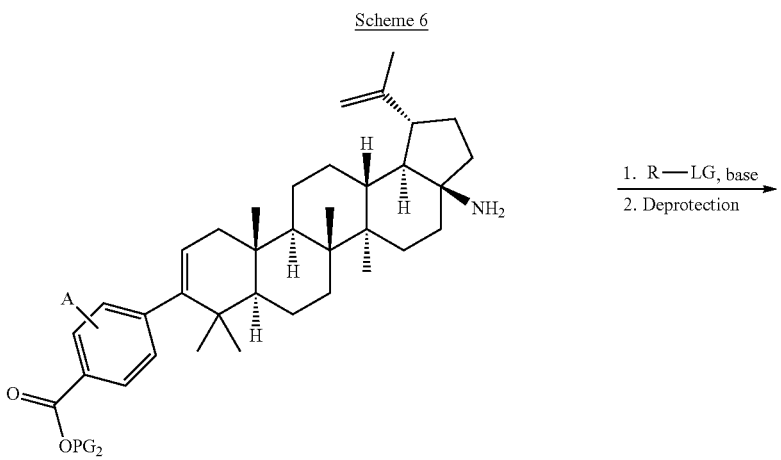

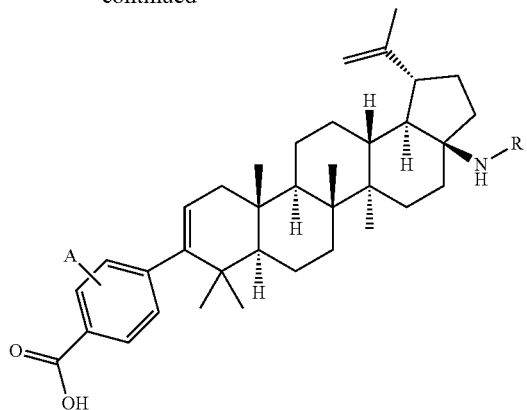

Some C-17 amines can be prepared by alkylation of the C-17 primary amine with an alkylating agent (R-LG), where LG is a leaving group such as, but not limited to Br, Cl, I, mesylate, tosylate or triflate in the presence of a base. Heating may be needed in some cases. Hydrolysis of the carboxylic ester renders the benzoic acid product.

Scheme 7

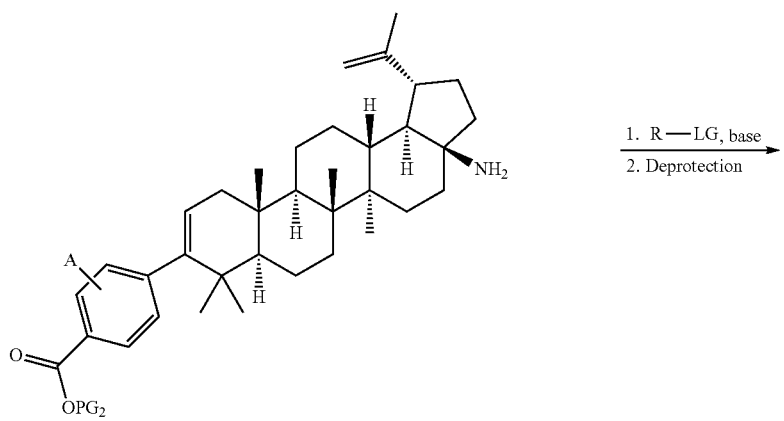

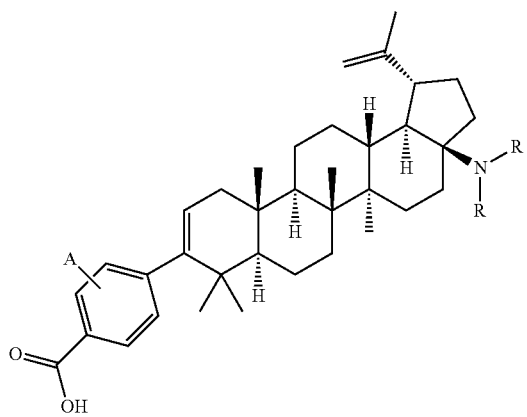

In some cases, by prolonging the reaction times and heating the reaction mixture, the dialkylated product can also be formed.

Scheme 8

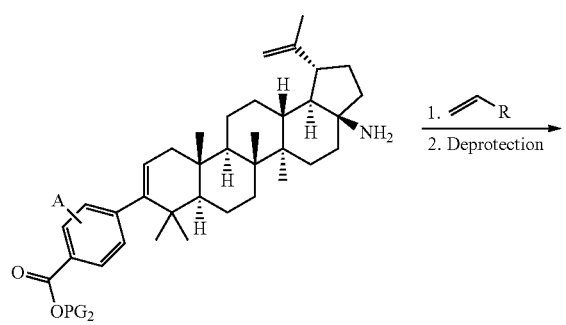

Alternatively, some C-17 amines can be prepared by 1,4-addition to Michael acceptors followed by hydrolysis of the ester.

Substituents R, R' and R" may contain functional groups (i.e. COOH, COOR, OH, NHR) that can be further modified by methods know to those skilled in the art. The modification can be carried out before or after the final deprotection of the carboxylic acid is performed depending on the nature of the functional group.

Alternatively, the C-17 secondary amine can be further modified (i.e. alkylated, acylated, sulfonylated, etc.) using some of the methods described above or other standard methods known to those skilled in the art. Saturation of the isopropenyl group can be accomplished by hydrogenation under standard conditions of the final products.

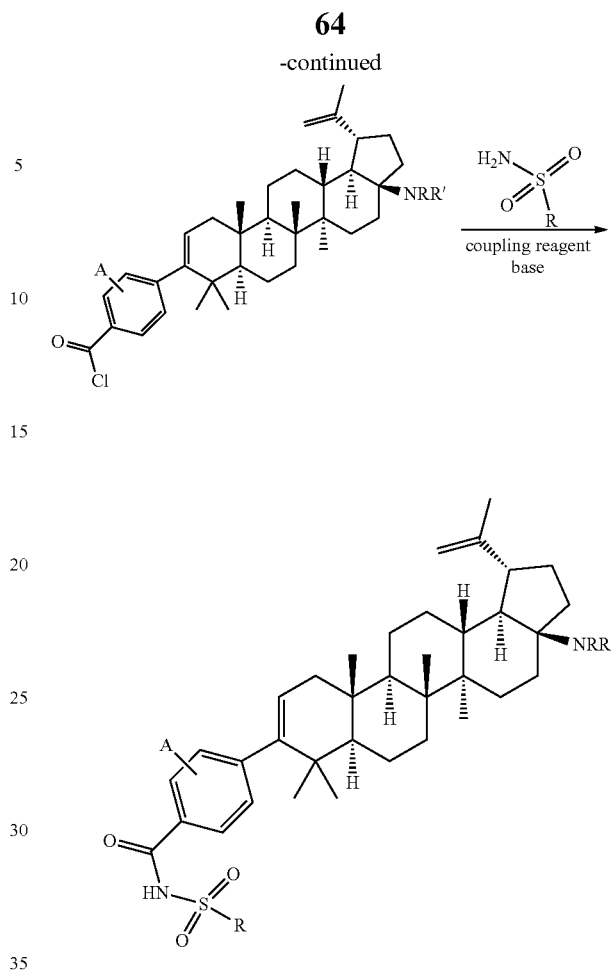

The benzoic acid can be further modified by methods known to those skilled in the art. An example of such modifications is shown in scheme 9: The free benzoic acid can be converted into the corresponding acid chloride and then treated with the corresponding nucleophile, for example a sulfonyl amide or urea sulfamide, in the presence of a base to afford a sulfonyl amide or acylsulfamide derivative.

Compounds of formula I where the modification in the C-3 position differs from benzoic acid can be prepared by selecting the corresponding boronic acid in the palladium-catalyzed cross coupling step shown in Scheme 1 (Scheme 10). Then the C-28 position can be modified using the chemistry methods described in the above schemes to obtain the corresponding C-17 amino derivatives.

Scheme 9

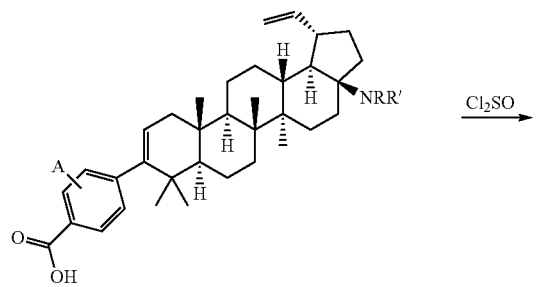

Scheme 10

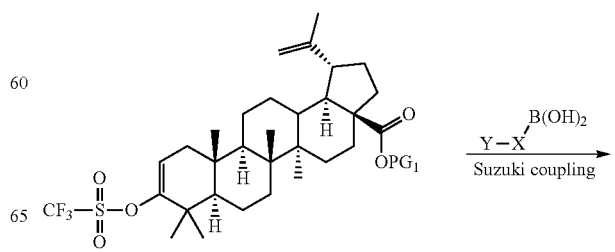

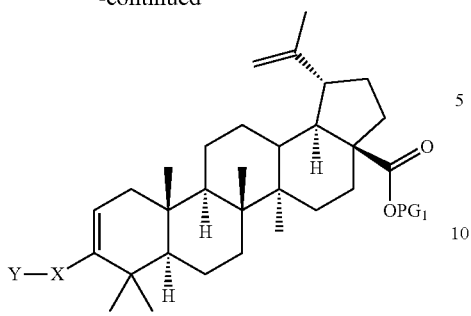

Alternatively, compounds of formula I can be prepared from betulinic acid as described in Scheme 11. Curtius rearrangement of betulinic acid can be accomplished without protection of the $C_{1-3}$ hydroxyl group to render the C-17 isocyanate which upon acid hydrolysis affords the C-17 amine. The C-17 amine is then selectively protected with an amine protective group (i.e F-moc, Boc) to then perform the oxidation of the $C_{1-3}$ hydroxy group to a ketone under standard conditions (i.e. PCC, Dess-Martin reagent, etc). Conversion of the ketone into its triflate can be accomplished by methods known to those skilled in the art. The protective group in the amino group is then taken off to produce the C-17 unsubstituted amine Installation of the C-3 moiety is accomplished via Suzuki coupling of the triflate with the corresponding boronic acid as described above. The C-17 amino group can then be derivatized as shown above in previous schemes (alkyaltion, acylation, etc).

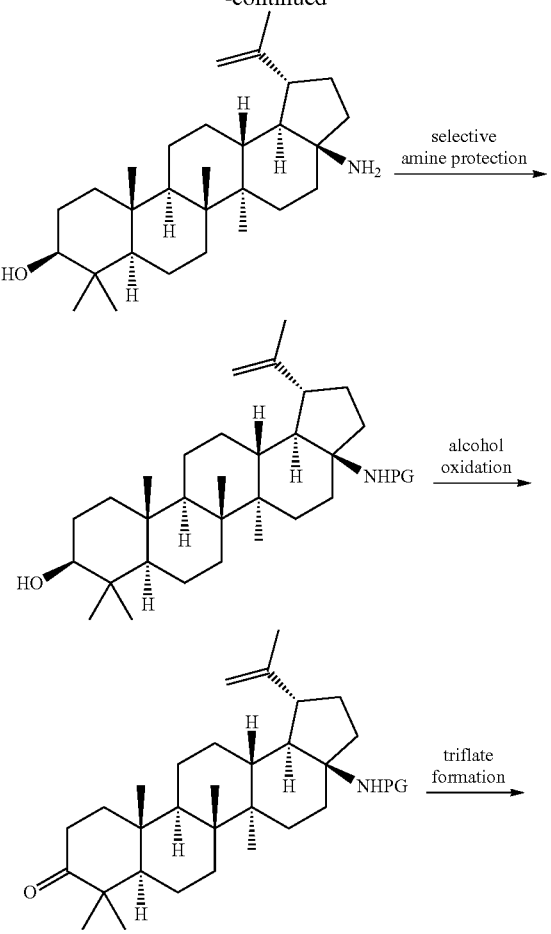

Scheme 11

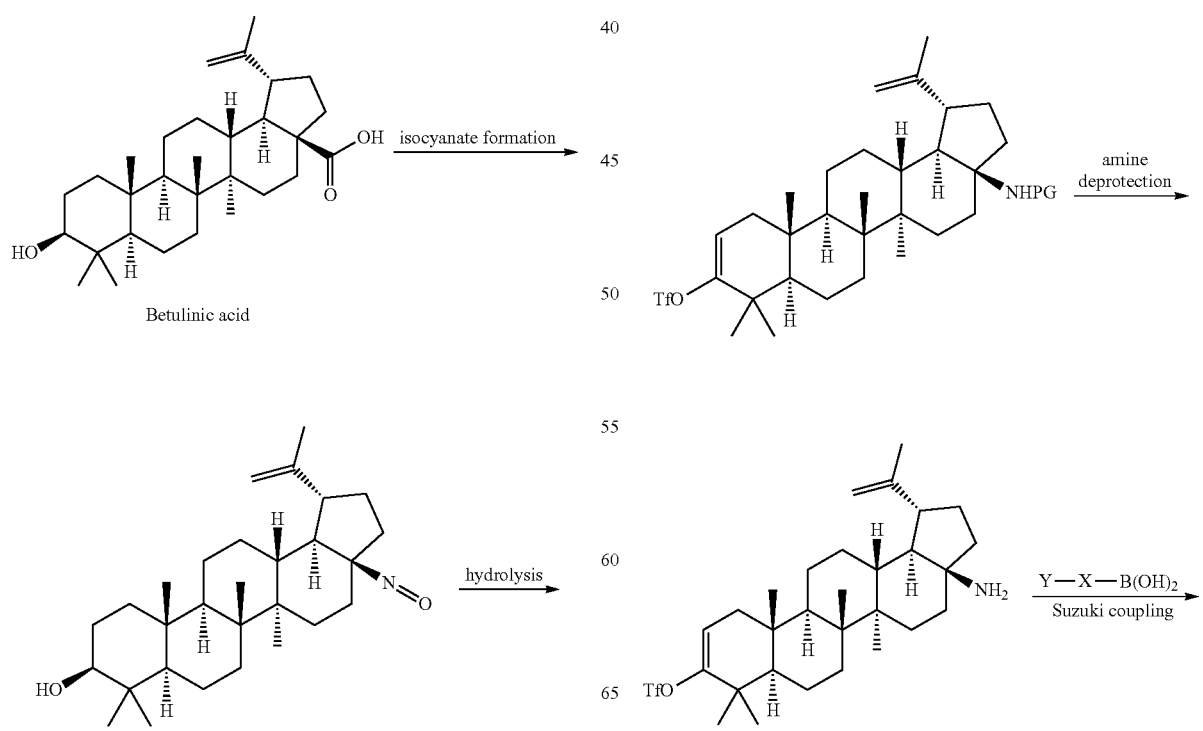

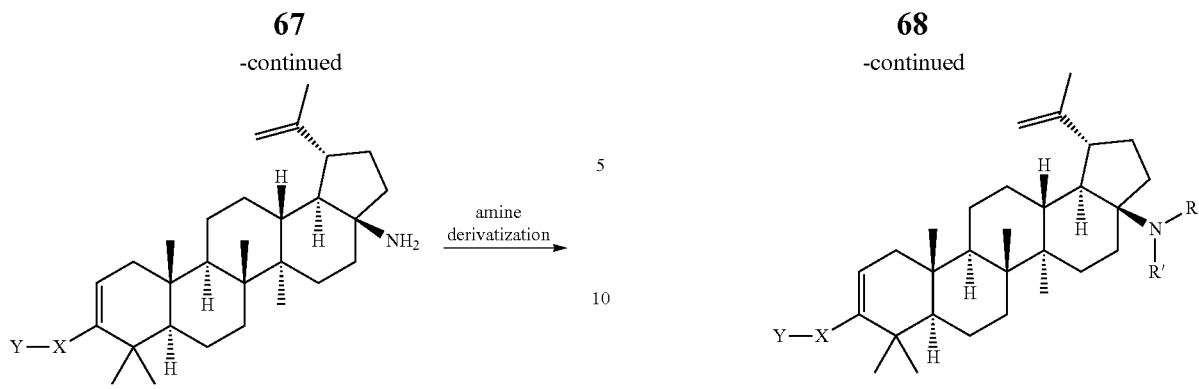
Compounds of formula II can be prepared using the chemistry methods described above for compounds of formula I, with one extra step which consists of saturation of the double bonds, as shown below in Scheme 12:
Scheme 12
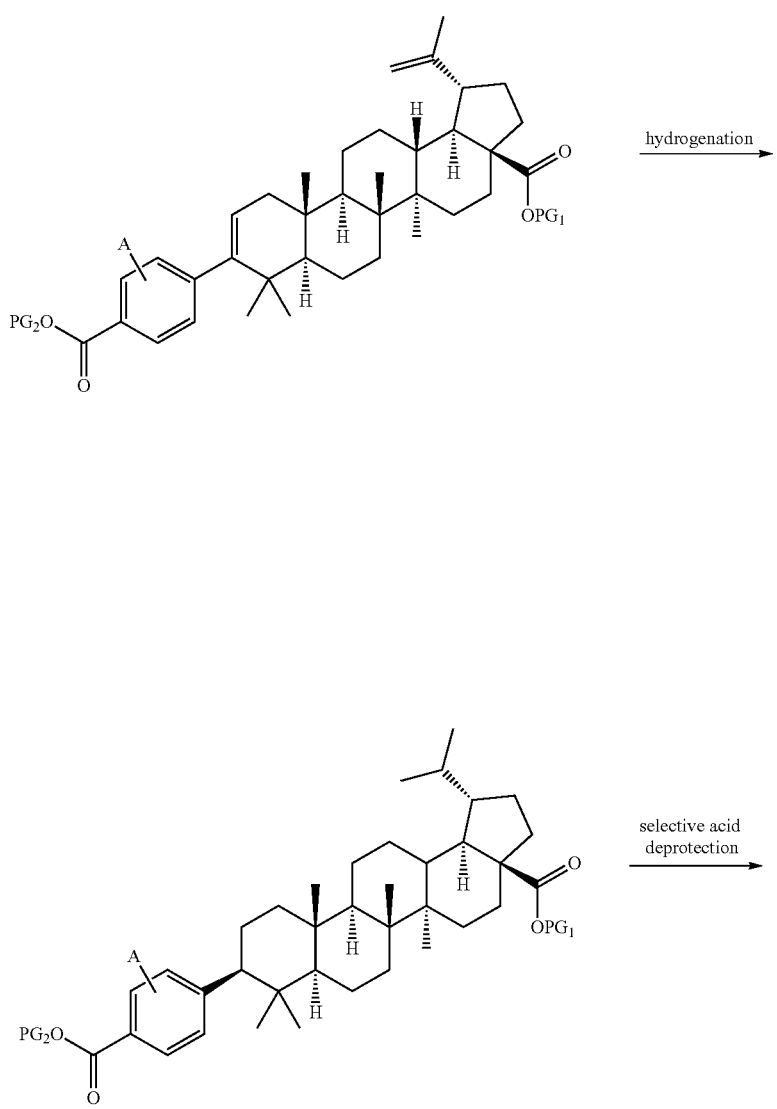

-continued
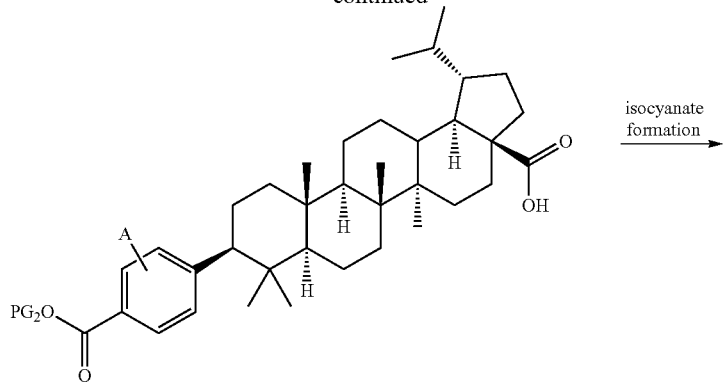
isocyanate formation →
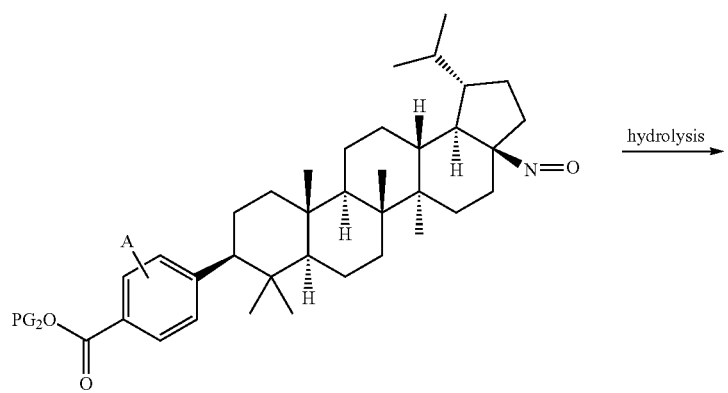
hydrolysis →
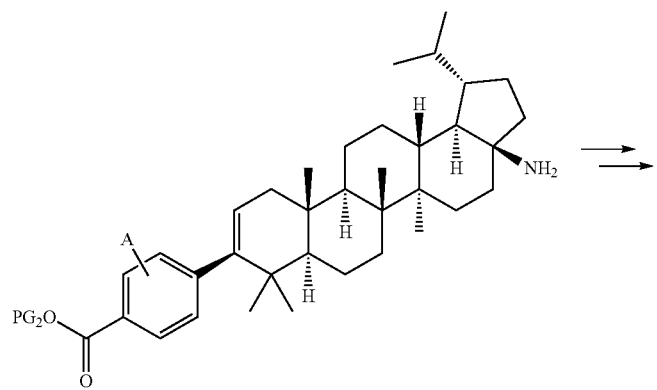
→→
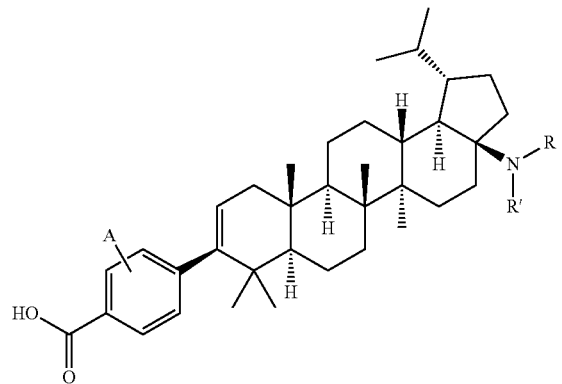

Compounds of formula III can be prepared in the same manner described above for compounds of formula I and II using oleanoic or ursolic acid as starting materials instead of betulinic acid.

EXAMPLES

The following examples illustrate typical syntheses of the compounds of Formulas I, II and III as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B or Varian Gemini 300 at 300 MHz as stated). The chemical shifts were reported in ppm on the δ scale relative to δTMS=0. The following internal references were used for the residual protons in the following solvents: $CDCl_3$ ($δ_H$ 7.26), $CD_3OD$ ($δ_H$ 3.30), Acetic-d4 (Acetic Acid $d_4$) ($δ_H$ 11.6, 2.07), DMSO mix or DMSO-D6_$CDCl_3$ (($_H$ 2.50 and 8.25) (ratio 75%:25%), and DMSO-D6 ($δ_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Methods:

Method 1
Start % B=0, Final % B=100 over 2 minute gradient, hold at 100% B
Flow Rate=4 mL/min
Wavelength=220 nm
Solvent A=95% water, 5% methanol, 10 mM ammonium acetate
Solvent B=5% water, 95% methanol, 10 mM ammonium acetate
Column=Phenomenex Luna C18, 5 μm, 3.0×50 mm Method 2
Start % B=0, Final % B=100 over 2 minute gradient, hold at 100% B
Flow Rate=1 mL/min
Wavelength=220 nm
Solvent A=90% water, 10% acetonitrile, 0.1% TFA
Solvent B=10% water, 90% acetonitrile, 0.1% TFA
Column=Phenomenex Luna C18, 3 μm, 2.0×30 mm Method 3
Start % B=0, Final % B=100 over 2 minute gradient, hold at 100% B
Flow Rate=4 mL/min
Wavelength=220 nm
Solvent A=95% water, 5% methanol, 10 mM ammonium acetate
Solvent B=5% water, 95% methanol, 10 mM ammonium acetate
Column=Waters Xbridge C18, 5 μm, 4.6×50 mm Method 4
Start % B=0, Final % B=100 over 2 minute gradient, hold at 100% B
Flow Rate=0.8 mL/min
Wavelength=220 nm
Solvent A=95% water, 5% methanol, 10 mM ammonium acetate
Solvent B=5% water, 95% methanol, 10 mM ammonium acetate
Column=Waters Xbridge C18, 3.5 μm, 2.1×50 mm Method 5
Start % B=15, Final % B=100 over 2 minute gradient, hold at 100% B
Flow Rate=1 mL/min
Wavelength=220 nm
Solvent A=95% water, 5% acetonitrile, 10 mM ammonium acetate
Solvent B=5% water, 95% acetonitrile, 10 mM ammonium acetate
Column=Phenomenex Luna C18, 3 μm, 2.0×30 mm Method 6
Start % B=0, Final % B=100 over 2 minute gradient, hold at 100% B
Flow Rate=1 ml/min
Wavelength=220 nm
Solvent A=95% water, 5% acetonitrile, 10 mM ammonium acetate
Solvent B=5% water, 95% acetonitrile, 10 mM ammonium acetate
Column=Phenomenex Luna C18, 3 μm, 2.0×30 mm Method 7
Start % B=25, Final % B=100 over 2 minute gradient, hold at 100% B
Flow Rate=1 ml/min
Wavelength=220 nm
Solvent A=95% water, 5% acetonitrile, 10 mM ammonium acetate
Solvent B=5% water, 95% acetonitrile, 10 mM ammonium acetate
Column=Phenomenex Luna C18, 3 μm, 2.0×30 mm Method 8
Start % B=0, Final % B=100 over 4 minute gradient, hold at 100% B
Flow Rate=5 ml/min
Wavelength=220 nm
Solvent A=90% water, 10% methanol, 0.1% TFA
Solvent B=10% water, 90% methanol, 0.1% TFA
Column=Phenomenex Luna C18, 10 μm 3.0×50 mm Method 9
Start % B=20, Final % B=100 over 2 minute gradient, hold at 100% B
Flow Rate=1 ml/min
Wavelength=220 nm
Solvent A=95% water, 5% acetonitrile, 10 mM ammonium acetate
Solvent B=5% water, 95% acetonitrile, 10 mM ammonium acetate
Column=Phenomenex Luna C18, 3 μm, 2.0×30 mm Method 10
Start % B=0, Final % B=100 over 2 minute gradient, hold at 100% B
Flow Rate=1 mL/min
Wavelength=220 nm
Solvent A=95% water, 5% methanol, 10 mM ammonium acetate
Solvent B=5% water, 95% methanol, 10 mM ammonium acetate Column=Phenomenex Luna C18, 3 μm, 2.0×30 mm
Method 11
Start % B=0, Final % B=100 over 2 minute gradient, hold at 100% B
Flow Rate=1 mL/min
Wavelength=220 nm
Solvent A=90% water, 10% methanol, 0.1% TFA
Solvent B=10% water, 90% methanol, 0.1% TFA
Column=Phenomenex Luna C18, 3 μm, 2.0×30 mm
Method 12
Start % B=30, Final % B=100 over 1 minute gradient
Flow Rate=0.8 mL/min
Wavelength=220 nm
Solvent A=90% water, 10% methanol, 0.1% TFA
Solvent B=10% water, 90% methanol, 0.1% TFA
Column=Xbridge Phenyl 2.1×50 mm 2.5 μm
Method 13
Start % B=20, Final % B=100 over 2 minute gradient
Flow Rate=0.8 mL/min
Wavelength=254 nm
Solvent A=90% water, 10% methanol, 0.1% TFA
Solvent B=10% water, 90% methanol, 0.1% TFA
Column=Xbridge Phenyl 2.1×50 mm 2.5 μm
Method 14
Start % B=0, Final % B=100 over 4 minute gradient, hold at 100% B
Flow Rate=1 mL/min
Wavelength=220 nm
Solvent A=95% water, 5% acetonitrile, 10 mM ammonium acetate
Solvent B=5% water, 95% acetonitrile, 10 mM ammonium acetate
Column=Waters BEH C18, 1.7 μm, 2.0×50 mm
Method 15
Start % B=0, Final % B=100 over 4 minute gradient, hold at 100% B
Flow Rate=0.5 mL/min
Wavelength=220 nm
Solvent A=95% water, 5% methanol, 10 mM ammonium acetate
Solvent B=5% water, 95% methanol, 10 mM ammonium acetate
Column=Waters BEH C18, 1.7 μm, 2.0×50 mm
Method 16
Start % B=0, Final % B=100 over 4 minute gradient, hold at 100% B
Flow Rate=1 mL/min
Wavelength=220 nm
Solvent A=90% water, 10% methanol, 0.1% TFA
Solvent B=10% water, 90% methanol, 0.1% TFA
Column=Phenomenex Luna C18, 3 μm, 2.0×30 mm
Method 17
Start % B=10%, Final % B=100 over 1 minute gradient, hold at 100% B
Flow Rate=0.8 mL/min
Wavelength=220 nm
Solvent A=90% water, 10% methanol, 0.1% TFA
Solvent B=10% water, 90% methanol, 0.1% TFA
Column=Phenomenex-luna, 2.0×30 mm, 3.0 μm
Prep HPLC methods:
Prep HPLC Method 1
Start % B=35, Final % B=100 over 10 minute gradient, hold at 100% B for 8 minutes
Flow Rate=100 mL/min
Solvent A=90% water, 10% acetonitrile, 0.1% TFA
Solvent B=10% water, 90% acetonitrile, 0.1% TFA
Column=Phenomenex Luna C8(2), 10 μm, 50×250 mm (100 A)
Prep HPLC Method 2
Start % B=15, Final % B=100 over 12 minute gradient, hold at 100% B for 6 minutes
Flow Rate=50 mL/min
Solvent A=90% water, 10% acetonitrile, 0.1% TFA
Solvent B=10% water, 90% acetonitrile, 0.1% TFA
Column=Waters Sunfire C18, 5 μm, 30×100 mm
Prep HPLC Method 3
Start % B=20, Final % B=100 over 8 minute gradient, hold at 100% B for 10 minutes
Flow Rate=50 mL/min
Solvent A=90% water, 10% acetonitrile, 0.1% TFA
Solvent B=10% water, 90% acetonitrile, 0.1% TFA
Column=Waters Sunfire C18, 5 μm, 30×100 mm
Prep HPLC Method 4
Start % B=20, Final % B=100 over 15 minute gradient, hold at 100% B for 8 minutes
Flow Rate=100 mL/min
Solvent A=90% water, 10% acetonitrile, 0.1% TFA
Solvent B=10% water, 90% acetonitrile, 0.1% TFA
Column=Phenomenex Luna C8(2), 10 μm, 50×250 mm (100 A)
Prep HPLC Method 5:
Start % B=15, Final % B=100 over 20 minute gradient, hold at 100% B for 4 minutes
Flow Rate=50 mL/min
Solvent A=90% water, 10% acetonitrile, 0.1% TFA
Solvent B=10% water, 90% acetonitrile, 0.1% TFA
Column=Waters Sunfire C18, 5 μm, 30×100 mm
Prep HPLC Method 6
Start % B=30, Final % B=100 over 20 minute gradient, hold at 100% B for 6 minutes
Flow Rate=40 mL/min
Solvent A=90% water, 10% methanol, 0.1% TFA
Solvent B=10% water, 90% methanol, 0.1% TFA
Column=Phenomenex Luna C18(2), 5 μm, 30×100 mm
Prep HPLC Method 7
Start % B=0, Final % B=100 over 30 minute gradient, hold at 100% B for 8 minutes
Flow Rate=50 mL/min
Solvent A=90% water, 10% acetonitrile, 0.1% TFA
Solvent B=10% water, 90% acetonitrile, 0.1% TFA
Column=Waters Xbridge Phenyl, 5 μm, 30×100 mm
Prep HPLC Method 8
Start % B=0, Final % B=100 over 15 minute gradient, hold at 100% B for 10 minutes
Flow Rate=50 mL/min
Solvent A=90% water, 10% acetonitrile, 0.1% TFA
Solvent B=10% water, 90% acetonitrile, 0.1% TFA
Column=Waters Xbridge Phenyl, 5 μm, 30×100 mm
Prep HPLC Method 9
Start % B=30, Final % B=100 over 20 minute gradient, hold at 100% B for 10 minutes
Flow Rate=50 mL/min
Solvent A=90% water, 10% acetonitrile, 0.1% TFA
Solvent B=10% water, 90% acetonitrile, 0.1% TFA
Column=Waters Sunfire C18, 5 μm, 30×100 mm
Prep HPLC Method 10
Start % B=0, Final % B=100 over 20 minute gradient, hold at 100% B for 4 minutes
Flow Rate=50 mL/min
Solvent A=90% water, 10% acetonitrile, 0.1% TFA
Solvent B=10% water, 90% acetonitrile, 0.1% TFA
Column=Waters Xbridge Phenyl, 5 μm, 30×100 mm Prep HPLC Method 11
Start % B=20, Final % B=100 over 10 min gradient, hold at 100% B for 15 min
Flow Rate=50 ml/min
Wavelength=220
Solvent Pair=Water–Methanol–TFA
Solvent A=90% Water–10% Methanol–0.1% TFA
Solvent B=10% Water–90% Methanol–0.1% TFA
Column=Waters Sunfire C18, 5 μm, 30×150 mm
Analytical HPLC Methods:
Analytical HPLC Method 1
Start % B=10
Final % B=100
Gradient Time=15 min
Flow Rate=1 ml/min
Wavelength1=220
Wavelength2=254
Solvent A=10 mM amm. bicarb (pH=9.5)/95% water/5% methanol
Solvent B=10 mM amm. bicarb (pH=9.5)/5% water/95% methanol
Column=Xbridge Phenyl 3.5 um, 3.0×150 mm
Analytical HPLC Method 2
Start % B=10
Final % B=100
Gradient Time=15 min
Flow Rate=1 ml/min
Wavelength1=220
Wavelength2=254
Solvent A=0.1% TFA/95% water/5% acetonitrile
Solvent B=0.1% TFA/5% water/95% acetonitrile
Column=Xbridge Phenyl 3.5 um, 3.0×150 mm Preparation of Compounds

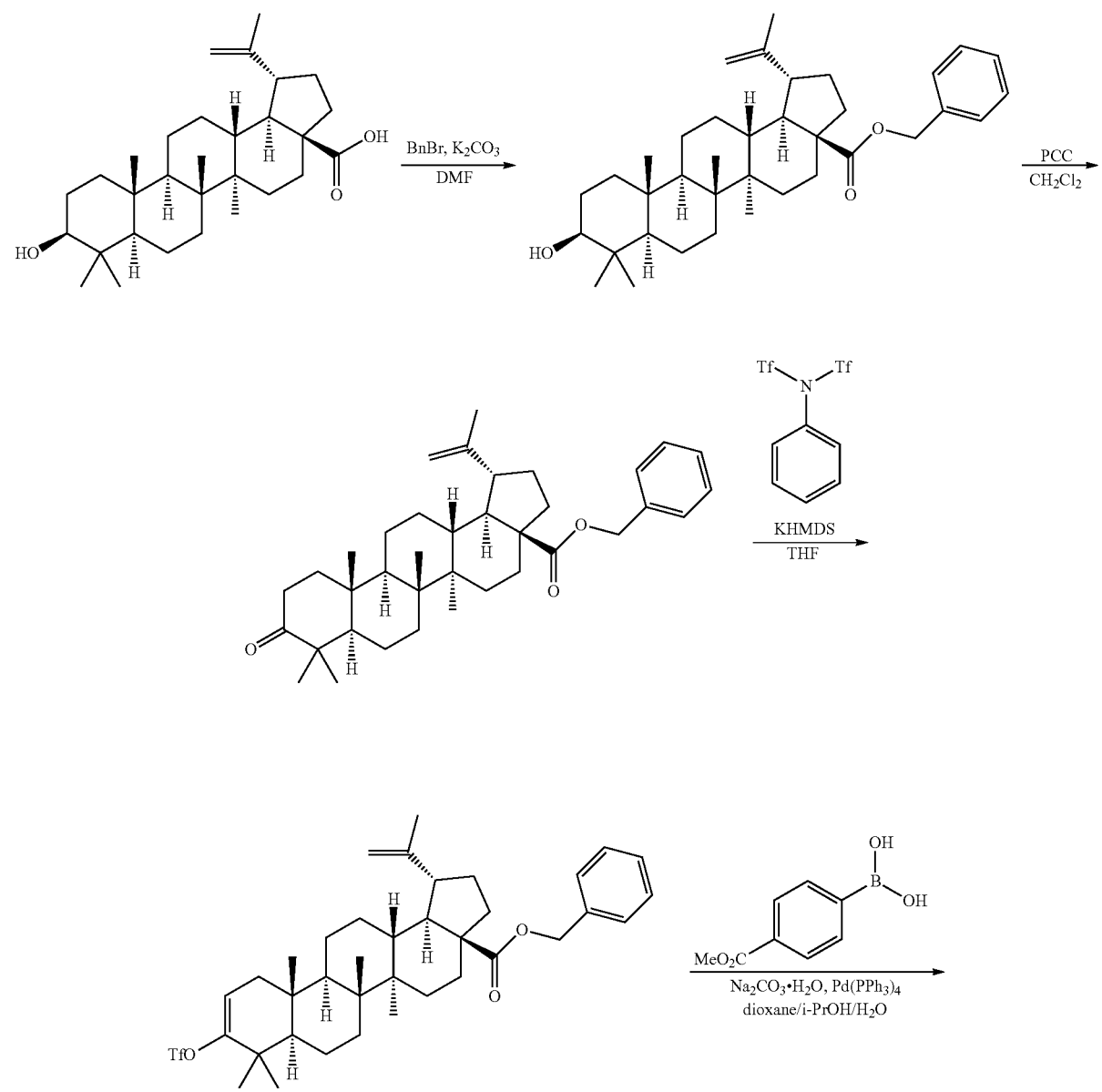

-continued
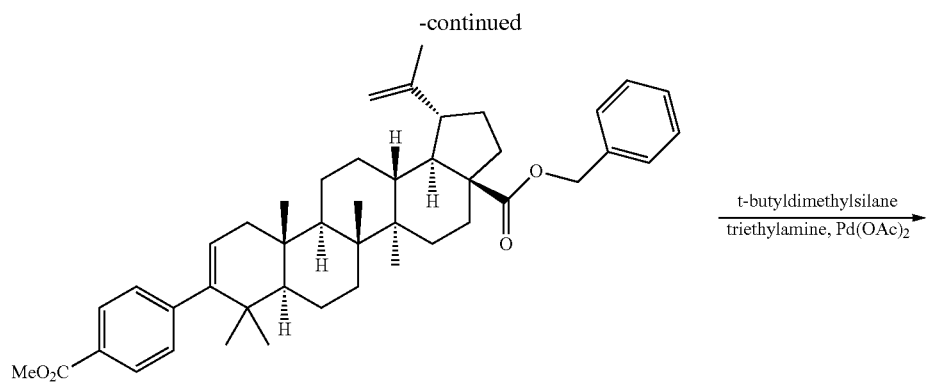
t-butyldimethylsilane
triethylamine, Pd(OAc)₂
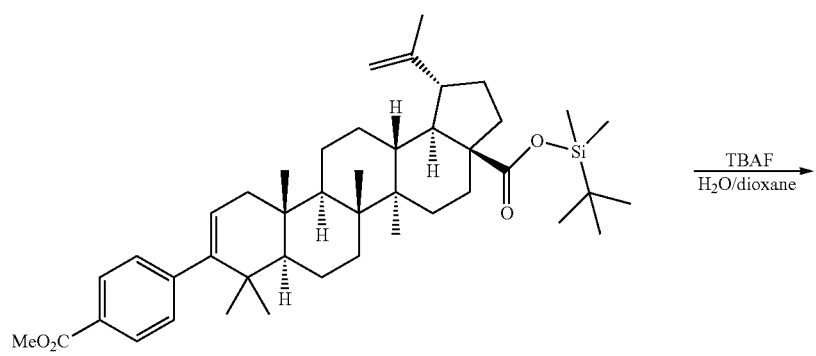
TBAF
H₂O/dioxane
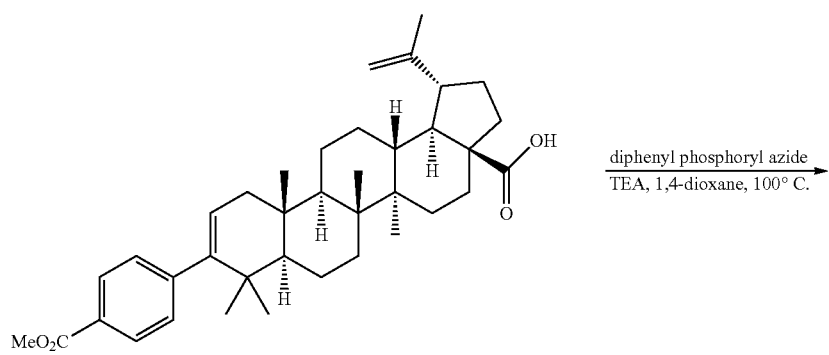
diphenyl phosphoryl azide
TEA, 1,4-dioxane, 100° C.
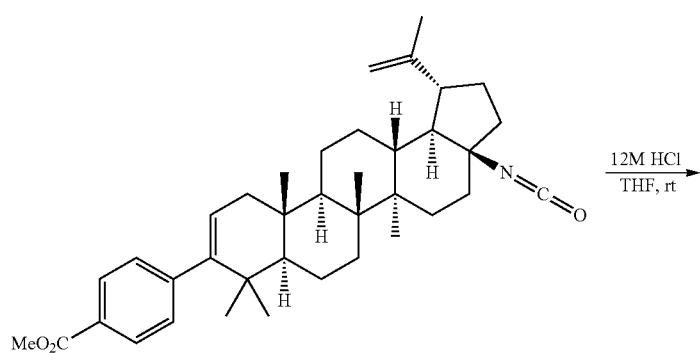
12M HCl
THF, rt

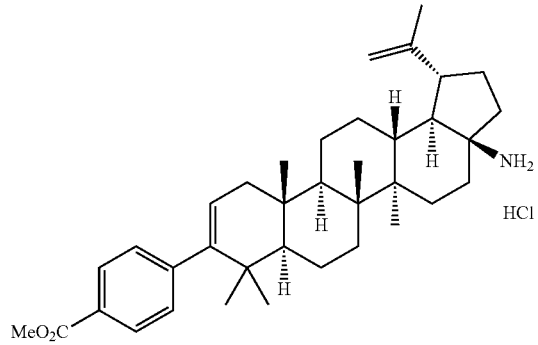

Preparation of (1R,3aS,5aR,5bR,7aR,9S,11aR,11bR, 13aR,13bR)-benzyl 9-hydroxy-5a,5b,8,8,11a-pentamethyl-1-(prop-1-en-2-yl)icosahydro-1H-cyclopenta[a]chrysene-3a-carboxylate

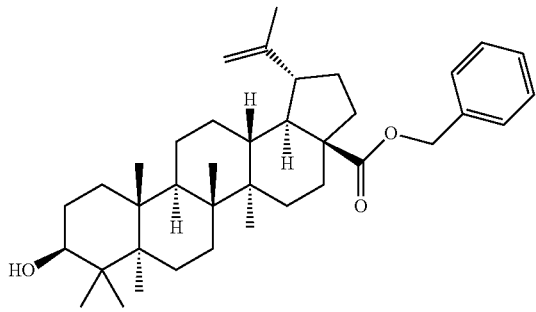

To a suspension of betulinic acid (12 g, 26.3 mmol) and potassium carbonate (7.26 g, 52.6 mmol) in DMF (150 mL) was added benzyl bromide (3.28 mL, 27.6 mmol). The mixture was heated to 60° C. for 3.5 h, and then it was cooled to rt. Solids started to precipitate upon cooling. The mixture was diluted water (200 mL) and the solids that formed were collected by filtration to give the title compound (13.92 g, 25.5 mmol, 97% yield) as a white solid. $^1$H NMR (500 MHz, CHLOROFORM-d) δ ppm 7.39-7.28 (m, 5H), 5.16-5.06 (m, 2H), 4.71 (d, J=1.83 Hz, 1H), 4.59 (s, 1H), 3.17 (ddd, J=11.44, 5.65, 5.49 Hz, 1H), 3.01 (td, J=10.99, 4.88 Hz, 1H), 2.27 (ddd, J=12.36, 3.20, 3.05 Hz, 1H), 2.21-2.13 (m, 1H), 1.93-1.81 (m, 2H), 1.67 (s, 3H), 0.95 (s, 3H), 0.93 (s, 3H), 1.71-0.82 (m, 20H), 0.79 (s, 3H), 0.75 (s, 3H), 0.74 (s, 3H).

Preparation of (1R,3aS,5aR,5bR,7aR,11aR,11bR, 13aR,13bR)-benzyl 5a,5b,8,8,11a-pentamethyl-9-oxo-1-(prop-1-en-2-yl)icosahydro-1H-cyclopenta[a]chrysene-3a-carboxylate

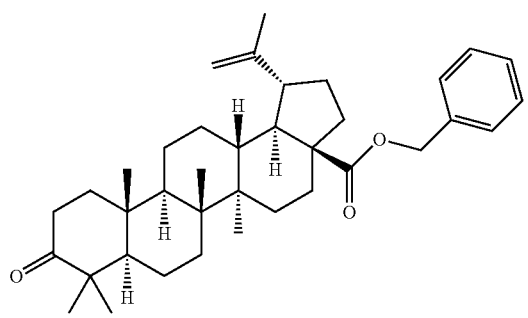

To a solution of (1R,3aS,5aR,5bR,7aR,9S,11aR,11bR, 13aR,13bR)-benzyl 9-hydroxy-5a,5b,8,8,11a-pentamethyl-1-(prop-1-en-2-yl)icosahydro-1H-cyclopenta[a]chrysene-3a-carboxylate (7.1 g, 12.98 mmol) in dichloromethane (100 mL) was added PCC (4.20 g, 19.48 mmol). After stirring for five minutes, the mixture turned a deep crimson color. The mixture was further stirred for 5.5 h. The mixture was filtered through a pad of celite and silica gel which was washed with dichloromethane and then with a 1:1 mixture of ethyl acetate: hexanes. The filtrate was concentrated under reduced pressure to give the title compound (6.92 g, 12.7 mmol, 98% yield) as a white foam. $^1$H NMR (500 MHz, CHLOROFORM-d) δ ppm 7.38-7.28 (m, 5H), 5.17-5.06 (m, 2H), 4.72 (d, J=1.83 Hz, 1H), 4.59 (s, 1H), 3.01 (td, J=10.99, 4.88 Hz, 1H), 2.51-2.43 (m, 1H), 2.42-2.34 (m, 1H), 2.28 (dt, J=12.59, 3.17 Hz, 1H), 2.21 (td, J=12.28, 3.51 Hz, 1H), 1.94-1.82 (m, 3H), 1.67 (s, 3H), 1.05 (s, 3H), 1.01 (s, 3H), 1.73-0.95 (m, 17H), 0.94 (s, 3H), 0.89 (s, 3H), 0.78 (s, 3H).

Preparation of (1R,3aS,5aR,5bR,7aR,11aR,11bR, 13aR,13bR)-benzyl 5a,5b,8,8,11a-pentamethyl-1-(prop-1-en-2-yl)-9-(trifluoromethylsulfonyloxy)-2,3, 3a,4,5,5a,5b,6,7,7a,8,11,11a,11b,12,13,13a,13b-octadecahydro-1H-cyclopenta[a]chrysene-3a-carboxylate

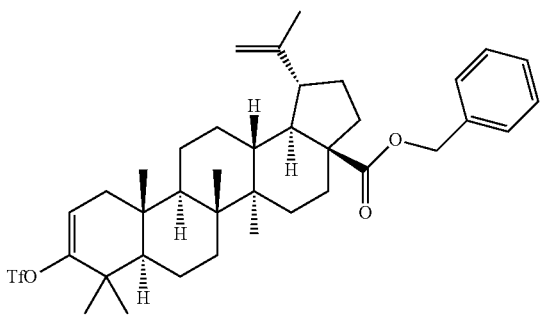

A solution of (1R,3aS,5aR,5bR,7aR,11aR,11bR,13aR, 13bR)-benzyl 5a,5b,8,8,11a-pentamethyl-9-oxo-1-(prop-1-en-2-yl)icosahydro-1H-cyclopenta[a]chrysene-3a-carboxylate (29.0 g, 53.2 mmol) in THF (200 mL) was cooled to −78° C. To the solution was added KHMDS (0.5 M in toluene) (213 mL, 106 mmol). The yellow solution was stirred at −78° C. for 25 minutes and a solution of 1,1,1-trifluoro-N-phenyl-N-(trifluoromethyl)sulfonyl methanesulfonamide (20.92 g, 58.6 mmol) in THF (70 mL) and toluene (30 mL) was added via cannula. The solution was stirred at −78° C. for 3 h. Then, an additional 1.0 g of 1,1,1-trifluoro-N-phenyl-N-(trifluoromethyl)sulfonyl methanesulfonamide was added and the mixture was stirred at −78° C. After stirring for 1 h, the mixture was quenched with water (300 mL) and the mixture was extracted with ethyl acetate (3×200 mL). The combined organic layers were dried with MgSO$_4$. The drying agent was removed by filtration, and the filtrate was concentrated under reduced pressure to give the title compound (40.0 g, 59.1 mmol) as a yellow solid. Product Rf=0.57 by silica gel TLC, 5% EtOAc in hexanes, visualized using Hanessian's stain. $^1$H NMR (500 MHz, CHLOROFORM-d) δ ppm 7.29-7.41 (m, 5H), 5.54 (dd, J=6.71, 1.53 Hz, 1H), 5.13-5.18 (m, 1H), 5.05-5.12 (m, 1H), 4.72 (d, J=1.53 Hz, 1H), 4.59 (s, 1H), 3.02 (td, J=10.99, 4.58 Hz, 1H), 2.25-2.31 (m, 1H), 2.22 (td, J=12.21, 3.36 Hz, 1H), 2.14 (dd, J=17.09, 6.71 Hz, 1H), 1.81-1.96 (m, 2H), 1.67 (s, 3H), 1.10 (s, 3H), 1.00 (s, 3H), 0.94 (s, 3H), 0.91-1.77 (m, 17H), 0.88 (s, 3H), 0.77 (s, 3H).

Preparation of (1R,3aS,5aR,5bR,7aR,11aS,11bR, 13aR,13bR)-benzyl 9-(4-(methoxycarbonyl)phenyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysene-3a-carboxylate

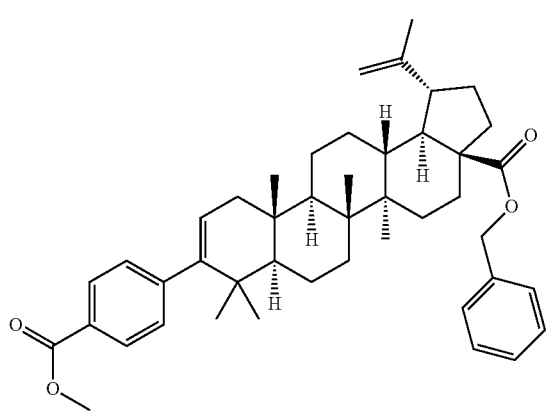

To a solution of (1R,3aS,5aR,5bR,7aR,11aR,11bR,13bR)-benzyl 5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysene-3a-carboxylate (6.21 g, 9.18 mmol) in dioxane (25 mL) was added 2-propanol (25 mL) and water (15 mL) followed by sodium carbonate monohydrate (3.42 g, 27.5 mmol), 4-methoxycarbonylphenylboronic acid (2.478 g, 13.77 mmol), and tetrakis(triphenylphosphine)palladium(0) (0.318 g, 0.275 mmol). The flask was attached to a reflux condenser, flushed with N$_2$ and heated to reflux overnight. The mixture was then cooled to rt and diluted with water (75 mL). The mixture was extracted with ethyl acetate (3×75 mL) and washed with brine (75 mL). The combined organic layers were dried with MgSO$_4$, filtered, and concentrated under reduced pressure. The residue was adsorbed to silica gel and purified by silica gel flash chromatography using a 0-20% ethyl acetate in hexanes gradient. The fractions containing the expected product were combined and concentrated under reduced pressure to give the title compound (4.16 g, 6.28 mmol, 68.4% yield) as a white foam. $^1$H NMR (500 MHz, CHLOROFORM-d) δ ppm 7.92 (d, J=8.24 Hz, 2H), 7.40-7.29 (m, 5H), 7.19 (d, J=8.24 Hz, 2H), 5.28 (dd, J=6.10, 1.83 Hz, 1H), 5.19-5.07 (m, 2H), 4.73 (d, J=1.83 Hz, 1H), 4.60 (s, 1H), 3.90 (s, 3H), 3.04 (td, J=10.91, 4.73 Hz, 1H), 2.20-2.32 (m, 2H), 2.09 (dd, J=17.24, 6.26 Hz, 1H), 1.95-1.82 (m, 2H), 1.69 (s, 3H), 0.97 (s, 3H), 0.95 (s, 3H), 0.92 (s, 3H), 0.91 (s, 3H), 1.75-0.87 (m, 17H), 0.82 (s, 3H).

Preparation of (1R,3aS,5aR,5bR,7aR,11aS,11bR, 13aR,13bR)-tert-butyldimethylsilyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate

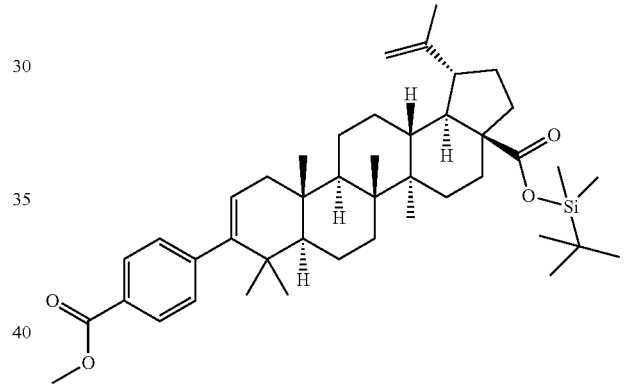

To a solution of (1R,3aS,5aR,5bR,7aR,11aS,11bR,13aR,13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (3.82 g, 5.76 mmol) in dichloroethane (100 mL) was added triethylamine (1.285 mL, 9.22 mmol), tert-butyldimethylsilane (1.912 mL, 11.52 mmol), and palladium(II) acetate (0.647 g, 2.88 mmol). The mixture was flushed with N$_2$ and heated to 60° C. After 2 h, the reaction was cooled to rt, filtered through a pad of celite and silica gel to remove the solids which were washed with 25% EtOAc in hexanes. The filtrate was concentrated under reduced pressure and treated with acetic acid (25 mL), THF (10 mL) and water (3 mL). After stirring for 1 h the solids formed were collected by filtration and washed with water to give the title compound (3.62 g, 5.27 mmol, 91% yield) as a white solid. $^1$H NMR (400 MHz, CHLOROFORM-d) δ ppm 7.94 (d, J=8.28 Hz, 2H), 7.21 (d, J=8.28 Hz, 2H), 5.30 (dd, J=6.15, 1.63 Hz, 1H), 4.75 (d, J=1.76 Hz, 1H), 4.62 (s, 1H), 3.92 (s, 4H), 3.08 (td, J=10.92, 4.27 Hz, 1H), 2.35-2.22 (m, 2H), 2.17-2.06 (m, 1H), 2.02-1.84 (m, 2H), 1.71 (s, 3H), 1.01 (s, 6H), 0.99 (br. s., 3H), 0.98 (s, 9H), 0.94 (s, 6H), 1.78-0.90 (m, 16H), 0.32-0.28 (m, 6H).

Preparation of (1R,3aS,5aR,5bR,7aR,11aS,11bR, 13aR,13bR)-9-(4-(methoxycarbonyl)phenyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysene-3a-carboxylic acid

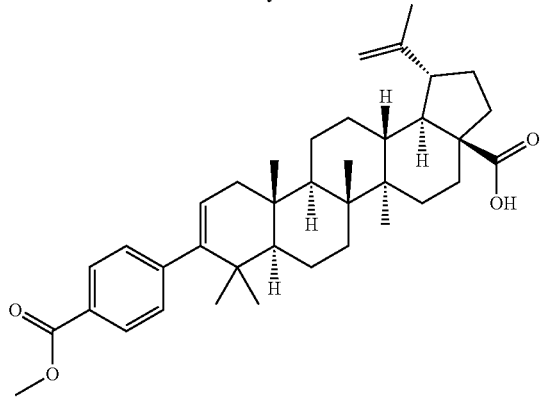

To solution of (1R,3aS,5aR,5bR,7aR,11aS,11bR,13aR, 13bR)-tert-butyldimethylsilyl 9-(4-(methoxycarbonyl)phenyl)-5a,5b,8,8,11a-pentamethyl-1-(prop-1-en-2-yl)-2,3,3a, 4,5,5a,5b,6,7,7a,8,11,11a,11b,12,13,13a,13b-octadecahydro-1H-cyclopenta[a]chrysene-3a-carboxylate (3.12 g, 4.54 mmol) in dioxane (25 mL) was added TBAF (75% wt in water) (2.375 g, 6.81 mmol) and the mixture was stirred at rt for 4 h. The reaction mixture was diluted with 1N HCl (25 mL) and water (5 mL) and extracted with dichloromethane (3×100 mL). The combined organic layers were dried over $Na_2SO_4$, filtered, and partially concentrated under reduced pressure to about 10 mL volume. To the partially concentrated mixture was added 1N HCl (50 mL). The solids that formed were collected by filtration and washed with water to give the title compound (2.58 g, 4.50 mmol, 99% yield) as a white solid. LCMS: m/e 571.47 (M–H)⁻, 3.60 min (method 1). $^1$H NMR (500 MHz, CHLOROFORM-d) δ ppm 9.80 (br. s., 1H), 7.92 (d, J=8.24 Hz, 2H), 7.18 (d, J=8.24 Hz, 2H), 5.32-5.26 (m, 1H), 4.75 (s, 1H), 4.62 (br. s., 1H), 3.90 (s, 3H), 3.07-2.99 (m, 1H), 2.33-2.21 (m, 2H), 2.10 (dd, J=17.09, 6.10 Hz, 1H), 2.06-1.94 (m, 2H), 1.70 (s, 3H), 1.01 (br. s., 3H), 1.00 (br. s., 3H), 0.98 (s, 3H), 0.91 (s, 6H), 1.79-0.89 (m, 17H).

Preparation of methyl 4-((1R,3aS,5aR,5bR,7aR, 11aS,11bR,13aR,13bR)-3a-isocyanato-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoate

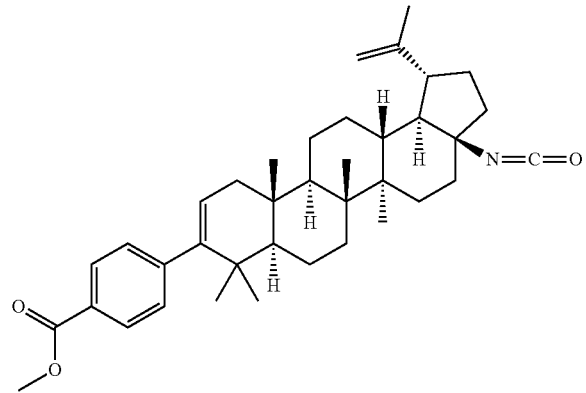

To a slurry of (1R,3aS,5aR,5bR,7aR,11aS,11bR,13aR, 13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysene-3a-carboxylic acid (10 g, 17.46 mmol) in 1,4-dioxane (200 mL) was added triethylamine (4.38 mL, 31.4 mmol) followed by diphenyl phosphoryl azide (5.82 mL, 26.2 mmol). The resulting white slurry was heated to 100° C. After 5 h, the reaction was allowed to cool to rt and was then diluted with EtOAc and washed with 1N NaOH (2×70 mL). The combined aqueous layer was extracted with EtOAc (2×150 mL). The combined organic layer was dried over $Na_2SO_4$, filtered and concentrated to a slurry (75 mL) which was stored in a refrigerator overnight. The slurry was filtered and the white solid product was washed with $Et_2O$. The liquid filtrate was concentrated to a yellow slurry which was filtered and washed with $Et_2O$ to give more white solid product. The two batches of white solid were combined and dried in vacuo to give the title compound (8.6 g, 15.09 mmol, 86% yield) as a white solid. $^1$H NMR (500 MHz, CHLOROFORM-d) δ ppm 8.0 (2H, d, J=8.2 Hz), 7.2 (2H, d, J=8.2 Hz), 5.3 (1H, d, J=4.6 Hz), 4.8 (1H, s), 4.7 (1H, s), 3.9 (3H, s), 2.6 (1H, td, J=10.8, 5.8 Hz), 2.1-2.2 (2H, m), 1.8-2.0 (4H, m), 1.7-1.8 (1H, m), 1.7 (3H, s), 1.5-1.7 (5H, m), 1.4-1.5 (5H, m), 1.3-1.4 (2H, m), 1.2-1.3 (2H, m), 1.1 (3H, s), 1.1-1.1 (1H, m), 1.0 (3H, s), 1.0 (3H, s), 1.0 (3H, br. s.), 1.0 (3H, br. s.). $^{13}$C NMR (CHLOROFORM-d) δ ppm 14.2, 15.4, 16.2, 19.2, 19.5, 20.8, 21.0, 24.7, 27.4, 29.0, 29.2, 33.3, 36.0, 37.2, 39.0, 39.0, 40.3, 41.5, 41.8, 47.8, 49.0, 49.2, 51.7, 52.6, 66.8, 71.3, 110.2, 121.3, 123.7, 127.6, 128.2, 129.8, 146.0, 148.4, 148.6, 166.9.

Preparation of methyl 4-((1R,3aS,5aR,5bR,7aR, 11aS,11bR,13aR,13bR)-3a-amino-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate

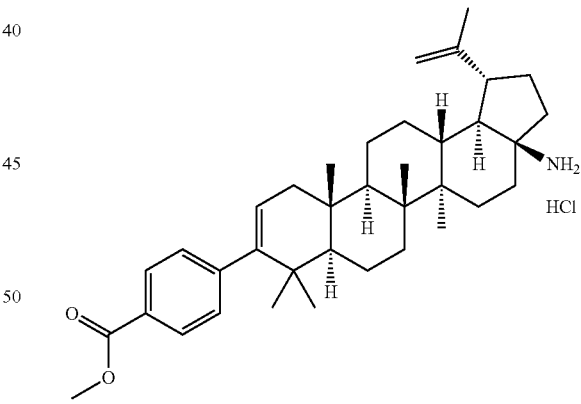

To a cloudy solution of methyl 4-((1R,3aS,5aR,5bR,7aR, 11aS,11bR,13aR,13bR)-3a-isocyanato-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)benzoate (5.47 g, 9.60 mmol) in THF (100 mL) was added concentrated hydrochloric acid (19.83 mL, 240 mmol). The resulting homogeneous mixture was stirred at rt for 72 h, the reaction mixture was concentrated to dryness to give methyl 4-((1R,3aS,5aR,5bR,7aR,11aS,11bR,13aR, 13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, HCl (4.98 g, 8.58 mmol, 89% yield) as a white solid. LCMS: m/e 544.5 (M+H)+, 3.26 min (method 6). ¹H NMR (500 MHz, 1:1 CDCl₃:MeOD, MeOD lock) δ ppm 7.9 (2H, d, J=8.5 Hz), 7.3 (1H, t, J=7.8 Hz), 7.2 (2H, d, J=8.5 Hz), 7.1 (1H, t, J=7.3 Hz), 5.3 (1H, d, J=4.6 Hz), 4.8 (1H, s), 4.7 (1H, br. s.), 3.9 (2H, s), 3.6 (2H, dt, J=15.6, 6.6 Hz), 3.3 (1H, dt, J=3.1, 1.6 Hz), 2.6 (1H, td, J=11.0, 6.1 Hz), 2.1 (1H, dd, J=17.1, 6.4 Hz), 2.0 (1H, d, J=13.4 Hz), 1.9-2.0 (1H, m), 1.8-1.9 (2H, m), 1.7-1.7 (3H, m), 1.6-1.7 (3H, m), 1.5-1.6 (3H, m), 1.5-1.5 (2H, m), 1.4 (1H, br. s.), 1.3-1.4 (1H, m), 1.2-1.3 (1H, m), 1.1-1.2 (2H, m), 1.1-1.1 (1H, m), 1.0 (3H, s), 1.0 (3H, s), 0.9 (3H, s), 0.9 (3H, s).

Example 1

Preparation of 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

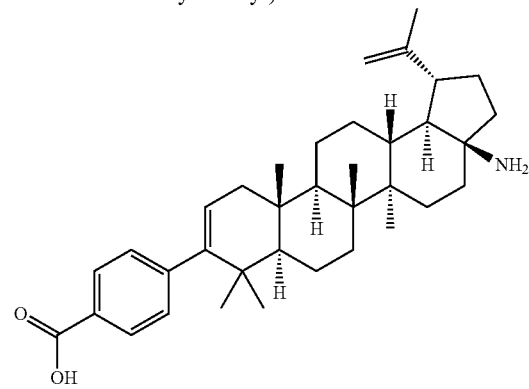

The title compound was formed as a byproduct during the preparation of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate. Purification by reverse phase preparative HPLC gave an off-white solid (100 mg, 3.5% yield) mono-TFA salt. LCMS: m/z 530 (M+H+), retention time 2.29 min (method 11). ¹H NMR (500 MHz, 1:1 mixture of CDCl₃ and MeOD, MeOD lock) δ ppm 0.94 (br. s., 3H) 0.95 (br. s., 3H) 1.02 (s, 3H) 1.06 (s, 3H) 1.09-1.22 (m, 4H) 1.22-1.30 (m, 1H) 1.30-1.47 (m, 3H) 1.49-1.57 (m, 4H) 1.58-1.72 (m, 6H) 1.73 (s, 3H) 1.74-1.91 (m, 4H) 1.91-1.99 (m, 1H) 2.02-2.18 (m, 2H) 2.51-2.63 (m, 1H) 4.71 (s, 1H) 4.81 (s, 1H) 5.29 (d, J=4.88 Hz, 1H) 7.20 (d, J=8.24 Hz, 2H) 7.92 (d, J=8.24 Hz, 2H).

Section 1. Ureas

Example 2

Preparation of 4-((1R,3aS,5aR,5bR,7aR,11aS,11bR,13aR,13bR)-3a-((1-(tert-butoxycarbonylamino)cyclopropyl)methylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

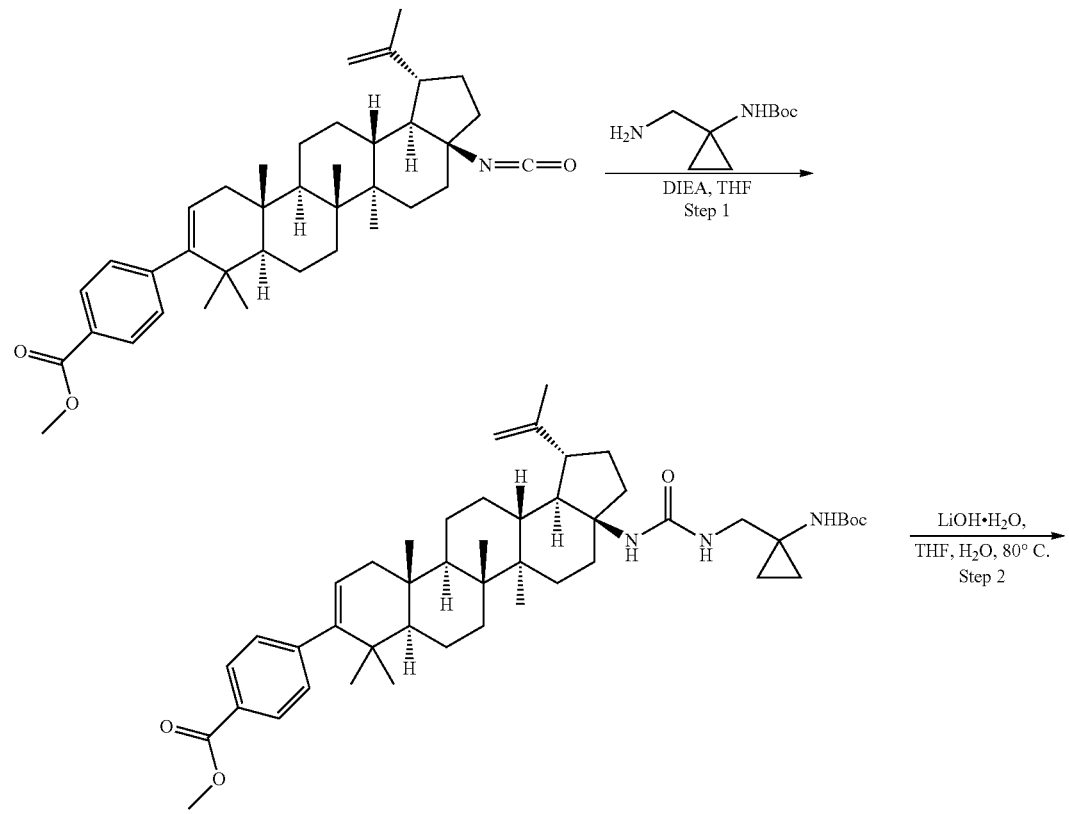

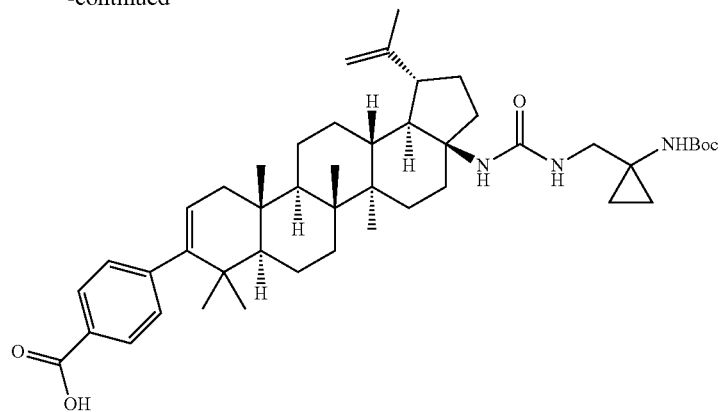

Step 1. Preparation of methyl 4-((1R,3aS,5aR,5bR,7aR,11aS,11bR,13aR,13bR)-3a-((1-(tert-butoxycarbonylamino)cyclopropyl)methylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

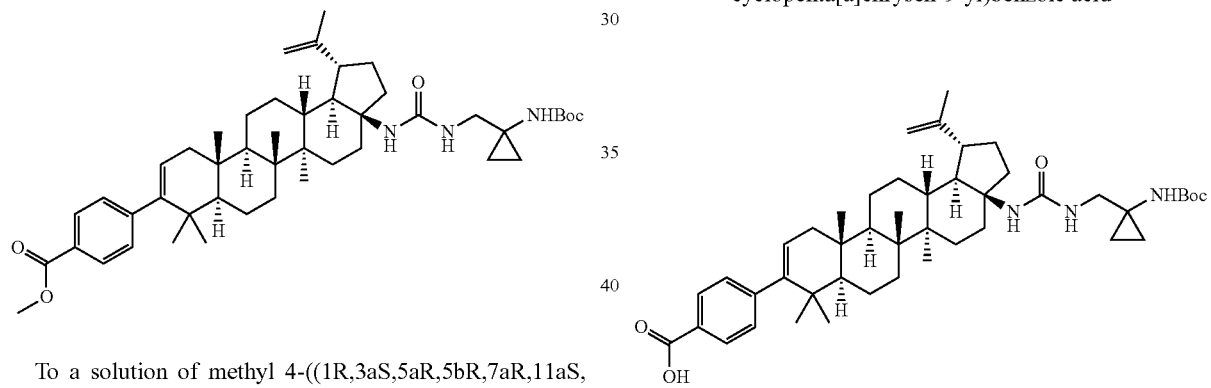

To a solution of methyl 4-((1R,3aS,5aR,5bR,7aR,11aS,11bR,13aR,13bR)-3a-isocyanato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (600 mg, 1.053 mmol) and N,N-diisopropyethyllamine (0.734 mL, 4.21 mmol) in THF (6 mL) was added tert-butyl 1-(aminomethyl)cyclopropylcarbamate (294 mg, 1.579 mmol). The resulting mixture was stirred at rt. After 16 h, the solvent was concentrated. The crude material was dissolved in THF (1 mL) and MeOH (2 mL), filtered and purified by reverse phase preparative HPLC (method 1) to give the title compound (499.5 mg, 58% yield) as a white solid. LCMS: m/e 756.7 (M+H)$^+$, 2.75 min (method 7). $^1$H NMR (500 MHz, CHLOROFORM-d) δ ppm 8.0 (2H, d, J=8.5 Hz), 7.2 (2H, d, J=8.5 Hz), 5.3-5.3 (1H, m), 5.1 (1H, br. s.), 4.8 (1H, s), 4.7 (1H, s), 3.9 (3H, s), 3.5-3.5 (1H, m), 3.4 (1H, d, J=14.3 Hz), 2.8 (1H, br. s.), 2.6 (1H, d, J=12.8 Hz), 2.4 (1H, dd, J=12.2, 8.2 Hz), 2.1 (1H, dd, J=17.4, 6.4 Hz), 1.9-2.1 (2H, m), 1.8 (1H, d, J=13.4 Hz), 1.7-1.8 (1H, m), 1.7 (3H, s), 1.7-1.7 (2H, m), 1.5-1.7 (3H, m), 1.5 (9H, s), 1.4-1.5 (5H, m), 1.2-1.3 (1H, m), 1.1-1.2 (2H, m), 1.1 (3H, s), 1.0 (3H, s), 1.0 (3H, s), 0.9 (6H, s), 0.8-0.9 (3H, m). $^{13}$C NMR (CHLOROFORM-d) δ ppm 14.1, 15.4, 16.1, 19.0, 19.5, 20.7, 20.8, 24.8, 27.0, 28.1, 29.1, 29.2, 29.4, 31.4, 33.2, 35.1, 36.0, 36.6, 37.2, 40.4, 41.4, 41.6, 46.0, 49.1, 49.6, 51.7, 52.5, 77.3, 80.1, 109.9, 123.7, 127.6, 128.2, 129.8, 146.0, 148.4, 149.2, 167.0.

Step 2. Preparation of 4-((1R,3aS,5aR,5bR,7aR,11aS,11bR,13aR,13bR)-3a-((1-(tert-butoxycarbonylamino)cyclopropyl)methylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid To a solution of methyl 4-((1R,3aS,5aR,5bR,7aR,11aS,11bR,13aR,13bR)-3a-(3-((1-(tert-butoxycarbonylamino)cyclopropyl)methyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (91 mg, 0.12 mmol) in THF (5 mL) was added a solution of lithium hydroxide monohydrate (20.2 mg, 0.481 mmol) in water (1.00 mL). The reaction mixture was stirred at 80° C. for 3 h. The reaction was concentrated and purified by reversed phase preparative HPLC using prep HPLC method 2. HPLC fractions containing product peaks were treated with saturated aqueous NaHCO$_3$ solution (100 mL), combined and concentrated. The resulting residue was triturated with H$_2$O (8 mL) and extracted with a mixture of THF (30 mL) and EtOAc (50 mL). The organic layer was washed with brine, dried over MgSO$_4$, filtered and concentrated to give the title compound (58.1 mg, 0.069 mmol, 57.7% yield) as a white solid. LCMS: m/e 742.6 (M+H)$^+$, 2.13 min (method 6). $^1$H NMR (500 MHz, MeOD) δ ppm 7.9 (2H, d, J=7.9 Hz), 7.2 (2H, d, J=8.2 Hz), 5.3 (1H, d, J=6.1 Hz), 4.8 (1H, s), 4.6 (1H, s), 3.9-4.0 (1H, m), 3.3 (2H, d, J=9.5 Hz), 2.7 (1H, br. s.), 2.6 (1H, d, J=13.4 Hz), 2.4 (1H, dd, J=11.7, 8.7 Hz), 2.2 (1H, dd, J=17.2, 6.3 Hz), 1.9-2.0 (3H, m), 1.7-1.8 (2H, m), 1.7 (3H, s), 1.7-1.7 (1H, m), 1.5-1.6 (3H, m), 1.5-1.5 (6H, m), 1.5 (9H, s), 1.4 (2H, d, J=2.1 Hz), 1.2-1.4 (6H, m), 1.2 (3H, s), 1.1-1.1 (2H, m), 1.0 (6H, br. s.), 1.0 (3H, s), 1.0 (3H, s), 0.9-0.9 (1H, m). $^{13}$C NMR (MeOD) δ ppm 11.2, 13.9, 15.5, 16.1, 18.4, 18.6, 20.0, 20.7, 21.6, 23.9, 25.6, 27.5, 27.8, 29.1, 29.1, 29.8, 29.9, 30.0, 33.8, 35.7, 36.5, 37.6, 37.7, 40.8, 41.9, 42.1, 49.9, 49.9, 53.3, 63.8, 67.3, 79.2, 109.5, 124.1, 128.7, 130.1, 146.8, 150.4, 157.5, 159.2.
Example 3
Preparation of 4-((1R,3aS,5aR,5bR,7aR,11aS,11bR,13aR,13bR)-3a-(3-(2-(dimethylamino)ethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid
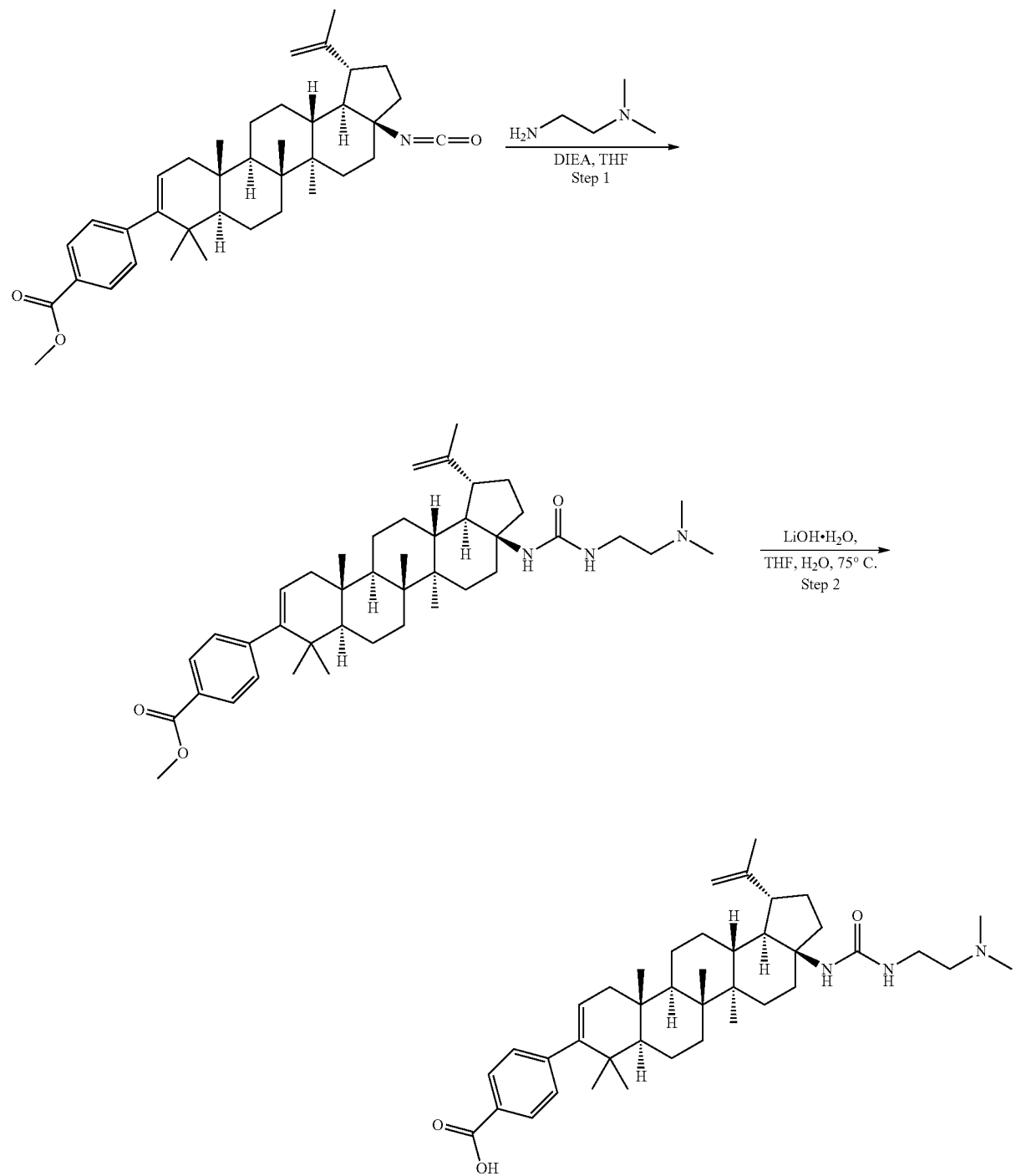

Step 1. Preparation of methyl 4-((1R,3aS,5aR,5bR, 7aR,11aS,11bR,13aR,13bR)-3a-(3-(2-(dimethylamino)ethyl)ureido)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate

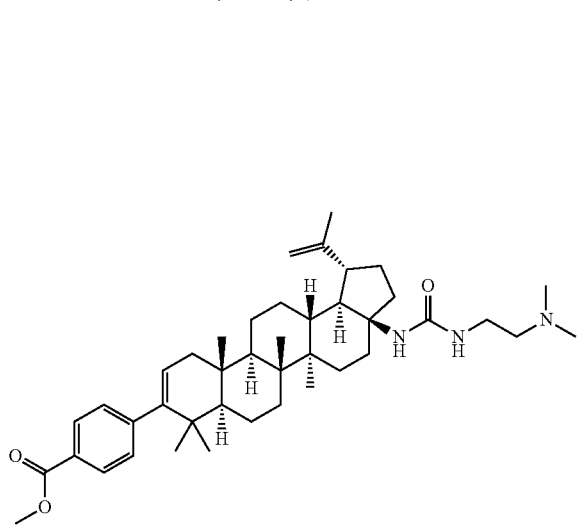

To a solution of methyl 4-((1R,3aS,5aR,5bR,7aR,11aS, 11bR,13aR,13bR)-3a-isocyanato-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate (610.0 mg, 1.071 mmol) in THF (10 mL) was added N,N-diisopropylethylamine (0.559 mL, 3.21 mmol) and N,N-dimethylethylenediamine (0.353 mL, 3.21 mmol). The reaction mixture was stirred at 25° C. After 18 h, the reaction mixture was diluted with EtOAc (50 mL) and treated with 1N HCl (5 mL). The mixture was concentrated to a paste and then triturated with EtOAc, filtered and washed with Et₂O. The white solid was saved and the liquid filtrate was concentrated and the trituration and filtration steps were repeated twice more. The combined white solid product was dried in a vacuum oven to give the title compound (650.0 mg, 0.958 mmol, 90% yield). LCMS: m/e 658.4 (M+H)⁺, 4.25 min (method 8). ¹H NMR (500 MHz, CHLOROFORM-d) δ ppm 7.9 (2H, d, J=8.5 Hz), 7.2 (2H, d, J=8.2 Hz), 5.3 (1H, dd, J=6.3, 1.7 Hz), 4.8 (1H, s), 4.6 (1H, s), 3.9 (3H, s), 3.7-3.8 (1H, m), 3.5-3.6 (1H, m), 3.2 (2H, br. s.), 2.9 (6H, br. s.), 2.7-2.7 (1H, m), 2.6 (1H, d, J=13.4 Hz), 2.4 (1H, dd, J=11.6, 8.2 Hz), 2.1 (1H, dd, J=17.2, 6.3 Hz), 2.0-2.1 (1H, m), 1.8-1.9 (1H, m), 1.8 (1H, d, J=12.8 Hz), 1.7 (3H, s), 1.7 (1H, d, J=6.7 Hz), 1.6-1.7 (1H, m), 1.5-1.6 (2H, m), 1.5 (4H, d, J=2.7 Hz), 1.3-1.4 (5H, m), 1.2-1.3 (1H, m), 1.1 (3H, s), 1.0-1.1 (2H, m), 1.0 (3H, s), 1.0-1.0 (3H, m), 0.9 (6H, s). ¹³C NMR (CHLOROFORM-d) δ ppm 14.2, 15.8, 16.3, 18.4, 19.2, 19.5, 20.7, 21.1, 25.0, 27.1, 29.1, 29.5, 29.6, 33.3, 35.3, 35.4, 36.0, 37.2, 37.3, 40.3, 41.4, 41.7, 43.4, 46.7, 49.3, 51.7, 52.6, 53.4, 58.9, 63.9, 77.3, 109.8, 123.9, 127.6, 128.2, 129.8, 145.9, 148.5, 149.4, 157.5, 167.0.

Step 2. Preparation of 4-((1R,3aS,5aR,5bR,7aR, 11aS,11bR,13aR,13bR)-3a-(3-(2-(dimethylamino)ethyl)ureido)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

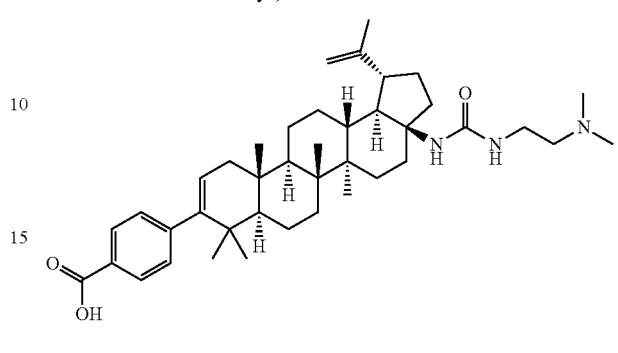

To a cloudy solution of methyl 4-((1R,3aS,5aR,5bR,7aR, 11aS,11bR,13aR,13bR)-3a-(3-(2-(dimethylamino)ethyl) ureido)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoate (0.255 g, 0.388 mmol) in THF (5 mL) was added a solution of lithium hydroxide monohydrate (0.049 g, 1.16 mmol) in water (1.00 mL). The reaction mixture was heated to 75° C. for 18 h. Then, the reaction was treated with 1N HCl (1 mL) and concentrated in vacuo, absorbed onto silica gel (3.5 g), loaded onto a silica gel column (12 g cartridge) and eluted with 90:10 DCM:MeOH to give the title compound (237 mg, 0.368 mmol, 95% yield) as a white solid. LCMS: m/e 644.4 (M+H)⁺, 3.95 min (method 8). ¹H NMR (500 MHz, MeOD) δ ppm 7.9 (2H, d, J=8.2 Hz), 7.2 (2H, d, J=8.2 Hz), 5.9 (1H, s), 5.3-5.3 (1H, m), 4.8 (1H, d, J=1.8 Hz), 4.6 (1H, s), 3.7-3.8 (1H, m), 3.4-3.6 (2H, m), 3.4 (1H, s), 3.2-3.3 (2H, m), 2.9 (6H, s), 2.7 (1H, td, J=11.1, 5.0 Hz), 2.6 (1H, dd, J=10.2, 3.2 Hz), 2.4 (1H, dd, J=12.1, 8.1 Hz), 2.2 (1H, dd, J=17.4, 6.4 Hz), 1.9-2.0 (2H, m), 1.8 (1H, d, J=13.4 Hz), 1.7 (3H, s), 1.7 (1H, br. s.), 1.7-1.7 (1H, m), 1.6-1.6 (2H, m), 1.5-1.6 (4H, m), 1.4-1.4 (5H, m), 1.3-1.4 (3H, m), 1.2 (3H, s), 1.1-1.1 (1H, m), 1.0-1.1 (6H, m), 1.0 (3H, s), 1.0 (3H, s). ¹³C NMR (MeOD) δ ppm 14.5, 16.3, 16.8, 19.2, 20.6, 21.3, 22.2, 26.3, 28.2, 29.7, 30.4, 30.5, 34.5, 36.2, 36.4, 37.1, 38.2, 38.4, 41.5, 42.6, 42.8, 43.6, 48.1, 49.0, 49.3, 49.3, 50.4, 50.6, 54.0, 55.6, 59.9, 64.9, 110.3, 111.1, 124.8, 129.3, 130.7, 147.5, 150.9, 160.4.

Example 4

Preparation of 4-((1R,3aS,5aR,5bR,7aR,11aS,11bR, 13aR,13bR)-3a-(3-(1-carboxycyclopropyl)ureido)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoic acid

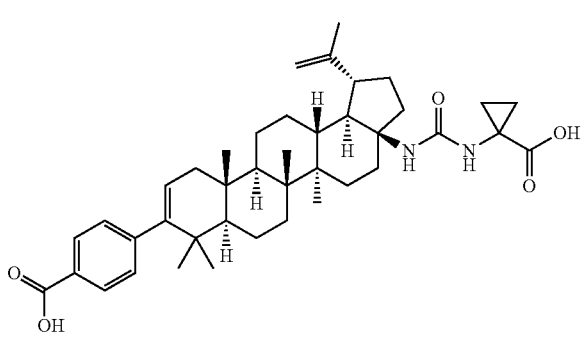

The title compound was prepared in 25% yield from methyl 4-((1R,3aS,5aR,5bR,7aR,11aS,11bR,13aR,13bR)-3a-isocyanato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(2-(dimethylamino)ethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 1-aminocyclopropane-1-carboxylic acid ethyl ester hydrochloride was used instead of N,N-dimethylethylenediamine in Step 1. LCMS: m/e 657.3 (M+H)+, 4.18 min (method 8). $^1$H NMR (500 MHz, MeOD) δ ppm 7.9 (2H, d, J=8.2 Hz), 7.2 (2H, d, J=8.2 Hz), 5.3-5.5 (1H, m), 4.8 (1H, br. s.), 4.6 (1H, br. s.), 3.7-3.8 (1H, m), 3.6-3.6 (1H, m), 3.5-3.6 (1H, m), 2.5-2.7 (2H, m), 2.4 (1H, dd, J=12.1, 8.4 Hz), 2.2 (1H, dd, J=17.1, 6.4 Hz), 2.0 (1H, d, J=11.9 Hz), 1.9 (2H, dt, J=6.6, 3.2 Hz), 1.8-1.9 (2H, m), 1.7-1.8 (4H, m), 1.4-1.7 (7H, m), 1.4 (3H, td, J=13.1, 4.0 Hz), 1.3 (3H, t, J=11.7 Hz), 1.2 (3H, s), 1.1-1.1 (3H, m), 1.1 (3H, d, J=2.4 Hz), 1.0 (3H, s), 1.0 (2H, s), 0.9 (1H, m).

Example 5

Preparation of 4-((1R,3aS,5aR,5bR,7aR,11aS,11bR,13aR,13bR)-5a,5b,8,8,11a-pentamethyl-3a-(3-(2-methyl-1-morpholinopropan-2-yl)ureido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

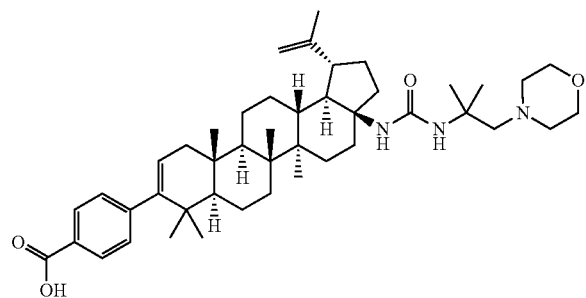

The title compound was prepared in 16% yield from methyl 4-((1R,3aS,5aR,5bR,7aR,11aS,11bR,13aR,13bR)-3a-isocyanato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(2-(dimethylamino)ethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-methyl-2-morpholinopropan-1-amine was used instead of N,N-dimethylethylenediamine in Step 1. LCMS: m/e 714.3 (M+H)+, 3.97 min (method 8). $^1$H NMR (500 MHz, MeOD) δ ppm 7.9 (2H, d, J=8.2 Hz), 7.2 (2H, d, J=8.2 Hz), 5.3 (1H, d, J=4.6 Hz), 4.7 (1H, br. s.), 2.5-2.7 (1H, m), 2.2 (1H, dd, J=16.9, 6.0 Hz), 2.1 (1H, dd, J=13.3, 9.9 Hz), 1.9-2.0 (2H, m), 1.8-1.9 (3H, m), 1.8 (3H, br. s.), 1.7-1.8 (1H, m), 1.6-1.7 (5H, m), 1.5-1.6 (3H, m), 1.4 (2H, d, J=13.4 Hz), 1.3-1.4 (1H, m), 1.2 (3H, br. s.), 1.1 (3H, br. s.), 1.1 (3H, br. s.), 1.0 (3H, br. s.), 1.0 (3H, br. s.).

Example 6

Preparation of 4-((1R,3aS,5aR,5bR,7aR,11aS,11bR,13aR,13bR)-5a,5b,8,8,11a-pentamethyl-3a-(3-(2-methyl-2-morpholinopropyl)ureido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

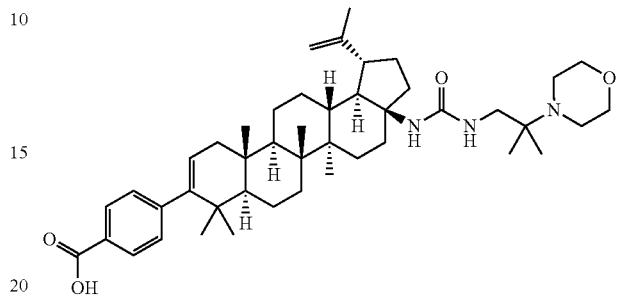

The title compound was prepared in 20% yield from methyl 4-((1R,3aS,5aR,5bR,7aR,11aS,11bR,13aR,13bR)-3a-isocyanato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(2-(dimethylamino)ethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-methyl-2-morpholinopropan-1-amine was used instead of N,N-dimethylethylenediamine in Step 1. LCMS: m/e 714.3 (M+H)+, 3.95 min (method 8). $^1$H NMR (500 MHz, MeOD) δ ppm 7.9 (2H, d, J=8.2 Hz), 7.2 (2H, d, J=8.2 Hz), 5.3 (1H, d, J=6.1 Hz), 4.8 (1H, s), 4.7 (1H, s), 4.1 (2H, d, J=12.2 Hz), 3.7-3.9 (2H, m), 3.5-3.6 (2H, m), 3.4-3.5 (2H, m), 3.2 (2H, t, J=11.9 Hz), 2.6-2.7 (2H, m), 2.4 (1H, dd, J=12.1, 8.4 Hz), 2.2 (1H, dd, J=17.1, 6.1 Hz), 2.0 (1H, t, J=10.8 Hz), 1.8-1.9 (1H, m), 1.8 (1H, br. s.), 1.7 (3H, s), 1.7 (1H, td, J=13.3, 3.4 Hz), 1.6-1.6 (2H, m), 1.5-1.6 (4H, m), 1.4-1.5 (3H, m), 1.4-1.4 (6H, m), 1.3 (1H, d, J=9.5 Hz), 1.1 (3H, s), 1.1 (3H, br. s.), 1.1 (3H, br. s.), 1.0 (3H, s), 1.0 (3H, s).

Example 7

Preparation of 4-((1R,3aS,5aR,5bR,7aR,11aS,11bR,13aR,13bR)-3a-(3-(1-((diethylamino)methyl)cyclopropyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

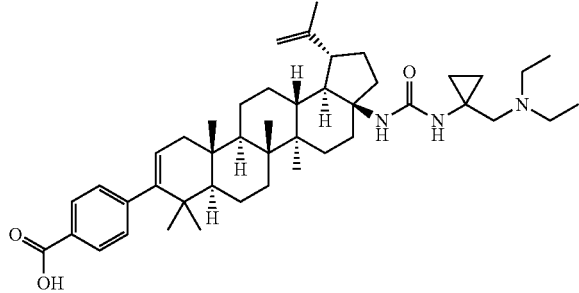

The title compound was prepared in 25% yield from methyl 4-((1R,3aS,5aR,5bR,7aR,11aS,11bR,13aR,13bR)-3a-isocyanato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(2-(dimethylamino)ethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 1-((diethylamino)methyl)cyclopropanamine, 2 HCl was used instead of N,N-dimethylethylenediamine in Step 1. LCMS: m/e 698.3 (M+H)$^+$, 3.97 min (method 8). $^1$H NMR (500 MHz, MeOD) δ ppm 7.9-8.0 (2H, m), 7.2-7.3 (2H, m), 5.3 (1H, dd, J=4.0, 1.8 Hz), 4.8 (1H, br. s.), 4.7 (1H, br. s.), 3.2-3.3 (4H, m), 2.6 (1H, d, J=12.8 Hz), 2.5-2.6 (1H, m), 2.3-2.4 (1H, m), 2.2 (1H, dd, J=16.0, 5.3 Hz), 1.9-2.0 (1H, m), 1.7-1.8 (3H, m), 1.7 (3H, br. s.), 1.6-1.7 (4H, m), 1.5 (4H, d, J=7.3 Hz), 1.4-1.5 (2H, m), 1.4 (8H, dd, J=7.0, 5.2 Hz), 1.3 (2H, br. s.), 1.1-1.2 (1H, m), 1.1 (3H, br. s.), 1.1 (6H, br. s.), 1.0 (3H, d, J=1.5 Hz), 1.0 (3H, br. s.), 0.9 (3H, br. s.).

The title compound was prepared from methyl 4-((1R,3aS,5aR,5bR,7aR,11aS,11bR,13aR,13bR)-3a-isocyanato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(2-(dimethylamino)ethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 1-(piperidin-1-ylmethyl)cyclopropanamine, 2 HCl was used instead of N,N-dimethylethylenediamine in Step 1. LCMS: m/e 710.6 (M+H)$^+$, 2.00 min (method 6). $^1$H NMR (500 MHz, MeOD) δ ppm 7.9 (2H, d, J=7.9 Hz), 7.2 (2H, d, J=7.9 Hz), 5.3 (1H, d, J=4.9 Hz), 4.8 (1H, s), 4.7 (1H, s), 3.5-3.7 (2H, m), 3.3 (1H, s), 3.2-3.3 (2H, m), 3.0 (2H, ddd, J=12.0, 8.5, 3.7 Hz), 2.6 (1H, d, J=13.4 Hz), 2.6 (1H, td, J=10.9, 5.0 Hz), 2.4 (1H, dd, J=11.9, 8.2 Hz), 2.2 (1H, dd, J=17.1, 6.4 Hz), 1.9-2.1 (3H, m), 1.7-1.9 (5H, m), 1.7 (3H, s), 1.7-1.7 (1H, m), 1.5-1.7 (8H, m), 1.3-1.5 (6H, m), 1.2-1.2 (1H, m), 1.1 (1H, d, J=4.0 Hz), 1.1 (3H, s), 1.1 (6H, br. s.), 1.0 (3H, s), 1.0 (3H, s), 0.9-0.9 (2H, m).

Example 8

Preparation of 4-((1R,3aS,5aR,5bR,7aR,11aS,11bR,13aR,13bR)-5a,5b,8,8,11a-pentamethyl-3a-(3-(1-(piperidin-1-ylmethyl)cyclopropyl)ureido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

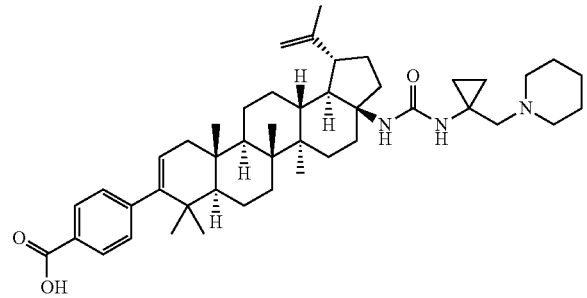

Example 9

Preparation of 4-((1R,3aS,5aR,5bR,7aR,11aS,11bR,13aR,13bR)-3a-(4-((3S,4S)-4-(dimethylamino)tetrahydrofuran-3-yl)piperazine-1-carboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

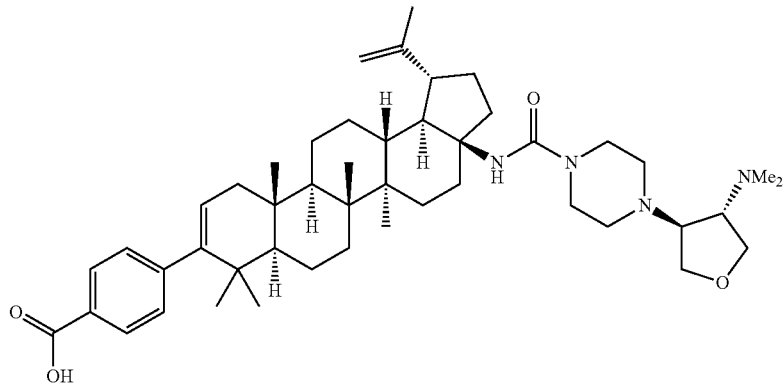

The title compound was prepared in 20% yield from methyl 4-((1R,3aS,5aR,5bR,7aR,11aS,11bR,13aR,13bR)-3a-isocyanato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(2-(dimethylamino)ethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except (3S,4S)—N,N-dimethyl-4-(piperazin-1-yl)tetrahydrofuran-3-amine was used instead of N,N-dimethylethylenediamine in Step 1. LCMS: m/e 755.6 (M+H)$^+$, 1.85 min (method 6). $^1$H NMR (500 MHz, METHANOL-d$_4$) δ=7.93 (d, J=8.2 Hz, 2H), 7.23 (d, J=8.2 Hz, 2H), 5.31 (d, J=6.1 Hz, 1H), 4.78 (s, 1H), 4.64 (br. s., 1H), 4.09 (d, J=3.4 Hz, 1H), 4.05 (d, J=4.9 Hz, 2H), 4.02 (td, J=3.5, 6.8 Hz, 1H), 3.96 (td, J=5.1, 10.1 Hz, 1H), 3.73 (d, J=5.2 Hz, 1H), 3.56-3.41 (m, 4H), 2.96 (s, 6H), 2.87-2.66 (m, 5H), 2.59 (d, J=13.1 Hz, 1H), 2.45 (dd, J=8.7, 11.7 Hz, 1H), 2.16 (dd, J=6.4, 17.1 Hz, 1H), 1.97-1.90 (m, 1H), 1.90-1.82 (m, 1H), 1.82-1.74 (m, 2H), 1.73 (s, 3H), 1.66-1.54 (m, 3H), 1.51 (d, J=12.5 Hz, 4H), 1.45-1.26 (m, 6H), 1.23-1.15 (m, 2H), 1.13 (s, 3H), 1.10 (d, J=13.4 Hz, 2H), 1.06 (s, 3H), 1.04 (s, 3H), 0.97 (s, 3H), 0.95 (s, 3H).

General Procedure for C-17 Urea Formation:

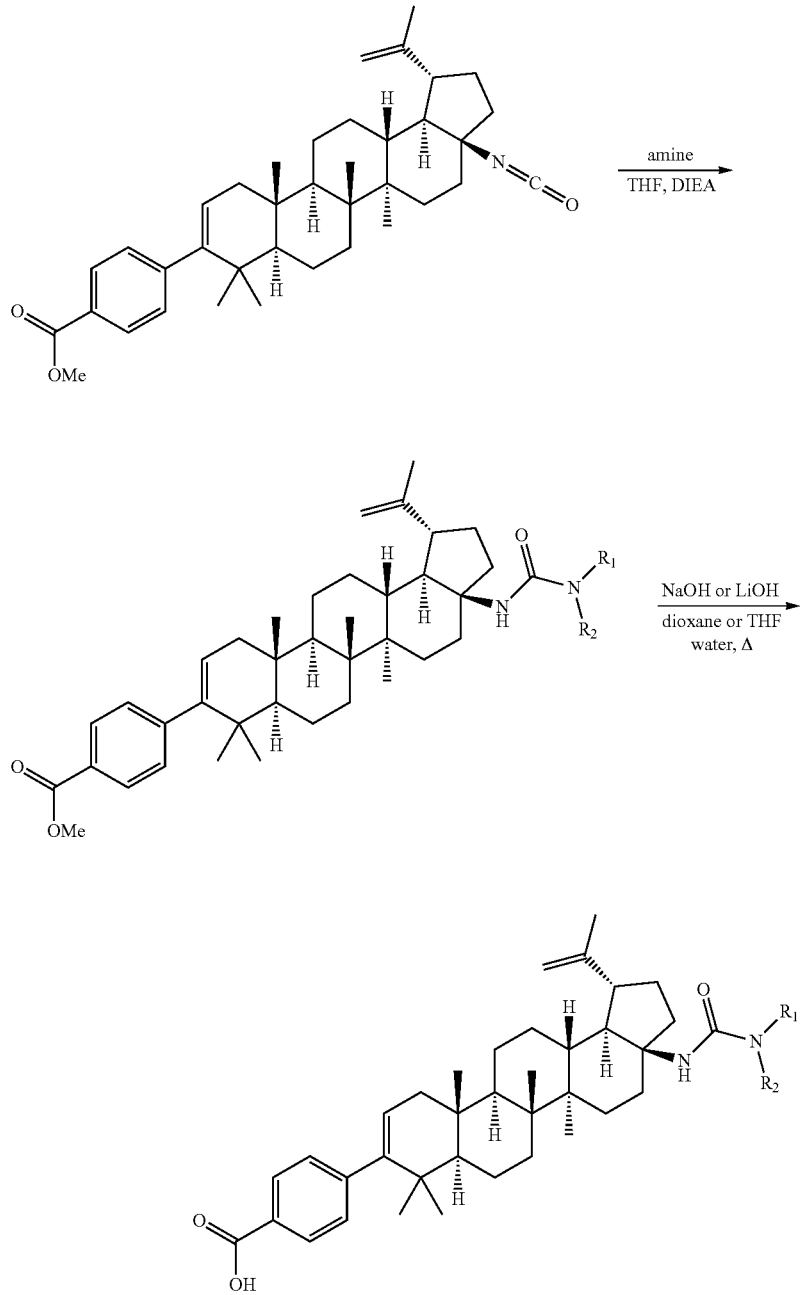

Step 1: General Procedure for the Preparation of C-17 Urea Methyl Esters.

To a solution of methyl 4-((1R,3aS,5aR,5bR,7aR,11aS,11bR,13aR,13bR)-3a-isocyanato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate in THF (approximately 0.1 M) was added Hunig's base (3-9 equiv.) and the amine (3 equiv.). The mixture was stirred at rt for 2-72 h. The reaction mixture was concentrated and redissolved in a mixture of THF and methanol and often a couple drops of water were added. The mixture was filtered and purified by reverse phase preparative HPLC.

Step 2: General Procedures for Hydrolysis of the Benzoic Ester Using NaOH or LiOH.H$_2$O.

The C-17 urea formed in Step 1 above was dissolved in either 1,4-dioxane or THF to give approximately a 0.1M solution. Aqueous 1N NaOH (4 eq.) was added to the mixture and it was heated to 50-85° C. After heating for 2-48 h, the mixture was cooled to rt. The crude mixture was purified by reverse phase preparative HPLC.

Alternatively, the ester hydrolysis can be carried out as follows: The C-17 urea formed in Step 1 above was dissolved in either 1,4-dioxane or THF to give approximately a 0.1M solution. To the solution was added water (ratio 4:1 or 5:1 organic 1,4-dioxane or THF:water) followed by LiOH.H$_2$O (5-12 equiv.). The mixture was heated to 50-85° C. After heating for as little as 60 seconds to as long as 24 h, the mixture was cooled to rt. The crude mixture was purified by reverse phase preparative HPLC.

Example 10

Preparation of 4-((1R,3aS,5aR,5bR,7aR,11aS,11bR,13aR,13bR)-3a-(3-(3-(dimethylamino)propyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

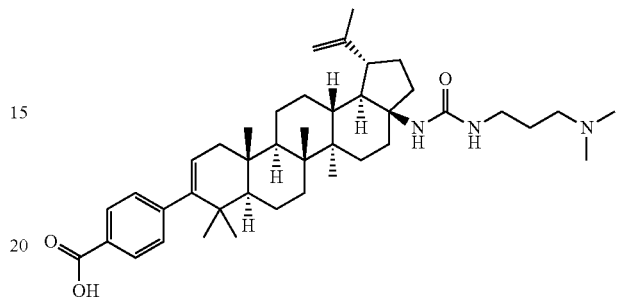

The title compound was prepared following the general procedures described above for the C-17 urea formation and subsequent ester hydrolysis using N1,N1-dimethylpropane-1,3-diamine as the reactant amine. The mono-TFA salt product was isolated after reverse phase preparative HPLC purification as a white solid (60 mg, 32.7% yield). LCMS: m/z 658 (M+H$^+$), retention time 1.86 min (method 2). $^1$H NMR (500 MHz, MeOD) δ ppm 0.97 (s, 3H), 0.99 (s, 3H), 1.07 (s, 6H), 1.11-1.13 (m, 1H), 1.15 (s, 3H), 1.17-1.22 (m, 1H), 1.28-1.48 (m, 5H), 1.48-1.64 (m, 6H), 1.64-1.83 (m, 7H), 1.83-2.01 (m, 4H), 2.18 (dd, J=17.09, 6.41 Hz, 1H), 2.37 (dd, J=12.21, 8.24 Hz, 1H), 2.58-2.68 (m, 2H), 2.90 (s, 6H), 3.13 (td, J=7.02, 1.83 Hz, 2H), 3.25 (td, J=6.49, 0.76 Hz, 1H), 4.66 (s, 1H), 4.78 (d, J=1.53 Hz, 1H), 5.33 (dd, J=6.10, 1.22 Hz, 1H), 7.25 (m, J=8.24 Hz, 2H), 7.95 (m, J=8.24 Hz, 2H).

Example 11

Preparation of 4-((1R,3aS,5aR,5bR,7aR,11aS,11bR,13aR,13bR)-5a,5b,8,8,11a-pentamethyl-3a-(3-(3-morpholinopropyl)ureido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

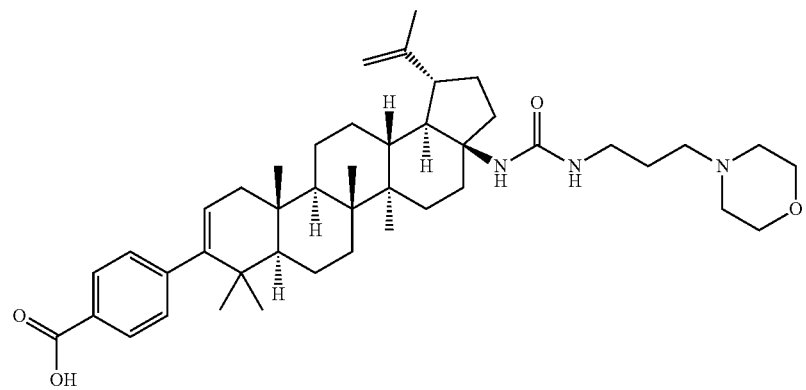

The title compound was prepared following the general procedures described above for the C-17 urea formation and subsequent ester hydrolysis using 3-morpholinopropan-1-amine as the reactant amine. The mono-TFA salt product was isolated after reverse phase preparative HPLC purification as a white solid (85 mg, 43% yield). LCMS: m/z 700 (M+H$^+$), retention time 1.89 min (method 2). $^1$H NMR (500 MHz, MeOD) δ ppm 0.97 (s, 3H), 0.99 (s, 3H), 1.07 (s, 6H), 1.11-1.13 (m, 1H), 1.15 (s, 3H), 1.17-1.21 (m, 1H), 1.28-1.47 (m, 5H), 1.50-1.63 (m, 6H), 1.64-1.72 (m, 1H), 1.74 (br. s., 1H), 1.75 (s, 3H), 1.76-1.83 (m, 2H), 1.87 (td, J=12.21, 3.36 Hz, 1H), 1.91-1.99 (m, 3H), 2.18 (dd, J=17.09, 6.41 Hz, 1H), 2.35 (dd, J=12.05, 8.09 Hz, 1H), 2.58-2.67 (m, 2H), 3.11-3.20 (m, 4H), 3.25-3.31 (m, 2H), 3.45 (t, J=12.97 Hz, 2H), 3.81 (t, J=12.51 Hz, 2H), 4.11 (d, J=12.82 Hz, 2H), 4.66 (s, 1H), 4.78 (s, 1H), 5.33 (dd, J=6.10, 1.83 Hz, 1H), 7.24 (m, J=8.55 Hz, 2H), 7.95 (m, J=8.55 Hz, 2H).

Example 12

Preparation of 4-((1R,3aS,5aR,5bR,7aR,11aS,11bR,13aR,13bR)-5a,5b,8,8,11a-pentamethyl-3a-(3-(3-(2-methyl-1H-imidazol-1-yl)propyl)ureido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

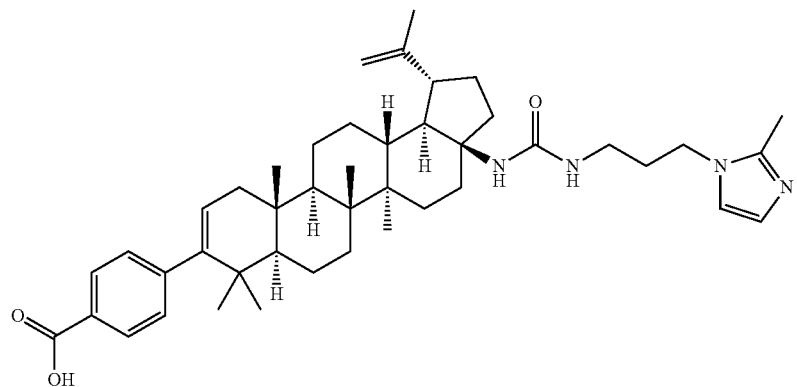

The title compound was prepared following the general procedures described above for the C-17 urea formation and subsequent ester hydrolysis using 3-(2-methyl-1H-imidazol-1-yl)propan-1-amine dihydrochloride as the reactant amine. The mono-TFA salt product was isolated after reverse phase preparative HPLC purification as a white solid (40 mg, 21% yield). LCMS: m/z 709 (M+H$^+$), retention time 1.83 min (method 2). $^1$H NMR (500 MHz, MeOD) δ ppm 0.97 (s, 3H), 0.99 (s, 3H), 1.07 (s, 6H), 1.12 (d, J=13.43 Hz, 1H), 1.15 (s, 3H), 1.17-1.22 (m, 1H), 1.27-1.46 (m, 5H), 1.47-1.64 (m, 6H), 1.66-1.82 (m, 7H), 1.83-1.98 (m, 2H), 2.04 (quin, J=6.94 Hz, 2H), 2.18 (dd, J=17.09, 6.41 Hz, 1H), 2.38 (dd, J=12.36, 8.09 Hz, 1H), 2.58-2.65 (m, 2H), 2.66 (s, 3H), 3.18 (t, J=6.71 Hz, 2H), 4.18 (t, J=7.17 Hz, 2H), 4.66 (s, 1H), 4.78 (d, J=1.83 Hz, 1H), 5.33 (dd, J=6.26, 1.68 Hz, 1H), 7.24 (m, J=8.55 Hz, 2H), 7.47 (d, J=1.83 Hz, 1H), 7.59 (d, J=2.14 Hz, 1H), 7.95 (m, J=8.24 Hz, 2H).

Example 13

Preparation of 4-((1R,3aS,5aR,5bR,7aR,11aS,11bR,13aR,13bR)-3a-(3-(2-(1H-imidazol-4-yl)ethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

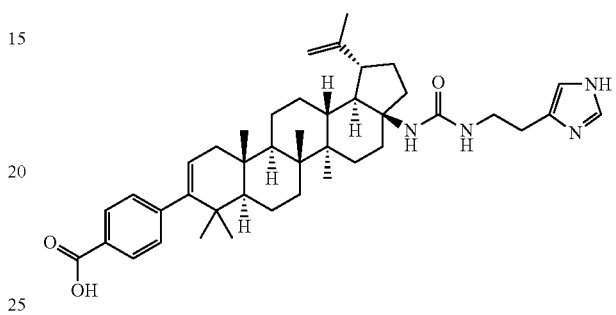

The title compound was prepared following the general procedures described above for the C-17 urea formation and subsequent ester hydrolysis using histamine as the reactant amine. The mono-TFA salt product was isolated after reverse phase preparative HPLC purification as a white solid (23 mg, 11% yield). LCMS: m/z 667 (M+H$^+$), retention time 1.79 min (method 2). $^1$H NMR (500 MHz, MeOD) δ ppm 0.97 (s, 3H), 0.99 (s, 3H), 1.05 (s, 3H), 1.06 (s, 3H), 1.07-1.11 (m, 1H), 1.12 (s, 3H), 1.13-1.20 (m, 1H), 1.26-1.45 (m, 5H), 1.49-1.68 (m, 7H), 1.71 (d, J=11.60 Hz, 1H), 1.74 (s, 3H), 1.75-1.94 (m, 4H), 2.17 (dd, J=17.09, 6.41 Hz, 1H), 2.31 (dd, J=12.36, 8.09 Hz, 1H), 2.54-2.64 (m, 2H), 2.90 (t, J=6.71 Hz, 2H), 3.45 (t, J=6.87 Hz, 2H), 4.65 (s, 1H), 4.76 (d, J=1.83 Hz, 1H), 5.33 (dd, J=6.10, 1.83 Hz, 1H), 7.24 (d, J=8.24 Hz, 2H), 7.34 (s, 1H), 7.94 (d, J=8.24 Hz, 2H), 8.84 (d, J=1.22 Hz, 1H).

Example 14

Preparation of 4-((1R,3aS,5aR,5bR,7aR,11aS,11bR, 13aR,13bR)-3a-(3-(3-(1H-imidazol-1-yl)propyl) ureido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

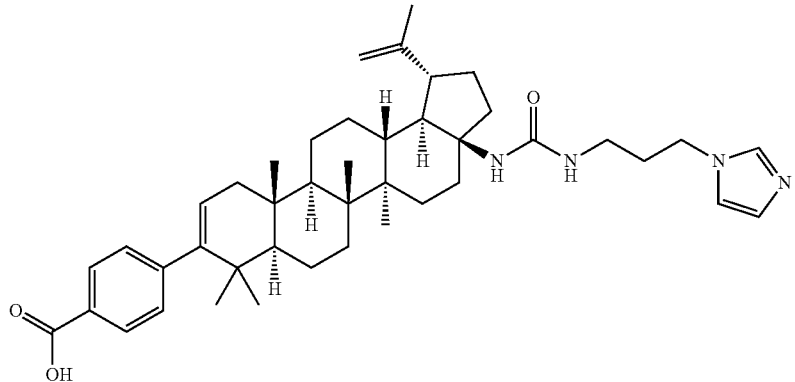

The title compound was prepared following the general procedures described above for the C-17 urea formation and subsequent ester hydrolysis using 3-(1H-imidazol-1-yl)propan-1-amine as the reactant amine. The mono-TFA salt product was isolated after reverse phase preparative HPLC purification as a white solid (109 mg, 53% yield). LCMS: m/z 681 (M+H$^+$), retention time 1.82 min (method 2). $^1$H NMR (500 MHz, MeOD) δ ppm 0.97 (s, 3H), 0.99 (s, 3H), 1.06 (s, 6H), 1.09-1.14 (m, 1H), 1.15 (s, 3H), 1.17-1.21 (m, 1H), 1.27-1.46 (m, 5H), 1.47-1.63 (m, 6H), 1.64-1.73 (m, 2H), 1.75 (s, 3H), 1.76-1.82 (m, 2H), 1.83-2.00 (m, 2H), 2.07 (qd, J=7.07, 6.87 Hz, 2H), 2.18 (dd, J=17.09, 6.41 Hz, 1H), 2.39 (dd, J=12.36, 8.09 Hz, 1H), 2.58-2.68 (m, 2H), 3.11-3.23 (m, 2H), 4.31 (t, J=6.87 Hz, 2H), 4.66 (s, 1H), 4.78 (d, J=1.83 Hz, 1H), 5.33 (dd, J=6.10, 1.83 Hz, 1H), 7.24 (m, J=8.54 Hz, 2H), 7.60 (t, J=1.53 Hz, 1H), 7.71 (t, J=1.68 Hz, 1H), 7.94 (m, J=8.54 Hz, 2H), 9.00 (s, 1H).

Example 15

Preparation of 4-((1R,3aS,5aR,5bR,7aR,11aS,11bR, 13aR,13bR)-5a,5b,8,8,11a-pentamethyl-3a-(piperidine-1-carboxamido)-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) benzoic acid

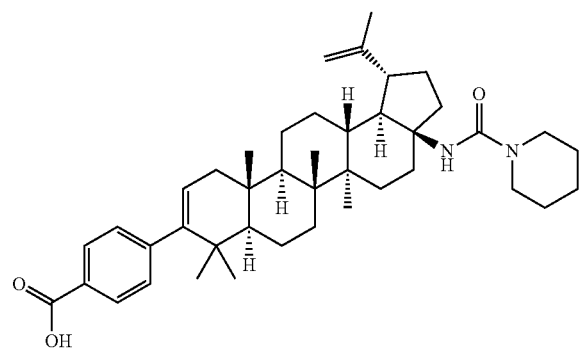

The title compound was prepared following the general procedures described above for the C-17 urea formation and subsequent ester hydrolysis using piperidine as the reactant amine. The product was isolated after reverse phase preparative HPLC purification as a white solid (10 mg, 6% yield). LCMS: m/z 641 (M+H$^+$), retention time 2.67 min (method 2). $^1$H NMR (500 MHz, MeOD) δ ppm 0.97 (s, 3H), 0.99 (s, 3H), 1.07 (s, 3H), 1.08 (s, 3H), 1.12 (dt, J=13.81, 3.17 Hz, 1H), 1.16 (s, 3H), 1.17-1.22 (m, 1H), 1.28-1.47 (m, 5H), 1.48-1.65 (m, 11H), 1.65-1.70 (m, 2H), 1.71-1.90 (m, 7H), 1.91-2.02 (m, 1H), 2.14-2.21 (m, 1H), 2.49 (dd, J=12.36, 8.09 Hz, 1H), 2.59-2.71 (m, 2H), 3.35-3.48 (m, 4H), 4.63-4.67 (m, 1H), 4.80 (d, J=1.83 Hz, 1H), 5.33 (dd, J=6.10, 1.83 Hz, 1H), 7.25 (m, J=8.24 Hz, 2H), 7.94 (m, J=8.24 Hz, 2H).

Example 16

Preparation of 4-((1R,3aS,5aR,5bR,7aR,11aS,11bR, 13aR,13bR)-3a-(3-(carboxymethyl)ureido)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

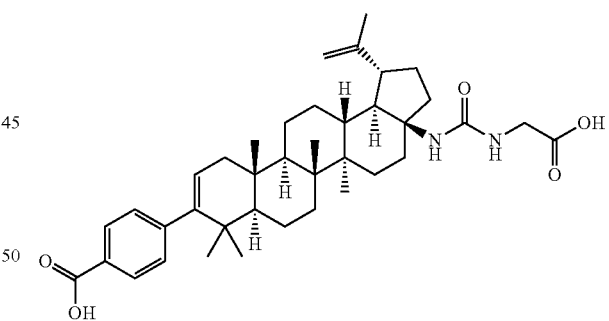

The title compound was prepared following the general procedures described above for the C-17 urea formation and subsequent ester hydrolysis using glycine methyl ester hydrochloride as the reactant amine. The product was isolated after reverse phase preparative HPLC purification as a white solid (59 mg, 45% yield). LCMS: m/z 631 (M+H$^+$), retention time 2.17 min (method 2). $^1$H NMR (500 MHz, 1:1 mixture of CDCl3 and MeOD, MeOD lock) δ ppm 0.94 (s, 3H), 0.95 (s, 3H), 1.02 (s, 6H), 1.04-1.11 (m, 2H), 1.12 (s, 3H), 1.23-1.41 (m, 5H), 1.42-1.61 (m, 6H), 1.65 (t, J=11.60 Hz, 1H), 1.68-1.79 (m, 6H), 1.85 (td, J=12.21, 3.36 Hz, 1H), 1.92-2.05 (m, 1H), 2.13 (dd, J=17.09, 6.41 Hz, 1H), 2.36 (dd, J=12.36, 8.09 Hz, 1H), 2.55-2.66 (m, 2H), 3.80-3.95 (m, 2H), 4.58-4.64 (m, 1H), 4.74 (d, J=1.83 Hz, 2H), 5.29 (dd, J=6.26, 1.68 Hz, 1H), 7.19-7.23 (m, 2H), 7.91-7.95 (m, 2H).

Example 17

Preparation of 4-((1R,3aS,5aR,5bR,7aR,11aS,11bR, 13aR,13bR)-3a-(3-((S)-1-carboxyethyl)ureido)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

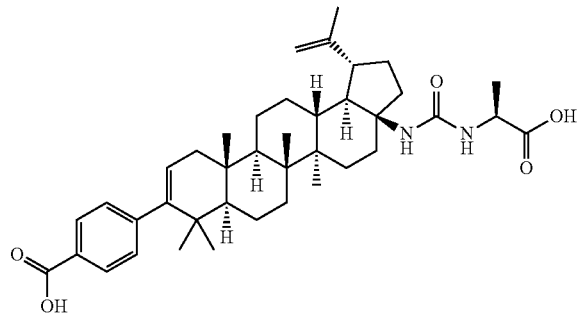

The title compound was prepared following the general procedures described above for the C-17 urea formation and subsequent ester hydrolysis using L-alanine methyl ester hydrochloride as the reactant amine. The product was isolated after reverse phase preparative HPLC purification as a white solid (74 mg, 54% yield). LCMS: m/z 645 (M+H$^+$), retention time 2.26 min (method 2). $^1$H NMR (500 MHz, 1:1 mixture of CDCl3 and MeOD, MeOD lock) δ ppm 0.93 (br. s., 3H), 0.94 (br. s., 3H), 0.99 (s, 6H), 1.02-1.09 (m, 2H), 1.10 (s, 3H), 1.19-1.35 (m, 5H), 1.37 (d, J=7.32 Hz, 3H), 1.39-1.57 (m, 6H), 1.63 (t, J=11.60 Hz, 1H), 1.66-1.76 (m, 6H), 1.76-1.85 (m, 1H), 1.88-1.99 (m, 1H), 2.11 (dd, J=17.09, 6.41 Hz, 1H), 2.35 (dd, J=12.36, 8.09 Hz, 1H), 2.50-2.61 (m, 2H), 4.28 (q, J=7.02 Hz, 1H), 4.61 (br. s., 1H), 4.72 (br. s., 1H), 5.26-5.31 (m, 1H), 7.20 (d, J=8.24 Hz, 2H), 7.92 (d, J=8.55 Hz, 2H).

Example 18

Preparation of 4-((1R,3aS,5aR,5bR,7aR,11aS,11bR, 13aR,13bR)-3a-(3-((S)-1-carboxy-2-hydroxyethyl) ureido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

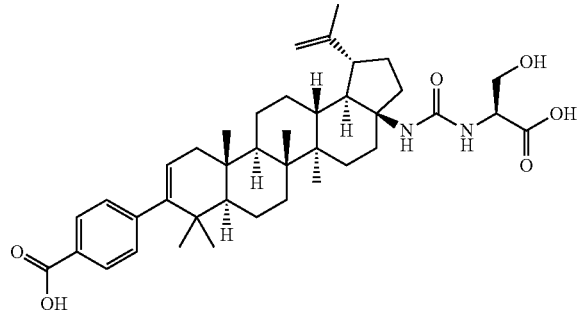

The title compound was prepared following the general procedures described above for the C-17 urea formation and subsequent ester hydrolysis using L-serine methyl ester hydrochloride as the reactant amine. The product was isolated after reverse phase preparative HPLC purification as a white solid (70 mg, 48% yield). LCMS: m/z 661 (M+H$^+$), retention time 2.19 min (method 2). $^1$H NMR (500 MHz, 1:1 mixture of CDCl3 and MeOD, MeOD lock) δ ppm 0.93 (br. s., 3H), 0.93 (s, 3H), 0.99 (br. s., 3H), 1.00 (s, 3H), 1.03-1.09 (m, 2H), 1.11 (s, 3H), 1.21-1.41 (m, 5H), 1.41-1.57 (m, 6H), 1.64 (t, J=11.60 Hz, 1H), 1.67-1.77 (m, 6H), 1.84 (td, J=12.21, 3.36 Hz, 1H), 1.88-1.99 (m, 1H), 2.11 (dd, J=17.09, 6.41 Hz, 1H), 2.35 (dd, J=12.21, 8.24 Hz, 1H), 2.54-2.63 (m, 2H), 3.80 (dd, J=10.99, 3.66 Hz, 1H), 3.93 (dd, J=10.99, 4.27 Hz, 1H), 4.37 (t, J=3.97 Hz, 1H), 4.61 (br. s., 1H), 4.72 (d, J=1.53 Hz, 1H), 5.28 (dd, J=6.26, 1.68 Hz, 1H), 7.20 (m, J=8.54 Hz, 2H), 7.92 (m, J=8.24 Hz, 2H).

Example 19

Preparation of 4-((1R,3aS,5aR,5bR,7aR,11aS,11bR, 13aR,13bR)-3a-(3-((R)-1-carboxyethyl)ureido)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

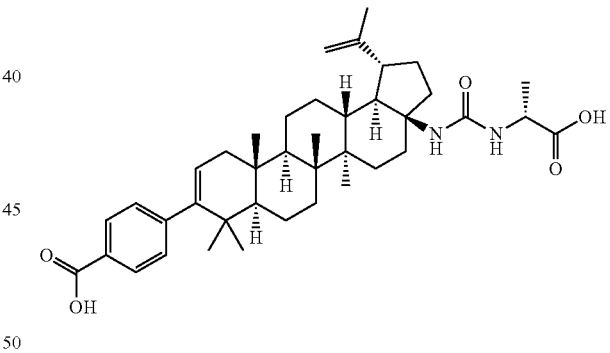

The title compound was prepared following the general procedures described above for the C-17 urea formation and subsequent ester hydrolysis using D-alanine methyl ester hydrochloride as the reactant amine. The product was isolated after reverse phase preparative HPLC purification as a white solid (68 mg, 50% yield). LCMS: m/z 645 (M+H$^+$), retention time 2.23 min (method 2). $^1$H NMR (500 MHz, 1:1 mixture of CDCl3 and MeOD, MeOD lock) δ ppm 0.93 (br. s., 3H), 0.94 (br. s., 3H), 1.00 (s, 6H), 1.03-1.14 (m, 5H), 1.20-1.36 (m, 5H), 1.37 (d, J=7.02 Hz, 3H), 1.40-1.58 (m, 6H), 1.58-1.68 (m, 2H), 1.68-1.75 (m, 5H), 1.75-1.83 (m, 1H), 1.92-2.03 (m, 1H), 2.11 (dd, J=17.09, 6.41 Hz, 1H), 2.34 (dd, J=12.21, 8.24 Hz, 1H), 2.51-2.60 (m, 2H), 4.27 (q, J=7.32 Hz, 1H), 4.60 (br.

s., 2H), 4.72 (d, J=1.53 Hz, 1H), 5.28 (dd, J=6.10, 1.53 Hz, 1H), 7.20 (m, J=8.55 Hz, 2H), 7.92 (m, J=8.24 Hz, 2H).

Example 20

Preparation of 4-((1R,3aS,5aR,5bR,7aR,11aS,11bR,13aR,13bR)-3a-(3-((R)-1-carboxy-2-hydroxyethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

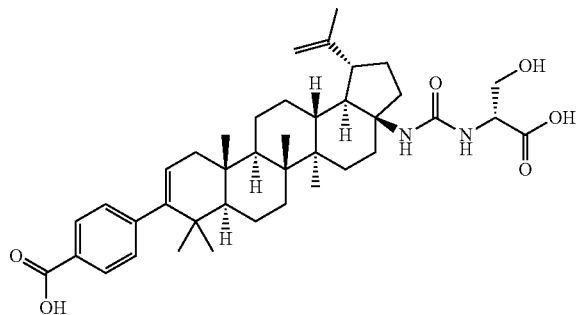

The title compound was prepared following the general procedures described above for the C-17 urea formation and subsequent ester hydrolysis using D-serine methyl ester hydrochloride as the reactant amine. The product was isolated after reverse phase preparative HPLC purification as a white solid (51 mg, 34% yield). LCMS: m/z 661 (M+H$^+$), retention time 2.11 min (method 2). $^1$H NMR (500 MHz, 1:1 mixture of CDCl3 and MeOD, MeOD lock) δ ppm 0.92 (br. s., 6H), 0.98 (br. s., 6H), 1.02-1.14 (m, 5H), 1.17-1.38 (m, 5H), 1.39-1.58 (m, 6H), 1.58-1.75 (m, 7H), 1.76-1.86 (m, 1H), 1.90-2.04 (m, 1H), 2.04-2.13 (m, 1H), 2.36 (t, J=9.77 Hz, 1H), 2.56 (d, J=12.51 Hz, 2H), 3.81 (d, J=10.99 Hz, 1H), 3.94 (d, J=10.99 Hz, 1H), 4.35 (d, J=2.44 Hz, 1H), 4.60 (br. s., 1H), 4.71 (br. s., 1H), 5.28 (br. s., 1H), 7.19 (m, J=7.32 Hz, 2H), 7.92 (m, J=7.63 Hz, 2H).

Example 21

Preparation of 4-((1R,3aS,5aR,5bR,7aR,11aS,11bR,13aR,13bR)-3a-(((2-(1,1-dioxido-4-thiomorpholinyl)ethyl)carbamoyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

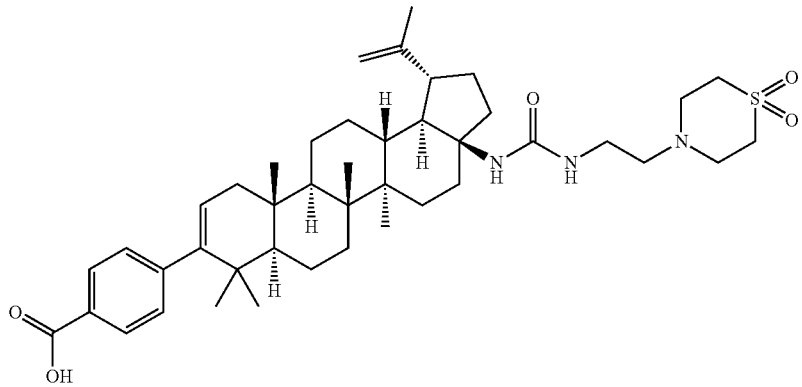

The title compound was prepared following the general procedures described above for the C-17 urea formation and subsequent ester hydrolysis using 4-(2-aminoethyl)thiomorpholine 1,1-dioxide as the reactant amine. The mono-TFA salt product was isolated after reverse phase preparative HPLC purification as a white solid (121 mg, 74% yield). LCMS: m/z 734 (M+H$^+$), retention time 2.49 min (method 11). $^1$H NMR (500 MHz, 1:1 mixture of CDCl3 and MeOD, MeOD lock) δ ppm 0.94 (s, 3H), 0.95 (s, 3H), 1.02 (br. s., 3H), 1.03 (br. s., 3H), 1.10 (s, 3H), 1.11-1.17 (m, 2H), 1.21-1.60 (m, 11H), 1.63-1.82 (m, 8H), 1.86-2.00 (m, 1H), 2.13 (dd, J=17.24, 6.26 Hz, 1H), 2.35 (dd, J=12.05, 8.39 Hz, 1H), 2.52-2.63 (m, 2H), 3.20 (br. s., 2H), 3.39-3.52 (m, 6H), 3.69 (br. s., 4H), 4.63 (s, 1H), 4.75 (d, J=1.22 Hz, 1H), 5.29 (d, J=4.58 Hz, 1H), 7.21 (m, J=8.24 Hz, 2H), 7.93 (m, J=8.24 Hz, 2H).

Example 22

Preparation of 4-((1R,3aS,5aR,5bR,7aR,11aS,11bR,13aR,13bR)-3a-(((3-(1,1-dioxido-4-thiomorpholinyl)propyl)carbamoyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

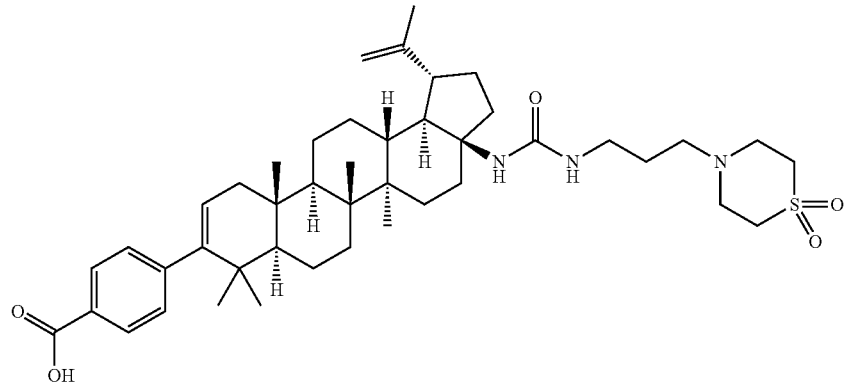

The title compound was prepared following the general procedures described above for the C-17 urea formation and subsequent ester hydrolysis using 4-(3-aminopropyl)thiomorpholine 1,1-dioxide as the reactant amine. The mono-TFA salt product was isolated after reverse phase preparative HPLC purification as a white solid (115 mg, 59% yield). LCMS: m/z 748 (M+H$^+$), retention time 2.44 min (method 11). $^1$H NMR (500 MHz, 1:1 mixture of CDCl3 and MeOD, MeOD lock) δ ppm 0.95 (s, 3H), 0.96 (s, 3H), 1.02 (br. s., 3H), 1.03 (br. s., 3H), 1.11 (s, 3H), 1.12-1.18 (m, 2H), 1.24-1.44 (m, 5H), 1.44-1.60 (m, 6H), 1.63-1.80 (m, 8H), 1.85-1.99 (m, 3H), 2.14 (dd, J=17.09, 6.41 Hz, 1H), 2.32 (dd, J=12.05, 8.09 Hz, 1H), 2.52-2.63 (m, 2H), 3.14 (t, J=7.02 Hz, 2H), 3.19-3.30 (m, 2H), 3.50 (d, J=4.58 Hz, 4H), 3.65 (d, J=5.19 Hz, 4H), 4.63 (s, 1H), 4.75 (s, 1H), 5.27-5.32 (m, 1H), 7.21 (m, J=8.24 Hz, 2H), 7.93 (m, J=8.24 Hz, 2H).

Example 23

Preparation of 4-((1R,3aS,5aR,5bR,7aR,11aS,11bR,13aR,13bR)-3a-(3-(2-((2-hydroxyethyl)(methyl)amino)ethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

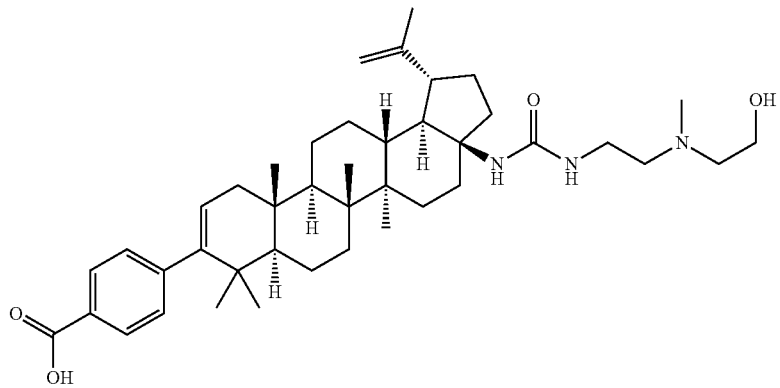

The title compound was prepared following the general procedures described above for the C-17 urea formation and subsequent ester hydrolysis using 2-((2-aminoethyl)(methyl)amino)ethanol as the reactant amine. The mono-TFA salt product was isolated after reverse phase preparative HPLC purification as a white solid (43 mg, 69% yield). LCMS: m/z 674 (M+H$^+$), retention time 2.41 min (method 11). $^1$H NMR (500 MHz, 1:1 mixture of CDCl3 and MeOD, MeOD lock) δ ppm 0.93 (br. s., 3H), 0.94 (br. s., 3H), 1.00 (br. s., 3H), 1.00 (br. s., 3H), 1.08 (s, 3H), 1.08-1.15 (m, 2H), 1.22-1.39 (m, 5H), 1.40-1.56 (m, 6H), 1.59-1.79 (m, 8H), 1.85-1.99 (m, 1H), 2.11 (dd, J=17.09, 6.41 Hz, 1H), 2.35 (br. s., 1H), 2.48-2.61 (m, 2H), 2.96 (s, 3H), 3.09-3.61 (m, 6H), 3.87 (t, J=5.19

Hz, 2H), 4.61 (br. s., 1H), 4.73 (br. s., 1H), 5.24-5.31 (m, 1H), 7.20 (d, J=8.24 Hz, 2H), 7.92 (d, J=8.24 Hz, 2H).

Example 24

Preparation of 4-((1R,3aS,5aR,5bR,7aR,11aS,11bR, 13aR,13bR)-3a-(3-(2-(dimethylamino)ethyl)-3-methylureido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

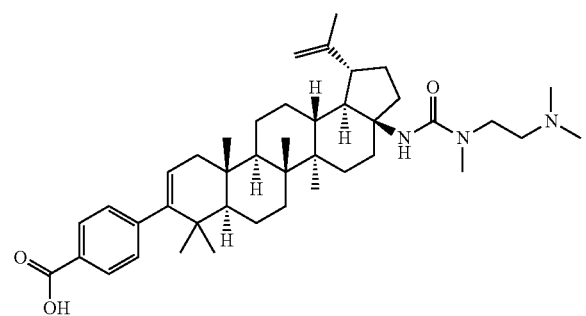

The title compound was prepared following the general procedures described above for the C-17 urea formation and subsequent ester hydrolysis using N1,N1,N2-trimethylethane-1,2-diamine as the reactant amine. The mono-TFA salt product was isolated after reverse phase preparative HPLC purification as a white solid (34 mg, 57% yield). LCMS: m/z 658 (M+H$^+$), retention time 2.41 min (method 11). $^1$H NMR (500 MHz, 1:1 mixture of CDCl3 and MeOD, MeOD lock) δ ppm 0.93 (br. s., 3H), 0.94 (br. s., 3H), 1.00 (s, 3H), 1.03 (s, 3H), 1.10 (s, 3H), 1.10-1.20 (m, 2H), 1.20-1.28 (m, 1H), 1.31-1.42 (m, 4H), 1.44-1.58 (m, 7H), 1.62-1.80 (m, 7H), 1.88-2.01 (m, 1H), 2.12 (dd, J=17.09, 6.10 Hz, 1H), 2.41-2.56 (m, 3H), 2.92 (s, 6H), 3.03 (s, 3H), 3.18-3.31 (m, 2H), 3.51 (ddd, J=15.11, 5.95, 5.80 Hz, 1H), 3.73-3.83 (m, 1H), 4.54 (s, 1H), 4.64 (br. s., 1H), 4.75 (s, 1H), 5.25-5.31 (m, 1H), 7.20 (d, J=8.24 Hz, 2H), 7.92 (d, J=8.24 Hz, 2H).

Example 25

Preparation of 4-((1R,3aS,5aR,5bR,7aR,11aS,11bR, 13aR,13bR)-3a-(3-(2-(1H-imidazol-1-yl)ethyl)-3-methylureido)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

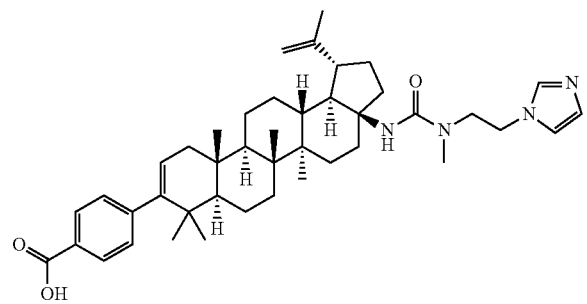

The title compound was prepared following the general procedures described above for the C-17 urea formation and subsequent ester hydrolysis using 2-(1H-imidazol-1-yl)-N-methylethanamine, 2 HCl as the reactant amine. The mono-TFA salt product was isolated after reverse phase preparative HPLC purification as a white solid (35 mg, 56% yield). LCMS: m/z 681 (M+H$^+$), retention time 2.39 min (method 11). $^1$H NMR (500 MHz, 1:1 mixture of CDCl3 and MeOD, MeOD lock) δ ppm 0.94 (br. s., 3H), 0.94 (br. s., 3H), 1.00 (s, 3H), 1.02 (s, 3H), 1.09 (s, 3H), 1.09-1.19 (m, 2H), 1.23-1.42 (m, 5H), 1.43-1.54 (m, 6H), 1.54-1.60 (m, 1H), 1.61-1.76 (m, 7H), 1.80-1.94 (m, 1H), 2.12 (dd, J=17.24, 6.26 Hz, 1H), 2.29 (dd, J=12.67, 8.09 Hz, 1H), 2.35-2.51 (m, 2H), 3.01 (s, 3H), 3.65 (dt, J=14.57, 5.84 Hz, 1H), 3.79-3.89 (m, 1H), 4.33-4.43 (m, 2H), 4.64 (br. s., 1H), 4.74 (br. s., 1H), 5.25-5.31 (m, 1H), 7.20 (d, J=8.55 Hz, 2H), 7.41 (t, J=1.53 Hz, 1H), 7.51 (t, J=1.68 Hz, 1H), 7.92 (d, J=8.24 Hz, 2H), 8.88 (d, J=1.22 Hz, 1H).

Example 26

Preparation of 4-((1R,3aS,5aR,5bR,7aR,11aS,11bR, 13aR,13bR)-3a-(3-(2-acetamidoethyl)ureido)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) benzoic acid

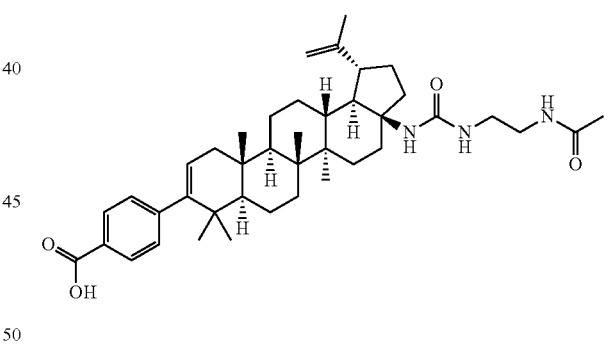

The title compound was prepared following the general procedures described above for the C-17 urea formation and subsequent ester hydrolysis using N-(2-aminoethyl)acetamide as the reactant amine. The product was isolated after reverse phase preparative HPLC purification as a white solid (24 mg, 48% yield). LCMS: m/z 658 (M+H$^+$), retention time 2.73 min (method 11). $^1$H NMR (500 MHz, 1:1 mixture of CDCl3 and MeOD, MeOD lock) δ ppm 0.93 (br. s., 3H), 0.94 (br. s., 3H), 1.00 (br. s., 3H), 1.04-1.15 (m, 5H), 1.21-1.41 (m, 6H), 1.41-1.58 (m, 6H), 1.58-1.67 (m, 2H), 1.70 (s, 3H), 1.70-1.82 (m, 3H), 1.86-1.94 (m, 1H), 1.96 (s, 3H), 2.11 (dd, J=17.40, 6.41 Hz, 1H), 2.34 (dd, J=12.05, 8.09 Hz, 1H), 2.49-2.61 (m, 2H), 3.19-3.27 (m, 4H), 4.61 (br. s., 1H), 4.72 (s, 1H), 5.25-5.31 (m, 1H), 7.20 (d, J=8.55 Hz, 2H), 7.92 (d, J=8.24 Hz, 2H).

Example 27

Preparation of 4-((1R,3aS,5aR,5bR,7aR,11aS,11bR, 13aR,13bR)-5a,5b,8,8,11a-pentamethyl-3a-(3-(2-(2-oxopiperidin-1-yl)ethyl)ureido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

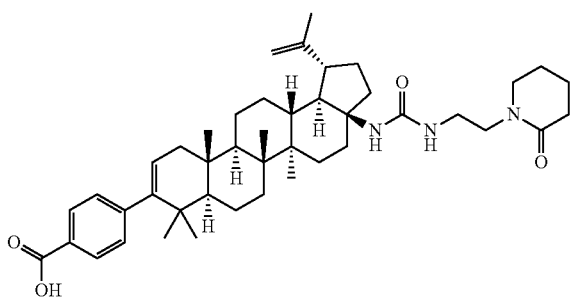

The title compound was prepared following the general procedures described above for the C-17 urea formation and subsequent ester hydrolysis using 1-(2-aminoethyl)piperidin-2-one hydrobromide as the reactant amine. The product was isolated after reverse phase preparative HPLC purification as a white solid (37 mg, 68% yield). LCMS: m/z 698 (M+H$^+$), retention time 2.83 min (method 11). $^1$H NMR (500 MHz, 1:1 mixture of CDCl3 and MeOD, MeOD lock) δ ppm 0.93 (br. s., 3H), 0.94 (br. s., 3H), 1.00 (s, 6H), 1.04-1.14 (m, 5H), 1.21-1.41 (m, 5H), 1.41-1.58 (m, 6H), 1.58-1.67 (m, 2H), 1.70 (s, 3H), 1.70-1.85 (m, 7H), 1.86-1.97 (m, 1H), 2.11 (dd, J=17.09, 6.10 Hz, 1H), 2.29-2.39 (m, 3H), 2.50-2.61 (m, 2H), 3.30-3.32 (m, 1H), 3.40 (t, J=5.34 Hz, 2H), 3.45 (t, J=5.95 Hz, 2H), 4.61 (br. s., 1H), 4.72 (br. s., 1H), 5.25-5.31 (m, 1H), 7.20 (d, J=8.24 Hz, 2H), 7.92 (d, J=8.24 Hz, 2H).

Example 28

Preparation of 4-((1R,3aS,5aR,5bR,7aR,11aS,11bR, 13aR,13bR)-5a,5b,8,8,11a-pentamethyl-3a-(3-(2-(2-oxopyrrolidin-1-yl)ethyl)ureido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

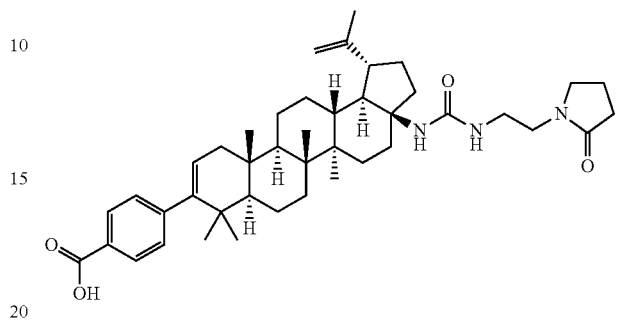

The title compound was prepared following the general procedures described above for the C-17 urea formation and subsequent ester hydrolysis using 1-(2-aminoethyl)pyrrolidin-2-one oxalic acid salt as the reactant amine. The product was isolated after reverse phase preparative HPLC purification as a white solid (37 mg, 67% yield). LCMS: m/z 684 (M+H$^+$), retention time 2.78 min (method 11). $^1$H NMR (500 MHz, 1:1 mixture of CDCl3 and MeOD, MeOD lock) δ ppm 0.93 (s, 3H), 0.94 (s, 3H), 1.00 (s, 6H), 1.04-1.15 (m, 5H), 1.21-1.41 (m, 6H), 1.41-1.59 (m, 6H), 1.59-1.67 (m, 2H), 1.67-1.81 (m, 6H), 1.86-1.97 (m, 1H), 2.00-2.08 (m, 2H), 2.11 (dd, J=17.09, 6.41 Hz, 1H), 2.33 (dd, J=12.36, 8.09 Hz, 1H), 2.38 (t, J=8.09 Hz, 2H), 2.50-2.60 (m, 2H), 3.28-3.32 (m, 2H), 3.53 (t, J=7.32 Hz, 2H), 4.61 (s, 1H), 4.72 (d, J=1.53 Hz, 1H), 5.28 (dd, J=5.95, 1.68 Hz, 1H), 7.20 (m, J=8.54 Hz, 2H), 7.92 (m, J=8.24 Hz, 2H).

Example 29

Preparation of 4-((1R,3aS,5aR,5bR,7aR,11aS,11bR, 13aR,13bR)-5a,5b,8,8,11a-pentamethyl-3a-(3-(3-(2-oxopyrrolidin-1-yl)propyl)ureido)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

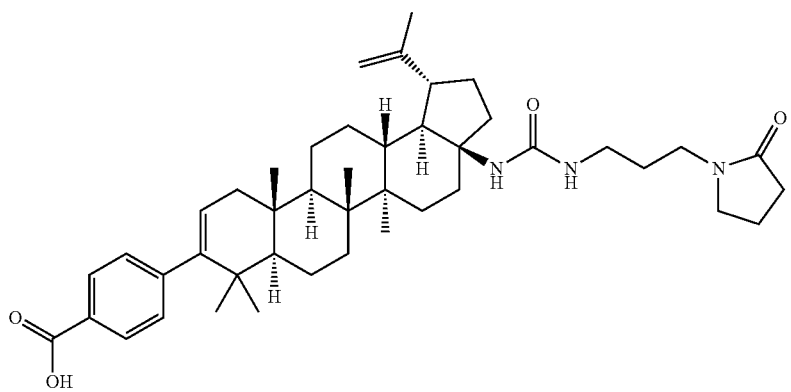

The title compound was prepared following the general procedures described above for the C-17 urea formation and subsequent ester hydrolysis using 1-(3-aminopropyl)pyrrolidin-2-one as the reactant amine. The product was isolated after reverse phase preparative HPLC purification as a white solid (38 mg, 69% yield). LCMS: m/z 698 (M+H+), retention time 2.79 min (method 11). ¹H NMR (500 MHz, 1:1 mixture of CDCl3 and MeOD, MeOD lock) δ ppm 0.93 (br. s., 3H), 0.94 (br. s., 3H), 1.00 (br. s., 3H), 1.00 (s, 3H), 1.04-1.16 (m, 5H), 1.21-1.41 (m, 5H), 1.41-1.59 (m, 6H), 1.59-1.76 (m, 9H), 1.80 (td, J=12.21, 3.05 Hz, 1H), 1.88-2.00 (m, 1H), 2.03-2.16 (m, 3H), 2.36 (dd, J=12.21, 8.24 Hz, 1H), 2.42 (t, J=8.09 Hz, 2H), 2.51-2.64 (m, 2H), 3.09 (t, J=6.56 Hz, 2H), 3.25-3.38 (m, 2H), 3.47 (t, J=7.17 Hz, 2H), 4.61 (s, 1H), 4.73 (d, J=1.53 Hz, 1H), 5.25-5.32 (m, 1H), 7.20 (m, J=8.24 Hz, 2H), 7.92 (m, J=8.24 Hz, 2H).

Example 30

Preparation of 4-((1R,3aS,5aR,5bR,7aR,11aS,11bR,13aR,13bR)-3a-(3,3-bis(3-(dimethylamino)propyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

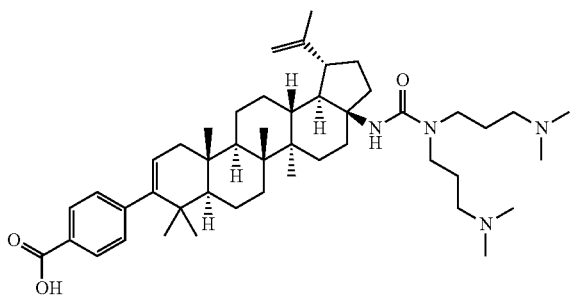

The title compound was prepared following the general procedures described above for the C-17 urea formation and subsequent ester hydrolysis using N1-(3-(dimethylamino)propyl)-N3,N3-dimethylpropane-1,3-diamine as the reactant amine. The bis-TFA salt product was isolated after reverse phase preparative HPLC purification as a white solid (15 mg, 20% yield). LCMS: m/z 743 (M+H+), retention time 2.27 min (method 11). ¹H NMR (500 MHz, 1:1 mixture of CDCl3 and MeOD, MeOD lock) δ ppm 0.94 (s, 3H), 0.94 (s, 3H), 1.00 (s, 3H), 1.05 (s, 3H), 1.09 (s, 3H), 1.11-1.19 (m, 2H), 1.26 (d, J=6.71 Hz, 1H), 1.30-1.44 (m, 3H), 1.44-1.62 (m, 8H), 1.63-1.81 (m, 7H), 1.83-1.95 (m, 1H), 2.02 (br. s., 4H), 2.13 (dd, J=17.09, 6.41 Hz, 1H), 2.41 (dd, J=12.51, 8.24 Hz, 1H), 2.51 (td, J=10.91, 5.04 Hz, 1H), 2.59 (d, J=13.43 Hz, 1H), 2.89 (s, 12H), 3.13 (t, J=7.02 Hz, 4H), 3.34-3.43 (m, 4H), 4.76 (s, 1H), 5.26-5.33 (m, 1H), 7.20 (m, J=8.55 Hz, 2H), 7.92 (m, J=8.24 Hz, 2H).

Example 31

Preparation of 4-((1R,3aS,5aR,5bR,7aR,11aS,11bR,13aR,13bR)-3a-(3-(2-(dimethylamino)-2-oxoethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

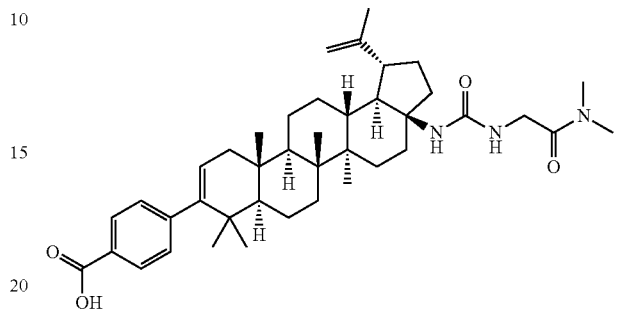

The title compound was prepared following the general procedures described above for the C-17 urea formation and subsequent ester hydrolysis using 2-amino-N,N-dimethylacetamide as the reactant amine. The product was isolated after reverse phase preparative HPLC purification as a white solid (7 mg, 14% yield). LCMS: m/z 658 (M+H+), retention time 2.77 min (method 11). ¹H NMR (500 MHz, 1:1 mixture of CDCl3 and MeOD, MeOD lock) δ ppm 0.93 (s, 3H), 0.94 (s, 3H), 1.01 (s, 6H), 1.05-1.16 (m, 5H), 1.21-1.41 (m, 6H), 1.41-1.57 (m, 6H), 1.60-1.78 (m, 7H), 1.84 (td, J=12.28, 3.51 Hz, 1H), 1.91-2.01 (m, 1H), 2.12 (dd, J=17.09, 6.41 Hz, 1H), 2.36 (dd, J=12.21, 7.93 Hz, 1H), 2.55-2.64 (m, 2H), 2.98 (s, 3H), 3.03 (s, 3H), 3.89-4.07 (m, 2H), 4.61 (d, J=1.22 Hz, 1H), 4.73 (d, J=1.83 Hz, 1H), 5.29 (dd, J=6.10, 1.83 Hz, 1H), 7.20 (d, J=8.54 Hz, 2H), 7.92 (d, J=8.24 Hz, 2H).

Example 32

Preparation of 4-((1R,3aS,5aR,5bR,7aR,11aS,11bR,13aR,13bR)-3a-(3,3-dimethylureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

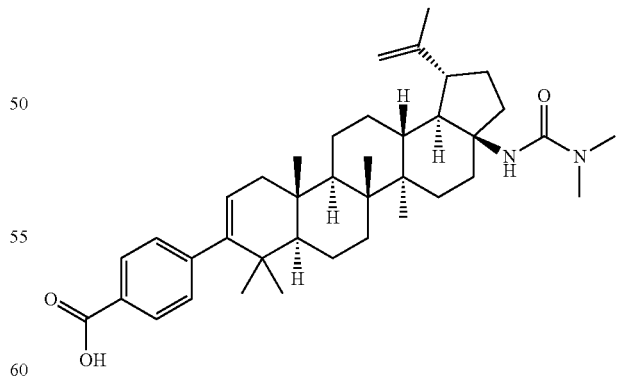

The title compound was formed as a byproduct during the preparation of 4-((1R,3aS,5aR,5bR,7aR,11aS,11bR,13aR,13bR)-3a-(3-(2-(dimethylamino)-2-oxoethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid. Hydrolysis of the penultimate methyl ester by the general procedure as described and purification by reverse phase preparative HPLC gave a white solid (13 mg, 29% yield). LCMS: m/z 601 (M+H$^+$), retention time 2.90 min (method 11). $^1$H NMR (500 MHz, 1:1 mixture of CDCl3 and MeOD, MeOD lock) δ ppm 0.94 (s, 3H), 0.94 (s, 3H), 1.00 (s, 3H), 1.03 (s, 3H), 1.10 (s, 3H), 1.11-1.19 (m, 2H), 1.24-1.44 (m, 6H), 1.45-1.60 (m, 7H), 1.61-1.66 (m, 1H), 1.69 (d, J=5.49 Hz, 2H), 1.71 (s, 3H), 1.72-1.78 (m, 2H), 1.91-2.01 (m, 1H), 2.12 (dd, J=17.09, 6.41 Hz, 1H), 2.42-2.52 (m, 2H), 2.56 (dt, J=13.20, 3.32 Hz, 1H), 2.95 (s, 6H), 4.63 (d, J=1.53 Hz, 1H), 4.74 (d, J=1.83 Hz, 1H), 5.29 (dd, J=6.26, 1.68 Hz, 1H), 7.20 (m, J=8.24 Hz, 2H), 7.92 (m, J=8.24 Hz, 2H).

Example 33

Preparation of 4-((1R,3aS,5aR,5bR,7aR,11aS,11bR, 13aR,13bR)-3a-(3-(2-carboxyethyl)ureido)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

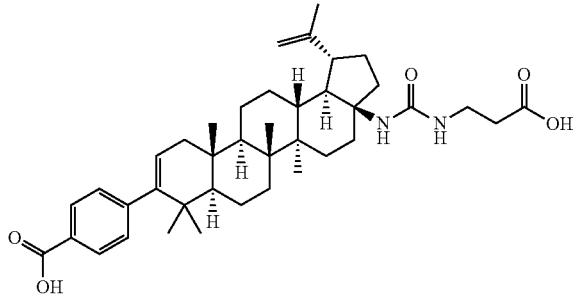

The title compound was prepared following the general procedures described above for the C-17 urea formation and subsequent ester hydrolysis using methyl-3-aminopropanoate HCl as the reactant amine. The product was isolated after reverse phase preparative HPLC purification as a white solid (33 mg, 67% yield). LCMS: m/z 645 (M+H$^+$), retention time 2.69 min (method 11). $^1$H NMR (500 MHz, 1:1 mixture of CDCl3 and MeOD, MeOD lock) δ ppm 0.93 (br. s., 3H), 0.94 (s, 3H), 1.00 (s, 6H), 1.03-1.14 (m, 5H), 1.21-1.40 (m, 5H), 1.40-1.58 (m, 6H), 1.58-1.67 (m, 2H), 1.67-1.75 (m, 5H), 1.75-1.83 (m, 1H), 1.87-1.98 (m, 1H), 2.11 (dd, J=17.09, 6.41 Hz, 1H), 2.34 (dd, J=12.05, 8.09 Hz, 1H), 2.49 (t, J=6.26 Hz, 2H), 2.51-2.63 (m, 2H), 3.37 (td, J=6.33, 3.81 Hz, 2H), 4.60 (s, 1H), 4.72 (d, J=1.83 Hz, 1H), 5.28 (d, J=6.10, 1.53 Hz, 1H), 7.20 (m, J=8.54 Hz, 2H), 7.92 (m, J=8.24 Hz, 2H).

Example 34

Preparation of 4-((1R,3aS,5aR,5bR,7aR,11aS,11bR, 13aR,13bR)-5a,5b,8,8,11a-pentamethyl-3a-(4-methyl-1,4-diazepane-1-carboxamido)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

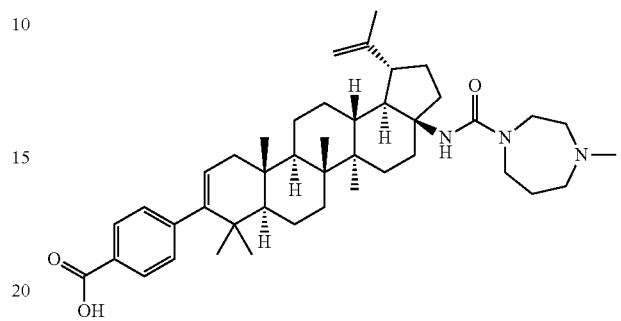

The title compound was prepared following the general procedures described above for the C-17 urea formation and subsequent ester hydrolysis using 1-methyl-1,4-diazepane as the reactant amine. The mono-TFA salt product was isolated after reverse phase preparative HPLC purification as a white solid (30 mg, 48% yield). LCMS: m/z 670 (M+H$^+$), retention time 2.41 min (method 11). $^1$H NMR (400 MHz, 1:1 mixture of CDCl3 and MeOD, MeOD lock) δ ppm 0.94 (s, 6H), 1.00 (s, 3H), 1.04 (s, 3H), 1.09 (s, 3H), 1.10-1.22 (m, 3H), 1.22-1.45 (m, 5H), 1.45-1.64 (m, 8H), 1.64-1.81 (m, 7H), 1.87-2.01 (m, 1H), 2.12 (dd, J=17.19, 6.40 Hz, 1H), 2.33 (br. s., 2H), 2.40-2.53 (m, 2H), 2.58 (d, J=13.30 Hz, 1H), 2.92 (s, 3H), 3.54 (br. s., 2H), 4.64 (s, 1H), 4.75 (d, J=1.00 Hz, 1H), 5.26-5.33 (m, 1H), 7.20 (m, J=8.28 Hz, 2H), 7.92 (m, J=8.28 Hz, 2H).

Example 35

Preparation of 4-((1R,3aS,5aR,5bR,7aR,11aS,11bR, 13aR,13bR)-3a-(4-acetyl-1,4-diazepane-1-carboxamido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

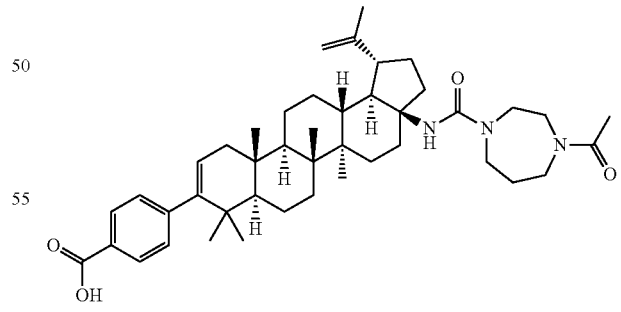

The title compound was prepared following the general procedures described above for the C-17 urea formation and subsequent ester hydrolysis using 1-[1,4-diazepan1-yl]ethanone as the reactant amine. The product was isolated after reverse phase preparative HPLC purification as a white solid (27 mg, 48% yield). LCMS: m/z 698 (M+H$^+$), retention time 2.74 min (method 11). $^1$H NMR (400 MHz, 1:1 mixture of CDCl3 and MeOD, MeOD lock) δ ppm 0.94 (br. s., 3H), 0.94 (br. s., 3H), 1.01 (s, 3H), 1.03 (s, 3H), 1.09 (s, 3H), 1.10-1.19 (m, 2H), 1.21-1.66 (m, 14H), 1.67-1.78 (m, 6H), 1.85-2.02 (m, 3H), 2.11 (s, 2H), 2.12-2.17 (m, 2H), 2.34-2.50 (m, 2H), 2.54-2.64 (m, 1H), 3.41-3.48 (m, 2H), 3.50-3.64 (m, 5H), 4.63 (br. s., 1H), 4.75 (d, J=9.16 Hz, 1H), 5.29 (d, J=4.58 Hz, 1H), 7.20 (d, J=8.24 Hz, 2H), 7.92 (d, J=8.24 Hz, 2H).

Example 36

Preparation of 4-((1R,3aS,5aR,5bR,7aR,11aS,11bR, 13aR,13bR)-3a-(methoxycarbonylamino)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

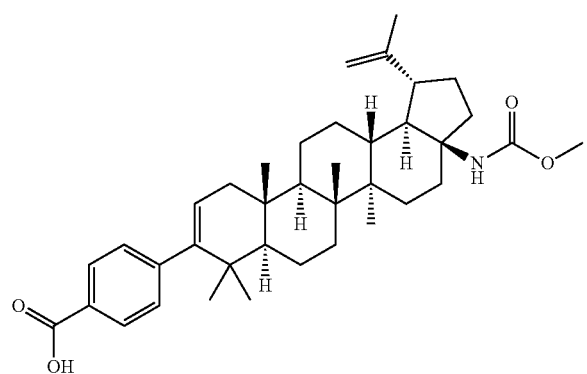

The title compound was formed as a byproduct during the urea formation step in the preparation of 4-((1R,3aS,5aR, 5bR,7aR,11aS,11bR,13aR,13bR)-3a-(4-acetyl-1,4-diazepane-1-carboxamido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoic acid. Hydrolysis of the penultimate methyl ester by the general procedure as described and purification by reverse phase preparative HPLC gave a white solid (6 mg, 13% yield). LCMS: m/z 588 (M+H⁺), retention time 3.07 min (method 11). ¹H NMR (500 MHz, 1:1 mixture of CDCl3 and MeOD, MeOD lock) δ ppm 0.93 (s, 3H), 0.94 (s, 3H), 1.00 (s, 3H), 1.01 (s, 3H), 1.09 (s, 3H), 1.09-1.16 (m, 2H), 1.23-1.27 (m, 1H), 1.28-1.44 (m, 5H), 1.45-1.57 (m, 6H), 1.59-1.77 (m, 9H), 1.88-2.00 (m, 1H), 2.12 (dd, J=17.09, 6.41 Hz, 1H), 2.28-2.39 (m, 1H), 2.45-2.58 (m, 2H), 3.62 (br. s., 3H), 4.62 (d, J=1.53 Hz, 1H), 4.74 (d, J=1.83 Hz, 1H), 5.29 (dd, J=6.26, 1.68 Hz, 1H), 7.20 (d, J=8.24 Hz, 2H), 7.92 (d, J=8.24 Hz, 2H).

Example 37

Preparation of 4-((1R,3aS,5aR,5bR,7aR,11aS,11bR, 13aR,13bR)-3a-(4-cyclopentyl-3-oxopiperazine-1-carboxamido)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

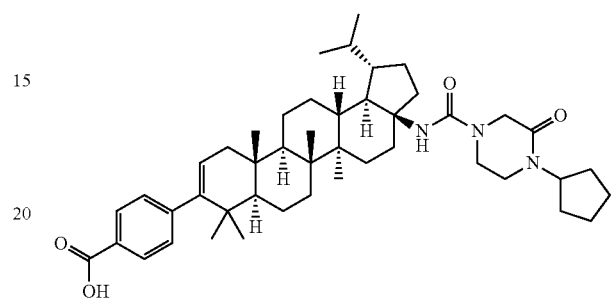

The title compound was prepared following the general procedures described above for the C-17 urea formation and subsequent ester hydrolysis using 1-cyclopentylpiperazin-2-one, HCl, 0.5 H₂O as the reactant amine. The product was isolated after reverse phase preparative HPLC purification as a white solid (18 mg, 28% yield). LCMS: m/z 724 (M+H⁺), retention time 2.97 min (method 11). ¹H NMR (500 MHz, 1:1 mixture of CDCl3 and MeOD, MeOD lock) δ ppm 0.93 (br. s., 3H), 0.94 (br. s., 3H), 1.00 (s, 3H), 1.03 (s, 3H), 1.09 (s, 3H), 1.11-1.19 (m, 2H), 1.24 (d, J=8.85 Hz, 1H), 1.30-1.42 (m, 4H), 1.43-1.60 (m, 10H), 1.62-1.67 (m, 2H), 1.67-1.80 (m, 9H), 1.82-1.90 (m, 2H), 1.90-2.00 (m, 1H), 2.12 (dd, J=17.09, 6.41 Hz, 1H), 2.40-2.60 (m, 3H), 3.35-3.41 (m, 2H), 3.53-3.68 (m, 2H), 3.94-4.04 (m, 1H), 4.04-4.13 (m, 1H), 4.63 (br. s., 1H), 4.75 (s, 1H), 4.90 (quin, J=8.47 Hz, 1H), 5.25-5.31 (m, 1H), 5.34-5.38 (m, 1H), 7.20 (d, J=8.24 Hz, 2H), 7.92 (d, J=8.24 Hz, 2H).

Example 38

Preparation of 4-((1R,3aS,5aR,5bR,7aR,11aS,11bR, 13aR,13bR)-3a-(4-(2-hydroxyethyl)piperazine-1-carboxamido)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

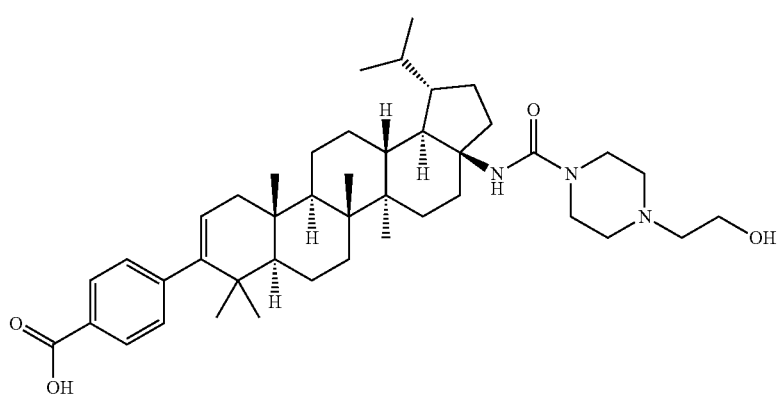

The title compound was prepared following the general procedures described above for the C-17 urea formation and subsequent ester hydrolysis using 2-(piperazin-1-yl)ethanol as the reactant amine. The mono-TFA salt product was isolated after reverse phase preparative HPLC purification as a white solid (12 mg, 18% yield). LCMS: m/z 686 (M+H$^+$), retention time 2.41 min (method 11). $^1$H NMR (500 MHz, 1:1 mixture of CDCl3 and MeOD, MeOD lock) δ ppm 0.94 (s, 3H), 0.94 (s, 3H), 1.00 (s, 3H), 1.04 (s, 3H), 1.08 (s, 3H), 1.09-1.19 (m, 2H), 1.24-1.28 (m, 1H), 1.32-1.43 (m, 4H), 1.44-1.59 (m, 7H), 1.67-1.80 (m, 7H), 1.86-1.98 (m, 1H), 2.12 (dd, J=17.24, 6.26 Hz, 1H), 2.42 (dd, J=12.36, 8.09 Hz, 1H), 2.53-2.65 (m, 2H), 3.23-3.29 (m, 3H), 3.92 (dd, J=5.95, 4.43 Hz, 2H), 4.75 (d, J=1.53 Hz, 1H), 5.29 (dd, J=6.10, 1.83 Hz, 1H), 7.20 (m, J=8.24 Hz, 2H), 7.92 (m, J=8.54 Hz, 2H).

Example 39

Preparation of 4-((1R,3aS,5aR,5bR,7aR,11aS,11bR,13aR,13bR)-3a-(4-(2-(dimethylamino)ethyl)piperazine-1-carboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

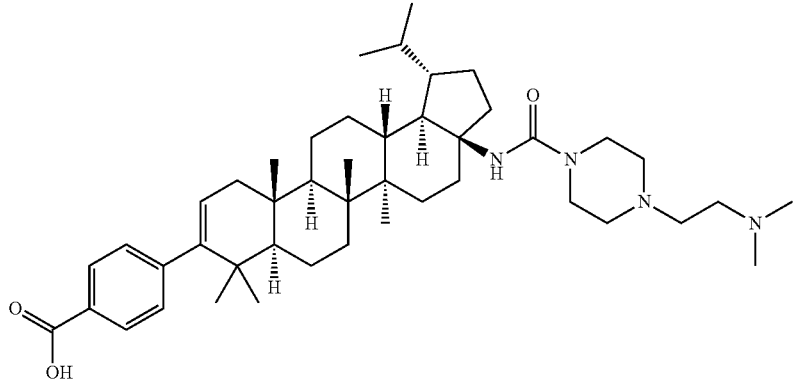

The title compound was prepared following the general procedures described above for the C-17 urea formation and subsequent ester hydrolysis using N,N-dimethyl-2-(piperazin-1-yl)ethanamine as the reactant amine. The bis-TFA salt product was isolated after reverse phase preparative HPLC purification as a white solid (15 mg, 19% yield). LCMS: m/z 713 (M+H$^+$), retention time 2.44 min (method 11). $^1$H NMR (500 MHz, 1:1 mixture of CDCl3 and MeOD, MeOD lock) δ ppm 0.94 (s, 3H), 0.94 (s, 3H), 1.00 (s, 3H), 1.03 (s, 3H), 1.08 (s, 3H), 1.09-1.20 (m, 2H), 1.24-1.44 (m, 7H), 1.44-1.62 (m, 7H), 1.64-1.79 (m, 7H), 1.88-2.00 (m, 1H), 2.12 (dd, J=17.09, 6.41 Hz, 1H), 2.44 (dd, J=12.21, 8.24 Hz, 1H), 2.51 (dt, J=10.15, 5.15 Hz, 1H), 2.57 (d, J=13.12 Hz, 1H), 2.73 (br. s., 4H), 2.87-2.99 (m, 8H), 3.39-3.55 (m, 4H), 4.75 (s, 1H), 5.29 (d, J=4.58 Hz, 1H), 7.20 (m, J=8.24 Hz, 2H), 7.92 (m, J=8.24 Hz, 2H).

Example 40

Preparation of 4-((1R,3aS,5aR,5bR,7aR,11aS,11bR,13aR,13bR)-5a,5b,8,8,11a-pentamethyl-3a-(4-(1-methylpiperidin-4-yl)piperazine-1-carboxamido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

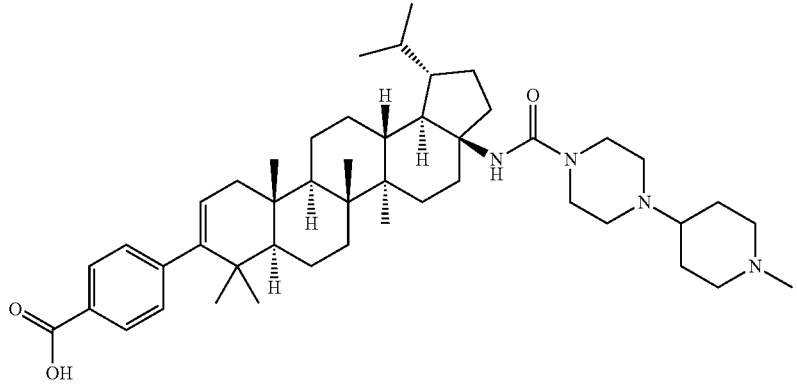

The title compound was prepared following the general procedures described above for the C-17 urea formation and subsequent ester hydrolysis using 1-(1-methylpiperidin-4-yl)piperazine as the reactant amine. The bis-TFA salt product was isolated after reverse phase preparative HPLC purification as a white solid (48 mg, 61% yield). LCMS: m/z 739 (M+H$^+$), retention time 2.41 min (method 11). $^1$H NMR (500 MHz, 1:1 mixture of CDCl3 and MeOD, MeOD lock) δ ppm 0.93 (s, 3H), 0.94 (s, 3H), 1.00 (s, 3H), 1.03 (s, 3H), 1.08 (s, 3H), 1.09-1.19 (m, 2H), 1.23-1.28 (m, 1H), 1.29-1.44 (m, 4H), 1.44-1.64 (m, 9H), 1.65-1.79 (m, 7H), 1.87-1.99 (m, 1H), 1.99-2.08 (m, 2H), 2.12 (dd, J=17.09, 6.41 Hz, 1H), 2.40-2.60 (m, 3H), 2.77-2.93 (m, 5H), 3.03-3.13 (m, 1H), 3.35 (br. s., 4H), 3.47 (br. s., 4H), 3.99-4.15 (m, 2H), 4.63 (s, 1H), 4.75 (d, J=1.22 Hz, 1H), 5.29 (dd, J=6.10, 1.53 Hz, 1H), 7.20 (m, J=8.54 Hz, 2H), 7.92 (m, J=8.24 Hz, 2H).

Example 41

Preparation of 4-((1R,3aS,5aR,5bR,7aR,11aS,11bR,13aR,13bR)-3a-(4-acetylpiperazine-1-carboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

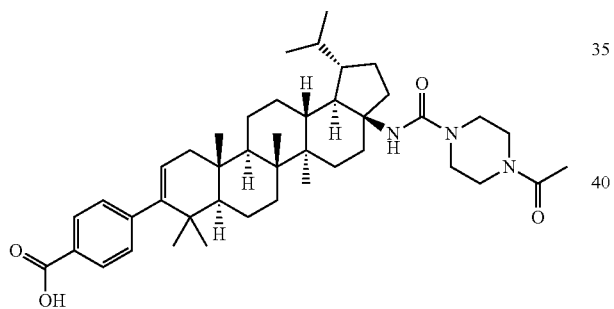

The title compound was prepared following the general procedures described above for the C-17 urea formation and subsequent ester hydrolysis using 1-(piperazin-1-yl)ethanone as the reactant amine. The product was isolated after reverse phase preparative HPLC purification as a white solid (6 mg, 11% yield). LCMS: m/z 684 (M+H$^+$), retention time 2.81 min (method 11). $^1$H NMR (500 MHz, 1:1 mixture of CDCl3 and MeOD, MeOD lock) δ ppm 0.94 (br. s., 3H), 0.94 (s, 3H), 1.01 (s, 3H), 1.04 (s, 3H), 1.09 (s, 3H), 1.10-1.20 (m, 2H), 1.24-1.28 (m, 2H), 1.29-1.45 (m, 4H), 1.45-1.62 (m, 7H), 1.64-1.79 (m, 7H), 1.89-2.00 (m, 1H), 2.08-2.16 (m, 4H), 2.46 (dd, J=12.36, 8.09 Hz, 1H), 2.52 (td, J=10.60, 5.34 Hz, 1H), 2.58 (ddd, J=13.35, 3.36, 3.13 Hz, 1H), 3.35-3.48 (m, 3H), 3.49-3.60 (m, 3H), 3.60-3.73 (m, 2H), 4.75 (d, J=1.53 Hz, 1H), 5.29 (dd, J=6.10, 1.53 Hz, 1H), 7.20 (m, J=8.54 Hz, 2H), 7.92 (m, J=8.54 Hz, 2H).

Example 42

Preparation of 4-((1R,3aS,5aR,5bR,7aR,11aS,11bR,13aR,13bR)-5a,5b,8,8,11a-pentamethyl-3a-(5-oxo-1,4-diazepane-1-carboxamido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

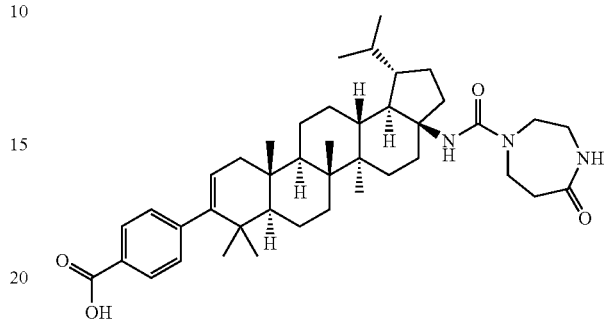

The title compound was prepared following the general procedures described above for the C-17 urea formation and subsequent ester hydrolysis using 1,4-diazepan-5-one as the reactant amine. The product was isolated after reverse phase preparative HPLC purification as a white solid (26 mg, 46% yield). LCMS: m/z 670 (M+H$^+$), retention time 2.70 min (method 11). $^1$H NMR (500 MHz, 1:1 mixture of CDCl3 and MeOD, MeOD lock) δ ppm 0.94 (s, 3H), 0.94 (s, 3H), 1.01 (s, 3H), 1.04 (s, 3H), 1.09 (s, 3H), 1.10-1.19 (m, 2H), 1.26 (dd, J=7.17, 3.20 Hz, 1H), 1.31-1.43 (m, 5H), 1.45-1.54 (m, 6H), 1.55-1.60 (m, 2H), 1.63-1.80 (m, 7H), 1.88-1.99 (m, 1H), 2.13 (dd, J=16.94, 6.26 Hz, 1H), 2.44-2.53 (m, 2H), 2.60 (ddd, J=13.50, 2.82, 2.59 Hz, 1H), 2.68 (t, J=5.19 Hz, 2H), 3.49-3.68 (m, 4H), 4.57 (s, 1H), 4.75 (d, J=1.53 Hz, 1H), 5.29 (dd, J=6.10, 1.53 Hz, 1H), 7.20 (d, J=8.54 Hz, 2H), 7.92 (d, J=8.54 Hz, 2H).

Example 43

Preparation of 4-((1R,3aS,5aR,5bR,7aR,11aS,11bR,13aR,13bR)-3a-(3-(2-aminoethyl)-3-(2-carboxyethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

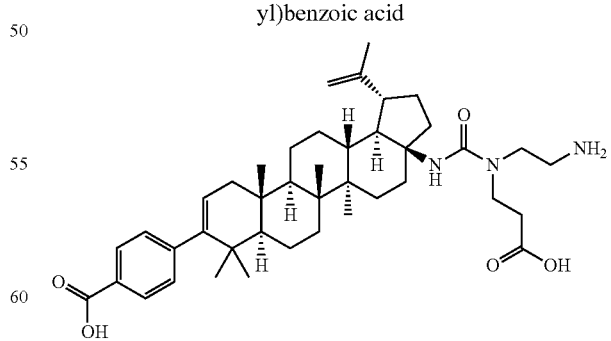

The title compound was formed as a byproduct during the ester hydrolysis step in the preparation of 4-((1R,3aS,5aR,5bR,7aR,11aS,11bR,13aR,13bR)-5a,5b,8,8,11a-pentamethyl-3a-(5-oxo-1,4-diazepane-1-carboxamido)-1-(prop-1- en-2-yl)-2,3,3a,4,5,5a,5b,6,7,7a,8,11,11a,11b,12,13,13a, 13b-octadecahydro-1H-cyclopenta[a]chrysen-9-yl)benzoic acid. Purification by reverse phase preparative HPLC gave a white solid (10 mg, 15% yield) mono-TFA salt. LCMS: m/z 688 (M+H$^+$), retention time 2.40 min (method 11). $^1$H NMR (500 MHz, 1:1 mixture of CDCl3 and MeOD, MeOD lock) δ ppm 0.94 (s, 6H), 1.01 (s, 3H), 1.04 (s, 3H), 1.07-1.17 (m, 5H), 1.23-1.42 (m, 7H), 1.44-1.62 (m, 7H), 1.67-1.81 (m, 6H), 1.84-2.00 (m, 2H), 2.13 (dd, J=17.39, 6.41 Hz, 1H), 2.38 (dd, J=11.90, 7.93 Hz, 1H), 2.51-2.58 (m, 1H), 2.59-2.66 (m, 1H), 2.66-2.73 (m, 1H), 2.77 (td, J=10.83, 4.58 Hz, 1H), 2.99-3.10 (m, 2H), 3.36-3.46 (m, 3H), 3.76 (ddd, J=15.56, 9.31, 3.81 Hz, 1H), 4.76 (d, J=1.83 Hz, 1H), 5.29 (dd, J=6.10, 1.53 Hz, 1H), 7.20 (m, J=8.24 Hz, 2H), 7.92 (m, J=8.24 Hz, 2H).

Example 44

Preparation of 4-((1R,3aS,5aR,5bR,7aR,11aS,11bR, 13aR,13bR)-5a,5b,8,8,11a-pentamethyl-3a-(3-methyl-3-(2-(pyrrolidin-1-yl)ethyl)ureido)-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

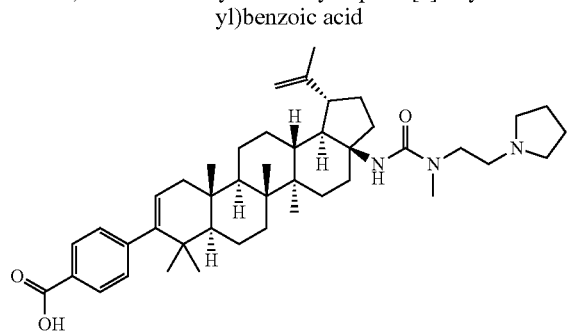

The title compound was prepared following the general procedures described above for the C-17 urea formation and subsequent ester hydrolysis using N-methyl-2-(pyrrolidin-1-yl)ethanamine as the reactant amine. The product was isolated after reverse phase preparative HPLC purification as a white solid (34 mg, 54% yield) mono-TFA salt. LCMS: m/z 684 (M+H$^+$), retention time 2.41 min (method 11). $^1$H NMR (500 MHz, 1:1 mixture of CDCl3 and MeOD, MeOD lock) δ ppm 0.94 (br. s., 3H), 0.94 (br. s., 3H), 1.00 (s, 3H), 1.04 (s, 3H), 1.10 (s, 3H), 1.10-1.21 (m, 2H), 1.26 (dd, J=10.68, 2.75 Hz, 1H), 1.32-1.43 (m, 4H), 1.45-1.59 (m, 7H), 1.62-1.81 (m, 8H), 1.87-2.00 (m, 1H), 2.08 (br. s., 4H), 2.12 (dd, J=17.09, 6.41 Hz, 1H), 2.41-2.57 (m, 3H), 3.03 (s, 3H), 3.06 (br. s., 2H), 3.25-3.39 (m, 2H), 3.52 (dt, J=14.65, 6.26 Hz, 1H), 3.63-3.83 (m, 3H), 4.64 (br. s., 1H), 4.75 (s, 1H), 5.26-5.32 (m, 1H), 7.20 (d, J=7.93 Hz, 2H), 7.92 (d, J=8.24 Hz, 2H).

Example 45

Preparation of 4-((1R,3aS,5aR,5bR,7aR,11aS,11bR, 13aR,13bR)-5a,5b,8,8,11a-pentamethyl-3a-(piperazine-1-carboxamido)-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) benzoic acid The title compound was prepared following the general procedures described above for the C-17 urea formation and subsequent ester hydrolysis using 1-(piperazin-1-yl)ethanone as the reactant amine. The product was isolated after reverse phase preparative HPLC purification as a white solid (5 mg, 8% yield) mono-TFA salt. LCMS: m/z 642 (M+H$^+$), retention time 2.42 min (method 11). $^1$H NMR (500 MHz, 1:1 mixture of CDCl3 and MeOD, MeOD lock) δ ppm 0.94 (s, 3H), 0.94 (s, 3H), 1.00 (s, 3H), 1.04 (s, 3H), 1.08 (s, 3H), 1.09-1.19 (m, 2H), 1.26 (dd, J=8.09, 2.29 Hz, 1H), 1.29-1.44 (m, 4H), 1.44-1.51 (m, 4H), 1.51-1.62 (m, 3H), 1.67-1.80 (m, 7H), 1.87-1.97 (m, 1H), 2.12 (dd, J=17.09, 6.41 Hz, 1H), 2.43 (dd, J=12.36, 8.09 Hz, 1H), 2.53-2.63 (m, 2H), 3.13-3.27 (m, 4H), 3.55-3.68 (m, 4H), 4.75 (d, J=1.53 Hz, 1H), 4.95 (s, 1H), 5.29 (dd, J=6.10, 1.53 Hz, 1H), 7.20 (d, J=8.54 Hz, 2H), 7.92 (d, J=8.24 Hz, 2H).

Example 46

Preparation of 4-((1R,3aS,5aR,5bR,7aR,11aS,11bR, 13aR,13bR)-3a-(3-(3-(dimethylamino)propyl)-3-methylureido)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

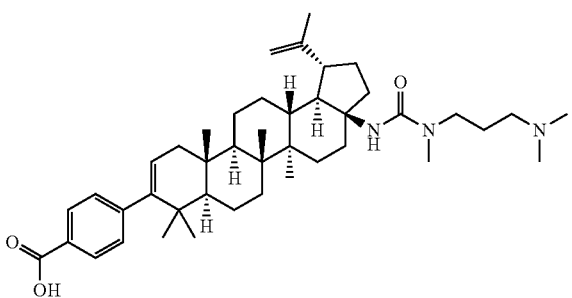

The title compound was prepared following the general procedures described above for the C-17 urea formation and subsequent ester hydrolysis using N1,N1,N3-trimethylpropane-1,3-diamine as the reactant amine. The product was isolated after reverse phase preparative HPLC purification as a white solid (21 mg, 31% yield) mono-TFA salt. LCMS: m/z 672 (M+H$^+$), retention time 1.86 min (method 2). $^1$H NMR (500 MHz, 1:1 mixture of CDCl3 and MeOD, MeOD lock) δ ppm 0.94 (s, 3H) 0.94 (s, 3H) 1.01 (s, 3H) 1.05 (s, 3H) 1.07-1.20 (m, 5H) 1.24-1.29 (m, 2H) 1.33-1.39 (m, 2H) 1.40-1.59 (m, 9H) 1.62-1.80 (m, 7H) 1.88-2.02 (m, 3H) 2.13 (dd, J=17.09, 6.41 Hz, 1H) 2.43 (dd, J=12.51, 8.24 Hz, 1H) 2.46-2.55 (m, 2H) 2.87 (s, 6H) 2.98-3.10 (m, 5H) 3.34-3.49 (m, 2H) 4.76 (d, J=1.22 Hz, 1H) 5.29 (dd, J=6.10, 1.83 Hz, 1H) 7.20 (m, J=8.24 Hz, 2H) 7.92 (m, J=8.24 Hz, 2H).

Example 47

Preparation of 4-((1R,3aS,5aR,5bR,7aR,11aS,11bR,13aR,13bR)-5a,5b,8,8,11a-pentamethyl-3a-(3-(2-(methylsulfonamido)ethyl)ureido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

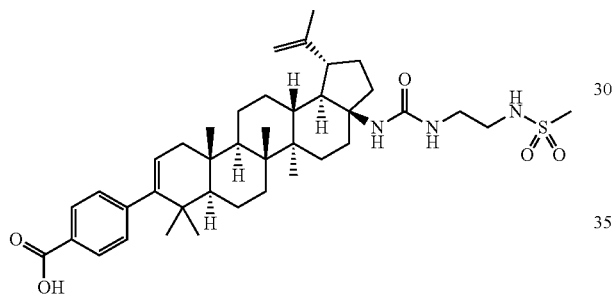

The title compound was prepared following the general procedures described above for the C-17 urea formation and subsequent ester hydrolysis using N-(2-aminoethyl)methanesulfonamide hydrochloride as the reactant amine. The product was isolated after reverse phase preparative HPLC purification as a white solid (28 mg, 51% yield). LCMS: m/z 694 (M+H$^+$), retention time 2.17 min (method 2). $^1$H NMR (400 MHz, 1:1 mixture of CDCl3 and MeOD, MeOD lock) δ ppm 0.93 (br. s., 3H) 0.94 (s, 3H) 1.00 (s, 6H) 1.04-1.16 (m, 5H) 1.23-1.43 (m, 6H) 1.45-1.56 (m, 5H) 1.59-1.83 (m, 8H) 1.87-2.00 (m, 1H) 2.11 (dd, J=17.19, 6.40 Hz, 1H) 2.36 (dd, J=12.05, 8.28 Hz, 1H) 2.49-2.63 (m, 2H) 2.95 (s, 3H) 3.09-3.17 (m, 2H) 3.20-3.30 (m, 2H) 4.61 (s, 1H) 4.72 (d, J=1.76 Hz, 1H) 5.29 (dd, J=6.02, 1.51 Hz, 1H) 7.20 (m, J=8.28 Hz, 2H) 7.92 (m, J=8.28 Hz, 2H).

Example 48

Preparation of 4-((1R,3aS,5aR,5bR,7aR,11aS,11bR,13aR,13bR)-3a-(3-(2-(1H-indol-1-yl)ethyl)-3-methylureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

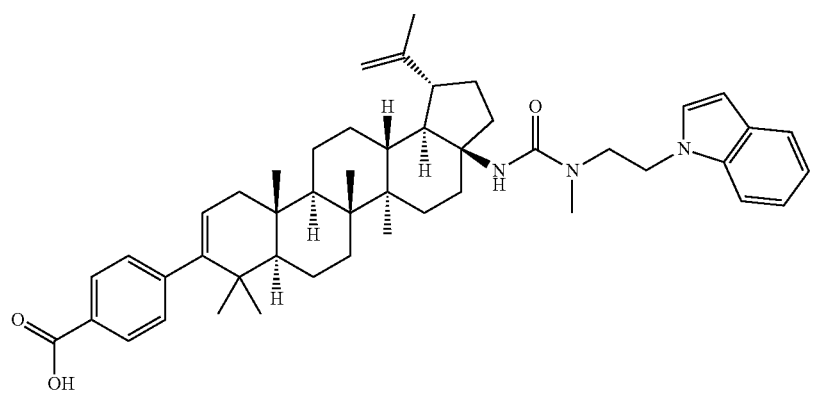

The title compound was prepared following the general procedures described above for the C-17 urea formation and subsequent ester hydrolysis using 2-(1H-indol-1-yl)-N-methylethanamine as the reactant amine. The product was isolated after reverse phase preparative HPLC purification as a white solid (30 mg, 39% yield) mono-TFA salt. LCMS: m/z 730 (M+H$^+$), retention time 2.73 min (method 2). $^1$H NMR (500 MHz, 1:1 mixture of CDCl3 and MeOD, MeOD lock) δ ppm 0.94 (br. s., 3H) 0.94 (br. s., 3H) 0.95 (br. s., 3H) 0.97 (s, 3H) 0.99 (s, 3H) 1.01-1.12 (m, 2H) 1.21-1.29 (m, 3H) 1.32-1.37 (m, 2H) 1.38-1.53 (m, 7H) 1.54-1.73 (m, 7H) 1.79-1.92 (m, 1H) 2.09 (dd, J=17.09, 6.41 Hz, 1H) 2.19 (td, J=10.61, 4.43 Hz, 1H) 2.42 (s, 3H) 2.48-2.57 (m, 2H) 3.60 (ddd, J=14.50, 5.49, 5.34 Hz, 1H) 3.71 (ddd, J=14.65, 5.65, 5.34 Hz, 1H) 4.28-4.39 (m, 1H) 4.60 (br. s., 1H) 4.69 (s, 1H) 5.27 (d, J=6.10 Hz, 1H) 6.51 (d, J=3.05 Hz, 1H) 7.05-7.12 (m, 2H) 7.15-7.22 (m, 3H) 7.38 (d, J=8.24 Hz, 1H) 7.61 (d, J=7.93 Hz, 1H) 7.92 (d, J=8.24 Hz, 2H).

Example 49

Preparation of 4-((1R,3aS,5aR,5bR,7aR,11aS,11bR,13aR,13bR)-5a,5b,8,8,11a-pentamethyl-3a-(3-(3-(N-methylmethylsulfonamido)propyl)ureido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

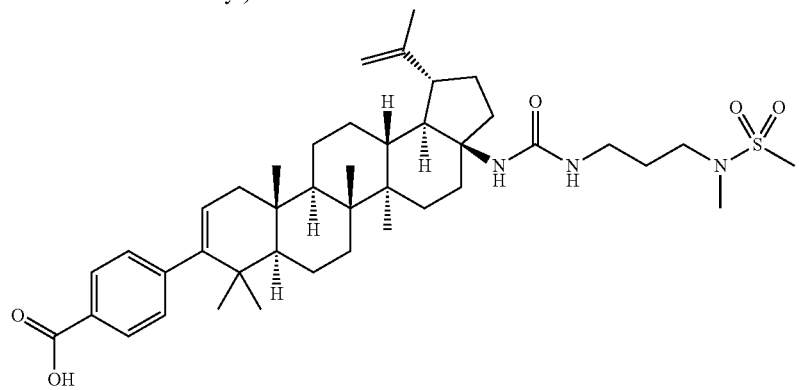

The title compound was prepared following the general procedures described above for the C-17 urea formation and subsequent ester hydrolysis using N-(3-aminopropyl)-N-methylmethanesulfonamide as the reactant amine. The product was isolated after reverse phase preparative HPLC purification as a white solid (36 mg, 62% yield). LCMS: m/z 730 (M+H$^+$), retention time 2.25 min (method 2). $^1$H NMR (500 MHz, 1:1 mixture of CDCl3 and MeOD, MeOD lock) δ ppm 0.93 (s, 3H) 0.94 (s, 3H) 1.00 (s, 6H) 1.05-1.15 (m, 5H) 1.21-1.41 (m, 5H) 1.41-1.59 (m, 6H) 1.62-1.81 (m, 10H) 1.88-1.99 (m, 1H) 2.11 (dd, J=17.09, 6.41 Hz, 1H) 2.35 (dd, J=12.36, 8.09 Hz, 1H) 2.50-2.63 (m, 2H) 2.85 (s, 3H) 2.86 (s, 3H) 3.12-3.23 (m, 4H) 4.61 (s, 1H) 4.72 (d, J=1.53 Hz, 1H) 5.25-5.32 (m, 1H) 7.20 (m, J=8.24 Hz, 2H) 7.92 (m, J=8.24 Hz, 2H).

Example 50

Preparation of 4-((1R,3aS,5aR,5bR,7aR,11aS,11bR,13aR,13bR)-5a,5b,8,8,11a-pentamethyl-3a-(3-(2-(N-methylmethylsulfonamido)ethyl)ureido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

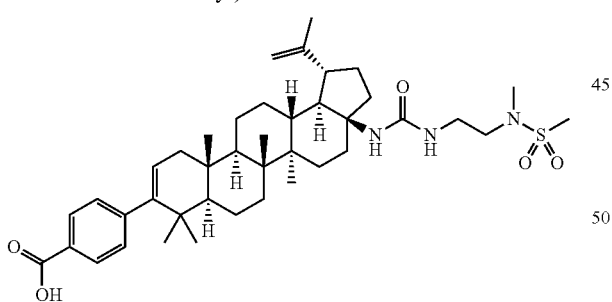

The title compound was prepared following the general procedures described above for the C-17 urea formation and subsequent ester hydrolysis using N-(2-aminoethyl)-N-methylmethanesulfonamide as the reactant amine. The product was isolated after reverse phase preparative HPLC purification as a white solid (37 mg, 65% yield). LCMS: m/z 708 (M+H$^+$), retention time 2.25 min (method 2). $^1$H NMR (500 MHz, 1:1 mixture of CDCl3 and MeOD, MeOD lock) δ ppm 0.93 (br. s., 3H) 0.94 (s, 3H) 1.00 (s, 6H) 1.04-1.15 (m, 5H) 1.21-1.41 (m, 5H) 1.41-1.58 (m, 6H) 1.59-1.75 (m, 7H) 1.75-1.83 (m, 1H) 1.88-2.00 (m, 1H) 2.11 (dd, J=17.09, 6.41 Hz, 1H) 2.36 (dd, J=12.36, 8.09 Hz, 1H) 2.51-2.64 (m, 2H) 2.86 (s, 3H) 2.91 (s, 3H) 3.18-3.25 (m, 2H) 3.31 (t, J=5.49 Hz, 2H) 4.61 (s, 1H) 4.72 (d, J=1.53 Hz, 1H) 5.28 (dd, J=6.26, 1.68 Hz, 1H) 7.20 (d, J=8.54 Hz, 2H) 7.92 (d, J=8.24 Hz, 2H).

Example 51

Preparation of 4-((1R,3aS,5aR,5bR,7aR,11aS,11bR,13aR,13bR)-3a-(4-(2-hydroxyethyl)-1,4-diazepane-1-carboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

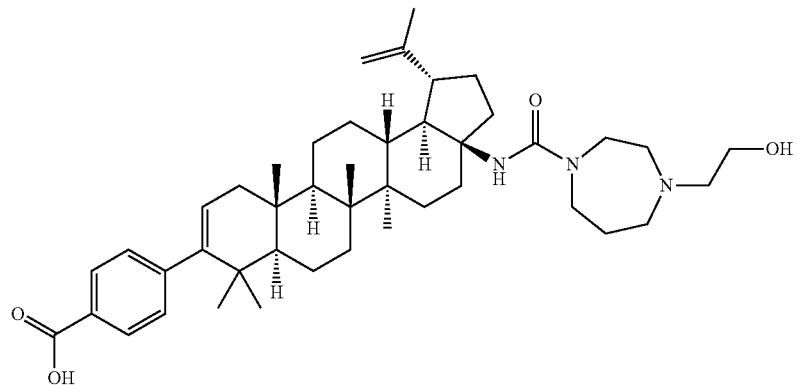

The title compound was prepared following the general procedures described above for the C-17 urea formation and subsequent ester hydrolysis using 2-(1,4-diazepan-1-yl)ethanol as the reactant amine. The product was isolated after reverse phase preparative HPLC purification as a white solid (49 mg, 72% yield) mono-TFA salt. LCMS: m/z 700 (M+H$^+$), retention time 1.77 min (method 2). $^1$H NMR (400 MHz, 1:1 mixture of CDCl3 and MeOD, MeOD lock) δ ppm 0.94 (s, 3H) 0.94 (s, 3H) 1.00 (s, 3H) 1.04 (s, 3H) 1.09 (s, 3H) 1.10-1.18 (m, 2H) 1.18-1.64 (m, 13H) 1.64-1.82 (m, 7H) 1.85-2.01 (m, 1H) 2.12 (dd, J=17.19, 6.40 Hz, 1H) 2.29-2.41 (m, 2H) 2.41-2.53 (m, 2H) 2.58 (d, J=13.30 Hz, 1H) 3.25-3.32 (m, 2H) 3.35-3.63 (m, 6H) 3.69-4.00 (m, 4H) 4.64 (br. s., 1H) 4.75 (s, 1H) 5.29 (d, J=4.77 Hz, 1H) 7.19 (m, 2H) 7.91 (m, 2H).

The title compound was prepared following the general procedures described above for the C-17 urea formation and subsequent ester hydrolysis using 2-(2-(dimethylamino)ethylamino)ethanol as the reactant amine. The product was isolated after reverse phase preparative HPLC purification as a white solid (35 mg, 51% yield) mono-TFA salt. LCMS: m/z 688 (M+H$^+$), retention time 1.79 min (method 2). $^1$H NMR (500 MHz, 1:1 mixture of CDCl3 and MeOD, MeOD lock) δ ppm 0.93 (br. s., 3H) 0.94 (br. s., 3H) 1.01 (br. s., 3H) 1.02 (br. s., 3H) 1.06-1.18 (m, 5H) 1.20-1.66 (m, 12H) 1.66-1.81 (m, 7H) 1.81-2.01 (m, 2H) 2.12 (dd, J=17.09, 6.41 Hz, 1H) 2.37 (dd, J=12.05, 8.09 Hz, 1H) 2.46-2.61 (m, 2H) 2.93 (s, 6H) 3.21-3.31 (m, 2H) 3.48-3.61 (m, 3H) 3.72-3.79 (m, 2H) 4.61 (br. s., 1H) 4.74 (br. s., 1H) 5.23-5.35 (m, 1H) 7.20 (d, J=8.24 Hz, 2H) 7.92 (d, J=8.24 Hz, 2H).

Example 52

Preparation of 4-((1R,3aS,5aR,5bR,7aR,11aS,11bR,13aR,13bR)-3a-(3-(2-(dimethylamino)ethyl)-3-(2-hydroxyethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

Example 53

Preparation of 4-((1R,3aS,5aR,5bR,7aR,11aS,11bR,13aR,13bR)-3a-(3-(carboxymethyl)-3-(2-morpholinoethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

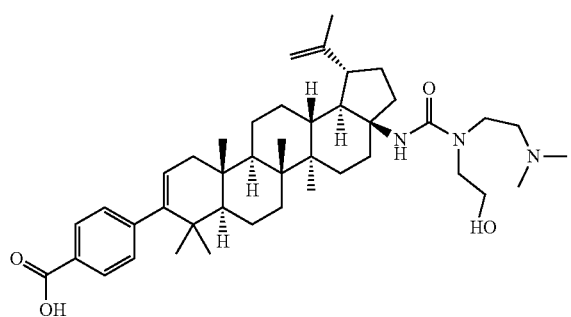

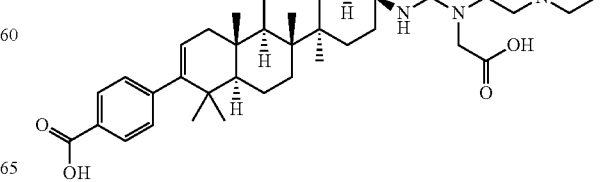

The title compound was prepared following the general procedures described above for the C-17 urea formation and subsequent ester hydrolysis using ethyl 2-(2-morpholinoethylamino)acetate as the reactant amine. The product was isolated after reverse phase preparative HPLC purification as a white solid (5 mg, 6% yield) mono-TFA salt. LCMS: m/z 744 (M+H$^+$), retention time 1.81 min (method 2). $^1$H NMR (500 MHz, 1:1 mixture of CDCl3 and MeOD, MeOD lock) δ ppm 0.94 (br. s., 3H) 0.94 (s, 3H) 1.01 (s, 3H) 1.02 (s, 3H) 1.10 (d, J=2.44 Hz, 1H) 1.11-1.16 (m, 4H) 1.19-1.64 (m, 12H) 1.64-1.80 (m, 7H) 1.87-1.98 (m, 1H) 2.13 (dd, J=17.09, 6.41 Hz, 1H) 2.35 (dd, J=12.51, 8.24 Hz, 1H) 2.47-2.59 (m, 2H) 3.23-3.30 (m, 2H) 3.37 (s, 3H) 3.58 (td, J=10.38, 4.88 Hz, 1H) 3.70-4.03 (m, 6H) 4.72 (s, 1H) 4.78 (d, J=1.53 Hz, 1H) 5.29 (dd, J=6.10, 1.53 Hz, 1H) 7.20 (m, J=8.24 Hz, 2H) 7.92 (m, J=8.24 Hz, 2H).

Example 54

Preparation of 4-((1R,3aS,5aR,5bR,7aR,11aS,11bR,13aR,13bR)-5a,5b,8,8,11a-pentamethyl-3a-(4-methylpiperazine-1-carboxamido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

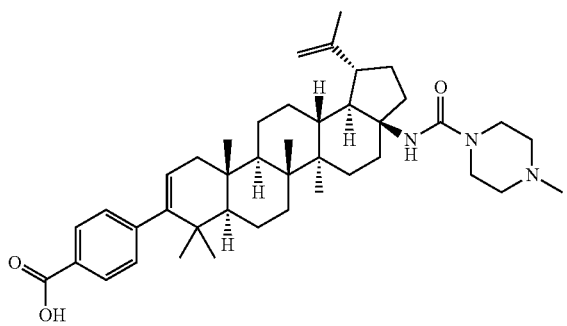

The title compound was prepared following the general procedures described above for the C-17 urea formation and subsequent ester hydrolysis using 1-methylpiperazine as the reactant amine. The product was isolated after reverse phase preparative HPLC purification as a white solid (49 mg, 75% yield) mono-TFA salt. LCMS: m/z 656 (M+H$^+$), retention time 2.44 min (method 11). $^1$H NMR (500 MHz, 1:1 mixture of CDCl3 and MeOD, MeOD lock) δ ppm 0.94 (br. s., 3H) 0.94 (s, 3H) 1.00 (s, 3H) 1.03 (s, 3H) 1.05-1.19 (m, 5H) 1.23-1.28 (m, 1H) 1.31-1.42 (m, 4H) 1.44-1.59 (m, 7H) 1.64-1.81 (m, 7H) 1.86-1.98 (m, 1H) 2.12 (dd, J=17.24, 6.26 Hz, 1H) 2.42 (dd, J=12.36, 8.39 Hz, 1H) 2.51-2.65 (m, 2H) 2.90 (s, 3H) 3.34 (br. s., 4H) 3.96 (br. s., 2H) 4.64 (br. s., 1H) 4.75 (d, J=1.22 Hz, 1H) 5.29 (dd, J=6.26, 1.68 Hz, 1H) 7.20 (m, J=8.24 Hz, 2H) 7.92 (m, J=8.55 Hz, 2H).

Example 55

Preparation of 4-((1R,3aS,5aR,5bR,7aR,11aS,11bR,13aR,13bR)-3a-(1,4-diazepane-1-carboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

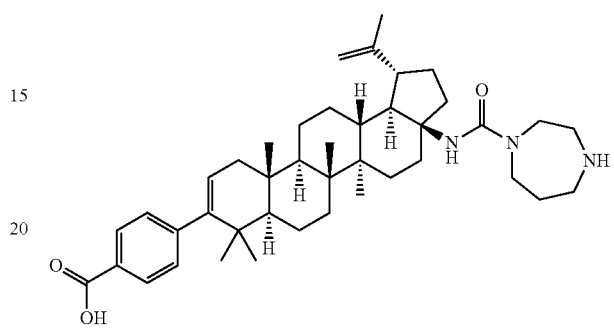

The title compound was prepared following the general procedures described above for the C-17 urea formation and subsequent ester hydrolysis using homopiperazine as the reactant amine. The product was isolated after reverse phase preparative HPLC purification as a white solid (33 mg, 53% yield) mono-TFA salt. LCMS: m/z 656 (M+H$^+$), retention time 2.43 min (method 11). $^1$H NMR (400 MHz, 1:1 mixture of CDCl3 and MeOD, MeOD lock) δ ppm 0.94 (s, 6H) 1.00 (s, 3H) 1.04 (s, 3H) 1.09 (s, 3H) 1.10-1.22 (m, 2H) 1.24-1.30 (m, 1H) 1.34-1.59 (m, 11H) 1.64-1.82 (m, 7H) 1.86-2.01 (m, 1H) 2.12 (dd, J=17.07, 6.27 Hz, 1H) 2.18-2.29 (m, 2H) 2.42-2.53 (m, 2H) 2.59 (d, J=13.30 Hz, 1H) 3.20-3.31 (m, 4H) 3.48-3.62 (m, 2H) 3.76 (t, J=4.27 Hz, 2H) 4.47 (s, 1H) 4.64 (s, 1H) 4.75 (s, 1H) 5.29 (d, J=4.77 Hz, 1H) 7.20 (m, J=8.03 Hz, 2H) 7.92 (m, J=8.03 Hz, 2H).

Example 56

Preparation of 4-((1R,3aS,5aR,5bR,7aR,11aS,11bR,13aR,13bR)-3a-(2-(carboxymethyl)-3-oxopiperazine-1-carboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

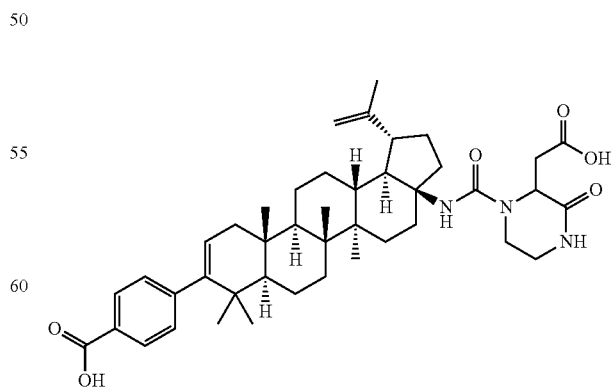

The title compound was prepared following the general procedures described above for the C-17 urea formation and subsequent ester hydrolysis using ethyl 2-(3-oxopiperazin-2-yl)acetate as the reactant amine. The product was isolated after reverse phase preparative HPLC purification as a white solid (38 mg, 64% yield). LCMS: m/z 714 (M+H$^+$), retention time 2.66 min (method 11). This material is a diastereomeric mixture in a ratio of approximately 1:1. $^1$H NMR (400 MHz, 1:1 mixture of CDCl3 and MeOD, MeOD lock) δ ppm 0.91-0.97 (m, 6H) 0.97-1.04 (m, 6H) 1.05-1.17 (m, 5H) 1.19-1.64 (m, 13H) 1.65-1.80 (m, 7H) 1.80-2.08 (m, 3H) 2.12 (dt, J=17.07, 6.02 Hz, 1H) 2.23 (dd, J=12.30, 8.28 Hz, 0.5H) 2.34-2.44 (m, 0.5H) 2.58 (d, J=13.30 Hz, 0.5H) 2.65-2.76 (m, 1H) 2.80-2.96 (m, 2H) 2.97-3.13 (m, 2H) 3.14-3.24 (m, 1H) 3.50-3.64 (m, 1.5H) 3.94-4.03 (m, 0.5H) 4.07 (dd, J=13.80, 2.76 Hz, 0.5H) 4.70-4.80 (m, 2H) 5.25-5.32 (m, 1H) 7.19 (d, J=8.03 Hz, 2H) 7.92 (d, 2H).

(m, 1H) 4.64 (d, J=1.22 Hz, 1H) 4.76 (d, J=1.22 Hz, 1H) 5.29 (dd, J=6.26, 1.68 Hz, 1H) 7.20 (d, J=8.24 Hz, 2H) 7.92 (d, J=8.55 Hz, 2H).

Example 58

Preparation of 4-((1R,3aS,5aR,5bR,7aR,11aS,11bR,13aR,13bR)-3a-(3-(2-aminoethyl)-3-(carboxymethyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

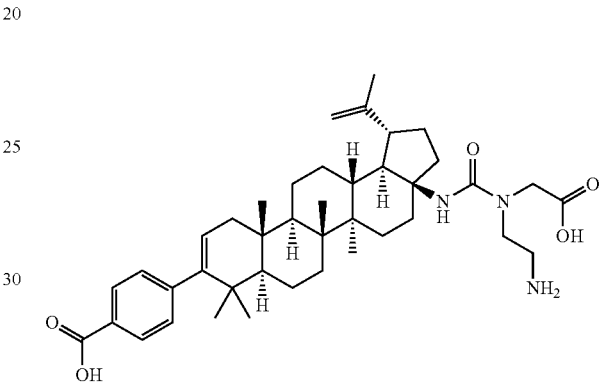

Example 57

Preparation of 4-((1R,3aS,5aR,5bR,7aR,11aS,11bR,13aR,13bR)-5a,5b,8,8,11a-pentamethyl-3a-(3-oxopiperazine-1-carboxamido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

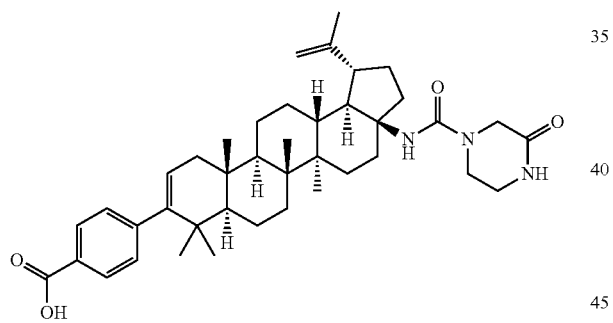

The title compound was prepared following the general procedures described above for the C-17 urea formation and subsequent ester hydrolysis using piperazin-2-one as the reactant amine. The product was isolated after reverse phase preparative HPLC purification as a white solid (7 mg, 12% yield). LCMS: m/z 656 (M+H$^+$), retention time 2.71 min (method 11). $^1$H NMR (500 MHz, 1:1 mixture of CDCl3 and MeOD, MeOD lock) δ ppm 0.94 (s, 3H) 0.94 (s, 3H) 1.00 (s, 3H) 1.03 (s, 3H) 1.10 (s, 3H) 1.10-1.20 (m, 2H) 1.25 (d, J=10.07 Hz, 1H) 1.29-1.44 (m, 4H) 1.44-1.63 (m, 7H) 1.65-1.80 (m, 7H) 1.89-2.00 (m, 1H) 2.13 (dd, J=17.09, 6.41 Hz, 1H) 2.46 (dd, J=12.51, 8.24 Hz, 1H) 2.49-2.61 (m, 2H) 3.36-3.45 (m, 2H) 3.54-3.67 (m, 2H) 3.91-4.02 (m, 1H) 4.02-4.13

The title compound was formed as a byproduct during the ester hydrolysis step in the preparation of 4-((1R,3aS,5aR,5bR,7aR,11aS,11bR,13aR,13bR)-5a,5b,8,8,11a-pentamethyl-3a-(3-oxopiperazine-1-carboxamido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid. Purification by reverse phase preparative HPLC gave a white solid (22 mg, 33% yield) mono-TFA salt. LCMS: m/z 674 (M+H$^+$), retention time 2.41 min (method 11). $^1$H NMR (400 MHz, 1:1 mixture of CDCl3 and MeOD, MeOD lock) δ ppm 0.94 (s, 3H) 0.94 (s, 3H) 1.01 (s, 3H) 1.02 (s, 3H) 1.07-1.18 (m, 5H) 1.20-1.59 (m, 12H) 1.60-1.79 (m, 8H) 1.86-2.01 (m, 1H) 2.12 (dd, J=17.07, 6.27 Hz, 1H) 2.37-2.51 (m, 2H) 2.51-2.60 (m, 1H) 3.05-3.18 (m, 2H) 3.47 (ddd, J=15.37, 5.46, 5.27 Hz, 1H) 3.70-3.82 (m, 1H) 3.93-4.06 (m, 2H) 4.62 (s, 1H) 4.75 (d, J=1.51 Hz, 1H) 5.29 (dd, J=6.02, 1.51 Hz, 1H) 7.20 (m, J=8.28 Hz, 2H) 7.92 (m, J=8.28 Hz, 2H).

Example 59

Preparation of 4-((1R,3aS,5aR,5bR,7aR,11aS,11bR,13aR,13bR)-3a-(4-(tert-butoxycarbonyl)-2-(carboxymethyl)piperazine-1-carboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

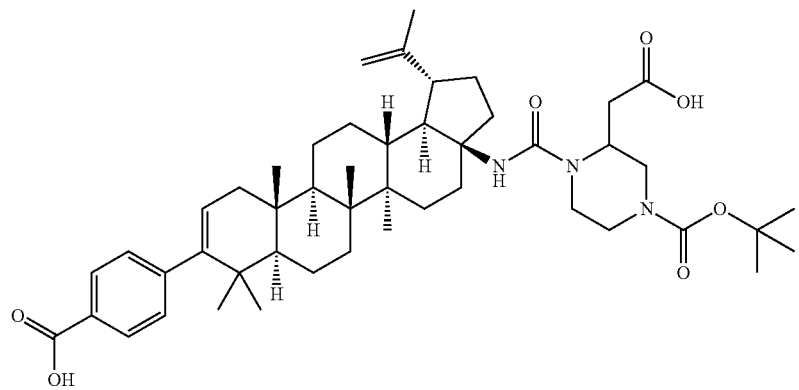

The title compound was prepared following the general procedures described above for the C-17 urea formation and subsequent ester hydrolysis using tert-butyl 3-(2-methoxy-2-oxoethyl)piperazine-1-carboxylate as the reactant amine. The product was isolated after reverse phase preparative HPLC purification as a white solid (39 mg, 63% yield). LCMS: m/z 800 (M+H⁺), retention time 2.94 min (method 11). This material is a diastereomeric mixture in a ratio of approximately 2:1. ¹H NMR (500 MHz, 1:1 mixture of CDCl3 and MeOD, MeOD lock) δ ppm ¹H NMR (500 MHz, MeOD) δ ppm 0.89-0.97 (m, 6H) 0.97-1.05 (m, 6H) 1.05-1.18 (m, 5H) 1.25 (d, J=3.36 Hz, 1H) 1.29-1.44 (m, 5H) 1.48 (d, J=5.80 Hz, 13H) 1.51-1.62 (m, 3H) 1.65-1.80 (m, 7H) 1.81-2.00 (m, 2H) 2.12 (ddd, J=17.09, 6.10, 3.66 Hz, 1H) 2.27-2.42 (m, 1H) 2.57 (dd, J=17.24, 4.12 Hz, 1H) 2.63 (dd, J=12.82, 9.77 Hz, 2H) 2.75 (br. s., 0.5H) 2.88 (d, J=7.02 Hz, 1.5H) 2.95-3.04 (m, 1H) 3.09 (br. s., 0.5H) 3.80 (d, J=11.60 Hz, 0.5H) 3.91 (d, J=12.21 Hz, 0.5H) 4.03 (d, J=10.38 Hz, 1H) 5.29 (dd, J=4.27, 2.14 Hz, 1H) 7.20 (dd, J=8.24, 2.44 Hz, 2H) 7.92 (d, J=7.32 Hz, 2H).

Example 60

Preparation of 4-((1R,3aS,5aR,5bR,7aR,11aS,11bR,13aR,13bR)-3a-(3-(5-(dimethylamino)pentyl)ureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

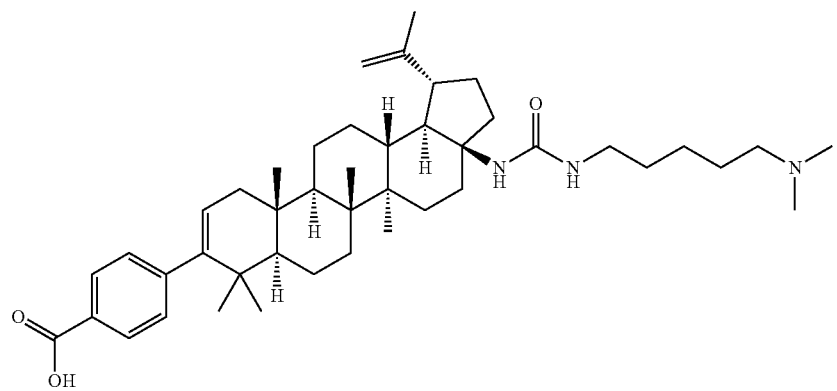

The title compound was prepared following the general procedures described above for the C-17 urea formation and subsequent ester hydrolysis using N1,N1-dimethylpentane-1,5-diamine as the reactant amine. The mono-TFA salt product was isolated after reverse phase preparative HPLC purification as a white solid (21 mg, 57% yield). LCMS: m/z 686 (M+H$^+$), retention time 2.44 min (method 11). $^1$H NMR (500 MHz, 1:1 mixture of CDCl3 and MeOD, MeOD lock) δ ppm 0.93 (br. s., 3H) 0.94 (s, 3H) 1.00 (br. s., 3H) 1.01 (br. s., 3H) 1.04-1.16 (m, 5H) 1.23-1.26 (m, 1H) 1.28-1.44 (m, 7H) 1.44-1.59 (m, 7H) 1.59-1.67 (m, 2H) 1.67-1.84 (m, 8H) 1.86-1.98 (m, 1H) 2.12 (dd, J=17.40, 6.41 Hz, 1H) 2.34 (dd, J=12.21, 8.24 Hz, 1H) 2.50-2.63 (m, 2H) 2.86 (s, 6H) 3.03-3.17 (m, 4H) 4.61 (s, 1H) 4.72 (d, J=1.53 Hz, 1H) 5.24-5.32 (m, 1H) 7.20 (m, J=8.24 Hz, 2H) 7.92 (m, J=8.24 Hz, 2H).

Example 61

Preparation of 4-((1R,3aS,5aR,5bR,7aR,11aS,11bR, 13aR,13bR)-3a-(4-(tert-butoxycarbonyl)-2-(hydroxymethyl)piperazine-1-carboxamido)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

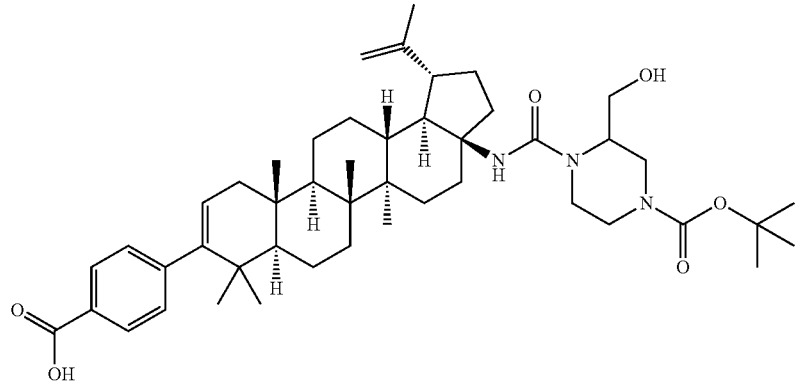

The title compound was prepared following the general procedures described above for the C-17 urea formation and subsequent ester hydrolysis using tert-butyl 3-(hydroxymethyl)piperazine-1-carboxylate as the reactant amine. The product was isolated as a mixture of two diastereomers after reverse phase preparative HPLC purification as a white solid (68 mg, 60% yield). LCMS: m/z 772 (M+H$^+$), retention time 2.91 and 2.99 min (method 11). This material is a diastereomeric mixture in a ratio of approximately 5:4. $^1$H NMR (400 MHz, 1:1 mixture of CDCl3 and MeOD, MeOD lock) δ ppm 0.89-0.98 (m, 6H) 0.98-1.04 (m, 6H) 1.05-1.18 (m, 5H) 1.20-1.44 (m, 6H) 1.47 (d, J=2.26 Hz, 9H) 1.48-1.61 (m, 6H) 1.62-1.77 (m, 7H) 1.80-2.01 (m, 2H) 2.12 (dd, J=16.81, 6.02 Hz, 1H) 2.32-2.42 (m, 1H) 2.46-2.56 (m, 1H) 2.60 (dd, J=13.30, 2.51 Hz, 1H) 2.98-3.15 (m, 2H) 3.21 (ddd, J=18.63, 13.87, 4.64 Hz, 1H) 3.61-3.69 (m, 1H) 3.71-3.91 (m, 4H) 3.94-4.06 (m, 1H) 4.61 (d, J=8.78 Hz, 1H) 4.74 (dd, J=10.79, 1.25 Hz, 1H) 5.24-5.33 (m, 1H) 7.20 (dd, J=8.41, 1.88 Hz, 2H) 7.86-7.92 (m, 1H) 7.93 (s, 1H).

Example 62

Preparation of 4-(tert-butoxycarbonyl)-1-((1R,3aS, 5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-3a-ylcarbamoyl)piperazine-2-carboxylic acid

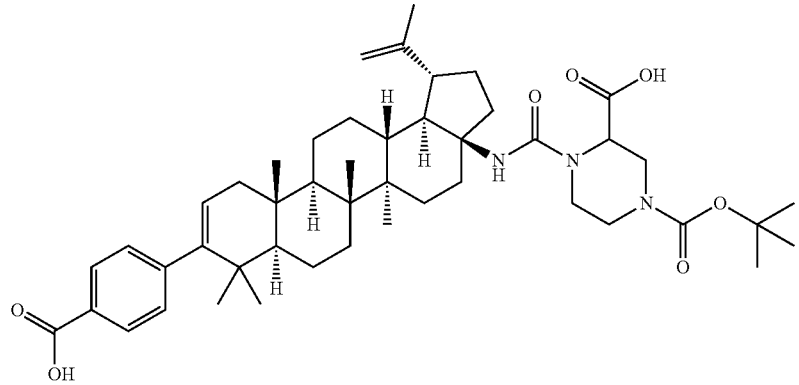

The title compound was prepared following the general procedures described above for the C-17 urea formation and subsequent ester hydrolysis using 1-tert-butyl 3-methyl piperazine-1,3-dicarboxylate as the reactant amine. The product was isolated as a mixture of two diastereomers after reverse phase preparative HPLC purification as a white solid (76 mg, 62% yield). LCMS: m/z 786 (M+H+), retention time 2.84 min (method 11). This material is a diastereomeric mixture in a ratio of approximately 1:1. ¹H NMR (500 MHz, 1:1 mixture of CDCl3 and MeOD, MeOD lock) δ ppm 0.93 (br. s., 3H) 0.94 (br. s., 3H) 1.01 (s, 3H) 1.02 (s, 3H) 1.04-1.18 (m, 5H) 1.19-1.43 (m, 6H) 1.46 (d, J=2.75 Hz, 9H) 1.47-1.61 (m, 6H) 1.61-1.80 (m, 8H) 1.91-2.05 (m, 1H) 2.12 (dd, J=17.09, 6.41 Hz, 1H) 2.43 (dd, J=12.21, 8.24 Hz, 1H) 2.46-2.53 (m, 1H) 2.53-2.62 (m, 1H) 2.98 (br. s., 1H) 3.17 (d, J=9.77 Hz, 1H) 3.35-3.44 (m, 1H) 3.50 (d, J=9.77 Hz, 1H) 4.09 (br. s., 1H) 4.60 (d, J=13.73 Hz, 1H) 4.63 (br. s., 1H) 4.68 (br. s., 1H) 4.75 (br. s., 1H) 5.29 (d, J=4.58 Hz, 1H) 7.20 (d, J=8.24 Hz, 2H) 7.92 (d, J=8.24 Hz, 2H).

Example 63

Preparation of 4-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-ylcarbamoyl)piperazine-2-carboxylic acid

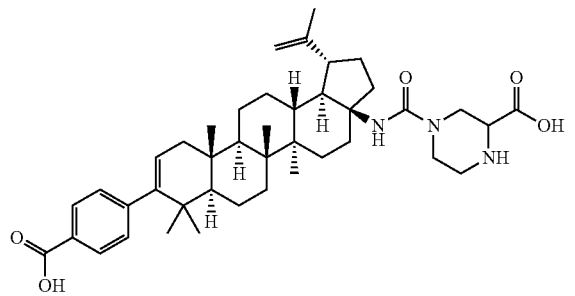

The title compound was prepared following the general procedures described above for the C-17 urea formation and subsequent ester hydrolysis using methyl piperazine-2-carboxylate as the reactant amine. The product was isolated as a mixture of two diastereomers after reverse phase preparative HPLC purification as a white solid (75 mg, 41% yield) mono-TFA salt. LCMS: m/z 686 (M+H+), retention time 2.46 min (method 11). This material is a diastereomeric mixture in a ratio of approximately 1:1. ¹H NMR (500 MHz, 1:1 mixture of CDCl3 and MeOD, MeOD lock) δ ppm 0.93 (br. s., 3H) 0.93 (br. s., 3H) 0.99 (s, 3H) 1.02 (s, 3H) 1.05-1.18 (m, 5H) 1.25 (d, J=7.63 Hz, 1H) 1.28-1.42 (m, 4H) 1.42-1.52 (m, 5H) 1.52-1.64 (m, 2H) 1.65-1.84 (m, 7H) 1.87-1.99 (m, 1H) 2.11 (dd, J=17.09, 6.41 Hz, 1H) 2.41 (td, J=11.90, 8.85 Hz, 1H) 2.55 (dd, J=13.43, 2.75 Hz, 1H) 2.63 (tt, J=10.72, 5.46 Hz, 1H) 3.07-3.18 (m, 0.5H) 3.19-3.27 (m, 0.5H) 3.34-3.51 (m, 2H) 3.57-3.71 (m, 1H) 3.71-3.83 (m, 1H) 3.98-4.05 (m, 0.5H) 4.07-4.16 (m, 1H) 4.16-4.25 (m, 0.5H) 4.63 (s, 1H) 4.76 (br. s., 1H) 5.28 (d, J=4.88 Hz, 1H) 7.19 (m, J=8.24 Hz, 2H) 7.92 (m, J=8.24 Hz, 2H).

Example 64

Preparation of 4-((1R,3aS,5aR,5bR,7aR,11aS,11bR,13aR,13bR)-3a-(6-hydroxy-1,4-diazepane-1-carboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

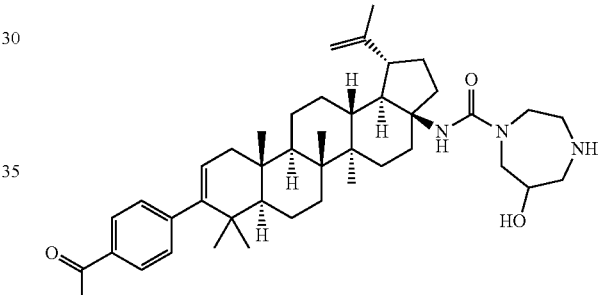

The title compound was prepared following the general procedures described above for the C-17 urea formation and subsequent ester hydrolysis using 1,4-diazepan-6-ol dihydrobromide as the reactant amine. The product was isolated as a mixture of two diastereomers after reverse phase preparative HPLC purification as a white solid (30 mg, 35% yield) mono-TFA salt. LCMS: m/z 672 (M+H+), retention time 2.42 min (method 11). This material is a diastereomeric mixture in a ratio of approximately 1:1. ¹H NMR (500 MHz, 1:1 mixture of CDCl3 and MeOD, MeOD lock) δ ppm 0.89-0.96 (m, 6H) 0.97-1.05 (m, 6H) 1.05-1.17 (m, 5H) 1.22-1.42 (m, 6H) 1.42-1.60 (m, 7H) 1.64-1.80 (m, 7H) 1.82-2.02 (m, 2H) 2.12 (dd, J=17.09, 6.10 Hz, 1H) 2.49-2.65 (m, 2H) 3.12-3.32 (m, 4H) 3.36-3.44 (m, 1H) 3.45-3.53 (m, 1H) 3.78 (d, J=15.56 Hz, 0.5H) 3.95 (d, J=15.56 Hz, 0.5H) 4.25-4.44 (m, 2H) 4.62 (d, J=8.85 Hz, 1H) 4.71 (br. s., 0.5H) 4.75 (br. s., 0.5H) 5.29 (d, J=6.10 Hz, 1H) 5.69 (s, 0.5H) 5.74 (s, 0.5H) 7.20 (dd, J=8.24, 1.53 Hz, 2H) 7.92 (d, J=7.93 Hz, 2H).

Example 65

Preparation of 4-((1R,3aS,5aR,5bR,7aR,11aS,11bR, 13aR,13bR)-3a-(((2-(1,1-dioxido-4-thiomorpholinyl) ethyl)(2-hydroxyethyl)carbamoyl)amino)-1-isopropenyl-5a,5b,8,8,11a-pentamethyl-2,3,3a,4,5,5a,5b,6, 7,7a,8,11,11a,11b,12,13,13a,13b-octadecahydro-1H-cyclopenta[a]chrysen-9-yl)benzoic acid

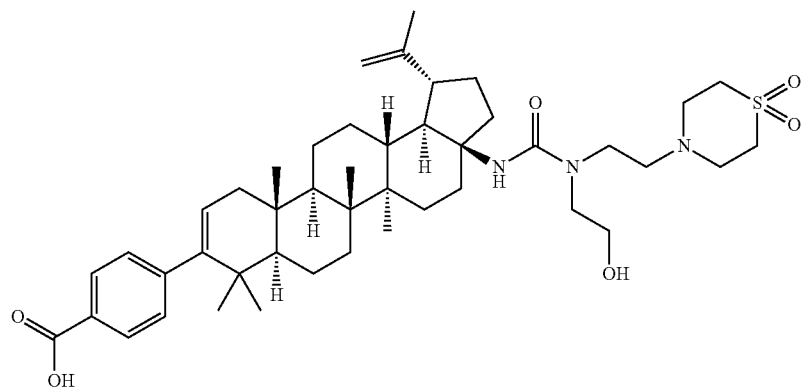

The title compound was prepared following the general procedures described for the C-17 urea formation and subsequent ester hydrolysis using the mixture of 2-((tert-butyl(dimethyl)silyl)oxy)-N-(2-(1,1-dioxido-4-thiomorpholinyl) ethyl)ethanamine and 2-((2-(1,1-dioxido-4-thiomorpholinyl) ethyl)amino)ethanol acquired in Step 3 below as the reactant amine. The urea formation step gave the desilylated material directly as the major product of the reaction, so no desilylation step was necessary. After ester hydrolysis, the mono-TFA salt product was isolated by reverse phase preparative HPLC purification as a white solid (96 mg, 57% yield). LCMS: m/z 778 (M+H$^+$), retention time 2.43 min (method 11). $^1$H NMR (400 MHz, 1:1 mixture of CDCl3 and MeOD, MeOD lock) δ ppm 0.94 (br. s., 3H) 0.94 (s, 3H) 1.01 (br. s., 3H) 1.02 (s, 3H) 1.06-1.16 (m, 5H) 1.20-1.45 (m, 6H) 1.45-1.64 (m, 6H) 1.64-1.79 (m, 6H) 1.81-2.00 (m, 2H) 2.12 (dd, J=17.07, 6.27 Hz, 1H) 2.38 (dd, J=11.80, 8.03 Hz, 1H) 2.48-2.63 (m, 2H) 3.16 (br. s., 2H) 3.30 (br. s., 1H) 3.37 (br. s., 4H) 3.43-3.58 (m, 3H) 3.60 (br. s., 4H) 3.76 (br. s., 2H) 4.61 (d, J=1.51 Hz, 1H) 4.73 (d, J=1.25 Hz, 1H) 5.29 (d, J=4.77 Hz, 1H) 7.20 (m, J=8.28 Hz, 2H) 7.92 (m, J=8.28 Hz, 2H).

Synthesis of amine used in preparation of 4-((1R, 3aS,5aR,5bR,7aR,11aS,11bR,13aR,13bR)-3a-(((2-(1,1-dioxido-4-thiomorpholinyl)ethyl)(2-hydroxyethyl)carbamoyl)amino)-1-isopropenyl-5a,5b,8,8, 11a-pentamethyl-2,3,3a,4,5,5a,5b,6,7,7a,8,11,11a, 11b,12,13,13a,13b-octadecahydro-1H-cyclopenta[a] chrysen-9-yl)benzoic acid

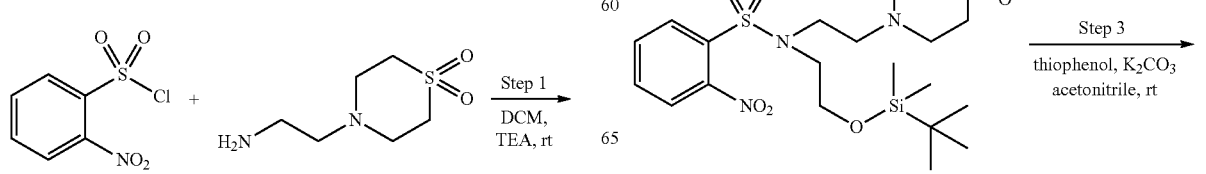

-continued

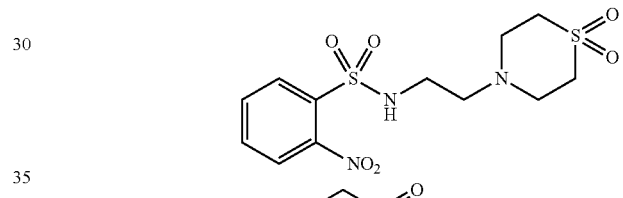

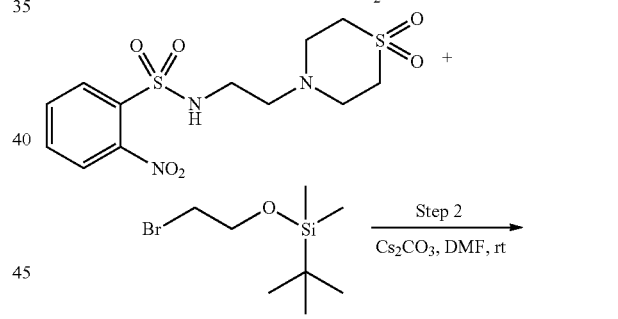

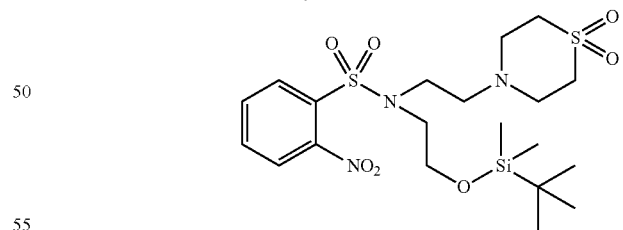

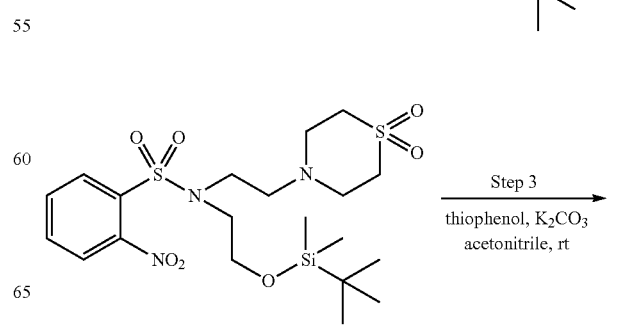

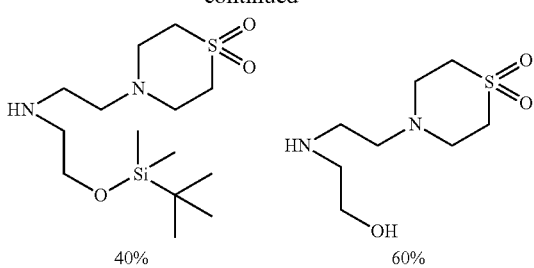

40%   60%

Step 1. Preparation of N-(2-(1,1-dioxido-4-thiomorpholinyl)ethyl)-2-nitrobenzenesulfonamide

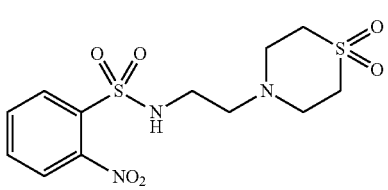 [SMILES: O=[N+]([O-])c1ccccc1S(=O)(=O)NCCN1CCS(=O)(=O)CC1]

A mixture of 4-(2-aminoethyl)thiomorpholine 1,1-dioxide (2.00 g, 11.2 mmol) and triethylamine (1.42 g, 14.0 mmol) in DCM (100 mL) was cooled in an ice bath and treated slowly with 2-nitrobenzene-1-sulfonyl chloride (2.49 g, 11.2 mmol). The mixture was removed from the ice bath and stirred at rt for 18 h. The resulting mixture was washed with water (2×50 mL) and the combined aqueous washes were extracted with DCM (50 mL). The organic phases were combined, dried over anhydrous sodium sulfate, filtered and concentrated in vacuo to a yellow solid. Purification by silica gel chromatography (linear gradient 100% DCM to 100:1 DCM:MeOH) gave the title compound as a pale yellow solid (3.47 g, 85% yield). LCMS: m/z 364 (M+H$^+$), retention time 0.98 min (method 11). $^1$H NMR (500 MHz, CHLOROFORM-d) δ ppm 2.71 (t, J=5.49 Hz, 2H) 2.96 (br. s., 4H) 3.05 (br. s., 4H) 3.20 (q, J=5.49 Hz, 2H) 5.93 (br. s., 1H) 7.73-7.84 (m, 2H) 7.84-7.93 (m, 1H) 8.11-8.23 (m, 1H).

Step 2. Preparation of N-(2-((tert-butyl(dimethyl)silyl)oxy)ethyl)-N-(2-(1,1-dioxido-4-thiomorpholinyl)ethyl)-2-nitrobenzenesulfonamide

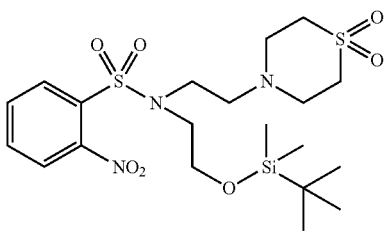 [SMILES: CC(C)(C)[Si](C)(C)OCCN(CCN1CCS(=O)(=O)CC1)S(=O)(=O)c1ccccc1[N+](=O)[O-]]

N-(2-(1,1-dioxido-4-thiomorpholinyl)ethyl)-2-nitrobenzenesulfonamide (0.400 g, 1.10 mmol) was combined with cesium carbonate (0.538 g, 1.65 mmol) in DMF (5 mL). The slurry was stirred at rt for 30 min, then to it was added (2-bromoethoxy)(tert-butyl)dimethylsilane (0.527 g, 2.20 mmol). The resulting mixture was stirred at rt for 18 h. Dilution with ethyl acetate (60 mL) and water (40 mL) followed by shaking gave a separation of phases. The organic phase was isolated, washed with water (2×30 mL) and brine (25 mL), dried over anhydrous magnesium sulfate, filtered and concentrated in vacuo to a residue. Purification by silica gel chromatography (gradient 100% DCM to 100:1 DCM:MeOH) gave the title compound as a yellow solid (0.560 g, 98% yield). LCMS: m/z 522 (M+H$^+$), retention time 2.22 min (method 11). $^1$H NMR (500 MHz, CHLOROFORM-d) δ ppm 0.01 (s, 6H) 0.86 (s, 9H) 2.75 (t, J=5.95 Hz, 2H) 3.05 (s, 8H) 3.44 (t, J=5.49 Hz, 2H) 3.57 (t, J=6.41 Hz, 2H) 3.70 (t, J=5.49 Hz, 2H) 7.63-7.78 (m, 3H) 8.02-8.11 (m, 1H).

Step 3. Preparation of a mixture of 2-((tert-butyl(dimethyl)silyl)oxy)-N-(2-(1,1-dioxido-4-thiomorpholinyl)ethyl)ethanamine and 2-((2-(1,1-dioxido-4-thiomorpholinyl)ethyl)amino)ethanol

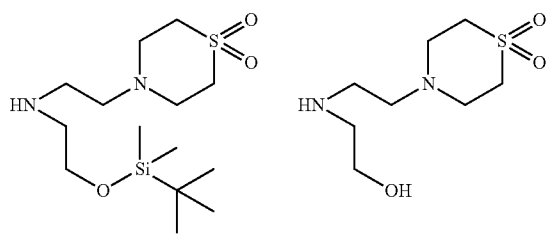 [SMILES: CC(C)(C)[Si](C)(C)OCCNCCN1CCS(=O)(=O)CC1 ; O=S1(=O)CCN(CCNCCO)CC1]

N-(2-((tert-butyl(dimethyl)silyl)oxy)ethyl)-N-(2-(1,1-dioxido-4-thiomorpholinyl)ethyl)-2-nitrobenzenesulfonamide (0.550 g, 1.05 mmol) and thiophenol (0.348 g, 3.16 mmol) were combined in dry acetonitrile (10 mL). Potassium carbonate (0.583 g, 4.22 mmol) was added and the mixture was stirred at rt for 18 h. The mixture was diluted with ethyl acetate and filtered to remove unwanted solids. The crude filtrate was concentrated in vacuo, redissolved in methanol, and loaded onto a strong cation exchange resin cartridge to capture the desired product. Undesired materials were eluted from the cartridge with methanol, and then the desired material was released from the resin by elution with 2M ammonia in methanol. Concentration in vacuo gave a yellow oil (0.300 g, 85% yield). $^1$H NMR revealed that the material collected was a roughly 2:3 mixture of desired product and desilylated desired material. No further purification was performed and the mixture was carried forward to the next step.

Example 66

Preparation of 4-((1R,3aS,5aR,5bR,7aR,11aS,11bR,13aR,13bR)-3a-(((2-(1,1-dioxido-4-thiomorpholinyl)ethyl)(3-hydroxypropyl)carbamoyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

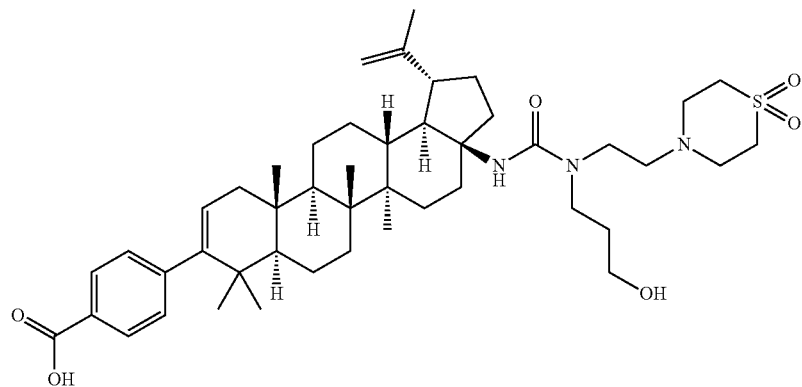

The title compound was prepared following the general procedures described for the C-17 urea formation and subsequent ester hydrolysis using 3-((tert-butyl(dimethyl)silyl)oxy)-N-(2-(1,1-dioxido-4-thiomorpholinyl)ethyl)-1-propanamine as the reactant amine (prepared as described below). The urea formation step gave the desilylated material directly as the major product of the reaction, so no desilylation step was necessary. After ester hydrolysis, the mono-TFA salt product was isolated by reverse phase preparative HPLC purification as a white solid (86 mg, 53% yield). LCMS: m/z 792 (M+H$^+$), retention time 2.45 min (method 11). $^1$H NMR (500 MHz, 1:1 mixture of CDCl3 and MeOD, MeOD lock) δ ppm 0.93 (br. s., 3H) 0.94 (br. s., 3H) 1.00 (s, 3H) 1.02 (s, 3H) 1.07-1.17 (m, 5H) 1.25 (d, J=7.02 Hz, 1H) 1.28-1.45 (m, 5H) 1.45-1.65 (m, 7H) 1.65-1.75 (m, 6H) 1.75-1.85 (m, 2H) 1.85-1.99 (m, 2H) 2.12 (dd, J=17.09, 6.41 Hz, 1H) 2.41 (dd, J=12.05, 8.09 Hz, 1H) 2.58 (d, J=13.43 Hz, 1H) 2.66 (td, J=10.91, 4.73 Hz, 1H) 3.09 (br. s., 2H) 3.39-3.52 (m, 2H) 3.54 (br. s., 4H) 3.55-3.63 (m, 2H) 3.67 (ddd, J=10.76, 5.26, 5.04 Hz, 1H) 4.62 (s, 1H) 4.75 (s, 1H) 5.29 (d, J=4.58 Hz, 1H) 7.20 (m, J=8.24 Hz, 2H) 7.92 (m, J=8.24 Hz, 2H).

Synthesis of amine used in preparation of 4-((1R,3aS,5aR,5bR,7aR,11aS,11bR,13aR,13bR)-3a-(((2-(1,1-dioxido-4-thiomorpholinyl)ethyl)(3-hydroxypropyl)carbamoyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

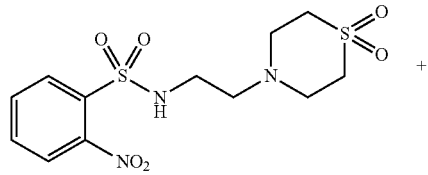

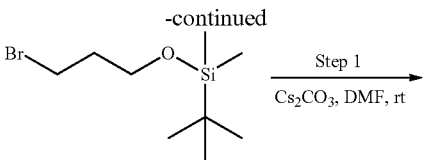

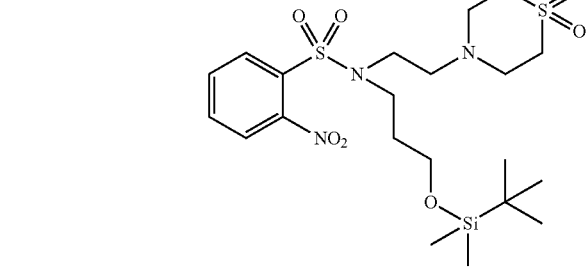

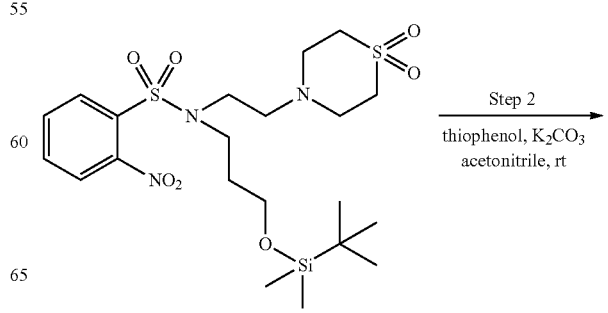

Step 1. Preparation of N-(3-((tert-butyl(dimethyl)silyl)oxy)propyl)-N-(2-(1,1-dioxido-4-thiomorpholinyl)ethyl)-2-nitrobenzenesulfonamide

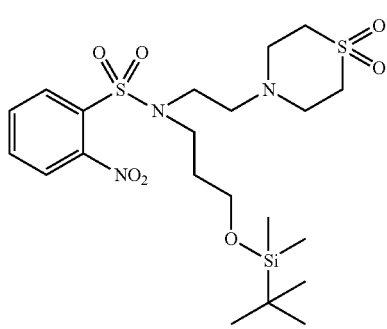 [SMILES: CC(C)(C)[Si](C)(C)OCCCN(CCN1CCS(=O)(=O)CC1)S(=O)(=O)c1ccccc1[N+](=O)[O-]]

N-(2-(1,1-dioxido-4-thiomorpholinyl)ethyl)-2-nitrobenzenesulfonamide (0.400 g, 1.10 mmol) was combined with cesium carbonate (0.538 g, 1.65 mmol) in DMF (5 mL). The slurry was stirred at rt for 30 min, then to it was added (3-bromopropoxy)(tert-butyl)dimethylsilane (0.558 g, 2.20 mmol). The resulting mixture was stirred at rt for 18 h. LCMS indicated incomplete conversion, so additional (3-bromopropoxy)(tert-butyl)dimethylsilane (0.558 g, 2.20 mmol) and cesium carbonate (0.538 g, 1.65 mmol) were added and the mixture was heated to 70° C. for 1 h. Dilution with ethyl acetate (60 mL) and water (40 mL) followed by shaking gave a separation of phases. The organic phase was isolated, washed with water (2×30 mL) and brine (25 mL), dried over anhydrous magnesium sulfate, filtered and concentrated in vacuo to a residue. Purification by silica gel chromatography (gradient 100% DCM to 100:1 DCM:MeOH) gave the title compound as a sticky yellow material, partially crystalline (0.548 g, 93% yield). LCMS: m/z 536 (M+H$^+$), retention time 2.26 min (method 11). $^1$H NMR (400 MHz, CHLOROFORM-d) δ ppm 0.02 (s, 6H) 0.87 (s, 9H) 1.63-1.75 (m, 2H) 2.72 (t, J=6.40 Hz, 2H) 3.07 (s, 8H) 3.32-3.40 (m, 2H) 3.47 (t, J=6.40 Hz, 2H) 3.56 (t, J=5.90 Hz, 2H) 7.63-7.76 (m, 3H) 8.08 (dd, J=7.53, 1.76 Hz, 1H).

Step 2. Preparation of 3-((tert-butyl(dimethyl)silyl)oxy)-N-(2-(1,1-dioxido-4-thiomorpholinyl)ethyl)-1-propanamine

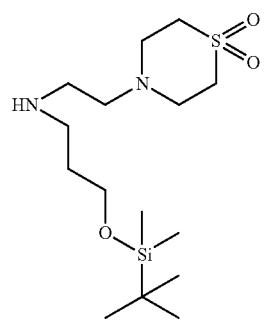 [SMILES: CC(C)(C)[Si](C)(C)OCCCNCCN1CCS(=O)(=O)CC1]

N-(3-((tert-butyl(dimethyl)silyl)oxy)propyl)-N-(2-(1,1-dioxido-4-thiomorpholinyl)ethyl)-2-nitrobenzenesulfonamide (0.540 g, 1.01 mmol) and thiophenol (0.333 g, 3.02 mmol) were combined in dry acetonitrile (10 mL). Potassium carbonate (0.557 g, 4.03 mmol) was added and the mixture was stirred at rt for 18 h. The mixture was diluted with ethyl acetate and filtered to remove unwanted solids. The crude filtrate was concentrated in vacuo, redissolved in methanol, and loaded onto a strong cation exchange resin cartridge to capture the desired product. Undesired materials were eluted from the cartridge with methanol, and then the desired material was released from the resin by elution with 2M ammonia in methanol. Concentration in vacuo gave the title compound as a yellow oil (0.294 g, 83% yield). No further purification was performed and the mixture was carried forward to the next step. LCMS: m/z 351 (M+H$^+$), $^1$H NMR (400 MHz, CHLOROFORM-d) δ ppm 0.06 (s, 6H) 0.90 (s, 9H) 1.75 (quin, J=6.46 Hz, 2H) 2.69-2.72 (m, 2H) 2.72-2.80 (m, 4H) 3.00-3.11 (m, 8H) 3.70 (t, J=6.02 Hz, 2H).

Example 67

Preparation of 4-((1R,3aS,5aR,5bR,7aR,11aS,11bR,13aR,13bR)-3a-(((2-(1,1-dioxido-4-thiomorpholinyl)ethyl)(2-methoxyethyl)carbamoyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

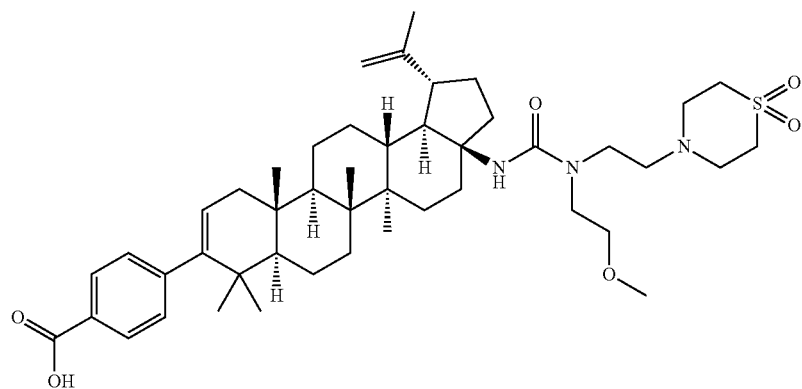

The title compound was prepared following the general procedures described for the C-17 urea formation and subsequent ester hydrolysis using 2-(1,1-dioxido-4-thiomorpholinyl)-N-(2-methoxyethyl)ethanamine (prepared as described below) as the reactant amine. After ester hydrolysis, the mono-TFA salt product was isolated by reverse phase preparative HPLC purification as a white solid (89 mg, 57% yield). LCMS: m/z 792 (M+H$^+$), retention time 2.48 min (method 11). $^1$H NMR (500 MHz, 1:1 mixture of CDCl3 and MeOD, MeOD lock) δ ppm 0.94 (br. s., 3H) 0.95 (s, 3H) 1.01 (s, 3H) 1.02 (s, 3H) 1.06-1.17 (m, 5H) 1.24-1.29 (m, 1H) 1.30-1.42 (m, 4H) 1.44-1.55 (m, 6H) 1.55-1.65 (m, 2H) 1.65-1.77 (m, 6H) 1.82 (td, J=12.13, 3.20 Hz, 1H) 1.86-1.98 (m, 1H) 2.13 (dd, J=17.09, 6.41 Hz, 1H) 2.38 (dd, J=12.36, 8.09 Hz, 1H) 2.47 (td, J=10.99, 5.19 Hz, 1H) 2.51-2.61 (m, 1H) 3.03-3.19 (m, 2H) 3.34-3.44 (m, 5H) 3.51 (s, 3H) 3.52-3.69 (m, 8H) 4.64 (s, 1H) 4.73 (s, 1H) 5.29 (d, J=4.58 Hz, 1H) 7.20 (m, J=8.24 Hz, 2H) 7.92 (m, J=8.24 Hz, 2H).

Synthesis of amine used in preparation of 4-((1R,3aS,5aR,5bR,7aR,11aS,11bR,13aR,13bR)-3a-(((2-(1,1-dioxido-4-thiomorpholinyl)ethyl)(2-methoxyethyl)carbamoyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

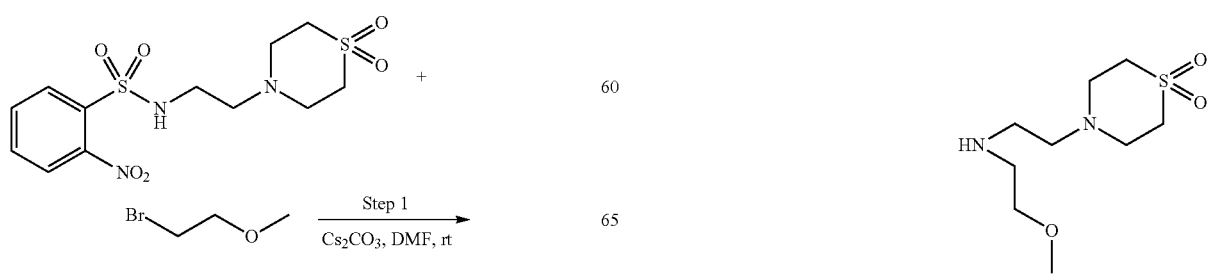

-continued

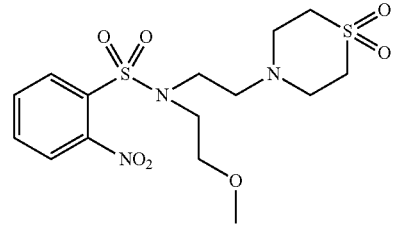

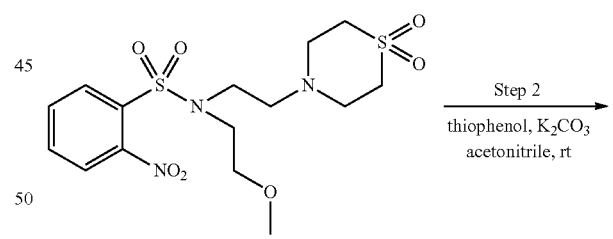

Step 1. Preparation of N-(2-(1,1-dioxido-4-thiomorpholinyl)ethyl)-N-(2-methoxyethyl)-2-nitrobenzenesulfonamide

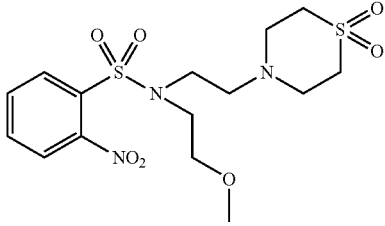 [SMILES: COCCN(CCN1CCS(=O)(=O)CC1)S(=O)(=O)c1ccccc1[N+](=O)[O-]]

N-(2-(1,1-dioxido-4-thiomorpholinyl)ethyl)-2-nitrobenzenesulfonamide (0.400 g, 1.10 mmol) was combined with cesium carbonate (0.538 g, 1.65 mmol) in DMF (5 mL). The slurry was stirred at rt for 30 min, then to it was added 1-bromo-2-methoxyethane (0.306 g, 2.20 mmol). The resulting mixture was stirred at rt for 72 h. LCMS indicated incomplete conversion, so additional 1-bromo-2-methoxyethane (0.306 g, 2.20 mmol) and cesium carbonate (0.538 g, 1.65 mmol) were added and the mixture was heated to 70° C. for 1 h. Dilution with ethyl acetate (60 mL) and water (40 mL) followed by shaking gave a separation of phases. The organic phase was isolated, washed with water (2×30 mL) and brine (25 mL), dried over anhydrous magnesium sulfate, filtered and concentrated in vacuo to a residue. Purification by silica gel chromatography (gradient 100% DCM to 60:1 DCM:MeOH) gave the title compound as a yellow oil (0.486 g, 105% yield). LCMS: m/z 422 (M+H$^+$), retention time 1.35 min (method 11). $^1$H NMR (500 MHz, CHLOROFORM-d) δ ppm 2.72 (t, J=6.41 Hz, 2H) 3.01 (s, 8H) 3.21 (s, 3H) 3.39-3.52 (m, 6H) 7.62-7.66 (m, 1H) 7.66-7.74 (m, J=7.48, 7.32, 7.32, 7.32, 1.68 Hz, 2H) 8.01 (dd, J=7.78, 1.68 Hz, 1H).

Step 2. Preparation of 2-(1,1-dioxido-4-thiomorpholinyl)-N-(2-methoxyethyl)ethanamine

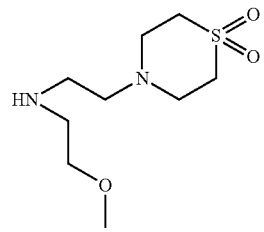

N-(2-(1,1-dioxido-4-thiomorpholinyl)ethyl)-N-(2-methoxyethyl)-2-nitrobenzenesulfonamide (0.470 g, 1.12 mmol) and thiophenol (0.369 g, 3.35 mmol) were combined in dry acetonitrile (10 mL). Potassium carbonate (0.616 g, 4.46 mmol) was added and the mixture was stirred at rt for 18 h. The mixture was diluted with ethyl acetate and filtered to remove unwanted solids. The crude filtrate was concentrated in vacuo, redissolved in methanol, and loaded onto a strong cation exchange resin cartridge to capture the desired product. Undesired materials were eluted from the cartridge with methanol, and then the desired material was released from the resin by elution with 2M ammonia in methanol. Concentration in vacuo gave the title compound as a yellow solid (0.222 g, 84% yield). No further purification was performed and the mixture was carried forward to the next step. LCMS: m/z 237 (M+H$^+$), $^1$H NMR (500 MHz, CHLOROFORM-d) δ ppm 2.15 (br. s., 1H) 2.66-2.71 (m, 2H) 2.71-2.77 (m, 2H) 2.82 (t, J=5.04 Hz, 2H) 2.97-3.05 (m, 4H) 3.05-3.10 (m, 4H) 3.37 (s, 3H) 3.51 (t, J=5.04 Hz, 2H).

Example 68

Preparation of 4-((1R,3aS,5aR,5bR,7aR,11aS,11bR,13aR,13bR)-3a-(((2-(1,1-dioxido-4-thiomorpholinyl)ethyl)(3-methoxypropyl)carbamoyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

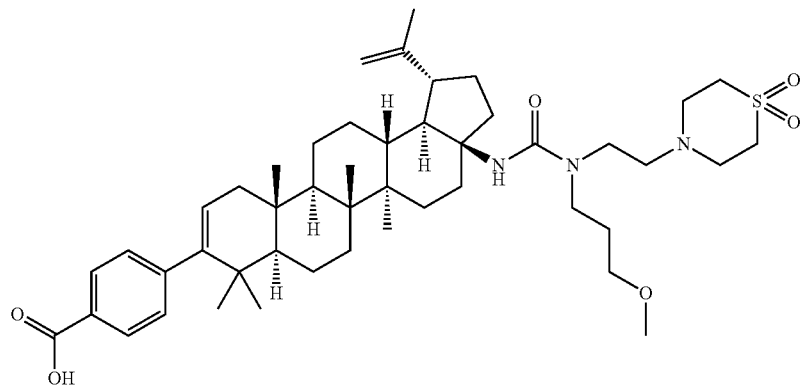

The title compound was prepared following the general procedures described for the C-17 urea formation and subsequent ester hydrolysis using N-(2-(1,1-dioxido-4-thiomorpholinyl)ethyl)-3-methoxy-1-propanamine (prepared as described below) as the reactant amine After ester hydrolysis, the mono-TFA salt product was isolated by reverse phase preparative HPLC purification as a white solid (132 mg, 82% yield). LCMS: m/z 806 (M+H⁺), retention time 2.52 min (method 11). ¹H NMR (400 MHz, 1:1 mixture of CDCl3 and MeOD, MeOD lock) δ ppm 0.94 (br. s., 3H) 0.95 (s, 3H) 1.01 (s, 3H) 1.03 (s, 3H) 1.10 (s, 3H) 1.11-1.21 (m, 2H) 1.21-1.42 (m, 5H) 1.43-1.65 (m, 8H) 1.65-1.77 (m, 6H) 1.77-1.98 (m, 5H) 2.12 (dd, J=17.07, 6.27 Hz, 1H) 2.40 (dd, J=12.17, 8.16 Hz, 1H) 2.55-2.67 (m, 2H) 3.01 (t, J=6.15 Hz, 2H) 3.29 (d, J=5.02 Hz, 4H) 3.34-3.42 (m, 1H) 3.42-3.59 (m, 11H) 4.74 (d, J=1.51 Hz, 1H) 5.24-5.34 (m, 1H) 7.20 (m, J=8.28 Hz, 2H) 7.92 (m, J=8.28 Hz, 2H).

Synthesis of amine used in preparation of 4-((1R,3aS,5aR,5bR,7aR,11aS,11bR,13aR,13bR)-3a-(((2-(1,1-dioxido-4-thiomorpholinyl)ethyl)(3-methoxypropyl)carbamoyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

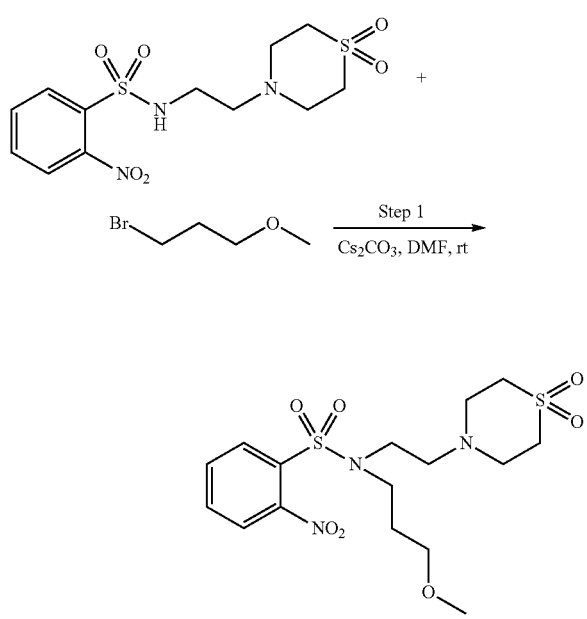

Step 1. Preparation of N-(2-(1,1-dioxido-4-thiomorpholinyl)ethyl)-N-(3-methoxypropyl)-2-nitrobenzenesulfonamide

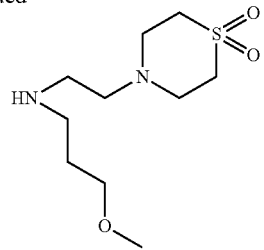

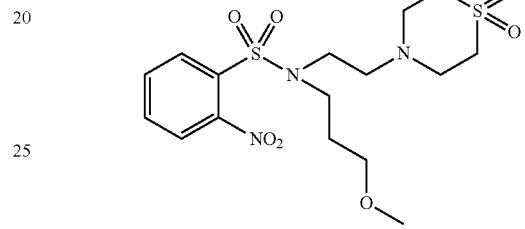

N-(2-(1,1-dioxido-4-thiomorpholinyl)ethyl)-2-nitrobenzenesulfonamide (0.400 g, 1.10 mmol) was combined with cesium carbonate (0.538 g, 1.65 mmol) in DMF (5 mL). The slurry was stirred at rt for 30 min, then to it was added 1-bromo-3-methoxypropane (0.337 g, 2.20 mmol). The resulting mixture was stirred at rt for 72 h. LCMS indicated incomplete conversion, so additional 1-bromo-3-methoxypropane (0.337 g, 2.20 mmol) and cesium carbonate (0.538 g, 1.65 mmol) were added and the mixture was heated to 70° C. for 1 hour. Dilution with ethyl acetate (60 mL) and water (40 mL) followed by shaking gave a separation of phases. The organic phase was isolated, washed with water (2×30 mL) and brine (25 mL), dried over anhydrous magnesium sulfate, filtered and concentrated in vacuo to a residue. Purification by silica gel chromatography (gradient 100% DCM to 60:1 DCM:MeOH) gave the title compound as a yellow oil (0.522 g, 109% yield). LCMS: m/z 436 (M+H⁺), retention time 1.50 min (method 11). ¹H NMR (500 MHz, CHLOROFORM-d) δ ppm 1.68-1.77 (m, 2H) 2.67 (t, J=6.26 Hz, 2H) 3.02 (br. s., 8H) 3.16 (s, 3H) 3.27 (t, J=5.80 Hz, 2H) 3.31-3.37 (m, 2H) 3.41 (t, J=6.26 Hz, 2H) 7.61-7.65 (m, 1H) 7.66-7.74 (m, 2H) 7.99-8.03 (m, 1H).

Step 2. Preparation of N-(2-(1,1-dioxido-4-thiomorpholinyl)ethyl)-3-methoxy-1-propanamine

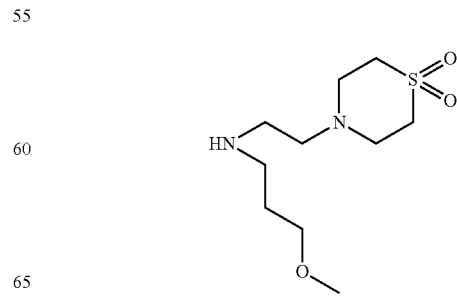

N-(2-(1,1-dioxido-4-thiomorpholinyl)ethyl)-N-(3-methoxypropyl)-2-nitrobenzenesulfonamide (0.510 g, 1.17 mmol) and thiophenol (0.387 g, 3.51 mmol) were combined in dry acetonitrile (10 mL). Potassium carbonate (0.647 g, 4.68 mmol) was added and the mixture was stirred at rt for 18 h. The mixture was diluted with ethyl acetate and filtered to remove unwanted solids. The crude filtrate was concentrated in vacuo, redissolved in methanol, and loaded onto a strong cation exchange resin cartridge to capture the desired product. Undesired materials were eluted from the cartridge with methanol, and then the desired material was released from the resin by elution with 2M ammonia in methanol. Concentration in vacuo gave a yellow oil (0.255 g, 87% yield). No further purification was performed and the mixture was carried forward to the next step. LCMS: m/z 251 (M+H$^+$), $^1$H NMR (400 MHz, CHLOROFORM-d) δ ppm 1.77 (quin, J=6.53 Hz, 2H) 2.13 (br. s., 2H) 2.62-2.68 (m, 2H) 2.68-2.75 (m, 4H) 2.93-3.11 (m, 8H) 3.32 (s, 3H) 3.44 (t, J=6.15 Hz, 2H).

Example 69

Preparation of 4-((1R,3aS,5aR,5bR,7aR,11aS,11bR,13aR,13bR)-3a-((bis(2-(1,1-dioxido-4-thiomorpholinyl)ethyl)carbamoyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

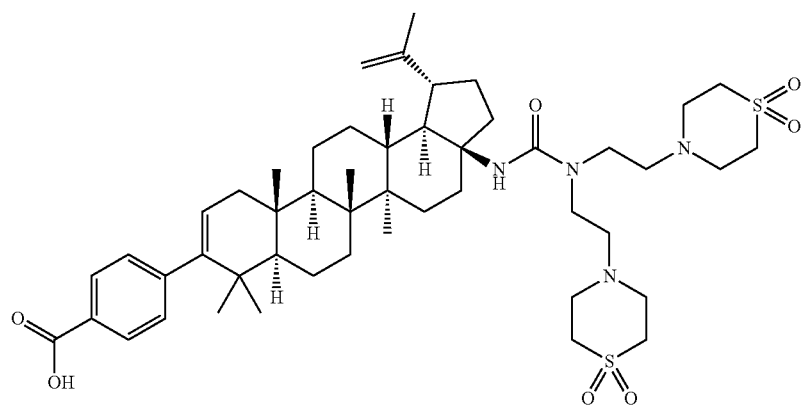

The title compound was prepared following the general procedures described for the C-17 urea formation and subsequent ester hydrolysis using 2-(1,1-dioxido-4-thiomorpholinyl)-N-(2-(1,1-dioxido-4-thiomorpholinyl)ethyl)ethanamine (prepared as described below) as the reactant amine After ester hydrolysis, the bis-TFA salt product was isolated by reverse phase preparative HPLC purification as a slightly yellow solid (109 mg, 64% yield). LCMS: m/z 895 (M+H$^+$), retention time 2.42 min (method 11). $^1$H NMR (500 MHz, 1:1 mixture of CDCl3 and MeOD, MeOD lock) δ ppm 0.94 (br. s., 3H) 0.95 (br. s., 3H) 1.01 (s, 3H) 1.04 (s, 3H) 1.12 (s, 3H) 1.13-1.22 (m, 2H) 1.23-1.32 (m, 2H) 1.33-1.43 (m, 2H) 1.43-1.63 (m, 8H) 1.64-1.81 (m, 7H) 1.84-1.96 (m, 1H) 2.13 (dd, J=17.24, 6.26 Hz, 1H) 2.38 (td, J=10.61, 5.04 Hz, 1H) 2.47 (dd, J=12.51, 8.24 Hz, 1H) 2.50-2.59 (m, 1H) 3.01 (br. s., 4H) 3.26 (br. s., 8H) 3.35-3.50 (m, 10H) 3.50-3.62 (m, 2H) 4.67 (s, 1H) 4.80 (s, 1H) 5.29 (dd, J=6.10, 1.53 Hz, 1H) 7.20 (d, J=8.24 Hz, 2H) 7.92 (d, J=8.55 Hz, 2H).

Synthesis of amine used in preparation of 4-((1R,3aS,5aR,5bR,7aR,11aS,11bR,13aR,13bR)-3a-((bis(2-(1,1-dioxido-4-thiomorpholinyl)ethyl)carbamoyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

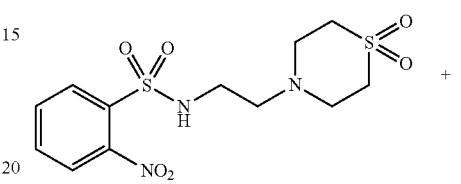

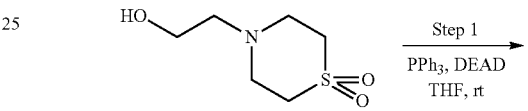

-continued

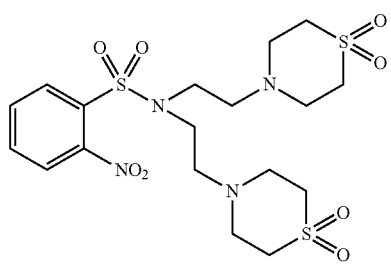

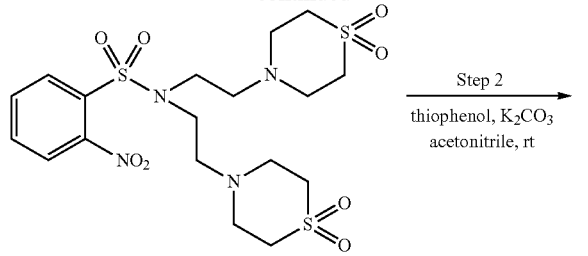

Step 2
thiophenol, K₂CO₃
acetonitrile, rt

Hz, 8H) 3.18 (d, J=5.80 Hz, 8H) 3.51 (t, J=6.71 Hz, 4H) 7.71-7.75 (m, 1H) 7.75-7.84 (m, 2H) 8.05 (d, J=7.63 Hz, 1H).

Step 2. Preparation of 2-(1,1-dioxido-4-thiomorpholinyl)-N-(2-(1,1-dioxido-4-thiomorpholinyl)ethyl)ethanamine

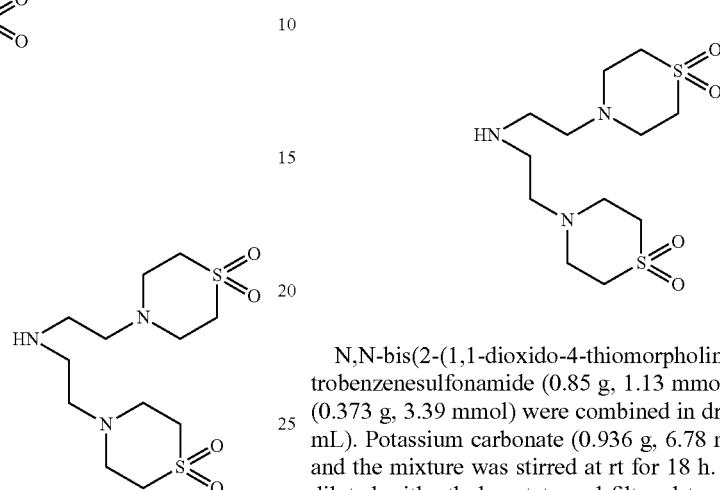

N,N-bis(2-(1,1-dioxido-4-thiomorpholinyl)ethyl)-2-nitrobenzenesulfonamide (0.85 g, 1.13 mmol) and thiophenol (0.373 g, 3.39 mmol) were combined in dry acetonitrile (10 mL). Potassium carbonate (0.936 g, 6.78 mmol) was added and the mixture was stirred at rt for 18 h. The mixture was diluted with ethyl acetate and filtered to remove unwanted solids. The crude filtrate was concentrated in vacuo, redissolved in methanol, and loaded onto a strong cation exchange resin cartridge to capture the desired product. Undesired materials were eluted from the cartridge with methanol, and then the desired material was released from the resin by elution with 2M ammonia in methanol. Concentration in vacuo gave a sticky yellow oil (0.381 g, 100% yield). No further purification was performed and the mixture was carried forward to the next step.

Step 1. Preparation of N,N-bis(2-(1,1-dioxido-4-thiomorpholinyl)ethyl)-2-nitrobenzenesulfonamide Example 69-1

Preparation of 4-((1R,3aS,5aR,5bR,7aR,11aS,11bR,13aR,13bR)-5a,5b,8,8,11a-pentamethyl-1-(prop-1-en-2-yl)-3a-ureido-2,3,3a,4,5,5a,5b,6,7,7a,8,11,11a,11b,12,13,13a,13b-octadecahydro-1H-cyclopenta[a]chrysen-9-yl)benzoic acid and 4-((1R,3aS,5aR,5bR,7aR,11aS,11bR,13aR,13bR)-3a-(1-carbamoylureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

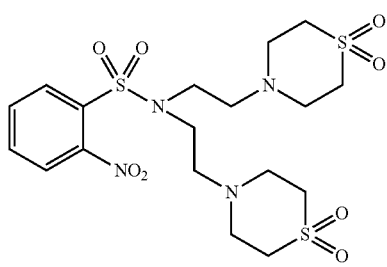 [SMILES: O=[N+]([O-])c1ccccc1S(=O)(=O)N(CCN1CCS(=O)(=O)CC1)CCN1CCS(=O)(=O)CC1]

N-(2-(1,1-dioxido-4-thiomorpholinyl)ethyl)-2-nitrobenzenesulfonamide (0.500 g, 1.38 mmol) was combined with 4-(2-hydroxyethyl)thiomorpholine 1,1-dioxide (0.296 g, 1.65 mmol) in THF (10 mL). To this mixture was added triphenylphosphine (0.541 g, 2.06 mmol) and diethyl azodicarboxylate (0.359 g, 2.06 mmol). The resulting mixture was stirred at rt for 72 h. The mixture was concentrated in vacuo, then redissolved in acetonitrile. Purification by reverse phase preparative HPLC gave the title compound as a pale yellow solid (0.863 g, 83% yield) bis-TFA salt. LCMS: m/z 525 (M+H⁺), retention time 1.25 min (method 11). ¹H NMR (500 MHz, MeOD) δ ppm 2.85 (t, J=6.71 Hz, 4H) 3.14 (d, J=5.49

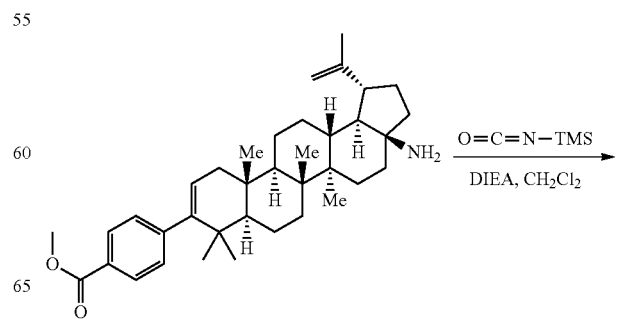

O=C=N—TMS
DIEA, CH₂Cl₂

161

-continued

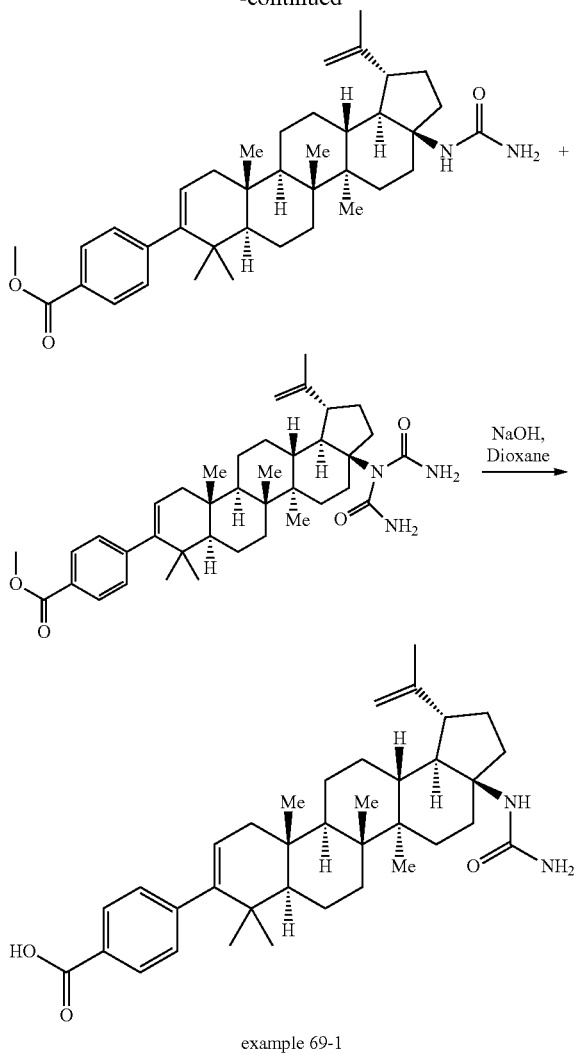

example 69-1

Step 1. To a solution of methyl 4-((1R,3aS,5aR,5bR,7aR, 11aS,11bR,13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate (50 mg, 0.092 mmol) in DCM (1 mL) was added diisopropylethylamine (0.016 mL, 0.092 mmol) and isocyanatotrimethylsilane (15.89 mg, 0.138 mmol). The resulting mixture was stirred at rt for 48 hours. LC-MS showed desired product at M+1=587.48 (2.87 min, method 13) and a side product M+1=630.48 (2.97 min, method 13). The volatiles were removed in vacuo. The crude products were obtained as yellow oil and were used in next step as is.

Step 2. 4-((1R,3aS,5aR,5bR,7aR,11aS,11bR,13aR,13bR)-5a,5b,8,8,11a-pentamethyl-1-(prop-1-en-2-yl)-3a-ureido-2, 3,3a,4,5,5a,5b,6,7,7a,8,11,11a,11b,12,13,13a,13b-octadecahydro-1H-cyclopenta[a]chrysen-9-yl)benzoic acid was prepared following the method described above for the synthesis of 4-((1R,3aS,5aR,5bR,7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoic acid, step 2. The product was isolated as white solid (15 mg, 28%). Example 69-1: LCMS: m/e 573.45 (M+H)+, 2.67 min (method 13). ¹H NMR (400 MHz, METHANOL-d₄) δ 7.94 (d, J=8.5 Hz, 2H), 7.24 (d, J=8.5 Hz, 2H), 5.32 (dd, J=6.1, 1.6 Hz, 1H), 4.78 (d, J=1.8 Hz, 1H), 4.67-4.63 (m, 1H), 2.69-2.59 (m, 2H), 2.40 (dd, J=12.2, 8.2 Hz, 1H), 2.17 (dd, J=17.2, 6.4 Hz, 1H), 2.04-1.84 (m, 2H), 1.74 (s, 3H), 1.82-1.67 (m, 3H), 1.63-1.48 (m, 6H), 1.46-1.26 (m, 6H), 1.16 (s, 3H), 1.22-1.08 (m, 2H), 1.06 (s, 3H), 1.06 (s, 3H), 0.99 (s, 3H), 0.97 (s, 3H).

Section 2. Carbamates

Example 70

Preparation of benzoic acid, 4-[(1R,3aS,5aR,5bR, 7aR,11aS,11bR,13aR,13bR)-3a-[[[3-(1,1-dioxido-4-thiomorpholinyl)propoxy]carbonyl]amino]-2,3,3a,4, 5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]

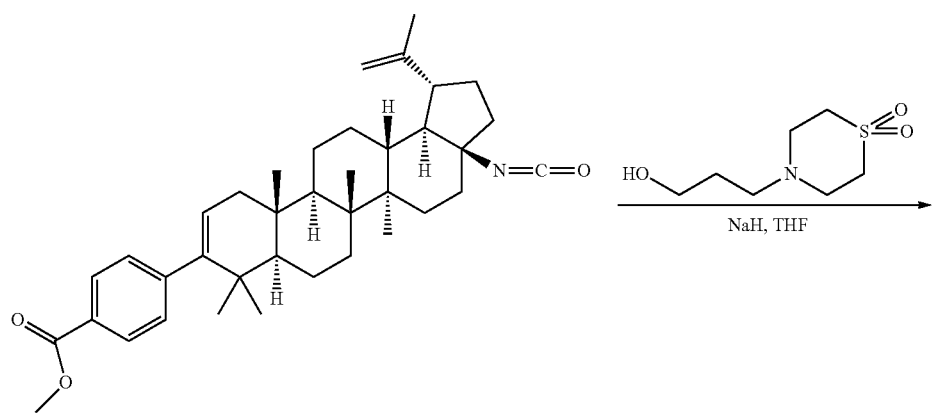

-continued

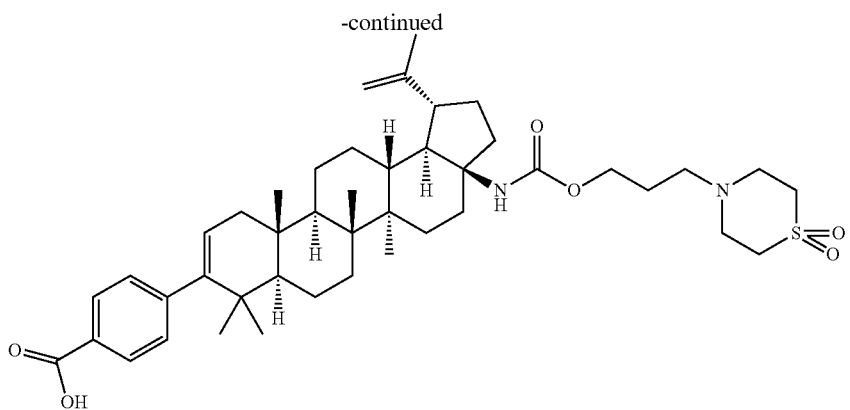

To a cloudy solution of 4-(3-hydroxypropyl)thiomorpholine 1,1-dioxide (407 mg, 2.106 mmol) in tetrahydrofuran (5 mL) was added sodium hydride (84 mg, 2.106 mmol). The resulting white slurry was stirred at rt. After 40 min, the resulting paste was diluted with tetrahydrofuran (5 mL) and was treated with methyl 4-((1R,3aS,5aR,5bR,7aR,11aS,11bR,13aR,13bR)-3a-isocyanato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (200 mg, 0.351 mmol) in one portion. The resulting white slurry was stirred at rt overnight. After 16 h, the reaction was poured into 0.1N HCl (20 mL) and extracted with 2×50 mL EtOAc. The combined organic layer was washed with brine, dried over MgSO$_4$, filtered and concentrated to give a white foam product. The crude material was dissolved in 2 mL THF, filtered and purified by reverse phase preparative HPLC using HPLC method 1 to give the mono-TFA salt of the title compound (123.1 mg, 0.143 mmol, 40.6% yield) as white solid. LCMS: m/e 749.5 (M+H)$^+$, 2.10 min (method 6). $^1$H NMR (500 MHz, 1:1 MeOD:CDCl$_3$) δ=7.92 (d, J=8.5 Hz, 2H), 7.20 (d, J=8.5 Hz, 2H), 5.29 (dd, J=1.8, 6.1 Hz, 1H), 4.75 (d, J=1.5 Hz, 1H), 4.63 (d, J=1.2 Hz, 1H), 4.09 (t, J=5.8 Hz, 2H), 3.42 (br. s., 3H), 2.98 (t, J=7.0 Hz, 2H), 2.57 (dt, J=5.3, 10.9 Hz, 1H), 2.51 (d, J=12.8 Hz, 1H), 2.35-2.28 (m, 1H), 2.12 (dd, J=6.4, 17.1 Hz, 1H), 2.02-1.88 (m, 3H), 1.82-1.65 (m, 7H), 1.65-1.45 (m, 6H), 1.45-1.19 (m, 6H), 1.15-1.10 (m, 2H), 1.09 (s, 3H), 1.02 (s, 3H), 1.01 (s, 3H), 0.95 (s, 3H), 0.94 (s, 3H). $^{13}$C NMR (1:1 MeOD:CDCl$_3$) δ ppm 15.2, 16.5, 17.2, 19.9, 20.7, 21.8, 22.3, 26.2, 26.5, 28.2, 29.9, 30.2, 30.5, 34.5, 37.2, 38.4, 38.6, 41.6, 42.7, 43.0, 48.2, 50.1, 50.5, 50.6, 51.9, 53.9, 54.6, 62.4, 64.9, 78.8, 111.0, 124.9, 129.3, 129.7, 131.0, 147.4, 149.8, 150.4, 156.3, 170.1.

Example 71

Preparation of benzoic acid, 4-[(1R,3aS,5aR,5bR,7aR,11aS,11bR,13aR,13bR)-3a-[[[2-(1,1-dioxido-4-thiomorpholinyl)ethoxy]carbonyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]

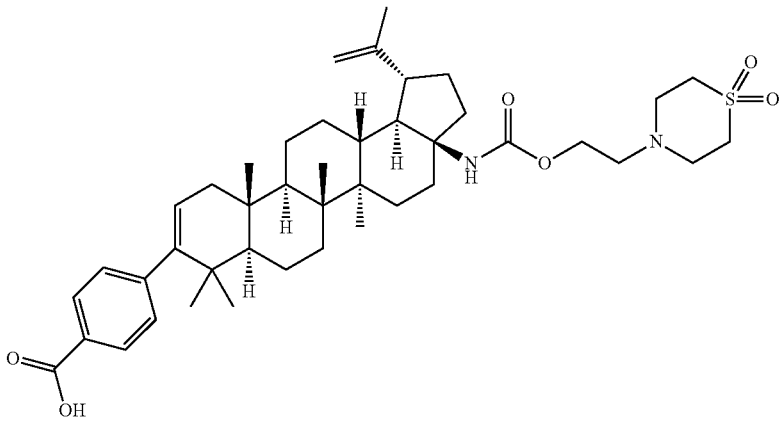

The title compound was prepared in 24% yield from methyl 4-((1R,3aS,5aR,5bR,7aR,11aS,11bR,13aR,13bR)-3a-isocyanato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of benzoic acid, 4-[(1R,3aS,5aR,5bR,7aR,11aS,11bR,13aR,13bR)-3a-[[[3-(1,1-dioxido-4-thiomorpholinyl)propoxy]carbonyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl], except 4-(2-hydroxyethyl)thiomorpholine 1,1-dioxide was used instead of 4-(3-hydroxypropyl)thiomorpholine 1,1-dioxide. LCMS: m/e 735.3 (M+H)$^+$, 2.63 min (method 6). $^1$H NMR (500 MHz, METHANOL-d$_4$) δ=7.95 (d, J=8.5 Hz, 2H), 7.25 (d, J=8.5 Hz, 2H), 5.33 (dd, J=1.7, 6.3 Hz, 1H), 4.79 (d, J=1.8 Hz, 1H), 4.66 (s, 1H), 4.38-4.28 (m, 1H), 4.27-4.19 (m, 1H), 3.56-3.43

(m, 3H), 3.31 (br. s., 2H), 3.17 (br. s., 2H), 2.71 (dt, J=5.3, 11.1 Hz, 1H), 2.57 (d, J=13.4 Hz, 1H), 2.33 (dd, J=8.4, 12.1 Hz, 1H), 2.18 (dd, J=6.4, 17.1 Hz, 1H), 2.00-1.89 (m, 2H), 1.84-1.76 (m, 2H), 1.75 (s, 3H), 1.73 (d, J=4.3 Hz, 1H), 1.71-1.64 (m, 1H), 1.62-1.56 (m, 2H), 1.56-1.48 (m, 4H), 1.47-1.35 (m, 4H), 1.31 (dt, J=4.0, 9.3 Hz, 2H), 1.15 (s, 3H), 1.12 (d, J=3.1 Hz, 1H), 1.07 (s, 6H), 0.99 (s, 3H), 0.97 (s, 3H).

Example 72

Preparation of benzoic acid, 4-[(1R,3aS,5aR,5bR,7aR,11aS,11bR,13aR,13bR)-3a-[[[4-(1,1-dioxido-4-thiomorpholinyl)butoxy]carbonyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]

methylethenyl)-1H-cyclopenta[a]chrysen-9-yl], except 4-(4-hydroxybutyl)thiomorpholine 1,1-dioxide was used instead of 4-(3-hydroxypropyl)thiomorpholine 1,1-dioxide. LCMS: m/e 763.5 (M+H)$^+$, 2.14 min (method 6). $^1$H NMR (500 MHz, METHANOL-d$_4$) δ=7.95 (d, J=8.2 Hz, 2H), 7.24 (d, J=8.2 Hz, 2H), 5.32 (dd, J=1.5, 6.1 Hz, 1H), 4.78 (d, J=1.5 Hz, 1H), 4.65 (s, 1H), 4.14-4.04 (m, 2H), 3.87-3.79 (m, 4H), 3.62-3.51 (m, 4H), 2.69 (dt, J=5.0, 11.1 Hz, 1H), 2.56 (d, J=13.4 Hz, 1H), 2.32 (dd, J=8.9, 11.3 Hz, 1H), 2.18 (dd, J=6.3, 17.2 Hz, 1H), 2.00-1.91 (m, 2H), 1.91-1.82 (m, 2H), 1.82-1.75 (m, 3H), 1.74 (s, 4H), 1.70-1.56 (m, 3H), 1.51 (d, J=11.0 Hz, 4H), 1.46-1.34 (m, 4H), 1.33-1.26 (m, 2H), 1.14 (s, 3H), 1.13-1.09 (m, 2H), 1.08-1.06 (m, 3H), 1.06 (s, 3H), 0.99 (s, 3H), 0.97 (s, 3H).

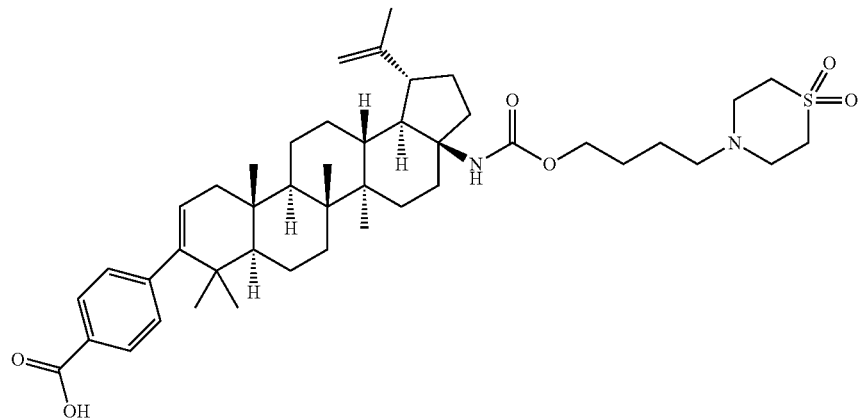

The title compound was prepared in 55% yield from methyl 4-((1R,3aS,5aR,5bR,7aR,11aS,11bR,13aR,13bR)-3a-isocyanato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of benzoic acid, 4-[(1R,3aS,5aR,5bR,7aR,11aS,11bR,13aR,13bR)-3a-[[[3-(1,1-dioxido-4-thiomorpholinyl)propoxy]carbonyl]amino]-2,3,3a,4,5,5a,5b,6,7,7a,8,11,11a,11b,12,13,13a,13b-octadecahydro-5a,5b,8,8,11a-pentamethyl-1-(1-

Section 3. Amides

Example 73

Preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

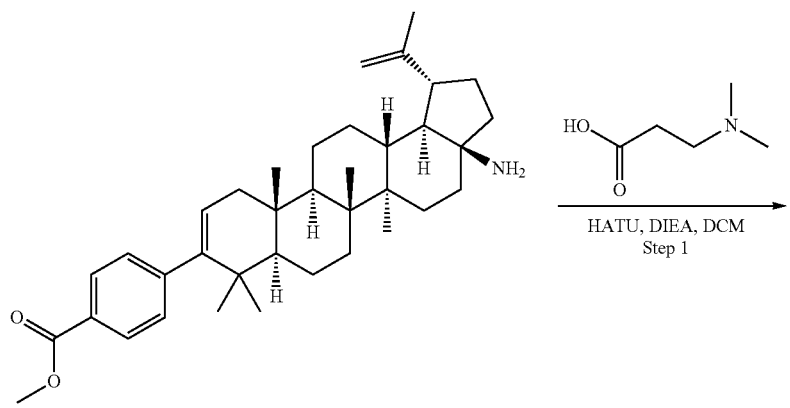

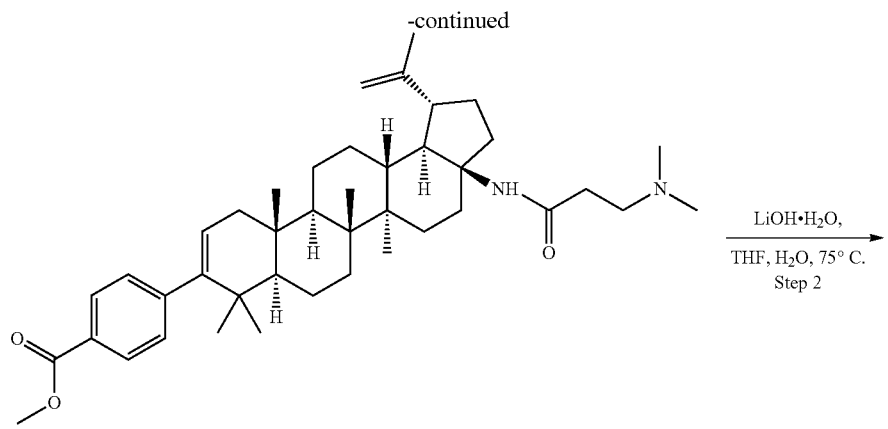

Step 1. Preparation of methyl 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

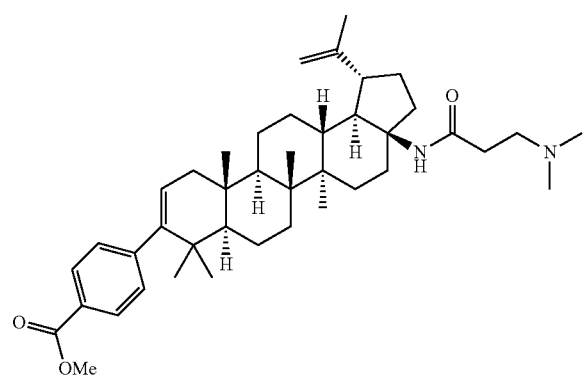

To a cloudy solution mixture of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.240 g, 0.441 mmol) in THF (5 mL) was added N,N-diisopropylethylamine (0.461 mL, 2.65 mmol), 2-(3H-[1,2,3]triazolo[4,5-b]pyridin-3-yl)-1,1,3,3-tetramethylisouronium hexafluorophosphate(V) (0.369 g, 0.971 mmol) and 3-(dimethylamino)propionic acid hydrochloride (0.136 g, 0.883 mmol). The reaction mixture was stirred at rt. After 16 h, the reaction mixture was diluted with EtOAc (50 mL), washed with 1N HCl (5 mL), 5% NaHCO₃, brine, dried over MgSO₄, filtered and concentrated to a viscous oil product. The crude material was dissolved in THF (1 mL) and MeOH (1.5 mL), filtered and purified by reverse phase preparative HPLC using HPLC method 4 to give methyl 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, TFA (93.8 mg, 0.116 mmol, 26.4% yield) as a white solid. LCMS: m/e 643.3 (M+H)⁺, 4.17 min (method 8). $^1$H NMR (500 MHz, 1:1 MeOD:CDCl₃) δ=7.97-7.85 (m, 2H), 7.29-7.23 (m, 2H), 7.21 (br. s., 1H), 5.32 (d, J=4.0 Hz, 1H), 4.80 (br. s., 1H), 4.67 (br. s., 1H), 3.97-3.88 (m, 3H), 3.43-3.37 (m, 2H), 2.92 (br. s., 6H), 2.84-2.77 (m, 2H), 2.77-2.68 (m, 2H), 2.46-2.38 (m, 1H), 2.22-2.13 (m, 1H), 2.05-1.88 (m, 2H), 1.83 (d, J=13.4 Hz, 1H), 1.75 (br. s., 5H), 1.66-1.49 (m, 7H), 1.48-1.34 (m, 4H), 1.32 (br. s., 1H), 1.16 (br. s., 4H), 1.07 (br. s., 6H), 0.98 (br. s., 3H), 0.96 (br. s., 3H). $^{13}$C NMR (1:1 MeOD:CDCl₃) δ ppm 13.8, 15.4, 16.0, 18.4, 19.9, 20.6, 21.4, 25.6, 27.5, 28.7, 29.0, 29.5, 29.7, 33.8, 34.8, 36.4, 37.5, 37.5, 40.8, 41.8, 42.1, 47.0, 49.5, 49.8, 51.5, 53.3, 54.5, 65.8, 102.7, 109.7, 124.3, 128.2, 128.5, 130.3, 146.7, 149.2, 150.1, 167.6, 170.3.

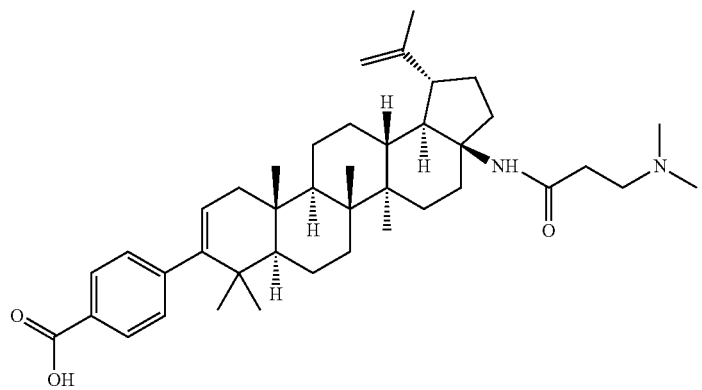

Step 2. Preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

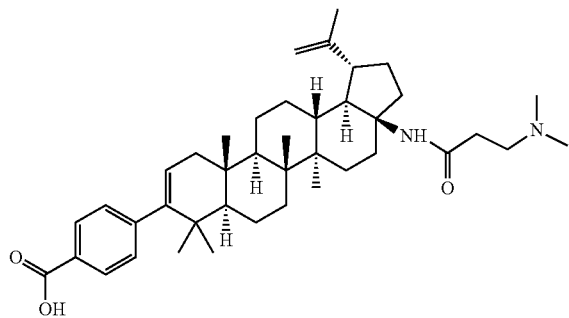

To a solution of methyl 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, TFA (87.9 mg, 0.116 mmol) in THF (5 mL) was added a solution of lithium hydroxide monohydrate (19.49 mg, 0.464 mmol) in water (1.00 mL). The reaction was stirred at 75° C. After 8 h, the reaction was concentrated to dryness. The crude material was dissolved in THF (1 mL) and MeOH (1.5 mL), filtered and purified by reverse phase preparative HPLC using HPLC method 1 to give the title compound (59.5 mg, 0.078 mmol, 67.6% yield) as a white solid. LCMS: m/e 629.4 (M+H)$^+$, 4.17 min (method 8). $^1$H NMR (500 MHz, METHANOL-d$_4$) δ=7.95 (d, J=8.2 Hz, 2H), 7.24 (d, J=8.2 Hz, 3H), 5.33 (dd, J=1.5, 6.1 Hz, 1H), 4.80 (d, J=1.5 Hz, 1H), 4.67 (s, 1H), 3.40 (t, J=6.6 Hz, 2H), 2.92 (s, 6H), 2.88-2.69 (m, 4H), 2.42 (dd, J=8.4, 12.4 Hz, 1H), 2.18 (dd, J=6.4, 17.1 Hz, 1H), 2.05-1.89 (m, 2H), 1.83 (d, J=11.3 Hz, 1H), 1.79-1.76 (m, 1H), 1.75 (s, 3H), 1.74-1.71 (m, 1H), 1.66-1.56 (m, 3H), 1.56-1.49 (m, 4H), 1.47-1.28 (m, 5H), 1.22-1.17 (m, 1H), 1.16 (s, 3H), 1.15-1.10 (m, 1H), 1.07 (s, 6H), 0.99 (s, 3H), 0.97 (s, 3H). $^{13}$C NMR (MeOD) δ ppm 14.5, 16.1, 16.8, 19.1, 20.6, 21.3, 22.1, 26.2, 28.2, 29.4, 29.7, 30.4, 34.5, 35.5, 37.1, 38.1, 38.2, 41.5, 42.5, 42.8, 43.2, 47.6, 49.3, 50.1, 50.5, 54.0, 55.1, 66.4, 110.4, 124.9, 129.5, 130.9, 147.4, 149.6, 150.8, 169.6, 171.0.

Example 74

Preparation of 4-((1R,3aS,5aR,5bR,7aR,11aS,11bR,13aR,13bR)-3a-(4-(dimethylamino)butanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

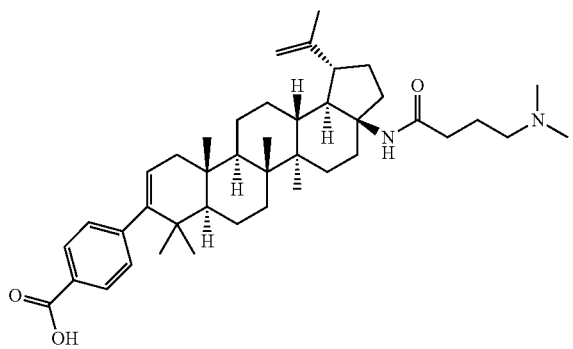

The title compound was prepared in 26% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid, except 4-(dimethylamino)butyric acid hydrochloride was used instead of 3-(dimethylamino)propionic acid hydrochloride in Step 1. LCMS: m/e 643.4 (M+H)$^+$, 4.19 min (method 8). $^1$H NMR (500 MHz, METHANOL-d$_4$) δ=7.95 (d, J=8.2 Hz, 2H), 7.24 (d, J=8.5 Hz, 2H), 5.33 (dd, J=1.7, 6.3 Hz, 1H), 4.80 (d, J=1.5 Hz, 1H), 4.67 (s, 1H), 3.21-3.14 (m, 2H), 2.93 (s, 6H), 2.82-2.67 (m, 2H), 2.49 (t, J=6.9 Hz, 2H), 2.41 (dd, J=8.2, 12.2 Hz, 1H), 2.18 (dd, J=6.4, 17.1 Hz, 1H), 2.06-1.96 (m, 3H), 1.96-1.86 (m, 1H), 1.85-1.79 (m, 1H), 1.77 (br. s., 1H), 1.75 (s, 3H), 1.73-1.69 (m, 1H), 1.64-1.56 (m, 3H), 1.55-1.48 (m, 4H), 1.47-1.38 (m, 3H), 1.35 (d, J=12.2 Hz, 1H), 1.33-1.27 (m, 1H), 1.21-1.17 (m, 1H), 1.15 (s, 3H), 1.12 (d, J=3.4 Hz, 1H), 1.07 (s, 6H), 0.99 (s, 3H), 0.97 (s, 3H).

Example 75

Preparation of 4-((1R,3aS,5aR,5bR,7aR,11aS,11bR,13aR,13bR)-5a,5b,8,8,11a-pentamethyl-3a-(3-(1-methyl-1H-imidazol-2-yl)propanamido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

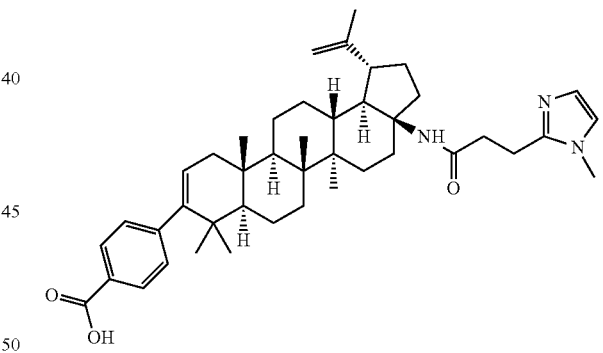

The title compound was prepared in 29% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid, except 3-(1-methyl-1H-imidazol-2-yl) propanoic acid was used instead of 3-(dimethylamino) propionic acid hydrochloride in Step 1. LCMS: m/e 666.4 (M+H)$^+$, 4.15 min (method 8). $^1$H NMR (500 MHz, METHANOL-d$_4$) δ=7.95 (d, J=8.5 Hz, 2H), 7.53-7.46 (m, 2H), 7.25

(d, J=8.2 Hz, 2H), 5.33 (dd, J=1.8, 6.1 Hz, 1H), 4.79 (d, J=1.5 Hz, 1H), 4.66 (s, 1H), 3.91 (s, 3H), 3.30-3.18 (m, 2H), 2.84-2.79 (m, 2H), 2.73 (dt, J=5.2, 11.1 Hz, 1H), 2.64 (d, J=12.5 Hz, 1H), 2.35 (dd, J=8.2, 12.2 Hz, 1H), 2.18 (dd, J=6.4, 17.4 Hz, 1H), 1.96 (dt, J=3.2, 12.1 Hz, 1H), 1.91-1.78 (m, 2H), 1.77 (s, 1H), 1.74 (s, 3H), 1.71-1.66 (m, 1H), 1.60 (br. s., 2H), 1.46-1.26 (m, 7H), 1.22-1.13 (m, 1H), 1.11 (s, 3H), 1.07 (s, 3H), 1.05 (s, 4H), 0.99 (s, 3H), 0.97 (s, 3H).

Example 76

Preparation of 4-((1R,3aS,5aR,5bR,7aR,11aS,11bR,13aR,13bR)-3a-(2-(dimethylamino)-2-oxoacetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

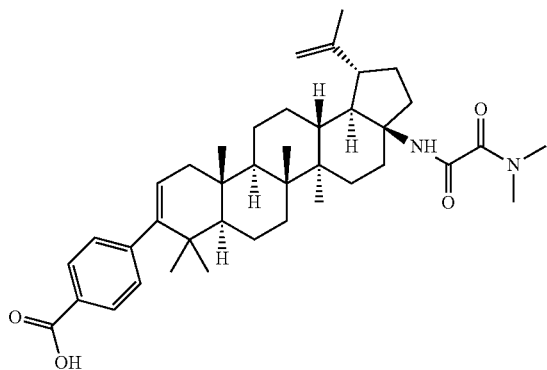

The title compound was prepared in 13% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except N,N-dimethyloxamic acid was used instead of 3-(dimethylamino)propionic acid hydrochloride in Step 1. LCMS: m/e 627.6 (M−H)⁻, 1.91 min (method 5). ¹H NMR (500 MHz, 2:1 MeOD:CDCl₃) δ=7.93 (d, J=8.2 Hz, 2H), 7.55 (s, 1H), 7.21 (d, J=8.2 Hz, 2H), 5.30 (dd, J=1.7, 6.3 Hz, 1H), 4.77 (d, J=1.2 Hz, 1H), 4.65 (s, 1H), 3.22 (s, 3H), 3.01 (s, 3H), 2.71-2.59 (m, 2H), 2.46 (dd, J=8.2, 11.9 Hz, 1H), 2.14 (dd, J=6.3, 17.2 Hz, 1H), 2.02-1.93 (m, 1H), 1.89 (dt, J=3.4, 12.2 Hz, 1H), 1.79 (d, J=13.1 Hz, 1H), 1.75 (d, J=3.7 Hz, 1H), 1.71 (br. s., 1H), 1.66 (dt, J=3.5, 13.5 Hz, 1H), 1.61-1.54 (m, 2H), 1.54-1.48 (m, 4H), 1.46 (br. s., 1H), 1.45-1.40 (m, 3H), 1.40-1.34 (m, 1H), 1.28 (br. s., 2H), 1.20-1.14 (m, 2H), 1.13 (s, 3H), 1.05 (s, 3H), 1.03 (s, 3H), 0.96 (s, 3H), 0.95 (s, 3H).

Example 77

Preparation of 4-((1R,3aS,5aR,5bR,7aR,11aS,11bR,13aR,13bR)-3a-(2-(1H-tetrazol-5-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

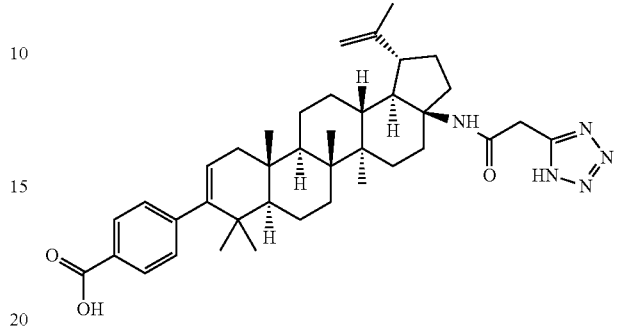

The title compound was prepared in 8% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except (1H-tetrazol-5-yl)-acetic acid was used instead of 3-(dimethylamino)propionic acid hydrochloride in Step 1. LCMS: m/e 640.5 (M+H)⁺, 1.58 min (method 6). ¹H NMR (500 MHz, METHANOL-d₄) δ=7.95 (d, J=8.2 Hz, 2H), 7.48 (s, 1H), 7.25 (d, J=8.2 Hz, 2H), 5.33 (dd, J=1.5, 6.1 Hz, 1H), 4.82 (d, J=1.8 Hz, 1H), 4.68 (s, 1H), 4.12-4.00 (m, 2H), 2.79 (dt, J=5.0, 11.2 Hz, 1H), 2.72-2.62 (m, 1H), 2.45-2.35 (m, 1H), 2.19 (dd, J=6.4, 17.1 Hz, 1H), 2.07-1.92 (m, 2H), 1.84 (d, J=11.6 Hz, 1H), 1.77 (br. s., 1H), 1.76 (s, 3H), 1.73 (d, J=7.3 Hz, 1H), 1.66-1.56 (m, 3H), 1.56-1.49 (m, 4H), 1.48-1.27 (m, 6H), 1.23-1.15 (m, 1H), 1.12 (s, 3H), 1.08 (s, 3H), 1.07 (s, 3H), 1.00 (s, 3H), 0.97 (s, 3H).

Example 78

Preparation of 4-((1R,3aS,5aR,5bR,7aR,11aS,11bR,13aR,13bR)-3a-(2-(1,3,4-thiadiazol-2-ylamino)-2-oxoacetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

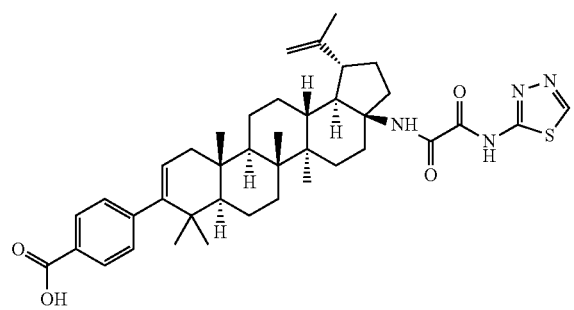

The title compound was prepared in 21% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octa decahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid, except 2-(1,3,4-thiadiazol-2-ylamino)-2-oxoacetic acid was used instead of 3-(dimethylamino)propionic acid hydrochloride in Step 1. LCMS: m/e 683.6 (M−H)⁻, 1.77 min (method 9). ¹H NMR (500 MHz, 2:1 MeOD:CDCl₃) δ=9.13 (s, 1H), 7.92 (d, J=8.5 Hz, 2H), 7.45 (s, 1H), 7.21 (d, J=8.2 Hz, 2H), 5.37-5.24 (m, 1H), 4.81-4.78 (m, 1H), 4.67 (s, 1H), 2.67-2.56 (m, 2H), 2.55-2.47 (m, 1H), 2.15 (dd, J=6.4, 17.1 Hz, 1H), 1.99-1.90 (m, 1H), 1.82 (dd, J=10.5, 16.3 Hz, 3H), 1.74 (s, 3H), 1.71 (br. s., 1H), 1.59-1.44 (m, 9H), 1.44-1.39 (m, 1H), 1.30-1.24 (m, 1H), 1.22-1.14 (m, 2H), 1.10 (s, 3H), 1.07 (s, 3H), 1.03 (s, 3H), 0.95 (s, 3H), 0.94 (s, 3H).

Example 79

Preparation of 4-((1R,3aS,5aR,5bR,7aR,11aS,11bR,13aR,13bR)-5a,5b,8,8,11a-pentamethyl-3a-(2-oxo-2-(thiazol-2-ylamino)acetamido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid The title compound was prepared in 23% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid, except 2-oxo-2-(thiazol-2-ylamino)acetic acid was used instead of 3-(dimethylamino)propionic acid hydrochloride in Step 1. LCMS: m/e 684.5 (M+H)⁺, 2.04 min (method 9). ¹H NMR (500 MHz, 1:1 MeOD:CDCl₃) δ=7.92 (d, J=8.5 Hz, 2H), 7.54 (d, J=3.7 Hz, 1H), 7.49 (s, 1H), 7.22-7.19 (m, 3H), 5.30 (dd, J=1.8, 6.1 Hz, 1H), 4.79 (d, J=1.2 Hz, 1H), 2.65-2.55 (m, 2H), 2.53-2.46 (m, 1H), 2.14 (dd, J=6.4, 17.1 Hz, 1H), 1.98-1.89 (m, 1H), 1.88-1.76 (m, 3H), 1.73 (s, 3H), 1.70 (s, 1H), 1.61-1.36 (m, 11H), 1.29-1.22 (m, 1H), 1.21-1.14 (m, 2H), 1.09 (s, 3H), 1.06 (s, 3H), 1.02 (s, 3H), 0.95-0.94 (m, 3H), 0.93 (s, 3H).

Example 80

Preparation of 4-((1R,3aS,5aR,5bR,7aR,11aS,11bR,13aR,13bR)-3a-(2-(cyclohexylamino)-2-oxoacetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

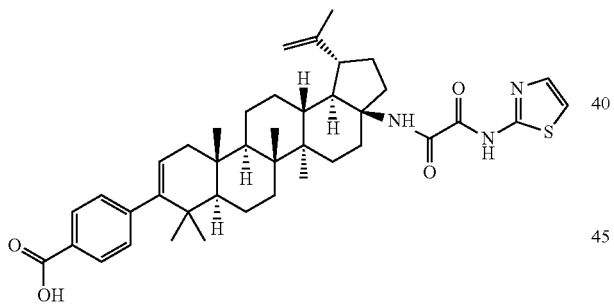

The title compound was prepared in 40% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid, except 2-(cyclohexylamino)-2-oxoacetic acid was used instead of 3-(dimethylamino)propionic acid hydrochloride in Step 1. LCMS: m/e 681.7 (M−H)⁻, 2.42 min (method 9). ¹H NMR (500 MHz, CHLOROFORM-d) δ=8.03 (d, J=8.5 Hz, 2H), 7.61 (s, 1H), 7.52 (d, J=8.5 Hz, 1H), 7.25 (d, J=8.2 Hz, 2H), 6.51 (br. s., 1H), 5.33 (d, J=4.6 Hz, 1H), 4.79 (d, J=1.2 Hz, 1H), 4.67 (s, 1H), 3.83-3.72 (m, 1H), 2.62-2.54 (m, 2H), 2.50 (dd, J=8.5, 11.6 Hz, 1H), 2.14 (dd, J=6.3, 17.2 Hz, 1H), 2.00-1.89 (m, 3H), 1.86-1.75 (m, 4H), 1.71-1.62 (m, 2H), 1.61-1.36 (m, 13H), 1.35-1.20 (m, 5H), 1.18-1.11 (m, 2H), 1.08 (s, 3H), 1.05-1.02 (m, 3H), 1.00 (s, 3H), 0.96 (s, 6H).

Example 81

Preparation of benzoic acid, 4-[(1R,3aS,5aR,5bR,7aR,11aS,11bR,13aR,13bR)-3a-[[3-(1,1-dioxido-4-thiomorpholinyl)-1-oxopropyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]

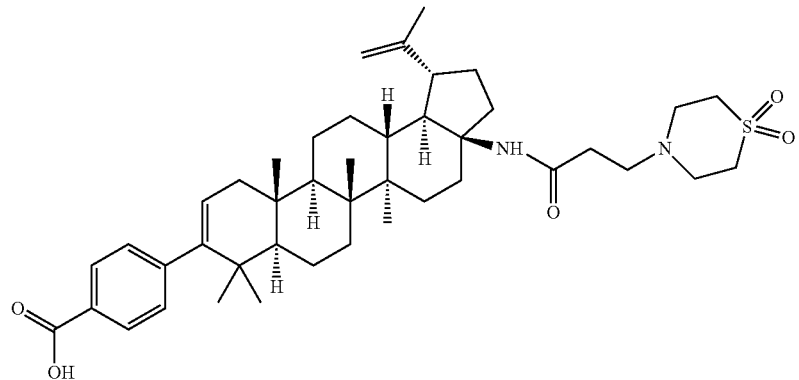

The title compound was prepared in 70% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid, except 3-(1,1-dioxo-1lamda-6,4-thiazinan-4-yl)propanoic acid hydrochloride was used instead of 3-(dimethylamino) propionic acid hydrochloride in Step 1. LCMS: m/e 719.5 (M+H)$^+$, 1.88 min (method 6). $^1$H NMR (500 MHz, 2:1 MeOD:CDCl$_3$) δ=7.93 (d, J=7.9 Hz, 2H), 7.25 (br. s., 1H), 7.21 (d, J=7.9 Hz, 2H), 5.30 (d, J=6.1 Hz, 1H), 4.78 (s, 1H), 4.66 (s, 1H), 3.47 (br. s., 4H), 3.36 (br. s., 4H), 3.19 (br. s., 2H), 2.72-2.59 (m, 4H), 2.40 (dd, J=8.9, 11.9 Hz, 1H), 2.15 (dd, J=6.3, 17.2 Hz, 1H), 1.98-1.86 (m, 2H), 1.80 (d, J=13.1 Hz, 1H), 1.73 (s, 3H), 1.71-1.66 (m, 1H), 1.63-1.43 (m, 8H), 1.42-1.23 (m, 5H), 1.22-1.13 (m, 2H), 1.12 (s, 3H), 1.05 (br. s., 3H), 1.04 (br. s., 3H), 0.97 (br. s., 3H), 0.95 (br. s., 3H).

The title compound was prepared in 61% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid, except 4-thiomorpholineacetic acid 1,1-dioxide was used instead of 3-(dimethylamino)propionic acid hydrochloride in Step 1. LCMS: m/e 704.5 (M+H)$^+$, 1.90 min (method 6). $^1$H NMR (500 MHz, 2:1 MeOD:CDCl$_3$) δ=7.93 (d, J=8.2 Hz, 2H), 7.23 (br. s., 1H), 7.21 (s, 2H), 5.31 (dd, J=1.7, 6.0 Hz, 1H), 4.78 (d, J=1.2 Hz, 1H), 4.67 (s, 1H), 3.29 (d, J=5.2 Hz, 4H), 3.24 (d, J=5.2 Hz, 4H), 2.67-2.60 (m, 1H), 2.53 (dt, J=5.5, 10.8 Hz, 1H), 2.47 (dd, J=8.1, 12.7 Hz, 1H), 2.16 (dd, J=6.3, 17.2 Hz, 1H), 1.94-1.78 (m, 3H), 1.76 (d, J=2.1 Hz, 1H), 1.74 (s, 3H), 1.62-1.49 (m, 7H), 1.47-1.33 (m, 4H), 1.31-1.25 (m, 1H), 1.21-1.13 (m, 2H), 1.12 (s, 3H), 1.07 (s, 3H), 1.05 (s, 3H), 0.97 (s, 3H), 0.96 (s, 3H).

Example 82

Preparation of benzoic acid, 4-[(1R,3aS,5aR,5bR,7aR,11aS,11bR,13aR,13bR)-3a-[[(1,1-dioxido-4-thiomorpholinyl)acetyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]

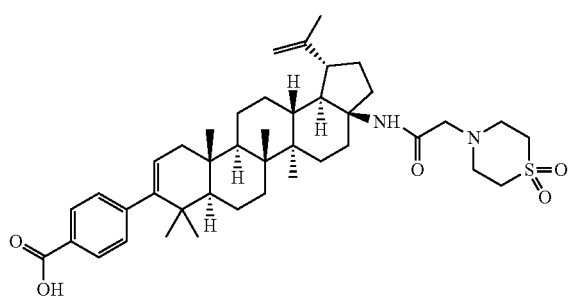

Example 83

Preparation of 4-((1R,3aS,5aR,5bR,7aR,11aS,11bR,13aR,13bR)-3a-(2-((2S,6R)-2,6-dimethylmorpholino)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

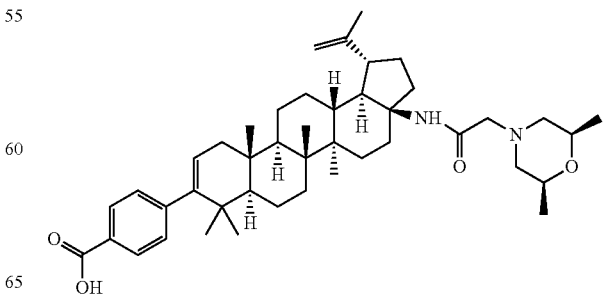

The title compound was prepared in 43% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except [(2R,6S)-2,6-dimethylmorpholin-4-yl]acetic acid was used instead of 3-(dimethylamino)propionic acid hydrochloride in Step 1. LCMS: m/e 685.6 (M+H)$^+$, 2.48 min (method 6). $^1$H NMR (500 MHz, 1:1 CDCl$_3$:MeOD) δ=7.92 (d, J=8.2 Hz, 2H), 7.20 (d, J=8.2 Hz, 2H), 5.29 (dd, J=1.5, 6.1 Hz, 1H), 4.75 (d, J=1.2 Hz, 1H), 3.89 (dd, J=6.3, 9.0 Hz, 2H), 3.64 (br. s., 1H), 3.24 (br. s., 2H), 2.69-2.49 (m, 4H), 2.39 (dd, J=8.1, 12.4 Hz, 1H), 2.13 (dd, J=6.4, 17.1 Hz, 1H), 1.93-1.76 (m, 3H), 1.74 (br. s., 1H), 1.72 (s, 3H), 1.70-1.66 (m, 1H), 1.60-1.42 (m, 8H), 1.42-1.30 (m, 3H), 1.25 (d, J=3.1 Hz, 3H), 1.24 (d, J=2.7 Hz, 3H), 1.18-1.11 (m, 2H), 1.08 (s, 3H), 1.03 (s, 3H), 1.01 (s, 3H), 0.95 (s, 3H), 0.94 (s, 3H).

Example 84

Preparation of 4-((1R,3aS,5aR,5bR,7aR,11aS,11bR,13aR,13bR)-3a-(2-(4-(2-hydroxyethyl)piperazin-1-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

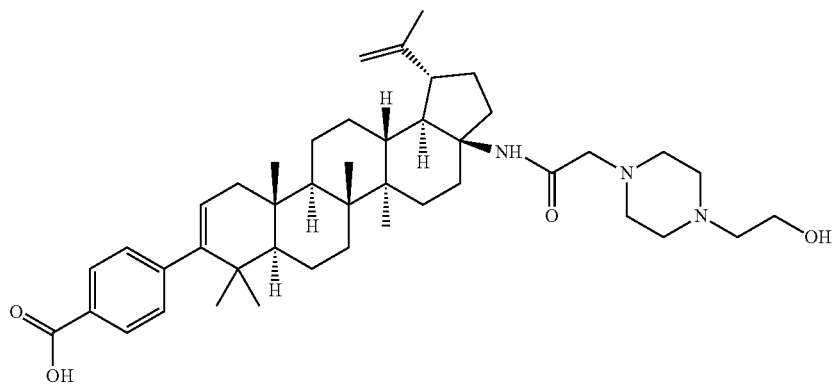

The title compound was prepared in 23% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except [4-(2-hydroxy-ethyl)-piperazine-1-yl]-acetic acid dihydrochloride was used instead of 3-(dimethylamino)propionic acid hydrochloride in Step 1. LCMS: m/e 700.6 (M+H)$^+$, 2.03 min (method 6). $^1$H NMR (500 MHz, 1:1 CDCl$_3$:MeOD) δ=7.92 (d, J=8.5 Hz, 2H), 7.20 (d, J=8.5 Hz, 2H), 6.96 (s, 1H), 5.30 (dd, J=1.7, 6.0 Hz, 1H), 4.76 (s, 1H), 4.66 (s, 1H), 3.93-3.89 (m, 2H), 3.42 (br. s., 2H), 3.30-3.25 (m, 2H), 3.22 (d, J=4.6 Hz, 2H), 2.97 (br. s., 3H), 2.68-2.60 (m, 1H), 2.55-2.47 (m, 1H), 2.44 (dd, J=8.2, 12.5 Hz, 1H), 2.13 (dd, J=6.4, 17.1 Hz, 1H), 1.91-1.77 (m, 2H), 1.75 (br. s., 1H), 1.72 (s, 3H), 1.72-1.68 (m, 1H), 1.62-1.31 (m, 11H), 1.30-1.24 (m, 1H), 1.15 (d, J=13.1 Hz, 2H), 1.08 (s, 3H), 1.05 (s, 3H), 1.02 (s, 3H), 0.95 (s, 3H), 0.94 (s, 3H).

Example 85

Preparation of 4-((1R,3aS,5aR,5bR,7aR,11aS,11bR, 13aR,13bR)-3a-(2-(4-ethylpiperazin-1-yl)acetamido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

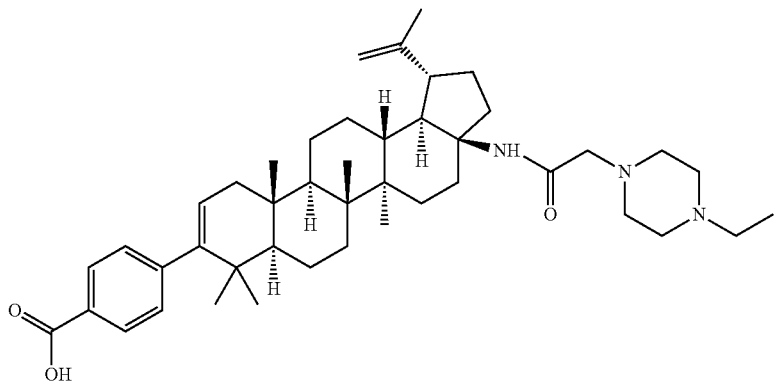

The title compound was prepared in 34% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid, except 2-(4-ethylpiperazin-1-yl)acetic acid was used instead of 3-(dimethylamino)propionic acid hydrochloride in Step 1. LCMS: m/e 684.6 (M+H)$^+$, 2.35 min (method 6). $^1$H NMR (500 MHz, 1:1 CDCl$_3$:MeOD) δ=7.92 (d, J=8.2 Hz, 2H), 7.20 (d, J=8.2 Hz, 2H), 6.90 (s, 1H), 5.29 (d, J=6.1 Hz, 1H), 4.75 (d, J=1.2 Hz, 1H), 3.27-3.14 (m, 5H), 2.96 (br. s., 3H), 2.64 (d, J=13.4 Hz, 1H), 2.55-2.38 (m, 2H), 2.13 (dd, J=6.4, 17.1 Hz, 1H), 1.92-1.76 (m, 2H), 1.74 (br. s., 1H), 1.72 (s, 3H), 1.70-1.67 (m, 1H), 1.61-1.41 (m, 9H), 1.37 (t, J=7.3 Hz, 4H), 1.35-1.31 (m, 1H), 1.29-1.23 (m, 1H), 1.18-1.12 (m, 2H), 1.06 (s, 3H), 1.03 (s, 3H), 1.01 (s, 2H), 0.94 (s, 3H), 0.94 (s, 3H).

Example 86

Preparation of 4-((1R,3aS,5aR,5bR,7aR,11aS,11bR, 13aR,13bR)-3a-(2-((2-methoxyethyl)(methyl)amino) acetamido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

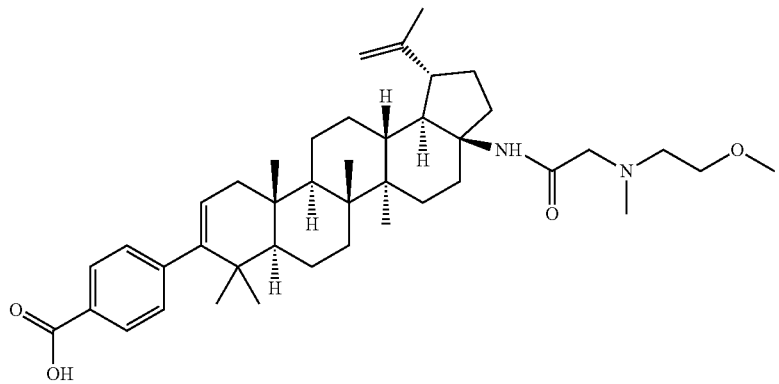

The title compound was prepared in 38% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)benzoic acid, except N-(2-methoxyethyl)-N-methylglycine was used instead of 3-(dimethylamino)propionic acid hydrochloride in Step 1. LCMS: m/e 659.6 (M+H)$^+$, 2.41 min (method 6). $^1$H NMR (500 MHz, 1:1 CDCl$_3$:MeOD) δ=7.92 (d, J=7.9 Hz, 2H), 7.43 (s, 1H), 7.20 (d, J=8.2 Hz, 2H), 5.29 (d, J=5.8 Hz, 1H), 4.75 (s, 1H), 3.96 (br. s., 2H), 3.73 (t, J=4.7 Hz, 2H), 3.42 (s, 3H), 3.40 (br. s., 2H), 2.94 (s, 3H), 2.73-2.61 (m, 2H), 2.36 (dd, J=8.4, 12.1 Hz, 1H), 2.12 (dd, J=6.1, 17.1 Hz, 1H), 1.88 (t, J=11.6 Hz, 2H), 1.77 (d, J=11.6 Hz, 1H), 1.73 (br. s., 1H), 1.71 (s, 3H), 1.70-1.65 (m, 1H), 1.58-1.30 (m, 11H), 1.25 (d, J=6.1 Hz, 1H), 1.18-1.10 (m, 2H), 1.09 (s, 3H), 1.02 (s, 3H), 1.01 (s, 3H), 0.94 (br. s., 3H), 0.93 (br. s., 3H).

Example 87

Preparation of 4-((1R,3aS,5aR,5bR,7aR,11aS,11bR,13aR,13bR)-5a,5b,8,8,11a-pentamethyl-3a-(2-(4-phenyl-1H-pyrazol-1-yl)acetamido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

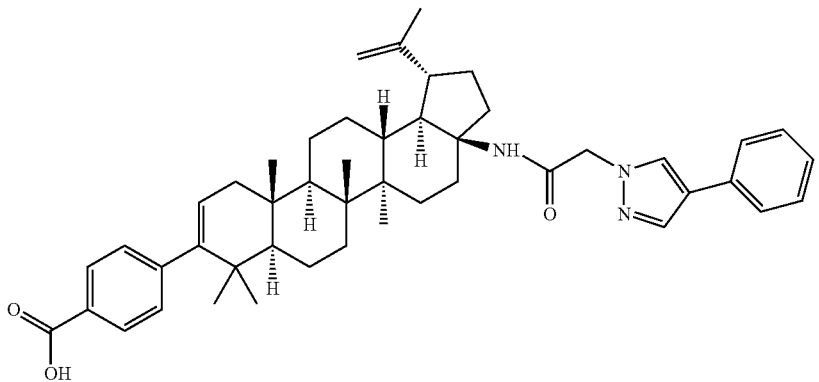

The title compound was prepared in 22% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-(3-phenyl-1H-pyrazol-1-yl)acetic acid was used instead of 3-(dimethylamino)propionic acid hydrochloride in Step 1. LCMS: m/e 714.6 (M+H)$^+$, 2.59 min (method 6). $^1$H NMR (500 MHz, 1:1 CDCl$_3$:MeOD) δ=7.91 (d, J=8.2 Hz, 4H), 7.67 (d, J=2.1 Hz, 1H), 7.42 (d, J=7.3 Hz, 2H), 7.40 (s, 1H), 7.37-7.31 (m, 1H), 7.18 (d, J=7.9 Hz, 2H), 5.24 (d, J=4.6 Hz, 1H), 4.86-4.75 (m, 2H), 4.59 (s, 1H), 3.37 (s, 3H), 2.50 (dd, J=2.4, 9.2 Hz, 1H), 2.47-2.38 (m, 2H), 1.97 (dd, J=6.4, 17.1 Hz, 1H), 1.93-1.83 (m, 1H), 1.64 (s, 3H), 1.60-1.52 (m, 2H), 1.50-1.37 (m, 4H), 1.37-1.27 (m, 7H), 1.26-1.19 (m, 1H), 1.16-1.11 (m, 1H), 1.00 (dd, J=2.4, 9.2 Hz, 1H), 0.90 (s, 3H), 0.89 (s, 6H), 0.79 (s, 3H), 0.61 (s, 3H), 0.49 (dd, J=4.3, 13.1 Hz, 1H).

Example 88

Preparation of 4-((1R,3aS,5aR,5bR,7aR,11aS,11bR,13aR,13bR)-3a-(2-(1H-1,2,3-triazol-1-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

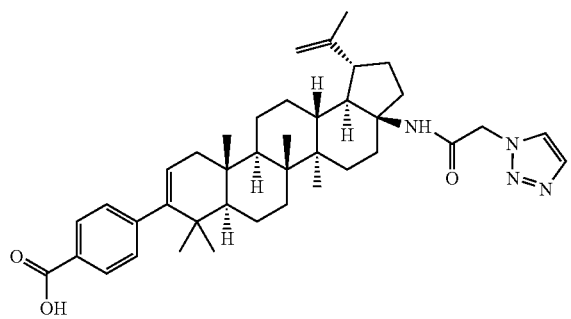

The title compound was prepared in 36% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 1H-1,2,3-triazole-1-acetic acid hydrochloride was used instead of 3-(dimethylamino)propionic acid hydrochloride in Step 1. LCMS: m/e 639.5 (M+H)$^+$, 2.04 min (method 6). $^1$H NMR (500 MHz, 1:1 CDCl$_3$:MeOD) δ=7.94 (d, J=0.9 Hz, 1H), 7.92 (d, J=8.5 Hz, 2H), 7.77 (d, J=0.9 Hz, 1H), 7.20 (d, J=8.5 Hz, 2H), 6.93 (s, 1H), 5.29 (dd, J=1.7, 6.3 Hz, 1H), 5.15 (s, 2H), 4.75 (d, J=1.5 Hz, 1H), 4.64 (br. s., 1H), 2.63-2.57 (m, 1H), 2.57-2.50 (m, 1H), 2.37 (dd, J=8.1, 12.7 Hz, 1H), 2.12 (dd, J=6.4, 17.1 Hz, 1H), 1.94-1.83 (m, 1H), 1.78-1.72 (m, 3H), 1.70 (s, 3H), 1.69-1.64 (m, 1H), 1.58-1.39 (m, 8H), 1.38-1.29 (m, 3H), 1.24 (dd, J=3.7, 10.4 Hz, 1H), 1.15-1.06 (m, 2H), 1.02 (s, 3H), 1.01 (s, 3H), 1.00 (s, 3H), 0.94 (s, 3H), 0.93 (s, 3H).

Example 89

Preparation of 4-((1R,3aS,5aR,5bR,7aR,11aS,11bR,13aR,13bR)-3a-(2-(1H-imidazol-1-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

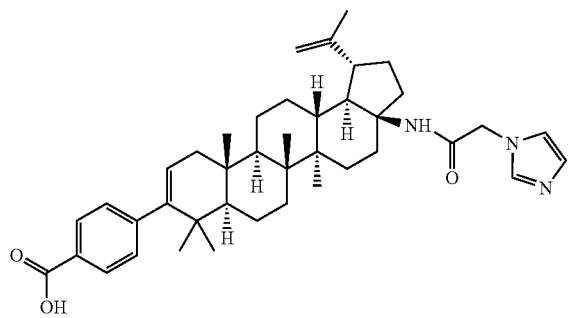

The title compound was prepared in 60% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except imidazol-1-ylacetic acid was used instead of 3-(dimethylamino)propionic acid hydrochloride in Step 1. LCMS: m/e 638.5 (M+H)$^+$, 2.05 min (method 6). $^1$H NMR (400 MHz, 1:1 CDCl$_3$:MeOD) δ=8.88 (s, 1H), 7.92 (d, J=8.3 Hz, 2H), 7.47 (ddd, J=1.6, 1.8, 9.7 Hz, 2H), 7.42 (s, 1H), 7.20 (d, J=8.5 Hz, 2H), 5.33-5.25 (m, 1H), 5.02 (d, J=5.0 Hz, 2H), 4.78 (d, J=1.3 Hz, 1H), 4.65 (d, J=1.8 Hz, 2H), 2.72 (dt, J=5.3, 11.0 Hz, 1H), 2.66-2.57 (m, 1H), 2.33 (dd, J=8.2, 12.7 Hz, 1H), 2.13 (dd, J=6.3, 17.1 Hz, 1H), 2.00-1.88 (m, 2H), 1.80 (d, J=14.6 Hz, 1H), 1.74 (br. s., 1H), 1.72 (s, 3H), 1.71-1.67 (m, 1H), 1.60-1.32 (m, 11H), 1.30-1.22 (m, 1H), 1.19-1.13 (m, 1H), 1.12 (s, 3H), 1.03 (s, 3H), 1.02 (s, 2H), 0.95 (s, 3H), 0.94 (br. s., 3H).

Example 90

Preparation of 4-((1R,3aS,5aR,5bR,7aR,11aS,11bR,13aR,13bR)-3a-(2-(1H-indol-1-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

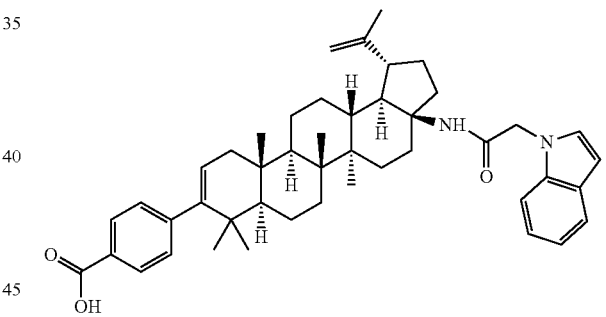

The title compound was prepared in 31% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-(1H-indol-1-yl)acetic acid was used instead of 3-(dimethylamino)propionic acid hydrochloride in Step 1. LCMS: m/e 687.6 (M+H)$^+$, 2.60 min (method 6). $^1$H NMR (400 MHz, 1:1 CDCl$_3$:MeOD) δ=7.92 (d, J=8.5 Hz, 2H), 7.72 (d, J=7.8 Hz, 1H), 7.40-7.35 (m, 1H), 7.32-7.25 (m, 1H), 7.24-7.16 (m, 4H), 6.71 (dd, J=0.8, 3.3 Hz, 1H), 5.27 (dd, J=1.6, 6.1 Hz, 1H), 4.90 (s, 1H), 4.83 (s, 2H), 4.44 (s, 1H), 4.33 (d, J=1.8 Hz, 1H), 2.48 (d, J=12.5 Hz, 1H), 2.39-2.31 (m, 1H), 2.08 (dd, J=6.4, 17.2 Hz, 1H), 1.64 (d, J=16.6 Hz, 1H), 1.54 (d, J=8.0 Hz, 2H), 1.50 (s, 3H), 1.39 (br. s., 3H), 1.37-1.23 (m, 6H), 1.23-1.13 (m, 4H), 1.04 (br. s., 1H), 1.00 (s, 4H), 0.95 (s, 3H), 0.92 (s, 3H), 0.87 (s, 3H), 0.82 (s, 3H).

Example 91 (Isomer 1) and Example 92 (Isomer 2)

Preparation of benzoic acid, 4-[(1R,3aS,5aR,5bR,7aR,11aS,11bR,13aR,13bR)-3a-[[(1,1-dioxido-4-thiomorpholinyl)phenylacetyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]

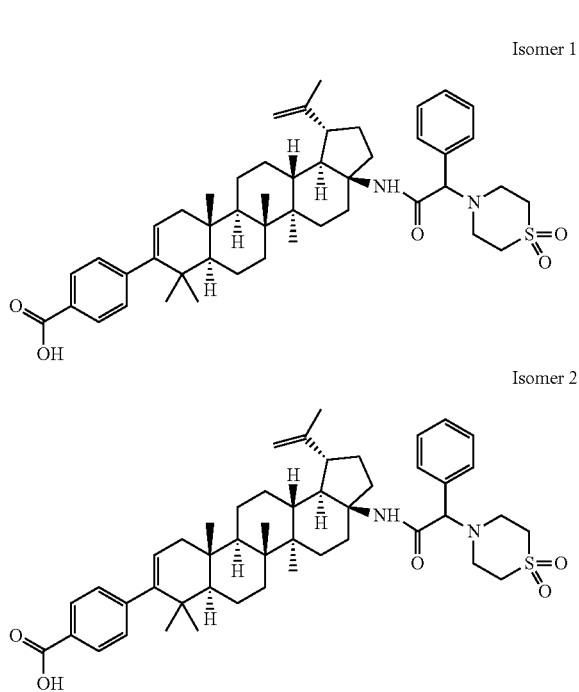

Isomer 1

Isomer 2

The title compounds were prepared in 21% and 11% yield, respectively, from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-(1,1-dioxo-1-lamda-6-4-thiazinan-4-yl)-2-phenylacetic acid was used instead of 3-(dimethylamino)propionic acid hydrochloride in Step 1. The two isomers formed in the reaction were separated by reverse phase preparative HPLC.

Isomer 1: LCMS: m/e 781.6 (M+H)$^+$, 2.21 min (method 6). $^1$H NMR (400 MHz, 1:1 CDCl$_3$:MeOD) δ=7.92 (d, J=8.5 Hz, 2H), 7.49-7.44 (m, 2H), 7.43-7.36 (m, 3H), 7.20 (d, J=8.3 Hz, 2H), 6.62 (s, 1H), 5.29 (dd, J=1.6, 6.1 Hz, 1H), 4.76 (d, J=1.3 Hz, 1H), 4.64 (br. s., 1H), 4.26 (s, 1H), 3.19-3.13 (m, 4H), 3.12-3.01 (m, 4H), 2.57-2.48 (m, 2H), 2.40 (dd, J=8.0, 11.8 Hz, 1H), 2.12 (dd, J=6.3, 17.1 Hz, 1H), 1.76 (d, J=14.6 Hz, 1H), 1.71 (br. s., 1H), 1.70 (s, 3H), 1.66 (d, J=11.0 Hz, 3H), 1.50 (d, J=16.3 Hz, 3H), 1.46-1.38 (m, 3H), 1.38-1.09 (m, 9H), 1.00 (s, 3H), 0.97 (s, 3H), 0.94 (s, 3H), 0.92 (s, 3H), 0.84 (s, 3H).

Isomer 2: LCMS: m/e 781.6 (M+H)$^+$, 2.22 min (method 6). $^1$H NMR (400 MHz, 1:1 CDCl$_3$:MeOD) δ=7.92 (d, J=8.3 Hz, 2H), 7.49-7.44 (m, 2H), 7.43-7.34 (m, 3H), 7.21 (d, J=8.3 Hz, 2H), 6.64 (s, 1H), 5.30 (dd, J=1.6, 6.1 Hz, 1H), 4.75 (s, 1H), 4.65 (s, 1H), 4.16 (s, 1H), 3.25-2.99 (m, 8H), 2.65-2.57 (m, 1H), 2.42 (dt, J=5.6, 10.9 Hz, 1H), 2.32 (dd, J=8.3, 12.5 Hz, 1H), 2.15 (dd, J=6.4, 16.9 Hz, 1H), 1.85-1.72 (m, 3H), 1.70 (s, 3H), 1.61-1.23 (m, 14H), 1.10 (s, 3H), 1.05 (s, 3H), 1.01 (s, 3H), 0.96 (s, 3H), 0.94 (s, 3H).

Example 93

Preparation of benzoic acid, 4-[(1R,3aS,5aR,5bR,7aR,11aS,11bR,13aR,13bR)-3a-[[2-(1,1-dioxido-4-thiomorpholinyl)-1-oxopropyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]

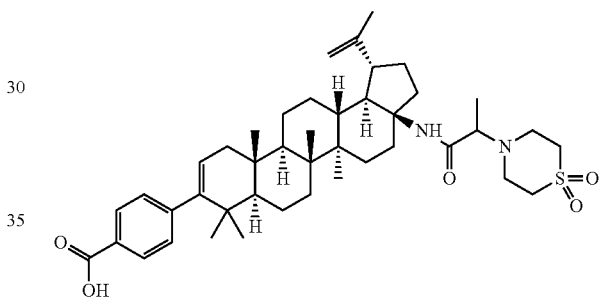

The title compound was prepared in 44% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-(1,1-dioxidothiomorpholin-4-yl)-propionic acid was used instead of 3-(dimethylamino)propionic acid hydrochloride in Step 1. LCMS: m/e 719.5 (M+H)$^+$, 2.03 min (method 6). $^1$H NMR (500 MHz, 1:1 CDCl$_3$:MeOD) δ=7.92 (d, J=8.2 Hz, 2H), 7.54 (s, 1H), 7.20 (d, J=7.9 Hz, 2H), 5.29 (d, J=5.2 Hz, 1H), 4.75 (d, J=10.4 Hz, 1H), 4.66 (br. s., 1H), 3.48-3.39 (m, 1H), 3.28-3.11 (m, 8H), 2.69-2.55 (m, 1H), 2.50-2.34 (m, 2H), 2.13 (dd, J=6.1, 17.1 Hz, 1H), 1.80 (d, J=11.6 Hz, 2H), 1.72 (s, 6H), 1.59-1.44 (m, 8H), 1.43-1.36 (m, 4H), 1.33 (dd, J=6.9, 14.8 Hz, 4H), 1.25 (d, J=6.7 Hz, 1H), 1.15 (d, J=11.0 Hz, 2H), 1.08 (s, 3H), 1.03 (s, 3H), 1.01 (s, 3H), 0.94 (br. s., 6H).

Example 94
Preparation of 4-((1R,3aS,5aR,5bR,7aR,11aS,11bR,13aR,13bR)-3a-(2-(3,3-difluoroazetidin-1-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
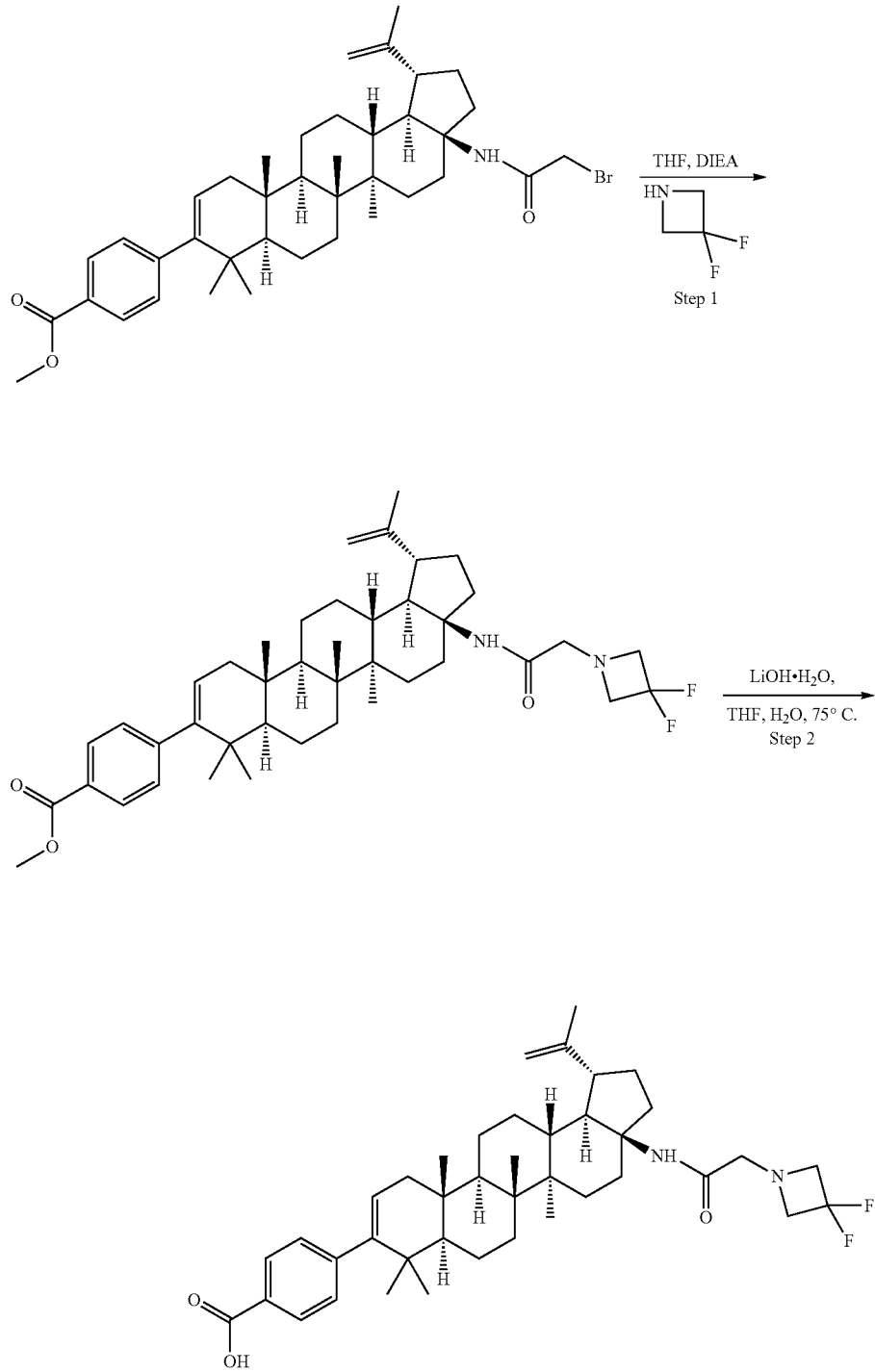

Step 1. Preparation of methyl 4-((1R,3aS,5aR,5bR, 7aR,11aS,11bR,13aR,13bR)-3a-(2-(3,3-difluoroaze-tidin-1-yl)acetamido)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate

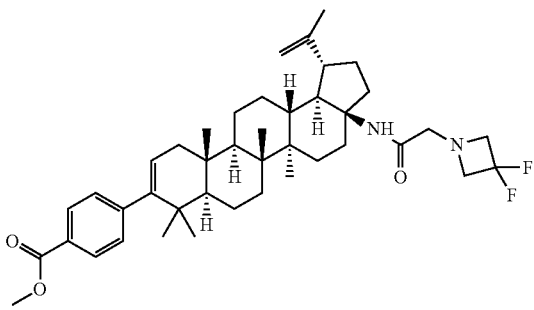

To a solution of methyl 4-((1R,3aS,5aR,5bR,7aR,11aS, 11bR,13aR,13bR)-3a-(2-bromoacetamido)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoate (129 mg, 0.194 mmol) in THF (3 mL) was added N,N-diisopropylethylamine (0.338 mL, 1.941 mmol) and 3,3-difluoroazetidine, HCl (126 mg, 0.970 mmol). The reaction mixture was stirred at 160° C. for 5 h. The mixture was concentrated and the crude residue was dissolved in THF (1.5 mL), filtered and purified by reverse phase preparative HPLC using Prep HPLC method 3 to give methyl 4-((1R,3aS,5aR,5bR,7aR,11aS,11bR,13aR,13bR)-3a-(2-(3, 3-difluoroazetidin-1-yl)acetamido)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate (28.8 mg, 0.043 mmol, 21.9% yield) as brown solid. LC/MS: m/e 677.5 (M+H)$^+$, 2.93 min (method 6).

Step 2. Preparation of give 4-((1R,3aS,5aR,5bR,7aR, 11aS,11bR,13aR,13bR)-3a-(2-(3,3-difluoroazetidin-1-yl)acetamido)-5a,5b,8,8,11a-pentamethyl-1-(prop-1-en-2-yl)-2,3,4,5,5a,5b,6,7,7a,8,11,11a,11b,12, 13,13a,13b-octadecahydro-1H-cyclopenta[a]chrysen-9-yl)benzoic acid, TFA

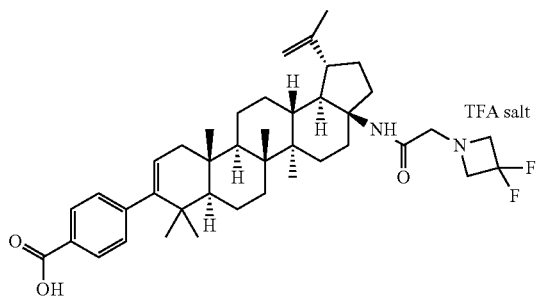

To a solution of methyl 4-((1R,3aS,5aR,5bR,7aR,11aS, 11bR,13aR,13bR)-3a-(2-(3,3-difluoroazetidin-1-yl)acetamido)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoate (28.8 mg, 0.043 mmol) in THF (Volume: 3 mL) was added a 0.753 molar solution of Li.HO.H$_2$O (0.340 mL, 0.170 mmol) in H$_2$O. The reaction was heated to 75° C. for 6 h and was then concentrated to a brown viscous oil. The crude residue was dissolved in THF (1.3 mL) and 0.2 mL 1N HCl, filtered and purified by reverse phase preparative HPLC using prep HPLC method 3 to give 4-((1R,3aS,5aR,5bR,7aR,11aS,11bR,13aR, 13bR)-3a-(2-(3,3-difluoroazetidin-1-yl)acetamido)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoic acid, TFA (17.6 mg, 0.022 mmol, 52.7% yield) as a light yellow solid. LCMS: m/e 663.7 (M+H)$^+$, 2.22 min (method 2). $^1$H NMR (500 MHz, 1:1 CDCl$_3$:METHANOL-d$_4$) δ 7.90 (d, J=8.2 Hz, 2H), 7.18 (d, J=8.2 Hz, 2H), 5.27 (d, J=4.6 Hz, 1H), 4.73 (s, 1H), 3.88 (t, J=12.5 Hz, 2H), 3.69-3.59 (m, 1H), 3.55-3.39 (m, 3H), 2.64-2.53 (m, 2H), 2.39 (dd, J=12.2, 8.2 Hz, 1H), 2.10 (dd, J=17.1, 6.4 Hz, 1H), 1.93-1.73 (m, 3H), 1.69 (s, 3H), 1.67 (d, J=4.6 Hz, 1H), 1.58-1.39 (m, 8H), 1.39-1.29 (m, 3H), 1.23 (d, J=10.1 Hz, 1H), 1.11 (d, J=13.7 Hz, 2H), 1.06 (s, 3H), 1.00 (s, 3H), 0.99 (s, 3H), 0.92 (br. s., 3H), 0.91 (br. s., 3H).

Example 95

Preparation of 4-((1R,3aS,5aR,5bR,7aR,11aS,11bR, 13aR,13bR)-5a,5b,8,8,11a-pentamethyl-3a-(2-(2-oxopyrrolidin-1-yl)acetamido)-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoic acid

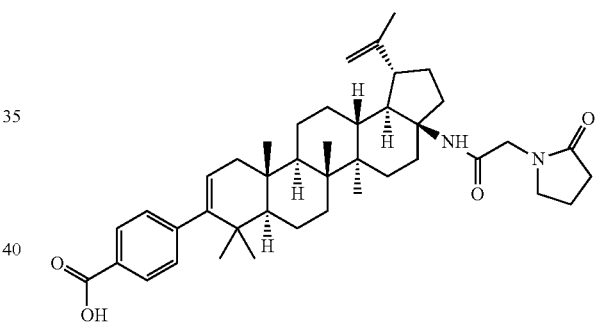

The title compound was prepared in 14% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid, except 2-(2-oxopyrrolidin-1-yl)acetic acid was used instead of 3-(dimethylamino)propionic acid hydrochloride in Step 1. LCMS: m/e 655.5 (M+H)$^+$, 1.99 min (method 6). $^1$H NMR (500 MHz, 1:1 CDCl$_3$:MeOD) δ=7.92 (d, J=7.9 Hz, 2H), 7.20 (d, J=7.9 Hz, 2H), 6.77 (s, 1H), 5.29 (d, J=4.7 Hz, 1H), 4.75 (d, J=1.3 Hz, 1H), 4.63 (s, 1H), 3.97-3.85 (m, 2H), 3.58-3.51 (m, 2H), 2.65-2.54 (m, 2H), 2.47 (t, J=8.0 Hz, 2H), 2.38 (dd, J=8.4, 12.5 Hz, 1H), 2.17-2.07 (m, 3H), 1.95-1.85 (m, 1H), 1.83-1.74 (m, 2H), 1.73 (br. s., 1H), 1.70 (s, 3H), 1.68-1.62 (m, 1H), 1.60-1.43 (m, 8H), 1.42-1.22 (m, 6H), 1.13 (br. s., 1H), 1.09 (s, 3H), 1.01 (s, 6H), 0.94 (s, 3H), 0.93 (s, 3H).

Example 96

Preparation of 4-((1R,3aS,5aR,5bR,7aR,11aS,11bR,13aR,13bR)-3a-(2-(4-isopropylpiperazin-1-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

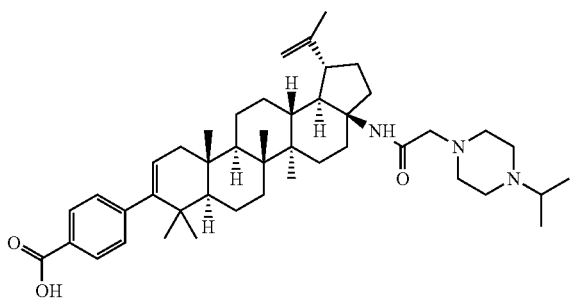

The title compound was prepared in 22% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except (4-isopropyl-piperazin-1-yl)-acetic acid was used instead of 3-(dimethylamino)propionic acid hydrochloride in Step 1. LCMS: m/e 698.6 (M+H)$^+$, 2.64 min (method 6). $^1$H NMR (500 MHz, 1:1 CDCl$_3$:MeOD) δ=7.92 (d, J=8.2 Hz, 2H), 7.37 (br. s., 1H), 7.20 (d, J=8.2 Hz, 2H), 6.34-6.03 (m, 1H), 5.29 (d, J=4.6 Hz, 1H), 4.76 (br. s., 1H), 4.70 (br. s., 1H), 3.95 (br. s., 1H), 3.84-3.55 (m, 8H), 3.17 (q, J=7.2 Hz, 2H), 2.64 (d, J=13.1 Hz, 2H), 2.39 (dd, J=8.1, 11.4 Hz, 1H), 2.12 (dd, J=6.3, 17.2 Hz, 1H), 1.96-1.84 (m, 2H), 1.79 (d, J=12.5 Hz, 1H), 1.76-1.65 (m, 5H), 1.59-1.40 (m, 14H), 1.35 (t, J=7.2 Hz, 4H), 1.29-1.21 (m, 1H), 1.15 (d, J=6.1 Hz, 1H), 1.10 (br. s., 3H), 1.02 (s, 3H), 1.01 (br. s., 2H), 0.94 (br. s., 3H), 0.93 (br. s., 3H).

Example 97

Preparation of 4-((1R,3aS,5aR,5bR,7aR,11aS,11bR,13aR,13bR)-5a,5b,8,8,11a-pentamethyl-3a-(2-morpholinoacetamido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

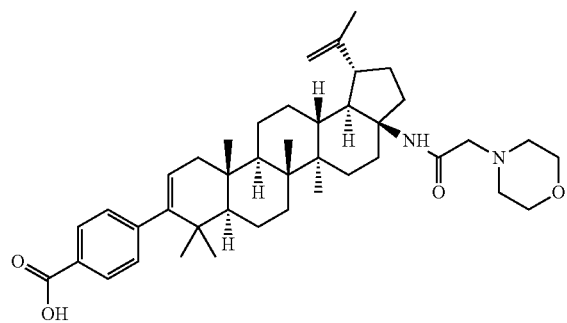

The title compound was prepared in 40% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except morpholin-4-yl-acetic acid was used instead of 3-(dimethylamino)propionic acid hydrochloride in Step 1. LCMS: m/e 657.6 (M+H)$^+$, 2.20 min (method 6). $^1$H NMR (500 MHz, 1:1 CDCl$_3$:MeOD) δ=7.91 (d, J=7.9 Hz, 2H), 7.48 (br. s., 1H), 7.19 (d, J=8.2 Hz, 2H), 5.28 (d, J=4.9 Hz, 1H), 4.77 (br. s., 1H), 4.12-3.79 (m, 6H), 3.57-3.40 (m, 2H), 3.22-3.11 (m, 1H), 2.74 (br. s., 1H), 2.65 (d, J=12.8 Hz, 1H), 2.42-2.29 (m, 1H), 2.12 (dd, J=6.1, 17.1 Hz, 1H), 2.03-1.85 (m, 2H), 1.79 (d, J=12.8 Hz, 1H), 1.72 (br. s., 1H), 1.71 (s, 3H), 1.69 (br. s., 1H), 1.60-1.30 (m, 12H), 1.24 (d, J=5.8 Hz, 1H), 1.14 (br. s., 1H), 1.10 (br. s., 4H), 1.02 (br. s., 3H), 1.00 (br. s., 3H), 0.93 (br. s., 3H), 0.92 (br. s., 3H).

Example 98

Preparation of 4-((1R,3aS,5aR,5bR,7aR,11aS,11bR,13aR,13bR)-5a,5b,8,8,11a-pentamethyl-1-(prop-1-en-2-yl)-3a-(2-thiomorpholinoacetamido)-2,3,3a,4,5,5a,5b,6,7,7a,8,11,11a,11b,12,13,13a,13b-octadecahydro-1H-cyclopenta[a]chrysen-9-yl)benzoic acid

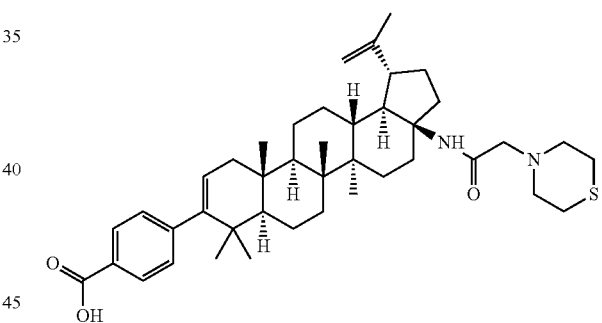

The title compound was prepared in 44% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-thiomorpholinoacetic acid was used instead of 3-(dimethylamino)propionic acid hydrochloride in Step 1. LCMS: m/e 671.8 (M−H)$^−$, 2.37 min (method 6). $^1$H NMR (500 MHz, 1:1 CDCl$_3$:MeOD) δ=7.92 (d, J=8.2 Hz, 2H), 7.47 (s, 1H), 7.20 (d, J=8.2 Hz, 2H), 5.29 (d, J=4.3 Hz, 1H), 4.75 (s, 1H), 3.79-3.63 (m, 2H), 3.58 (td, J=6.5, 12.9 Hz, 1H), 3.47-3.35 (m, 3H), 2.95 (br. s., 4H), 2.68-2.57 (m, 2H), 2.37 (dd, J=8.4, 12.4 Hz, 1H), 2.13 (dd, J=6.4, 17.1 Hz, 1H), 1.92-1.82 (m, 2H), 1.81-1.76 (m, 1H), 1.73 (br. s., 1H), 1.71 (s, 3H), 1.69-1.64 (m, 1H), 1.60-1.31 (m, 12H), 1.30-1.22 (m, 1H), 1.19-1.11 (m, 2H), 1.09 (s, 3H), 1.03 (s, 3H), 1.01 (s, 3H), 0.94 (br. s., 3H), 0.93 (br. s., 3H).

Example 99

Preparation of benzoic acid, 4-[(1R,3aS,5aR,5bR, 7aR,11aS,11bR,13aR,13bR)-3a-[[3-cyclohexyl-2-(1, 1-dioxido-4-thiomorpholinyl)-1-oxopropyl]amino]- 2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]

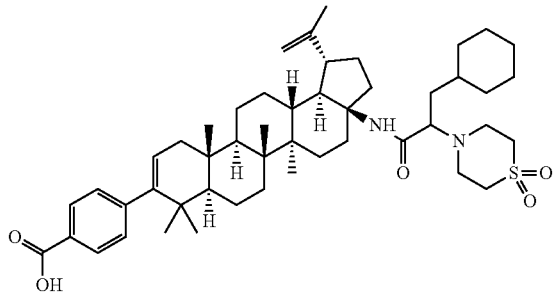

The title compound was prepared in 23% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid, except 3-cyclohexyl-2-(1,1-dioxo-1lambda6,- 4,thiazinan-4-yl)propanoic acid was used instead of 3-(dimethylamino)propionic acid hydrochloride in Step 1. LCMS: m/e 801.6 (M+H)$^+$, 2.43 min (method 6). $^1$H NMR (500 MHz, 1:1 CDCl$_3$:MeOD) δ=7.92 (d, J=8.2 Hz, 2H), 7.20 (d, J=8.2 Hz, 2H), 6.56 (s, 1H), 5.29 (d, J=4.6 Hz, 1H), 4.76 (s, 1H), 3.58 (td, J=6.6, 13.4 Hz, 1H), 3.44 (dd, J=5.0, 9.6 Hz, 1H), 3.30-3.25 (m, 3H), 3.24-3.15 (m, 2H), 3.14-3.06 (m, 2H), 2.68 (d, J=13.4 Hz, 1H), 2.56 (dt, J=5.6, 11.1 Hz, 1H), 2.41 (dd, J=8.4, 12.7 Hz, 1H), 2.13 (dd, J=6.3, 17.2 Hz, 1H), 1.92-1.75 (m, 5H), 1.73 (br. s., 1H), 1.72 (s, 3H), 1.70-1.64 (m, 4H), 1.61-1.40 (m, 10H), 1.40-1.29 (m, 3H), 1.28-1.11 (m, 7H), 1.09 (s, 3H), 1.03 (s, 3H), 1.01 (s, 3H), 0.97 (d, J=3.1 Hz, 1H), 0.94 (br. s., 3H), 0.93 (br. s., 3H).

Example 100

Preparation of benzoic acid, 4-[(1R,3aS,5aR,5bR, 7aR,11aS,11bR,13aR,13bR)-2,3,3a,4,5,5a,5b,6,7,7a, 8,11,11a,11b,12,13,13a,13b-octadecahydro-5a,5b,8, 8,11a-pentamethyl-1-(1-methylethenyl)-3a-[[[methyl (tetrahydro-1,1-dioxido-3-thienyl)amino]acetyl] amino]-1H-cyclopenta[a]chrysen-9-yl]

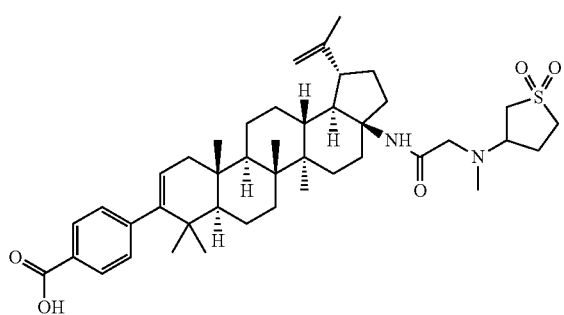

The title compound was prepared in 17% yield from methyl 4-((1R,3aS,5aR,5bR,7aR,11aS,11bR,13aR,13bR)- 3a-amino-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid, except N-(1,1-dioxidotetrahydro-3-thienyl)-N-methylglycine was used instead of 3-(dimethylamino) propionic acid hydrochloride in Step 1. LCMS: m/e 719.5 (M+H)$^+$, 2.00 min (method 6). $^1$H NMR (500 MHz, CDCl$_3$: MeOD) δ=7.92 (d, J=8.2 Hz, 2H), 7.30 (d, J=7.6 Hz, 1H), 7.20 (d, J=8.2 Hz, 2H), 5.29 (d, J=4.9 Hz, 1H), 3.80 (br. s., 1H), 3.40 (dd, J=7.6, 13.4 Hz, 1H), 3.30-3.05 (m, 4H), 2.60 (br. s., 1H), 2.57 (d, J=1.5 Hz, 3H), 2.55-2.41 (m, 3H), 2.23 (quin, J=10.6 Hz, 1H), 2.13 (dd, J=6.1, 17.1 Hz, 1H), 1.91-1.76 (m, 2H), 1.73 (br. s., 1H), 1.71 (s, 3H), 1.70 (br. s., 1H), 1.60-1.29 (m, 12H), 1.25 (d, J=7.0 Hz, 1H), 1.21-1.11 (m, 3H), 1.09 (s, 3H), 1.03 (s, 3H), 1.01 (s, 3H), 0.94 (s, 3H), 0.93 (br. s., 3H).

Example 101

Preparation of benzoic acid, 4-[(1R,3aS,5aR,5bR, 7aR,11aS,11bR,13aR,13bR)-3a-[[3-(1,1-dioxido-4-thiomorpholinyl)-1-oxo-3-(2-thienyl)propyl]amino]- 2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl

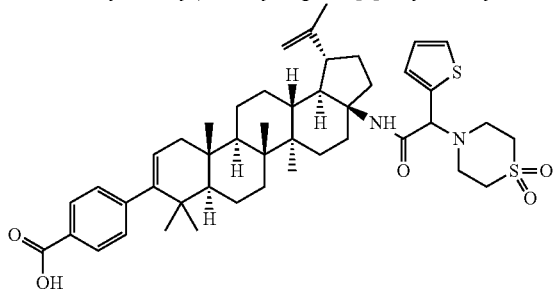

The title compound was prepared in 39% yield from methyl 4-((1R,3aS,5aR,5bR,7aR,11aS,11bR,13aR,13bR)- 3a-amino-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid, except 3-(1,1-dioxo-1lambda-6,4-thiazinan-4-yl)-3-(2-thienyl)propanoic acid was used instead of 3-(dimethylamino)propionic acid hydrochloride in Step 1. LCMS: m/e 801.6 (M+H)$^+$, 2.16 min (method 6). $^1$H NMR (500 MHz, 1:1 CDCl$_3$:MeOD) δ=7.92 (d, J=8.2 Hz, 2H), 7.36-7.28 (m, 1H), 7.20 (d, J=8.2 Hz, 2H), 7.05-6.91 (m, 2H), 6.59 (s, 1H), 5.29 (d, J=4.9 Hz, 1H), 4.74 (d, J=7.6 Hz, 1H), 4.60-4.52 (m, 2H), 3.18-3.05 (m, 6H), 3.04-2.93 (m, 2H), 2.91-2.72 (m, 2H), 2.68-2.49 (m, 2H), 2.48-2.40 (m, 1H), 2.27 (dd, J=8.5, 11.9 Hz, 1H), 2.12 (dd, J=4.9, 17.1 Hz, 1H), 1.93-1.72 (m, 3H), 1.69 (d, J=7.9 Hz, 3H), 1.64 (d, J=11.6 Hz, 1H), 1.61-1.38 (m, 8H), 1.37-1.19 (m, 5H), 1.13 (br. s., 1H), 1.11 (br. s., 15H), 1.10 (br. s., 2H), 1.02 (br. s., 1H), 1.01 (br. s., 2H), 1.01 (br. s., 1H), 1.00 (br. s., 2H), 0.95 (br. s., 1H), 0.95 (br. s., 2H), 0.93 (s, 3H).

Example 102

Preparation of 4-((1R,3aS,5aR,5bR,7aR,11aS,11bR,13aR,13bR)-5a,5b,8,8,11a-pentamethyl-1-(prop-1-en-2-yl)-3a-(2-(pyrazin-2-yl)acetamido)-2,3,3a,4,5,5a,5b,6,7,7a,8,11,11a,11b,12,13,13a,13b-octadecahydro-1H-cyclopenta[a]chrysen-9-yl)benzoic acid

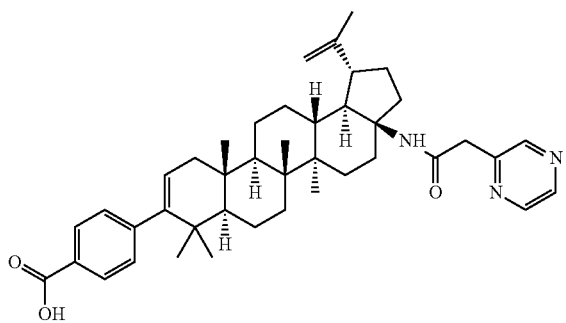

The title compound was prepared in 14% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-pyrazine acetic acid was used instead of 3-(dimethylamino)propionic acid hydrochloride in Step 1. LCMS: m/e 650.6 (M+H)$^+$, 2.12 min (method 6). $^1$H NMR (500 MHz, 1:1 CDCl$_3$:MeOD) δ=8.68-8.50 (m, 3H), 7.92 (d, J=8.2 Hz, 2H), 7.20 (d, J=8.2 Hz, 3H), 5.29 (dd, J=1.7, 6.0 Hz, 1H), 4.76 (s, 1H), 3.79 (q, J=14.3 Hz, 2H), 2.66-2.53 (m, 2H), 2.42-2.31 (m, 1H), 2.12 (dd, J=6.4, 17.1 Hz, 1H), 1.91-1.74 (m, 3H), 1.72 (br. s., 1H), 1.71 (s, 2H), 1.67 (d, J=11.9 Hz, 2H), 1.57-1.18 (m, 13H), 1.17-1.02 (m, 3H), 1.00 (br. s., 3H), 1.00 (br. s., 3H), 0.94 (s, 3H), 0.92 (br. s., 3H), 0.92 (br. s., 3H).

Example 103

Preparation of 4-((1R,3aS,5aR,5bR,7aR,11aS,11bR,13aR,13bR)-3a-(2-(1H-tetrazol-1-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

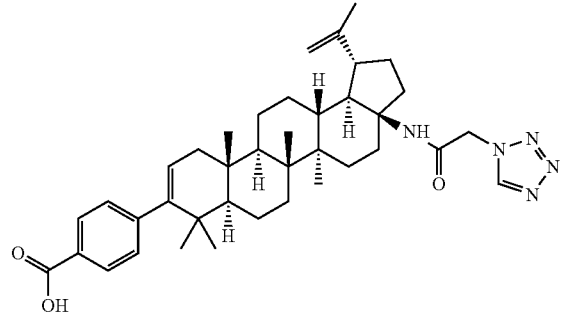

The title compound was prepared in 33% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 1-H-tetrazole-1-acetic acid was used instead of 3-(dimethylamino)propionic acid hydrochloride in Step 1. LCMS: m/e 638.7 (M−H)$^-$, 1.98 min (method 6). $^1$H NMR (500 MHz, 1:1 CDCl$_3$:MeOD) δ=9.10 (s, 1H), 7.93 (d, J=8.2 Hz, 2H), 7.39 (s, 1H), 7.21 (d, J=8.2 Hz, 2H), 5.30 (dd, J=1.5, 6.1 Hz, 1H), 5.27 (d, J=1.5 Hz, 2H), 4.78 (d, J=1.2 Hz, 1H), 4.65 (s, 1H), 2.71 (dt, J=5.2, 11.1 Hz, 1H), 2.64-2.56 (m, 1H), 2.34 (dd, J=8.1, 12.7 Hz, 1H), 2.13 (dd, J=6.4, 17.1 Hz, 1H), 2.00-1.86 (m, 2H), 1.80 (d, J=11.0 Hz, 1H), 1.74 (br. s., 1H), 1.72 (s, 3H), 1.71-1.66 (m, 1H), 1.62-1.30 (m, 11H), 1.29-1.22 (m, 1H), 1.20-1.14 (m, 1H), 1.12 (s, 3H), 1.10 (d, J=4.3 Hz, 1H), 1.03 (s, 6H), 0.95 (s, 3H), 0.94 (s, 3H).

Example 104

Preparation of 4-((1R,3aS,5aR,5bR,7aR,11aS,11bR,13aR,13bR)-3a-(2-(7-chloro-2-oxo-2,4-dihydro-1H-benzo[d][1,3]oxazin-1-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

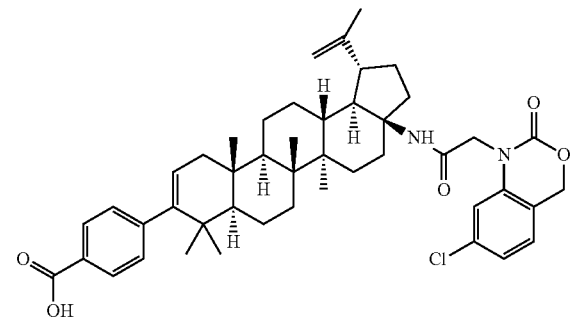

The title compound was prepared in 36% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-(6-chloro-3-oxo-2H-benzo[b][1,4]oxazin-4(3H)-yl)acetic acid was used instead of 3-(dimethylamino)propionic acid hydrochloride in Step 1. LCMS: m/e 653.5 (M+H)$^+$, 2.29 min (method 6). $^1$H NMR (500 MHz, 1:1 CDCl$_3$:MeOD) δ=7.92 (d, J=8.5 Hz, 2H), 7.21 (d, J=8.5 Hz, 2H), 7.05-7.01 (m, 1H), 7.01-6.97 (m, 2H), 6.83 (s, 1H), 5.29 (dd, J=1.7, 6.3 Hz, 1H), 4.73 (d, J=1.8 Hz, 1H), 4.70 (d, J=1.2 Hz, 2H), 4.66 (br. s., 1H), 4.63 (s, 1H), 4.57-4.50 (m, 1H), 2.65-2.57 (m, 1H), 2.51-2.34 (m, 2H), 2.13 (dd, J=6.4, 17.1 Hz, 1H), 1.96-1.85 (m, 1H), 1.83-1.72 (m, 3H), 1.70 (s, 3H), 1.69-1.64 (m, 1H), 1.63-1.55 (m, 2H), 1.54-1.45

(m, 4H), 1.45-1.30 (m, 5H), 1.30-1.23 (m, 1H), 1.18-1.12 (m, 2H), 1.10 (s, 3H), 1.02 (s, 6H), 0.95 (s, 3H), 0.94 (s, 3H).

Example 105

Preparation of 4-((1R,3aS,5aR,5bR,7aR,11aS,11bR, 13aR,13bR)-5a,5b,8,8,11a-pentamethyl-3a-(2-(2-oxooxazolidin-3-yl)acetamido)-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl) benzoic acid

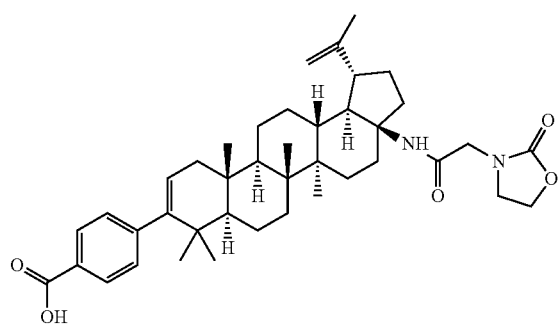

The title compound was prepared in 29% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid, except 2-(2-oxooxazolidin-3-yl)acetic acid was used instead of 3-(dimethylamino)propionic acid hydrochloride in Step 1. LCMS: m/e 657.5 (M+H)+, 1.97 min (method 6). ¹H NMR (500 MHz, 1:1 CDCl₃:MeOD) δ=7.92 (d, J=8.2 Hz, 2H), 7.20 (d, J=8.5 Hz, 2H), 6.82 (s, 1H), 5.29 (dd, J=1.7, 6.3 Hz, 1H), 4.76 (d, J=1.5 Hz, 1H), 4.64 (s, 2H), 4.43 (dt, J=1.7, 8.2 Hz, 2H), 3.98-3.84 (m, 2H), 3.74 (t, J=8.1 Hz, 2H), 2.69-2.56 (m, 2H), 2.40 (dd, J=8.1, 12.4 Hz, 1H), 2.13 (dd, J=6.4, 17.1 Hz, 1H), 1.98-1.81 (m, 2H), 1.81-1.75 (m, 1H), 1.73 (br. s., 1H), 1.71 (s, 3H), 1.70-1.65 (m, 1H), 1.61-1.43 (m, 7H), 1.42-1.29 (m, 4H), 1.29-1.21 (m, 2H), 1.16-1.12 (m, 1H), 1.10 (s, 3H), 1.02 (s, 3H), 1.02 (s, 3H), 0.95 (s, 3H), 0.94 (s, 3H).

Example 106

Preparation of 4-((1R,3aS,5aR,5bR,7aR,11aS,11bR, 13aR,13bR)-3a-(2-(2-hydroxyethylamino)acetamido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

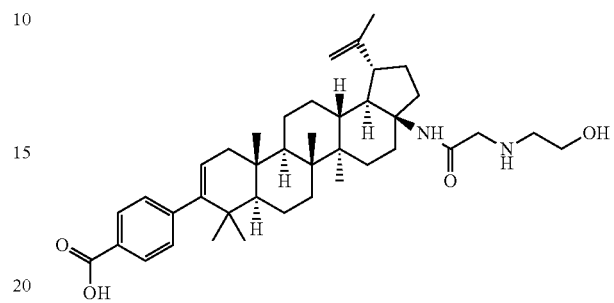

The title compound was prepared in 14% yield as a by-product during the above described preparation of 4-((1R, 3aS,5aR,5bR,7aR,11aS,11bR,13aR,13bR)-5a,5b,8,8,11a-pentamethyl-3a-(2-(2-oxooxazolidin-3-yl)acetamido)-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid. LCMS: m/e 631.5 (M+H)+, 1.94 min (method 6). ¹H NMR (500 MHz, 1:1 CDCl₃:MeOD) δ=7.92 (d, J=8.2 Hz, 2H), 7.20 (d, J=8.2 Hz, 2H), 5.29 (d, J=4.6 Hz, 1H), 4.76 (s, 1H), 4.65 (s, 1H), 3.87-3.75 (m, 4H), 3.17-3.12 (m, 2H), 2.73-2.62 (m, 2H), 2.37 (dd, J=8.4, 12.1 Hz, 1H), 2.13 (dd, J=6.3, 17.2 Hz, 1H), 2.16-2.09 (m, 1H), 1.95-1.85 (m, 2H), 1.79 (d, J=11.0 Hz, 1H), 1.74 (br. s., 1H), 1.72 (s, 3H), 1.71-1.66 (m, 1H), 1.58-1.47 (m, 6H), 1.47-1.32 (m, 5H), 1.30-1.23 (m, 1H), 1.16-1.11 (m, 2H), 1.10 (s, 3H), 1.03 (s, 3H), 1.02 (s, 3H), 0.95 (s, 3H), 0.94 (br. s., 3H).

Example 107

Preparation of 4-((1R,3aS,5aR,5bR,7aR,11aS,11bR, 13aR,13bR)-5a,5b,8,8,11a-pentamethyl-3a-(2-((S)-2-oxo-4-phenyloxazolidin-3-yl)acetamido)-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)benzoic acid

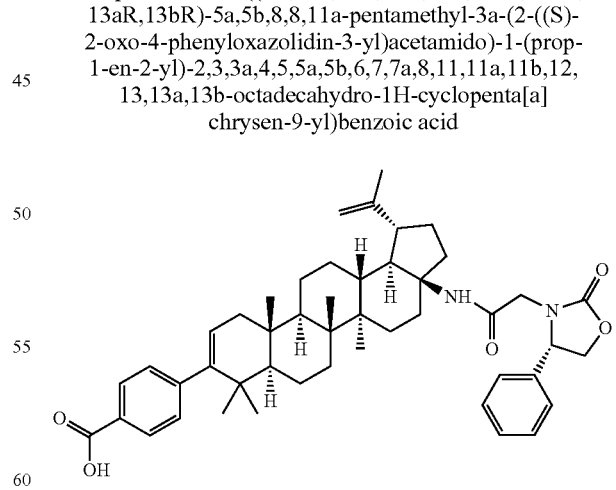

The title compound was prepared in 30% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except (S)-(+)-2-oxo-4-phenyl-3-oxazolidineacetic acid was used instead of 3-(dimethylamino)propionic acid hydrochloride in Step 1. LCMS: m/e 733.5 (M+H)+, 2.25 min (method 6). 1H NMR (400 MHz, 1:1 CDCl3:MeOD) δ=7.92 (d, J=8.3 Hz, 2H), 7.47-7.39 (m, 3H), 7.37-7.32 (m, 2H), 7.20 (d, J=8.3 Hz, 2H), 6.60 (s, 1H), 5.28 (d, J=4.5 Hz, 1H), 5.04 (t, J=8.3 Hz, 1H), 4.75 (t, J=8.9 Hz, 1H), 4.71 (s, 1H), 4.61 (br. s., 1H), 4.25-4.19 (m, 1H), 4.04 (d, J=16.3 Hz, 1H), 3.40 (d, J=16.3 Hz, 1H), 2.65-2.59 (m, 1H), 2.47 (dt, J=4.8, 11.0 Hz, 1H), 2.37 (dd, J=8.2, 11.7 Hz, 1H), 2.11 (dd, J=6.3, 17.1 Hz, 1H), 1.84-1.70 (m, 4H), 1.69 (s, 3H), 1.66-1.59 (m, 1H), 1.58-1.40 (m, 7H), 1.39-1.22 (m, 6H), 1.09 (br. s., 1H), 1.07 (s, 3H), 1.00 (s, 6H), 0.95 (s, 3H), 0.94 (br. s., 3H).

δ=7.92 (d, J=8.3 Hz, 2H), 7.49-7.45 (m, 3H), 7.45-7.40 (m, 2H), 7.19 (d, J=8.3 Hz, 2H), 5.28 (d, J=4.8 Hz, 1H), 4.71 (s, 1H), 4.62 (br. s., 2H), 4.35 (dd, J=4.9, 7.7 Hz, 1H), 4.04-3.90 (m, 2H), 3.72-3.55 (m, 2H), 2.60-2.50 (m, 2H), 2.36 (dd, J=8.5, 12.0 Hz, 1H), 2.10 (dd, J=6.4, 17.2 Hz, 1H), 1.91-1.75 (m, 2H), 1.73 (d, J=7.3 Hz, 2H), 1.69 (s, 3H), 1.65-1.60 (m, 1H), 1.50-1.37 (m, 6H), 1.37-1.19 (m, 7H), 1.07 (d, J=18.6 Hz, 3H), 0.99 (s, 6H), 0.97 (s, 3H), 0.94 (br. s., 3H), 0.94 (br. s., 3H).

Example 109

Preparation of 4-((1R,3aS,5aR,5bR,7aR,11aS,11bR,13aR,13bR)-3a-(2-((S)-3-(tert-butoxycarbonylamino)-2-oxopyrrolidin-1-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

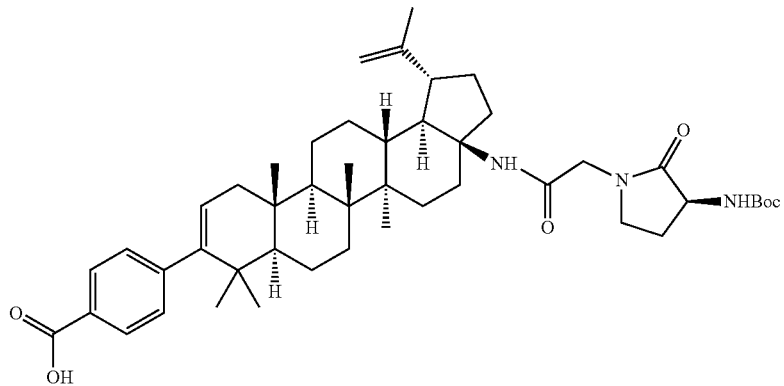

The title compound was prepared in 34% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except (S)-2-(3-(tert-butoxycarbonylamino)-2-oxopyrrolidin-1-yl)acetic acid was used instead of 3-(dimethylamino)propionic acid hydrochloride in Step 1. LCMS: m/e 770.6 (M+H)+, 2.07 min (method 6). 1H NMR (400 MHz, 1:1 CDCl3:MeOD) δ=7.92 (d, J=8.0 Hz, 2H), 7.20 (d, J=8.0 Hz, 2H), 6.83-6.60 (m, 1H), 5.29 (d, J=4.8 Hz, 1H), 4.76 (s, 1H), 4.63 (br. s., 1H), 4.32-4.16 (m, 1H), 4.07-3.84 (m, 2H), 3.44 (d, J=7.0 Hz, 2H), 2.70-2.56 (m, 2H), 2.55-2.44 (m, 1H), 2.43-2.31 (m, 1H), 2.13 (dd, J=6.3, 17.1 Hz, 1H), 2.08-1.95 (m, 1H), 1.94-1.82 (m, 2H), 1.81-1.73 (m, 2H), 1.71 (s, 3H), 1.68-1.62 (m, 1H), 1.61-1.48 (m, 6H), 1.46 (s, 9H), 1.43-1.22 (m, 6H), 1.13 (br. s., 1H), 1.10 (d, J=3.8 Hz, 3H), 1.02 (s, 6H), 0.95 (br. s., 3H), 0.94 (br. s., 3H).

Example 108

Preparation of 4-((1R,3aS,5aR,5bR,7aR,11aS,11bR,13aR,13bR)-3a-(2-((S)-2-hydroxy-1-phenylethylamino)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

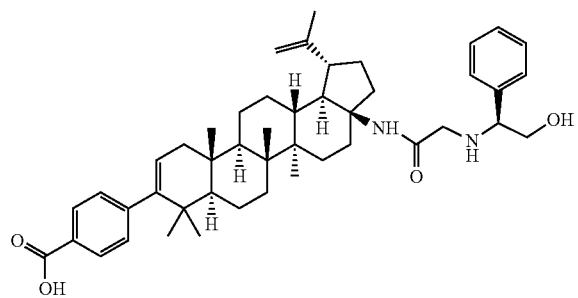

The title compound was prepared in 8% yield as a by-product during the above described preparation of 4-((1R,3aS,5aR,5bR,7aR,11aS,11bR,13aR,13bR)-5a,5b,8,8,11a-pentamethyl-3a-(2-((S)-2-oxo-4-phenyloxazolidin-3-yl)acetamido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid. LCMS: m/e 707.5 (M+H)+, 2.18 min (method 6). 1H NMR (400 MHz, 1:1 CDCl3:MeOD)

Example 110 (Isomer 1) and Example 111 (Isomer 2)

Preparation of benzoic acid, 4-[(1R,3aS,5aR,5bR, 7aR,11aS,11bR,13aR,13bR)-3a-[[2-(1,1-dioxido-4-thiomorpholinyl)-3-methyl-1-oxobutyl]amino]-2,3, 3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]

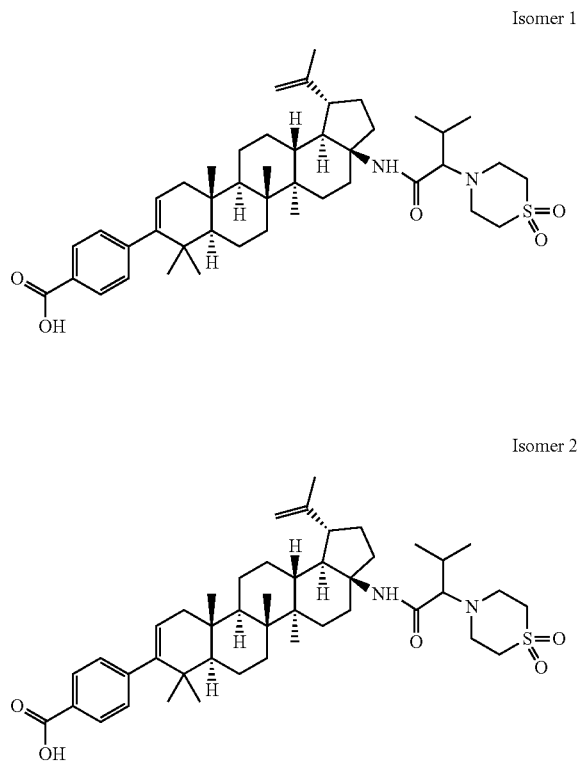

The title compounds were prepared in 9% yield each from methyl 4-((1R,3aS,5aR,5bR,7aR,11aS,11bR,13aR,13bR)-3a-amino-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid, except 2-(1,1-dioxo-1-lamda-6,4-thiazinan-4-yl)-3-methylbutanoic acid (91 mg, 0.388 mmol) was used instead of 3-(dimethylamino)propionic acid hydrochloride in Step 1. The two isomers formed in the reaction were separated by reverse phase preparative HPLC.

Isomer 1: LCMS: m/e 747.5 (M+H)$^+$, 2.23 min (method 6). $^1$H NMR (500 MHz, 1:1 CDCl$_3$:MeOD) δ=7.92 (d, J=8.2 Hz, 2H), 7.20 (d, J=8.5 Hz, 2H), 6.42 (s, 1H), 5.29 (dd, J=1.5, 6.1 Hz, 1H), 4.75 (d, J=1.5 Hz, 1H), 4.64 (br. s., 1H), 3.31-3.23 (m, 2H), 3.16-3.07 (m, 4H), 3.06-2.97 (m, 2H), 2.84 (d, J=10.4 Hz, 1H), 2.77-2.71 (m, 1H), 2.63 (dt, J=5.5, 11.1 Hz, 1H), 2.42 (dd, J=8.2, 12.5 Hz, 1H), 2.12 (dd, J=6.4, 17.1 Hz, 1H), 2.03 (qd, J=6.5, 16.9 Hz, 1H), 1.91-1.81 (m, 2H), 1.78 (d, J=12.2 Hz, 1H), 1.73 (br. s., 1H), 1.71 (s, 3H), 1.68 (d, J=11.3 Hz, 1H), 1.62 (dd, J=3.4, 13.4 Hz, 1H), 1.57 (d, J=4.9 Hz, 1H), 1.51 (br. s., 3H), 1.47 (d, J=12.5 Hz, 1H), 1.44-1.28 (m, 5H), 1.28-1.23 (m, 2H), 1.18 (d, J=13.7 Hz, 1H), 1.11 (dd, J=4.0, 12.8 Hz, 1H), 1.08 (s, 3H), 1.02 (s, 3H), 1.01 (s, 4H), 0.99 (s, 2H), 0.94 (s, 3H), 0.94 (br. s., 3H), 0.90 (d, J=6.4 Hz, 3H).

Isomer 2: LCMS: m/e 747.5 (M+H)$^+$, 2.29 min (method 6). $^1$H NMR (500 MHz, 1:1 CDCl$_3$:MeOD) δ=7.92 (d, J=8.5 Hz, 2H), 7.20 (d, J=8.2 Hz, 2H), 6.40 (s, 1H), 5.29 (dd, J=1.5, 6.1 Hz, 1H), 4.76 (d, J=1.5 Hz, 1H), 4.64 (s, 1H), 3.77-3.72 (m, 1H), 3.23-3.14 (m, 2H), 3.13-3.06 (m, 4H), 3.05-2.99 (m, 2H), 2.80 (d, J=10.4 Hz, 1H), 2.74-2.67 (m, 1H), 2.61 (dt, J=5.3, 11.1 Hz, 1H), 2.49 (dd, J=8.4, 12.7 Hz, 1H), 2.12 (dd, J=6.4, 17.1 Hz, 1H), 2.08-2.01 (m, 1H), 1.99-1.91 (m, 1H), 1.88 (ddd, J=3.1, 3.3, 6.8 Hz, 1H), 1.86-1.82 (m, 1H), 1.78 (d, J=11.0 Hz, 1H), 1.72 (br. s., 1H), 1.71 (s, 3H), 1.69 (d, J=4.6 Hz, 1H), 1.67-1.63 (m, 1H), 1.61-1.53 (m, 2H), 1.51 (br. s., 1H), 1.48 (br. s., 2H), 1.47-1.41 (m, 2H), 1.12 (dd, J=3.4, 13.4 Hz, 2H), 1.07 (s, 3H), 1.01 (br. s., 3H), 1.00 (s, 3H), 0.99 (s, 3H), 0.97 (d, J=6.7 Hz, 3H), 0.93 (s, 3H), 0.93 (s, 3H).

Example 112

Preparation of benzoic acid, 4-[(1R,3aS,5aR,5bR, 7aR,11aS,11bR,13aR,13bR)-2,3,3a,4,5,5a,5b,6,7,7a, 8,11,11a,11b,12,13,13a,13b-octadecahydro-5a,5b,8, 8,11a-pentamethyl-1-(1-methylethenyl)-3a-[[3-methyl-1-oxo-2-[(tetrahydro-1,1-dioxido-3-thienyl) amino]butyl]amino]-1H-cyclopenta[a]chrysen-9-yl]

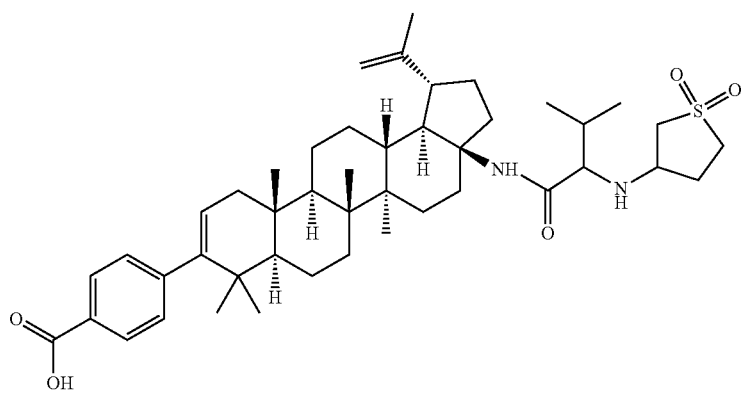

The title compound was prepared in 30% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid, except 2-(1,1-dioxo-tetrahydro-1lambda6-thiophene-3-yl-amino)-3-methylbutyric acid was used instead of 3-(dimethylamino)propionic acid hydrochloride in Step 1. LCMS: m/e 747.5 (M+H)$^+$, 2.09 min (method 6). $^1$H NMR (500 MHz, 1:1 CDCl$_3$:MeOD) δ=7.92 (d, J=8.2 Hz, 2H), 7.25 (br. s., 1H), 7.19 (d, J=8.2 Hz, 2H), 5.28 (d, J=4.9 Hz, 1H), 4.78 (s, 1H), 4.65 (br. s., 1H), 3.73 (ddd, J=6.6, 6.7, 9.3 Hz, 1H), 3.47 (dd, J=7.2, 13.3 Hz, 1H), 3.41 (dt, J=4.1, 8.6 Hz, 1H), 3.27 (br. s., 1H), 3.17-3.07 (m, 1H), 2.75-2.63 (m, 2H), 2.59 (dd, J=7.2, 13.0 Hz, 1H), 2.43 (dd, J=8.5, 12.2 Hz, 1H), 2.35 (dd, J=8.9, 12.8 Hz, 1H), 2.25-2.16 (m, 1H), 2.12 (dd, J=6.3, 17.2 Hz, 1H), 1.91-1.76 (m, 3H), 1.74 (br. s., 1H), 1.71 (s, 3H), 1.69 (br. s., 1H), 1.58-1.47 (m, 6H), 1.46-1.35 (m, 4H), 1.35-1.28 (m, 1H), 1.25 (d, J=9.8 Hz, 1H), 1.18-1.12 (m, 2H), 1.10 (d, J=6.7 Hz, 3H), 1.08 (s, 3H), 1.06 (d, J=7.3 Hz, 3H), 1.03 (s, 3H), 1.00 (s, 3H), 0.93 (s, 3H), 0.93 (br. s., 3H).

Example 113

Preparation of 4-((1R,3aS,5aR,5bR,7aR,11aS,11bR,13aR,13bR)-5a,5b,8,8,11a-pentamethyl-3a-(1-(methylsulfonyl)pyrrolidine-2-carboxamido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

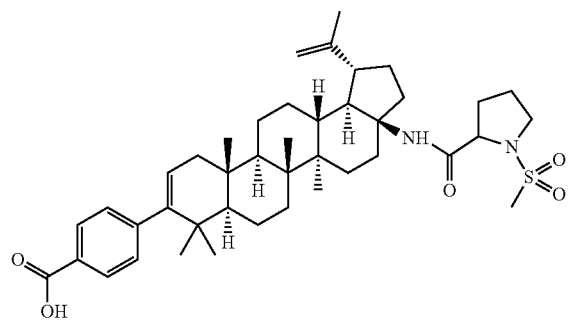

The title compound was prepared in 17% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 1-(methylsulfonyl)pyrrolidine-2-carboxylic acid was used instead of 3-(dimethylamino) propionic acid hydrochloride in Step 1. LCMS: m/e 705.5 (M+H)$^+$, 2.04 min (method 6). $^1$H NMR (500 MHz, 1:1 CDCl$_3$:MeOD) δ=7.92 (d, J=8.5 Hz, 2H), 7.20 (d, J=8.2 Hz, 2H), 6.88 (s, 1H), 5.29 (dd, J=1.5, 6.1 Hz, 1H), 4.76 (d, J=1.5 Hz, 1H), 4.10 (dd, J=3.1, 8.8 Hz, 1H), 3.60 (ddd, J=3.5, 7.0, 10.2 Hz, 1H), 3.40 (dt, J=6.4, 9.6 Hz, 1H), 2.96 (s, 3H), 2.62-2.52 (m, 2H), 2.42 (dd, J=8.2, 11.6 Hz, 1H), 2.31 (dddd, J=3.2, 3.4, 6.4, 9.7 Hz, 1H), 2.21-2.16 (m, 1H), 2.16-2.10 (m, 1H), 2.03 (tdd, J=3.2, 6.6, 13.0 Hz, 1H), 1.99-1.89 (m, 2H), 1.82-1.75 (m, 1H), 1.75-1.72 (m, 1H), 1.70 (s, 3H), 1.69-1.66 (m, 1H), 1.58-1.46 (m, 6H), 1.46-1.29 (m, 5H), 1.28-1.22 (m, 1H), 1.14 (d, J=13.1 Hz, 2H), 1.09 (s, 3H), 1.03 (s, 3H), 1.01 (s, 3H), 0.93 (s, 6H).

Example 114

Preparation of 4-((1R,3aS,5aR,5bR,7aR,11aS,11bR,13aR,13bR)-3a-((S)-1-(tert-butoxycarbonyl)-4,4-difluoropyrrolidine-2-carboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

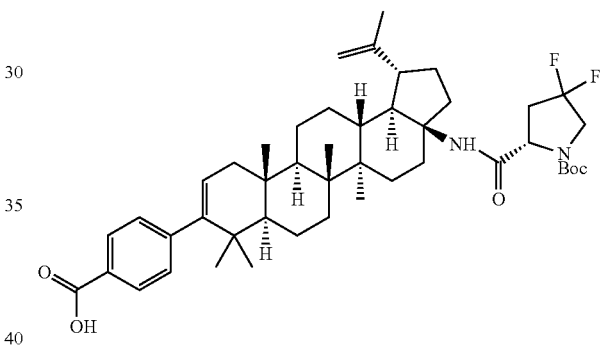

The title compound was prepared in 29% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid, except (S)-1-(tert-butoxycarbonyl)-4,4-difluoropyrrolidine-2-carboxylic acid was used instead of 3-(dimethylamino)propionic acid hydrochloride in Step 1. LCMS: m/e 763.5 (M+H)$^+$, 2.55 min (method 6). $^1$H NMR (500 MHz, 1:1 CDCl$_3$:MeOD) δ=7.92 (d, J=8.5 Hz, 2H), 7.20 (d, J=8.5 Hz, 2H), 6.46 (br. s., 1H), 5.29 (dd, J=1.7, 6.3 Hz, 1H), 4.72 (s, 1H), 4.63 (br. s., 1H), 4.50 (d, J=9.2 Hz, 1H), 3.84 (br. s., 1H), 3.72 (td, J=6.7, 13.4 Hz, 1H), 2.84 (br. s., 1H), 2.55 (d, J=13.4 Hz, 1H), 2.51-2.37 (m, 2H), 2.12 (dd, J=6.4, 17.1 Hz, 1H), 1.96 (br. s., 1H), 1.73 (br. s., 1H), 1.70 (s, 4H), 1.61 (br. s., 2H), 1.56 (br. s., 9H), 1.53-1.45 (m, 5H), 1.45-1.37 (m, 3H), 1.36-1.29 (m, 2H), 1.28-1.23 (m, 1H), 1.17-1.09 (m, 2H), 1.08 (s, 3H), 1.02 (s, 6H), 0.94 (s, 3H), 0.93 (s, 3H).

Example 115

Preparation of 4-((1R,3aS,5aR,5bR,7aR,11aS,11bR, 13aR,13bR)-5a,5b,8,8,11a-pentamethyl-1-(prop-1-en-2-yl)-3a-(2-(thiophene-2-sulfonamido)acetamido)-2,3,3a,4,5,5a,5b,6,7,7a,8,11,11a,11b,12,13, 13a,13b-octadecahydro-1H-cyclopenta[a]chrysen-9-yl)benzoic acid

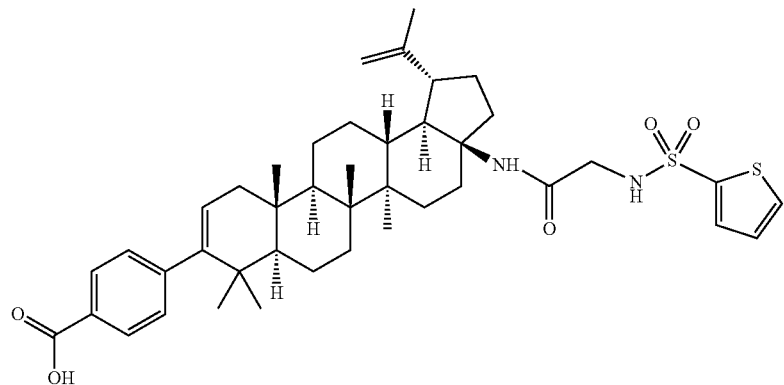

The title compound was prepared in 31% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid, except 2-(thiophene-2-sulfonamido)acetic acid was used instead of 3-(dimethylamino)propionic acid hydrochloride in Step 1. LCMS: m/e 733.6 (M+H)$^+$, 2.06 min (method 6). $^1$H NMR (500 MHz, 1:1 CDCl$_3$:MeOD) δ=7.92 (d, J=8.5 Hz, 2H), 7.73 (dd, J=1.4, 5.0 Hz, 1H), 7.66 (dd, J=1.2, 3.7 Hz, 1H), 7.20 (d, J=8.2 Hz, 2H), 7.16 (dd, J=3.8, 5.0 Hz, 1H), 6.88 (s, 1H), 5.32-5.26 (m, 1H), 4.78 (d, J=1.5 Hz, 1H), 3.58-3.45 (m, 2H), 2.63-2.57 (m, 1H), 2.56-2.50 (m, 1H), 2.42 (dd, J=8.2, 12.2 Hz, 1H), 2.13 (dd, J=6.3, 17.2 Hz, 1H), 1.98-1.88 (m, 1H), 1.87-1.76 (m, 2H), 1.73 (br. s., 1H), 1.72 (s, 3H), 1.70-1.66 (m, 1H), 1.63-1.53 (m, 3H), 1.53-1.46 (m, 4H), 1.45-1.37 (m, 3H), 1.37-1.30 (m, 2H), 1.28-1.22 (m, 1H), 1.14 (s, 3H), 1.10 (d, J=3.1 Hz, 1H), 1.03 (s, 3H), 1.02 (s, 3H), 0.94 (s, 3H), 0.94 (br. s., 3H).

Example 116

Preparation of benzoic acid, 4-[(1R,3aS,5aR,5bR, 7aR,11aS,11bR,13aR,13bR)-2,3,3a,4,5,5a,5b,6,7,7a, 8,11,11a,11b,12,13,13a,13b-octadecahydro-5a,5b,8, 8,11a-pentamethyl-1-(1-methylethenyl)-3a-[[1-oxo-2-[(tetrahydro-1,1-dioxido-3-thienyl)amino]butyl] amino]-1H-cyclopenta[a]chrysen-9-yl]

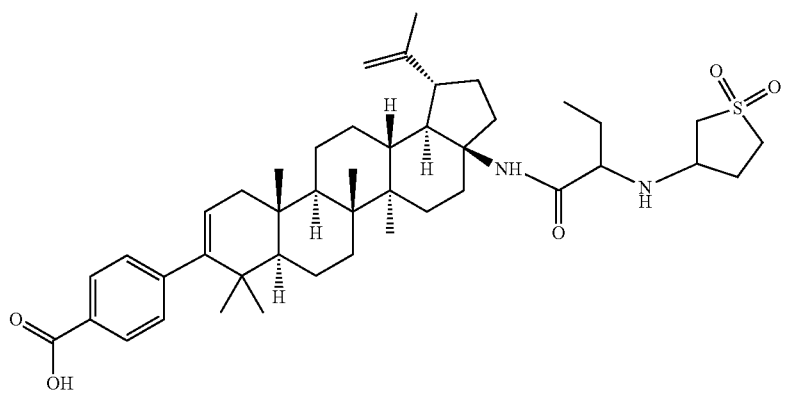

The title compound was prepared in 19% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid, except 2-(1,1-dioxo-tetrahydro-1lambda6-thiophene-3-yl-amino)-butyric acid was used instead of 3-(dimethylamino)propionic acid hydrochloride in Step 1. LCMS: m/e 733.6 (M+H)$^+$, 2.00 min (method 6). $^1$H NMR (500 MHz, 1:1 CDCl$_3$:MeOD) δ=7.92 (d, J=8.2 Hz, 2H), 7.38 (br. s., 1H), 7.20 (d, J=8.2 Hz, 2H), 5.29 (d, J=4.6 Hz, 1H), 4.77 (d, J=8.5 Hz, 1H), 3.77 (br. s., 1H), 3.51-3.36 (m, 2H), 3.22-3.09 (m, 2H), 2.65 (d, J=15.9 Hz, 3H), 2.37 (br. s., 2H), 2.13 (dd, J=6.4, 17.4 Hz, 1H), 1.96-1.77 (m, 5H), 1.73 (br. s., 1H), 1.73 (s, 3H), 1.72-1.67 (m, 1H), 1.61-1.52 (m, 2H), 1.50 (d, J=2.1 Hz, 3H), 1.48-1.30 (m, 6H), 1.29-1.23 (m, 1H), 1.22-1.14 (m, 2H), 1.12 (s, 2H), 1.09 (d, J=1.8 Hz, 2H), 1.08-1.05 (m, 1H), 1.04 (d, J=1.8 Hz, 4H), 1.03 (d, J=4.0 Hz, 4H), 0.95 (br. s., 3H), 0.94 (br. s., 3H).

Example 117

Preparation of benzoic acid, 4-[(1R,3aS,5aR,5bR,7aR,11aS,11bR,13aR,13bR)-2,3,3a,4,5,5a,5b,6,7,7a,8,11,11a,11b,12,13,13a,13b-octadecahydro-5a,5b,8,8,11a-pentamethyl-1-(1-methylethenyl)-3a-[[[(tetrahydro-1,1-dioxido-2H-1,2-thiazin-2-yl)acetyl]amino]-1H-cyclopenta[a]chrysen-9-yl]

The title compound was prepared in 13% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(3-(dimethylamino)propanamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid, except (1,1-dioxo-1,6-[1,2]thiazinan-2-yl) acetic acid was used instead of 3-(dimethylamino)propionic acid hydrochloride in Step 1. LCMS: m/e 705.5 (M+H)$^+$, 2.01 min (method 6). $^1$H NMR (500 MHz, METHANOL-d$_4$) δ=7.92 (d, J=8.5 Hz, 2H), 7.20 (d, J=8.5 Hz, 2H), 6.83 (s, 1H), 5.32-5.26 (m, 1H), 4.77 (d, J=1.5 Hz, 1H), 4.64 (s, 1H), 3.83-3.72 (m, 2H), 3.63-3.46 (m, 2H), 3.37 (s, 2H), 3.21-3.11 (m, 2H), 2.62-2.54 (m, 1H), 2.53-2.50 (m, 1H), 2.49-2.41 (m, 1H), 2.32-2.23 (m, 2H), 2.13 (dd, J=6.6, 17.2 Hz, 1H), 1.99-1.87 (m, 1H), 1.78 (br. s., 1H), 1.77-1.73 (m, 3H), 1.72 (s, 3H), 1.71-1.67 (m, 1H), 1.62-1.51 (m, 3H), 1.48 (d, J=5.2 Hz, 3H), 1.46-1.31 (m, 5H), 1.28-1.23 (m, 1H), 1.14 (d, J=13.4 Hz, 2H), 1.11 (s, 3H), 1.03 (s, 3H), 1.02 (s, 3H), 0.94 (s, 3H), 0.94 (s, 3H).

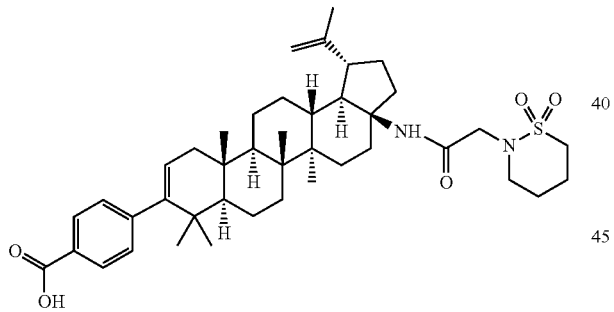

Example 118

Preparation of 4-((1R,3aS,5aR,5bR,7aR,11aS,11bR,13aR,13bR)-3a-(2-(4,4-difluoropiperidin-1-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

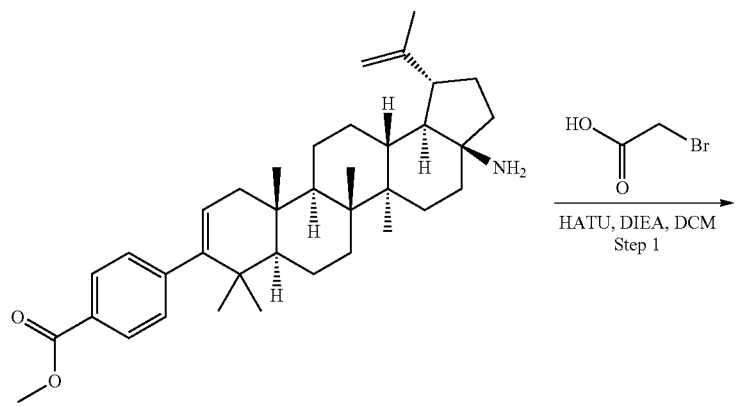

-continued
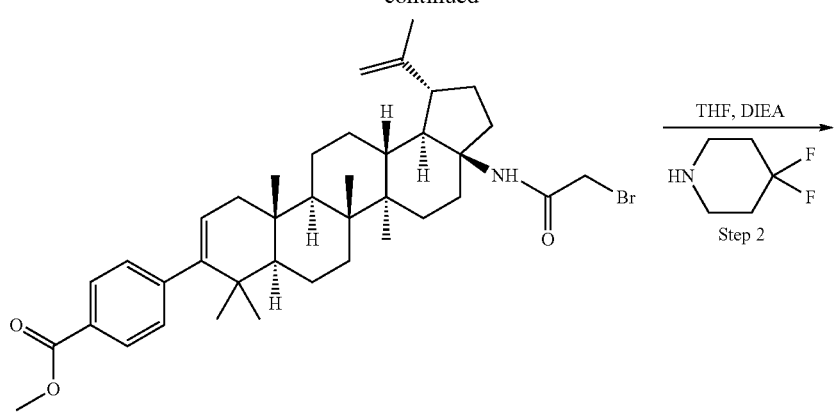
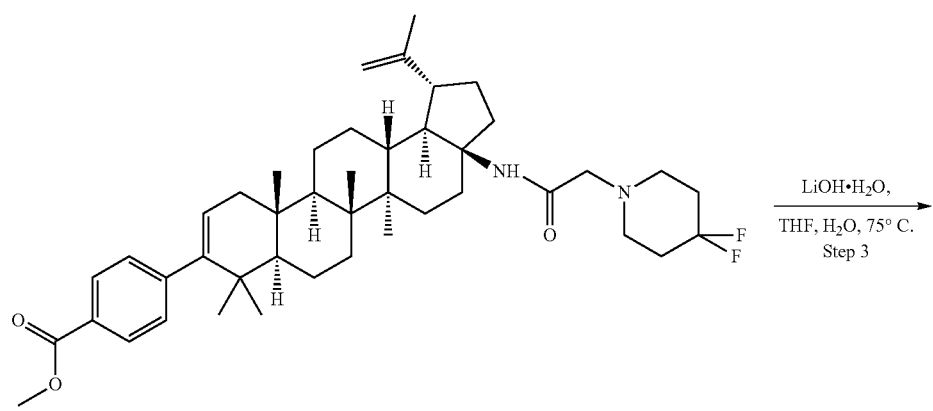
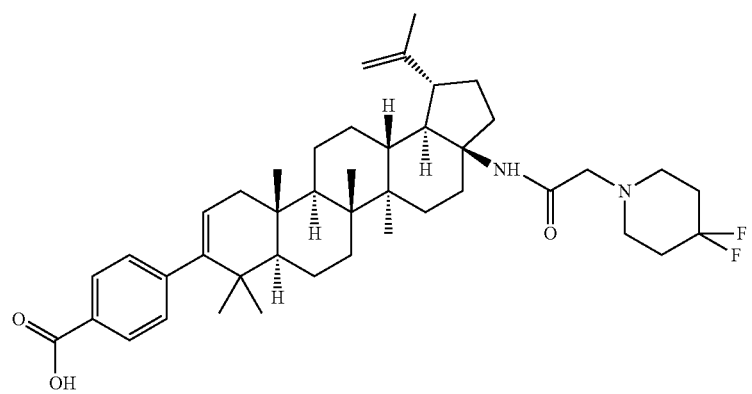
example 118

Step 1. Preparation of methyl 4-((1R,3aS,5aR,5bR, 7aR,11aS,11bR,13aR,13bR)-3a-(2-bromoacetamido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate

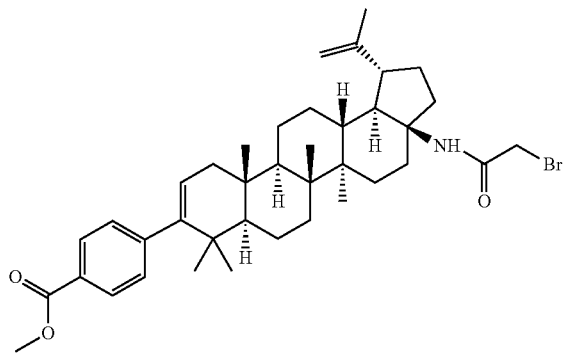

To a solution of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate, HCl (403 mg, 0.694 mmol) in DCM (10 mL) was added N,N-diisopropylethylamine (0.484 mL, 2.78 mmol), bromoacetic acid (106 mg, 0.764 mmol) and 2-(3H-[1,2,3] triazolo[4,5-β]pyridin-3-yl)-1,1,3,3-tetramethylisouronium hexafluorophosphate(V) (317 mg, 0.833 mmol). The reaction mixture was stirred at rt for 15 h. Then, the reaction was concentrated and the crude residue was dissolved in THF (3.0 mL) filtered and purified by reverse phase preparative HPLC using HPLC method 3 to give methyl 4-((1R,3aS,5aR,5bR, 7aR,11aS,11bR,13aR,13bR)-3a-(2-bromoacetamido)-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)benzoate (148.9 mg, 0.224 mmol, 32.3% yield) as white solid. LCMS: m/e 664.6 (M+H)$^+$, 2.41 min (method 6).

Step 2. Preparation of methyl 4-((1R,3aS,5aR,5bR, 7aR,11aS,11bR,13aR,13bR)-3a-(2-(4,4-difluoropiperidin-1-yl)acetamido)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate

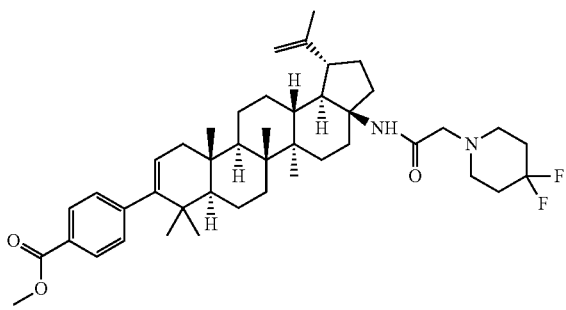

To a solution of methyl 4-((1R,3aS,5aR,5bR,7aR,11aS, 11bR,13aR,13bR)-3a-(2-bromoacetamido)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoate (30 mg, 0.045 mmol) in THF (3 mL) was added N,N-diisopropylethylamine (0.039 mL, 0.226 mmol) and 4,4-difluoropiperidine, HCl (21.34 mg, 0.135 mmol). The reaction mixture was stirred at 80° C. for 18 h. Additional N,N-diisopropylethylamine (0.078 mL, 0.452 mmol) and 4,4-difluoropiperidine, HCl (40 mg, 0.354 mmol) were added, and the mixture was heated to 150° C. in a microwave for 7.5 h. The mixture was concentrated to brown viscous oil. The crude residue was dissolved in THF (1.5 mL), filtered and purified by reverse phase preparative HPLC using HPLC method 3 to give methyl 4-((1R,3aS,5aR,5bR,7aR, 11aS,11bR,13aR,13bR)-3a-(2-(4,4-difluoropiperidin-1-yl) acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, TFA (13.1 mg, 0.016 mmol, 35.4% yield) as white solid. LCMS: m/e 705.6 (M+H)$^+$, 2.95 min (method 6). $^1$H NMR (500 MHz, CHLOROFORM-d) δ=7.94 (d, J=8.5 Hz, 2H), 7.90-7.80 (m, 1H), 7.21 (d, J=8.2 Hz, 2H), 6.32 (s, 1H), 5.31 (dd, J=1.4, 6.0 Hz, 1H), 4.77 (s, 1H), 4.67 (s, 1H), 3.93 (s, 3H), 3.72-3.61 (m, 3H), 3.51-3.41 (m, 5H), 2.83 (d, J=2.7 Hz, 2H), 2.63 (d, J=13.1 Hz, 1H), 2.56 (dt, J=5.3, 10.9 Hz, 1H), 2.39 (dd, J=8.2, 12.8 Hz, 1H), 2.12 (dd, J=6.4, 17.1 Hz, 1H), 1.91-1.81 (m, 1H), 1.79-1.73 (m, 2H), 1.72 (s, 3H), 1.70-1.64 (m, 1H), 1.54-1.40 (m, 7H), 1.39-1.26 (m, 3H), 1.26-1.21 (m, 1H), 1.18-1.09 (m, 2H), 1.04 (s, 3H), 1.02 (s, 3H), 1.00 (s, 3H), 0.95 (br. s., 3H), 0.94 (br. s., 3H).

Step 3. Preparation of 4-((1R,3aS,5aR,5bR,7aR, 11aS,11bR,13aR,13bR)-3a-(2-(4,4-difluoropiperidin-1-yl)acetamido)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid

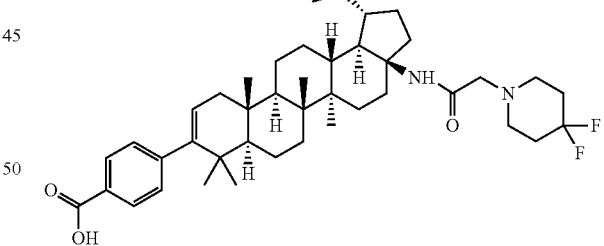

To a solution of methyl 4-((1R,3aS,5aR,5bR,7aR,11aS, 11bR,13aR,13bR)-3a-(2-(4,4-difluoropiperidin-1-yl)acetamido)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoate (13.1 mg, 0.019 mmol) in THF (3 mL) was added a 0.753 molar aqueous solution of LiOH.H$_2$O (0.149 mL, 0.074 mmol). The reaction was heated to 75° C. for 6 h. The reaction was concentrated to brown viscous oil, and the crude material was purified by reverse phase preparative HPLC using HPLC method 3 to give 4-((1R,3aS,5aR,5bR,7aR,11aS,11bR,13aR, 13bR)-3a-(2-(4,4-difluoropiperidin-1-yl)acetamido)-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)benzoic acid, TFA (9.4 mg, 0.012 mmol, 62.8% yield) as white solid. LCMS: m/e 691.6 (M+H)+, 2.34 min (method 6). ¹H NMR (500 MHz, METHANOL-d₄) δ=7.92 (d, J=8.2 Hz, 2H), 7.43 (s, 1H), 7.20 (d, J=8.5 Hz, 2H), 5.30 (dd, J=1.7, 6.3 Hz, 1H), 4.75 (d, J=1.2 Hz, 1H), 4.66 (d, J=1.5 Hz, 1H), 3.71-3.58 (m, 2H), 3.24 (br. s., 3H), 2.67-2.61 (m, 1H), 2.57 (dt, J=5.3, 11.1 Hz, 1H), 2.41 (dd, J=8.2, 12.5 Hz, 1H), 2.33-2.22 (m, 4H), 2.13 (dd, J=6.4, 17.1 Hz, 1H), 1.95-1.83 (m, 1H), 1.81 (d, J=9.2 Hz, 2H), 1.74 (br. s., 1H), 1.72 (s, 3H), 1.71-1.67 (m, 1H), 1.59-1.43 (m, 8H), 1.42-1.31 (m, 3H), 1.29-1.23 (m, 1H), 1.18-1.12 (m, 2H), 1.09 (s, 3H), 1.04 (s, 3H), 1.02 (s, 3H), 0.95 (s, 3H), 0.94 (br. s., 3H).

Example 119

Preparation of 4-((1R,3aS,5aR,5bR,7aR,11aS,11bR,13aR,13bR)-3a-(2-(3,3-difluoropyrrolidin-1-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

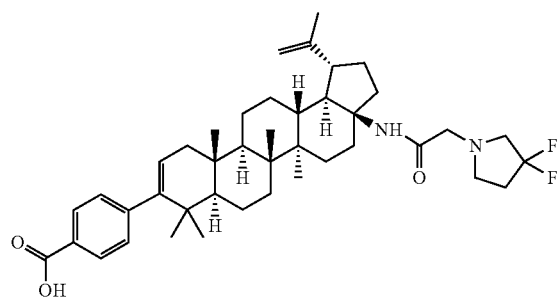

The title compound was prepared in 38% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-(2-(4,4-difluoropiperidin-1-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except and 3,3-difluoropyrrolidine, HCl was used instead of 4,4-difluoropiperidine, HCl in Step 2. LCMS: m/e 677.5 (M+H)+, 2.26 min (method 6). ¹H NMR (500 MHz, 1:1 CDCl₃:MeOD) δ=7.92 (d, J=8.2 Hz, 2H), 7.40 (s, 1H), 7.20 (d, J=8.2 Hz, 2H), 5.29 (dd, J=1.7, 6.3 Hz, 1H), 4.75 (d, J=1.2 Hz, 1H), 4.65 (s, 1H), 3.59-3.44 (m, 2H), 3.43-3.36 (m, 1H), 3.31-3.20 (m, 2H), 2.63-2.55 (m, 1H), 2.55-2.47 (m, 3H), 2.47-2.39 (m, 1H), 2.13 (dd, J=6.4, 17.1 Hz, 1H), 1.94-1.83 (m, 1H), 1.81-1.76 (m, 2H), 1.76-1.73 (m, 1H), 1.72 (s, 3H), 1.70-1.65 (m, 1H), 1.57-1.46 (m, 6H), 1.46-1.40 (m, 2H), 1.39-1.31 (m, 2H), 1.26 (dd, J=2.7, 10.7 Hz, 1H), 1.19-1.10 (m, 2H), 1.09 (s, 3H), 1.03 (s, 3H), 1.02 (s, 3H), 0.95 (s, 3H), 0.94 (s, 3H).

General Procedure for Parallel Synthesis of C-17 Amides:

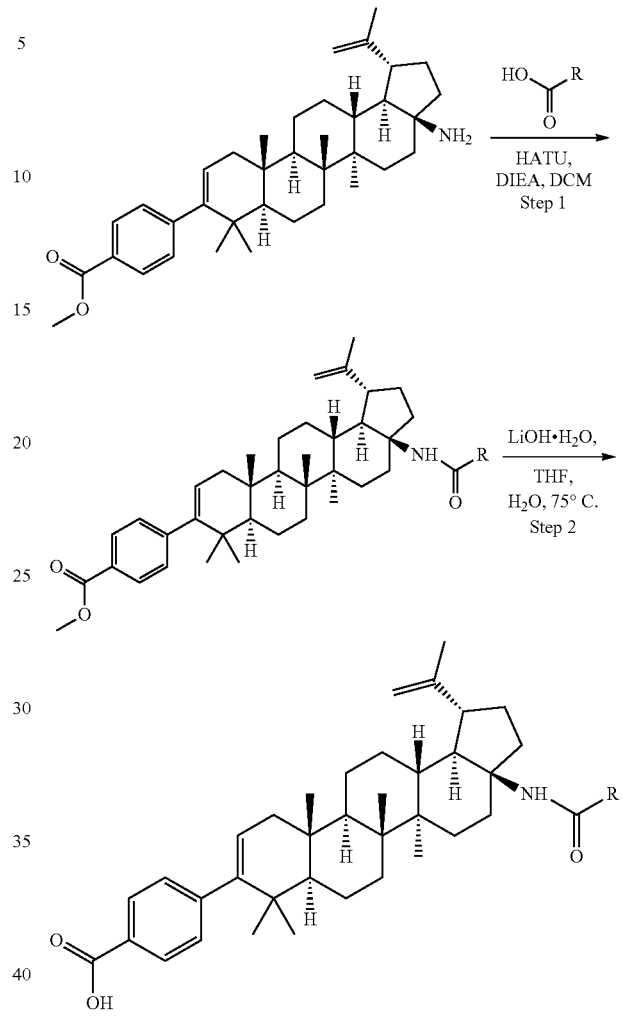

A stock solution of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, HCl (0.990 g, 1.7 mmol) and DIPEA (1.10 g, 8.52 mmol) in DCE (13 mL) was prepared. A stock solution of the HATU (1.94 g, 5.11 mmol) in DCE (13 mL) was prepared. To each of the carboxylic acids (0.393 mmol) weighed into 16×100 mm Wheaton vials was added 1 mL of the stock HATU solution. The vials were capped and shaken at rt for 10 min before adding 1 mL of the stock methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, HCl/DIPEA solution to each vial. The vials were capped and shaken at rt for 18 h. Samples were concentrated. A stock solution of lithium hydroxide monohydrate (0.286 g, 6.81 mmol) in water (6.50 mL) was prepared. To each of the reaction vials was added 2.5 mL of THF and 0.5 mL of the stock lithium hydroxide solution. The vials were capped and the reactions were stirred at 75° C. for 18 h. Added an additional 0.5 mL of the stock lithium hydroxide solution and stirred at 75° C. for an additional 48 h. Samples were concentrated, redissolved in a small quantity of a mixture of THF and methanol, filtered and purified by reverse phase preparative HPLC.

Example 120

Preparation of benzoic acid, 4-[(1R,3aS,5aR,5bR, 7aR,11aS,11bR,13aR,13bR)-2,3,3a,4,5,5a,5b,6,7,7a, 8,11,11a,11b,12,13,13a,13b-octadecahydro-5a,5b,8, 8,11a-pentamethyl-1-(1-methylethenyl)-3a-[(3-pyridinylacetyl)amino]-1H-cyclopenta[a]chrysen-9-yl]

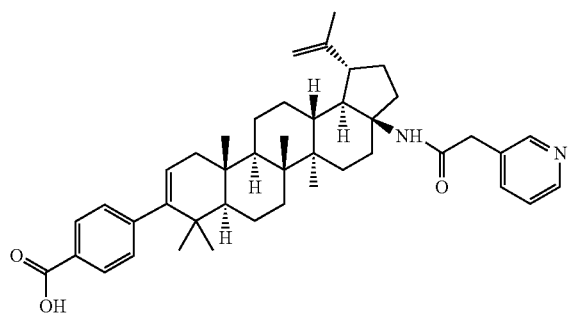

The title compound was prepared from methyl 4-((1R,3aS, 5aR,5bR,7aR,11aS,11bR,13aR,13bR)-3a-amino-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate following the general procedure described for the parallel synthesis of C-17 amides above, using pyridylacetic acid hydrochloride as the reacting carboxylic acid. LCMS: m/e 649.6 (M+H)$^+$, 4.09 min (method 3).

Example 121

Preparation of 4-((1R,3aS,5aR,5bR,7aR,11aS,11bR, 13aR,13bR)-5a,5b,8,8,11a-pentamethyl-1-(prop-1-en-2-yl)-3a-(2-(pyridin-3-yloxy)acetamido)-2,3,3a,4, 5,5a,5b,6,7,7a,8,11,11a,11b,12,13,13a,13b-octadecahydro-1H-cyclopenta[a]chrysen-9-yl) benzoic acid

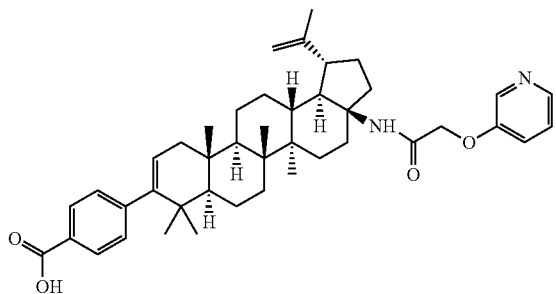

The title compound was prepared from methyl 4-((1R,3aS, 5aR,5bR,7aR,11aS,11bR,13aR,13bR)-3a-amino-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate following the general procedure described for the parallel synthesis of C-17 amides above, using 3-pyridyloxyacetic acid as the reacting carboxylic acid. LCMS: m/e 665.6 (M+H)$^+$, 4.37 min (method 3).

Example 122

Preparation of 4-((1R,3aS,5aR,5bR,7aR,11aS,11bR, 13aR,13bR)-5a,5b,8,8,11a-pentamethyl-3a-(2-(piperidin-1-yl)acetamido)-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) benzoic acid

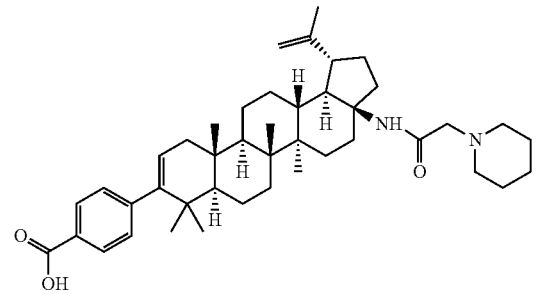

The title compound was prepared from methyl 4-((1R,3aS, 5aR,5bR,7aR,11aS,11bR,13aR,13bR)-3a-amino-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate following the general procedure described for the parallel synthesis of C-17 amides above, using piperidin-1-ylacetic acid hydrochloride as the reacting carboxylic acid. LCMS: m/e 655.7 (M+H)$^+$, 4.68 min (method 3).

Example 123

Preparation of 4-((1R,3aS,5aR,5bR,7aR,11aS,11bR, 13aR,13bR)-3a-(2-(diisopropylamino)acetamido)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

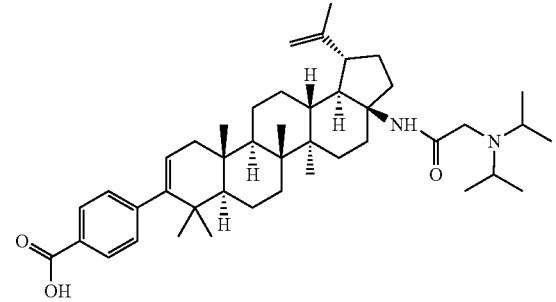

The title compound was prepared from methyl 4-((1R,3aS, 5aR,5bR,7aR,11aS,11bR,13aR,13bR)-3a-amino-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate following the general procedure described for the parallel synthesis of C-17 amides above, using diisopropylamino-acetic acid as the reacting carboxylic acid. LCMS: m/e 671.7 (M+H)$^+$, 4.99 min (method 3). $^1$H NMR (599 MHz, <DMSO_CDCl$_3$>) δ=8.45-8.37 (m, 1H), 7.89 (d, J=8.2 Hz, 2H), 7.69-7.65 (m, 1H), 7.24-7.20 (m, 2H), 5.31-5.24 (m, 1H), 4.79-4.73 (m, 1H), 4.67-4.62 (m, 1H), 3.95 (br. s., 2H), 3.66 (d, J=5.9 Hz, 3H), 2.94 (s, 1H), 2.78 (s, 1H), 2.74 (br. s., 1H), 2.63 (d, J=13.5 Hz, 1H), 2.30 (t, J=9.1 Hz, 1H), 2.13 (dd, J=6.2, 16.7 Hz, 1H), 2.07-1.98 (m, 1H), 1.75 (br. s., 1H), 1.72 (s, 4H), 1.69-1.61 (m, 1H), 1.52-1.41 (m, 8H), 1.36-1.33 (m, 3H), 1.33-1.31 (m, 2H), 1.30-1.28 (m, 3H), 1.28-1.25 (m, 3H), 1.09 (s, 6H), 1.01 (s, 6H), 0.93 (br. s., 6H).

Example 124

Preparation of 4-((1R,3aS,5aR,5bR,7aR,11aS,11bR, 13aR,13bR)-5a,5b,8,8,11a-pentamethyl-3a-(2-(2-methylpiperidin-1-yl)acetamido)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

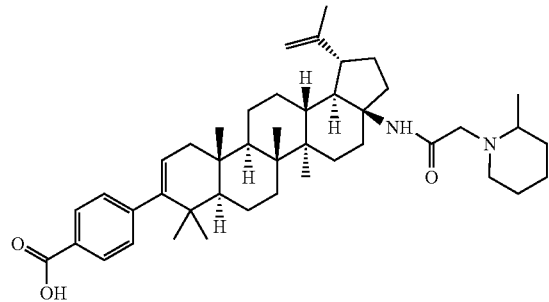

The title compound was prepared from methyl 4-((1R,3aS, 5aR,5bR,7aR,11aS,11bR,13aR,13bR)-3a-amino-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate following the general procedure described for the parallel synthesis of C-17 amides above, using (2-methylpiperidin-1-yl)acetic acid as the reacting carboxylic acid. LCMS: m/e 669.7 (M+H)$^+$, 4.73 min (method 3).

Example 125

Preparation of 4-((1R,3aS,5aR,5bR,7aR,11aS,11bR, 13aR,13bR)-3a-(2-(4-fluorophenylamino)acetamido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

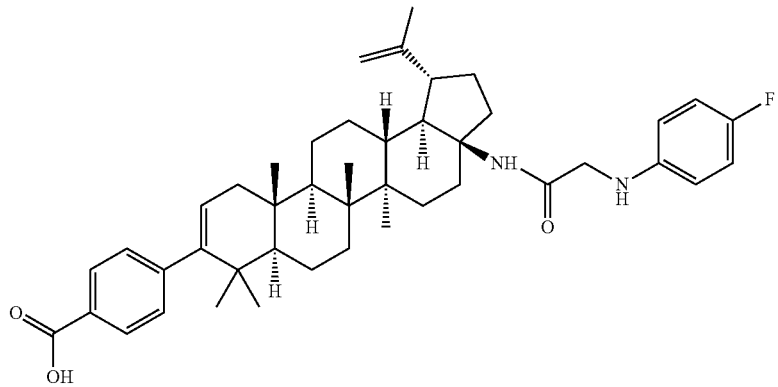

The title compound was prepared from methyl 4-((1R,3aS, 5aR,5bR,7aR,11aS,11bR,13aR,13bR)-3a-amino-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate following the general procedure described for the parallel synthesis of C-17 amides above, using (4-fluorophenylamino)acetic acid as the reacting carboxylic acid. LCMS: m/e 681.7 (M+H)$^+$, 6.62 min (method 3).

Example 126

Preparation of 4-((1R,3aS,5aR,5bR,7aR,11aS,11bR,13aR,13bR)-5a,5b,8,8,11a-pentamethyl-1-(prop-1-en-2-yl)-3a-(2-(pyrimidin-2-yl)acetamido)-2,3,3a,4,5,5a,5b,6,7,7a,8,11,11a,11b,12,13,13a,13b-octadecahydro-1H-cyclopenta[a]chrysen-9-yl)benzoic acid

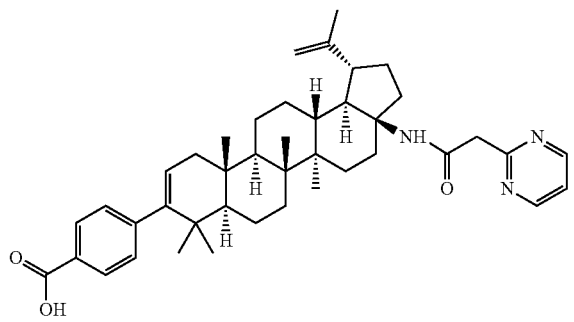

The title compound was prepared from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure described for the parallel synthesis of C-17 amides above, using 2-pyrimidine acetic acid as the reacting carboxylic acid. LCMS: m/e 650.6 (M+H)+, 5.57 min (method 3). $^1$H NMR (599 MHz, <DMSO_CDCl$_3$>) δ=8.78 (d, J=4.7 Hz, 2H), 7.88 (d, J=8.2 Hz, 2H), 7.29 (s, 1H), 7.22 (d, J=7.6 Hz, 2H), 5.28 (d, J=5.3 Hz, 1H), 4.75 (s, 1H), 4.62 (br. s., 1H), 3.93 (s, 1H), 3.82 (d, J=14.6 Hz, 1H), 2.77-2.72 (m, 1H), 2.63 (d, J=12.9 Hz, 1H), 2.40-2.32 (m, 1H), 2.16-2.04 (m, 1H), 2.00-1.81 (m, 2H), 1.73 (br. s., 2H), 1.71 (s, 3H), 1.67-1.52 (m, 4H), 1.50-1.39 (m, 7H), 1.36-1.20 (m, 7H), 0.99 (br. s., 6H), 0.98 (br. s., 3H), 0.93 (br. s., 3H), 0.93 (br. s., 3H).

Example 127

Preparation of 4-((1R,3aS,5aR,5bR,7aR,11aS,11bR,13aR,13bR)-5a,5b,8,8,11a-pentamethyl-1-(prop-1-en-2-yl)-3a-(2-(pyridin-2-yl)acetamido)-2,3,3a,4,5,5a,5b,6,7,7a,8,11,11a,11b,12,13,13a,13b-octadecahydro-1H-cyclopenta[a]chrysen-9-yl)benzoic acid

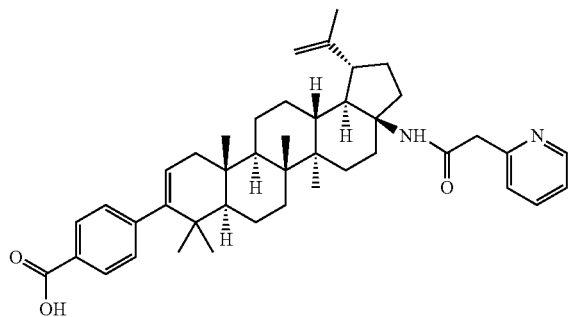

The title compound was prepared from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure described for the parallel synthesis of C-17 amides above, using 2-pyridylacetic acid hydrochloride as the reacting carboxylic acid. LCMS: m/e 649.6 (M+H)+, 4.23 min (method 3).

Example 128

Preparation of 4-((1R,3aS,5aR,5bR,7aR,11aS,11bR,13aR,13bR)-5a,5b,8,8,11a-pentamethyl-1-(prop-1-en-2-yl)-3a-(2-(pyridin-3-yl)acetamido)-2,3,3a,4,5,5a,5b,6,7,7a,8,11,11a,11b,12,13,13a,13b-octadecahydro-1H-cyclopenta[a]chrysen-9-yl)benzoic acid

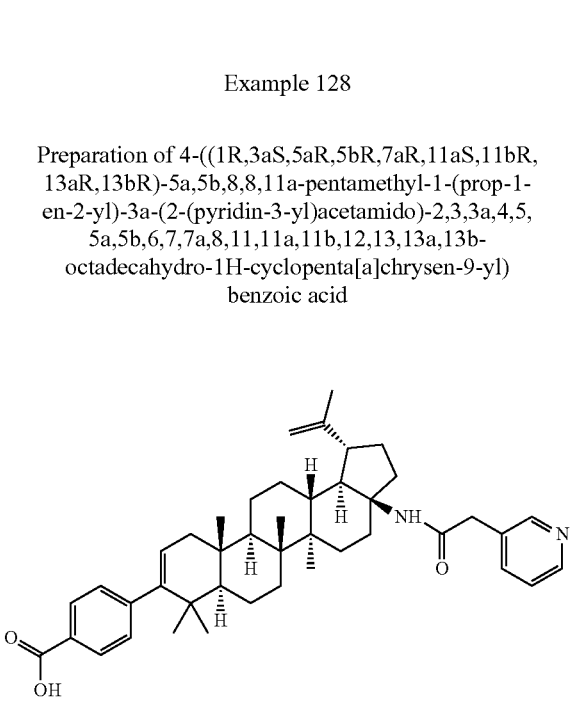

The title compound was prepared from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure described for the parallel synthesis of C-17 amides above, using 3-pyridylacetic acid hydrochloride as the reacting carboxylic acid. LCMS: m/e 649.6 (M+H)+, 4.07 min (method 3). $^1$H NMR (599 MHz, <DMSO_CDCl$_3$>) δ=8.49 (d, J=5.3 Hz, 2H), 7.88 (s, 2H), 7.33 (d, J=5.3 Hz, 2H), 7.22 (d, J=8.2 Hz, 2H), 7.17 (s, 1H), 5.28 (d, J=5.3 Hz, 1H), 4.86-4.81 (m, 1H), 4.76 (s, 1H), 4.63 (br. s., 1H), 3.66 (d, J=12.9 Hz, 1H), 3.49 (d, J=12.9 Hz, 1H), 2.85-2.79 (m, 1H), 2.60-2.56 (m, 1H), 2.35-2.28 (m, 1H), 2.12 (dd, J=6.4, 17.0 Hz, 1H), 2.06 (t, J=11.1 Hz, 1H), 1.87-1.79 (m, 1H), 1.73 (br. s., 2H), 1.71 (s, 3H), 1.61-1.50 (m, 2H), 1.50-1.35 (m, 6H), 1.37-1.27 (m, 3H), 1.24 (d, J=9.4 Hz, 3H), 1.13-1.05 (m, J=12.9 Hz, 1H), 1.03-1.00 (m, 6H), 0.97 (s, 3H), 0.94 (s, 3H), 0.93 (s, 3H).

Example 129

Preparation of 4-((1S,3aS,5aR,5bR,7aR,11aS,11bR,13aR,13bR)-3a-(((1,1-dioxido-4-thiomorpholinyl)acetyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

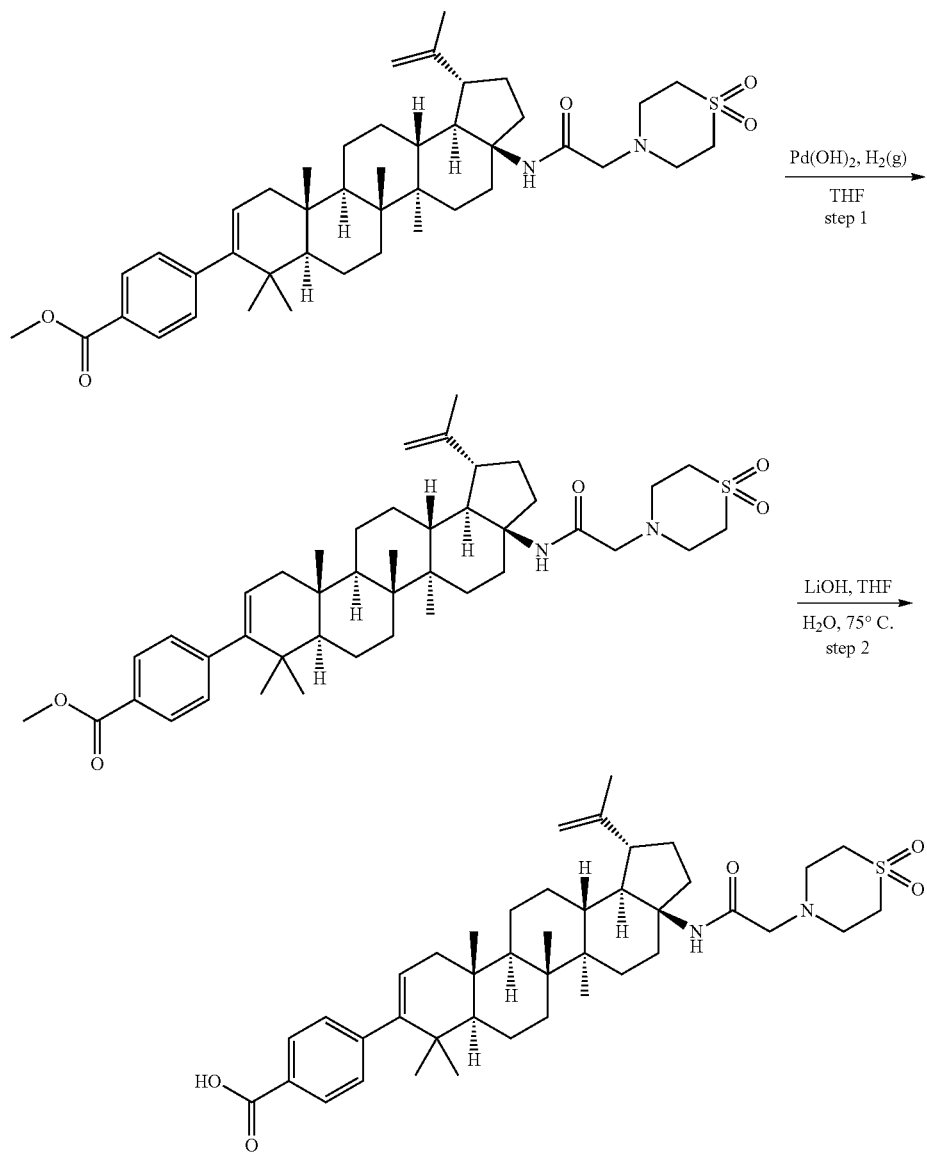

Step 1. Preparation of methyl 4-[(1S,3aS,5aR,5bR,7aR,11aS,11bR,13aR,13bR)-3a-[[2-(1,1-dioxo-1,4-thiazinan-4-yl)acetyl]amino]-1-isopropyl-5a,5b,8,8,11a-pentamethyl-1,2,3,4,5,6,7,7a,11,11b,12,13,13a,13b-tetradecahydrocyclopenta[a]chrysen-9-yl]benzoate A solution of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoate (152 mg, 0.211 mmol) in THF (10 mL) was flushed with $N_2$ (g) and palladium hydroxide (44.5 mg, 0.063 mmol) was added. The reaction mixture was purged with $H_2$ (g) then stirred under $H_2$ (g) atmosphere. After 68 h, the reaction was purged with $N_2$ (g), the catalyst was removed by filtering through celite and washed with DCM. The resulting liquid filtrate was concentrated to a viscous oil which was dissolved in THF (2.0 mL) filtered and injected into reverse phase HPLC for purification using HPLC method 5 to give the title compound (28.8 mg, 0.040 mmol, 18.89% yield; 62.8% yield based on recovered starting material). LCMS: m/z 721.6

(M+H⁺), retention time 2.655 min (method 6). ¹H NMR (500 MHz, CHLOROFORM-d) δ=8.47 (br. s., 2H), 7.95 (d, J=8.2 Hz, 2H), 7.22 (d, J=8.5 Hz, 2H), 6.98 (s, 1H), 5.32 (dd, J=1.5, 6.1 Hz, 1H), 3.94 (s, 3H), 3.69-3.61 (m, 1H), 3.58-3.52 (m, 4H), 3.31-3.27 (m, 3H), 2.65 (d, J=11.6 Hz, 1H), 2.37 (dd, J=7.5, 12.7 Hz, 1H), 2.20-2.11 (m, 1H), 1.98-1.86 (m, 1H), 1.72 (d, J=15.9 Hz, 3H), 1.62-1.52 (m, 3H), 1.52-1.36 (m, 9H), 1.34-1.23 (m, 3H), 1.21-1.14 (m, 2H), 1.03 (s, 3H), 1.02 (br. s., 3H), 1.01 (br. s., 3H), 0.95 (s, 6H), 0.91 (d, J=7.0 Hz, 3H), 0.81 (d, J=6.7 Hz, 3H).

Step 2. Preparation of 4-((1S,3aS,5aR,5bR,7aR, 11aS,11bR,13aR,13bR)-3a-(((1,1-dioxido-4-thiomorpholinyl)acetyl)amino)-1-isopropyl-5a,5b,8,8, 11a-pentamethyl-2,3,3a,4,5,5a,5b,6,7,7a,8,11,11a, 11b,12,13,13a,13b-octadecahydro-1H-cyclopenta[a]chrysen-9-yl)benzoic acid To a solution of methyl 4-[(1S,3aS,5aR,5bR,7aR,11aS, 11bR,13aR,13bR)-3a-[[2-(1,1-dioxo-1,4-thiazinan-4-yl) acetyl]amino]-1-isopropyl-5a,5b,8,8,11a-pentamethyl-1,2, 3,4,5,6,7,7a,11,11b,12,13,13a,13b-tetradecahydrocyclopenta[a]chrysen-9-yl]benzoate, TFA (33 mg, 0.040 mmol) in THF (Volume: 3 mL) was added a 0.753 molar solution of lithium hydroxide monohydrate (0.316 mL, 0.158 mmol) in H₂O. The reaction mixture was heated to 75° C. After 5.5 h, the reaction was concentrated to dryness. The crude residue was dissolved in THF (1.2 mL), MeOH (0.3 mL) and 1N HCl (0.2 mL). The solution was filtered and injected into reverse phase HPLC for purification using HPLC method 3 to give 4-((1S,3aS,5aR,5bR,7aR,11aS, 11bR,13aR,13bR)-3a-(((1,1-dioxido-4-thiomorpholinyl) acetyl)amino)-1-isopropyl-5a,5b,8,8,11a-pentamethyl-2,3, 3a,4,5,5a,5b,6,7,7a,8,11,11a,11b,12,13,13a,13b-octadecahydro-1H-cyclopenta[a]chrysen-9-yl)benzoic acid, TFA (17.9 mg, 0.021 mmol, 54.1% yield) as a white solid. LCMS: m/z 707.6 (M+H⁺), retention time 2.030 min (method 6). ¹H NMR (500 MHz, METHANOL-d₄) δ=7.93 (d, J=8.5 Hz, 2H), 7.21 (d, J=8.5 Hz, 2H), 7.13 (s, 1H), 5.31 (dd, J=1.5, 6.1 Hz, 1H), 3.26-3.22 (m, 5H), 3.21-3.15 (m, 4H), 2.66-2.59 (m, 1H), 2.37 (dd, J=6.7, 12.5 Hz, 1H), 2.17 (dd, J=6.4, 17.1 Hz, 1H), 1.99-1.91 (m, 1H), 1.80-1.70 (m, 4H), 1.67-1.57 (m, 2H), 1.57-1.45 (m, 9H), 1.44-1.39 (m, 1H), 1.39-1.26 (m, 3H), 1.18-1.11 (m, 2H), 1.09 (s, 3H), 1.04 (s, 6H), 0.96 (s, 3H), 0.95 (s, 3H), 0.91 (d, J=7.0 Hz, 3H), 0.82 (d, J=6.7 Hz, 3H).

Example 130

Preparation of 4-((1S,3aS,5aR,5bR,7aS,9S,11aS, 11bR,13aR,13bR)-3a-(((1,1-dioxido-4-thiomorpholinyl)acetyl)amino)-1-isopropyl-5a,5b,8,8,11a-pentamethylicosahydro-1H-cyclopenta[a]chrysen-9-yl) benzoic acid

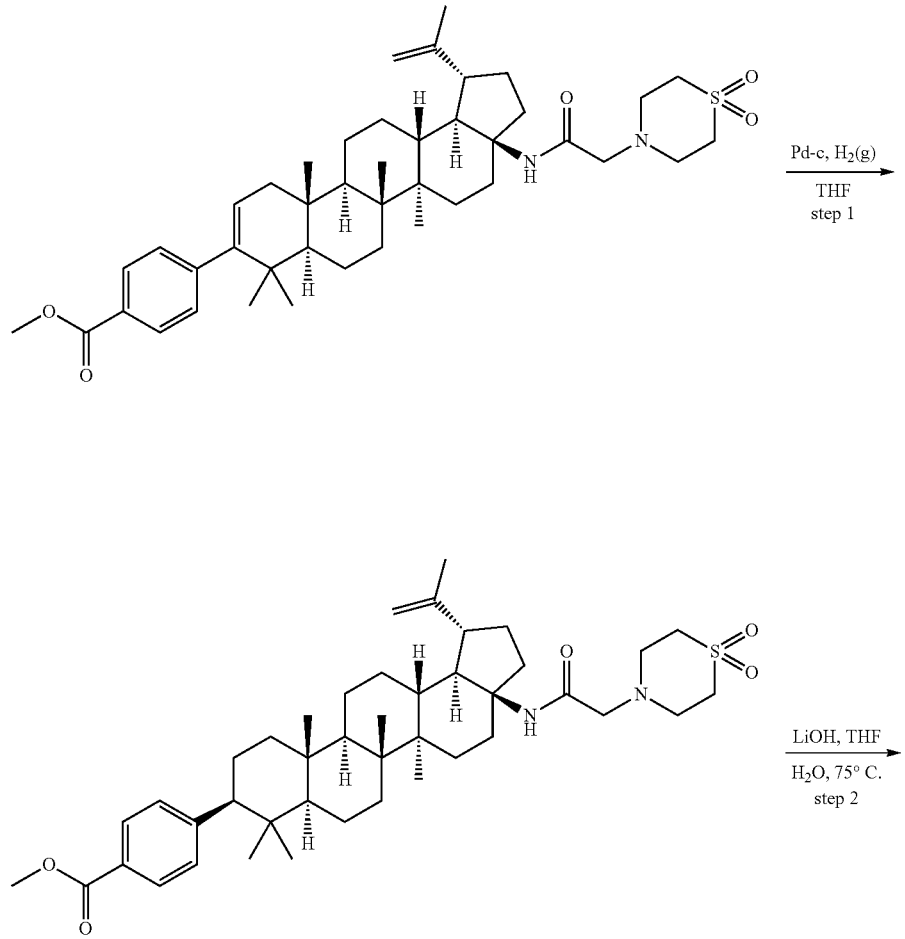

-continued

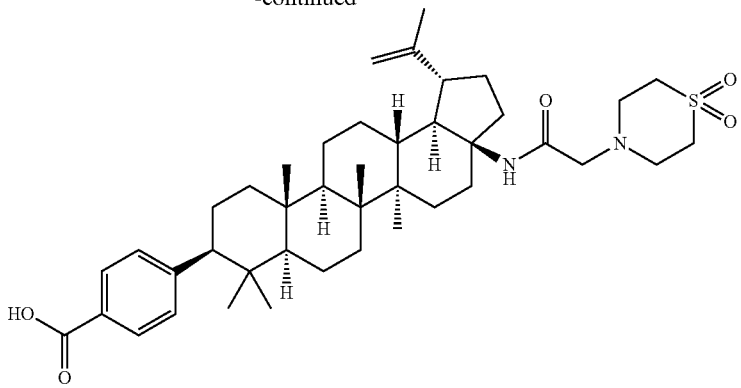

example 130

Step 1. Preparation of methyl 4-[(1S,5aR,5bR,7aS, 9S,11aS,11bR,13aR,13bR)-3a-[[2-(1,1-dioxo-1,4-thiazinan-4-yl)acetyl]amino]-1-isopropyl-5a,5b,8,8,11a-pentamethyl-1,2,3,4,5,6,7,7a,9,10,11,11b,12,13,13a,13b-hexadecahydrocyclopenta[a]chrysen-9-yl] benzoate To a solution of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoate (51 mg, 0.071 mmol) in THF (3 mL) was added palladium on activated charcoal (10% Pd content) (18 mg, 0.017 mmol). The reaction mixture was purged by bubbling H$_2$ (g) slowly into the mixture over 30 mins and then the mixture was stirred under H$_2$ (g) atmosphere. After 24 h, the reaction mixture was purged with N$_2$ (g) and more catalyst (36 mg, 0.034 mmol) was added. The reaction mixture was stirred under H$_2$ (g) for an additional 24 h. The mixture was then purged with N$_2$ (g), and the catalyst was filtered and washed with THF. The liquid filtrate was concentrated. The crude residue was purified by preparative HPLC using HPLC method 5 to give methyl 4-[(1S,5aR,5bR,7aS,9S,11aS,11bR,13aR,13bR)-3a-[[2-(1,1-dioxo-1,4-thiazinan-4-yl)acetyl]amino]-1-isopropyl-5a,5b,8,8,11a-pentamethyl-1,2,3,4,5,6,7,7a,9,10,11,11b,12,13,13a,13b-hexadecahydrocyclopenta[a]chrysen-9-yl]benzoate, TFA (24.4 mg, 0.029 mmol, 41.1% yield) as a white solid. LCMS: m/z 723.6 (M+H$^+$), retention time 2.648 min (method 6). $^1$H NMR (500 MHz, CHLOROFORM-d) δ=7.94 (d, J=8.2 Hz, 2H), 7.25 (d, J=8.2 Hz, 2H), 7.13 (br. s., 2H), 7.05 (s, 1H), 3.56-3.49 (m, 1H), 3.48-3.39 (m, 5H), 3.27-3.19 (m, 4H), 2.66 (d, J=12.5 Hz, 1H), 2.42 (dd, J=3.2, 13.3 Hz, 1H), 2.40-2.34 (m, 1H), 2.16-2.07 (m, 1H), 1.96-1.90 (m, 1H), 1.74-1.60 (m, 6H), 1.59-1.51 (m, 2H), 1.51-1.38 (m, 9H), 1.37-1.31 (m, 2H), 1.30-1.26 (m, 1H), 1.21-1.10 (m, 2H), 1.03 (s, 3H), 1.01 (s, 3H), 0.98 (s, 3H), 0.95 (s, 1H), 0.91 (d, J=7.0 Hz, 3H), 0.81 (d, J=6.7 Hz, 3H), 0.78 (s, 3H), 0.72 (s, 3H). $^{13}$C NMR (CHLOROFORM-d) δ ppm 167.7, 167.2, 149.5, 129.8, 129.4, 128.4, 128.3, 127.5, 65.9, 58.8, 57.3, 55.7, 51.8, 51.3, 49.9, 49.9, 48.2, 44.7, 41.9, 40.4, 40.3, 37.9, 37.4, 37.3, 34.5, 34.0, 29.4, 29.2, 28.1, 26.8, 26.2, 24.6, 22.6, 21.8, 20.4, 18.5, 17.4, 16.1, 15.6, 14.5, 14.1.

Step 2. Preparation 4-((1S,3aS,5aR,5bR,7aS,9S,11aS,11bR,13aR,13bR)-3a-(((1,1-dioxido-4-thiomorpholinyl)acetyl)amino)-1-isopropyl-5a,5b,8,8,11a-pentamethylicosahydro-1H-cyclopenta[a]chrysen-9-yl)benzoic acid To a solution of 4-[(1S,5aR,5bR,7aS,9S,11aS,11bR,13aR,13bR)-3a-[[2-(1,1-dioxo-1,4-thiazinan-4-yl)acetyl]amino]-1-isopropyl-5a,5b,8,8,11a-pentamethyl-1,2,3,4,5,6,7,7a,9,10,11,11b,12,13,13a,13b-hexadecahydrocyclopenta[a]chrysen-9-yl]benzoate, TFA (24.3 mg, 0.029 mmol) in THF (3 mL) was added a 0.753 molar aqueous solution of lithium hydroxide monohydrate (0.232 mL, 0.116 mmol). The reaction mixture was heated to 75° C. After 5.5 h, the reaction mixture was concentrated to dryness. The crude residue was dissolved in THF (1.2 mL), MeOH (0.3 mL) and 1N HCl (0.2 mL). The resulting solution was filtered and purified using prep HPLC method 3 to give 4-((1S,3aS,5aR,5bR,7aS,9S,11aS,11bR,13aR,13bR)-3a-(((1,1-dioxido-4-thiomorpholinyl)acetyl)amino)-1-isopropyl-5a,5b,8,8,11a-pentamethylicosahydro-1H-cyclopenta[a]chrysen-9-yl)benzoic acid, TFA (16.5 mg, 0.020 mmol, 69.1% yield) as a white solid. LCMS: m/z 709.6 (M+H$^+$), retention time 2.072 min (method 6). $^1$H NMR (500 MHz, METHANOL-d$_4$) δ=7.91 (d, J=8.2 Hz, 2H), 7.26 (d, J=8.2 Hz, 2H), 7.11 (s, 1H), 3.25-3.20 (m, 6H), 3.17 (d, J=5.5 Hz, 4H), 2.65-2.59 (m, 1H), 2.44 (dd, J=2.7, 13.1 Hz, 1H), 2.37 (dd, J=7.0, 12.5 Hz, 1H), 2.19-2.04 (m, 1H), 1.98-1.89 (m, 1H), 1.85 (d, J=13.1 Hz, 1H), 1.74 (dd, J=3.7, 7.9 Hz, 2H), 1.71-1.60 (m, 3H), 1.56-1.45 (m, 8H), 1.44-1.37 (m, 4H), 1.36-1.25 (m, 2H), 1.16-1.09 (m, 2H), 1.05 (s, 3H), 1.04 (s, 3H), 1.00 (s, 3H), 0.95 (d, J=2.1 Hz, 1H), 0.91 (d, J=6.7 Hz, 3H), 0.81 (d, J=6.7 Hz, 3H), 0.78 (s, 3H), 0.72 (s, 3H).

Example 130-1

Preparation of 4-((1R,3aS,5aR,5bR,7aR,11aS,11bR, 13aR,13bR)-3a-(carboxyformamido)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoic acid

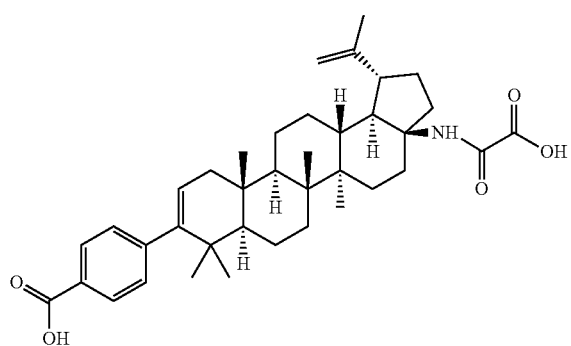

The title compounds was obtained in 25% yield as a by-product during the ester hydrolysis in Step 2 of the preparation of 4-((1R,3aS,5aR,5bR,7aR,11aS,11bR,13aR,13bR)-3a-(2-(dimethylamino)-2-oxoacetamido)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid. LCMS: m/e 600.5 (M−H)$^-$, 1.33 min (method 5). $^1$H NMR (500 MHz, CHLOROFORM-d) δ=8.02 (d, J=8.2 Hz, 2H), 7.26 (d, J=8.2 Hz, 3H), 5.33 (d, J=4.9 Hz, 1H), 4.80 (s, 1H), 4.70 (s, 1H), 3.84-3.80 (m, 1H), 2.59 (d, J=10.1 Hz, 1H), 2.54 (d, J=5.2 Hz, 1H), 2.46 (dd, J=8.4, 11.7 Hz, 1H), 2.18-2.11 (m, 1H), 1.91 (ddd, J=3.1, 3.3, 6.8 Hz, 2H), 1.83-1.75 (m, 2H), 1.74 (s, 3H), 1.62-1.34 (m, 12H), 1.28 (s, 1H), 1.27-1.12 (m, 3H), 1.07 (s, 3H), 1.05 (s, 3H), 1.02 (s, 3H), 0.97 (br. s., 3H), 0.96 (br. s., 3H).

Example 130-2

Preparation of 4-((1R,3aS,5aR,5bR,7aR,11aS,11bR, 13aR,13bR)-3a-(1-(tert-butoxycarbonylamino)cyclopropanecarboxamido)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoic acid

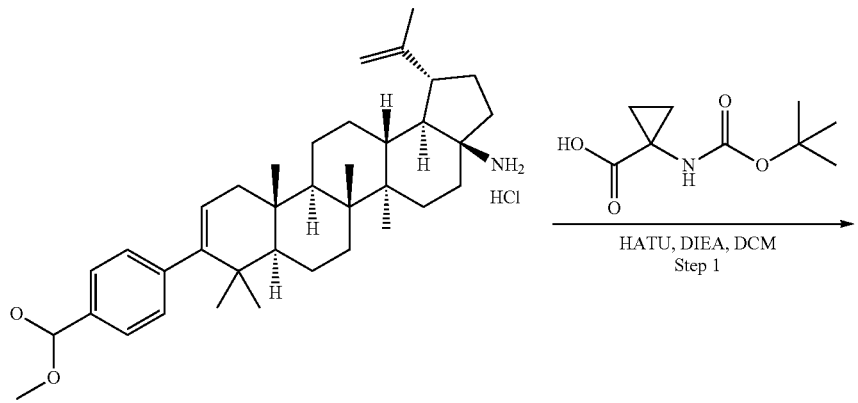

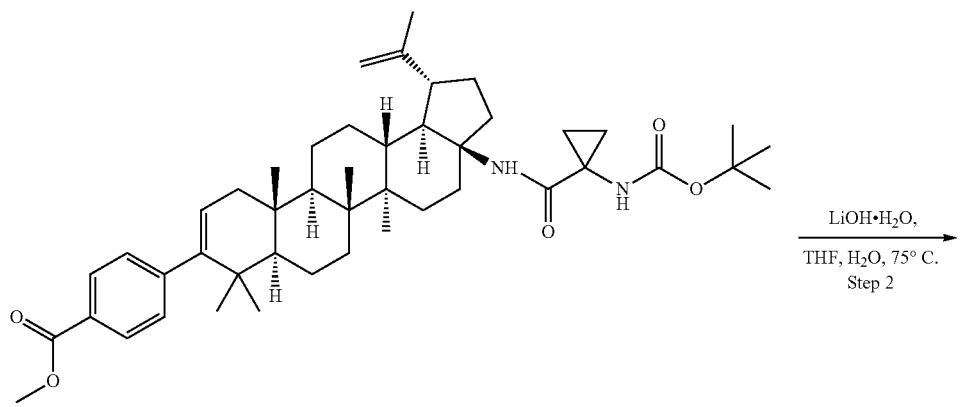

-continued

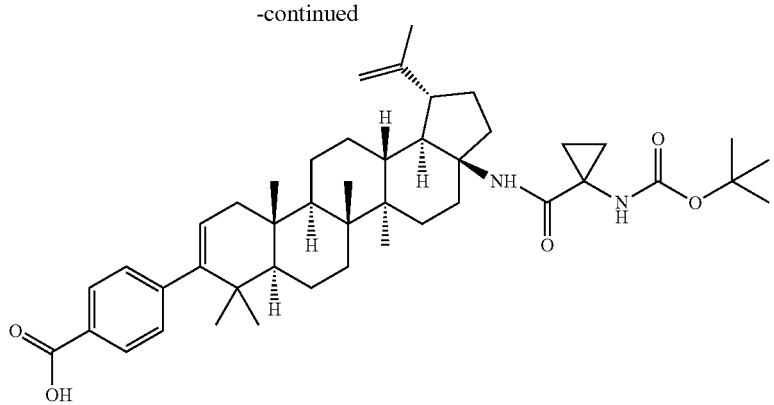

Step 1. Preparation of methyl 4-((1R,3aS,5aR,5bR,7aR,11aS,11bR,13aR,13bR)-3a-(1-(tert-butoxycarbonylamino)cyclopropanecarboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

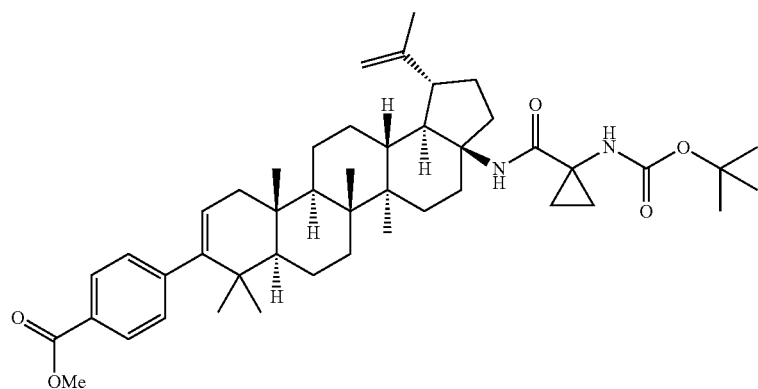

To a solution mixture of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.302 g, 0.555 mmol) and N,N-diisopropylethylamine (0.580 mL, 3.33 mmol) in DCM (5 mL) was added 2-(3H-[1,2,3]triazolo[4,5-b]pyridin-3-yl)-1,1,3,3-tetramethylisouronium hexafluorophosphate(V) (0.465 g, 1.222 mmol) and 1-(tert-butoxycarbonylamino)cyclopropanecarboxylic acid (0.223 g, 1.111 mmol). The reaction mixture was stirred at rt. After 18 h, the reaction was diluted with DCM (20 mL) and silica gel (4 g) was added. The mixture was concentrated to dryness and dried in vacuo to a free flowing powder. The material was loaded onto a silica gel column (25 g cartridge) gradient 100% hexanes to 25% EtOAc in hexanes over 240 mL, hold 25% EtOAc in hexanes to give methyl 4-((1R,3aS,5aR,5bR,7aR,11aS,11bR,13aR,13bR)-3a-(1-(tert-butoxycarbonylamino)cyclopropanecarboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (234 mg, 0.309 mmol, 55.6% yield) as a white solid. LCMS: m/e 727.4 (M+H)$^+$, 5.17 min (method 2). $^1$H NMR (500 MHz, CHLOROFORM-d) δ 7.97-7.89 (m, 2H), 7.20 (d, J=8.5 Hz, 2H), 6.47 (br. s., 1H), 5.30 (dd, J=6.3, 1.7 Hz, 1H), 5.16-5.06 (m, 1H), 4.72 (d, J=1.8 Hz, 1H), 4.62 (s, 1H), 4.19-4.09 (m, 1H), 3.92 (s, 3H), 2.66-2.60 (m, 1H), 2.49 (d, J=4.6 Hz, 2H), 2.11 (dd, J=17.1, 6.4 Hz, 1H), 2.07-1.96 (m, 1H), 1.53 (s, 9H), 1.46 (s, 3H), 1.43 (d, J=2.7 Hz, 1H), 1.37 (d, J=3.4 Hz, 1H), 1.34 (d, J=3.7 Hz, 1H), 1.26 (dd, J=7.0, 3.1 Hz, 1H), 1.19-1.16 (m, 1H), 1.12 (br. s., 3H), 1.10-1.07 (m, 1H), 1.01 (s, 3H), 1.01-0.99 (m, 3H), 0.94 (s, 3H), 0.94 (s, 3H).

Step 2. Preparation of 4-((1R,3aS,5aR,5bR,7aR,11aS,11bR,13aR,13bR)-3a-(1-(tert-butoxycarbonylamino)cyclopropanecarboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

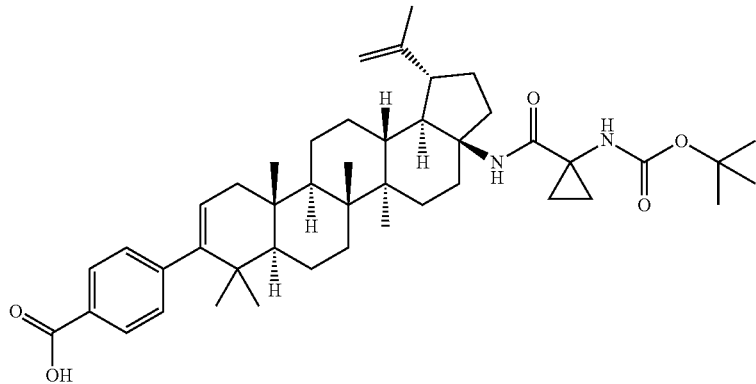

To a solution of methyl 4-((1R,3aS,5aR,5bR,7aR,11aS,11bR,13aR,13bR)-3a-(1-(tert-butoxycarbonylamino)cyclopropanecarboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (101 mg, 0.139 mmol) in THF (5 mL) was added a solution of lithium hydroxide monohydrate (17.49 mg, 0.417 mmol) in water (1.000 mL). The resulting mixture was stirred at 75° C. After 18 h, the reaction mixture was concentrated. The residue was redissolved in THF/MeOH, silica gel (2 g) was added and the mixture was concentrated to dryness. The absorbed material was loaded onto a silica gel column (25 g cartridge) and eluted with 0% B (solvent B=(90:10 DCM:MeOH, A=100% DCM) to 50% B for 180 mL, then hold at 50% B for 900 mL. Thus was obtained 4-((1R,3aS,5aR,5bR,7aR,11aS,11bR,13aR,13bR)-3a-(1-(tert-butoxycarbonylamino)cyclopropanecarboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (39 mg, 0.054 mmol, 38.6% yield) as white solid. LCMS: m/e 713.6 (M+H)$^+$, 2.32 min (method 1). $^1$H NMR (500 MHz, 1:1 CDCl$_3$:METHANOL-d$_4$) δ 7.92 (d, J=8.2 Hz, 2H), 7.20 (d, J=8.2 Hz, 3H), 6.62 (br. s., 1H), 5.33-5.24 (m, 1H), 4.72 (s, 1H), 4.63 (s, 1H), 2.61-2.36 (m, 3H), 2.13 (dd, J=17.2, 6.3 Hz, 1H), 2.04-1.95 (m, 1H), 1.73 (br. s., 1H), 1.71 (s, 3H), 1.41 (d, J=6.1 Hz, 2H), 1.26 (br. s., 9H), 1.15 (s, 3H), 1.10 (br. s., 1H), 1.03 (s, 3H), 1.02 (s, 3H), 0.95 (s, 3H), 0.94 (s, 3H), 0.88 (d, J=6.7 Hz, 2H), 0.86-0.83 (m, 2H).

Example 130-3

Preparation of 4-((1R,3aS,5aR,5bR,7aR,11aS,11bR,13aR,13bR)-3a-(1-(tert-butoxycarbonylamino)cyclopropanecarboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

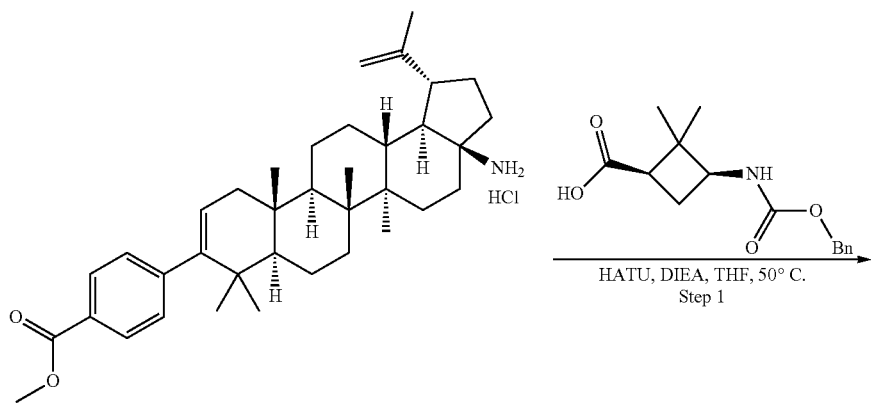

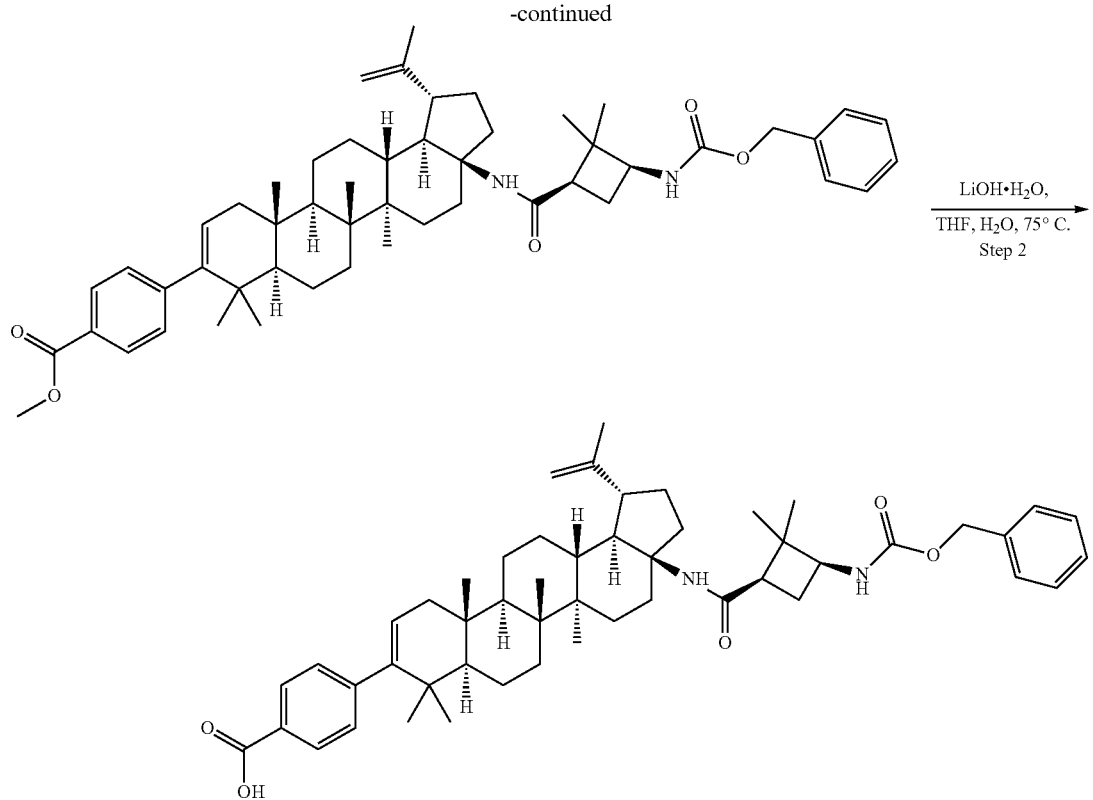

Step 1. Preparation of methyl 4-((1R,3aS,5aR,5bR,7aR,11aS,11bR,13aR,13bR)-3a-((1R,3S)-3-(((benzyloxy)carbonyl)amino)-2,2-dimethylcyclobutanecarboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To a solution of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, HCl (265 mg, 0.457 mmol) in tetrahydrofuran (5 mL) was added N,N-di-iso-propylethylamine (0.278 mL, 1.598 mmol), (1R,3S)-3-(((benzyloxy)carbonyl)amino)-2,2-dimethylcyclobutanecarboxylic acid (152 mg, 0.548 mmol) (for preparation see: J. Aguilera et al. *Tetrahedron Asymmetry* 2008, 19, 302) and O-(7-azabenzotriazol-1-yl)-N,N,N',N'-tetramethyluronium hexafluorophosphate (226 mg, 0.594 mmol). The reaction mixture was heated to 50° C. After 6 h, the mixture was dilute with EtOAc (30 mL) and washed with 1N HCl (5 mL). The aqueous layer was extracted with EtOAc (25 mL). The combined organic layer was washed with 5% NaHCO₃, brine, dried over MgSO₄, filtered and concentrated to afford a light brown viscous oil. The material was dissolved in DCM, loaded onto a silicagel column and eluted with 97:3 DCM:MeOH to give methyl 4-((1R,3aS,5aR,5bR,7aR,11aS,11bR,13aR,13bR)-3a-((1R,3S)-3-(((benzyloxy)carbonyl)amino)-2,2-dimethylcyclobutanecarboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (335 mg, 0.355 mmol, 78% yield) as brown foam. LC/MS: m/e 802.4 (M+H)⁺, 4.23 min (method 8). ¹H NMR (400 MHz, CHLOROFORM-d) δ 7.95 (d, J=8.3 Hz, 2H), 7.40-7.37 (m, 5H), 7.21 (d, J=8.3 Hz, 2H), 5.31 (d, J=4.6 Hz, 1H), 5.18-5.12 (m, 2H), 5.10-5.06 (m, 1H), 4.97 (s, 1H), 4.76 (s, 1H), 4.66 (s, 1H), 3.93 (s, 3H), 2.85 (s, 6H), 2.69-2.55 (m, 2H), 2.44-2.29 (m, 3H), 2.17-2.09 (m, 2H), 1.94-1.81 (m, 3H), 1.72 (s, 3H), 1.70-1.66 (m, 1H), 1.62-1.52 (m, 4H), 1.46 (d, J=7.3 Hz, 1H), 1.42 (d, J=2.7 Hz, 1H), 1.37 (s, 3H), 1.32-1.22 (m, 3H), 1.15 (d, J=11.7 Hz, 2H), 1.09 (s, 2H), 1.02 (s, 3H), 1.01 (s, 3H), 1.00 (s, 3H), 0.95 (s, 6H).

Step 2. Preparation of 4-((1R,3aS,5aR,5bR,7aR,11aS,11bR,13aR,13bR)-3a-((1R,3S)-3-(((benzyloxy)carbonyl)amino)-2,2-dimethylcyclobutanecarboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid To a solution of methyl 4-((1R,3aS,5aR,5bR,7aR,11aS,11bR,13aR,13bR)-3a-((1R,3S)-3-(((benzyloxy)carbonyl)amino)-2,2-dimethylcyclobutanecarboxamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (135 mg, 0.168 mmol) in THF (5 mL), MeOH (2 mL) was added a solution of lithium hydroxide monohydrate (0.014 mL, 0.504 mmol) in water (1 mL). The reaction mixture was stirred at 75° C. After 4 h, the mixture was concentrated to a white paste. The crude material was dissolved in THF (1.75 mL), MeOH (1 mL) and 1N HCl (0.25 mL) and injected into a reverse phase prep-HPLC using HPLC method 11 and dried in a vacuum oven to give the title compound (30.4 mg, 0.035 mmol, 21.09% yield) as white solid. LCMS: m/e 789.4 (M+H)⁺, 3.14 min (method 8). ¹H NMR (400 MHz, CHLOROFORM-d) δ 8.02 (d, J=8.3 Hz, 2H), 7.41-7.37 (m, 4H), 7.36 (d, J=3.4 Hz, 1H), 7.25 (d, J=8.3 Hz, 2H), 5.33 (d, J=4.6 Hz, 1H), 5.19-5.07 (m, 3H), 4.99 (br. s., 1H), 4.77 (s, 1H), 4.66 (s, 1H), 3.98-3.88 (m, 1H), 2.70-2.55 (m, 3H), 2.47-2.28 (m, 3H), 2.19-2.09 (m, 2H), 1.99-1.87 (m, 1H), 1.76 (d, J=7.8 Hz, 1H), 1.72 (s, 3H), 1.71-1.63 (m, 2H), 1.58 (d, J=8.1 Hz, 3H), 1.50 (br. s., 3H), 1.43 (br. s., 1H), 1.37 (br. s., 3H), 1.33 (d, J=12.2 Hz, 2H), 1.28 (s, 3H), 1.24 (d, J=7.1 Hz, 1H), 1.16 (d, J=12.2 Hz, 2H), 1.09 (s, 3H), 1.02 (s, 6H), 1.01 (br. s., 3H), 0.96 (s, 6H).
Section 4. Sulfonyl Amides
Example 131
Preparation of 4-((1R,3aS,5aR,5bR,7aR,11aS,11bR, 13aR,13bR)-5a,5b,8,8,11a-pentamethyl-1-(prop-1-en-2-yl)-3a-(pyridin-2-ylmethylsulfonamido)-2,3,3a, 4,5,5a,5b,6,7,7a,8,11,11a,11b,12,13,13a,13b-octadecahydro-1H-cyclopenta[a]chrysen-9-yl) benzoic acid
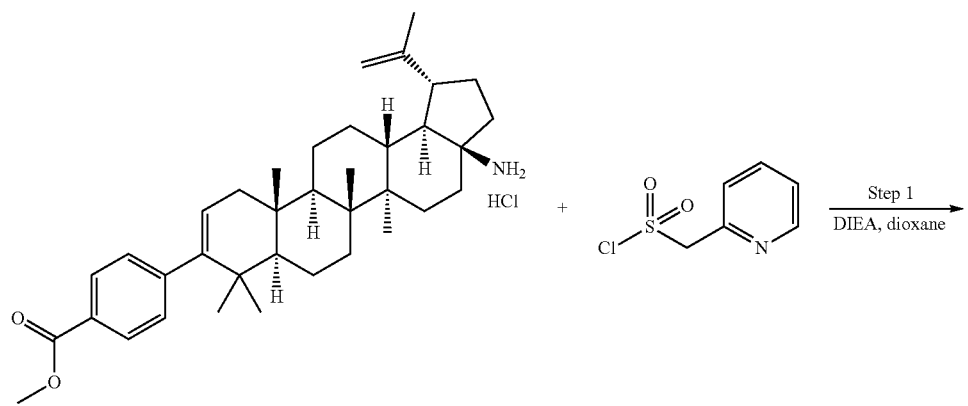
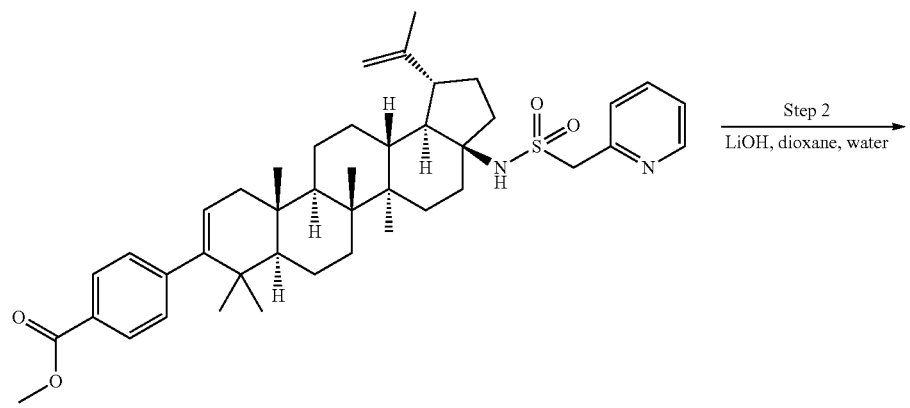

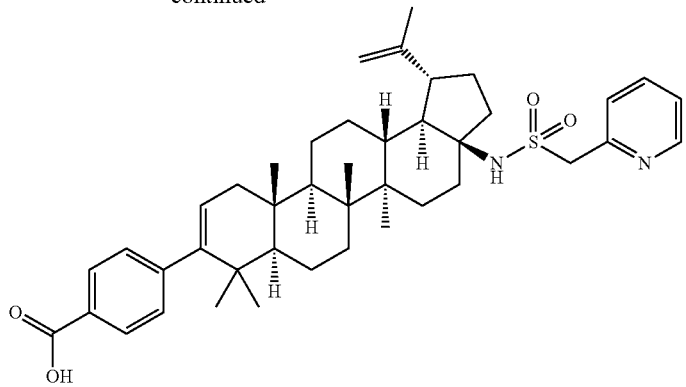

Step 1: Preparation of methyl 4-((1R,3aS,5aR,5bR, 7aR,11aS,11bR,13aR,13bR)-5a,5b,8,8,11a-pentamethyl-1-(prop-1-en-2-yl)-3a-(pyridin-2-ylmethylsulfonamido)-2,3,3a,4,5,5a,5b,6,7,7a,8,11,11a,11b,12, 13,13a,13b-octadecahydro-1H-cyclopenta[a]chrysen-9-yl)benzoate Step 2: Preparation of 4-((1R,3aS,5aR,5bR,7aR, 11aS,11bR,13aR,13bR)-5a,5b,8,8,11a-pentamethyl-1-(prop-1-en-2-yl)-3a-(pyridin-2-ylmethylsulfonamido)-2,3,3a,4,5,5a,5b,6,7,7a,8,11,11a,11b,12,13, 13a,13b-octadecahydro-1H-cyclopenta[a]chrysen-9-yl)benzoic acid

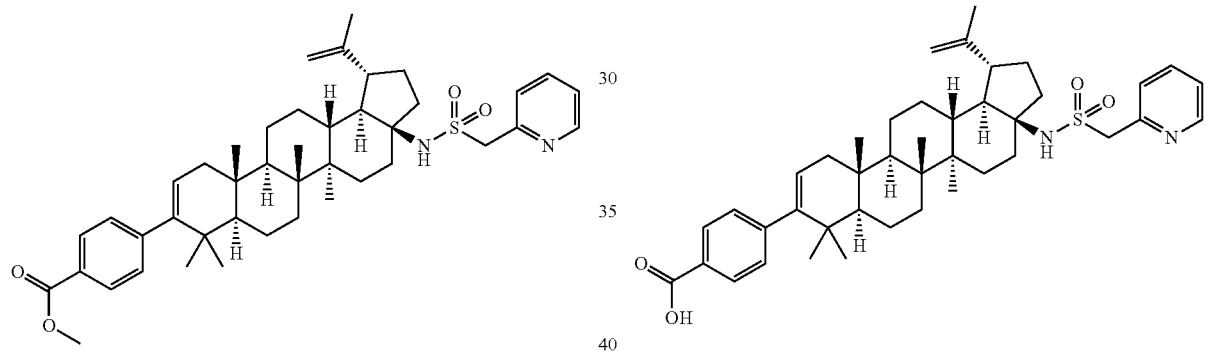

Methyl 4-((1R,3aS,5aR,5bR,7aR,11aS,11bR,13aR, 13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.100 g, 0.184 mmol) was combined with pyridin-2-ylmethanesulfonyl chloride, triflic acid salt (0.189 g, 0.552 mmol). To the mixture was added dry 1,4-dioxane (1.5 mL) followed by addition of DIPEA (0.095 g, 0.736 mmol). The mixture was shaken at rt for 3 h. The crude reaction mixture was concentrated, redissolved in a mixture of MeOH and THF, and purified by reverse phase preparative HPLC. The title compound was isolated as a mono-TFA salt white solid (66 mg, 44% yield). LCMS: m/z 699 (M+H$^+$), retention time 3.03 min (method 11). $^1$H NMR (400 MHz, 1:1 mixture of CDCl3 and MeOD, MeOD lock) δ ppm 0.93 (s, 3H) 0.94 (s, 3H) 1.01 (d, J=1.76 Hz, 6H) 1.07-1.20 (m, 5H) 1.21-1.28 (m, 1H) 1.34-1.57 (m, 11H) 1.63-1.78 (m, 6H) 1.78-1.95 (m, 2H) 1.95-2.05 (m, 1H) 2.12 (dd, J=17.19, 6.40 Hz, 1H) 2.31-2.41 (m, 1H) 2.41-2.51 (m, 1H) 2.61 (td, J=10.98, 4.64 Hz, 1H) 3.90 (s, 3H) 4.56-4.59 (m, 1H) 4.64 (br. s., 1H) 4.75 (d, J=1.51 Hz, 1H) 5.28 (dd, J=6.02, 1.51 Hz, 1H) 7.20 (m, J=8.28 Hz, 2H) 7.53 (br. s., 1H) 7.70 (d, J=6.27 Hz, 1H) 7.90 (m, J=8.28 Hz, 2H) 7.98 (t, J=7.78 Hz, 1H) 8.67 (br. s., 1H).

In a 1 dram vial with PTFE lined screw cap were combined methyl 4-((1R,3aS,5aR,5bR,7aR,11aS,11bR,13aR,13bR)-5a,5b,8,8,11a-pentamethyl-1-(prop-1-en-2-yl)-3a-(pyridin-2-ylmethylsulfonamido)-2,3,3a,4,5,5a,5b,6,7,7a,8,11,11a, 11b,12,13,13a,13b-octadecahydro-1H-cyclopenta[a] chrysen-9-yl)benzoate (0.060 g, 0.086 mmol), lithium hydroxide monohydrate (0.022 g, 0.515 mmol), 1,4-dioxane (0.8 mL) and water (0.4 mL). The vial was sealed and heated with stirring to 75° C. for 7 min. Small quantities of MeOH and THF were added to completely dissolve all solids, and the mixture was filtered and purified by reverse phase preparative HPLC. The mono-TFA salt product was isolated after purification as a white solid (56 mg, 96% yield). LCMS: m/z 685 (M+H$^+$), retention time 2.62 min (method 11). $^1$H NMR (500 MHz, 1:1 mixture of CDCl3 and MeOD, MeOD lock) δ ppm 0.94 (s, 3H) 0.95 (s, 3H) 1.02 (d, J=2.14 Hz, 6H) 1.09-1.20 (m, 5H) 1.22-1.29 (m, 1H) 1.29-1.40 (m, 1H) 1.40-1.60 (m, 9H) 1.65-1.80 (m, 6H) 1.82-2.02 (m, 3H) 2.13 (dd, J=17.09, 6.41 Hz, 1H) 2.33-2.41 (m, 1H) 2.41-2.49 (m, 1H) 2.64 (td, J=11.06, 4.73 Hz, 1H) 4.64 (s, 3H) 4.77 (d, J=1.53 Hz, 1H) 5.29 (dd, J=6.26, 1.68 Hz, 1H) 7.20 (d, J=8.54 Hz, 2H) 7.61-7.67 (m, 1H) 7.80 (d, J=7.93 Hz, 1H) 7.92 (d, J=8.24 Hz, 2H) 8.11 (td, J=7.78, 1.53 Hz, 1H) 8.69 (d, J=3.97 Hz, 1H).

Section 5. Amines
Example 132
Preparation of 4-((1R,3aS,5aR,5bR,7aR,11aS,11bR,13aR,13bR)-3a-((2-fluoropyridin-4-yl)methylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
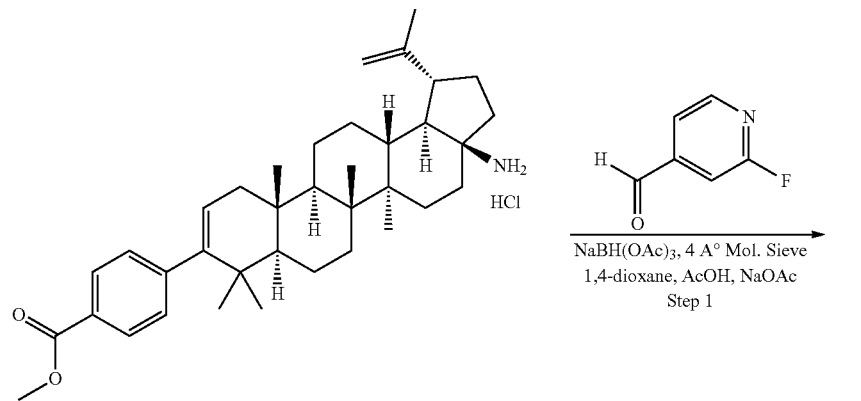
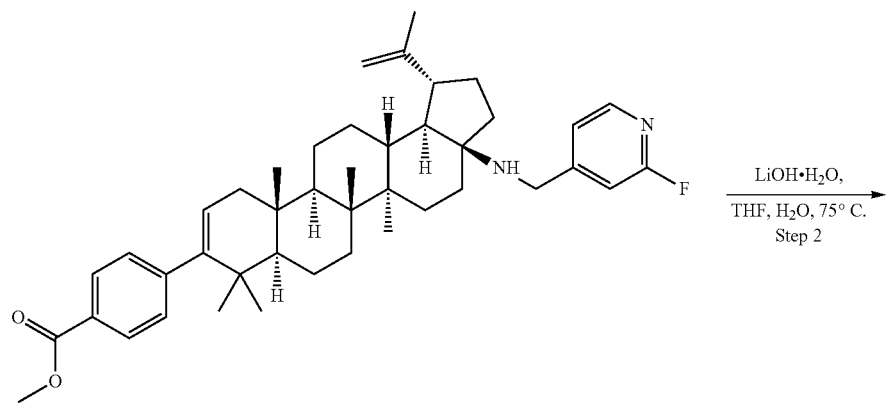
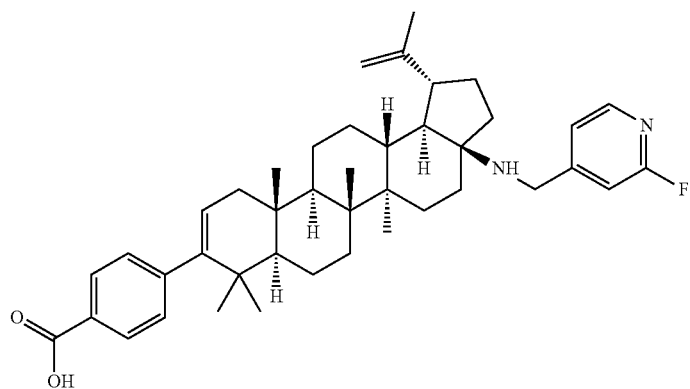

Step 1. Preparation of methyl 4-((1R,3aS,5aR,5bR, 7aR,11aS,11bR,13aR,13bR)-3a-((2-fluoropyridin-4-yl)methylamino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate

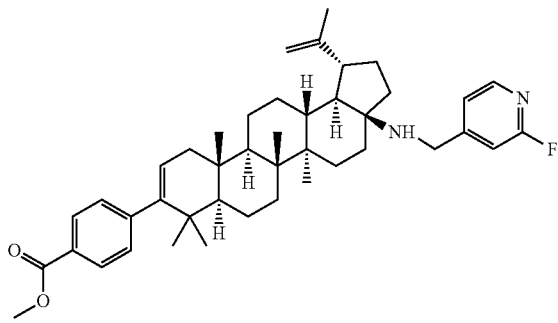

To a solution of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate, HCl (318 mg, 0.548 mmol) in DCE (10 mL) was added glacial acetic acid (0.314 mL, 5.48 mmol), sodium acetate (67.4 mg, 0.822 mmol), 2-fluoropyridine-4-carboxaldehyde (206 mg, 1.644 mmol) and 4 Å molecular sieves. The reaction mixture was heated to 65° C. for 18 h. To the reaction mixture was added sodium triacetoxyhydroborate (581 mg, 2.74 mmol) and the resulting mixture was heated to 65° C. for 7.5 h, then the mixture was left at rt for 48 h. The reaction was diluted with DCM (50 mL) and washed with saturated NaHCO₃ (20 mL). The aqueous layer was extracted with DCM (2×25 mL). The combined organic layer was dried over MgSO₄, filtered and concentrated. The resulting dark brown residue was dissolved in THF (3 mL) and MeOH (0.6 mL), filtered and purified by reverse phase preparative HPLC using HPLC method 3 to give methyl 4-((1R,3aS,5aR,5bR,7aR, 11aS,11bR,13aR,13bR)-3a-((2-fluoropyridin-4-yl)methylamino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoate, TFA (218.4 mg, 0.285 mmol, 52.0% yield) as a white solid. LCMS: m/e 653.4 (M+H)⁺, 2.69 min (method 6).

Step 2. Preparation of 4-((1R,3aS,5aR,5bR,7aR, 11aS,11bR,13aR,13bR)-3a-((2-fluoropyridin-4-yl)methylamino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

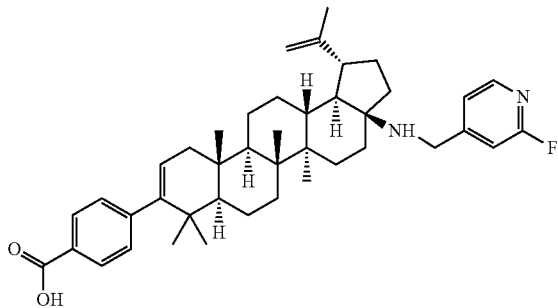

To a solution of methyl 4-((1R,3aS,5aR,5bR,7aR,11aS, 11bR,13aR,13bR)-3a-((2-fluoropyridin-4-yl)methylamino)-5a,5b,8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)benzoate, TFA (77.7 mg, 0.101 mmol) in THF (3 mL) was added a 0.753 molar aqueous solution of LiOH.H₂O (0.539 mL, 0.405 mmol). The reaction mixture was heated to 75° C. After 4 h, the reaction mixture was concentrated. The crude residue was dissolved in THF (1.5 mL) and MeOH (200 µL), filtered and purified by reverse phase preparative HPLC using HPLC method 3 to give 4-((1R,3aS,5aR,5bR,7aR,11aS,11bR,13aR,13bR)-3a-((2-fluoropyridin-4-yl)methylamino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)benzoic acid, TFA (30.6 mg, 0.037 mmol, 36.1% yield) as a white solid. LCMS: m/e 637.7 (M–H)⁻, 3.12 min (method 6). ¹H NMR (500 MHz, 1:1 CDCl₃:MeOD) δ=8.24 (d, J=5.2 Hz, 1H), 7.92 (d, J=8.2 Hz, 2H), 7.43 (d, J=5.2 Hz, 1H), 7.24 (s, 1H), 7.20 (d, J=8.5 Hz, 2H), 5.29 (dd, J=1.7, 6.3 Hz, 1H), 4.78 (s, 1H), 4.17 (br. s., 2H), 2.78-2.69 (m, 1H), 2.18-2.10 (m, 2H), 2.09-2.01 (m, 2H), 1.98 (dd, J=3.1, 11.9 Hz, 1H), 1.96-1.88 (m, 1H), 1.83-1.76 (m, 1H), 1.72 (s, 3H), 1.70-1.64 (m, 1H), 1.63-1.40 (m, 10H), 1.39-1.31 (m, 1H), 1.31-1.23 (m, 2H), 1.13 (s, 3H), 1.07 (s, 3H), 1.02 (s, 3H), 0.95 (s, 3H), 0.94 (s, 3H). ¹³C NMR (1:1 CDCl₃:MeOD) d ppm 15.3, 16.6, 17.4, 19.5, 20.6, 21.8, 22.2, 26.1, 27.6, 29.0, 29.5, 30.2, 33.9, 34.6, 37.2, 38.2, 38.4, 41.8, 42.8, 43.1, 45.7, 47.2, 49.7, 49.9, 50.3, 50.5, 53.9, 78.8, 123.1, 123.2, 124.9, 129.3, 129.7, 131.0, 147.4, 149.7, 164.0, 166.0, 170.1.

Example 133

Preparation of 4-((1R,3aS,5aR,5bR,7aR,11aS,11bR, 13aR,13bR)-3a-((5-fluoropyridin-2-yl)methylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoic acid

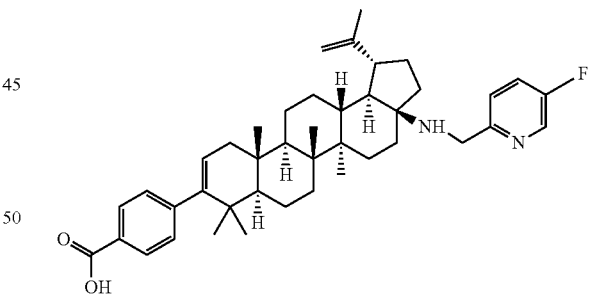

The title compound was prepared in 47% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-((2-fluoropyridin-4-yl)methylamino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoic acid, except 5-fluoro-2-formylpyridine was used instead of 2-fluoropyridine-4-carboxaldehyde in Step 1. LCMS: m/e 639.5 (M+H)⁺, 3.33 min (method 6). ¹H NMR (500 MHz, 1:1 CDCl₃:MeOD) δ=8.46 (d, J=2.7 Hz, 1H), 7.93 (d, J=8.2 Hz, 2H), 7.68 (dt, J=2.7, 8.2 Hz, 1H), 7.53 (dd, J=4.1, 8.7 Hz, 1H), 7.21 (d, J=8.5 Hz, 2H), 5.31 (dd, J=1.7, 6.3 Hz, 1H), 4.83 (s, 1H), 4.74 (s, 1H), 4.49 (d, J=15.3 Hz, 1H), 4.32 (d, J=15.0 Hz, 1H), 2.78 (dt, J=5.3, 10.9 Hz, 1H), 2.22-2.06 (m, 5H), 1.96 (dt, J=3.4, 12.2 Hz, 1H), 1.89-1.82 (m, 1H), 1.80 (d, J=10.7 Hz, 2H), 1.76 (s, 3H), 1.74-1.66 (m, 2H), 1.64-1.54 (m, 4H), 1.53-1.47 (m, 2H), 1.46-1.42 (m, 1H), 1.41-1.37 (m, 1H), 1.33 (s, 3H), 1.29 (dd, J=3.8, 9.9 Hz, 1H), 1.24 (dd, J=4.1, 13.0 Hz, 1H), 1.13 (s, 3H), 1.07 (s, 3H), 0.97 (s, 3H), 0.95 (s, 3H).

Example 134

Preparation of 4-((1R,3aS,5aR,5bR,7aR,11aS,11bR,13aR,13bR)-5a,5b,8,8,11a-pentamethyl-1-(prop-1-en-2-yl)-3a-((3-(trifluoromethyl)pyridin-2-yl)methylamino)-2,3,3a,4,5,5a,5b,6,7,7a,8,11,11a,11b,12,13,13a,13b-octadecahydro-1H-cyclopenta[a]chrysen-9-yl)benzoic acid

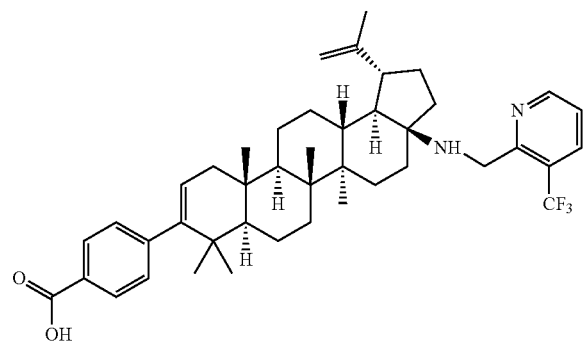

The title compound was prepared in 42% yield from methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the same procedure as described for the preparation of 4-((1R,3aS,5aR,5bR,7aR,11aS,11bR,13aR,13bR)-3a-((2-fluoropyridin-4-yl)methylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 3-trifluoromethylpyridine-2-carbaldehyde was used instead of 2-fluoropyridine-4-carboxaldehyde in Step 1. LCMS: m/e 689.6 (M+H)⁺, 4.12 min (method 6). ¹H NMR (500 MHz, 1:1 CDCl₃:MeOD) δ=8.83 (d, J=4.3 Hz, 1H), 8.28 (d, J=7.9 Hz, 1H), 7.93 (d, J=8.5 Hz, 2H), 7.72 (dd, J=5.0, 7.8 Hz, 1H), 7.21 (d, J=8.5 Hz, 2H), 5.31 (dd, J=1.5, 6.1 Hz, 1H), 4.85 (s, 1H), 4.76 (s, 1H), 4.44 (d, J=16.2 Hz, 1H), 2.80 (dt, J=5.5, 11.0 Hz, 1H), 2.25-2.10 (m, 5H), 2.02 (dt, J=3.5, 12.1 Hz, 1H), 1.92-1.79 (m, 2H), 1.78 (s, 3H), 1.76-1.68 (m, 3H), 1.64-1.54 (m, 4H), 1.52-1.43 (m, 3H), 1.40 (br. s., 1H), 1.36 (s, 3H), 1.32-1.22 (m, 2H), 1.16-1.13 (m, 3H), 1.08 (s, 3H), 0.97 (s, 3H), 0.95 (s, 3H).

Example 135

Preparation of 4-((1R,3aS,5aR,5bR,7aR,11aS,11bR,13aR,13bR)-3a-(2-(2-hydroxyethylsulfonyl)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

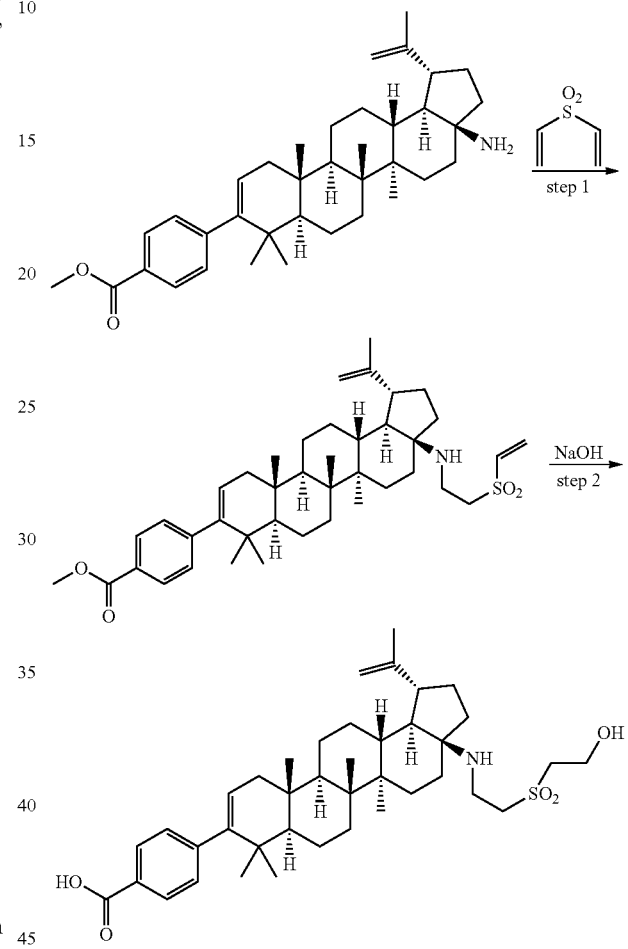

Step 1. Preparation of methyl 4-((1R,3aS,5aR,5bR,7aR,11aS,11bR,13aR,13bR)-5a,5b,8,8,11a-pentamethyl-1-(prop-1-en-2-yl)-3a-(2-(vinylsulfonyl)ethylamino)-2,3,3a,4,5,5a,5b,6,7,7a,8,11,11a,11b,12,13,13a,13b-octadecahydro-1H-cyclopenta[a]chrysen-9-yl)benzoate A mixture of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (30 mg, 0.055 mmol), TEA (0.023 mL, 0.165 mmol) and vinylsulfonylethene (19.5 mg, 0.165 mmol) in EtOH (1 mL) was heated for 3 h at 100° C. The reaction mixture was quenched with water, extracted with DCM (3×2 mL). The organic phases were combined, dried over sodium sulfate, filtered and concentrated under reduced pressure to provide the title compound as a brown oil (25 mg, 68%). LCMS: m/e 662.42 (M+H)⁺, 3.45 min (method 10).

Step 2. Preparation of 4-((1R,3aS,5aR,5bR,7aR, 11aS,11bR,13aR,13bR)-3a-(2-(2-hydroxyethylsulfonyl)ethylamino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)benzoic acid A mixture of methyl 4-((1R,3aS,5aR,5bR,7aR,11aS, 11bR,13aR,13bR)-5a,5b,8,8,11a-pentamethyl-1-(prop-1-en-2-yl)-3a-(2-(vinylsulfonyl)ethylamino)-2,3,3a,4,5,5a,5b, 6,7,7a,8,11,11a,11b,12,13,13a,13b-octadecahydro-1H-cyclopenta[a]chrysen-9-yl)benzoate (25 mg, 0.038 mmol) and sodium hydroxide (0.189 mL, 0.189 mmol) in dioxane (1 mL) was heated at 78° C. for 3 h. The reaction mixture was filtered and the clear solution was purified by prep HPLC to provide the title compound as a white solid (14 mg, 53%). LCMS: m/e 666.39 (M+H)$^+$, 2.48 min (method 10). $^1$H NMR (500 MHz, Acetic acid d4) δ ppm 8.03 (d, J=8.24 Hz, 2H), 7.30 (d, J=8.24 Hz, 2H), 5.37 (d, J=4.27 Hz, 1H), 4.87 (s, 1H), 4.75 (s, 1H), 4.31-4.01 (m, 3H), 3.93-3.74 (m, 3H), 3.68-3.41 (m, 2H), 3.06-2.73 (m, 1H), 2.48-1.26 (m, 22H), 1.76 (s, 3H), 1.23 (s, 3H), 1.14 (s, 3H), 1.09 (s, 3H), 1.02 (s, 3H), 1.00 (s, 3H).

The title compound was prepared following the method described above for the synthesis of 4-((1R,3aS,5aR,5bR, 7aR,11aS,11bR,13aR,13bR)-3a-(2-(2-hydroxyethylsulfonyl)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using methylsulfonylethene instead of vinylsulfonylethene in Step 1. The product was isolated as a white solid (6 mg, 39%). LCMS: m/e 636.37 (M+H)$^+$, 2.53 min (method 10). $^1$H NMR (500 MHz, Acetic acid d4) δ ppm 8.04 (d, J=8.24 Hz, 2H), 7.30 (d, J=8.24 Hz, 2H), 5.44-5.33 (m, 1H), 4.88 (s, 1H), 4.76 (s, 1H), 4.17-4.00 (m, 1H), 3.93-3.69 (m, 3H), 3.22 (s, 3H), 3.00-2.85 (m, 1H), 2.40-1.26 (m, 22H), 1.77 (s, 3H), 1.23 (s, 3H), 1.14 (s, 3H), 1.10 (s, 3H), 1.02 (s, 3H), 1.00 (s, 3H).

Example 136

Preparation of 4-((1R,3aS,5aR,5bR,7aR,11aS,11bR, 13aR,13bR)-5a,5b,8,8,11a-pentamethyl-3a-(2-(methylsulfonyl)ethylamino)-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

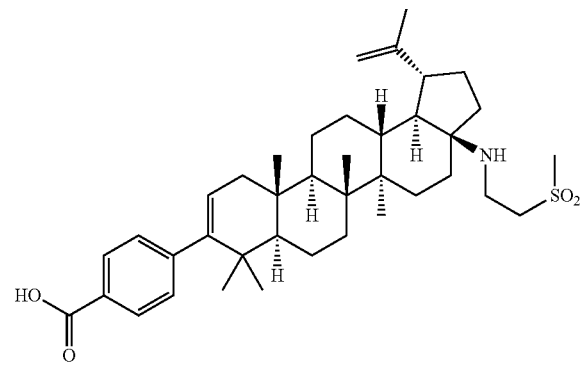

Example 137

Preparation of 4-((1R,3aS,5aR,5bR,7aR,11aS,11bR, 13aR,13bR)-3a-((2-(1,1-dioxido-4-thiomorpholinyl) ethyl)amino)-1-isopropenyl-5a,5b,8,8,11a-pentamethyl-2,3,3a,4,5,5a,5b,6,7,7a,8,11,11a,11b,12,13,13a, 13b-octadecahydro-1H-cyclopenta[a]chrysen-9-yl) benzoic acid

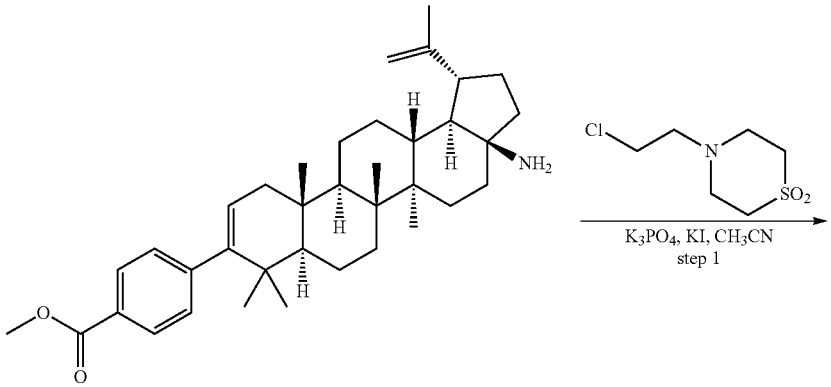

-continued

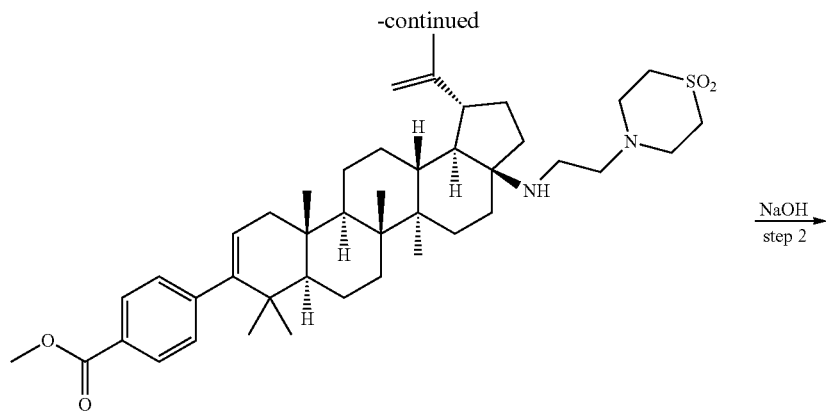

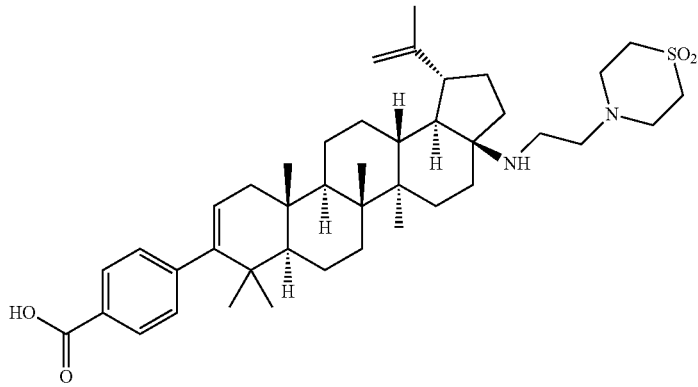

Step 1. Preparation of methyl 4-((1R,3aS,5aR,5bR, 7aR,11aS,11bR,13aR,13bR)-3a-((2-(1,1-dioxido-4-thiomorpholinyl)ethyl)amino)-1-isopropenyl-5a,5b, 8,8,11a-pentamethyl-2,3,3a,4,5,5a,5b,6,7,7a,8,11, 11a,11b,12,13,13a,13b-octadecahydro-1H-cyclopenta[a]chrysen-9-yl)benzoate A mixture of methyl 4-((1R,3aS,5aR,5bR,7aR,11aS, 11bR,13aR,13bR)-3a-amino-1-isopropenyl-5a,5b,8,8,11a-pentamethyl-2,3,3a,4,5,5a,5b,6,7,7a,8,11,11a,11b,12,13, 13a,13b-octadecahydro-1H-cyclopenta[a]chrysen-9-yl) benzoate (600 mg, 1.10 mmol), 4-(2-chloroethyl) thiomorpholine 1,1-dioxide (600 mg, 2.56 mmol) (prepared as described in WO2002045652), anhydrous potassium phosphate (3.00 g, 14.1 mmol) and potassium iodide (10 mg, 0.060 mmol) in acetonitrile (50 mL) was placed in 150 mL AceGlass resealable pressure vessel. The white suspension was blanketed with nitrogen. The vessel was sealed and warmed to 115-125° C. for 48 h. The crude reaction was filtered through a short bed of silica gel and washed with ethyl acetate. The filtrate was concentrated in vacuo and purified by silica gel chromatography eluted with ethyl acetate and hexanes (0-50%) to afford the title compound as a colorless foam (566 mg, 73%). $^1$H NMR (500 MHz, CHLOROFORM-d) δ 7.95 (d, J=8.2 Hz, 2H), 7.22 (d, J=8.2 Hz, 2H), 5.31 (d, J=4.6 Hz, 1H), 4.74 (d, J=1.8 Hz, 1H), 4.62 (s, 1H), 3.93 (s, 3H), 3.22-2.99 (m, 9H), 2.79-2.55 (m, 4H), 2.52-2.42 (m, 1H), 2.18-2.09 (m, 1H), 1.99-1.02 (m, 20H), 1.72 (s, 3H), 1.11 (s, 3H), 1.01 (s., 3H), 1.10 (s, 3H), 0.95 (s, 3H), 0.95 (s., 3H). LCMS: m/e 705.51 (M+H)$^+$, 3.01 min (method 10).

Step 2. Preparation of 4-[(1R,3aS,5aR,5bR,7aR, 11aS,11bR,13aR,13bR)-3a-[[2-(1,1-dioxido-4-thiomorpholinyl)ethyl]amino]-2,3,3a,4,5,5a,5b,6,7,7a,8, 11,11a,11b,12,13,13a,13b-octadecahydro-5a,5b,8,8, 11a-pentamethyl-1-(1-methylethenyl)-1H-cyclopenta [a]chrysen-9-yl]-benzoic acid A mixture of methyl 4-((1R,3aS,5aR,5bR,7aR,11aS, 11bR,13aR,13bR)-3a-((2-(1,1-dioxido-4-thiomorpholinyl) ethyl)amino)-1-isopropenyl-5a,5b,8,8,11a-pentamethyl-2,3, 3a,4,5,5a,5b,6,7,7a,8,11,11a,11b,12,13,13a,13b-octadecahydro-1H-cyclopenta[a]chrysen-9-yl)benzoate (500 mg, 0.709 mmol) and aqueous sodium hydroxide 10N (1.42 mL, 14.2 mmol) in dioxane (10 mL) was heated at 78° C. for 3 h. The reaction was filtered and the resulting clear solution was purified by prep HPLC to provide the title compound as white solid (200 mg, 39%). LCMS: m/e 691.59 (M+H)$^+$, 2.53 min (method 10). $^1$H NMR (500 MHz, Acetic acid d4) δ ppm 8.04 (d, J=8.24 Hz, 2H), 7.30 (d, J=8.24 Hz, 2H), 5.45-5.34 (m, 1H), 4.85 (s, 1H), 4.74 (s, 1H), 3.55-3.40 (m, 1H), 3.39-3.22 (m, 6H), 3.22-3.11 (m, 4H), 3.11-3.03 (m, 1H), 3.04-2.94 (m, 1H), 2.36-1.18 (m, 22H), 1.76 (s, 3H), 1.30 (s, 3H), 1.15 (s, 3H), 1.12 (s, 3H), 1.03 (s, 3H), 1.00 (s, 3H).

Example 138

Preparation of 4-((1R,3aS,5aR,5bR,7aR,11aS,11bR,13aR,13bR)-3a-(2-(tert-butoxycarbonylamino)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

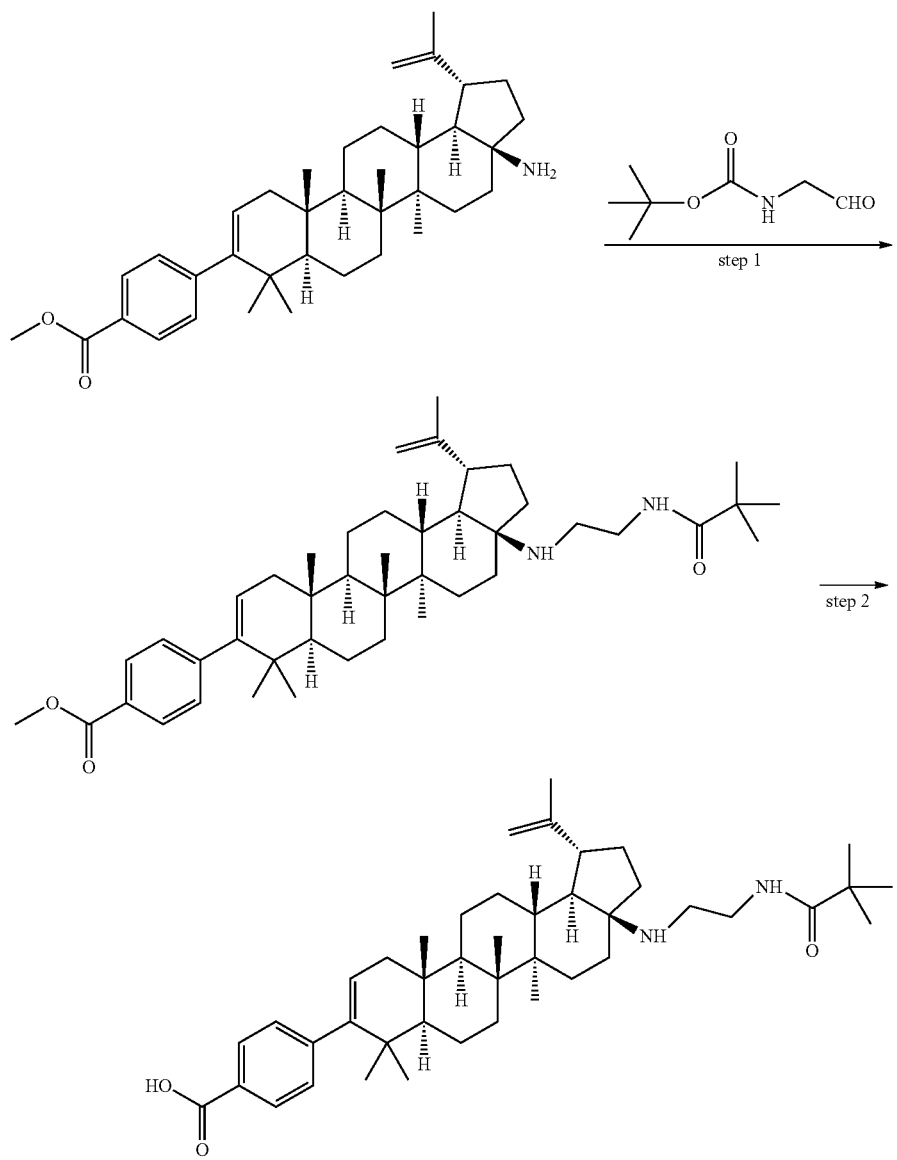

Step 1. Preparation of methyl 4-((1R,3aS,5aR,5bR,7aR,11aS,11bR,13aR,13bR)-3a-(2-(tert-butoxycarbonylamino)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (1.00 g, 1.84 mmol) in DCE (5 mL) was added tert-butyl 2-oxoethylcarbamate (1.17 g, 7.36 mmol) and tetraisopropoxytitanium (0.700 mL, 2.39 mmol). The reaction mixture was stirred for 1 h, then sodium triacetoxyborohydride (1.17 g, 5.52 mmol) was added. The reaction mixture was stirred for 18 h. The reaction mixture was quenched with sodium bicarbonate and was extracted with DCM (3×40 mL). The combined organic layers were dried over sodium sulfate, filtered and concentrated under reduced pressure. The residue was purified by silica gel chromatography using ethyl acetate and hexanes (20-100%) as the eluent to provide the title compound as a pale yellow oil. (900 mg, 71%). LCMS: m/e 688.24 (M+H)+, 2.51 min (method 11).

Step 2. Preparation of 4-((1R,3aS,5aR,5bR,7aR,11aS,11bR,13aR,13bR)-3a-(2-(tert-butoxycarbonylamino)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid The title compound was prepared following the hydrolysis method described above for the synthesis of 4-((1R,3aS,5aR,5bR,7aR,11aS,11bR,13aR,13bR)-3a-(2-(2-hydroxyethylsulfonyl)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using methyl 4-((1R,3aS,5aR,5bR,7aR,11aS,11bR,13aR,13bR)-3a-(2-(tert-butoxycarbonylamino)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (10 mg, 0.015 mmol) as starting material. The title compound was isolated as a white solid (4 mg, 39%). LCMS: m/e 673.45 (M+H)+, 2.65 min (method 10). $^1$H NMR (500 MHz, Acetic acid d4) δ ppm 8.04 (d, J=8.24 Hz, 2H), 7.30 (d, J=8.55 Hz, 2H), 5.51-5.32 (m, 1H), 4.87 (s, 1H), 4.75 (s, 1H), 3.82-3.53 (m, 1H), 3.53-3.24 (m, 3H), 3.04-2.83 (m, 1H), 2.37-1.15 (m, 22H), 1.77 (s, 3H), 1.53-1.49 (m, 9H), 1.27 (s, 3H), 1.14 (s, 3H), 1.11 (s, 3H), 1.02 (s, 3H), 1.00 (s, 3H).

Example 139

Preparation of 4-((1R,3aS,5aR,5bR,7aR,11aS,11bR,13aR,13bR)-3a-(2-aminoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

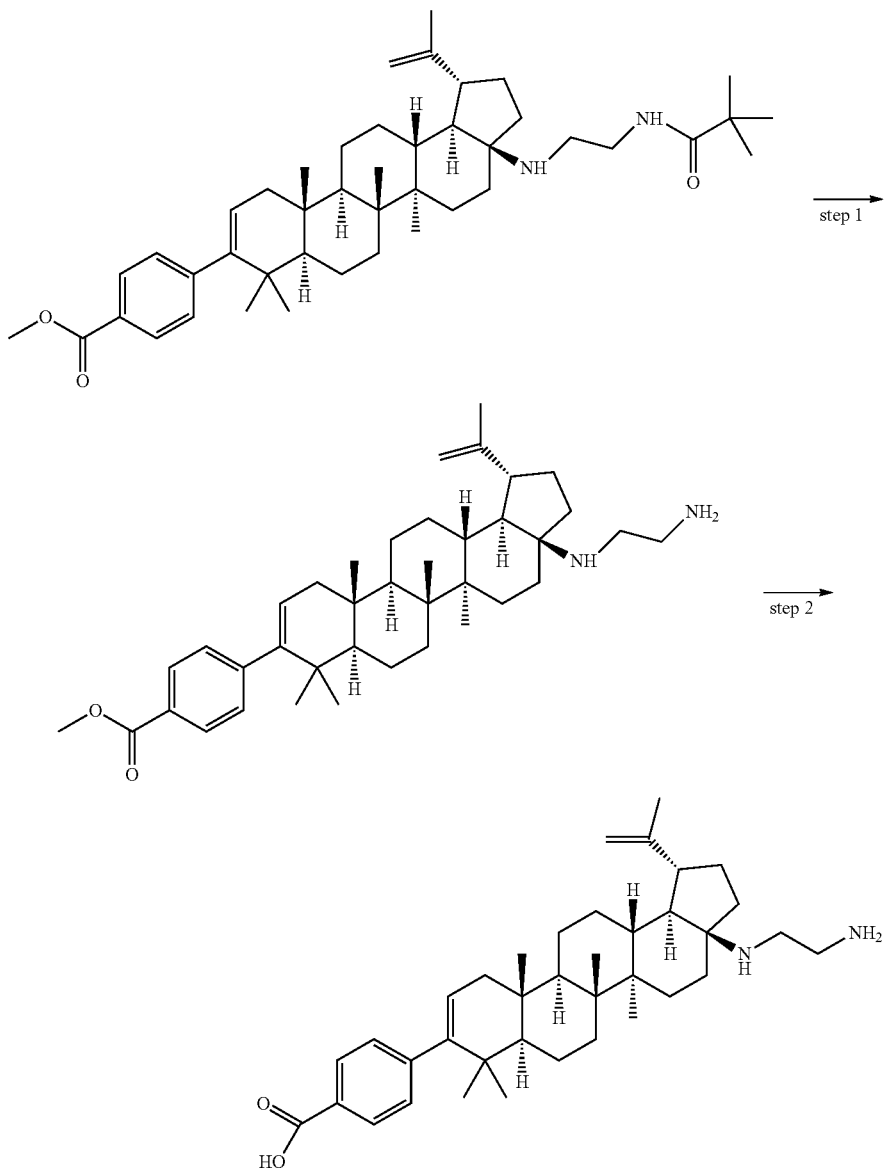

Step 1. Preparation of methyl 4-((1R,3aS,5aR,5bR, 7aR,11aS,11bR,13aR,13bR)-3a-(2-aminoethylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate To a solution of methyl 4-((1R,3aS,5aR,5bR,7aR,11aS, 11bR,13aR,13bR)-3a-(2-(tert-butoxycarbonylamino)ethylamino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoate (900 mg, 1.310 mmol) in dioxane (1 mL) was added HCl (4M in dioxane) (4.26 mL, 17.03 mmol) and the reaction mixture was stirred for 4 h at rt. The reaction mixture was concentrated under reduced pressure to provide the title compound as a brown solid (769 mg, 100%). LCMS: m/e 588.08 (M+H)$^+$, 2.44 min (method 11).

Step 2. Preparation of 4-((1R,3aS,5aR,5bR,7aR, 11aS,11bR,13aR,13bR)-3a-(2-aminoethylamino)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid The title compound was prepared following the hydrolysis method described above for the synthesis of 4-((1R,3aS,5aR, 5bR,7aR,11aS,11bR,13aR,13bR)-3a-(2-(2-hydroxyethylsulfonyl)ethylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoic acid using methyl 4-((1R,3aS,5aR,5bR,7aR,11aS,11bR, 13aR,13bR)-3a-(2-aminoethylamino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate (4 mg, 0.006 mmol) as starting material. The title compound was isolated as a white solid (2.4 mg, 67%). LCMS: m/e 573.2 (M+H)$^+$, 2.39 min (method 10). $^1$H NMR (500 MHz, Acetic acid d4) δ ppm 8.03 (d, J=8.24 Hz, 2H), 7.30 (d, J=8.24 Hz, 2H), 5.37 (d, J=4.27 Hz, 1H), 4.87 (s, 1H), 4.76 (s, 1H), 3.80-3.68 (m, 3H), 3.68-3.59 (m, 1H), 2.97-2.80 (m, 1H), 2.38-1.21 (m, 22H), 1.78 (s, 3H), 1.20 (s, 3H), 1.14 (s, 3H), 1.09 (s, 3H), 1.01 (s, 3H), 1.00 (s, 3H).

Examples 140 and 141

Preparation of 4-((1R,3aS,5aR,5bR,7aR,11aS,11bR, 13aR,13bR)-3a-(2-(2-carboxyethylamino)ethylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid and 3,3'-(2-((1R,3aS,5aR,5bR,7aR, 11aS,11bR,13aR,13bR)-9-(4-carboxyphenyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-3a-ylamino)ethylazanediyl)dipropanoic acid

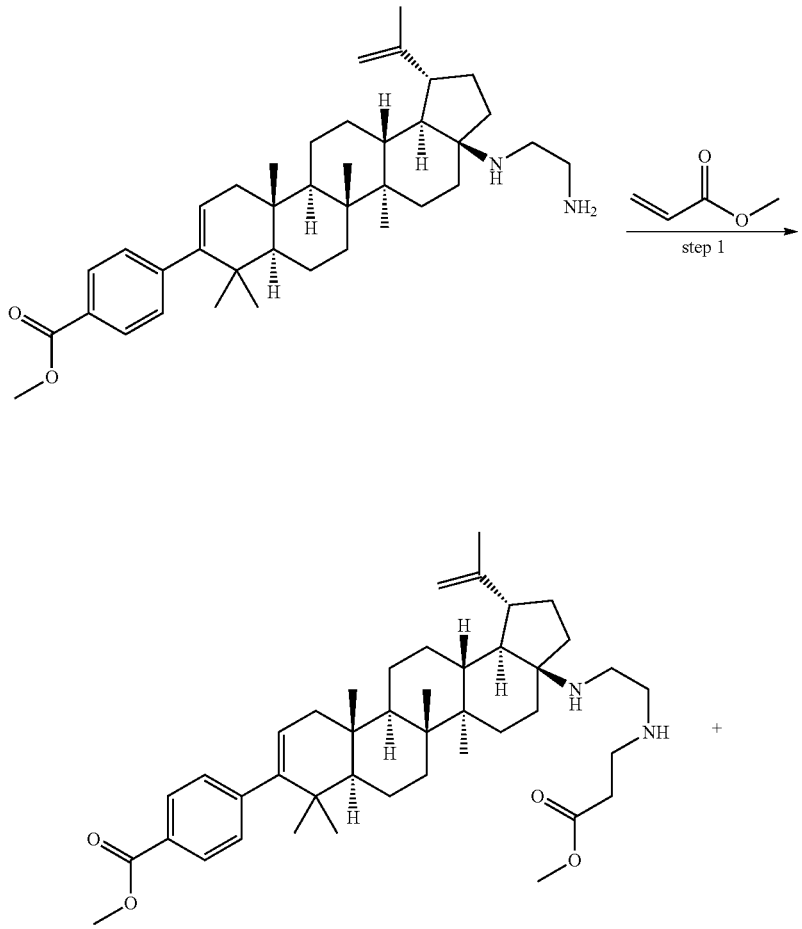

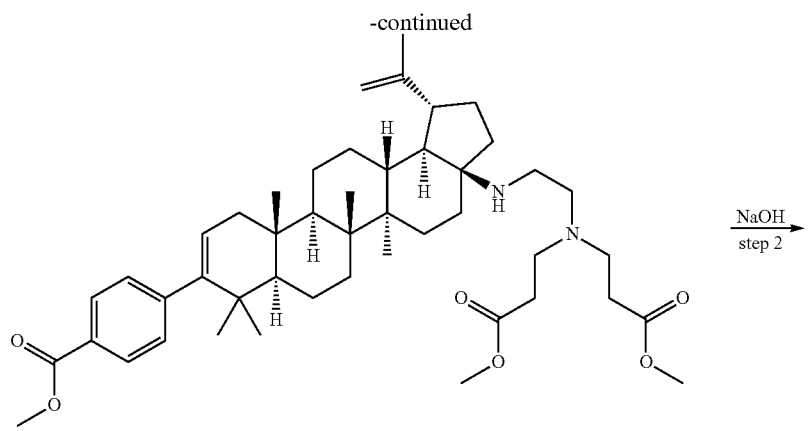

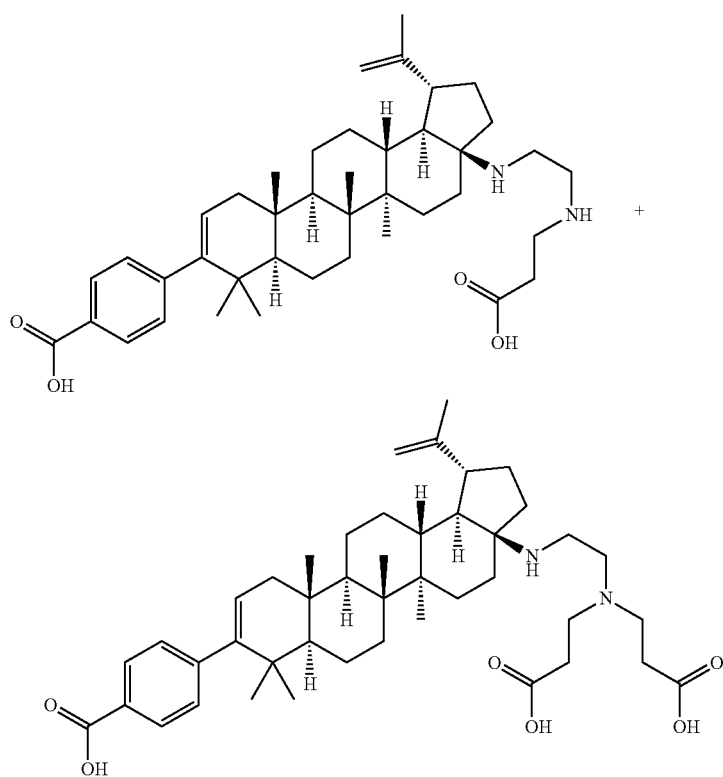

Step 1. Preparation of methyl 4-((1R,3aS,5aR,5bR, 7aR,11aS,11bR,13aR,13bR)-3a-(2-(3-methoxy-3-oxopropylamino)ethylamino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoate and dimethyl 3,3'-(2-((1R,3aS,5aR,5bR,7aR,11aS,11bR,13aR, 13bR)-9-(4-(methoxycarbonyl)phenyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-3a-ylamino)ethylazanediyl)dipropanoate Methyl acrylate (9.97 mg, 0.116 mmol) was added to a solution of methyl 4-((1R,3aS,5aR,5bR,7aR,11aS,11bR, 13aR,13bR)-3a-(2-aminoethylamino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate (34 mg, 0.058 mmol) in MeOH (2 mL) and the mixture was stirred for 16 h at room temperature. The reaction mixture was concentrated under reduced pressure to provide a mixture of the two title compounds as a brown oil (20 mg, 51%). LCMS: m/e 673.47 (M+H)$^+$, 2.96 min and 759.51 (M+H)$^+$, 3.43 min (method 10). The mixture was taken to the next step without further purification.

Step 2. Ester Hydrolysis

The mixture of esters from above (20 mg) in dioxane (1 mL) was treated with sodium hydroxide (0.297 mL, 0.297 mmol) at 78° C. for 3 hours. The reaction mixture was filtered and purified by prep. HPLC to provide the following two compounds:

Example 140

4-((1R,3aS,5aR,5bR,7aR,11aS,11bR,13aR,13bR)-3a-(2-(2-carboxyethylamino)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid White solid (16 mg, 43% over 2 steps). LCMS: m/e 645.44 (M+H)+, 2.37 min (method 10). 1H NMR (500 MHz, Acetic acid d4) δ ppm 8.04 (d, J=8.2 Hz, 2H), 7.30 (d, J=8.5 Hz, 2H), 5.37 (d, J=4.6 Hz, 1H), 4.87 (s, 1H), 4.75 (s, 1H), 3.78 (s., 2H), 3.77-3.59 (m, 2H), 3.45 (t, J=6.4 Hz, 2H), 2.90 (t, J=6.4 Hz, 2H), 2.87-2.72 (m, 1H), 2.42-1.22 (m, 22H), 1.78 (s, 3H), 1.20 (s, 3H), 1.13 (s, 3H), 1.09 (s, 3H), 1.02 (s, 3H), 1.00 (s, 3H).

Example 141

3,3'-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-ylamino)ethylazanediyl)dipropanoic acid White solid (5.7 mg, 57% over 2 steps). LCMS: m/e 717.51 (M+H)+, 2.25 min (method 10). 1H NMR (500 MHz, Acetic acid d4) δ ppm 8.03 (d, J=8.2 Hz, 2H), 7.29 (d, J=8.2 Hz, 2H), 5.36 (d, J=4.9 Hz, 1H), 4.88 (s, 1H), 4.76 (s, 1H), 3.83-3.66 (m, 4H), 3.51 (t, J=6.3 Hz, 4H), 2.93 (t, J=6.9 Hz, 4H), 2.88-2.74 (m, 1H), 2.42-1.22 (m, 22H), 1.78 (s, 3H), 1.19 (s, 3H), 1.14 (s, 3H), 1.08 (s, 3H), 1.01 (s, 3H), 0.99 (s, 3H).

Example 142

Preparation of 4-((1R,3aS,5aR,5bR,7aR,11aS,11bR,13aR,13bR)-3a-(2-(3-(dimethylamino)-3-oxopropylamino)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

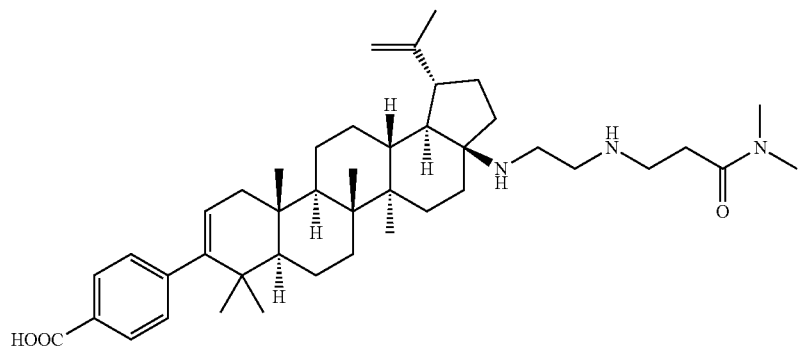

The title compound was prepared following the method described above for the synthesis of 4-((1R,3aS,5aR,5bR,7aR,11aS,11bR,13aR,13bR)-3a-(2-(2-carboxyethylamino)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using N,N-dimethylacrylamide as the Michael aceptor reagent in the first step. The product was isolated as a white solid (9 mg, 50%). LCMS: m/e 672.47 (M+H)+, 2.33 min (method 2). 1H NMR (500 MHz, Acetic acid d4) δ ppm 8.04 (d, J=8.2 Hz, 2H), 7.30 (d, J=8.2 Hz, 2H), 5.37 (d, J=4.6 Hz, 1H), 4.88 (s, 1H), 4.76 (s, 1H), 3.86-3.59 (m, 4H), 3.51-3.37 (m, 2H), 3.07 (s, 3H), 2.99 (s, 3H), 2.95 (t, J=5.6 Hz, 2H), 2.90-2.76 (m, 1H), 2.37-1.22 (m, 22H), 1.78 (s, 3H), 1.20 (s, 3H), 1.14 (s, 3H), 1.09 (s, 3H), 1.02 (s, 3H), 1.00 (s, 3H).

Example 142

Preparation of 4-((1R,3aS,5aR,5bR,7aR,11aS,11bR,13aR,13bR)-3a-(3-(tert-butoxycarbonylamino)propylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

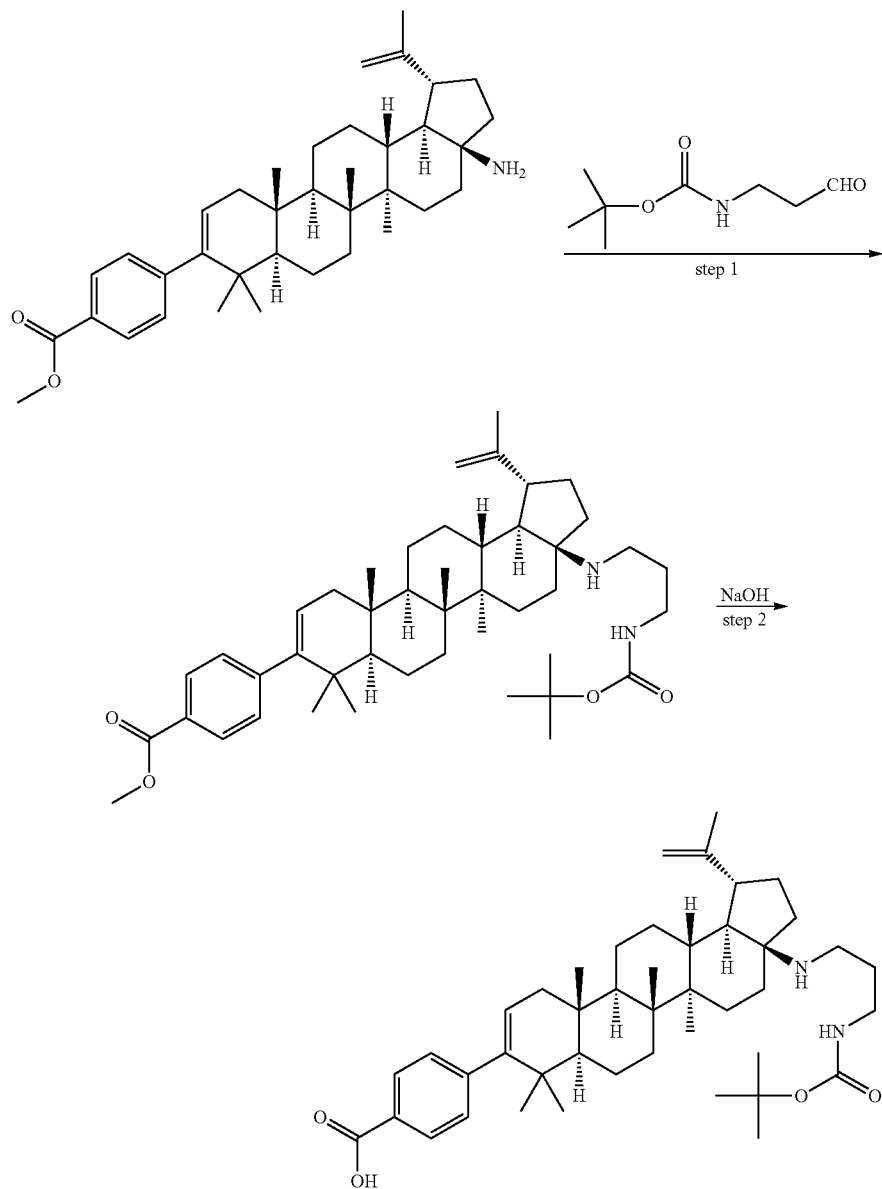

Step 1. Preparation of methyl 4-((1R,3aS,5aR,5bR,7aR,11aS,11bR,13aR,13bR)-3a-(3-(tert-butoxycarbonylamino)propylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate Acetic acid (0.013 mL, 0.221 mmol) and tert-butyl 3-oxopropylcarbamate (38.2 mg, 0.221 mmol) were added to a solution of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (40 mg, 0.074 mmol) in EtOH (1 mL) and dioxane (1.0 mL) and the mixture was stirred for 2 h at rt. Sodium triacetoxyborohydride (78 mg, 0.368 mmol) was added and the reaction mixture was stirred at 20° C. for two hours. The reaction was quenched with a saturated aqueous solution of sodium bicarbonate (3 mL), washed with 0.1N HCl (5 mL) and brine (5 mL) and extracted with DCM (3×5 mL). All the extracts were combined, dried over sodium sulfate, filtered and concentrated under reduced pressure to provide the title compound as pale yellow oil (28 mg, 54%). LCMS: m/e 701.51 (M+H)+, 4.0 min (method 10).

Step 2. Preparation of 4-((1R,3aS,5aR,5bR,7aR, 11aS,11bR,13aR,13bR)-3a-(3-(tert-butoxycarbonylamino)propylamino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoic acid The title compound was prepared following the hydrolysis method described above for the synthesis of 4-((1R,3aS,5aR, 5bR,7aR,11aS,11bR,13aR,13bR)-3a-(2-(2-hydroxyethylsulfonyl)ethylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoic acid using methyl 4-((1R,3aS,5aR,5bR,7aR,11aS,11bR, 13aR,13bR)-3a-(3-(tert-butoxycarbonylamino)propylamino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoate (5 mg, 0.007 mmol) as starting material. The title compound was isolated as a white solid (3 mg, 58%). LCMS: m/e 687.54 (M+H)+, 2.69 min (method 10). 1H NMR (500 MHz, Acetic acid d4) δ ppm 8.04 (d, J=8.24 Hz, 2H), 7.30 (d, J=8.24 Hz, 2H), 5.37 (d, J=4.58 Hz, 1H), 4.87 (s, 1H), 4.74 (s, 1H), 3.38-3.17 (m, 4H), 3.04-2.86 (m, 1H), 2.36-1.17 (m, 24H), 1.77 (s, 3H), 1.50 (s, 9H), 1.25 (s, 3H), 1.14 (s, 3H), 1.09 (s, 3H), 1.02 (s, 3H), 1.00 (s, 3H).

Example 144

Preparation of 4-[(1R,3aS,5aR,5bR,7aR,11aS,11bR, 13aR,13bR)-3a-[[3-(1,1-dioxido-4-thiomorpholinyl) propyl]amino]-2,3,3a,4,5,5a,5b,6,7,7a,8,11,11a,11b, 12,13,13a,13b-octadecahydro-5a,5b,8,8,11a-pentamethyl-1-(1-methylethenyl)-1H-cyclopenta[a] chrysen-9-yl]-benzoic acid

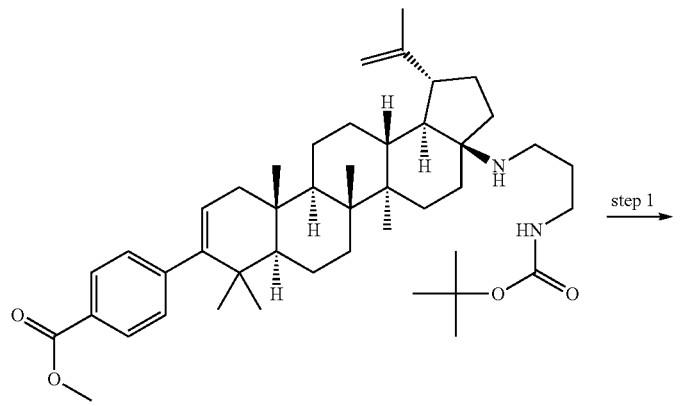

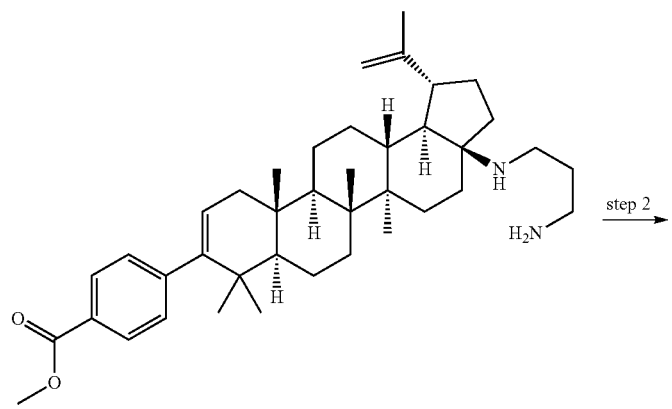

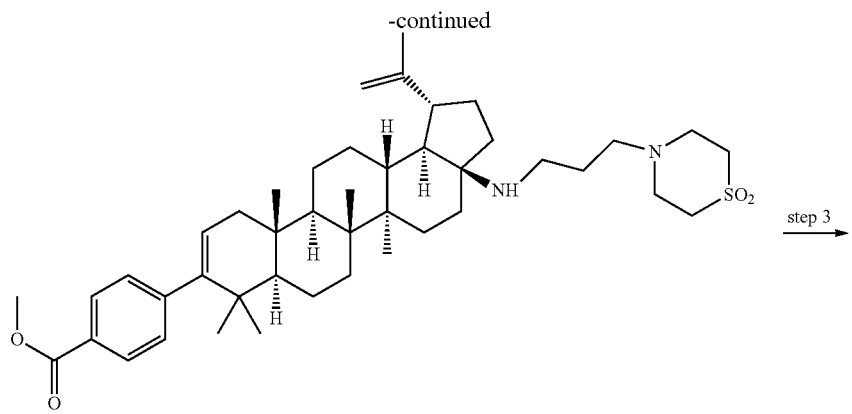

step 3

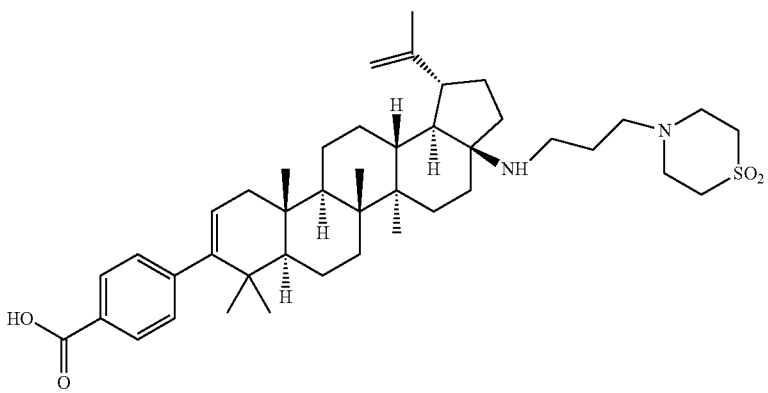

Step 1. Preparation of methyl 4-((1R,3aS,5aR,5bR,7aR,11aS,11bR,13aR,13bR)-3a-(3-aminopropylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate 4.0M HCl in dioxane (32.8 µl, 0.131 mmol) was added to a solution of methyl 4-((1R,3aS,5aR,5bR,7aR,11aS,11bR,13aR,13bR)-3a-(3-(tert-butoxycarbonylamino)propylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (23 mg, 0.033 mmol) in dioxane (1 mL) and the mixture was stirred for 6 h at room temperature. The reaction mixture was concentrated under reduced pressure to provide the title compound as a brown oil (15 mg, 76%). LCMS: m/e 601.48 (M+H)$^+$, 2.88 min (method 10).

Step 2. Preparation of methyl 4-((1R,3aS,5aR,5bR,7aR,11aS,11bR,13aR,13bR)-3a-((3-(1,1-dioxido-4-thiomorpholinyl)propyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid Vinylsulfonylethene (5.90 mg, 0.050 mmol) and triethylamine (6.96 µl, 0.050 mmol) were added to a mixture of methyl 4-((1R,3aS,5aR,5bR,7aR,11aS,11bR,13aR,13bR)-3a-(3-aminopropylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (15 mg, 0.025 mmol) in EtOH (1 mL). The reaction mixture was heated to 100° C. for 3 hours. The reaction mixture was concentrated under reduced pressure to provide the desired product as a brown solid (15 mg, 76%). LCMS: m/e 719.46 (M+H)$^+$, 3.68 min (method 10).

Step 3. Preparation of, 4-[(1R,3aS,5aR,5bR,7aR,11aS,11bR,13aR,13bR)-3a-[[3-(1,1-dioxido-4-thiomorpholinyl)propyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]-benzoic acid A mixture of methyl 4-((1R,3aS,5aR,5bR,7aR,11aS,11bR,13aR,13bR)-3a-((3-(1,1-dioxido-4-thiomorpholinyl)propyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid (15 mg, 0.021 mmol) and 1N sodium hydroxide (0.104 mL, 0.104 mmol) in dioxane (1 mL) was heated at 78° C. for 3 hours. The reaction mixture was purified by prep HPLC to provide the title compound as a white solid (9 mg, 58%). LCMS: m/e 705.49 (M+H)$^+$, 2.60 min (method 10). $^1$H NMR (400 MHz, Acetic acid d4) δ ppm 7.99 (d, J=8.28 Hz, 2H), 7.25 (d, J=8.28 Hz, 2H), 5.33 (d, J=4.77 Hz, 1H), 4.82 (s, 1H), 4.71 (s, 1H), 3.87 (br. s., 4H), 3.56 (d, J=4.27 Hz, 4H), 3.51-3.40 (m, 2H), 3.39-3.22 (m, 2H), 2.86-2.69 (m, 1H), 2.57-2.34 (m, 2H), 2.27-1.18 (m, 22H), 1.72 (s, 3H), 1.16 (s, 3H), 1.10 (s, 3H), 1.04 (s, 3H), 0.98 (s, 3H), 0.96 (s, 3H).

Example 145

Preparation of 4-((1R,3aS,5aR,5bR,7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

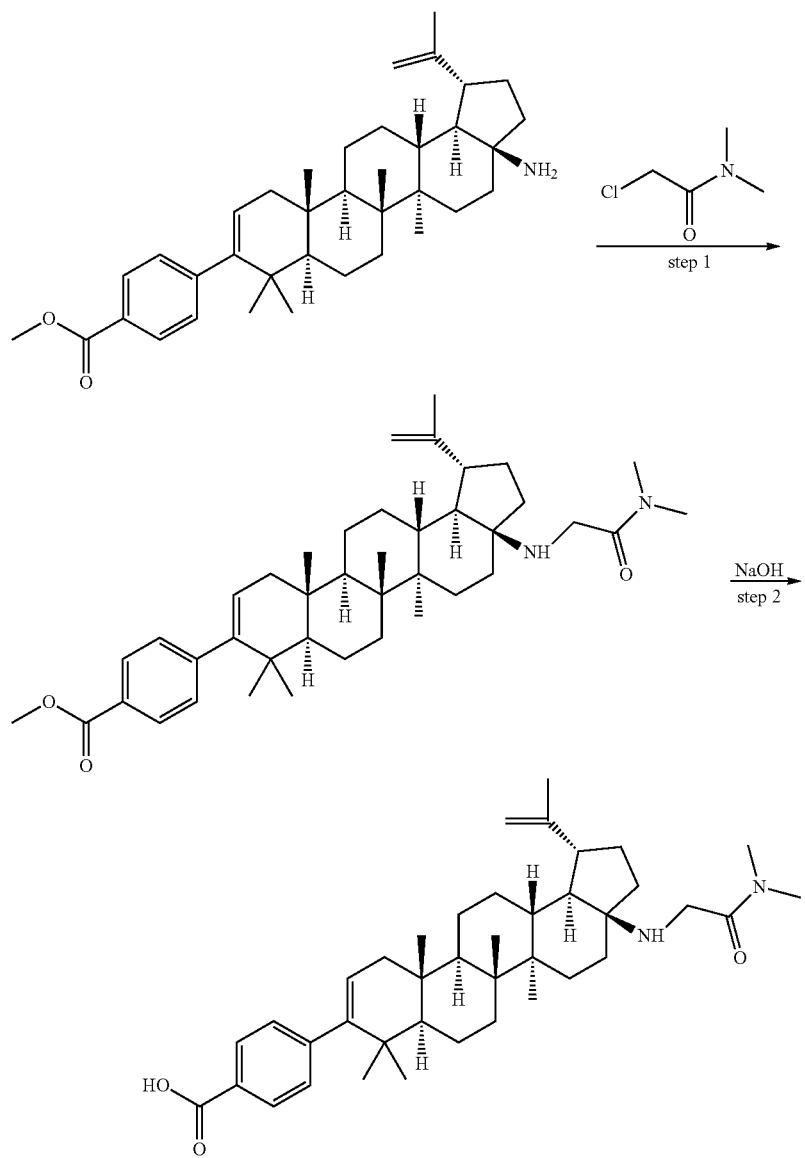

Step 1. Preparation of methyl 4-((1R,3aS,5aR,5bR,7aR,11aS,11bR,13aR,13bR)-3a-(2-(dimethylamino)-2-oxo ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate A mixture of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (50 mg, 0.092 mmol), 2-chloro-N,N-dimethylacetamide (33.5 mg, 0.276 mmol), potassium phosphate (78 mg, 0.368 mmol) and potassium iodide (36.6 mg, 0.221 mmol) in acetonitrile (1 mL) was heated at 120° C. for 33 h in a sealed tube. The reaction mixture was quenched with distilled water (5 mL) and extracted with DCM (3×5 mL). The combined organic layers were dried over sodium sulfate, filtered and concentrated under reduced pressure to provide the title compound as a pale yellow solid (30 mg, 52%). LCMS: m/e 629.51 (M+H)$^+$, 3.03 min (method 10). The product was used in the next step without further purification.

Step 2. Preparation of 4-((1R,3aS,5aR,5bR,7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid A mixture of methyl 4-((1R,3aS,5aR,5bR,7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (30 mg, 0.048 mmol) and aqueous 1N sodium hydroxide (0.048 mL, 0.048 mmol) in dioxane (1 mL) was heated up at 78° C. for 3 h. The reaction mixture was filtered and the clear solution was purified by prep HPLC to provide the title compound as a white solid (9.5 mg, 31%). LCMS: m/e 615.56 (M+H)$^+$, 2.52 min (method 10). $^1$H NMR (500 MHz, Acetic acid d4) δ ppm 8.04 (d, J=8.24 Hz, 2H), 7.30 (d, J=8.24 Hz, 2H), 5.38 (d, J=4.58 Hz, 1H), 4.89 (s, 1H), 4.76 (s, 1H), 4.52 (d, J=16.17 Hz, 1H), 4.04 (d, J=16.17 Hz, 1H), 3.08 (d, J=10.99 Hz, 6H), 3.01-2.86 (m, 1H), 2.37-1.22 (m, 22H), 1.79 (s, 3H), 1.30 (s, 3H), 1.14 (s, 3H), 1.10 (s, 3H), 1.03 (s, 3H), 1.00 (s, 3H).

Example 146

Preparation of 4-((1R,3aS,5aR,5bR,7aR,11aS,11bR,13aR,13bR)-5a,5b,8,8,11a-pentamethyl-3a-(2-(2-oxopyrrolidin-1-yl)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

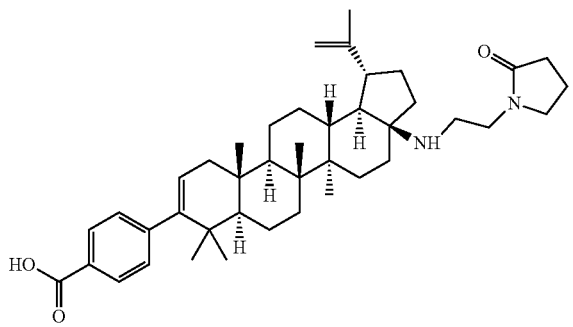

The title compound was prepared following the method described above for the synthesis of 4-((1R,3aS,5aR,5bR,7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 1-(2-chloroethyl)pyrrolidin-2-one as the alkylating reagent in Step 1. The product was isolated as a white solid (19 mg, 62%). LCMS: m/e 641.57 (M+H)$^+$, 2.58 min (method 10). $^1$H NMR (500 MHz, Acetic acid d4) δ ppm 8.04 (d, J=8.24 Hz, 2H), 7.30 (d, J=8.55 Hz, 2H), 5.37 (d, J=4.88 Hz, 1H), 4.91 (s, 1H), 4.76 (s, 1H), 3.89-3.73 (m, 3H), 3.55-3.45 (m, 1H), 2.93-2.80 (m, 1H), 2.57 (td, J=8.24, 3.97 Hz, 2H), 2.34-1.19 (m, 24H), 1.78 (s, 3H), 1.23 (s, 3H), 1.13 (s, 3H), 1.10 (s, 3H), 1.02 (s, 3H), 1.00 (s, 3H).

Example 147

Preparation of 4-((1R,3aS,5aR,5bR,7aR,11aS,11bR,13aR,13bR)-5a,5b,8,8,11a-pentamethyl-3a-(2-oxo-2-(pyrrolidin-1-yl)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

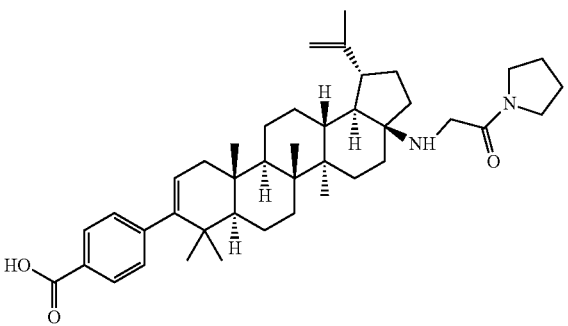

The title compound was prepared following the method described above for the synthesis of 4-((1R,3aS,5aR,5bR,7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 2-chloro-1-(pyrrolidin-1-yl)ethanone as the alkylating reagent in Step 1. The product was isolated as a white solid (19 mg, 46%). LCMS: m/e 641.46 (M+H)$^+$, 2.55 min (method 10). $^1$H NMR (500 MHz, Acetic acid d4) δ ppm 8.04 (d, J=8.24 Hz, 2H), 7.30 (d, J=8.24 Hz, 2H), 5.38 (d, J=4.58 Hz, 1H), 4.89 (s, 1H), 4.76 (s, 1H), 4.43 (d, J=16.48 Hz, 1H), 3.99 (d, J=16.17 Hz, 1H), 3.73-3.42 (m, 4H), 3.15-2.86 (m, 1H), 2.41-1.19 (m, 26H), 1.79 (s, 3H), 1.28 (s, 3H), 1.14 (s, 3H), 1.10 (s, 3H), 1.03 (s, 3H), 1.00 (s, 3H).

Example 148

Preparation of 4-((1R,3aS,5aR,5bR,7aR,11aS,11bR,13aR,13bR)-5a,5b,8,8,11a-pentamethyl-3a-(2-(methylamino)-2-oxoethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

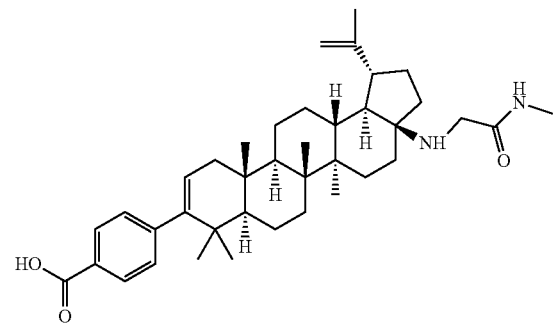

The title compound was prepared following the method described above for the synthesis of 4-((1R,3aS,5aR,5bR, 7aR,11aS,11bR,13aR,13bR)-3a-(2-(dimethylamino)-2-oxo-ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 2-chloro-N-methylacetamide as the alkylating reagent in Step 1. The product was isolated as a white solid (41 mg, 80%). LCMS: m/e 601.45 (M+H)+, 2.31 min (method 11). $^1$H NMR (500 MHz, Acetic acid d4) δ ppm 8.04 (d, J=8.24 Hz, 2H), 7.30 (d, J=8.24 Hz, 2H), 5.38 (d, J=4.58 Hz, 1H), 4.88 (s, 1H), 4.76 (s, 1H), 4.24 (d, J=15.56 Hz, 1H), 3.92 (d, J=15.26 Hz, 1H), 2.88 (s, 3H), 3.08-2.74 (m, 1H), 2.31-1.30 (m, 22H), 1.78 (s, 3H), 1.29 (s, 3H), 1.14 (s, 3H), 1.10 (s, 3H), 1.03 (s, 3H), 1.01 (s, 3H).

Example 149

Preparation of 4-((1R,3aS,5aR,5bR,7aR,11aS,11bR, 13aR,13bR)-3a-(2-(diethylamino)-2-oxoethyl-amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

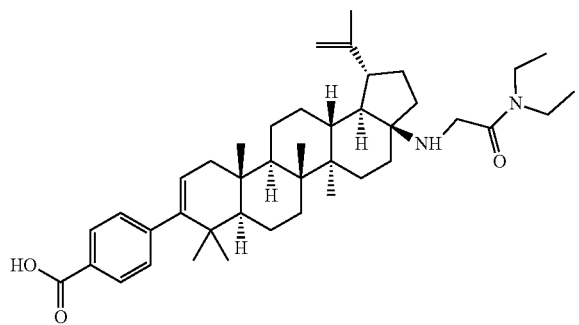

The title compound was prepared following the method described above for the synthesis of 4-((1R,3aS,5aR,5bR, 7aR,11aS,11bR,13aR,13bR)-3a-(2-(dimethylamino)-2-oxo-ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 2-chloro-N,N-diethylacetamide as alkylating reagent in Step 1. The product was isolated as a white solid (20 mg, 39%). LCMS: m/e 643.50 (M+H)+, 2.35 min (method 11). $^1$H NMR (400 MHz, CHLOROFORM-d) δ ppm 7.99 (d, J=8.28 Hz, 2H), 7.24 (d, J=8.28 Hz, 2H), 5.31 (d, J=4.52 Hz, 1H), 4.74 (d, J=1.76 Hz, 1H), 4.60 (s, 1H), 3.58-3.21 (m, 6H), 2.82-2.69 (m, 1H), 2.22-1.02 (m, 28H), 1.72 (s, 3H), 1.18 (s, 3H), 1.01 (s, 3H), 1.00 (s, 3H), 0.95 (s, 6H).

Example 150

Preparation of 4-((1R,3aS,5aR,5bR,7aR,11aS,11bR, 13aR,13bR)-3a-(2-(isopropylamino)-2-oxoethyl-amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

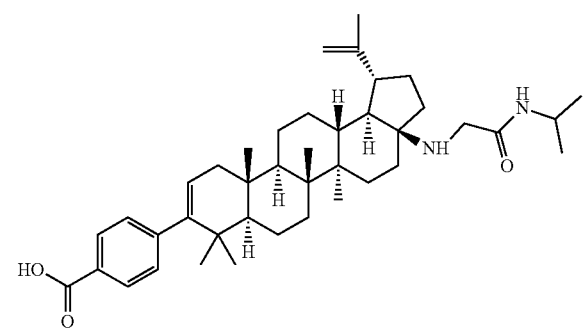

The title compound was prepared following the method described above for the synthesis of 4-((1R,3aS,5aR,5bR, 7aR,11aS,11bR,13aR,13bR)-3a-(2-(dimethylamino)-2-oxo-ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 2-chloro-N-isopropylacetamide as the alkylating reagent in Step 1. The product was isolated as a white solid (50 mg, 81%). LCMS: m/e 629.46 (M+H)+, 2.60 min (method 10). $^1$H NMR (400 MHz, Acetic acid d4) δ ppm 7.99 (d, J=8.53 Hz, 2H), 7.26 (d, J=8.53 Hz, 2H), 5.34 (d, J=4.77 Hz, 1H), 4.84 (s, 1H), 4.72 (s, 1H), 4.15 (d, J=15.31 Hz, 1H), 4.06 (dt, J=13.11, 6.62 Hz, 1H), 3.85 (d, J=15.31 Hz, 1H), 3.07-2.77 (m, 1H), 2.41-1.26 (m, 22H), 1.74 (s, 3H), 1.24 (s, 3H), 1.16 (d, J=6.53 Hz, 6H), 1.10 (s, 3H), 1.06 (s, 3H), 0.99 (s, 3H), 0.97 (s, 3H).

Example 151

Preparation of 4-((1R,3aS,5aR,5bR,7aR,11aS,11bR, 13aR,13bR)-3a-(2-hydroxyethylamino)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

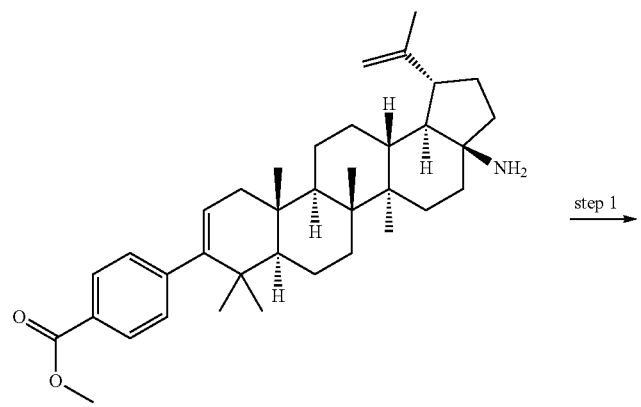

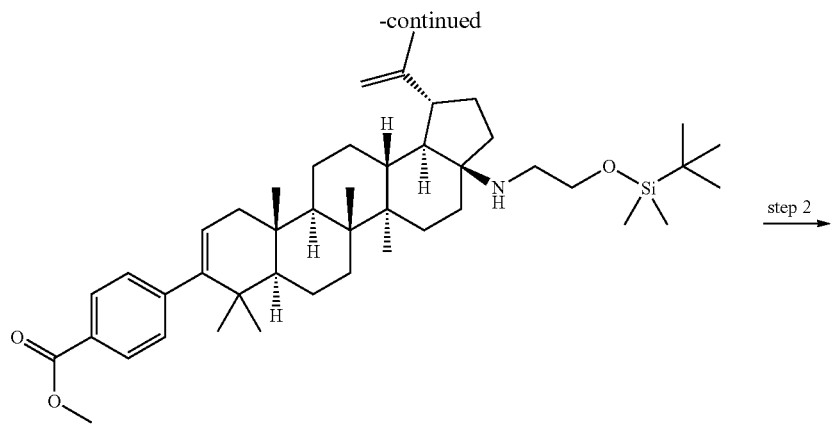

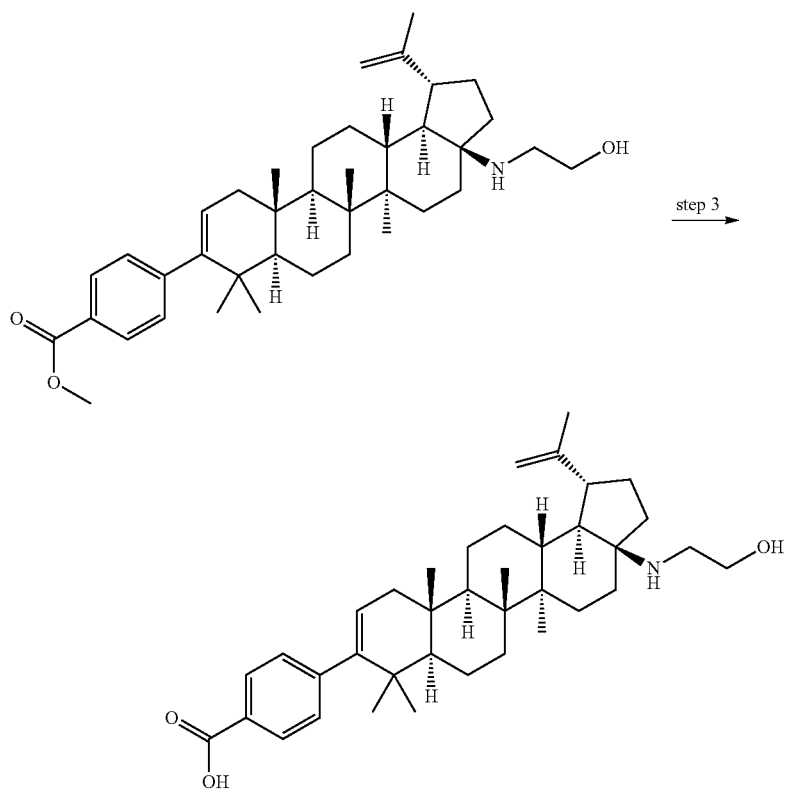

Step 1. Preparation of methyl 4-((1R,3aS,5aR,5bR, 7aR,11aS,11bR,13aR,13bR)-3a-(2-(tert-butyldimethylsilyloxy)ethylamino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate To a solution of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (300 mg, 0.552 mmol) in DCE (4 mL) was added (tert-butyldimethylsilyloxy)acetaldehyde (131 mL, 0.690 mmol) and titanium(IV) isopropoxide (0.202 mL, 0.690 mmol). The mixture was stirred at rt for 45 minutes and sodium triacetoxyborohydride (234 mg, 1.103 mmol) was added. The mixture was stirred at rt for 23 h and an additional 0.1 mL of (tert-butyldimethylsilyloxy)acetaldehyde and an additional 150 mg of sodium triacetoxyborohydride were added. The mixture was stirred at rt for an additional 22 h, then was diluted with 15 mL of sat. NaHCO$_3$ and was extracted with dichloromethane (3×15 mL). The combined organic layers were dried with Na$_2$SO$_4$, the drying agent was removed by filtration and the filtrate was concentrated under reduced pressure. The residue was adsorbed to silica gel and was purified by flash chromatography using a 0-10% EtOAc in hexanes gradient. The fractions containing the expected product were combined and were concentrated under reduced pressure to give the title compound (0.211 g, 0.301 mmol, 54.5% yield) as a clear yellow film. The product was used in the next step with no additional purification. LCMS: m/e 702.7 (M+H)$^+$, 2.35 min (method 2).

Step 2. Preparation of methyl 4-((1R,3aS,5aR,5bR, 7aR,11aS,11bR,13aR,13bR)-3a-(2-hydroxyethylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate To a solution of methyl 4-((1R,3aS,5aR,5bR,7aR,11aS, 11bR,13aR,13bR)-3a-(2-(tert-butyldimethylsilyloxy)ethylamino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoate (0.211 g, 0.301 mmol) in THF (2 mL) was added TBAF (1M in THF) (0.601 mL, 0.601 mmol). The mixture was stirred at rt for 2.75 h then was diluted with water (10 mL) and was extracted with dichloromethane (3×10 mL). The combined organic layers were dried with $Na_2SO_4$, the drying agent was removed by filtration and the filtrate was concentrated under reduced pressure. The residue was adsorbed to silica gel and was purified by flash chromatography using a 0-25% EtOAc in hexanes gradient. The title compound (93.4 mg, 0.159 mmol, 52.9% yield), was isolated as a colorless film. LCMS: m/e 588.6 (M+H)$^+$, 1.98 min (method 2). $^1$H NMR (500 MHz, CHLOROFORM-d) d ppm 7.91 (d, J=8.24 Hz, 2H), 7.18 (d, J=8.24 Hz, 2H), 5.27 (d, J=4.58 Hz, 1H), 4.70 (d, J=1.83 Hz, 1H), 4.59 (s, 1H), 3.89 (s, 3H), 3.54-3.64 (m, 2H), 2.52-2.69 (m, 3H), 2.09 (dd, J=17.09, 6.41 Hz, 1H), 1.68 (s, 3H), 1.07 (s, 3H), 0.98 (s, 3H), 0.97 (s, 3H), 0.93-2.05 (m, 21H), 0.91 (s, 3H), 0.91 (s, 3H).

Step 3. Preparation of 4-((1R,3aS,5aR,5bR,7aR, 11aS,11bR,13aR,13bR)-3a-(2-hydroxyethylamino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoic acid To a solution of methyl 4-((1R,3aS,5aR,5bR,7aR,11aS, 11bR,13aR,13bR)-3a-(2-hydroxyethylamino)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate (35 mg, 0.060 mmol) in dioxane (1 mL) was added NaOH (1N) (0.298 mL, 0.298 mmol). The mixture was heated to 85° C. for 15 h then was cooled to rt. The mixture was diluted with MeOH and was purified by prep HPLC. The fractions containing the expected product were combined and concentrated under reduced pressure to give the title compound (25 mg, 0.041 mmol, 69.5% yield) as a white solid. LCMS: m/e 574.5 (M+H)$^+$, 1.69 min (method 2). $^1$H NMR (500 MHz, Acetic acid d4) δ ppm 8.04 (2H, d, J=8.2 Hz), 7.30 (2H, d, J=8.2 Hz), 5.37 (1H, d, J=4.6 Hz), 4.86 (1H, s), 4.75 (1H, s), 3.95-4.11 (2H, m), 3.25-3.43 (2H, m), 2.90-2.98 (1H, m), 1.77 (3H, s), 1.21 (3H, s), 1.14 (3H, s), 1.09 (3H, s), 1.02 (3H, s), 1.00 (3H, s), 0.97-2.32 (22H, m).

Example 152

Preparation of 4-((1R,3aS,5aR,5bR,7aR,11aS,11bR, 13aR,13bR)-3a-(cyclopropylmethylamino)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

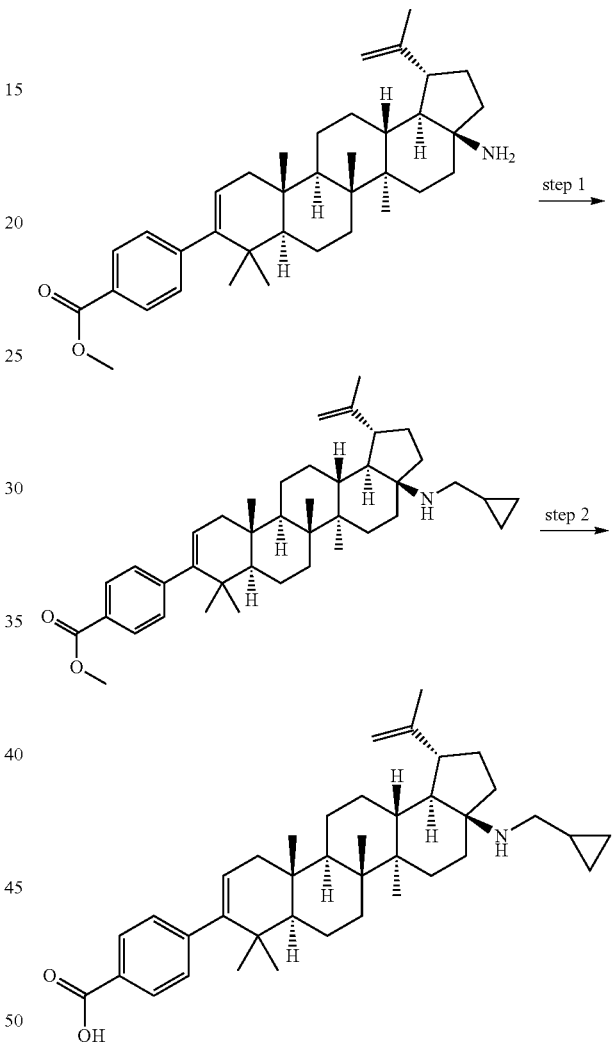

Step 1. Preparation of methyl 4-((1R,3aS,5aR,5bR, 7aR,11aS,11bR,13aR,13bR)-3a-(cyclopropylmethylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate To a solution of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (0.022 g, 0.040 mmol) in DCE (0.25 mL) was added cyclopropanecarbaldehyde (2.84 mg, 0.040 mmol) and titanium (IV) isopropoxide (0.015 mL, 0.051 mmol). The mixture was stirred at rt for 1 h and sodium triacetoxyborohydride (0.017 g, 0.081 mmol) was added. After stirring the mixture for 16.75 h, the mixture was diluted with 3 mL of water and was filtered through a pad of celite, then was extracted with dichloromethane (3×4 mL). The combined organic layers were dried with Na$_2$SO$_4$. The drying agent was removed by filtration and the filtrate was concentrated under reduced pressure to give the title compound (0.024 g, 0.040 mmol, 99% yield) as a clear film. The crude product was used in the next step with no additional purification. LCMS: m/e 598.6 (M+H)$^+$, 2.13 min (method 2).

Step 2. Preparation of 4-((1R,3aS,5aR,5bR,7aR, 11aS,11bR,13aR,13bR)-3a-(cyclopropylmethylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid To a cloudy mixture of methyl 4-((1R,3aS,5aR,5bR,7aR, 11aS,11bR,13aR,13bR)-3a-(cyclopropylmethylamino)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)benzoate (0.024 g, 0.040 mmol) in 1,4-dioxane (1.5 mL) was added NaOH (1N) (0.5 mL, 0.5 mmol). The mixture was heated to 65° C. After two hours, the mixture was cooled to rt and stirred at rt overnight. The mixture was filtered through plug of glass wool and was purified by prep HPLC to afford the title compound (0.007 g, 10.79 μmol, 26.9% yield) as a white film. LCMS: m/e 584.6 (M+H)$^+$, 1.83 min (method 2). $^1$H NMR (400 MHz, CHLOROFORM-d) δ ppm 8.00 (2H, d, J=8.0 Hz), 7.21 (2H, d, J=8.0 Hz), 5.31 (1H, d, J=5.0 Hz), 4.75 (1H, d, J=1.5 Hz), 4.61 (1H, s), 2.76 (1H, td, J=10.9, 5.6 Hz), 2.62 (1H, dd, J=11.2, 6.1 Hz), 2.23 (1H, dd, J=11.5, 7.8 Hz), 1.97-2.16 (3H, m), 1.82-1.95 (2H, m), 1.70 (3H, s), 1.16 (3H, s), 1.01 (3H, s), 1.00 (3H, s), 0.96 (3H, s), 0.95 (3H, s), 0.80-1.77 (19H, m), 0.48-0.58 (2H, m), 0.09-0.24 (2H, m).

Example 153

Preparation of tert-butyl 3-(((1R,3aS,5aR,5bR,7aR, 11aS,11bR,13aR,13bR)-9-(4-(methoxycarbonyl) phenyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-3a-ylamino)methyl)piperidine-1-carboxylate

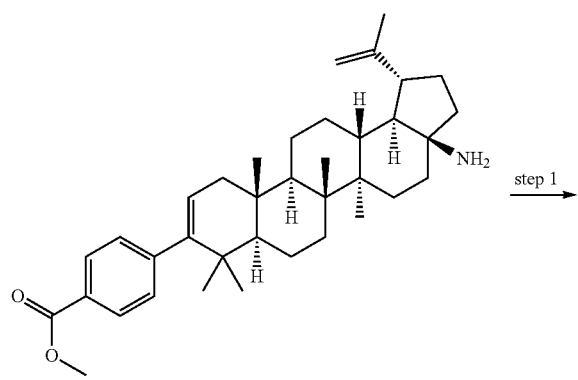

step 1

Step 1. Preparation of tert-butyl 3-(((1R,3aS,5aR, 5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-3a-ylamino)methyl)piperidine-1-carboxylate To a solution of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (30 mg, 0.055 mmol) in DCE (0.5 mL) was added 3-formyl-piperidine-1-carboxylic acid tert-butyl ester (14.71 mg, 0.069 mmol) and titanium(IV) isopropoxide (0.020 mL, 0.069 mmol). The mixture was stirred at rt for 1 h and sodium triacetoxyborohydride (23.38 mg, 0.110 mmol) was added. After stirring the mixture for 16.5 h, the mixture was diluted with 3 mL of sat. NaHCO$_3$ and was extracted with dichloromethane (3×5 mL). The combined organic layers were dried with Na$_2$SO$_4$. The drying agent was removed by filtration and the filtrate was concentrated under reduced pressure. The residue was adsorbed to silica gel and was purified by silica gel flash chromatography using a 0-10% EtOAc in hexanes gradient and a Thomson 12 g silica gel column. The fractions containing the expected product were combined and concentrated under reduced pressure to afford the title compound (29 mg, 0.039 mmol, 70.9% yield) as an off-white film. The product was used in the next step with no additional purification. LCMS: m/e 741.7 (M+H)$^+$, 3.76 min (method 2).

Step 2. Preparation of tert-butyl 3-(((1R,3aS,5aR, 5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-3a-ylamino)methyl)piperidine-1-carboxylate To a solution of tert-butyl 3-(((1R,3aS,5aR,5bR,7aR,11aS, 11bR,13aR,13bR)-9-(4-(methoxycarbonyl)phenyl)-5a,5b,8, 8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-ylamino)methyl)piperidine-1-carboxylate (0.029 g, 0.039 mmol) in dioxane (2 mL) was added NaOH (1N) (0.196 mL, 0.196 mmol). The mixture was heated to 85° C. overnight. After heating the mixture for 22 h, it was cooled to rt, diluted with MeOH, and purified by prep HPLC to afford the title compound (24 mg, 0.031 mmol, 80% yield) as a clear, colorless film. LCMS: m/e 727.7 (M+H)+, 2.00 min (method 2). $^1$H NMR (500 MHz, CHLOROFORM-d) δ ppm 7.98 (2H, d, J=7.9 Hz), 7.21 (2H, d, J=7.9 Hz), 5.29 (1H, d, J=5.5 Hz), 4.70 (1H, br. s.), 4.58 (1H, br. s.), 3.83-4.22 (4H, m), 2.46-2.85 (4H, m), 2.29 (2H, br. s.), 1.68 (3H, s), 1.47 (9H, d, J=4.6 Hz), 1.10 (3H, d, J=7.9 Hz), 0.98 (6H, br. s.), 0.93 (3H, s), 0.92 (3H, s), 0.77-2.15 (25H, m).

Example 154

Preparation of 4-((1R,3aS,5aR,5bR,7aR,11aS,11bR,13aR,13bR)-5a,5b,8,8,11a-pentamethyl-3a-(piperidin-3-ylmethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

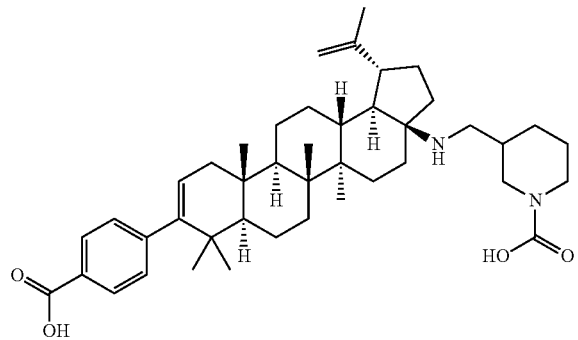

To a solution of 4-((1R,3aS,5aR,5bR,7aR,11aS,11bR,13aR,13bR)-3a-((1-(tert-butoxycarbonyl)piperidin-3-yl)methylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (0.019 g, 0.026 mmol) in DCM (1 mL) was added TFA (0.25 mL, 3.24 mmol). The mixture was stirred at rt for 1.75 h. Then, the mixture was concentrated under reduced pressure and purified by prep HPLC to give the title compound (14.2 mg, 0.021 mmol, 81% yield) as a white solid. LCMS: m/e 627.6 (M+H)+, 1.50 min (method 2). $^1$H NMR (500 MHz, Acetic acid d4) δ ppm 8.04 (2H, d, J=8.2 Hz), 7.30 (2H, d, J=7.9 Hz), 5.37 (1H, s), 4.85 (1H, d, J=5.5 Hz), 4.75 (1H, s), 2.98-3.83 (6H, m), 2.82-2.91 (1H, m), 2.57-2.72 (1H, m), 0.85-2.33 (44H, m).

Example 155

Preparation of 4-((1R,3aS,5aR,5bR,7aR,11aS,11bR,13aR,13bR)-3a-(furan-2-ylmethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

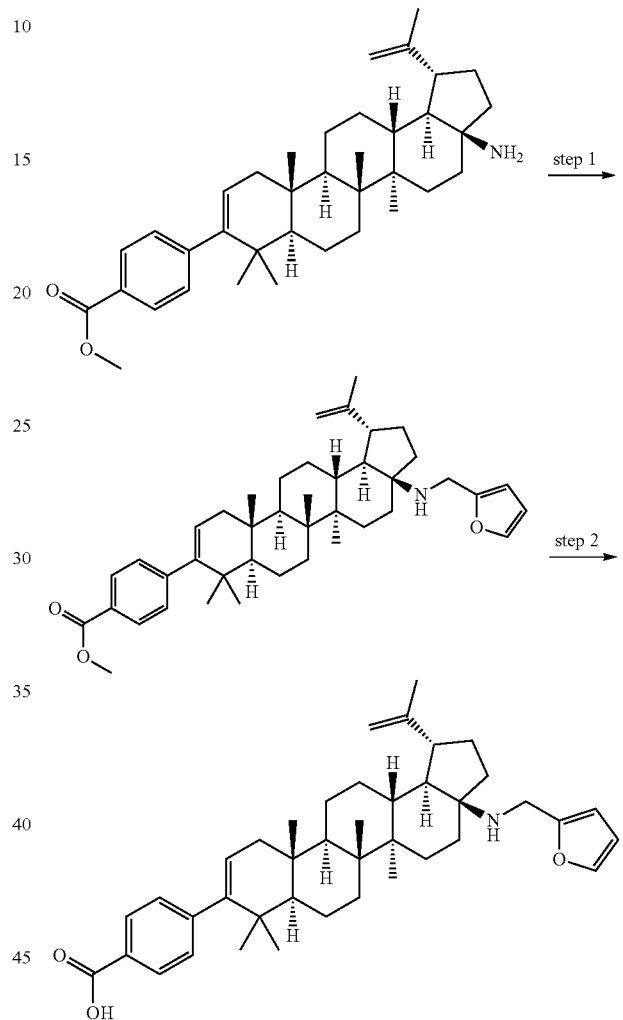

Step 1. Preparation of methyl 4-((1R,3aS,5aR,5bR,7aR,11aS,11bR,13aR,13bR)-3a-(furan-2-ylmethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To a solution of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (30 mg, 0.055 mmol) in DCE (0.5 mL) was added furfural (5.71 μL, 0.069 mmol) and titanium(IV) isopropoxide (0.020 mL, 0.069 mmol). The mixture was stirred at rt for 1 h and sodium triacetoxyborohydride (23.38 mg, 0.110 mmol) was added. After stirring the mixture for 16 h at rt an additional 5 μL of furfural was added along with an additional 0.025 g of sodium triacetoxborohydride. After stirring the mixture overnight at rt, it was purified by passing through a plug of silica gel and washing with 0-25% EtOAc in hexanes.

The fractions containing the product were combined and concentrated under reduced pressure to give the title compound (31 mg, 0.050 mmol, 90% yield) as a light-yellow film. The product was used in the next step with no additional purification. LCMS: m/e 625.6 (M+H)+, 3.08 min (method 2).

Step 2. Preparation of 4-((1R,3aS,5aR,5bR,7aR, 11aS,11bR,13aR,13bR)-3a-(furan-2-ylmethy- lamino)-5a,5b,8,8,11a-pentamethyl-1-(prop-1-en-2- yl)-2,3,3a,4,5,5a,5b,6,7,7a,8,11,11a,11b,12,13,13a, 13b-octadecahydro-1H-cyclopenta[a]chrysen-9-yl) benzoic acid To a solution of methyl 4-((1R,3aS,5aR,5bR,7aR,11aS, 11bR,13aR,13bR)-3a-(furan-2-ylmethylamino)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H- cyclopenta[a]chrysen-9-yl)benzoate (31 mg, 0.050 mmol) in 1,4-dioxane (2 mL) was added 1N NaOH (0.248 mL, 0.248 mmol). The mixture was heated to 85° C. for 22 h then was cooled to rt. The crude product was purified by prep HPLC. The fractions containing the expected product were combined and were concentrated under reduced pressure to afford the title compound (19.3 mg, 0.030 mmol, 60.5% yield) as a clear film. LCMS: m/e 610.69 (M+H)+, 2.35 min (method 2). $^1$H NMR (400 MHz, CHLOROFORM-d) d ppm 8.00 (d, J=7.78 Hz, 2H), 7.37 (d, J=1.00 Hz, 1H), 7.23 (d, J=7.78 Hz, 2H), 6.33 (dd, J=3.14, 1.88 Hz, 1H), 6.21 (d, J=2.76 Hz, 1H), 5.53 (br. s., 1H), 5.29-5.34 (m, 1H), 4.72 (d, J=1.76 Hz, 1H), 4.60 (s, 1H), 3.67 (s, 2H), 2.64 (td, J=10.85, 5.40 Hz, 1H), 1.71 (s, 3H), 1.10-1.15 (m, 3H), 1.01 (s, 3H), 1.00 (s, 3H), 0.97-2.18 (m, 22H), 0.96 (s, 6H).

Example 156

Preparation of 4-((1R,3aS,5aR,5bR,7aR,11aS,11bR, 13aR,13bR)-3a-(2,2-dimethoxyethylamino)-5a,5b,8, 8,11a-pentamethyl-1-(prop-1-en-2-yl)-2,3,3a,4,5,5a, 5b,6,7,7a,8,11,11a,11b,12,13,13a,13b- octadecahydro-1H-cyclopenta[a]chrysen-9-yl) benzoic acid

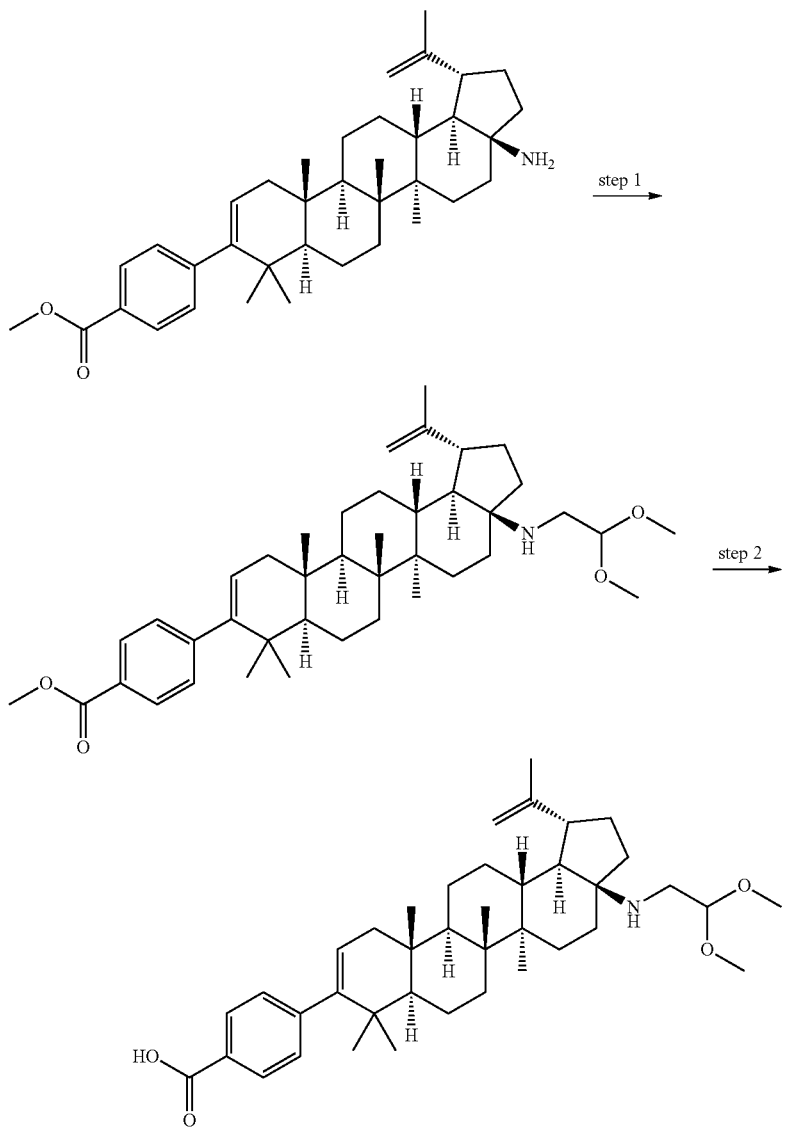

Step 1. Preparation of methyl 4-((1R,3aS,5aR,5bR, 7aR,11aS,11bR,13aR,13bR)-3a-(2,2-dimethoxyethylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate To a solution of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate, HCl (0.9 g, 1.551 mmol) in DCM (Volume: 15 mL) was added glyoxal 1,1-dimethyl acetal solution (45% in MTBE) (0.498 mL, 1.939 mmol), acetic acid (0.178 mL, 3.10 mmol), and sodium triacetoxyborohydride (0.493 g, 2.326 mmol). The mixture was stirred at rt. After 4 h of stirring, an additional 0.5 mL of glyoxal 1,1-dimethyl acetal solution (45% in MTBE) was added along with an additional 0.5 g of sodium triacetoxyborohydride. After a total of 7 h of stirring, the mixture was diluted with 25 mL of sat. NaHCO$_3$ and was extracted with dichloromethane (3×25 mL). The combined organic layers were dried with Na$_2$SO$_4$. The drying agent was removed by filtration and the filtrate was concentrated under reduced pressure. The residue was adsorbed to silica gel and was purified by flash chromatography using a 0-10% EtOAc in hexanes gradient to give the title compound (0.67 g, 1.060 mmol, 68.4% yield) as a white foam. LCMS: m/e 632.75 (M+H)$^+$, 2.45 min (method 11).

Step 2. Preparation of 4-((1R,3aS,5aR,5bR,7aR, 11aS,11bR,13aR,13bR)-3a-(2,2-dimethoxyethylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid To a solution of methyl 4-((1R,3aS,5aR,5bR,7aR,11aS, 11bR,13aR,13bR)-3a-(2,2-dimethoxyethylamino)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate (0.025 g, 0.040 mmol) in 1,4-dioxane (1 mL) was added NaOH (1N) (0.198 mL, 0.198 mmol). The mixture was heated to 85° C. After 6 h of heating, the mixture was cooled to rt, the reaction mixture was diluted with MeOH and was purified by prep HPLC. The fractions containing the expected product were combined and were concentrated under reduced pressure to give the title compound (17 mg, 0.026 mmol, 66.1% yield) as a clear film. LCMS: m/e 618.8 (M+H)$^+$, 2.28 min (method 11). $^1$H NMR (500 MHz, CHLOROFORM-d) d ppm 7.99 (d, J=7.93 Hz, 2H), 7.20 (d, J=7.93 Hz, 2H), 5.28 (d, J=4.88 Hz, 1H), 5.12 (br. s., 1H), 4.72 (s, 1H), 4.58 (s, 1H), 4.53 (t, J=5.49 Hz, 1H), 3.44 (s, 3H), 3.41 (s, 3H), 2.64-2.74 (m, 2H), 2.60 (dd, J=11.44, 6.56 Hz, 1H), 1.97-2.13 (m, 2H), 1.86-1.95 (m, 2H), 1.81 (dd, J=12.51, 8.24 Hz, 1H), 1.68 (s, 3H), 1.11 (s, 3H), 0.98 (s, 3H), 0.97 (br. s., 3H), 0.95-1.72 (m, 17H), 0.93 (br. s., 6H).

Example 157

Preparation of 4-((1R,3aS,5aR,5bR,7aR,11aS,11bR, 13aR,13bR)-3a-((2-carboxycyclopropyl)methylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

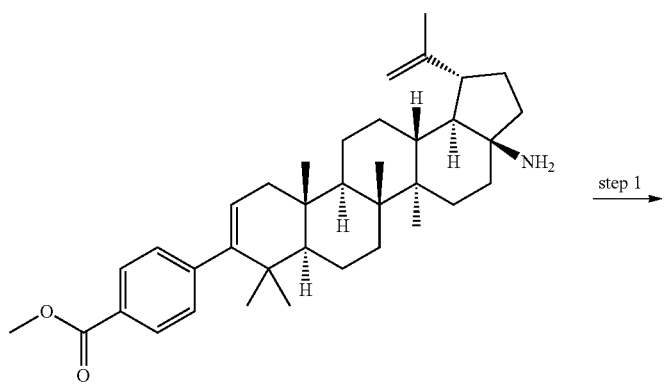

step 1

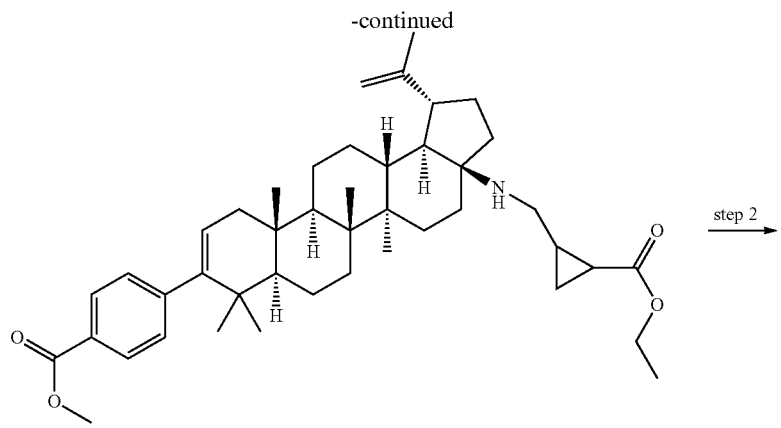

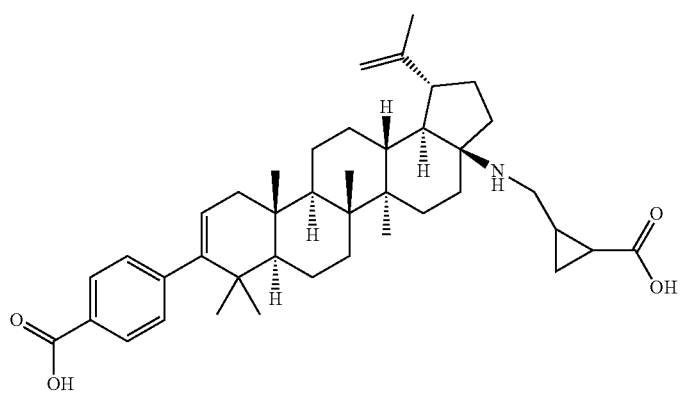

Step 1. Preparation of methyl 4-((1R,3aS,5aR,5bR, 7aR,11aS,11bR,13aR,13bR)-3a-((2-(ethoxycarbonyl)cyclopropyl)methylamino)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)benzoate To a solution of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (30 mg, 0.055 mmol) in DCE (0.5 mL) was added ethyl 2-formyl-1-cyclopropanecarboxylate (9.13 mL, 0.069 mmol) and titanium(IV) isopropoxide (0.020 mL, 0.069 mmol). The mixture was stirred at rt for 1 h and sodium triacetoxyborohydride (23.38 mg, 0.110 mmol) was added. After stirring the mixture for 16.25 h additional ethyl 2-formyl-1-cyclopropanecarboxylate (9.13 mL, 0.069 mmol) and sodium triacetoxyborohydride (23.38 mg, 0.110 mmol) were added and the mixture was again stirred at rt for 24 h. The reaction mixture was loaded directly onto a silica gel column and was purified by flash chromatography using a 0-25% EtOAc in hexanes gradient. The fractions containing the expected product were combined and concentrated under reduced pressure to give methyl 4-((1R,3aS,5aR,5bR,7aR, 11aS,11bR,13aR,13bR)-3a-((2-(ethoxycarbonyl)cyclopropyl)methylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (33 mg, 0.049 mmol, 89% yield). LCMS: m/e 670.8 (M+H)+, 2.47 min (method 11).

Step 2. Preparation of 4-((1R,3aS,5aR,5bR,7aR, 11aS,11bR,13aR,13bR)-3a-((2-carboxycyclopropyl) methylamino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid To a solution of methyl 4-((1R,3aS,5aR,5bR,7aR,11aS, 11bR,13aR,13bR)-3a-((2-(ethoxycarbonyl)cyclopropyl)methylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (33 mg, 0.049 mmol) in 1,4-dioxane (2 mL) was added NaOH (1N) (0.246 mL, 0.246 mmol). The mixture was heated to 85° C. for 22 h then was cooled to rt. An additional 0.25 mL of 1N NaOH was added to the mixture and it was again heated to 85° C. After stirring the mixture over the weekend, the reaction mixture was purified by prep HPLC. The fractions containing the expected product were combined and concentrated under reduced pressure. 1H NMR still showed impurities present, so the mixture was purified a second time by prep HPLC. The fractions containing the product were combined and concentrated under reduced pressure to give the title compound (8.3 mg, 0.012 mmol, 24.15% yield) as a white solid. LCMS: m/e 628.6 (M+H)⁺, 1.66 min (method 2).

Example 158

Preparation of 4-((1R,3aS,5aR,5bR,7aR,11aS,11bR,13aR,13bR)-5a,5b,8,8,11a-pentamethyl-1-(prop-1-en-2-yl)-3a-(thiophen-3-ylmethylamino)-2,3,3a,4,5,5a,5b,6,7,7a,8,11,11a,11b,12,13,13a,13b-octadecahydro-1H-cyclopenta[a]chrysen-9-yl)benzoic acid

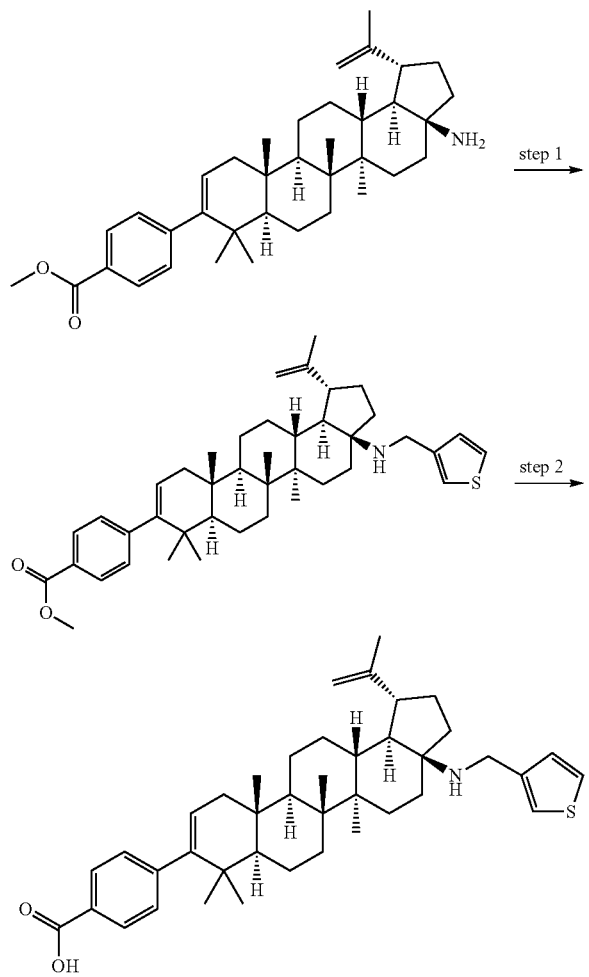

Step 1. Preparation of methyl 4-((1R,3aS,5aR,5bR,7aR,11aS,11bR,13aR,13bR)-5a,5b,8,8,11a-pentamethyl-1-(prop-1-en-2-yl)-3a-(thiophen-3-ylmethylamino)-2,3,3a,4,5,5a,5b,6,7,7a,8,11,11a,11b,12,13,13a,13b-octadecahydro-1H-cyclopenta[a]chrysen-9-yl)benzoate To a solution of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (30 mg, 0.055 mmol) in DCE (0.5 mL) was added 3-thiophenecarboxaldehyde (7.73 mg, 0.069 mmol) and titanium(IV) isopropoxide (0.020 mL, 0.069 mmol). The mixture was stirred at rt for 1 h and sodium triacetoxyborohydride (23.38 mg, 0.110 mmol) was added. The mixture was stirred for 18 h at rt. The reaction mixture was loaded directly onto a silica gel column and was purified by flash chromatography using a 0-25% EtOAc in hexanes gradient. The fractions containing the expected product were combined and were concentrated under reduced pressure to give the title compound (32 mg, 0.05 mmol, 91% yield). LCMS: m/e 640.6 (M+H)⁺, 2.13 min (method 2).

Step 2. Preparation of 4-((1R,3aS,5aR,5bR,7aR,11aS,11bR,13aR,13bR)-5a,5b,8,8,11a-pentamethyl-1-(prop-1-en-2-yl)-3a-(thiophen-3-ylmethylamino)-2,3,3a,4,5,5a,5b,6,7,7a,8,11,11a,11b,12,13,13a,13b-octadecahydro-1H-cyclopenta[a]chrysen-9-yl)benzoic acid To a solution of methyl 4-((1R,3aS,5aR,5bR,7aR,11aS,11bR,13aR,13bR)-5a,5b,8,8,11a-pentamethyl-1-(prop-1-en-2-yl)-3a-(thiophen-3-ylmethylamino)-2,3,3a,4,5,5a,5b,6,7,7a,8,11,11a,11b,12,13,13a,13b-octadecahydro-1H-cyclopenta[a]chrysen-9-yl)benzoate (32 mg, 0.050 mmol) in dioxane (1 mL) was added NaOH (1N) (0.250 mL, 0.250 mmol). The mixture was heated to 85° C. for 15 h. The mixture was cooled to rt and was purified by prep HPLC to give the title compound (18 mg, 0.027 mmol, 53.5% yield) as a white solid. LCMS: m/e 626.5 (M+H)⁺, 1.82 min (method 2). ¹H NMR (400 MHz, CHLOROFORM-d) δ ppm 8.00 (2H, d, J=8.3 Hz), 7.30 (1H, dd, J=4.8, 3.0 Hz), 7.24 (2H, d, J=8.3 Hz), 7.20 (1H, d, J=2.0 Hz), 7.12 (1H, dd, J=5.0, 1.0 Hz), 5.30-5.34 (1H, m), 4.72 (1H, d, J=1.8 Hz), 4.61 (1H, s), 2.61 (1H, td, J=10.7, 5.4 Hz), 1.89-2.17 (5H, m), 1.77-1.88 (1H, m), 1.72 (3H, s), 1.14 (3H, s), 1.02 (3H, s), 1.00 (3H, s), 0.94-1.74 (18H, m), 0.96 (6H, s).

Example 159

Preparation of 4-((1R,3aS,5aR,5bR,7aR,11aS,11bR,13aR,13bR)-5a,5b,8,8,11a-pentamethyl-3a-(2-morpholinoethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

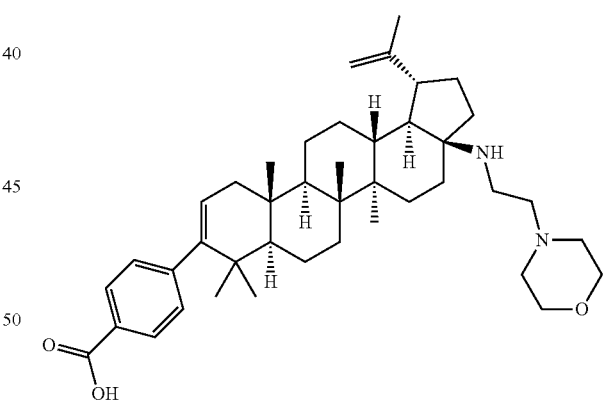

The title compound was prepared following the method described above for the synthesis of 4-((1R,3aS,5aR,5bR,7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 4-(2-chloroethyl)morpholine hydrochloride as the alkylating agent in Step 1. The product was isolated as a white solid (65 mg, 49.4%). LCMS: m/e 643.6 (MH⁺), 2.35 min (method 13). ¹H NMR (400 MHz, MeOD) δ ppm 7.95 (m, J=8.3 Hz, 2H), 7.24 (m, J=8.3 Hz, 2H), 5.31 (d, J=4.8 Hz, 1H), 4.86 (s, 1H), 4.74 (s, 1H), 3.82-3.99 (m, 4H), 3.37-3.58 (m, 4H), 3.21 (d, J=4.5 Hz, 2H), 3.19 (br. s., 2H), 2.67-2.86 (m, 1H), 2.02-2.26 (m, 5H), 1.83-1.90 (m, 1H), 1.64-1.81 (m, 8H), 1.45-1.64 (m, 7H), 1.34-1.45 (m, 2H), 1.27-1.34 (m, 1H), 1.15-1.27 (m, 4H), 1.12 (s, 3H), 1.04 (s, 3H), 0.99 (s, 3H), 0.93 (s, 3H).

Example 160

Preparation of 4-((1R,3aS,5aR,5bR,7aR,11aS,11bR, 13aR,13bR)-3a-(bis(2-morpholinoethyl)amino)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

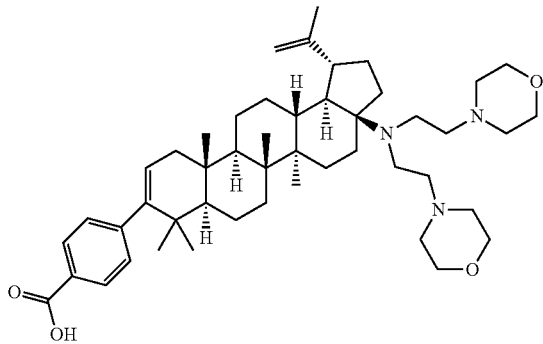

The title compound was obtained as a side product in the preparation 4-((1R,3aS,5aR,5bR,7aR,11aS,11bR,13aR, 13bR)-5a,5b,8,8,11a-pentamethyl-3a-(2-morpholinoethylamino)-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)benzoic acid. The product was isolated as a white solid (20 mg, 12.2%). LCMS: m/e 756.7 (MH+), 2.41 min (method 13). $^1$H NMR (400 MHz, MeOD) δ ppm 7.95 (m, J=8.3 Hz, 2H), 7.24 (m, J=8.3 Hz, 2H), 5.32 (d, J=4.8 Hz, 1H), 4.86 (s, 1H), 4.73 (s, 1H), 4.19 (t, J=7.5 Hz, 2H), 4.02-4.14 (m, 6H), 3.88 (t, J=4.4 Hz, 4H), 3.70-3.84 (m, 4H), 3.57 (br. s., 2H), 3.42-3.51 (m, 2H), 2.96-3.19 (m, 4H), 2.79 (br. s., 1H), 2.01-2.26 (m, 5H), 1.87-1.96 (m, 1H), 1.68-1.82 (m, 6H), 1.46-1.68 (m, 8H), 1.26-1.45 (m, 4H), 1.17-1.26 (m, 4H), 1.13 (s, 3H), 1.05 (s, 3H), 0.99 (s, 3H), 0.97 (s, 3H).

Example 161

Preparation of 4-((1R,3aS,5aR,5bR,7aR,11aS,11bR, 13aR,13bR)-5a,5b,8,8,11a-pentamethyl-1-(prop-1-en-2-yl)-3a-(thiazol-4-ylmethylamino)-2,3,3a,4,5,5a, 5b,6,7,7a,8,11,11a,11b,12,13,13a,13b-octadecahydro-1H-cyclopenta[a]chrysen-9-yl) benzoic acid

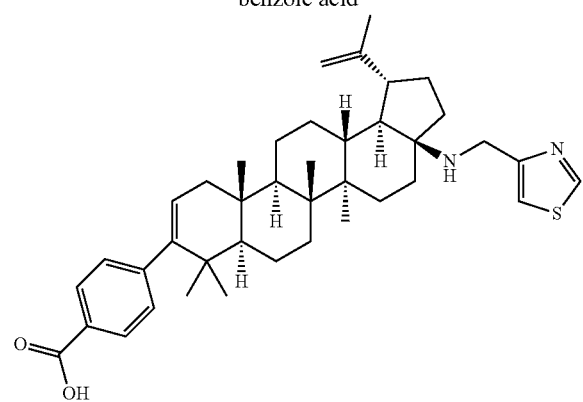

The title compound was prepared following the method described above for the synthesis of 4-((1R,3aS,5aR,5bR, 7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 4-(chloromethyl)thiazole as the alkylating agent in Step 1. MS: m/e 627.5 (M+H)+, 1.56 min (method 12). $^1$H NMR (400 MHz, CHLOROFORM-d) δ ppm 0.95 (s., 3H) 0.96 (s, 3H) 1.01 (s, 3H) 1.10 (s, 3H) 1.21 (s, 3H) 1.72 (s, 3H) 0.89-1.83 (m, 16H) 1.84-2.05 (m, 3H) 2.07-2.22 (m, 1H) 2.13 (dd, J=17.07, 6.53 Hz, 1H) 2.22-2.32 (m, 1H) 2.33-2.49 (m, 1H) 4.24 (d, J=14.05 Hz, 1H) 4.70 (s, 1H) 4.72 (d, J=13.55 Hz, 1H) 4.81 (s, 1H) 5.31 (dd, J=6.02, 1.51 Hz, 1H) 7.24 (d, J=8.28 Hz, 2H) 7.59 (s, 1H) 8.00 (d, J=8.28 Hz, 2H) 8.83 (s, 1H).

Example 162

Preparation of 4-((1R,3aS,5aR,5bR,7aR,11aS,11bR, 13aR,13bR)-5a,5b,8,8,11a-pentamethyl-3a-((2-methylthiazol-4-yl)methylamino)-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoic acid

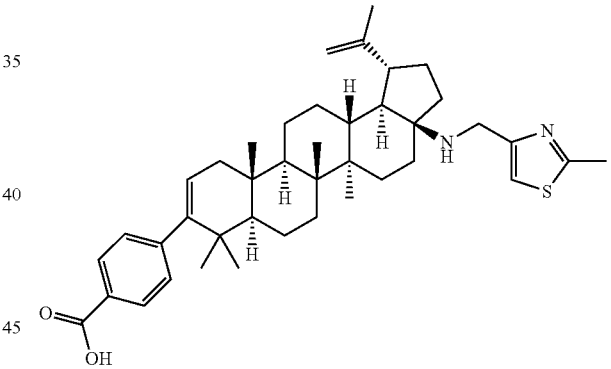

The title compound was prepared following the method described above for the synthesis of 4-((1R,3aS,5aR,5bR, 7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 4-(chloromethyl)-2-methylthiazole hydrochloride as the alkylating agent in Step 1. MS: m/e 641.5 (M+H)+, 1.56 min (method 12). $^1$H NMR (400 MHz, CHLOROFORM-d) δ ppm 0.96 (s, 3H) 0.97 (s, 3H) 1.02 (s, 3H) 1.10 (s, 3H) 1.26 (s, 3H) 1.71 (s, 3H) 0.88-1.83 (m, 16H) 1.89-2.04 (m, 3H) 2.08-2.21 (m, 1H) 2.14 (dd, J=17.19, 6.15 Hz, 1H) 2.22-2.30 (m, 1H) 2.33-2.45 (m, 1H) 2.68 (s, 3H) 4.09 (d, J=13.05 Hz, 1H)

4.64 (d, J=12.80 Hz, 1H) 4.69 (s, 1H) 4.80 (s, 1H) 5.32 (d, J=4.52 Hz, 1H) 7.24 (d, J=8.28 Hz, 2H) 7.28 (s, 1H) 8.00 (d, J=8.28 Hz, 2H).

Example 163

Preparation of 4-((1S,3aS,5aR,5bR,7aR,11aS,11bR,13aR,13bR)-3a-((2-(1,1-dioxido-4-thiomorpholinyl)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

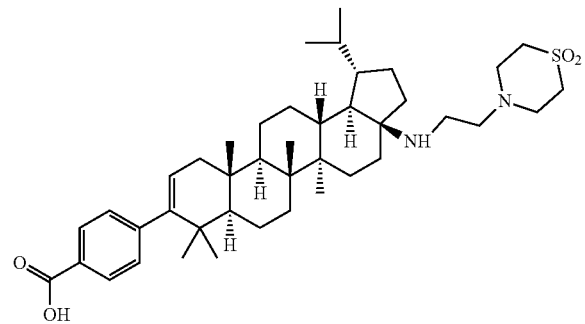

A mixture of 4-((1R,3aS,5aR,5bR,7aR,11aS,11bR,13aR,13bR)-3a-((2-(1,1-dioxido-4-thiomorpholinyl)ethyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid (100 mg, 0.145 mmol) and 10% Pd/C (90 mg, 0.087 mmol) in methanol (5 mL) and ethyl acetate (5 mL) was loaded onto a PARR shaker reactor and treated with hydrogen for 25 hours under 40 psi at room temperature. The reaction mixture was filtered through a celite pad to remove the catalyst. The filtrate was purified by HPLC to provide the title compound as a white solid (5.6 mg, 28%). LCMS: m/e 693.46 (M+H)$^+$, 2.46 min (method 10). $^1$H NMR (500 MHz, Acetic acid d4) δ ppm 8.04 (d, J=8.2 Hz, 2H), 7.31 (d, J=8.2 Hz, 2H), 5.39 (d, J=4.6 Hz, 1H), 3.50-3.36 (m, 1H), 3.36-3.21 (m, 6H), 3.21-2.98 (m, 5H), 2.31-1.29 (m, 24H), 1.29 (s, 3H), 1.13 (s, 6H), 1.03 (s, 3H), 1.01 (s, 3H), 0.94 (d, J=6.7 Hz, 3H), 0.86 (d, J=6.7 Hz, 3H).

Example 164

Preparation of N-(cyclopropylsulfonyl)-4-((1R,3aS,5aR,5bR,7aR,11aS,11bR,13aR,13bR)-3a-((2-(1,1-dioxido-4-thiomorpholinyl)ethyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzamide

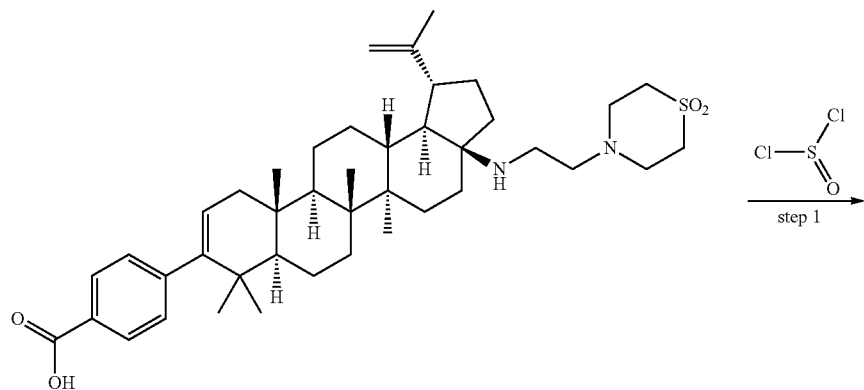

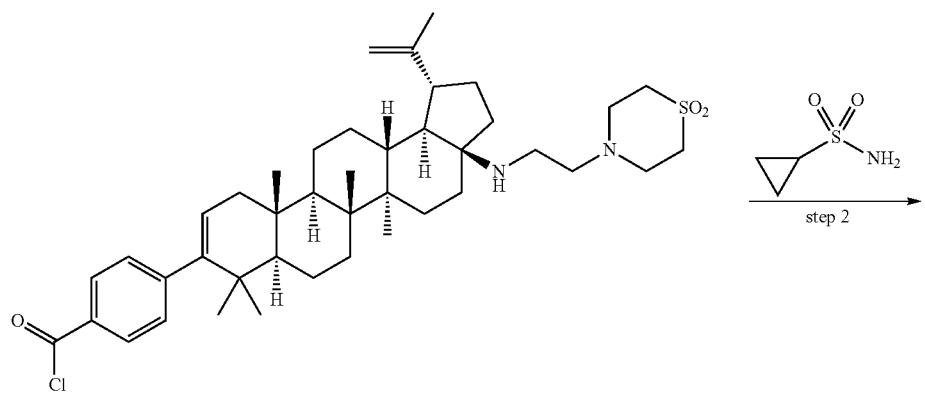

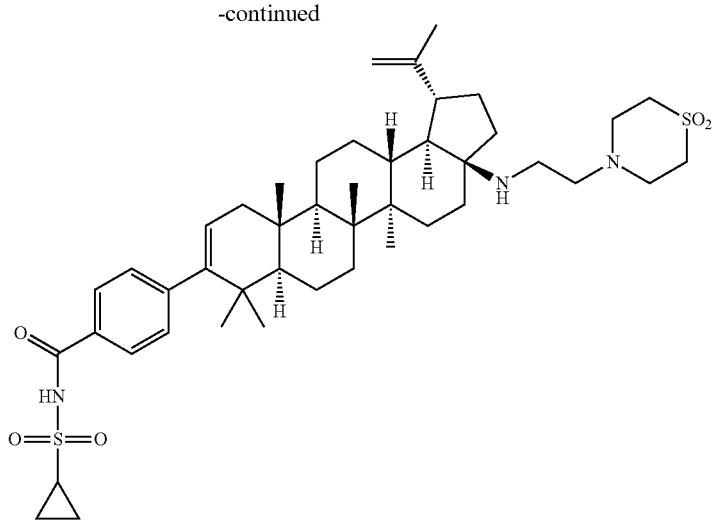

Step 1. Preparation of 4-((1R,3aS,5aR,5bR,7aR, 11aS,11bR,13aR,13bR)-3a-((2-(1,1-dioxido-4-thiomorpholinyl)ethyl)amino)-1-isopropenyl-5a,5b,8,8, 11a-pentamethyl-2,3,3a,4,5,5a,5b,6,7,7a,8,11,11a, 11b,12,13,13a,13b-octadecahydro-1H-cyclopenta[a]chrysen-9-yl)benzoyl chloride A mixture of 4-((1R,3aS,5aR,5bR,7aR,11aS,11bR,13aR, 13bR)-3a-((2-(1,1-dioxido-4-thiomorpholinyl)ethyl) amino)-1-isopropenyl-5a,5b,8,8,11a-pentamethyl-2,3,3a,4, 5,5a,5b,6,7,7a,8,11,11a,11b,12,13,13a,13b-octadecahydro-1H-cyclopenta[a]chrysen-9-yl)benzoic acid (200 mg, 0.289 mmol) and thionyl chloride (0.211 mL, 2.89 mmol) in dichloroethane (5 mL) was refluxed for 30 h. The reaction mixture was concentrated under reduced pressure to provide the title compound as a white solid (150 mg, 73%). LCMS: m/e 705.46 (M−Cl+OMe+H)+, 3.0 min (method 10).

Step 2. Preparation of N-(cyclopropylsulfonyl)-4-((1R,3aS,5aR,5bR,7aR,11aS,11bR,13aR,13bR)-3a-((2-(1,1-dioxido-4-thiomorpholinyl)ethyl)amino)-1-isopropenyl-5a,5b,8,8,11a-pentamethyl-2,3,3a,4,5, 5a,5b,6,7,7a,8,11,11a,11b,12,13,13a,13b-octadecahydro-1H-cyclopenta[a]chrysen-9-yl) benzamide A mixture of 4-((1R,3aS,5aR,5bR,7aR,11aS,11bR,13aR, 13bR)-3a-((2-(1,1-dioxido-4-thiomorpholinyl)ethyl) amino)-1-isopropenyl-5a,5b,8,8,11a-pentamethyl-2,3,3a,4, 5,5a,5b,6,7,7a,8,11,11a,11b,12,13,13a,13b-octadecahydro-1H-cyclopenta[a]chrysen-9-yl)benzoyl chloride (30 mg, 0.042 mmol), cyclopropanesulfonamide (6.15 mg, 0.051 mmol), Hunig's Base (0.022 mL, 0.127 mmol) and DMAP (2.58 mg, 0.021 mmol) in dichloromethane (1 mL) was stirred for 16 h at room temperature. The crude reaction mixture was purified by prep HPLC to provide the title compound as a white solid (4 mg, 11%). LCMS: m/e 794.53 (M+H)+, 2.44 min (method 10). $^1$H NMR (500 MHz, Acetic acid d4) δ ppm 7.94 (d, J=8.5 Hz, 2H), 7.32 (d, J=8.2 Hz, 2H), 5.38 (d, J=4.6 Hz, 1H), 4.84 (s, 1H), 4.74 (s, 1H), 3.56-3.39 (m, 1H), 3.38-3.21 (m, 7H), 3.21-3.11 (m, 3H), 3.11-3.03 (m, 2H), 3.01-2.89 (m, 1H), 2.41-1.16 (m, 26H), 1.76 (s, 3H), 1.29 (s, 3H), 1.15 (s, 3H), 1.11 (s, 3H), 1.03 (s, 3H), 1.00 (s, 3H).

Example 165

Preparation of 4-((1R,3aS,5aR,5bR,7aR,11aS,11bR, 13aR,13bR)-5a,5b,8,8,11a-pentamethyl-3a-(3-morpholinopropylamino)-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) benzoic acid

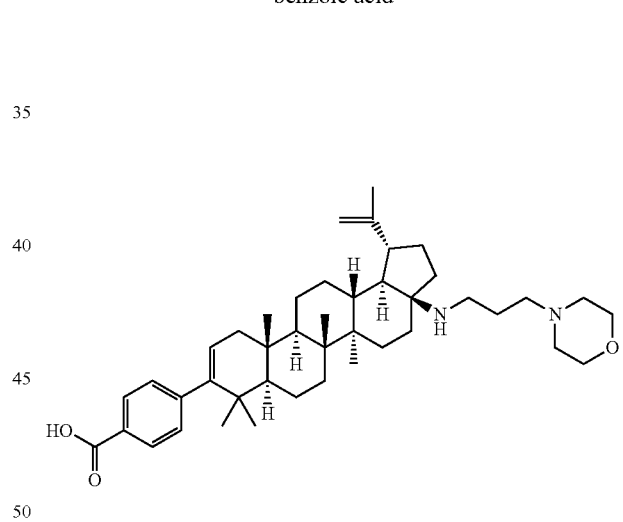

The title compound was prepared following the method described above for the synthesis of 4-((1R,3aS,5aR,5bR, 7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 4-(3-chloropropyl)morpholine hydrochloride as the alkylating reagent in Step 1. The product was isolated as a white solid (60 mg, 48.1%). LCMS: m/e 657.55 (M+H)+, 2.24 min (method 13). $^1$H NMR (400 MHz, METHANOL-$d_4$) δ 7.95 (d, J=8.3 Hz, 2H), 7.26 (d, J=8.3 Hz, 2H), 5.33 (d, J=4.5 Hz, 1H), 4.88 (s, 1H), 4.75 (s, 1H), 3.97 (m, 4H), 3.30-3.04 (m, 8H), 2.85-2.66 (m, 1H), 2.46-2.24 (m, 2H), 2.24-1.85 (m, 7H), 1.82-1.65 (m, 7H), 1.65-1.45 (m, 7H), 1.45-1.26 (m, 4H), 1.22 (s, 3H), 1.14 (s, 3H), 1.08 (s, 3H), 1.00 (s, 3H), 0.98 (s, 3H)

Example 166

Preparation of 4-((1R,3aS,5aR,5bR,7aR,11aS,11bR,13aR,13bR)-5a,5b,8,8,11a-pentamethyl-1-(prop-1-en-2-yl)-3a-((2-(pyridin-4-yl)ethyl)amino)-2,3,3a,4,5,5a,5b,6,7,7a,8,11,11a,11b,12,13,13a,13b-octadecahydro-1H-cyclopenta[a]chrysen-9-yl)benzoic acid

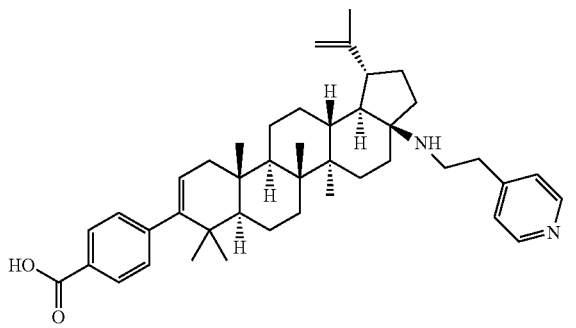

The title compound was prepared following the method described above for the synthesis of 4-((1R,3aS,5aR,5bR,7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 4-(2-chloroethyl)pyridine as the alkylating reagent in Step 1. The product was isolated as an off white solid (10 mg, 2.9%). LCMS: m/e 635.40 (M+H)+, 2.31 min (method 13). $^1$H NMR (400 MHz, METHANOL-$d_4$) δ 8.83 (d, J=5.8 Hz, 2H), 8.06 (d, J=6.0 Hz, 2H), 7.95 (d, J=8.5 Hz, 2H), 7.25 (d, J=8.3 Hz, 2H), 5.33 (d, J=4.5 Hz, 1H), 4.90 (s, 1H), 4.76 (s, 1H), 3.57-3.46 (m, 4H), 2.86-2.75 (m, 1H), 2.27-2.08 (m, 5H), 2.05-1.89 (m, 2H), 1.79 (s, 3H), 1.85-1.67 (m, 4H), 1.66-1.49 (m, 7H), 1.45-1.23 (m, 4H), 1.21 (s, 3H), 1.14 (s, 3H), 1.09 (s, 3H), 1.00 (s, 3H), 0.98 (s, 3H).

Example 167

Preparation of 4-((1R,3aS,5aR,5bR,7aR,11aS,11bR,13aR,13bR)-3a-(bis(2-(pyrrolidin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

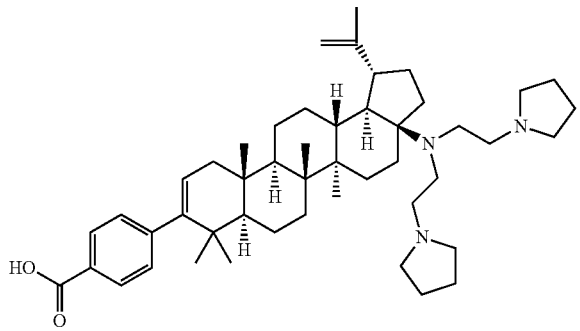

The title compound was prepared following the method described above for the synthesis of 4-((1R,3aS,5aR,5bR,7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 1-(2-chloroethyl)pyrrolidine hydrochloride as the alkylating reagent in Step 1. The product was isolated as a white solid (10 mg, 2.57%). LCMS: m/e 724.52 (M+H)+, 1.43 min (method 15). $^1$H NMR (400 MHz, METHANOL-d) δ 7.88 (d, J=8.0 Hz, 2H), 7.19 (d, J=8.0 Hz, 2H), 5.26 (d, J=4.8 Hz, 1H), 4.79 (s, 1H), 4.66 (s, 1H), 4.03-3.86 (m, 4H), 3.86-3.62 (m, 6H), 3.59-3.29 (m, 6H), 2.81-2.58 (m, 1H), 2.26 (br. s., 4H), 2.21-1.88 (m, 9H), 1.82 (d, J=13.1 Hz, 1H), 1.73-1.62 (m, 5H), 1.62-1.40 (m, 9H), 1.40-1.19 (m, 4H), 1.13 (s, 4H), 1.06 (s, 3H), 1.01 (s, 3H), 0.93 (s, 3H), 0.91 (s, 3H),

Example 168

Preparation of 4-((1R,3aS,5aR,5bR,7aR,11aS,11bR,13aR,13bR)-5a,5b,8,8,11a-pentamethyl-1-(prop-1-en-2-yl)-3a-(2-thiomorpholinoethylamino)-2,3,3a,4,5,5a,5b,6,7,7a,8,11,11a,11b,12,13,13a,13b-octadecahydro-1H-cyclopenta[a]chrysen-9-yl)benzoic acid

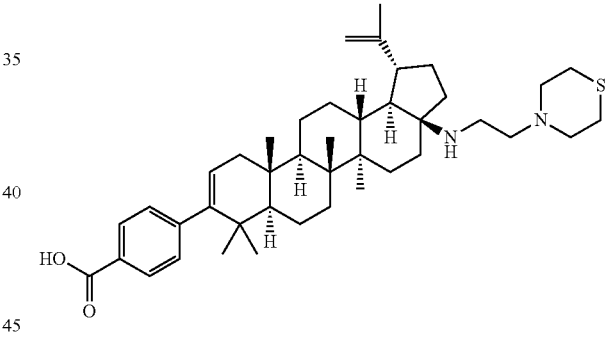

The title compound was prepared following the method described above for the synthesis of 4-((1R,3aS,5aR,5bR,7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 4-(2-chloroethyl)thiomorpholine hydrochloride (prepared as describe in WO 2009058859) as the alkylating reagent in Step 1. The product was isolated as a white solid (3 mg, 0.85%). LCMS: m/e 659.37 (M+H)+, 2.38 min (method 13). $^1$H NMR (400 MHz, CHLOROFORM-d) δ 8.00 (d, J=8.3 Hz, 2H), 7.21 (d, J=8.5 Hz, 2H), 5.32-5.19 (m, 1H), 4.77 (s, 1H), 4.65 (s, 1H), 3.11-2.98 (m, 1H), 2.89 (m, 5H), 2.75 (m, 5H), 2.67-2.57 (m, 1H), 2.31-2.16 (m, 1H), 2.14-1.85 (m, 6H), 1.71 (s, 7H), 1.59-1.40 (m, 6H), 1.38-1.15 (m, 8H), 1.08-0.96 (m, 10H), 0.94 (s, 3H)

Example 169

Preparation of 4-((1R,3aS,5aR,5bR,7aR,11aS,11bR,13aR,13bR)-3a-(3-(dimethylamino)propylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

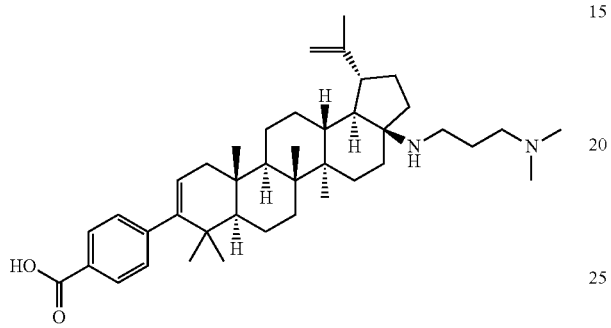

The title compound was prepared following the method described above for the synthesis of 4-((1R,3aS,5aR,5bR,7aR,11aS,11bR,13aR,13bR)-3a-(2-(dimethylamino)-2-oxo-ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 3-chloro-N,N-dimethylpropan-1-amine hydrochloride as the alkylating reagent in Step 1. The product was isolated as a white solid (3 mg, 0.85%). LCMS: m/e 615.75 (M+H)$^+$, 2.24 min (method 13). $^1$H NMR (400 MHz, METHANOL-d$_4$) δ 7.95 (d, J=8.0 Hz, 2H), 7.25 (d, J=8.0 Hz, 2H), 5.34 (s, 1H), 4.89 (s, 1H), 4.75 (s, 1H), 3.58-3.36 (m, 2H), 3.26 (br. s., 8H), 2.78 (d, J=7.5 Hz, 1H), 2.51-2.26 (m, 3H), 2.26-1.97 (m, 7H), 1.92 (m, 1H), 1.78 (m, 6H), 1.63-1.47 (m, 6H), 1.45-1.36 (m, 2H), 1.32-1.18 (m, 5H), 1.14 (s, 3H), 1.08 (s, 3H), 1.00 (s, 3H), 0.98 (s, 3H)

Example 170

Preparation of 1-(2-(((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)piperidine-4-carboxylic acid

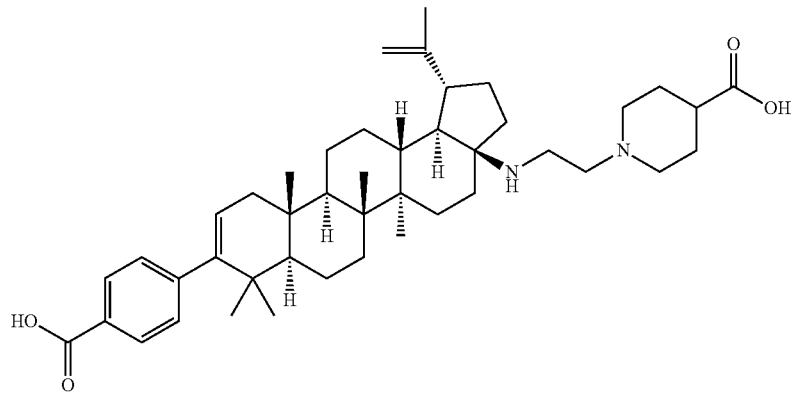

The title compound was prepared following the method described above for the synthesis of 4-((1R,3aS,5aR,5bR,7aR,11aS,11bR,13aR,13bR)-3a-(2-(dimethylamino)-2-oxo-ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using methyl 1-(2-chloroethyl)piperidine-4-carboxylate hydrochloride (prepared as described below) as the alkylating reagent in Step 1. The product was isolated as a white solid (8 mg, 83%). LCMS: m/e 685.6 (M+H)$^+$, 2.33 min (method 10). $^1$H NMR (400 MHz, METHANOL-d$_4$) δ 7.94 (d, J=8.3 Hz, 2H), 7.23 (d, J=8.3 Hz, 2H), 5.31 (d, J=4.5 Hz, 1H), 4.86 (s, 1H), 4.74 (s, 1H), 3.48-3.36 (m, 5H), 3.12-2.88 (m, 2H), 2.79-2.69 (m 1H), 2.68-2.60 (m, 1H), 2.24-2.11 (m, 4H), 2.11-2.00 (m, 4H), 1.97-1.81 (m, 3H), 1.77 (s, 3H), 1.81-1.71 (m, 2H), 1.70-1.46 (m, 10H), 1.45-1.27 (m, 4H), 1.21 (s, 3H), 1.12 (s, 3H), 1.06 (s, 3H), 0.98 (s, 3H), 0.97 (s, 3H).

Preparation of methyl 1-(2-chloroethyl)piperidine-4-carboxylate

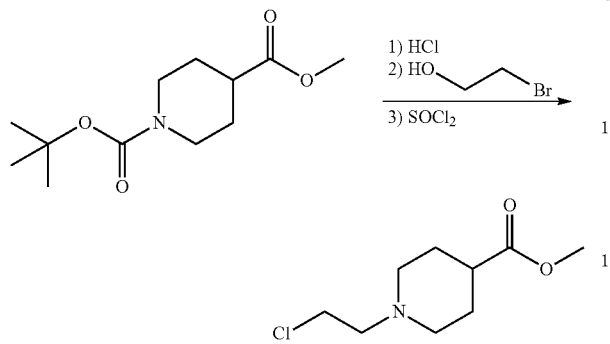

To a solution of 1-tert-butyl 4-methyl piperidine-1,4-dicarboxylate (5.4 g, 22.19 mmol) in ether was added hydrogen chloride (27.7 mL, 111 mmol) in dioxane. The resulted clear solution was stirred for 4 hours. Bubbles and white precipitates were observed. Then the solvent was removed and dried in vacuo. The residue was suspended in acetonitrile (50 mL), and 2-bromoethanol (1.567 mL, 22.19 mmol) was added followed by powdered $K_2CO_3$ (14.72 g, 107 mmol). After the reaction mixture was refluxed for 18 hours, it was filtered and concentrated. The residue was redissolved in water (50.0 mL) and extracted with ethyl acetate (50.0 mL). The organic layer was dried over sodium sulfate. After filtration the solvent was removed in vacuo. The residue was dissolved in DCE (50.0 mL) before sulfurous dichloride (2.428 mL, 33.3 mmol) was added. The reaction mixture was reflux for 3 hours, then all volatile was removed in vacuo, the resulting solid was suspended in ether, then filtered and washed with ether (50.0 mL), resuspended in ethyl acetate and neutralized with sodium bicarbonate. The organic layer was collected and dried with sodium sulfate to afford methyl 1-(2-chloroethyl)piperidine-4-carboxylate (1 g, 4.86 mmol, 21.91% yield) as a brown oil. $^1$H NMR (400 MHz, CHLOROFORM-d) δ 3.70 (s, 3H), 3.61 (t, J=7.0 Hz, 2H), 2.97-2.86 (m, 2H), 2.75 (t, J=7.2 Hz, 2H), 2.40-2.27 (m, 1H), 2.19 (m, 2H), 2.01-1.88 (m, 2H), 1.87-1.72 (m, 2H).

Example 171

Preparation of 4-((1R,3aS,5aR,5bR,7aR,11aS,11bR,13aR,13bR)-3a-(2-(4-(dimethylcarbamoyl)piperidin-1-yl)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

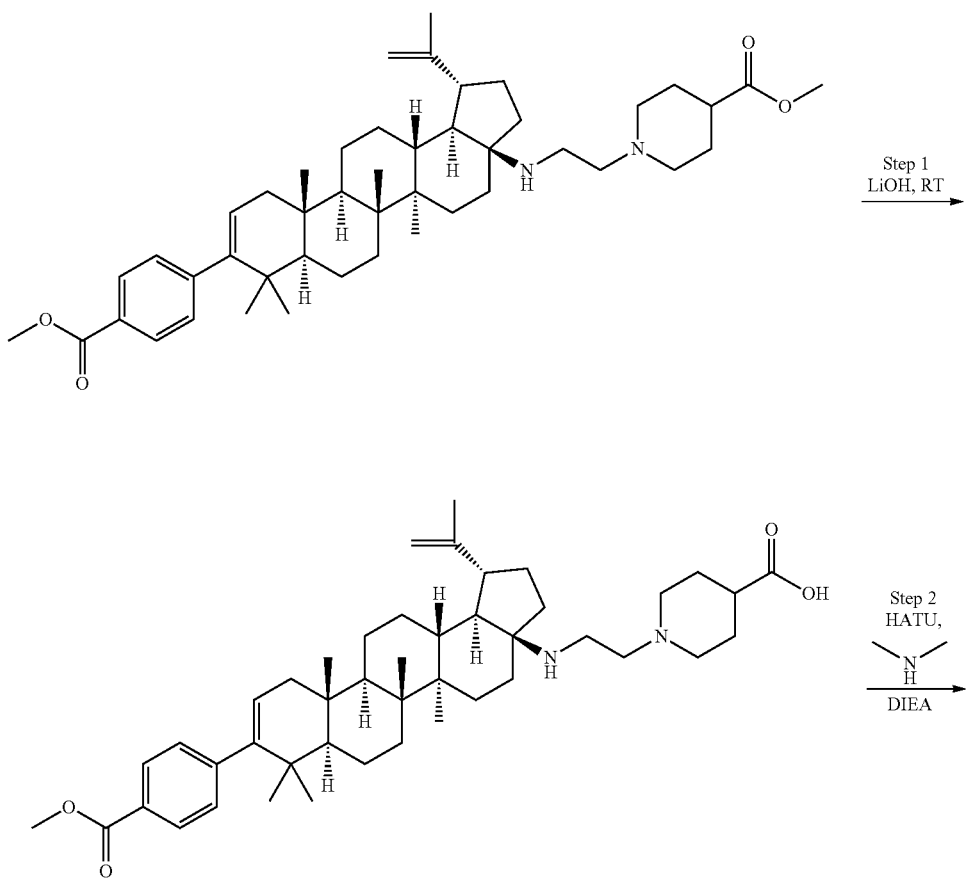

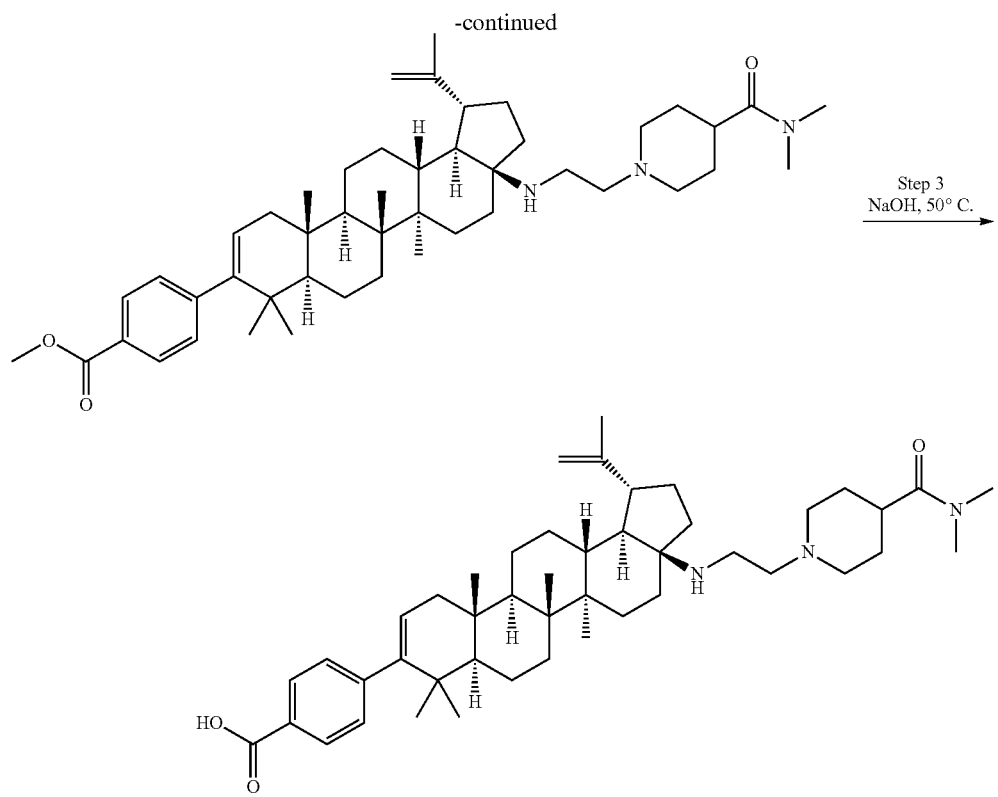

Step 1. To a solution of methyl 1-(2-(((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-ylamino)ethyl)piperidine-4-carboxylate (40 mg) in dioxane (1 mL) was added lithium hydroxide (2.7 mg, 0.112 mmol) in water (1 mL). A white precipitate was observed. The mixture was stirred at 25° C. for 3 hours. The desired product was observed at m/e 699.7 (M+H)+, 2.703 min, method 10. The reaction mixture was neutralized with 1 N HCl to pH-4 and diluted with methylene chloride (10 mL). The organic layer was then collected, dried over sodium sulfate and filtered. After removal of solvent, the crude product was obtained as an oil (40 mg, ~100%) which was used without further purification.

Step 2. To a solution of 1-(2-(((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)piperidine-4-carboxylic acid (40 mg, 0.057 mmol) in CH$_2$Cl$_2$ (5 ml) at rt was added dimethylamine (7.6 mg, 0.17 mmol) and HATU (65 mg, 0.18 mmol) followed by DIEA (29 mg, 0.23 mmol). The mixture was stirred for 3 hour at rt. The resulted mixture was diluted with ethyl acetate and washed with water. The organic layer was dried over sodium sulfate. The crude product was obtained after removal of solvent as a white solid (40 mg, ~100%) which was used without further purification Step 3. 4-((1R,3aS,5aR,5bR,7aR,11aS,11bR,13aR,13bR)-3a-(2-(4-(dimethylcarbamoyl)piperidin-1-yl)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid was prepared following step 2 of the method described above for the synthesis of 4-((1R,3aS,5aR,5bR,7aR,11aS,11bR,13aR,13bR)-3a-(2-(dimethylamino)-2-oxoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid. The product was isolated as a white solid (9 mg, 23.0%). LCMS: m/e 712.64 (M+H)+, 2.265 min (method 11). $^1$H NMR (400 MHz, METHANOL-d$_4$) δ 7.95 (d, J=8.3 Hz, 2H), 7.25 (d, J=8.3 Hz, 2H), 5.33 (d, J=4.5 Hz, 1H), 4.87 (s, 1H), 4.74 (s, 1H), 3.65-3.38 (m, 6H), 3.16 (s, 3H), 3.05 (m, 2H), 2.96 (s, 3H), 2.75 (m, 1H), 2.23-1.85 (m, 11H), 1.82-1.74 (m, 6H), 1.70-1.48 (m, 9H), 1.44-1.28 (m, 3H), 1.22 (m, 4H), 1.13 (s, 3H), 1.08 (s, 3H), 1.00 (s, 3H), 0.98 (s, 3H), Example 172

Preparation of 4-(1R,3aS,5aR,5bR,7aR,11aS,11bR,13aR,13bR)-3a-(2-(4,4-difluoropiperidin-1-yl)ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

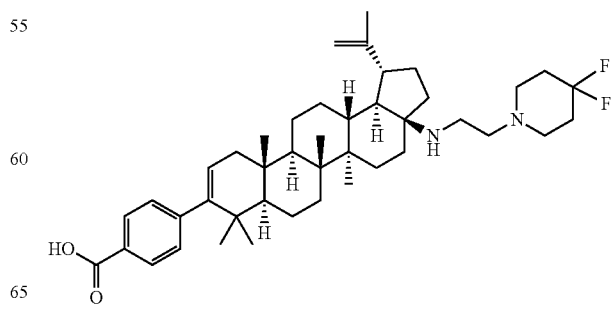

The title compound was prepared following the method described above for the synthesis of 4-((1R,3aS,5aR,5bR,7aR,11aS,11bR,13aR,13bR)-3a-((2-(4-(tert-butoxycarbonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 4,4-difluoropiperidine hydrochloride as the alkylating reagent in Step 3. The product was isolated as a white solid (20 mg, 58.3%). LCMS: m/e 677.57 (M+H)$^+$, 2.30 min (method 11). $^1$H NMR (400 MHz, CHLOROFORM-d) δ 7.97 (d, J=8.3 Hz, 2H), 7.22 (d, J=8.3 Hz, 2H), 5.27 (d, J=4.8 Hz, 1H), 4.82 (s, 1H), 4.70 (s, 1H), 3.32 (m, 1H), 3.19-3.05 (m, 1H), 2.94 (m, 2H), 2.83-2.68 (m, 5H), 2.36-2.21 (m, 2H), 2.15-1.90 (m, 7H), 1.74 (br. s., 7H), 1.60-1.45 (m, 6H), 1.44-1.30 (m, 4H), 1.26 (s, 2H), 1.18 (s, 3H), 1.06 (s, 4H) 0.98 (s, 3H), 0.97 (s, 3H), 0.95 (s, 3H). $^{19}$F NMR (376 MHz, CHLOROFORM-d) δ −98.39 (br. s., 2F)

Example 173

Preparation of 4-((1R,3aS,5aR,5bR,7aR,11aS,11bR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

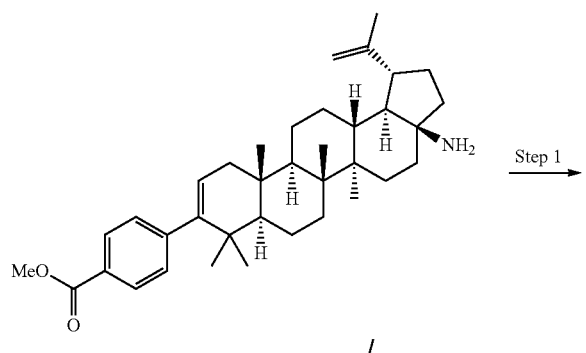

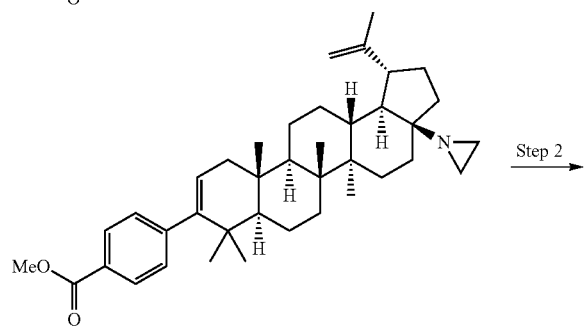

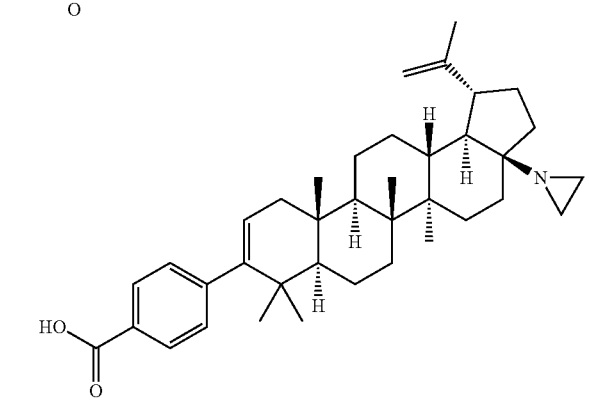

Step 1. Preparation of methyl 4-((1R,3aS,5aR,5bR,7aR,11aS,11bR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate. To a solution of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.160 g, 0.276 mmol) in a mixture of acetonitrile (25 mL) and dichloroethane (5 mL) was added anhydrous potassium phosphate (0.25 gm, 1.18 mmol). The resulting suspension was heated to 120° C. under nitrogen in a thick-walled tube for 24 hours. The cooled reaction suspension was filtered through a short bed of silica gel (Type-H), washed with ethyl acetate (60 mL). The clear filtrate was concentrated in vacuo to give a white solid (0.150 g, 96%). LCMS: m/e 570.5 (M+H)$^+$, 3.32 min (method 12, but modified to gradient over 3 minutes). $^1$H NMR (400 MHz, CHLOROFORM-d) δ 7.95 (d, J=8.3 Hz, 2H), 7.22 (d, J=8.5 Hz, 2H), 5.31 (dd, J=6.1, 1.6 Hz, 1H), 4.81-4.73 (m, 1H), 4.67-4.59 (m, 1H), 3.93 (s, 3H), 2.82-2.45 (m, 1H), 2.19-2.04 (m, 1H), 1.88-1.74 (m, 1H), 1.71 (s, 3H), 1.68 (br. s., 1H), 1.63-1.21 (m, 7H), 1.11 (s, 3H), 1.01 (s, 3H), 1.00 (s, 3H), 0.95 (s, 6H).

Step 2. To a solution of methyl 4-((1R,3aS,5aR,5bR,7aR,11aS,11bR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.150 g, 0.264 mmol) in a mixture of methanol (2 mL) and THF (6 mL) at rt was added a stock solution of lithium hydroxide (1.0 Molar, 2 mL, 2.0 mmol) forming a thick suspension. The mixture was kept at 50° C. under nitrogen for 60 hours. The reaction mixture was neutralized with HCl (0.5 Molar, 10 mL), the organic material was extracted into ethyl acetate (30 mL). While the 2-phase mixture was stirred at rt, a white precipitate slowly separated out. It was filtered to give 4-((1R,3aS,5aR,5bR,7aR,11aS,11bR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid as a white solid (99 mg, 68%). LCMS: m/e 592.5 (M+MeOH+Na)$^+$, 3.03 min (method 12, but modified to gradient over 3 minutes). Selected $^1$H NMR (400 MHz, CHLOROFORM-d) δ 8.01 (d, J=8.3 Hz, 2H), 7.24 (d, J=8.3 Hz, 2H), 5.28 (m, 1H), 4.94 (br. s, 1H), 4.73 (br. s, 1H), 1.74 (s, 3H), 1.20 (s, 3H), 1.09 (s, 3H), 1.01 (s, 3H), 0.99 (s, 3H), 0.97 (s, 3H).

Example 174

Preparation of 4-((1R,3aS,5aR,5bR,7aR,11aS,11bR,13aR,13bR)-3a-((1-(tert-butoxycarbonyl)piperidin-3-yl)methylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

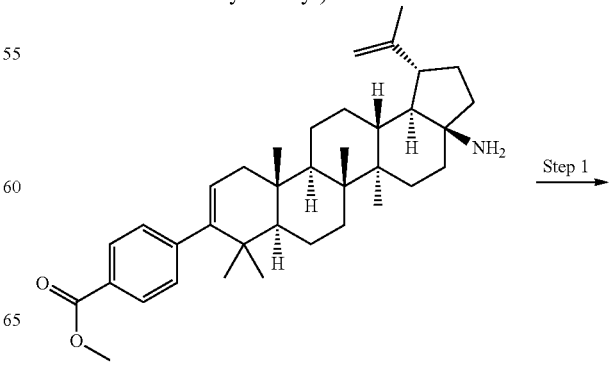

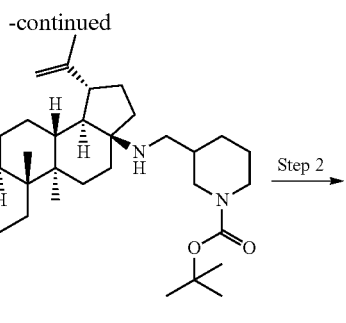

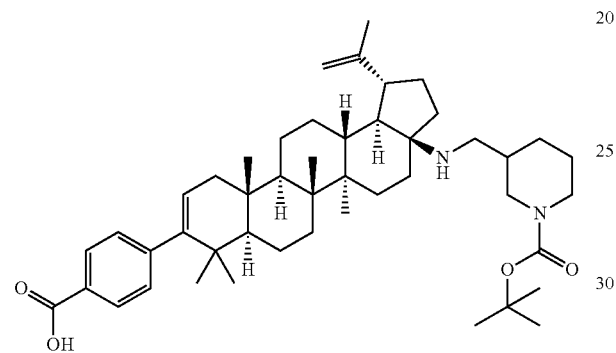

Step 1. Preparation of tert-butyl 3-((((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-ylamino)methyl)piperidine-1-carboxylate. To a solution of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (30 mg, 0.055 mmol) in dichloroethane (0.5 mL) was added 3-formyl-piperidine-1-carboxylic acid tert-butyl ester (14.71 mg, 0.069 mmol) and titanium (IV) isopropoxide (0.020 mL, 0.069 mmol). The mixture was stirred at rt for 1 h and sodium triacetoxyborohydride (23.38 mg, 0.110 mmol) was added. The mixture was stirred at rt for 16.5 h, then was diluted with 3 mL of sat. NaHCO$_3$ and was extracted with dichloromethane (3×5 mL). The combined organic layers were dried with Na$_2$SO$_4$, were filtered and were concentrated under reduced pressure. The residue was adsorbed to silica gel and was purified by flash chromatography using a 0-10% ethyl acetate in hexanes gradient and a Thomson 12 g silica gel column. The fractions containing the expected product were combined and concentrated under reduced pressure to give the title compound as an off-white foam. LCMS: m/e 741.7 (M+H)$^+$, 3.76 min (method 2).

Step 2. To a solution of tert-butyl 3-((((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-ylamino)methyl)piperidine-1-carboxylate (0.029 g, 0.039 mmol) in 1,4-dioxane (2 mL) was added NaOH (1N) (0.196 mL, 0.196 mmol). The mixture was heated to 85° C. for 22 h, then was cooled to rt, was diluted with MeOH, and was purified by prep HPLC. The fractions containing the expected product were combined and concentrated under reduced pressure to give 4-((1R,3aS,5aR,5bR,7aR,11aS,11bR,13aR,13bR)-3a-((1-(tert-butoxycarbonyl)piperidin-3-yl)methylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (24 mg, 0.031 mmol, 56% yield over 2 steps) as a clear, colorless film. LCMS: m/e 727.7 (M+H)$^+$, 2.00 min (method 2). $^1$H NMR (500 MHz, Chloroform-d) δppm 7.98 (d, J=7.93 Hz, 2H), 7.21 (d, J=7.93 Hz, 2H), 5.29 (d, J=5.49 Hz, 1H), 4.70 (br. s., 1H), 4.58 (br. s., 1H), 3.82-4.51 (m, 5H), 1.68 (s, 3H), 1.47 (d, J=4.58 Hz, 9H), 1.10 (d, J=7.93 Hz, 3H), 0.98 (br. s., 6H), 0.93 (s, 3H), 0.92 (s, 3H), 0.90-2.85 (m, 30H).

Example 175

Preparation of 4-((1R,3aS,5aR,5bR,7aR,11aS,11bR,13aR,13bR)-5a,5b,8,8,11a-pentamethyl-3a-(piperidin-3-ylmethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid To a solution of 4-((1R,3aS,5aR,5bR,7aR,11aS,11bR,13aR,13bR)-3a-((1-(tert-butoxycarbonyl)piperidin-3-yl)methylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (0.019 g, 0.026 mmol) in dichloromethane (1 mL) was added TFA (0.25 mL, 3.24 mmol). The mixture was stirred at rt for 1.75 h then was concentrated under reduced pressure. The residue was purified by prep HPLC. The fractions containing the expected product were combined and were concentrated under reduced pressure to give 4-((1R,3aS,5aR,5bR,7aR,11aS,11bR,13aR,13bR)-5a,5b,8,8,11a-pentamethyl-3a-(piperidin-3-ylmethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (14.2 mg, 0.021 mmol, 81% yield) as a white solid. LCMS: m/e 627.6 (M+H)$^+$, 1.50 min (method 2).

Examples 176 and 177
Preparation of 4-((1R,3aS,5aR,5bR,7aR,11aS,11bR,13aR,13bR)-5a,5b,8,8,11a-pentamethyl-3a-(methylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid and 4-((1R,3aS,5aR,5bR,7aR,11aS,11bR,13aR,13bR)-3a-(dimethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
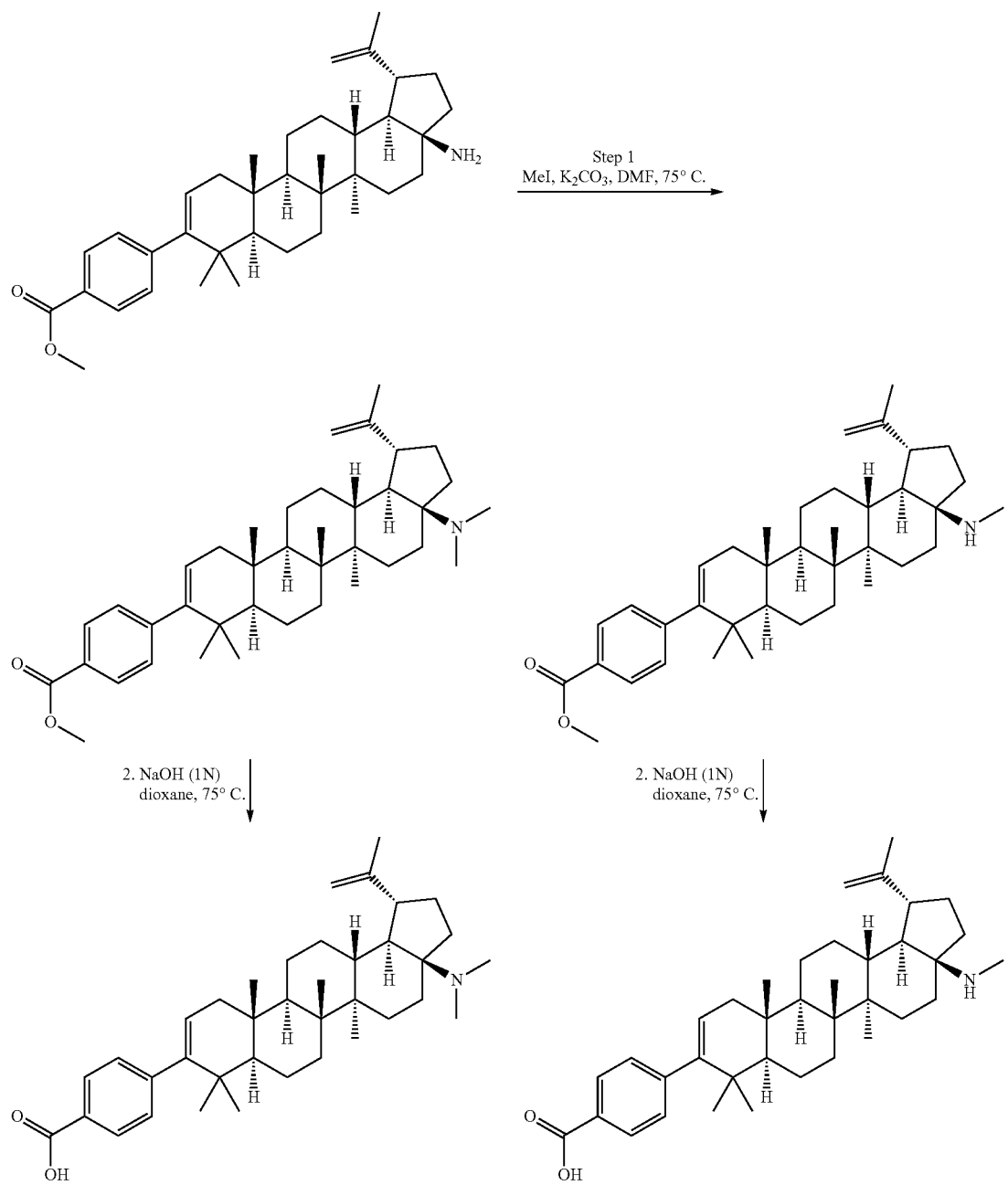
Example 176
Example 177

Step 1. To a sealable vial containing methyl 4-((1R,3aS,5aR, 5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoate, HCl (1.0 g, 1.72 mmol) was added potassium carbonate (0.48 g, 3.45 mmol). The mixture was diluted with DMF (15 mL) and methyl iodide (323 mL, 3.45 mmol) was added. The vial was sealed and the mixture was heated to 75° C. for 4 h then was cooled to rt. The vial was opened to the air and was stirred at rt overnight. The mixture was diluted with 20 mL of saturated aqueous sodium thiosulfate. Solids formed and were collected by filtration and were washed with water. The residue was purified by flash chromatography in silica gel using a 0-25% ethyl acetate in hexanes gradient with 0.1% ammonium hydroxide added to the mixture. Two main isolates were recovered from the column. The less polar product, methyl 4-((1R,3aS,5aR,5bR,7aR, 11aS,11bR,13aR,13bR)-3a-(dimethylamino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoate (0.247 g, 0.405 mmol, 23.5% yield) was recovered as a white foam. The more polar isolate, methyl 4-((1R,3aS,5aR,5bR,7aR,11aS,11bR,13aR,13bR)-5a,5b,8,8,11a-pentamethyl-3a-(methylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.5 g, 0.807 mmol, 46.8% yield), was recovered as a white solid. LCMS of the less polar isolate: m/e 572.6 (M+H)$^+$, 2.03 min (method 2). $^1$H NMR (400 MHz, Chloroform-d) δ=7.96-7.92 (m, 2H), 7.23-7.19 (m, 2H), 5.31-5.29 (m, 1H), 4.71 (d, J=2.0 Hz, 1H), 4.61 (dd, J=2.3, 1.3 Hz, 1H), 3.92 (s, 3H), 2.86 (td, J=11.2, 6.1 Hz, 1H), 2.34-2.24 (m, 7H), 2.12 (dd, J=17.1, 6.5 Hz, 1H), 2.04-1.80 (m, 5H), 1.70 (s, 3H), 1.10 (s, 3H), 1.02 (s, 3H), 1.00 (s, 3H), 0.94 (s, 3H), 0.94 (s, 3H), 1.74-0.85 (m, 15H). LCMS of the more polar isolate: m/e 558.6 (M+H)$^+$, 2.04 min (method 2). $^1$H NMR (400 MHz, Chloroform-d) =7.93 (d, J=8.0 Hz, 2H), 7.20 (d, J=8.3 Hz, 2H), 5.30 (dd, J=6.1, 1.6 Hz, 1H), 4.72 (d, J=2.0 Hz, 1H), 4.59 (s, 1H), 3.92 (s, 3H), 2.60 (td, J=10.9, 5.8 Hz, 1H), 2.24 (s, 3H), 2.11 (dd, J=17.2, 6.1 Hz, 1H), 2.03-1.91 (m, 2H), 1.88-1.79 (m, 2H), 1.09 (s, 3H), 1.00 (s, 3H), 0.99 (s, 3H), 0.94 (s, 3H), 0.93 (s, 3H), 1.69-0.91 (m, 20H).

Step 2. The saponification of the isolates were carried out independently:

Example 176

Preparation of 4-((1R,3aS,5aR,5bR,7aR,11aS,11bR, 13aR,13bR)-5a,5b,8,8,11a-pentamethyl-3a-(methylamino)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid, HCl To a solution of methyl 4-((1R,3aS,5aR,5bR,7aR,11aS, 11bR,13aR,13bR)-5a,5b,8,8,11a-pentamethyl-3a-(methylamino)-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate (88 mg, 0.158 mmol) in 1,4-dioxane (3 mL) was added NaOH (1M) (1 mL, 1.000 mmol). The mixture was heated to 75° C. for 17 h then was cooled to rt and was acidified with 3 mL of 1N HCl. Solids formed upon standing and were collected by filtration and were washed with water. The solids were dissolved and were purified by flash chromatography using a 0-40% methanol in ethyl acetate gradient and a Thomson 25 g silica gel column. The fractions containing the expected product were combined and were concentrated under reduced pressure then were redissolved in dichloromethane and methanol and were filtered through a plug of celite. The filtrate was concentrated under reduced pressure to give 4-((1R,3aS,5aR,5bR,7aR,11aS, 11bR,13aR,13bR)-5a,5b,8,8,11a-pentamethyl-3a-(methylamino)-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoic acid, HCl (40 mg, 0.065 mmol, 41% yield) as a white solid. LCMS: m/e 544.5 (M+H)$^+$, 1.79 min (method 2). $^1$H NMR (500 MHz, Acetic acid d$_4$) δ=8.01 (d, J=8.2 Hz, 2H), 7.27 (d, J=8.2 Hz, 2H), 5.34 (d, J=4.6 Hz, 1H), 4.84 (s, 1H), 4.71 (s, 1H), 2.85-2.77 (m, 1H), 2.74 (s, 3H), 1.75 (s, 3H), 1.16 (s, 3H), 1.10 (s, 3H), 1.06 (s, 3H), 0.99 (s, 3H), 0.97 (s, 3H), 2.24-0.95 (m, 22H).

Example 177

Preparation of 4-((1R,3aS,5aR,5bR,7aR,11aS,11bR, 13aR,13bR)-3a-(dimethylamino)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)benzoic acid To a suspension of methyl 4-((1R,3aS,5aR,5bR,7aR,11aS, 11bR,13aR,13bR)-3a-(dimethylamino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate, HCl (100 mg, 0.164 mmol) in 1,4-dioxane (3 mL) was added 1N NaOH (1 mL, 1.000 mmol) and the mixture was heated to 70° C. After 3.75 h the mixture was cooled to rt and was diluted with 2 mL of MeOH and then 1N HCl (6 mL) was added. The solids that formed were collected by filtration and were washed with water. The solids were dissolved in dioxane and methanol and were purified by prep HPLC. The fractions containing the expected product were combined and concentrated under reduced pressure to give 4-((1R,3aS,5aR,5bR,7aR,11aS,11bR,13aR,13bR)-3a-(dimethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (45 mg, 0.077 mmol, 46.6% yield) as a white solid. LCMS: m/e 558.3 (M+H)$^+$, 2.28 min (method 11). $^1$H NMR (500 MHz, Acetic acid d$_4$) δ ppm 8.04 (2H, d, J=8.2 Hz), 7.30 (2H, d, J=8.2 Hz), 5.37 (1H, d, J=4.9 Hz), 4.92 (1H, s), 4.77 (1H, s), 3.08 (7H, br. s.), 1.80 (3H, s), 1.22 (3H, s), 1.18 (3H, s), 1.09 (3H, s), 1.02 (3H, s), 1.00 (3H, s), 0.98-2.46 (22H, m).

Example 178

Preparation of 4-((1R,3aS,5aR,5bR,7aR,11aS,11bR, 13aR,13bR)-3a-(acetyl(2-(1,1-dioxido-4-thiomorpholinyl)ethyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

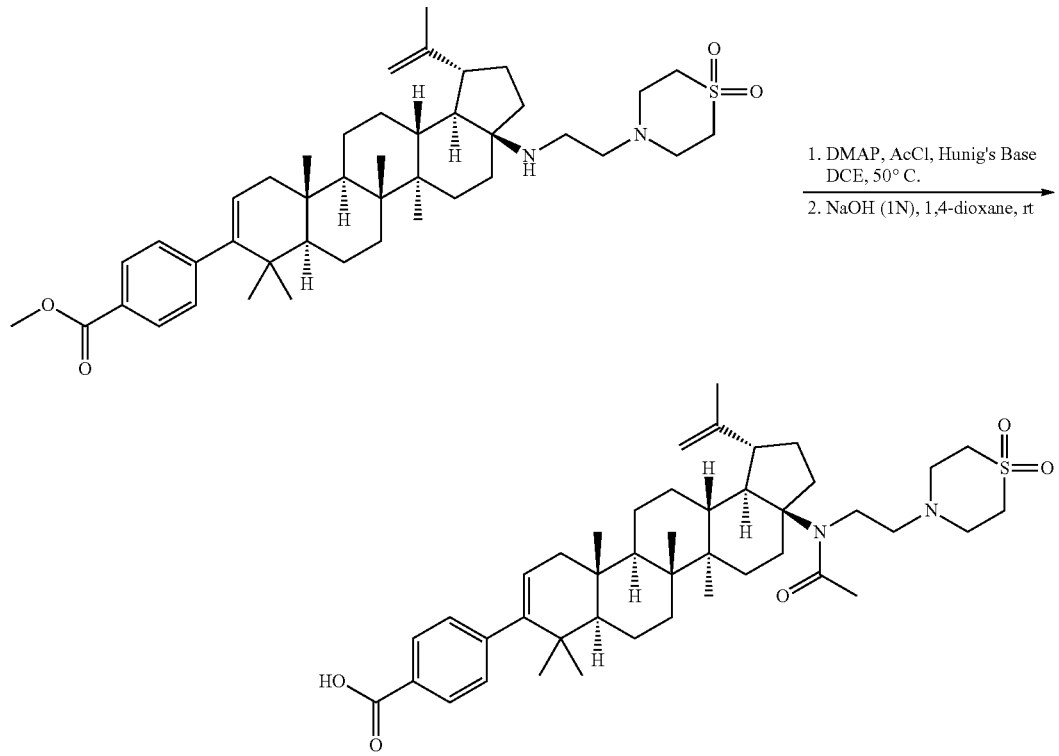

Step 1. Preparation of methyl 4-((1R,3aS,5aR,5bR,7aR,11aS,11bR,13aR,13bR)-3a-(acetyl(2-(1,1-dioxido-4-thiomorpholinyl)ethyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoate To a solution of methyl 4-((1R,3aS,5aR,5bR,7aR,11aS,11bR,13aR,13bR)-3a-(((1,1-dioxido-4-thiomorpholinyl)acetyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoate (0.05 g, 0.071 mmol) in dichloroethane (1 mL) and Hunig's base (0.062 mL, 0.355 mmol) was added acetyl chloride (0.020 mL, 0.284 mmol). The mixture was heated to 50° C. After heating the mixture for 71.25 h, the mixture was cooled to rt and was directly loaded onto a 12 g Thomson silica gel column and was purified by Biotage flash chromatography using a 0-5% MeOH in dichloromethane gradient. The fractions containing the expected product were combined and were concentrated under reduced pressure to give methyl 4-((1R,3aS,5aR,5bR,7aR,11aS,11bR,13aR,13bR)-3a-(acetyl(2-(1,1-dioxido-4-thiomorpholinyl)ethyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoate (40 mg, 0.054 mmol, 75%) as a clear, colorless film. LCMS: m/e 747.5 (M+H)$^+$, 2.26 min (method 2).

Step 2. To a solution of methyl 4-((1R,3aS,5aR,5bR,7aR,11aS,11bR,13aR,13bR)-3a-(acetyl(2-(1,1-dioxido-4-thiomorpholinyl)ethyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoate (40 mg, 0.054 mmol) in 1,4-dioxane (1 mL) was added NaOH (1N) (0.27 mL, 0.27 mmol). The mixture was stirred at rt for 16.5 h then was purified directly by prep HPLC. The fractions containing the expected product were combined and concentrated under reduced pressure to give 4-((1R,3aS,5aR,5bR,7aR,11aS,11bR,13aR,13bR)-3a-(acetyl(2-(1,1-dioxido-4-thiomorpholinyl)ethyl)amino)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid (14 mg, 0.018 mmol, 33%) as a white solid. LCMS: m/e 733.5 (M+H)$^+$, 1.96 min (method 2). $^1$H NMR (400 MHz, Chloroform-d) δ=7.99 (d, J=7.8 Hz, 2H), 7.22 (d, J=7.8 Hz, 2H), 5.23 (d, J=4.0 Hz, 1H), 4.85 (br. s., 1H), 4.68 (br. s., 1H), 3.65 (br. s., 2H), 3.40-3.04 (m, 8H), 2.97-2.46 (m, 4H), 1.74 (s, 3H), 1.27 (s, 3H), 1.03-0.98 (m, 9H), 0.95 (br. s., 3H), 0.89 (br. s., 3H), 2.20-0.71 (m, 21H).

Example 179

Preparation of 4-((1R,3aS,5aR,5bR,7aR,11aS,11bR, 13aR,13bR)-3a-((2-fluoroethyl)amino)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

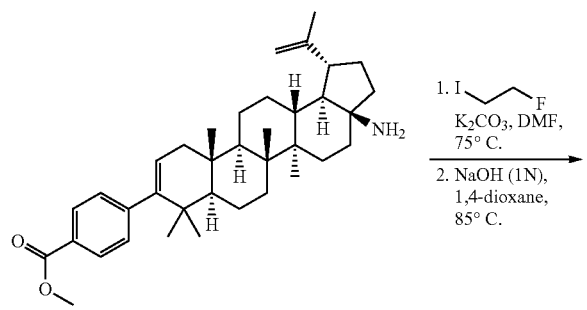

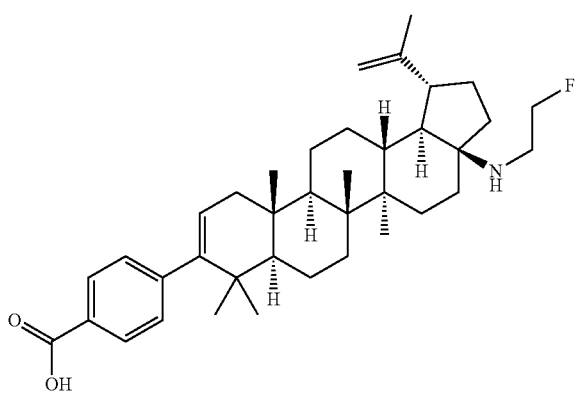

Step 1. Preparation of methyl 4-((1R,3aS,5aR,5bR, 7aR,11aS,11bR,13aR,13bR)-3a-((2-fluoroethyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate To a sealable vial containing methyl 4-((1R,3aS,5aR,5bR, 7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate, HCl (0.075 g, 0.129 mmol) was added potassium carbonate (0.036 g, 0.258 mmol). The mixture was diluted with DMF (1 mL) and 1-fluoro-2-iodoethane (0.032 ml, 0.388 mmol) was added. The vial was sealed and the mixture was heated to 75° C. for 26 h then was cooled to rt. The mixture was diluted with 3 mL of sat. aq. sodium thiosulfate and was extracted with dichloromethane (3×4 mL). The combined organic layers were dried with sodium sulfate, the drying agent was removed by filtration and the filtrate was concentrated under reduced pressure. The residue was dissolved in toluene and was loaded onto a Thomson 12 g silica gel column and was purified by Biotage flash chromatography using a 0-15% ethyl acetate in hexanes gradient with 0.1% ammonium hydroxide added to the mixture. The fractions containing the expected product were combined and concentrated under reduced pressure to give methyl 4-((1R, 3aS,5aR,5bR,7aR,11aS,11bR,13aR,13bR)-3a-((2-fluoroethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.062 g, 0.103 mmol, 80% yield) as a white foam. LCMS: m/e 590.6 (M+H)$^+$, 2.05 min (method 2). $^1$H NMR (400 MHz, chloroform-d) 7.94 (d, J=8.53 Hz, 2H), 7.21 (d, J=8.28 Hz, 2H), 5.30 (dd, J=2.01, 6.27 Hz, 1H), 4.73 (d, J=2.01 Hz, 1H), 4.58-4.64 (m, 2H), 4.50 (t, J=4.89 Hz, 1H), 3.92 (s, 3H), 2.57-2.85 (m, 3H), 2.11 (dd, J=6.40, 17.19 Hz, 1H), 1.71 (s, 3H), 1.10 (s, 3H), 1.00 (s, 3H), 0.99 (s, 3H), 0.94 (s, 3H), 0.94 (s, 3H), 0.86-2.05 (m, 21H).

Step 2. To a solution of methyl 4-((1R,3aS,5aR,5bR,7aR, 11aS,11bR,13aR,13bR)-3a-((2-fluoroethyl)amino)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate (0.059 g, 0.100 mmol) in 1,4-dioxane (2 mL) was added NaOH (1N) (0.5 mL, 0.500 mmol). The mixture was heated to 85° C. for 15.25 h, was cooled to rt, then was diluted with methanol and 1,4-dioxane and was purified by prep HPLC. The fractions containing the expected product were combined and concentrated under reduced pressure to give 4-((1R,3aS,5aR,5bR,7aR,11aS, 11bR,13aR,13bR)-3a-((2-fluoroethyl)amino)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoic acid (29.2 mg, 0.048 mmol, 48.2% yield) as a white solid. LCMS: m/e 576.6 (M+H)$^+$, 1.74 min (method 2). $^1$H NMR (400 MHz, Acetic acid d$_4$) δ 7.99 (d, J=8.53 Hz, 2H), 7.26 (d, J=8.28 Hz, 2H), 5.33 (d, J=4.77 Hz, 1H), 4.73-4.99 (m, 3H), 4.70 (s, 1H), 3.41-3.73 (m, 2H), 2.83-2.94 (m, 1H), 1.73 (s, 3H), 1.19 (s, 3H), 1.11 (s, 3H), 1.05 (s, 3H), 0.98 (s, 3H), 0.96 (s, 3H), 0.82-2.27 (m, 22H).

Example 180

Preparation of 4-((1R,3aS,5aR,5bR,7aR,11aS,11bR, 13aR,13bR)-3a-(ethylamino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid

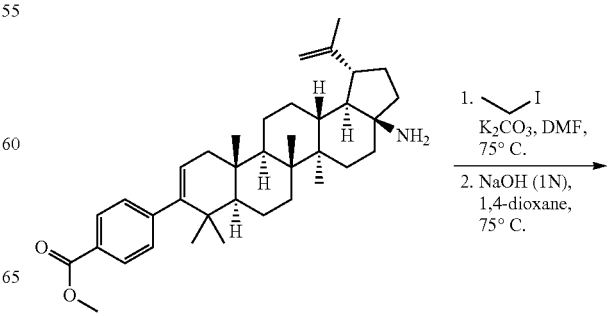

-continued

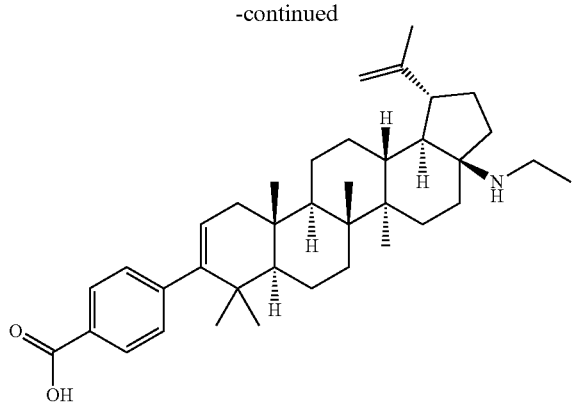

Step 1. Preparation of methyl 4-((1R,3aS,5aR,5bR,7aR,11aS,11bR,13aR,13bR)-3a-(ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To a sealable vial containing methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, HCl (0.075 g, 0.129 mmol) was added potassium carbonate (0.036 g, 0.258 mmol). The mixture was diluted with DMF (1 mL) and iodoethane (0.031 mL, 0.388 mmol) was added. The mixture was heated to 75° C. for 23 h then was cooled to rt. The mixture was diluted with 1 mL of DMF and additional iodoethane (0.031 mL, 0.388 mmol) was added to the mixture. The vial was sealed and heated to 75° C. for 24 h, then was concentrated under reduced pressure and was adsorbed to silica gel. The mixture was purified by flash chromatography using a 0-25% EtOAc in hexanes gradient with 0.1% ammonium hydroxide added and a Thomson 12 g silica gel column. The fractions containing the expected product were combined and were concentrated under reduced pressure to give methyl 4-((1R,3aS,5aR,5bR,7aR,11aS,11bR,13aR,13bR)-3a-(ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.039 g, 0.065 mmol, 50.1% yield) as a white foam. LCMS: m/e 572.7 (M+H)+, 2.16 min (method 2). $^1$H NMR (400 MHz, chloroform-d) δ 7.94 (d, J=8.28 Hz, 2H), 7.21 (d, J=8.53 Hz, 2H), 5.30 (dd, J=1.76, 6.27 Hz, 1H), 4.73 (d, J=2.51 Hz, 1H), 4.59 (dd, J=1.38, 2.38 Hz, 1H), 3.92 (s, 3H), 2.62 (dt, J=5.40, 10.98 Hz, 1H), 2.38-2.53 (m, 2H), 2.11 (dd, J=6.40, 17.19 Hz, 1H), 1.88-2.03 (m, 3H), 1.83 (dd, J=7.78, 12.55 Hz, 1H), 1.70 (s, 3H), 1.10 (s, 3H), 1.11 (t, J=7.03 Hz, 3H), 0.99 (s, 6H), 0.94 (s, 3H), 0.94 (s, 3H), 0.91-1.74 (m, 17H).

Step 2. To a solution of methyl 4-((1R,3aS,5aR,5bR,7aR,11aS,11bR,13aR,13bR)-3a-(ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.037 g, 0.065 mmol) in 1,4-dioxane (1.5 mL) was added NaOH (1N) (0.3 mL, 0.300 mmol). The mixture was heated to 75° C. for 18.5 h then was cooled to rt, was diluted with methanol and 1,4-dioxane, was filtered through a plug of glass wool and was purified by prep HPLC. The fractions containing the expected product were combined and were concentrated under reduced pressure to give 4-((1R,3aS,5aR,5bR,7aR,11aS,11bR,13aR,13bR)-3a-(ethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (0.023 g, 0.040 mmol, 61.2% yield) as a white solid. LCMS: m/e 558.6 (M+H)+, 1.77 min (method 2). $^1$H NMR (400 MHz, Acetic acid d$_4$) δ 7.99 (d, J=8.53 Hz, 2H), 7.26 (d, J=8.28 Hz, 2H), 5.33 (d, J=4.52 Hz, 1H), 4.82 (s, 1H), 4.69 (s, 1H), 3.23 (q, J=7.11 Hz, 2H), 2.81-2.92 (m, 1H), 1.72 (s, 3H), 1.40 (t, J=7.15 Hz, 3H), 1.19 (s, 3H), 1.09 (s, 3H), 1.05 (s, 3H), 0.98 (s, 3H), 0.96 (s, 3H), 0.83-2.24 (m, 22H).

Example 181

Preparation of 4-((1R,3aS,5aR,5bR,7aR,11aS,11bR,13aR,13bR)-3a-(isobutylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

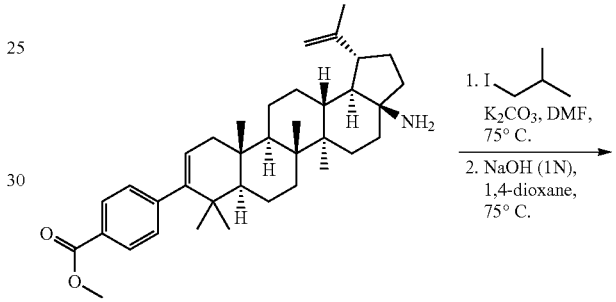

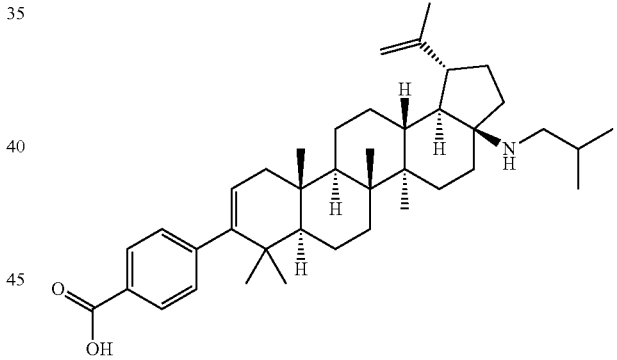

Step 1. Preparation of methyl 4-((1R,3aS,5aR,5bR,7aR,11aS,11bR,13aR,13bR)-3a-(isobutylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate. To a sealable vial containing methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, HCl (0.075 g, 0.129 mmol) was added potassium carbonate (0.036 g, 0.258 mmol). The mixture was diluted with DMF (1 mL) and isobutyl iodide (0.045 mL, 0.388 mmol) was added. The vial was sealed and the mixture was heated to 75° C. for 23 h, then the mixture was cooled to rt. LC/MS showed formation of the expected product, but starting material still remained. To the mixture was added additional isobutyl iodide (0.045 mL, 0.388 mmol) and the vial was sealed and heated to 75° C. for 48 h. The mixture was cooled to rt then was diluted with 5 mL of water. The solids that formed were collected by filtration then were washed with water to give the expected product, methyl 4-((1R,3aS,5aR,5bR,7aR,11aS,11bR,13aR,13bR)-3a-(isobutylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (53 mg, 0.075 mmol, 58.1% yield) as a light-yellow solid. The crude product was used in the next step with no additional purification. LCMS: m/e 600.6 (M+H)⁺, 2.14 min (method 2).

Step 2. To a solution of methyl 4-((1R,3aS,5aR,5bR,7aR,11aS,11bR,13aR,13bR)-3a-(isobutylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (52 mg, 0.087 mmol) in 1,4-dioxane (1.5 mL) was added NaOH (1N) (0.3 mL, 0.300 mmol). The mixture was heated to 75° C. for 67 h then was cooled to rt. The mixture was diluted with 1,4-dioxane and methanol, was filtered through a plug of glass wool, and was purified by prep HPLC. The fractions containing the expected product were combined and concentrated under reduced pressure to give 4-((1R,3aS,5aR,5bR,7aR,11aS,11bR,13aR,13bR)-3a-(isobutylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (25.2 mg, 0.041 mmol, 47.1% yield) as a white solid. LCMS: m/e 586.6 (M+H)⁺, 1.85 min (method 2). ¹H NMR (400 MHz, Acetic acid d₄) δ 8.00 (d, J=8.28 Hz, 2H), 7.26 (d, J=8.28 Hz, 2H), 5.33 (d, J=4.52 Hz, 1H), 4.81 (s, 1H), 4.69 (s, 1H), 3.15 (dd, J=5.02, 12.05 Hz, 1H), 2.88-2.98 (m, 1H), 2.78 (dd, J=9.03, 11.80 Hz, 1H), 1.72 (s, 3H), 1.22 (s, 3H), 1.10 (s, 3H), 1.09 (d, J=6.78 Hz, 3H), 1.06 (s, 3H), 1.01 (d, J=6.78 Hz, 3H), 0.98 (s, 3H), 0.96 (s, 3H), 0.83-2.31 (m, 23H).

Example 182

Preparation of 4-((1R,3aS,5aR,5bR,7aR,11aS,11bR,13aR,13bR)-5a,5b,8,8,11a-pentamethyl-1-(prop-1-en-2-yl)-3a-((3,3,3-trifluoropropyl)amino)-2,3,3a,4,5,5a,5b,6,7,7a,8,11,11a,11b,12,13,13a,13b-octadecahydro-1H-cyclopenta[a]chrysen-9-yl)benzoic acid

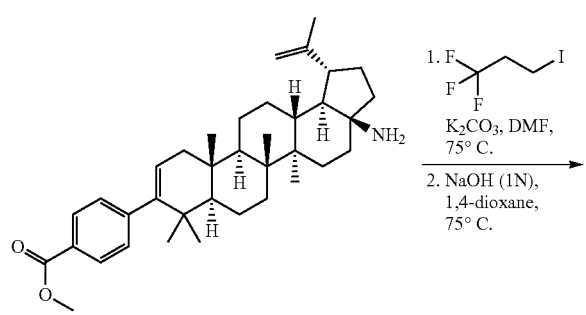

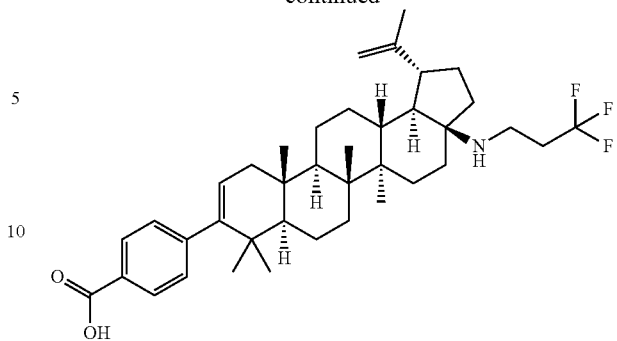

Step 1. Preparation of methyl 4-((1R,3aS,5aR,5bR,7aR,11aS,11bR,13aR,13bR)-5a,5b,8,8,11a-pentamethyl-1-(prop-1-en-2-yl)-3a-((3,3,3-trifluoropropyl)amino)-2,3,3a,4,5,5a,5b,6,7,7a,8,11,11a,11b,12,13,13a,13b-octadecahydro-1H-cyclopenta[a]chrysen-9-yl)benzoate To a sealable vial containing methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, HCl (0.075 g, 0.129 mmol) was added potassium carbonate (0.036 g, 0.258 mmol). The mixture was diluted with DMF (1 mL) and 1-iodo-3,3,3-trifluoropropane (0.045 mL, 0.388 mmol) was added. The vial was sealed and the mixture was heated to 75° C. for 23 h then was cooled to rt. LC/MS showed a mixture of starting material and product. An additional 0.045 mL of 1-Iodo-3,3,3-trifluoropropane was added and the mixture and was heated to 75° C. for 48 h then was cooled to rt. LC/MS showed further progression, but the reaction was still not complete. An additional 0.045 mL of 1-iodo-3,3,3-trifluoropropane was added and the mixture was heated to 75° C. for 71 h, then was cooled to rt and was concentrated under reduced pressure. The mixture was adsorbed to silica gel and was purified by flash chromatography using a 0-15% EtOAc in hexanes gradient with 0.1% ammonium hydroxide added to the mixture and a Thomson 12 g silica gel column. The fractions containing the expected product were combined and were concentrated under reduced pressure to give methyl 4-((1R,3aS,5aR,5bR,7aR,11aS,11bR,13aR,13bR)-5a,5b,8,8,11a-pentamethyl-1-(prop-1-en-2-yl)-3a-((3,3,3-trifluoropropyl)amino)-2,3,3a,4,5,5a,5b,6,7,7a,8,11,11a,11b,12,13,13a,13b-octadecahydro-1H-cyclopenta[a]chrysen-9-yl)benzoate (0.032 g, 0.044 mmol, 34.1% yield) as a white foam. LCMS: m/e 640.6 (M+H)⁺, 2.15 min (method 2). ¹H NMR (500 MHz, chloroform-d) δ 7.92 (d, J=8.24 Hz, 2H), 7.19 (d, J=8.24 Hz, 2H), 5.28 (dd, J=1.53, 6.10 Hz, 1H), 4.70 (d, J=1.83 Hz, 1H), 4.59 (s, 1H), 3.90 (s, 3H), 2.60-2.73 (m, 2H), 2.56 (dt, J=5.34, 10.91 Hz, 1H), 2.21-2.32 (m, 2H), 2.09 (dd, J=6.41, 17.09 Hz, 1H), 1.68 (s, 3H), 1.07 (s, 3H), 0.98 (s, 6H), 0.92 (s, 3H), 0.92 (br. s., 3H), 0.84-2.01 (m, 21H).

Step 2. To a solution of methyl 4-((1R,3aS,5aR,5bR,7aR,11aS,11bR,13aR,13bR)-5a,5b,8,8,11a-pentamethyl-1-(prop-1-en-2-yl)-3a-((3,3,3-trifluoropropyl)amino)-2,3,3a,4,5,5a,5b,6,7,7a,8,11,11a,11b,12,13,13a,13b-octadecahydro-1H-cyclopenta[a]chrysen-9-yl)benzoate (0.032 g, 0.050 mmol) in 1,4-dioxane (1 mL) was added NaOH (1N) (0.2 mL, 0.200 mmol). The mixture was heated to 75° C. for 22.5 h then was cooled to rt. The mixture was diluted with methanol, was filtered through a plug of glass wool and was purified by Prep HPLC. The fractions containing the expected product were combined and concentrated under reduced pressure to give 4-((1R,3aS,5aR,5bR,7aR,11aS,11bR,13aR,13bR)-5a,5b,8,8,11a-pentamethyl-1-(prop-1-en-2-yl)-3a-((3,3,3-trifluoropropyl)amino)-2,3,3a,4,5,5a,5b,6,7,7a,8,11,11a,11b,12,13,13a,13b-octadecahydro-1H-cyclopenta[a]chrysen-9-yl)benzoic acid (0.022 g, 0.033 mmol, 66.8% yield) as a white solid. LCMS: m/e 626.6 (M+H)$^+$, 1.87 min (method 2). $^1$H NMR (400 MHz, Acetic acid d$_4$) 67.99 (d, J=8.28 Hz, 2H), 7.25 (d, J=8.28 Hz, 2H), 5.33 (d, J=4.77 Hz, 1H), 4.82 (s, 1H), 4.70 (s, 1H), 3.36-3.51 (m, 2H), 2.81-2.97 (m, 3H), 2.12-2.28 (m, 4H), 1.72 (s, 3H), 1.17 (s, 3H), 1.09 (s, 3H), 1.05 (s, 3H), 0.98 (s, 3H), 0.96 (s, 3H), 0.82-2.11 (m, 18H).

Example 183

Preparation of 4-((1R,3aS,5aR,5bR,7aR,11aS,11bR,13aR,13bR)-3a-(4,5-dimethylthiazol-2-ylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

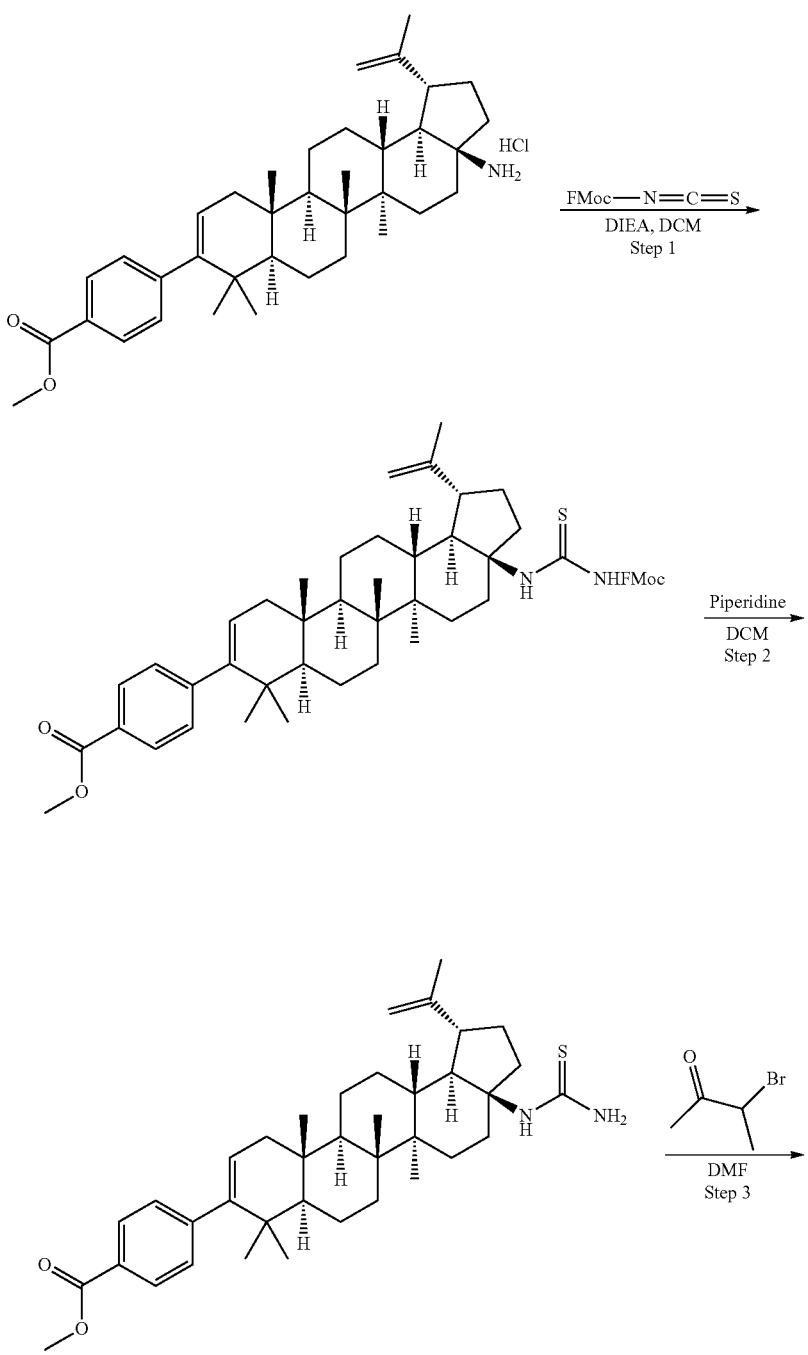

-continued

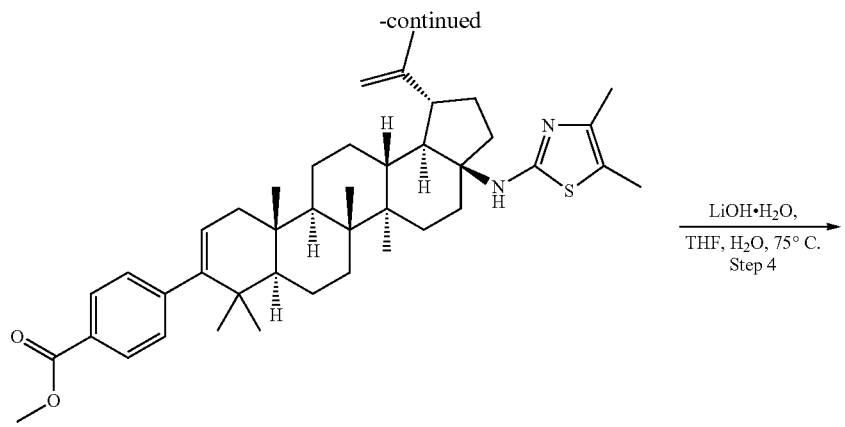

LiOH·H₂O,
THF, H₂O, 75° C.
Step 4

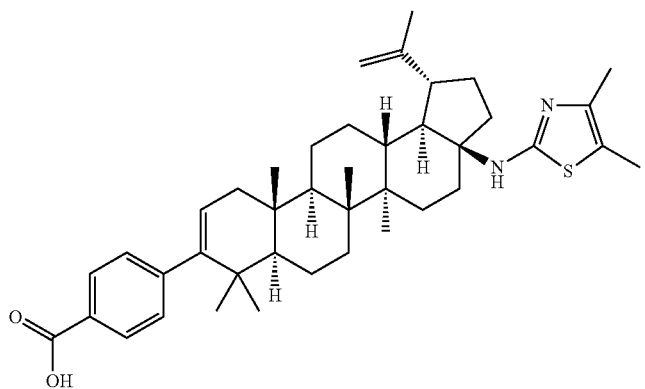

Step 1. Preparation of methyl 4-((1R,3aS,5aR,5bR, 7aR,11aS,11bR,13aR,13bR)-3a-(3-(((9H-fluoren-9-yl)methoxy)carbonyl)thioureido)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)benzoate

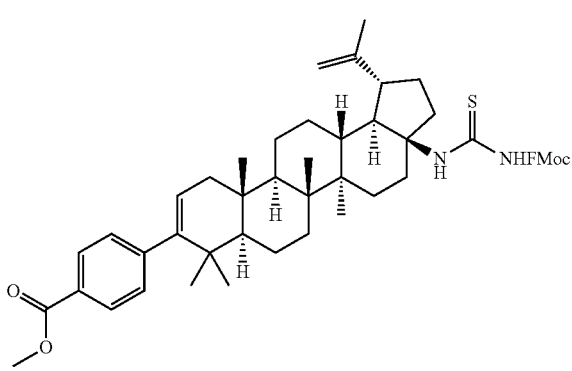

To a solution of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate, HCl (2 g, 3.45 mmol) in DCM (50 mL) was added N,N-diisopropylethylamine (3.00 mL, 17.23 mmol) and Fmoc-isothioisocyanate (1.939 g, 6.89 mmol). The reaction mixture was stirred at rt. After 3 h, the reaction was washed with 0.1 N HCl (50 mL). The aqueous layer was extracted with DCM (50 mL). The combined organic layer was washed with brine, dried over MgSO₄, filtered and concentrated to about 30 mL of DCM and treated with MeOH (100 mL). The mixture was concentrated to remove all DCM until approximately 50 mL of MeOH remained. The resulting yellow precipitate was filtered and washed with MeOH. The solid product was saved and the liquid filtrate was concentrated to effect more precipitation. The resulting solid was isolated by filtration and washed with MeOH. The combined solid product was dried in a 50° C. vacuum oven to give methyl 4-((1R, 3aS,5aR,5bR,7aR,11aS,11bR,13aR,13bR)-3a-(3-(((9H-fluoren-9-yl)methoxy)carbonyl)thioureido)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoate (2.52 g, 3.05 mmol, 89% yield) as a yellow solid. ¹H NMR (500 MHz, CHLOROFORM-d) δ 9.84 (s, 1H), 8.00 (s, 1H), 7.95 (d, J=8.2 Hz, 2H), 7.82 (d, J=7.6 Hz, 2H), 7.64 (t, J=8.2 Hz, 2H), 7.49-7.44 (m, 2H), 7.38 (tt, J=1.5, 7.4 Hz, 2H), 7.21 (d, J=8.5 Hz, 2H), 5.33-5.27 (m, 1H), 4.79 (s, 1H), 4.67 (s, 1H), 4.58-4.53 (m, 2H), 4.29 (t, J=6.9 Hz, 1H), 3.93 (s, 3H), 3.39 (d, J=13.7 Hz, 1H), 3.23 (dd, J=8.2, 12.8 Hz, 1H), 2.50 (dt, J=5.3, 10.8 Hz, 1H), 2.13 (dd, J=6.4, 17.1 Hz, 1H), 1.98-1.88 (m, 1H), 1.87-1.77 (m, 3H), 1.74 (s, 3H), 1.70 (d, J=17.4 Hz, 1H), 1.54-1.42 (m, 8H), 1.41-1.29

(m, 3H), 1.24 (d, J=10.4 Hz, 1H), 1.19-1.10 (m, 2H), 1.05 (s, 3H), 1.00 (s, 6H), 0.94 (s, 6H).

Step 2. Preparation of methyl 4-((1R,3aS,5aR,5bR,7aR,11aS,11bR,13aR,13bR)-5a,5b,8,8,11a-pentamethyl-1-(prop-1-en-2-yl)-3a-thioureido-2,3,3a,4,5,5a,5b,6,7,7a,8,11,11a,11b,12,13,13a,13b-octadecahydro-1H-cyclopenta[a]chrysen-9-yl)benzoate

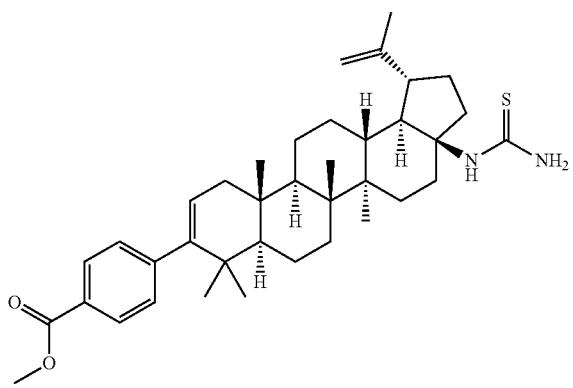

To a solution of methyl 4-((1R,3aS,5aR,5bR,7aR,11aS,11bR,13aR,13bR)-3a-(3-(((9H-fluoren-9-yl)methoxy)carbonyl)thioureido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (2.51 g, 3.04 mmol) in DCM (30 mL) was added piperidine (1.502 mL, 15.21 mmol). The resulting brown reaction mixture was stirred at rt for 5 h. The reaction was concentrated and triturated with MeOH to give white solid product and fulvene adduct. This material was then re-dissolved in hot DCM and allowed to cool to rt. The resulting white precipitate was filtered and washed with cold DCM. The liquid filtrate was concentrated and more white precipitate was filtered. The combined white solid product was dried in a vacuum oven. The liquid filtrate was concentrated and loaded onto a column of SiO$_2$ (90 g) and eluted with DCM (1 L) to remove top spot by-product then the desired product was eluted with 97:3 DCM:MeOH. After drying in a vacuum oven all solid product was combined to give methyl 4-((1R,3aS,5aR,5bR,7aR,11aS,11bR,13aR,13bR)-5a,5b,8,8,11a-pentamethyl-1-(prop-1-en-2-yl)-3a-thioureido-2,3,3a,4,5,5a,5b,6,7,7a,8,11,11a,11b,12,13,13a,13b-octadecahydro-1H-cyclopenta[a]chrysen-9-yl)benzoate (1.7 g, 2.82 mmol, 93% yield) as a white solid. LCMS: m/e 603.5 (M+H)$^+$, 2.51 min (method 1). $^1$H NMR (500 MHz, CHLOROFORM-d) δ 7.94 (d, J=7.9 Hz, 2H), 7.28 (s, 1H), 7.21 (d, J=7.9 Hz, 2H), 6.07 (br. s., 1H), 5.94 (br. s., 1H), 5.34-5.28 (m, 2H), 4.78 (s, 1H), 4.68 (br. s., 1H), 3.92 (s, 3H), 2.64-2.55 (m, 1H), 2.17-2.02 (m, 2H), 1.85-1.74 (m, 3H), 1.71 (s, 3H), 1.67 (br. s., 1H), 1.60-1.38 (m, 10H), 1.35-1.35 (m, 1H), 1.27-1.17 (m, 2H), 1.13 (s, 4H), 1.02 (s, 3H), 1.00 (s, 3H), 0.95 (br. s., 3H), 0.94 (s, 3H), 0.91-0.90 (m, 1H). $^{13}$C NMR (126 MHz, CHLOROFORM-d) δ 182.0, 167.4, 148.8, 148.4, 146.4, 130.2, 128.6, 128.0, 124.0, 111.0, 66.8, 53.5, 53.0, 52.1, 50.3, 49.5, 46.8, 42.0, 41.8, 40.6, 37.9, 37.6, 36.4, 34.2, 33.5, 29.7, 29.5, 29.5, 27.6, 25.1, 21.3, 21.1, 19.8, 19.4, 16.5, 15.9, 14.6.

Step 3. Preparation of methyl 4-((1R,3aS,5aR,5bR,7aR,11aS,11bR,13aR,13bR)-3a-(4,5-dimethylthiazol-2-ylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

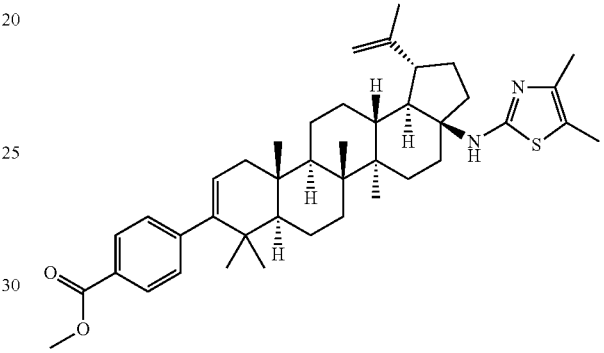

To a solution of methyl 4-((1R,3aS,5aR,5bR,7aR,11aS,11bR,13aR,13bR)-5a,5b,8,8,11a-pentamethyl-1-(prop-1-en-2-yl)-3a-thioureido-2,3,3a,4,5,5a,5b,6,7,7a,8,11,11a,11b,12,13,13a,13b-octadecahydro-1H-cyclopenta[a]chrysen-9-yl)benzoate (150 mg, 0.249 mmol) in DMF (5 mL) was added N,N-diisopropylethylamine (0.173 mL, 0.995 mmol) and 3-bromobutan-2-one (56.4 mg, 0.373 mmol). The reaction mixture was stirred at rt. After 18 h, the reaction mixture was poured into a separatory funnel containing H$_2$O (10 mL) and extracted with EtOAc (50 mL). The organic layer was washed with brine, dried over MgSO$_4$, filtered and concentrated to white solid. The material was redissolved in DCM (5 mL) and MeOH was added to effect precipitation. The mixture was concentrated to remove most of DCM and the resulting white precipitate was filtered, washed with cold MeOH, and dried in a vacuum oven to give methyl 4-((1R,3aS,5aR,5bR,7aR,11aS,11bR,13aR,13bR)-3a-(4,5-dimethylthiazol-2-ylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (121 mg, 0.175 mmol, 70.5% yield) as a white solid. LCMS: m/e 655.3 (M+H)$^+$, 2.72 min (method 2). $^1$H NMR (500 MHz, CHLOROFORM-d) δ 7.95 (d, J=8.2 Hz, 2H), 7.21 (d, J=8.2 Hz, 2H), 5.31 (d, J=4.6 Hz, 1H), 4.76 (br. s., 1H), 4.65 (s, 1H), 3.93 (s, 3H), 2.43 (d, J=10.4 Hz, 1H), 2.21 (s, 3H), 2.15 (s, 3H), 2.11 (d, J=6.7 Hz, 1H), 2.07-1.96 (m, 1H), 1.80-1.65 (m, 6H), 1.57-1.36 (m, 8H), 1.35-1.27 (m, 2H), 1.23 (d, J=10.1 Hz, 1H), 1.17-1.11 (m, 1H), 1.09 (s, 3H), 1.03 (s, 3H), 1.00 (s, 3H), 0.94 (s, 6H).

Step 4. Preparation of 4-((1R,3aS,5aR,5bR,7aR, 11aS,11bR,13aR,13bR)-3a-(4,5-dimethylthiazol-2-ylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid, TFA

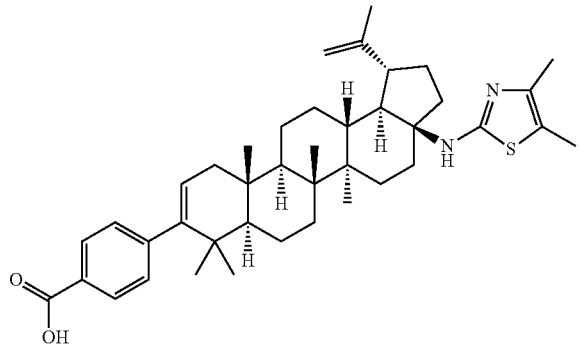

To a solution of methyl 4-((1R,3aS,5aR,5bR,7aR,11aS, 11bR,13aR,13bR)-3a-(4,5-dimethylthiazol-2-ylamino)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)benzoate (107 mg, 0.163 mmol) in THF (3 mL) was added a solution of lithium hydroxide monohydrate (20.57 mg, 0.490 mmol) in water (1.000 mL). The reaction was heated to 75° C. for 6 h. The reaction mixture was concentrated, redissolved in MeOH (2 mL) and THF (1 mL) filtered and was then injected (2 injections) into reverse phase HPLC for purification using Prep HPLC method 3 to give 4-((1R,3aS,5aR,5bR,7aR,11aS,11bR,13aR, 13bR)-3a-(4,5-dimethylthiazol-2-ylamino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid, TFA (58.3 mg, 0.073 mmol, 44.4% yield) as a white solid. LCMS: m/e 641.3 (M+H)$^+$, 2.51 min (method 2). $^1$H NMR (500 MHz, CHLOROFORM-d) δ 10.10 (s, 1H), 8.02 (d, J=8.2 Hz, 2H), 7.25 (d, J=8.2 Hz, 2H), 5.33 (d, J=4.6 Hz, 1H), 4.84 (s, 1H), 4.69 (s, 1H), 2.97 (dt, J=5.2, 11.0 Hz, 1H), 2.48 (d, J=13.7 Hz, 1H), 2.32-2.25 (m, 2H), 2.23 (s, 3H), 2.20 (s, 3H), 2.16 (dd, J=6.4, 17.1 Hz, 1H), 2.03-1.89 (m, 1H), 1.89-1.79 (m, 2H), 1.74 (s, 3H), 1.71 (br. s., 1H), 1.60-1.34 (m, 11H), 1.26-1.19 (m, 1H), 1.12 (d, J=13.4 Hz, 1H), 1.06 (s, 3H), 1.03 (s, 3H), 1.01 (s, 3H), 0.96 (s, 3H), 0.94 (s, 3H). $^{13}$C NMR (126 MHz, CHLOROFORM-d) δ 171.0, 164.9, 149.8, 148.9, 146.2, 132.4, 130.3, 129.2, 127.0, 124.4, 117.7, 111.4, 110.7, 68.1, 53.1, 50.3, 49.8, 45.4, 41.9, 40.8, 37.6, 36.5, 36.4, 33.8, 33.1, 29.6, 27.3, 25.3, 21.2, 19.9, 19.6, 16.5, 15.7, 14.5, 11.4, 10.8.

Examples 184A and 184B

Preparation of 4-((1R,3aS,5aR,5bR,7aR,11aS,11bR, 13aR,13bR)-3a-((4-ethylthiazol-2-yl)(2-oxobutyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid and 4-((1R,3aS,5aR,5bR,7aR,11aS, 11bR,13aR,13bR)-3a-(4-ethylthiazol-2-ylamino)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

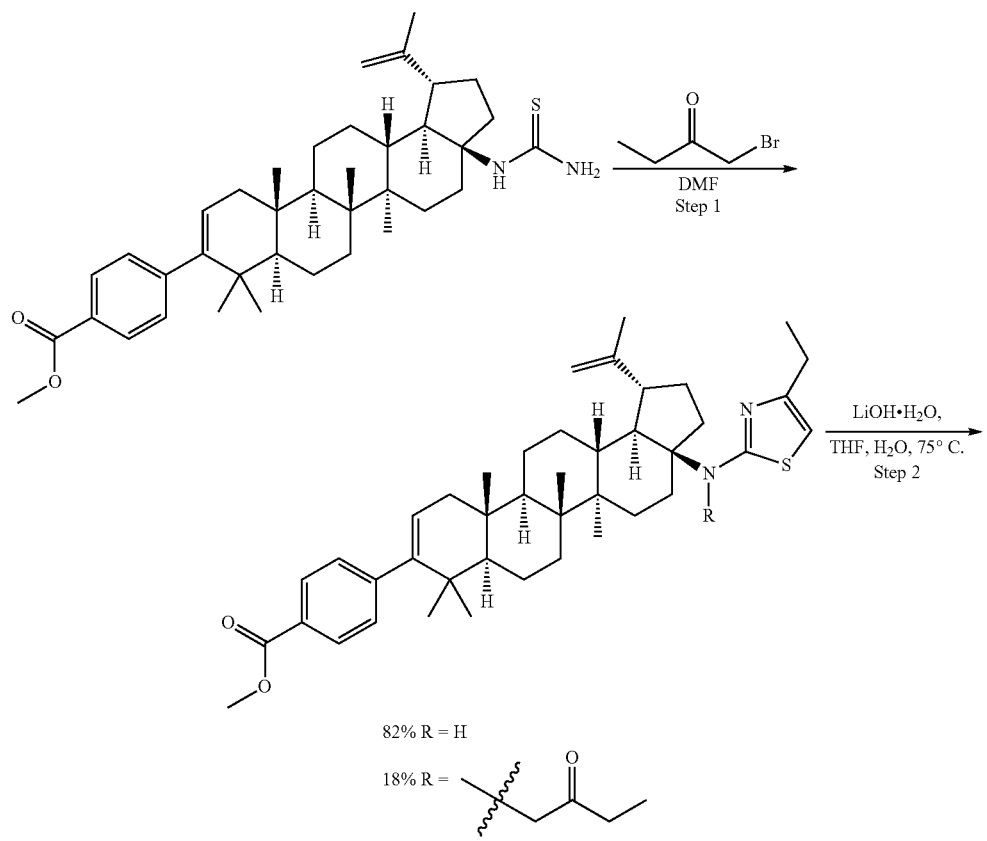

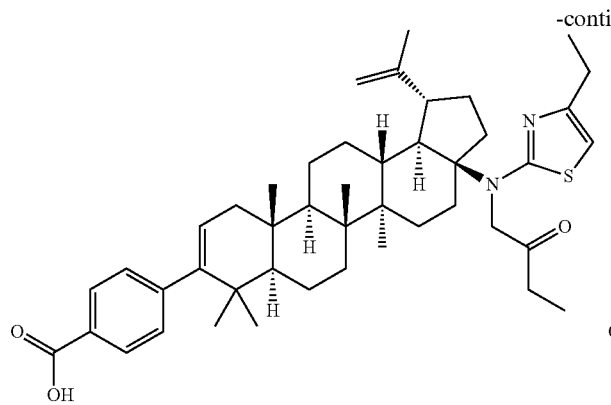

Example 184A

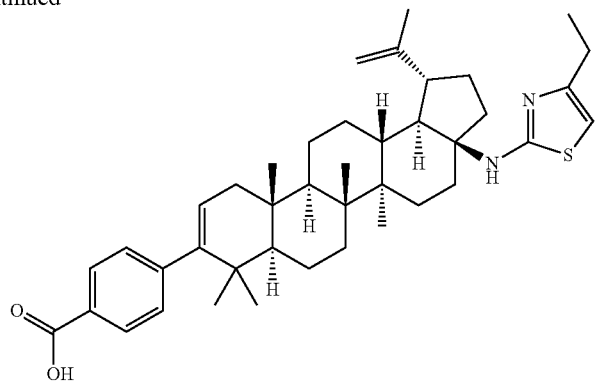

Example 184B (1:4)

Step 1. Preparation of methyl 4-((1R,3aS,5aR,5bR, 7aR,11aS,11bR,13aR,13bR)-3a-((4-ethylthiazol-2-yl)(2-oxobutyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate and methyl 4-((1R,3aS,5aR, 5bR,7aR,11aS,11bR,13aR,13bR)-3a-(4-ethylthiazol-2-ylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate

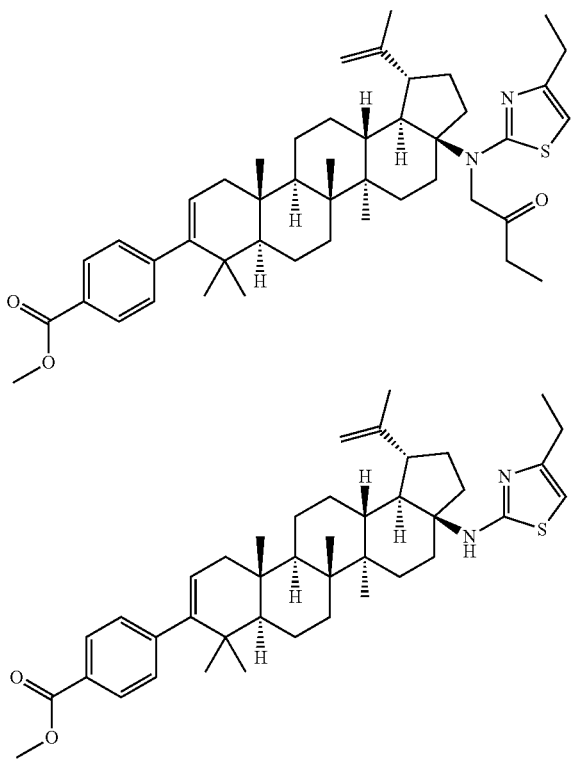

To a solution of methyl 4-((1R,3aS,5aR,5bR,7aR,11aS, 11bR,13aR,13bR)-5a,5b,8,8,11a-pentamethyl-1-(prop-1-en-2-yl)-3a-thioureido-2,3,3a,4,5,5a,5b,6,7,7a,8,11,11a, 11b,12,13,13a,13b-octadecahydro-1H-cyclopenta[a] chrysen-9-yl)benzoate (158 mg, 0.262 mmol) in DMF (3 mL) was added N,N-diisopropylethylamine (0.183 mL, 1.048 mmol) and 1-bromobutan-2-one (0.042 mL, 0.393 mmol).

The reaction mixture was stirred at rt. After 16 h, the reaction mixture was poured into H$_2$O (5 mL) and extracted with EtOAc (50 mL). The organic layer was washed with brine, dried over MgSO$_4$, filtered and concentrated. The crude material was dissolved in DCM and treated with MeOH to effect precipitation. The mixture was concentrated to remove all DCM and the resulting white precipitate was filtered and washed with MeOH. The product was dried in a vacuum oven to give a mixture of methyl 4-((1R,3aS,5aR,5bR,7aR,11aS, 11bR,13aR,13bR)-3a-((4-ethylthiazol-2-yl)(2-oxobutyl) amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoate and methyl 4-((1R,3aS,5aR,5bR,7aR,11aS,11bR,13aR,13bR)-3a-(4-ethylthiazol-2-ylamino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate as a white solid in quantitative yield (173 mg, 0.264 mmol). LC/MS: m/e 725.4 (M+H)$^+$, 2.70 min and m/e 655.3 (M+H)$^+$, 2.95 min (method 9), respectively. Reversed phased analytical HPLC showed ratio of major product with rt=23.45 min (m/e 655.3 (M+H)$^+$) to minor product with rt=26.86 min (m/e 725.4 (M+H)$^+$) of 82%:18% (using analytical HPLC method 1).

Step 2. Preparation of 4-((1R,3aS,5aR,5bR,7aR, 11aS,11bR,13aR,13bR)-3a-((4-ethylthiazol-2-yl)(2-oxobutyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid, TFA and 4-((1R,3aS,5aR, 5bR,7aR,11aS,11bR,13aR,13bR)-3a-(4-ethylthiazol-2-ylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid, TFA

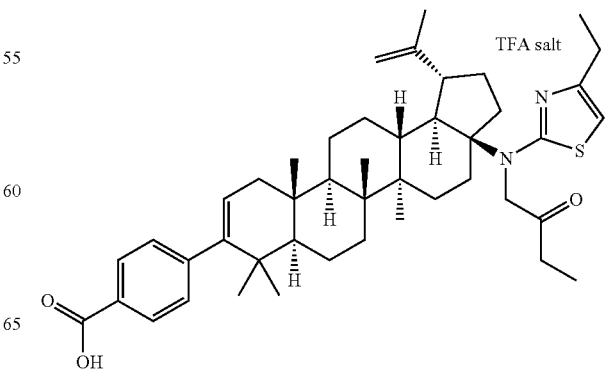

TFA salt

-continued

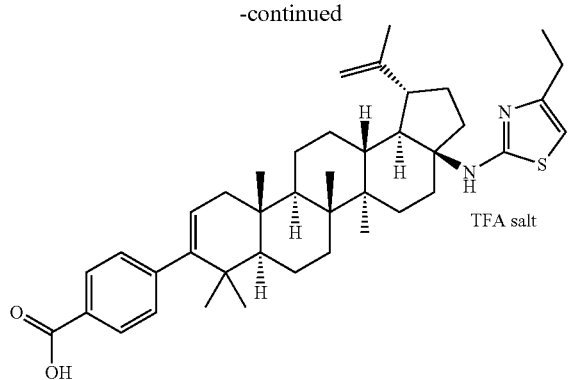

TFA salt

To a mixture of methyl 4-((1R,3aS,5aR,5bR,7aR,11aS,11bR,13aR,13bR)-3a-((4-ethylthiazol-2-yl)(2-oxobutyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate and methyl 4-((1R,3aS,5aR,5bR,7aR,11aS,11bR,13aR,13bR)-3a-(4-ethylthiazol-2-ylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate in THF (3 mL) was added a solution of Li.HO.H$_2$O (32.7 mg, 0.779 mmol) in water (1.50 mL). The reaction was heated to 75° C. for 6 h. The reaction mixture was concentrated, redissolved in MeOH (2 mL) and THF (1 mL) filtered and was then injected (2 injections) into reverse phase HPLC for purification using Prep HPLC method 3 to give 4-((1R,3aS,5aR,5bR,7aR,11aS,11bR,13aR,13bR)-3a-((4-ethylthiazol-2-yl)(2-oxobutyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, TFA (22.3 mg, 0.027 mmol, 10.31% yield) and 4-((1R,3aS,5aR,5bR,7aR,11aS,11bR,13aR,13bR)-3a-(4-ethylthiazol-2-ylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, TFA (91.7 mg, 0.118 mmol, 45.4% yield) both as a white solid.

Example 184A

LC/MS: m/e 711.4 (M+H)$^+$, 2.45 min (method 11), $^1$H NMR (500 MHz, CHLOROFORM-d) δ 8.14 (br. s., 1H), 7.97 (d, J=7.9 Hz, 2H), 7.21 (d, J=8.2 Hz, 2H), 6.56-6.45 (m, 1H), 6.32 (s, 1H), 5.26 (d, J=5.2 Hz, 1H), 5.16 (d, J=19.5 Hz, 1H), 4.84 (s, 1H), 4.67 (br. s., 1H), 3.11-2.98 (m, 1H), 2.89-2.77 (m, 1H), 2.73-2.61 (m, 2H), 2.54-2.47 (m, 1H), 2.43 (dd, J=7.6, 16.2 Hz, 1H), 2.30-2.22 (m, 1H), 2.21-2.11 (m, 1H), 2.11-1.98 (m, 2H), 1.95-1.87 (m, 1H), 1.71 (s, 3H), 1.63 (d, J=16.2 Hz, 2H), 1.51 (d, J=11.0 Hz, 2H), 1.48-1.37 (m, 6H), 1.34-1.25 (m, 6H), 1.23-1.19 (m, 1H), 1.16 (t, J=7.2 Hz, 3H), 1.11 (d, J=10.7 Hz, 1H), 1.00 (br. s., 3H), 0.99 (br. s., 3H), 0.96 (br. s., 6H), 0.95 (br. s., 2H). $^{13}$C NMR (126 MHz, CHLOROFORM-d) δ 203.2, 170.6, 167.1, 149.4, 148.6, 146.3, 144.3, 130.2, 129.1, 127.8, 124.6, 110.7, 100.1, 70.7, 55.2, 53.0, 50.7, 49.4, 44.3, 42.0, 41.8, 40.7, 37.6, 36.4, 36.3, 33.6, 33.4, 32.7, 29.6, 29.4, 27.3, 27.2, 25.2, 21.5, 21.2, 20.7, 19.8, 19.7, 16.5, 15.5, 14.5, 10.8, 7.3.

Example 184B

LC/MS: m/e 641.3 (M+H)$^+$, 2.51 min (method 11), $^1$H NMR (500 MHz, CHLOROFORM-d) δ 10.17 (s, 1H), 8.02 (d, J=8.2 Hz, 2H), 7.25 (d, J=8.2 Hz, 2H), 6.07 (s, 1H), 5.33 (d, J=4.6 Hz, 1H), 4.85 (s, 1H), 4.70 (s, 1H), 2.97 (dt, J=5.0, 11.1 Hz, 1H), 2.71 (dq, J=0.9, 7.5 Hz, 2H), 2.53-2.45 (m, 1H), 2.32 (dd, J=7.8, 13.0 Hz, 1H), 2.26 (dt, J=2.9, 12.1 Hz, 1H), 2.16 (dd, J=6.3, 17.2 Hz, 1H), 2.05-1.92 (m, 1H), 1.90-1.79 (m, 2H), 1.74 (s, 3H), 1.69 (d, J=16.8 Hz, 1H), 1.60-1.35 (m, 11H), 1.30 (t, J=7.6 Hz, 3H), 1.23 (dd, J=4.1, 9.6 Hz, 1H), 1.13 (d, J=13.1 Hz, 1H), 1.06 (s, 3H), 1.03 (s, 3H), 1.01 (s, 3H), 0.96 (s, 3H), 0.95 (s, 3H). $^{13}$C NMR (126 MHz, CHLOROFORM-d) δ 171.5, 167.1, 163.3, 163.0, 149.8, 148.8, 146.2, 144.6, 130.3, 129.3, 127.1, 124.4, 117.5, 115.2, 110.8, 98.3, 68.3, 53.1, 50.3, 49.7, 45.4, 41.9, 40.8, 37.6, 36.5, 36.4, 33.8, 32.8, 29.6, 27.3, 27.1, 25.3, 21.7, 21.2, 19.8, 19.6, 16.5, 15.7, 14.5, 11.8.

Example 185

Preparation of 4-((1R,3aS,5aR,5bR,7aR,11aS,11bR,13aR,13bR)-3a-(4-tert-butylthiazol-2-ylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

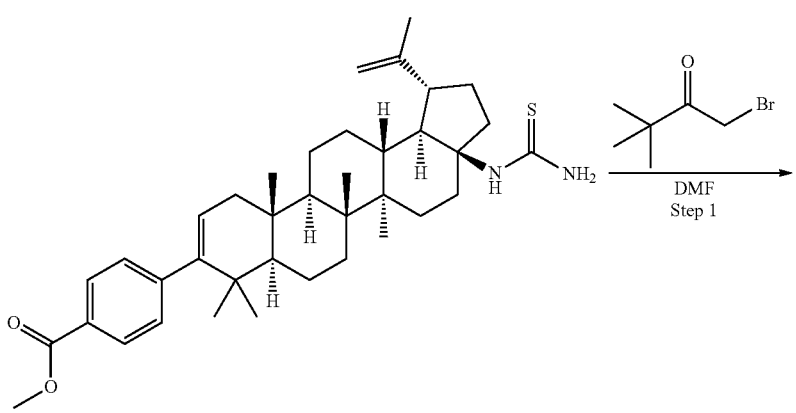

-continued

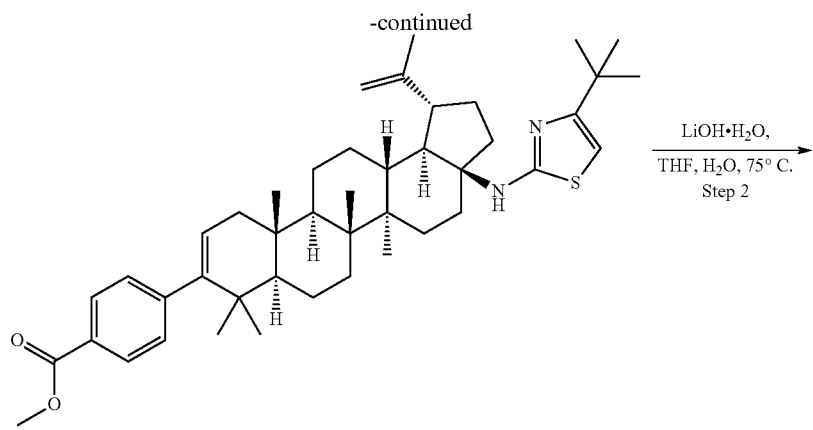

LiOH·H₂O,
─────────────→
THF, H₂O, 75° C.
Step 2

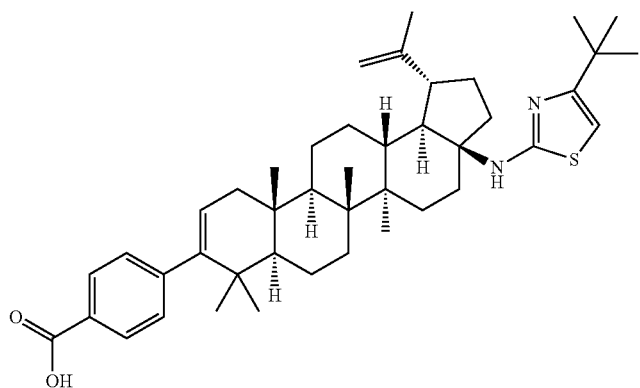

Step 1. Preparation of 4-((1R,3aS,5aR,5bR,7aR,11aS,11bR,13aR,13bR)-3a-(4-tert-butylthiazol-2-ylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

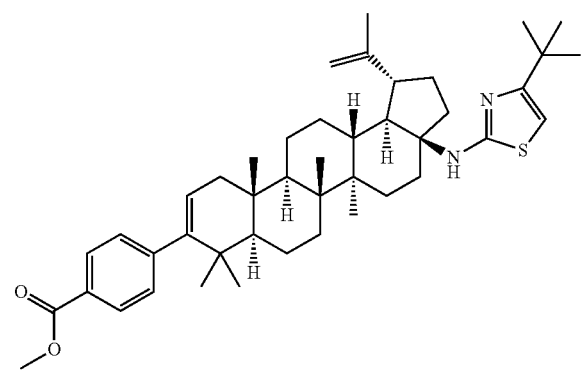

To a solution of methyl 4-((1R,3aS,5aR,5bR,7aR,11aS,11bR,13aR,13bR)-5a,5b,8,8,11a-pentamethyl-1-(prop-1-en-2-yl)-3a-thioureido-2,3,3a,4,5,5a,5b,6,7,7a,8,11,11a,11b,12,13,13a,13b-octadecahydro-1H-cyclopenta[a]chrysen-9-yl)benzoate (150 mg, 0.249 mmol) in DMF (3 mL) was added N,N-diisopropylethylamine (0.217 mL, 1.244 mmol) and 1-bromopinacolone (0.056 mL, 0.373 mmol). The reaction mixture was stirred at rt overnight. After 18 h, the reaction mixture was poured into a separatory funnel containing H₂O (5 mL) and extracted with EtOAc (50 mL). The organic layer was washed with brine, dried over MgSO₄, filtered and concentrated to white solid. The material was redissolved in DCM (3 mL), MeOH wash added and concentrated to remove most of the DCM. The resulting white precipitate was filtered, washed with cold MeOH, and dried in a vacuum oven to give methyl 4-((1R,3aS,5aR,5bR,7aR,11aS,11bR,13aR,13bR)-3a-(4-tert-butylthiazol-2-ylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (154.0 mg, 0.225 mmol, 91% yield) as a white solid. LC/MS: m/e 683.4 (M+H)⁺, 2.88 min (method 11). ¹H NMR (500 MHz, CHLOROFORM-d) δ 7.95 (d, J=8.2 Hz, 2H), 7.22 (d, J=8.2 Hz, 2H), 6.06 (s, 1H), 5.31 (d, J=4.6 Hz, 1H), 4.88 (s, 1H), 4.77 (s, 1H), 4.66 (s, 1H), 3.93 (s, 3H), 2.72 (d, J=13.7 Hz, 1H), 2.68-2.62 (m, 1H), 2.55 (dd, J=8.1, 12.7 Hz, 1H), 2.13 (dd, J=6.4, 17.1 Hz, 1H), 2.07-1.98 (m, 1H), 1.92-1.83 (m, 1H), 1.82-1.76 (m, 1H), 1.74 (s, 3H), 1.73-1.66 (m, 2H), 1.61 (s, 1H), 1.57-1.49 (m, 3H), 1.49-1.40 (m, 4H), 1.40-1.31 (m, 3H), 1.29 (s, 9H), 1.27-1.21 (m, 1H), 1.18-1.12 (m, 1H), 1.10 (s, 3H), 1.04 (s, 3H), 1.01 (s, 3H), 0.95 (s, 6H).

Step 2. Preparation of 4-((1R,3aS,5aR,5bR,7aR, 11aS,11bR,13aR,13bR)-3a-(4-tert-butylthiazol-2-ylamino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid, TFA

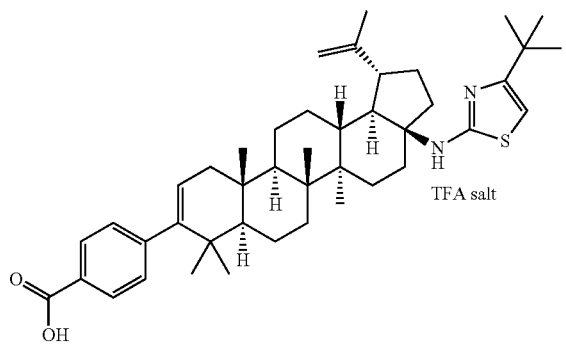

To a solution of methyl 4-((1R,3aS,5aR,5bR,7aR,11aS, 11bR,13aR,13bR)-3a-(4-tert-butylthiazol-2-ylamino)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)benzoate (139 mg, 0.204 mmol) in THF (3 mL) was added a solution of lithium hydroxide monohydrate (25.6 mg, 0.611 mmol) in water (1 mL). The reaction was heated to 75° C. for 6 h. The reaction mixture was concentrated, redissolved in MeOH (2 mL) and THF (1 mL) filtered and was then injected (2 injections) into reverse phase HPLC for purification using Prep HPLC method 3 to give 4-((1R,3aS,5aR,5bR,7aR,11aS,11bR,13aR,13bR)-3a-(4-tert-butylthiazol-2-ylamino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid, TFA (49.3 mg, 0.059 mmol, 28.8% yield) as a white solid. LC/MS: m/e 669.4 (M+H)$^+$, 2.61 min (method 11). $^1$H NMR (500 MHz, CHLOROFORM-d) δ 8.02 (d, J=7.9 Hz, 2H), 7.25 (d, J=8.2 Hz, 2H), 6.05 (s, 1H), 5.33 (d, J=4.9 Hz, 1H), 4.86 (s, 1H), 4.70 (s, 1H), 3.52 (s, 1H), 3.03 (dt, J=5.0, 10.9 Hz, 1H), 2.54 (d, J=14.0 Hz, 1H), 2.34 (dd, J=8.1, 12.7 Hz, 1H), 2.31-2.22 (m, 1H), 2.16 (dd, J=6.3, 17.2 Hz, 1H), 2.09-1.96 (m, 1H), 1.92-1.80 (m, 2H), 1.75 (s, 3H), 1.69 (d, J=16.8 Hz, 1H), 1.58 (br. S., 1H), 1.53-1.42 (m, 8H), 1.39 (s, 9H), 1.28 (s, 2H), 1.23 (d, J=9.2 Hz, 2H), 1.13 (d, J=13.7 Hz, 1H), 1.08 (s, 4H), 1.04 (s, 3H), 1.01 (s, 3H), 0.95 (br. S., 3H), 0.95 (br. S., 3H). $^{13}$C NMR (126 MHz, CHLOROFORM-d) δ 170.9, 167.4, 151.7, 149.5, 148.3, 145.6, 129.9, 128.8, 126.5, 124.0, 110.5, 96.6, 68.0, 52.7, 50.0, 49.3, 44.9, 41.5, 41.5, 40.3, 37.2, 36.1, 36.0, 33.5, 33.4, 32.3, 29.2, 29.2, 28.5, 27.0, 26.8, 24.9, 20.8, 20.7, 19.4, 19.3, 16.1, 15.4, 14.1.

Example 186

Preparation of 4-((1R,3aS,5aR,5bR,7aR,11aS,11bR, 13aR,13bR)-5a,5b,8,8,11a-pentamethyl-1-(prop-1-en-2-yl)-3a-(4-(thiophen-3-yl)thiazol-2-ylamino)-2, 3,3a,4,5,5a,5b,6,7,7a,8,11,11a,11b,12,13,13a,13b-octadecahydro-1H-cyclopenta[a]chrysen-9-yl) benzoic acid and 4-((1R,3aS,5aR,5bR,7aR,11aS, 11bR,13aR,13bR)-5a,5b,8,8,11a-pentamethyl-3a-((2-oxo-2-(thiophen-3-yl)ethyl)(4-(thiophen-3-yl) thiazol-2-yl)amino)-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

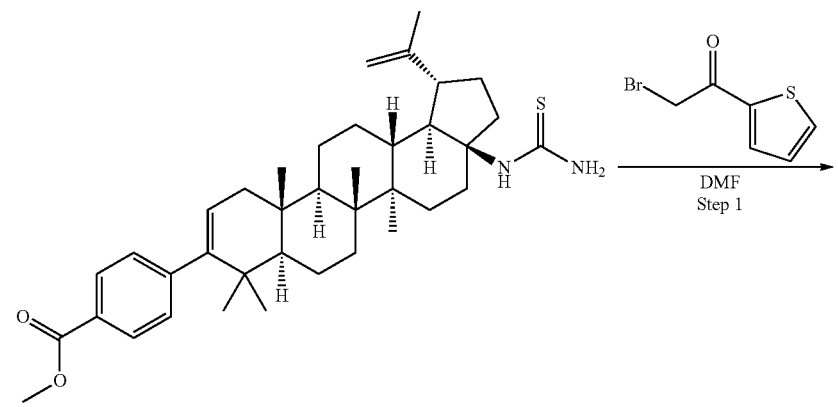

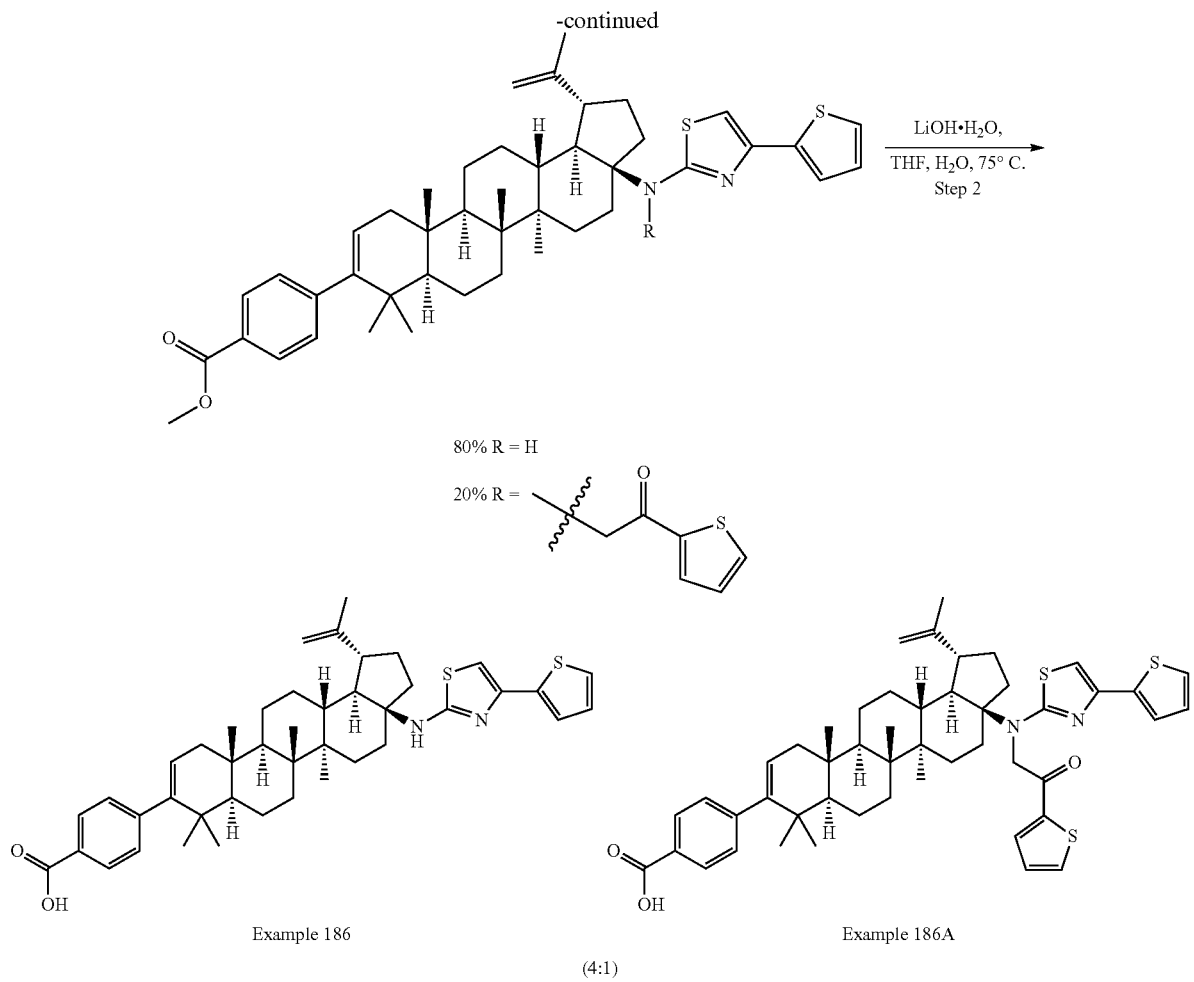

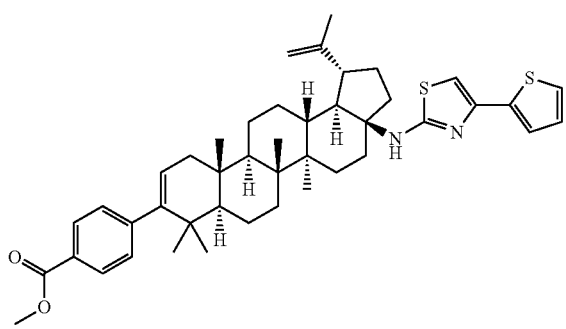

Example 186

(4:1)

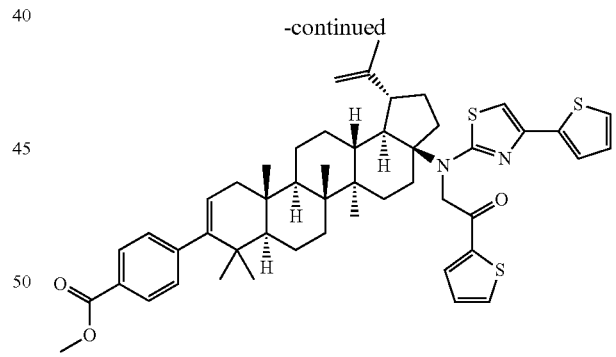

Step 1. Preparation of methyl 4-((1R,3aS,5aR,5bR,7aR,11aS,11bR,13aR,13bR)-5a,5b,8,8,11a-pentamethyl-1-(prop-1-en-2-yl)-3a-(4-(thiophen-3-yl)thiazol-2-ylamino)-2,3,3a,4,5,5a,5b,6,7,7a,8,11,11a,11b,12,13,13a,13b-octadecahydro-1H-cyclopenta[a]chrysen-9-yl)benzoate and methyl 4-((1R,3aS,5aR,5bR,7aR,11aS,11bR,13aR,13bR)-5a,5b,8,8,11a-pentamethyl-3a-((2-oxo-2-(thiophen-3-yl)ethyl)(4-(thiophen-3-yl)thiazol-2-yl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To a solution of methyl 4-((1R,3aS,5aR,5bR,7aR,11aS,11bR,13aR,13bR)-5a,5b,8,8,11a-pentamethyl-1-(prop-1-en-2-yl)-3a-thioureido-2,3,3a,4,5,5a,5b,6,7,7a,8,11,11a,11b,12,13,13a,13b-octadecahydro-1H-cyclopenta[a]chrysen-9-yl)benzoate (150 mg, 0.249 mmol) in DMF (3 mL) was added N,N-diisopropylethylamine (0.217 mL, 1.244 mmol) and 2-bromo-1-(thiophen-3-yl)ethanone (77 mg, 0.373 mmol). The reaction mixture was stirred at rt overnight. After 18 h, the reaction mixture was poured into a separatory funnel containing H$_2$O (5 mL) and extracted with EtOAc (50 mL). The organic layer was washed with brine, dried over MgSO$_4$, filtered and concentrated to white solid. The material was redissolved in DCM (3 mL). MeOH was added and the mixture was concentrated to remove most of DCM. The resulting white precipitate was filtered, washed with cold MeOH, and dried in a vacuum oven to give a 4:1 mixture of (as determined by HPLC integration) methyl 4-((1R,3aS,5aR,5bR,7aR,11aS,11bR,13aR,13bR)-5a,5b,8,8,11a-pentamethyl-1-(prop-1-en-2-yl)-3a-(4-(thiophen-3-yl)thiazol-2-ylamino)-2,3,3a,4,5,5a,5b,6,7,7a,8,11,11a,11b,12,13,13a,13b-octadecahydro-1H-cyclopenta[a]chrysen-9-yl)benzoate and methyl 4-((1R,3aS,5aR,5bR,7aR,11aS,11bR,13aR,13bR)-5a,5b,8,8,11a-pentamethyl-3a-((2-oxo-2-(thiophen-3-yl)ethyl)(4-(thiophen-3-yl)thiazol-2-yl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (134 mg, 82% yield) as white solid. LC/MS: m/e 709.3 (M+H)$^+$, 3.62 min and m/e 833.3 (M+H)$^+$, 2.63 min (method 9), respectively. Reverse phased analytical HPLC showed ratio of major product with rt=16.04 min (m/e 709.3 (M+H)$^+$) to minor product with rt=15.42 min (m/e 833.3 (M+H)$^+$) product of 80%:20% (using analytical HPLC method 2).

Step 2. Preparation of 4-((1R,3aS,5aR,5bR,7aR,11aS,11bR,13aR,13bR)-5a,5b,8,8,11a-pentamethyl-1-(prop-1-en-2-yl)-3a-(4-(thiophen-3-yl)thiazol-2-ylamino)-2,3,3a,4,5,5a,5b,6,7,7a,8,11,11a,11b,12,13,13a,13b-octadecahydro-1H-cyclopenta[a]chrysen-9-yl)benzoic acid, TFA and 4-((1R,3aS,5aR,5bR,7aR,11aS,11bR,13aR,13bR)-5a,5b,8,8,11a-pentamethyl-3a-((2-oxo-2-(thiophen-3-yl)ethyl)(4-(thiophen-3-yl)thiazol-2-yl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, TFA To a mixture of methyl 4-((1R,3aS,5aR,5bR,7aR,11aS,11bR,13aR,13bR)-5a,5b,8,8,11a-pentamethyl-1-(prop-1-en-2-yl)-3a-(4-(thiophen-3-yl)thiazol-2-ylamino)-2,3,3a,4,5,5a,5b,6,7,7a,8,11,11a,11b,12,13,13a,13b-octadecahydro-1H-cyclopenta[a]chrysen-9-yl)benzoate (119.36 mg, 0.168 mmol) and methyl 4-((1R,3aS,5aR,5bR,7aR,11aS,11bR,13aR,13bR)-5a,5b,8,8,11a-pentamethyl-3a-((2-oxo-2-(thiophen-3-yl)ethyl)(4-(thiophen-3-yl)thiazol-2-yl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (29.84 mg, 0.036 mmol) in THF (3 mL) was added a solution of lithium hydroxide monohydrate (25.4 mg, 0.606 mmol) in water (1 mL). The reaction was heated to 75° C. for 6 h. The reaction mixture was concentrated, redissolved in MeOH (2 mL) and THF (1 mL) filtered and was then injected (2 injections) onto reverse phase HPLC for purification using Prep HPLC method 3 to give 4-((1R,3aS,5aR,5bR,7aR,11aS,11bR,13aR,13bR)-5a,5b,8,8,11a-pentamethyl-1-(prop-1-en-2-yl)-3a-(4-(thiophen-3-yl)thiazol-2-ylamino)-2,3,3a,4,5,5a,5b,6,7,7a,8,11,11a,11b,12,13,13a,13b-octadecahydro-1H-cyclopenta[a]chrysen-9-yl)benzoic acid, TFA (110.7 mg, 0.134 mmol, 80% yield) and 4-((1R,3aS,5aR,5bR,7aR,11aS,11bR,13aR,13bR)-5a,5b,8,8,11a-pentamethyl-3a-((2-oxo-2-(thiophen-3-yl)ethyl)(4-(thiophen-3-yl)thiazol-2-yl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, TFA (13.4 mg, 0.016 mmol, 9.52% yield).

Example 186

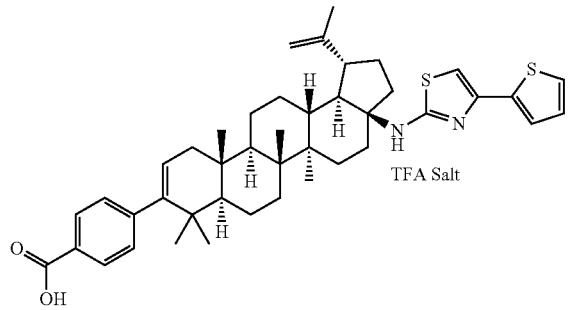

TFA Salt

LC/MS: m/e 695.3 (M+H)$^+$, 2.92 min (method 11). $^1$H NMR (500 MHz, CHLOROFORM-d) δ 8.12 (br. s., 1H), 8.03 (d, J=8.2 Hz, 2H), 7.42-7.39 (m, 1H), 7.38-7.36 (m, 1H), 7.25 (d, J=8.2 Hz, 2H), 6.52 (s, 1H), 5.33 (d, J=4.6 Hz, 1H), 4.86 (s, 1H), 4.71 (s, 1H), 3.04 (dt, J=5.0, 11.1 Hz, 1H), 2.58 (d, J=14.0 Hz, 1H), 2.39 (dd, J=7.9, 12.8 Hz, 1H), 2.33-2.25 (m, 1H), 2.15 (dd, J=6.4, 17.1 Hz, 1H), 2.06-1.98 (m, 1H), 1.92-1.82 (m, 2H), 1.76 (s, 3H), 1.70 (d, J=17.1 Hz, 1H), 1.64-1.56 (m, 1H), 1.55-1.47 (m, 5H), 1.46-1.37 (m, 5H), 1.23 (d, J=10.1 Hz, 1H), 1.15 (d, J=13.1 Hz, 1H), 1.06 (s, 3H), 1.05 (s, 3H), 0.99 (s, 3H), 0.95 (s, 3H), 0.94 (s, 3H). $^{13}$C NMR (126 MHz, CHLOROFORM-d) δ 171.2, 167.1, 163.3, 149.3, 148.5, 145.9, 129.9, 128.8, 127.0, 126.9, 124.7, 124.4, 123.9, 117.4, 115.1, 110.4, 98.1, 68.0, 52.6, 50.0, 49.3, 45.0, 41.6, 41.5, 40.4, 37.2, 36.2, 36.0, 33.4, 32.6, 29.2, 29.2, 27.0, 26.9, 24.9, 20.8, 19.5, 19.2, 16.1, 15.3, 14.1.

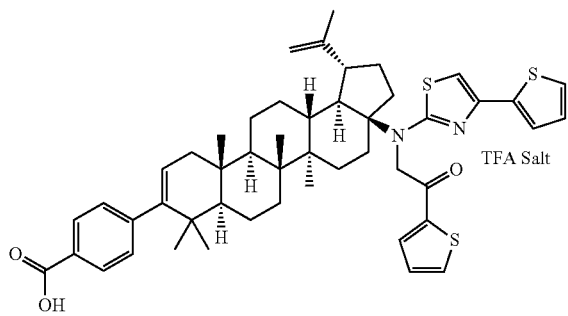

TFA Salt

Example 186A

LC/MS: m/e 818.4 (M+H)$^+$, 2.50 min (method 11).

Examples 187 and 187A

Preparation of 4-((1R,3aS,5aR,5bR,7aR,11aS,11bR,13aR,13bR)-5a,5b,8,8,11a-pentamethyl-1-(prop-1-en-2-yl)-3a-(4-(pyridin-2-yl)thiazol-2-ylamino)-2,3,3a,4,5,5a,5b,6,7,7a,8,11,11a,11b,12,13,13a,13b-octadecahydro-1H-cyclopenta[a]chrysen-9-yl) benzoic acid and 4-((1R,3aS,5aR,5bR,7aR,11aS,11bR,13aR,13bR)-5a,5b,8,8,11a-pentamethyl-3a-((2-oxo-2-(pyridin-2-yl)ethyl)(4-(pyridin-2-yl)thiazol-2-yl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

91% R = H

9% R = (2-oxo-2-(pyridin-2-yl)ethyl group)

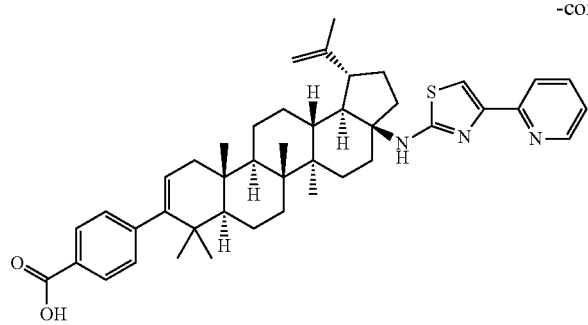
Example 187

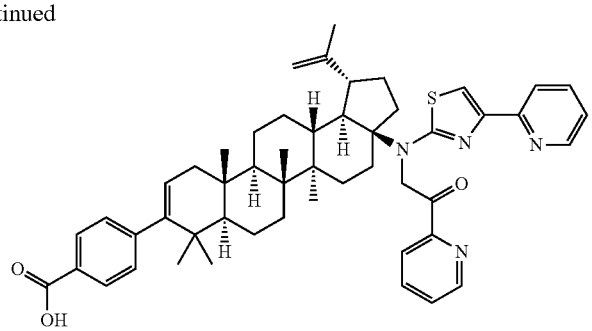
Example 187A (7:1)

Step 1. Preparation of methyl 4-((1R,3aS,5aR,5bR,7aR,11aS,11bR,13aR,13bR)-5a,5b,8,8,11a-pentamethyl-1-(prop-1-en-2-yl)-3a-(4-(pyridin-2-yl)thiazol-2-ylamino)-2,3,3a,4,5,5a,5b,6,7,7a,8,11,11a,11b,12,13,13a,13b-octadecahydro-1H-cyclopenta[a]chrysen-9-yl)benzoate and methyl 4-((1R,3aS,5aR,5bR,7aR,11aS,11bR,13aR,13bR)-5a,5b,8,8,11a-pentamethyl-3a-((2-oxo-2-(pyridin-2-yl)ethyl)(4-(pyridin-2-yl)thiazol-2-yl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

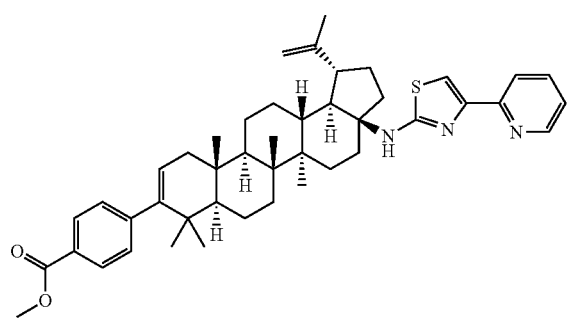
major

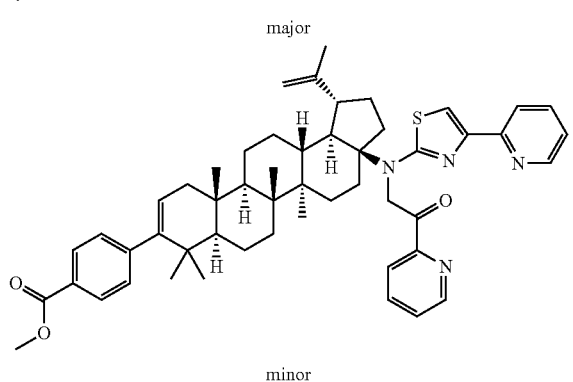
minor

To a solution of methyl 4-((1R,3aS,5aR,5bR,7aR,11aS,11bR,13aR,13bR)-5a,5b,8,8,11a-pentamethyl-1-(prop-1-en-2-yl)-3a-thioureido-2,3,3a,4,5,5a,5b,6,7,7a,8,11,11a,11b,12,13,13a,13b-octadecahydro-1H-cyclopenta[a]chrysen-9-yl)benzoate (150 mg, 0.249 mmol) was added N,N-diisopropylethylamine (0.217 mL, 1.244 mmol) and 2-bromo-1-(pyridin-2-yl)ethanone, hydrobromide (116 mg, 0.373 mmol). The reaction mixture was stirred at rt overnight. After 18 h, the reaction mixture was poured into a separatory funnel containing H₂O (5 mL) and extracted with EtOAc (50 mL). The organic layer was washed with brine, dried over MgSO₄, filtered and concentrated to brown solid. The material was redissolved in DCM (3 mL), MeOH was added and the resulting mixture was concentrated to remove most of DCM. The resulting white precipitate was filtered, washed with cold MeOH, and dried in a vacuum oven to give a 91:9 mixture (as determined by HPLC integration) of methyl 4-((1R,3aS,5aR,5bR,7aR,11aS,11bR,13aR,13bR)-5a,5b,8,8,11a-pentamethyl-1-(prop-1-en-2-yl)-3a-(4-(pyridin-2-yl)thiazol-2-ylamino)-2,3,3a,4,5,5a,5b,6,7,7a,8,11,11a,11b,12,13,13a,13b-octadecahydro-1H-cyclopenta[a]chrysen-9-yl)benzoate and methyl 4-((1R,3aS,5aR,5bR,7aR,11aS,11bR,13aR,13bR)-5a,5b,8,8,11a-pentamethyl-3a-((2-oxo-2-(pyridin-2-yl)ethyl)(4-(pyridin-2-yl)thiazol-2-yl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (137 mg, 76.57% yield) as brown solid. LC/MS: m/e 704.3 (M+H)⁺, 3.72 min and m/e 823.4 (M+H)⁺, 2.56 min (method 9), respectively. Reversed phased analytical HPLC showed ratio of major product with rt=22.43 min (m/e 704.3 (M+H)⁺) to minor product with rt=23.61 min (m/e 823.4 (M+H)⁺) product of 91%:9% (using analytical HPLC method 1).

Step 2. Preparation of 4-((1R,3aS,5aR,5bR,7aR,11aS,11bR,13aR,13bR)-5a,5b,8,8,11a-pentamethyl-1-(prop-1-en-2-yl)-3a-(4-(pyridin-2-yl)thiazol-2-ylamino)-2,3,3a,4,5,5a,5b,6,7,7a,8,11,11a,11b,12,13,13a,13b-octadecahydro-1H-cyclopenta[a]chrysen-9-yl)benzoic acid, TFA and 4-((1R,3aS,5aR,5bR,7aR,11aS,11bR,13aR,13bR)-5a,5b,8,8,11a-pentamethyl-3a-((2-oxo-2-(pyridin-2-yl)ethyl)(4-(pyridin-2-yl)thiazol-2-yl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, TFA

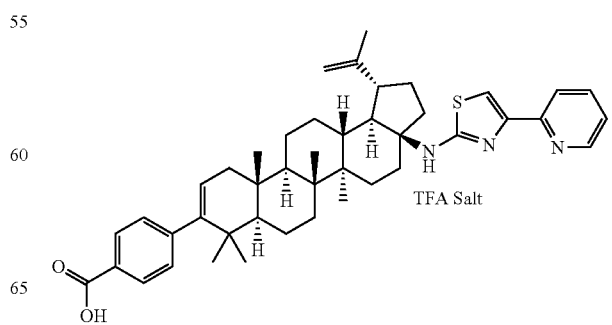
TFA Salt 52.6, 49.9, 49.3, 45.2, 41.6, 41.5, 40.4, 37.2, 36.5, 36.0, 33.3, 32.7, 29.2, 29.2, 26.9, 24.9, 20.8, 19.4, 19.2, 16.1, 15.4, 14.2.

Example 187A

LC/MS: m/e 809.5 (M+H)⁺, 2.38 min (method 11).

Example 188

Preparation of 4-((1R,3aS,5aR,5bR,7aR,11aS,11bR, 13aR,13bR)-5a,5b,8,8,11a-pentamethyl-1-(prop-1-en-2-yl)-3a-(2-(pyridin-2-ylamino)ethylamino)-2,3, 3a,4,5,5a,5b,6,7,7a,8,11,11a,11b,12,13,13a,13b-octadecahydro-1H-cyclopenta[a]chrysen-9-yl) benzoic acid

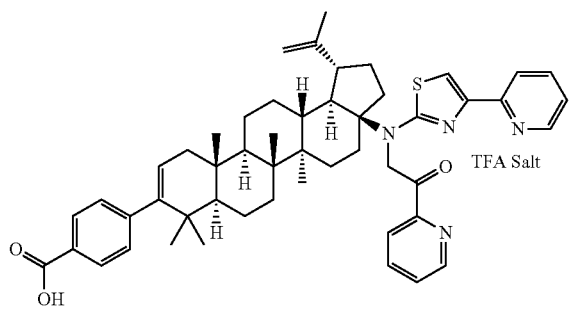

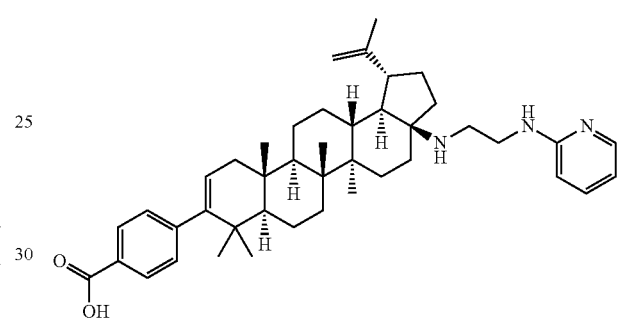

Mixture of methyl 4-((1R,3aS,5aR,5bR,7aR,11aS,11bR, 13aR,13bR)-5a,5b,8,8,11a-pentamethyl-1-(prop-1-en-2-yl)-3a-(4-(pyridin-2-yl)thiazol-2-ylamino)-2,3,3a,4,5,5a,5b,6,7, 7a,8,11,11a,11b,12,13,13a,13b-octadecahydro-1H-cyclopenta[a]chrysen-9-yl)benzoate (117.66 mg, 0.167 mmol) and methyl 4-((1R,3aS,5aR,5bR,7aR,11aS,11bR, 13aR,13bR)-5a,5b,8,8,11a-pentamethyl-3a-((2-oxo-2-(pyridin-2-yl)ethyl)(4-(pyridin-2-yl)thiazol-2-yl)amino)-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (19.6 mg, 0.024 mmol) in THF (3 mL) was added a solution of lithium hydroxide monohydrate (25.2 mg, 0.602 mmol) in water (1 mL). The reaction was heated to 75° C. for 6 h. The reaction mixture was concentrated, redissolved in MeOH (2 mL) and THF (1 mL) filtered and was injected onto reverse phase HPLC for purification using Prep HPLC method 3 to give 4-((1R,3aS,5aR,5bR,7aR,11aS,11bR,13aR, 13bR)-5a,5b,8,8,11a-pentamethyl-1-(prop-1-en-2-yl)-3a-(4-(pyridin-2-yl)thiazol-2-ylamino)-2,3,3a,4,5,5a,5b,6,7,7a,8, 11,11a,11b,12,13,13a,13b-octadecahydro-1H-cyclopenta[a] chrysen-9-yl)benzoic acid, TFA (70.2 mg, 0.085 mmol, 50.7% yield) and 4-((1R,3aS,5aR,5bR,7aR,11aS,11bR, 13aR,13bR)-5a,5b,8,8,11a-pentamethyl-3a-((2-oxo-2-(pyridin-2-yl)ethyl)(4-(pyridin-2-yl)thiazol-2-yl)amino)-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid, TFA (10.3 mg, 0.011 mmol, 6.86% yield).

Example 187

LC/MS: m/e 690.3 (M+H)⁺, 2.53 min (method 11). ¹H NMR (500 MHz, CHLOROFORM-d) δ 9.67 (br. s., 1H), 8.73 (td, J=0.9, 5.0 Hz, 1H), 8.14 (d, J=7.9 Hz, 1H), 8.02 (d, J=8.2 Hz, 2H), 7.96 (dt, J=1.7, 7.9 Hz, 1H), 7.42 (s, 1H), 7.40 (ddd, J=0.9, 4.9, 7.6 Hz, 1H), 7.25 (d, J=8.5 Hz, 2H), 5.33 (d, J=4.6 Hz, 1H), 4.86 (s, 1H), 4.71 (s, 1H), 2.99 (dt, J=4.9, 11.0 Hz, 1H), 2.64-2.58 (m, 1H), 2.41 (dd, J=8.1, 12.7 Hz, 1H), 2.23 (dt, J=3.1, 12.1 Hz, 1H), 2.16 (dd, J=6.3, 17.2 Hz, 1H), 2.06-2.00 (m, 1H), 1.90 (t, J=11.7 Hz, 1H), 1.85 (d, J=12.5 Hz, 1H), 1.76 (s, 3H), 1.70 (d, J=17.1 Hz, 1H), 1.64-1.55 (m, 1H), 1.55-1.39 (m, 9H), 1.30-1.21 (m, 1H), 1.17 (d, J=13.1 Hz, 1H), 1.08 (s, 3H), 1.06 (s, 3H), 1.01 (s, 3H), 0.95 (s, 3H), 0.95 (s, 3H). ¹³C NMR (126 MHz, CHLOROFORM-d) δ 170.8, 167.4, 149.3, 148.4, 146.3, 145.9, 141.1, 138.6, 129.9, 128.8, 126.8, 123.9, 123.9, 121.2, 110.4, 104.8, 77.3, 68.1, In a 1 dram vial under nitrogen were combined (2R)-1-[(1R)-1-[bis(1,1-dimethylethyl)phosphino]ethyl]-2-(dicyclohexylphosphino)ferrocene (CAS#158923-11-6) (2.101 mg, 3.79 µmol), palladium(II) acetate (0.851 mg, 3.79 µmol) and dry DME (0.5 ml). The contents of the vial were stirred for 10 min, and were then added all at once to a separate mixture of 2-bromopyridine (0.012 g, 0.076 mmol) and sodium tert-butoxide (0.032 g, 0.333 mmol) in dry DME (0.5 mL) contained in a separate 1 dram vial. The resulting mixture was allowed to stir very briefly (1 min) before TBDMSCl (0.025 g, 0.167 mmol) was added. The vial was shaken briefly, and solid methyl 4-((1R,3aS,5aR,5bR,7aR,11aS, 11bR,13aR,13bR)-3a-(2-aminoethylamino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoate bis HCl salt (0.050 g, 0.076 mmol) was added in one portion. A mild exotherm resulted upon the final addition. The mixture was heated to 110° C. for 15 min. LCMS indicated essentially complete consumption of starting material. To the mixture was added water (0.5 mL) and methanol (1.5 mL) and the resulting mixture was stirred for 2 days. Purification of the crude mixture by reverse phase preparative HPLC using Prep HPLC Method 6 gave the title compound (0.0092 g, 13.1% yield) as a beige powder bis TFA salt. LCMS: m/e 650.4 (M+H)⁺, 3.76 min (method 16). ¹H NMR (500 MHz, 1:1 mixture of CDCl3 and MeOD, MeOD lock) δ ppm 8.01 (d, J=4.9 Hz, 1H), 7.95-7.88 (m, J=8.2 Hz, 2H), 7.72 (t, J=7.3 Hz, 1H), 7.23-7.16 (m, J=8.2 Hz, 2H), 6.92 (d, J=8.2 Hz, 1H), 6.85 (t, J=6.3 Hz, 1H), 5.29 (d, J=4.9 Hz, 1H), 4.86 (s, 1H), 4.74 (br. s., 1H), 3.90-3.72 (m, 2H), 3.23-3.14 (m, 1H), 2.78-2.67 (m, 1H), 2.17-2.04 (m, 2H), 2.03-1.82 (m, 5H), 1.73 (s, 3H), 1.71-1.66 (m, 1H), 1.65-1.46 (m, 6H), 1.45-1.22 (m, 9H), 1.21-1.09 (m, 1H), 1.06 (s, 3H), 0.99

(br. s., 3H), 0.98 (br. s., 3H), 0.94 (s, 3H), 0.93 (br. s., 3H), 0.91-0.84 (m, J=6.7, 3.4 Hz, 1H).

Example 189

Preparation of 4-((1R,3aS,5aR,5bR,7aR,11aS,11bR, 13aR,13bR)-5a,5b,8,8,11a-pentamethyl-1-(prop-1-en-2-yl)-3a-(2-(pyridin-3-ylamino)ethylamino)-2,3, 3a,4,5,5a,5b,6,7,7a,8,11,11a,11b,12,13,13a,13b-octadecahydro-1H-cyclopenta[a]chrysen-9-yl) benzoic acid

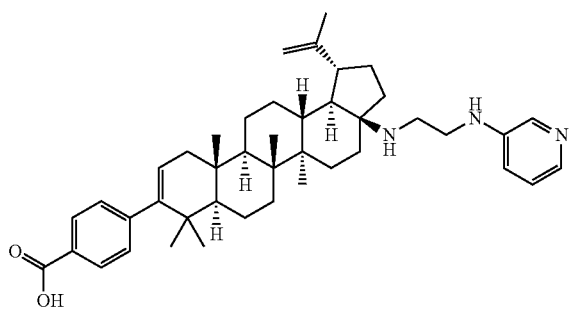

In a 1 dram vial under nitrogen were combined (2R)-1-[(1R)-1-[bis(1,1-dimethylethyl)phosphino]ethyl]-2-(dicyclohexylphosphino)ferrocene (CAS#158923-11-6) (2.101 mg, 3.79 mmol), palladium(II) acetate (0.851 mg, 3.79 mmol) and dry DME (0.5 ml). The contents of the vial were stirred for 10 min, and were then added all at once to a separate mixture of 3-bromopyridine (0.014 g, 0.091 mmol) and sodium tert-butoxide, 2.0M solution in THF (0.167 mL, 0.333 mmol) in dry DME (0.333 mL) contained in a separate 1 dram vial. The resulting mixture was allowed to stir very briefly (1 min) before solid methyl 4-((1R,3aS,5aR,5bR,7aR, 11aS,11bR,13aR,13bR)-3a-(2-aminoethylamino)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate bis HCl salt (0.050 g, 0.076 mmol) was added in one portion. The mixture was heated to 110° C. overnight. To the mixture was added lithium hydroxide monohydrate (6.4 mg, 0.152 mmol) with water (0.2 mL) and methanol (0.5 mL) and the resulting mixture was stirred for 4 days. Purification of the crude mixture by reverse phase preparative HPLC using Prep HPLC Method 7 gave the title compound (0.0407 g, 57.5% yield) as a beige powder bis TFA salt. LCMS: m/e 650.4 (M+H)$^+$, 2.26 min (method 11). $^1$H NMR (500 MHz, 1:1 mixture of CDCl3 and MeOD, MeOD lock) δ ppm 8.26 (d, J=2.4 Hz, 1H), 8.02 (d, J=4.9 Hz, 1H), 7.94-7.87 (m, J=8.2 Hz, 2H), 7.77 (dd, J=8.9, 1.5 Hz, 1H), 7.67 (dd, J=8.9, 5.2 Hz, 1H), 7.22-7.14 (m, 2H), 5.28 (dd, J=6.3, 1.7 Hz, 1H), 4.82 (s, 1H), 4.74 (s, 1H), 3.89-3.78 (m, 1H), 3.70 (dt, J=14.6, 4.5 Hz, 1H), 3.30-3.23 (m, 2H), 2.85 (td, J=11.1, 5.5 Hz, 1H), 2.21-2.05 (m, 3H), 2.03-1.94 (m, 2H), 1.94-1.85 (m, 1H), 1.85-1.76 (m, 1H), 1.72 (s, 3H), 1.70-1.64 (m, 1H), 1.64-1.51 (m, 3H), 1.51-1.44 (m, 3H), 1.43-1.20 (m, 6H), 1.19-1.08 (m, 2H), 1.07-1.04 (m, 3H), 1.04-1.00 (m, 3H), 0.99 (s, 3H), 0.95-0.88 (m, 7H).

Example 190

Preparation of 4-((1R,3aS,5aR,5bR,7aR,11aS,11bR, 13aR,13bR)-5a,5b,8,8,11a-pentamethyl-1-(prop-1-en-2-yl)-3a-(2-(pyridin-4-ylamino)ethylamino)-2,3, 3a,4,5,5a,5b,6,7,7a,8,11,11a,11b,12,13,13a,13b-octadecahydro-1H-cyclopenta[a]chrysen-9-yl) benzoic acid

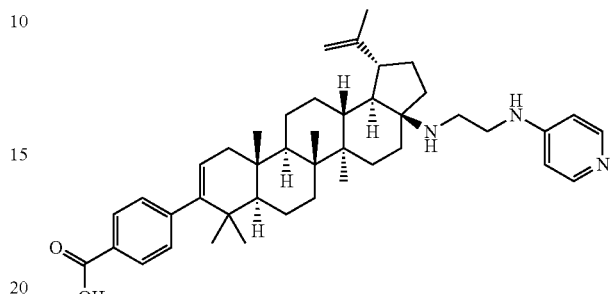

The title compound was prepared following a similar procedure as described for the synthesis of 4-((1R,3aS,5aR,5bR, 7aR,11aS,11bR,13aR,13bR)-5a,5b,8,8,11a-pentamethyl-1-(prop-1-en-2-yl)-3a-(2-(pyridin-3-ylamino)ethylamino)-2,3, 3a,4,5,5a,5b,6,7,7a,8,11,11a,11b,12,13,13a,13b-octadecahydro-1H-cyclopenta[a]chrysen-9-yl)benzoic acid, except 4-bromopyridine hydrochloride (0.018 g, 0.091 mmol) was used in place of 3-bromopyridine, and an additional 1.2 equivalents of sodium tert-butoxide, 2.0M solution in THF (for a total of 5.6 equivalents, 0.212 mL, 0.424 mmol) was employed. The product was isolated after reverse phase preparative HPLC purification using Prep HPLC Method 7 as a beige solid (74 mg, 54% yield) bis TFA salt. LCMS: m/e 650.4 (M+H)$^+$, 3.85 min (method 16). $^1$H NMR (500 MHz, 1:1 mixture of CDCl3 and MeOD, MeOD lock) δ ppm 8.19-7.97 (m, 2H), 7.91 (d, J=8.2 Hz, 2H), 7.19 (d, J=8.2 Hz, 2H), 7.06 (br. s., 2H), 5.28 (d, J=4.6 Hz, 1H), 4.83 (s, 1H), 4.73 (s, 1H), 3.96-3.81 (m, 2H), 3.31-3.19 (m, 2H), 2.88-2.76 (m, 1H), 2.18-2.03 (m, 3H), 1.97 (dd, J=10.4, 6.4 Hz, 3H), 1.83 (d, J=12.5 Hz, 1H), 1.72 (s, 3H), 1.68 (br. s., 1H), 1.66-1.45 (m, 7H), 1.44-1.28 (m, 5H), 1.24 (d, J=8.2 Hz, 1H), 1.18-1.11 (m, 1H), 1.09 (s, 3H), 1.06 (s, 3H), 1.01 (s, 3H), 0.93 (s, 3H), 0.92 (s, 3H).

Example 191

Preparation of 4-((1R,3aS,5aR,5bR,7aR,11aS,11bR, 13aR,13bR)-5a,5b,8,8,11a-pentamethyl-3a-(2-(1-methyl-1H-imidazol-2-ylamino)ethylamino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid

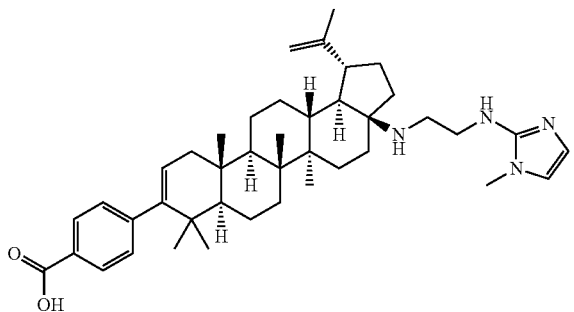

The title compound was prepared following a similar procedure as described for the synthesis of 4-((1R,3aS,5aR,5bR,7aR,11aS,11bR,13aR,13bR)-5a,5b,8,8,11a-pentamethyl-1-(prop-1-en-2-yl)-3a-(2-(pyridin-3-ylamino)ethylamino)-2,3,3a,4,5,5a,5b,6,7,7a,8,11,11a,11b,12,13,13a,13b-octadecahydro-1H-cyclopenta[a]chrysen-9-yl)benzoic acid, except 2-bromo-1-methyl-1H-imidazole (0.015 g, 8.88 μL, 0.091 mmol) was used in place of 3-bromopyridine. Also, addition of LiOH, water and methanol were unnecessary for this example, as the ester hydrolysis occurred spontaneously during the course of the amination reaction. The product was isolated after reverse phase preparative HPLC purification using Prep HPLC Method 8 as a beige solid (38.1 mg, 51.5% yield) bis TFA salt. LCMS: m/e 653.4 (M+H)$^+$, 3.88 min (method 16). $^1$H NMR (500 MHz, 1:1 mixture of CDCl3 and MeOD, MeOD lock) δ ppm 7.91 (d, J=8.2 Hz, 2H), 7.19 (d, J=7.9 Hz, 2H), 6.86 (s, 1H), 6.83-6.79 (m, 1H), 5.28 (d, J=5.5 Hz, 1H), 4.84 (s, 1H), 4.73 (s, 1H), 4.71 (br. s., 1H), 3.98-3.82 (m, 2H), 3.58 (s, 3H), 3.25 (br. s., 1H), 2.89-2.78 (m, 1H), 2.18-2.07 (m, 3H), 2.05-1.92 (m, 3H), 1.90-1.79 (m, 1H), 1.72 (s, 4H), 1.69 (br. s., 1H), 1.62-1.54 (m, 3H), 1.53-1.47 (m, 3H), 1.46-1.34 (m, 5H), 1.28-1.20 (m, 2H), 1.18-1.12 (m, 1H), 1.11 (s, 3H), 1.09-1.03 (m, 4H), 1.01 (s, 3H), 0.93 (br. s., 3H), 0.93 (br. s., 3H).

Example 192

Preparation of 4-((1R,3aS,5aR,5bR,7aR,11aS,11bR,13aR,13bR)-5a,5b,8,8,11a-pentamethyl-3a-(2-(phenylamino)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

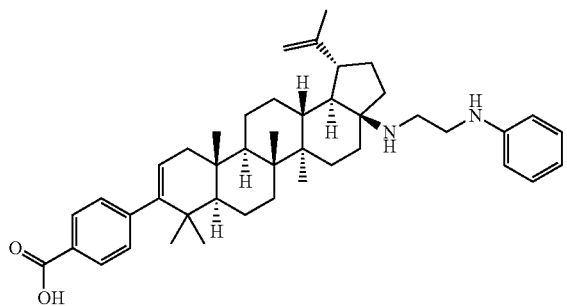

The title compound was prepared following a similar procedure as described for the synthesis of 4-((1R,3aS,5aR,5bR,7aR,11aS,11bR,13aR,13bR)-5a,5b,8,8,11a-pentamethyl-1-(prop-1-en-2-yl)-3a-(2-(pyridin-3-ylamino)ethylamino)-2,3,3a,4,5,5a,5b,6,7,7a,8,11,11a,11b,12,13,13a,13b-octadecahydro-1H-cyclopenta[a]chrysen-9-yl)benzoic acid, except bromobenzene (0.014 g, 9.58 μL, 0.091 mmol) was used in place of 3-bromopyridine. The product was isolated after reverse phase preparative HPLC purification using Prep HPLC Method 7 as a beige solid (29.7 mg, 42% yield) bis TFA salt. LCMS: m/e 649.4 (M+H)$^+$, 2.42 min (method 11). $^1$H NMR (500 MHz, 1:1 mixture of CDCl3 and MeOD, MeOD lock) δ ppm 7.94-7.88 (m, J=7.9 Hz, 2H), 7.22 (t, J=7.8 Hz, 2H), 7.20-7.15 (m, J=8.2 Hz, 2H), 6.82 (t, J=7.3 Hz, 1H), 6.75 (d, J=7.9 Hz, 2H), 5.27 (d, J=5.5 Hz, 1H), 4.81 (s, 1H), 4.73 (s, 1H), 3.68-3.58 (m, 1H), 3.58-3.51 (m, 1H), 3.25-3.17 (m, 2H), 2.82 (td, J=11.0, 5.2 Hz, 1H), 2.18-2.05 (m, 2H), 2.01-1.92 (m, 2H), 1.90 (br. s., 1H), 1.83-1.72 (m, 2H), 1.71 (s, 3H), 1.68 (d, J=17.4 Hz, 1H), 1.64-1.46 (m, 6H), 1.45-1.30 (m, 5H), 1.27-1.11 (m, 4H), 1.10-1.02 (m, 2H), 1.02-0.99 (m, 6H), 0.98 (s, 3H), 0.93 (s, 3H), 0.91 (s, 3H).

Example 193

Preparation of 4-((1R,3aS,5aR,5bR,7aR,11aS,11bR,13aR,13bR)-5a,5b,8,8,11a-pentamethyl-1-(prop-1-en-2-yl)-3a-(2-(thiazol-2-ylamino)ethylamino)-2,3,3a,4,5,5a,5b,6,7,7a,8,11,11a,11b,12,13,13a,13b-octadecahydro-1H-cyclopenta[a]chrysen-9-yl)benzoic acid

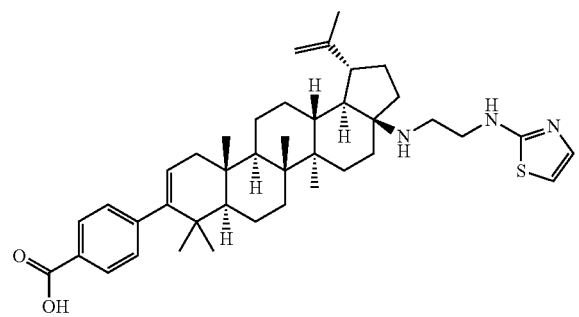

The title compound was prepared following a similar procedure as described for the synthesis of 4-((1R,3aS,5aR,5bR,7aR,11aS,11bR,13aR,13bR)-5a,5b,8,8,11a-pentamethyl-1-(prop-1-en-2-yl)-3a-(2-(pyridin-3-ylamino)ethylamino)-2,3,3a,4,5,5a,5b,6,7,7a,8,11,11a,11b,12,13,13a,13b-octadecahydro-1H-cyclopenta[a]chrysen-9-yl)benzoic acid, except 2-bromothiazole (0.015 g, 0.091 mmol) was used in place of 3-bromopyridine. The product was isolated after reverse phase preparative HPLC purification using Prep HPLC Method 7 as a beige solid (12.8 mg, 18% yield) bis TFA salt. LCMS: m/e 656.4 (M+H)$^+$, 2.38 min (method 11). $^1$H NMR (500 MHz, 1:1 mixture of CDCl3 and MeOD, MeOD lock) δ ppm 7.91 (d, J=8.2 Hz, 2H), 7.19 (d, J=8.2 Hz, 2H), 7.08 (d, J=3.7 Hz, 1H), 6.68 (d, J=4.0 Hz, 1H), 5.28 (d, J=4.6 Hz, 1H), 4.86 (s, 1H), 4.74 (br. s., 1H), 3.69 (dd, J=9.9, 5.3 Hz, 1H), 3.43-3.36 (m, 1H), 2.13 (dd, J=17.2, 6.3 Hz, 1H), 2.05 (d, J=15.0 Hz, 1H), 2.01-1.79 (m, 6H), 1.73 (s, 4H), 1.70-1.46 (m, 8H), 1.46-1.27 (m, 6H), 1.27-1.22 (m, 2H), 1.22-1.10 (m, 2H), 1.07 (s, 3H), 1.04 (s, 3H), 1.00 (s, 3H), 0.93 (s, 3H), 0.92 (s, 3H).

Example 194

Preparation of 4-((1R,3aS,5aR,5bR,7aR,11aS,11bR,13aR,13bR)-5a,5b,8,8,11a-pentamethyl-3a-(2-(6-methylpyridazin-3-ylamino)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

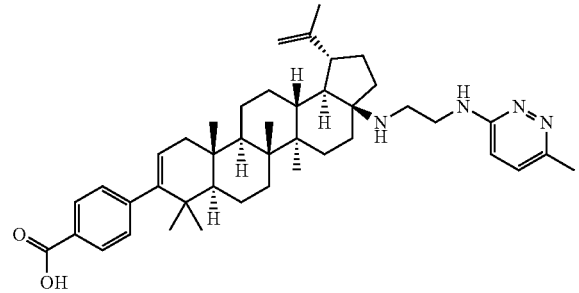

In a 1 dram vial under nitrogen were combined (2R)-1-[(1R)-1-[bis(1,1-dimethylethyl)phosphino]ethyl]-2-(dicyclohexylphosphino)ferrocene (CAS#158923-11-6) (2.52 mg, 4.55 mmol), palladium(II) acetate (1.02 mg, 4.55 mmol)

and dry DME (0.5 ml). The contents of the vial were stirred for 10 min, and were then added all at once to a separate mixture of 3-bromo-6-methylpyridazine (0.017 g, 0.100 mmol) and sodium tert-butoxide, 2.0M solution in THF (0.200 mL, 0.400 mmol) in dry DME (0.500 mL) contained in a separate 1 dram vial. The resulting mixture was allowed to stir very briefly (1 min) before solid methyl 4-((1R,3aS,5aR,5bR,7aR,11aS,11bR,13aR,13bR)-3a-(2-aminoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate bis HCl salt (0.060 g, 0.091 mmol) was added in one portion. The mixture was heated to 110° C. overnight. Iterative purification of the crude mixture by reverse phase preparative HPLC first using Prep HPLC Method 9 and then repurification by Prep HPLC Method 10 gave the title compound (0.0070 g, 8.3% yield) as a white glassy solid bis TFA salt. LCMS: m/e 665.5 (M+H)$^+$, 2.22 min (method 11). $^1$H NMR (500 MHz, 1:1 mixture of CDCl$_3$ and MeOD, MeOD lock) δ ppm 7.90 (d, J=8.5 Hz, 2H), 7.49-7.42 (m, 1H), 7.32-7.23 (m, 1H), 7.18 (d, J=8.2 Hz, 2H), 5.27 (dd, J=6.0, 1.4 Hz, 1H), 4.88 (br. s., 1H), 4.72 (br. s., 1H), 3.94-3.84 (m, 1H), 3.84-3.73 (m, 1H), 3.26-3.13 (m, 1H), 2.84 (d, J=12.5 Hz, 1H), 2.57 (s, 3H), 2.12 (dd, J=16.9, 6.3 Hz, 1H), 2.05 (d, J=15.6 Hz, 1H), 2.01-1.91 (m, 2H), 1.91-1.74 (m, 2H), 1.70 (s, 3H), 1.69-1.59 (m, 2H), 1.59-1.43 (m, 4H), 1.43-1.28 (m, 4H), 1.28-1.18 (m, 4H), 1.18-1.06 (m, 2H), 1.05 (s, 3H), 0.99 (s, 3H), 0.97 (s, 3H), 0.92 (s, 3H), 0.92-0.89 (m, 3H).

The title compound was prepared following a similar procedure as described for the synthesis of 4-((1R,3aS,5aR,5bR,7aR,11aS,11bR,13aR,13bR)-5a,5b,8,8,11a-pentamethyl-3a-(2-(6-methylpyridazin-3-ylamino)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 4-bromopyrimidine (0.016 g, 0.100 mmol) was used in place of 3-bromo-6-methylpyridazine. The reaction did not produce the intended product but instead produced the byproduct title compound as the major isolate. Iterative purification of the crude mixture by reverse phase preparative HPLC first using Prep HPLC Method 9 and then repurification by Prep HPLC Method 10 gave the title compound as a white glassy solid (7.5 mg, 9.6% yield) mono TFA salt. LCMS: m/e 615.5 (M+H)$^+$, 2.42 min (method 11). $^1$H NMR (500 MHz, 1:1 mixture of CDCl3 and MeOD, MeOD lock) δ ppm 8.18 (s, 1H), 7.94-7.84 (m, J=8.2 Hz, 2H), 7.24-7.13 (m, J=8.2 Hz, 2H), 5.27 (d, J=4.6 Hz, 1H), 4.83 (s, 1H), 4.72 (br. s., 1H), 3.89 (s, 3H), 3.61 (br. s., 2H), 3.18 (br. s., 2H), 2.71 (td, J=11.1, 6.3 Hz, 2H), 2.12-1.92 (m, 6H), 1.90-1.76 (m, 3H), 1.76-1.66 (m, 5H), 1.66-1.43 (m, 9H), 1.42-1.33 (m, 3H), 1.24 (br. s., 2H), 1.17 (s, 3H), 1.07 (s, 3H), 1.01 (s, 3H), 0.93 (s, 3H), 0.92 (br. s., 3H).

Example 195

Preparation of 4-((1R,3aS,5aR,5bR,7aR,11aS,11bR,13aR,13bR)-3a-(2-acetamidoethylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

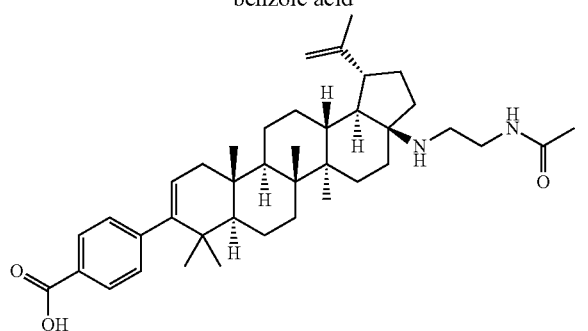

Example 196

Preparation of 4-((1R,3aS,5aR,5bR,7aR,11aS,11bR,13aR,13bR)-5a,5b,8,8,11a-pentamethyl-3a-(2-(5-(methylthio)pyridin-2-ylamino)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

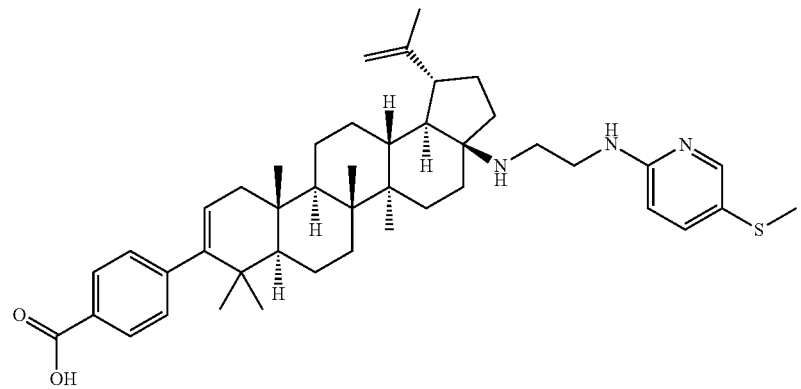

The title compound was prepared following a similar procedure as described for the synthesis of 4-((1R,3aS,5aR,5bR,7aR,11aS,11bR,13aR,13bR)-5a,5b,8,8,11a-pentamethyl-3a-(2-(6-methylpyridazin-3-ylamino)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-bromo-5-(methylthio)pyridine (0.020 g, 0.100 mmol) was used in place of 3-bromo-6-methylpyridazine. Iterative purification of the crude mixture by reverse phase preparative HPLC first using Prep HPLC Method 9 and then repurification by Prep HPLC Method 10 gave the title compound as a white glassy solid (5.2 mg, 5.9% yield) bis TFA salt. LCMS: m/e 696.5 (M+H)+, 2.34 min (method 11). ¹H NMR (500 MHz, 1:1 mixture of CDCl3 and MeOD, MeOD lock) δ ppm 8.03 (d, J=1.8 Hz, 1H), 7.93-7.88 (m, J=8.2 Hz, 2H), 7.61-7.57 (m, 1H), 7.21-7.14 (m, J=8.2 Hz, 2H), 6.71 (d, J=8.9 Hz, 1H), 5.27 (dd, J=6.1, 1.5 Hz, 1H), 4.87 (s, 1H), 4.75 (br. s., 1H), 4.72 (br. s., 1H), 3.80-3.72 (m, 1H), 3.72-3.63 (m, 1H), 3.18-3.09 (m, 1H), 2.72-2.64 (m, 1H), 2.39 (s, 3H), 2.11 (dd, J=17.1, 6.4 Hz, 1H), 2.08-2.01 (m, 1H), 2.00-1.90 (m, 3H), 1.90-1.74 (m, 3H), 1.72 (s, 3H), 1.71-1.66 (m, 2H), 1.65-1.44 (m, 7H), 1.44-1.33 (m, 3H), 1.33-1.12 (m, 7H), 1.04 (s, 3H), 0.97 (s, 3H), 0.91 (br. s., 3H), 0.91 (br. s., 3H), 0.87 (s, 3H).

Example 197

Preparation of 4-((1R,3aS,5aR,5bR,7aR,11aS,11bR,13aR,13bR)-5a,5b,8,8,11a-pentamethyl-3a-(2-(4-(methylthio)pyrimidin-2-ylamino)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

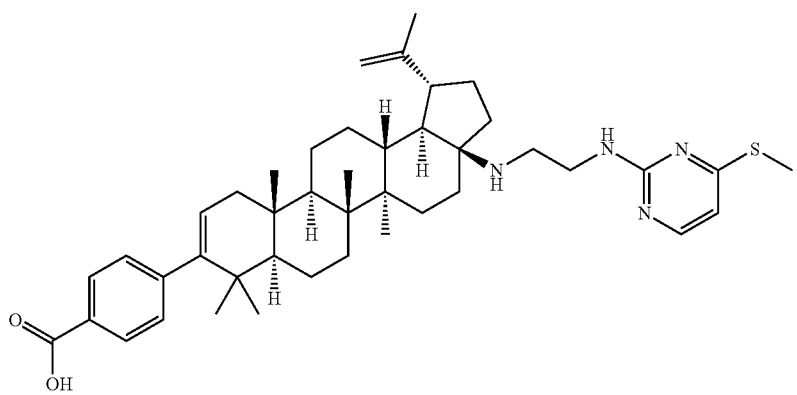

The title compound was prepared following a similar procedure as described for the synthesis of 4-((1R,3aS,5aR,5bR,7aR,11aS,11bR,13aR,13bR)-5a,5b,8,8,11a-pentamethyl-3a-(2-(6-methylpyridazin-3-ylamino)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-chloro-4-(methylthio)pyrimidine (0.016 g, 0.100 mmol) was used in place of 3-bromo-6-methylpyridazine. Iterative purification of the crude mixture by reverse phase preparative HPLC first using Prep HPLC Method 9 and then repurification by Prep HPLC Method 10 gave the title compound as a white glassy solid (12.0 mg, 14% yield) bis TFA salt. LCMS: m/e 697.5 (M+H)+, 2.30 min (method 11). ¹H NMR (500 MHz, 1:1 mixture of CDCl3 and MeOD, MeOD lock) δ ppm 7.99-7.85 (m, 3H), 7.17 (d, J=8.2 Hz, 2H), 6.75-6.63 (m, 1H), 5.26 (d, J=4.6 Hz, 1H), 4.82 (s, 1H), 4.70 (br. s., 1H), 3.96 (s, 1H), 3.85 (br. s., 2H), 3.43-3.34 (m, 1H), 3.25 (br. s., 1H), 2.72 (br. s., 1H), 2.55 (s, 3H), 2.10 (dd, J=17.1, 6.4 Hz, 1H), 2.04 (d, J=15.3 Hz, 1H), 2.01-1.89 (m, 3H), 1.89-1.77 (m, 2H), 1.70 (s, 4H), 1.68-1.49 (m, 5H), 1.46 (d, J=7.3 Hz, 3H), 1.42-1.18 (m, 7H), 1.18-1.06 (m, 2H), 1.03 (s, 3H), 0.97 (s, 3H), 0.95 (s, 3H), 0.92 (s, 3H), 0.91 (br. s., 3H).

Example 198

Preparation of 4-((1R,3aS,5aR,5bR,7aR,11aS,11bR,13aR,13bR)-5a,5b,8,8,11a-pentamethyl-3a-(2-(6-(methylthio)pyridin-2-ylamino)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

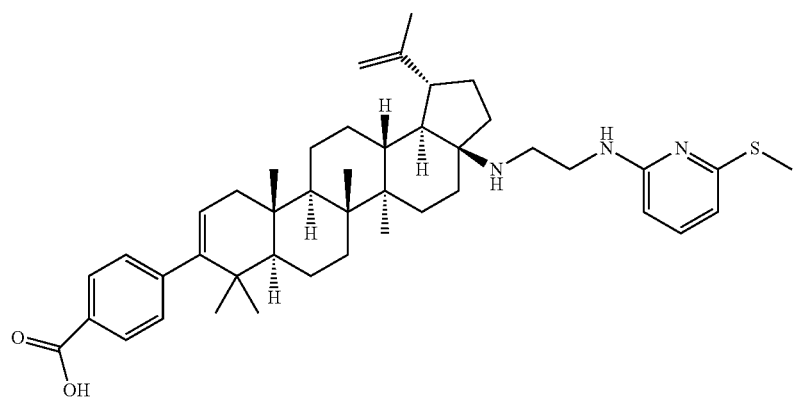

The title compound was prepared following a similar procedure as described for the synthesis of 4-((1R,3aS,5aR,5bR,7aR,11aS,11bR,13aR,13bR)-5a,5b,8,8,11a-pentamethyl-3a-(2-(6-methylpyridazin-3-ylamino)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-bromo-6-(methylthio)pyridine (0.020 g, 0.100 mmol) was used in place of 3-bromo-6-methylpyridazine. Iterative purification of the crude mixture by reverse phase preparative HPLC first using Prep HPLC Method 9 and then repurification by Prep HPLC Method 10 gave the title compound as a white glassy solid (10.3 mg, 12% yield) bis TFA salt. LCMS: m/e 696.5 (M+H)$^+$, 2.34 min (method 11). $^1$H NMR (500 MHz, 1:1 mixture of CDCl3 and MeOD, MeOD lock) δ ppm 7.95-7.85 (m, J=8.2 Hz, 2H), 7.39 (t, J=7.8 Hz, 1H), 7.20-7.12 (m, J=8.2 Hz, 2H), 6.53 (d, J=7.6 Hz, 1H), 6.37 (d, J=7.9 Hz, 1H), 5.25 (d, J=4.6 Hz, 1H), 4.85 (s, 1H), 4.72 (br. s., 1H), 3.96 (s, 1H), 3.78-3.59 (m, 2H), 3.28-3.13 (m, 2H), 2.95-2.83 (m, 1H), 2.49 (s, 3H), 2.08-1.86 (m, 6H), 1.78-1.69 (m, 4H), 1.69-1.52 (m, 5H), 1.52-1.31 (m, 6H), 1.31-1.07 (m, 7H), 1.01 (s, 3H), 0.95-0.83 (m, 9H), 0.57 (s, 3H).

Example 199

Preparation of 4-((1R,3aS,5aR,5bR,7aR,11aS,11bR,13aR,13bR)-5a,5b,8,8,11a-pentamethyl-1-(prop-1-en-2-yl)-3a-(2-(pyrimidin-2-ylamino)ethylamino)-2,3,3a,4,5,5a,5b,6,7,7a,8,11,11a,11b,12,13,13a,13b-octadecahydro-1H-cyclopenta[a]chrysen-9-yl)benzoic acid

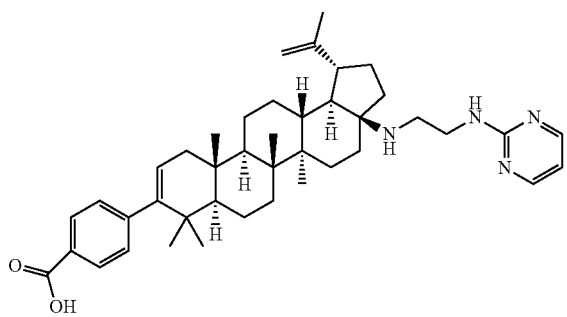

The title compound was prepared following a similar procedure as described for the synthesis of 4-((1R,3aS,5aR,5bR,7aR,11aS,11bR,13aR,13bR)-5a,5b,8,8,11a-pentamethyl-3a-(2-(6-methylpyridazin-3-ylamino)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 2-bromopyrimidine (0.016 g, 0.100 mmol) was used in place of 3-bromo-6-methylpyridazine. Iterative purification of the crude mixture by reverse phase preparative HPLC first using Prep HPLC Method 9 and then repurification by Prep HPLC Method 10 gave the title compound as a white glassy solid (8.0 mg, 8.2% yield) bis TFA salt. LCMS: m/e 651.5 (M+H)$^+$, 2.27 min (method 11).

Example 200

Preparation of 4-((1R,3aS,5aR,5bR,7aR,11aS,11bR,13aR,13bR)-5a,5b,8,8,11a-pentamethyl-1-(prop-1-en-2-yl)-3a-(2-(pyridazin-3-ylamino)ethylamino)-2,3,3a,4,5,5a,5b,6,7,7a,8,11,11a,11b,12,13,13a,13b-octadecahydro-1H-cyclopenta[a]chrysen-9-yl)benzoic acid

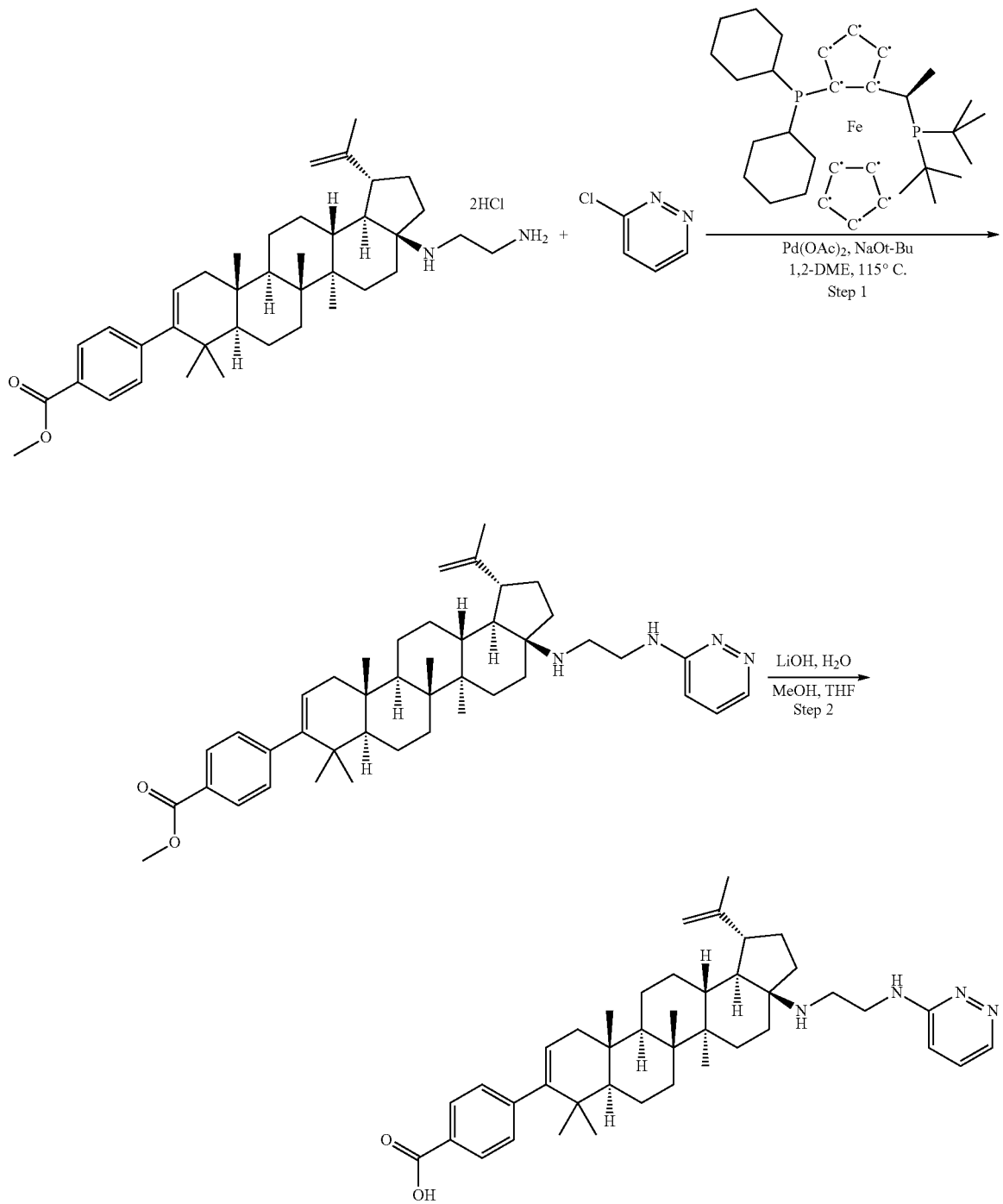

Step 1. Preparation of methyl 4-((1R,3aS,5aR,5bR, 7aR,11aS,11bR,13aR,13bR)-5a,5b,8,8,11a-pentamethyl-1-(prop-1-en-2-yl)-3a-(2-(pyridazin-3-ylamino)ethylamino)-2,3,3a,4,5,5a,5b,6,7,7a,8,11,11a,11b,12,13,13a,13b-octadecahydro-1H-cyclopenta[a]chrysen-9-yl)benzoate The title compound was prepared following a similar procedure as described for the synthesis of 4-((1R,3aS,5aR,5bR,7aR,11aS,11bR,13aR,13bR)-5a,5b,8,8,11a-pentamethyl-3a-(2-(6-methylpyridazin-3-ylamino)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, except 3-chloropyridazine (0.011 g, 0.100 mmol) was used in place of 3-bromo-6-methylpyridazine. Purification of the crude mixture by reverse phase preparative HPLC using Prep HPLC Method 9 gave the title compound as a white glassy solid (4.9 mg, 6.0% yield) bis TFA salt. LCMS: m/e 665.5 (M+H)$^+$, 2.40 min (method 11).

Step 2. Preparation of 4-((1R,3aS,5aR,5bR,7aR,11aS,11bR,13aR,13bR)-5a,5b,8,8,11a-pentamethyl-1-(prop-1-en-2-yl)-3a-(2-(pyridazin-3-ylamino)ethylamino)-2,3,3a,4,5,5a,5b,6,7,7a,8,11,11a,11b,12,13,13a,13b-octadecahydro-1H-cyclopenta[a]chrysen-9-yl)benzoic acid A solution of methyl 4-((1R,3aS,5aR,5bR,7aR,11aS,11bR,13aR,13bR)-5a,5b,8,8,11a-pentamethyl-1-(prop-1-en-2-yl)-3a-(2-(pyridazin-3-ylamino)ethylamino)-2,3,3a,4,5,5a,5b,6,7,7a,8,11,11a,11b,12,13,13a,13b-octadecahydro-1H-cyclopenta[a]chrysen-9-yl)benzoate and lithium hydroxide monohydrate (2.3 mg, 0.055 mmol) in a mixture of water (0.5 mL), THF (0.25 mL) and MeOH (0.25 mL) was stirred at rt for 2.5 days. Purification of the crude mixture by reverse phase preparative HPLC using Prep HPLC Method 10 gave the title compound as a white solid (5.0 mg, 100% yield) bis TFA salt. LCMS: m/e 651.5 (M+H)$^+$, 2.26 min (method 11).

Example 201

Preparation of 4-((1R,3aS,5aR,5bR,7aR,11aS,11bR,13aR,13bR)-5a,5b,8,8,11a-pentamethyl-3a-(2-(5-(methylsulfonyl)pyridin-2-ylamino)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

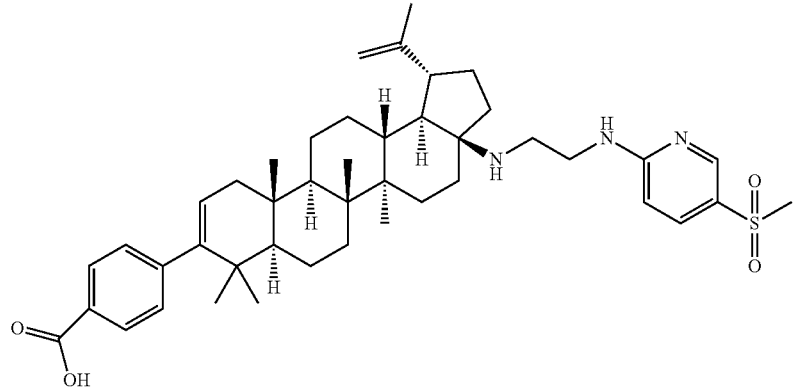

The title compound was prepared following a similar procedure as described for the synthesis of 4-((1R,3aS,5aR,5bR,7aR,11aS,11bR,13aR,13bR)-5a,5b,8,8,11a-pentamethyl-1-(prop-1-en-2-yl)-3a-(2-(pyridazin-3-ylamino)ethylamino)-2,3,3a,4,5,5a,5b,6,7,7a,8,11,11a,11b,12,13,13a,13b-octadecahydro-1H-cyclopenta[a]chrysen-9-yl)benzoic acid, except 2-bromo-5-(methylsulfonyl)pyridine (0.024 g, 0.100 mmol) was used in place of 3-chloropyridazine. Purification of the crude Step 2 mixture by reverse phase preparative HPLC using Prep HPLC Method 10 gave the title compound as an off-white solid (10.6 mg, 11.9% yield over 2 steps) bis TFA salt. LCMS: m/e 728.5 (M+H)$^+$, 2.22 min (method 11). $^1$H NMR (500 MHz, 1:1 mixture of CDCl3 and MeOD, MeOD lock) δ ppm 8.61 (d, J=1.8 Hz, 1H), 7.95-7.87 (m, 3H), 7.19 (d, J=8.2 Hz, 2H), 6.80 (d, J=8.9 Hz, 1H), 5.29 (d, J=4.6 Hz, 1H), 4.90 (s, 1H), 4.82 (br. s., 1H), 3.96-3.85 (m, 1H), 3.85-3.71 (m, 1H), 3.42 (br. s., 1H), 3.37 (s, 3H), 3.27-3.18 (m, 1H), 3.10 (s, 3H), 2.70 (br. s., 1H), 2.14 (dd, J=17.2, 6.3 Hz, 1H), 2.10-1.95 (m, 5H), 1.91-1.77 (m, 3H), 1.74 (s, 3H), 1.71 (d, J=17.4 Hz, 2H), 1.65-1.47 (m, 6H), 1.47-1.34 (m, 3H), 1.34-1.11 (m, 6H), 1.06 (s, 3H), 1.00 (s, 3H), 0.94 (s, 6H), 0.93 (s, 3H).

Section 6. F-Benzoic Acid Derivatives
Example A1
Preparation of 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-fluorobenzoic acid
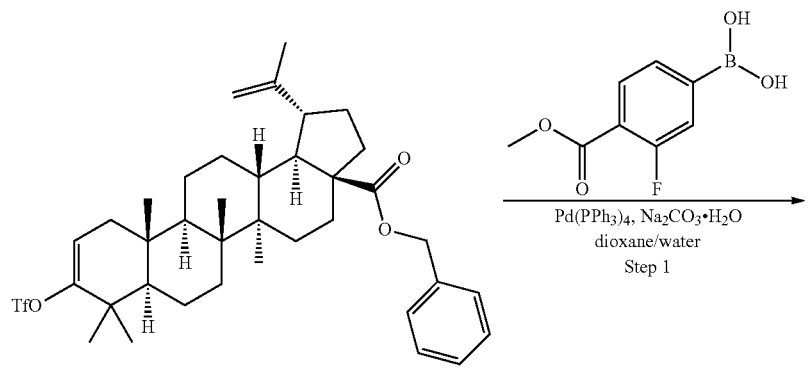
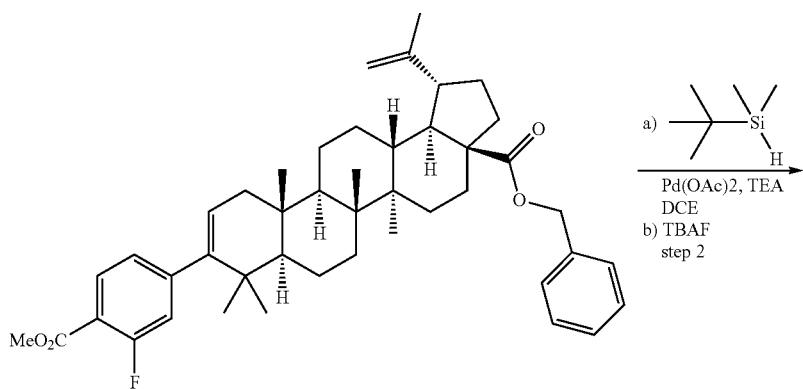
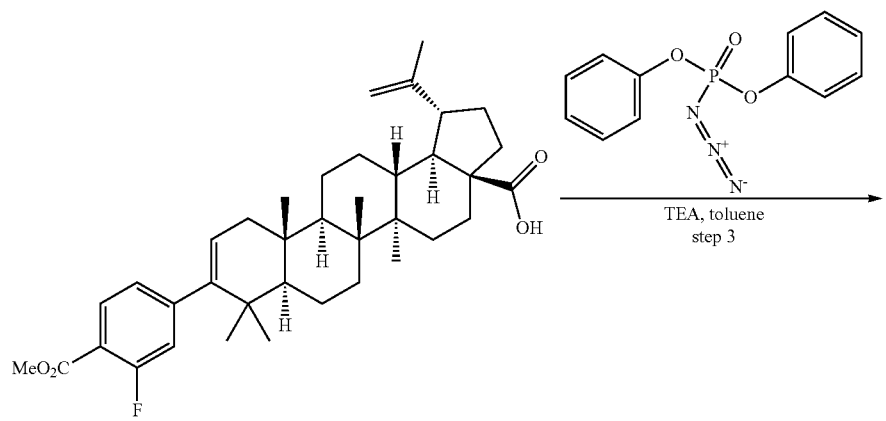

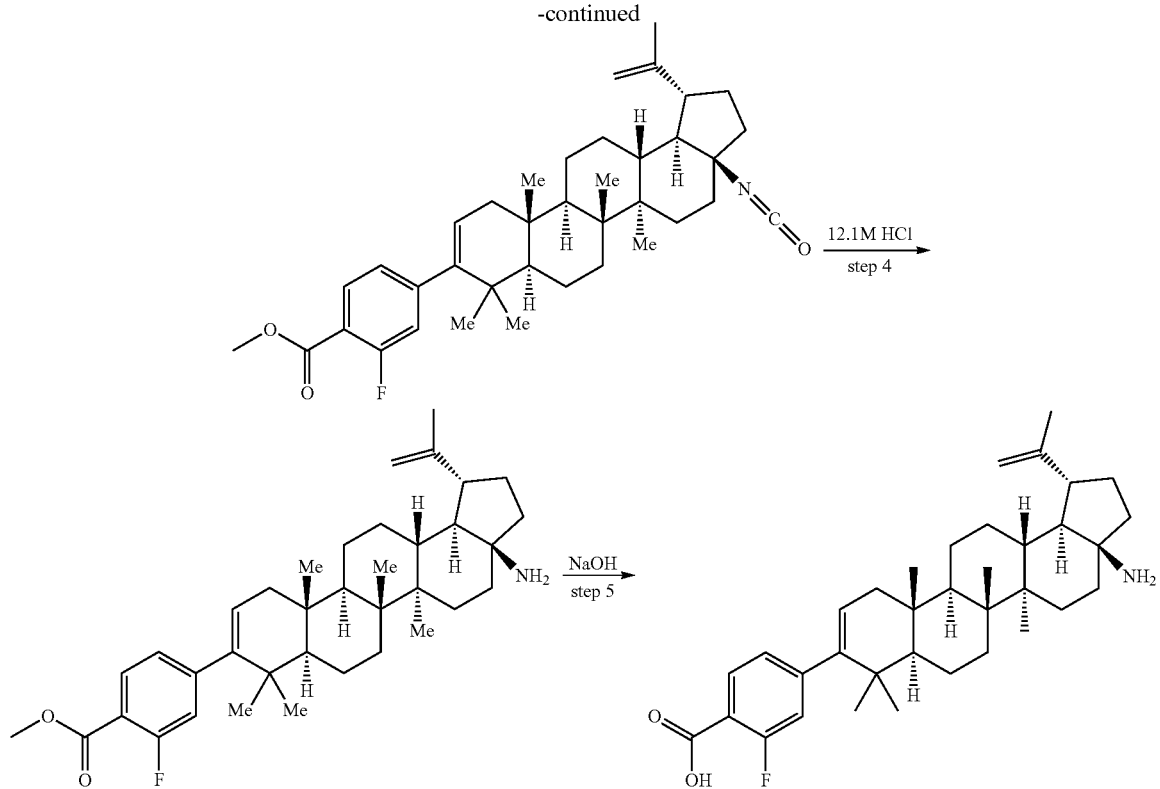

Step 1. Preparation of (1R,3aS,5aR,5bR,7aR,11aS, 11bR,13aR,13bR)-benzyl 9-(3-fluoro-4-(methoxy-carbonyl)phenyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysene-3a-carboxylate A suspension of (1R,3aS,5aR,5bR,7aR,11aR,11bR,13aR, 13bR)-benzyl 5a,5b,8,8,11a-pentamethyl-1-(prop-1-en-2-yl)-9-(trifluoromethylsulfonyloxy)-2,3,3a,4,5,5a,5b,6,7,7a, 8,11,11a,11b,12,13,13a,13b-octadecahydro-1H-cyclopenta [a]chrysene-3a-carboxylate (4.0 g, 5.91 mmol), 3-fluoro-4-(methoxycarbonyl)phenylboronic acid (1.287 g, 6.50 mmol), sodium carbonate monohydrate (2.198 g, 17.73 mmol), and Pd(PPh$_3$)$_4$ (0.205 g, 0.177 mmol) in 1,4-dioxane (24 mL) and water (6 mL) was flushed with N$_2$ and the mixture was heated to reflux. After 2 h of heating, the mixture was cooled to rt. The mixture was diluted with water (40 mL) and was extracted with dichloromethane (3×40 mL). The combined organic layers were dried with Na$_2$SO$_4$. The drying agent was removed by filtration and the filtrate was concentrated under reduced pressure. The residue was dissolved in DCM and was filtered through a pad of celite and silica gel, washing with a 25% EtOAc in hexanes solution. The filtrate was concentrated under reduced pressure to give the title compound (3.59 g, 5.27 mmol, 89% yield) as a dark grey foam. The crude product was used in the next step with no additional purification. $^1$H NMR (500 MHz, CHLOROFORM-d) δ ppm 7.80 (1H, t, J=7.8 Hz), 7.29-7.42 (5H, m), 6.96 (1H, d, J=7.9 Hz), 6.91 (1H, d, J=11.9 Hz), 5.28-5.33 (1H, m), 5.16 (1H, d, J=12.5 Hz), 5.09 (1H, d, J=12.2 Hz), 4.73 (1H, s), 4.59 (1H, br. s.), 3.92 (3H, s), 3.03 (1H, td, J=10.8, 4.7 Hz), 2.20-2.33 (2H, m), 2.09 (1H, dd, J=17.1, 6.4 Hz), 1.81-1.97 (2H, m), 1.68 (3H, s), 0.96 (3H, s), 0.92 (3H, s), 0.92 (3H, s), 0.91 (3H, s), 0.81 (3H, s), 0.79-1.75 (17H, m).

Step 2. Preparation of (1R,3aS,5aR,5bR,7aR,11aS, 11bR,13aR,13bR)-9-(3-fluoro-4-(methoxycarbonyl) phenyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysene-3a-carboxylic acid To a solution of (1R,3aS,5aR,5bR,7aR,11aS,11bR,13aR, 13bR)-benzyl 9-(3-fluoro-4-(methoxycarbonyl)phenyl)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysene-3a-carboxylate (3.59 g, 5.27 mmol) in DCE (25 mL) was added TEA (1.176 mL, 8.44 mmol), t-butyldimethylsilane (1.749 mL, 10.54 mmol), and palladium(II) acetate (0.118 g, 0.527 mmol). The mixture was flushed with N$_2$ and heated to 60° C. for 1 h. The mixture was cooled to rt and was filtered through a plug of celite and silica gel (washed with 25% EtOAc in hexanes). The filtrate was concentrated under reduced pressure. The residue was diluted with 25 mL of dioxane and TBAF (75% in water) (2.76 g, 7.91 mmol) was added. The mixture was stirred for 30 minutes at rt then was diluted with 50 mL of 1N HCl. The solids that formed were collected by filtration and were washed with water to give the title compound (2.95 g, 4.99 mmol, 95% yield) as a white solid. $^1$H NMR (400 MHz, CHLOROFORM-d) δ ppm 7.83 (1H, t, J=7.9 Hz), 6.90-7.00 (2H, m), 5.34 (1H, dd, J=6.1, 1.6 Hz), 4.77 (1H, d, J=2.0 Hz), 4.64 (1H, s), 3.94 (3H, s), 3.04 (1H, td, J=10.7, 4.8 Hz), 2.24-2.34 (2H, m), 2.13 (1H, dd, J=17.3, 6.3 Hz), 1.96-2.06 (2H, m), 1.72 (3H, s), 1.03 (3H, s), 1.02 (3H, s), 0.98 (3H, s), 0.93-0.96 (6H, m), 0.91-1.80 (17H, m).

Step 3. Preparation of methyl 2-fluoro-4-((1R,3aS, 5aR,5bR,7aR,11aS,11bR,13aR,13bR)-3a-isocy-anato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoate To a solution of (1R,3aS,5aR,5bR,7aR,11aS,11bR,13aR, 13bR)-9-(3-fluoro-4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid (2.95 g, 4.99 mmol) in toluene (50 mL) and TEA (1.39 mL, 9.99 mmol) was added diphenyl phosphorazidate (1.614 mL, 7.49 mmol) and the mixture was heated to reflux. After 3 h, the reaction mixture was concentrated under reduced pressure, was adsorbed to silica gel, and was purified by flash chromatography using a 0-10% EtOAc in hexanes gradient to give the title compound as a white solid. The material was used in the next step with no additional purification. $^1$H NMR (500 MHz, Chloroform-d) δ ppm 7.81 (1H, t, J=7.8 Hz), 6.96 (1H, dd, J=7.9, 1.5 Hz), 6.92 (1H, dd, J=11.9, 1.5 Hz), 5.31 (1H, dd, J=6.3, 1.7 Hz), 4.75 (1H, s), 4.64 (1H, s), 3.92 (3H, s), 2.55 (1H, td, J=10.8, 5.8 Hz), 2.05-2.16 (2H, m), 1.76-1.92 (4H, m), 1.68 (3H, s), 1.09-1.11 (3H, m), 0.97 (3H, s), 0.96 (3H, s), 0.94 (3H, s), 0.92 (3H, s), 0.88-1.75 (16H, m).

Step 4. Preparation of methyl 4-((1R,3aS,5aR,5bR, 7aR,11aS,11bR,13aR,13bR)-3a-amino-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-2-fluorobenzoate dihydrochloride To a solution of crude methyl 2-fluoro-4-((1R,3aS,5aR, 5bR,7aR,11aS,11bR,13aR,13bR)-3a-isocyanato-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (2.93 g, 4.99 mmol) in THF (35 mL) was added 12N HCl (10 mL, 121 mmol). After stirring the mixture for 24 h, the mixture was diluted with water (100 mL) until solids precipitated. The solids were collected by filtration and were washed with water to afford the title compound (2.75 g, 4.33 mmol, 87% yield), as an off-white solid that was used in the next step with no additional purification. LCMS: m/e 562 (M+H)$^+$, 1.96 min (method 2).

Step 5. Preparation of 4-((1R,3aS,5aR,5bR,7aR, 11aS,11bR,13aR,13bR)-3a-amino-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)-2-fluorobenzoic acid To a solution of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-2-fluorobenzoate (100 mg, 0.178 mmol) in 1,4-dioxane (2 mL) was added 1N NaOH (0.890 mL, 0.890 mmol). Solids formed upon the addition of the NaOH. The mixture was heated to 60° C. After 20 minutes of heating, the mixture still contained solids. The mixture was further diluted with 1 mL of MeOH and 2 mL of dioxane then was heated to 60° C. overnight (solids did not completely dissolve).

After 21 h of heating, the mixture was cooled to rt. The mixture was diluted with 3 mL of water and the solids that remained were collected by filtration and were washed with water then with ether to give 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-2-fluorobenzoic acid (67 mg, 0.113 mmol, 63.2% yield) as a white solid. LCMS: m/e 548.4 (M+H)$^+$, 2.29 min (method 11).

Example A2

Preparation of benzoic acid, 4-[(1R,3aS,5aR,5bR, 7aR,11aS,11bR,13aR,13bR)-3a-[[2-(1,1-dioxido-4-thiomorpholinyl)ethyl]amino]-2,3,3a,4,5,5a,5b,6,7, 7a,8,11,11a,11b,12,13,13a,13b-octadecahydro-5a,5b, 8,8,11a-pentamethyl-1-(1-methylethenyl)-1H-cyclopenta[a]chrysen-9-yl]-2-fluoro-, HCl

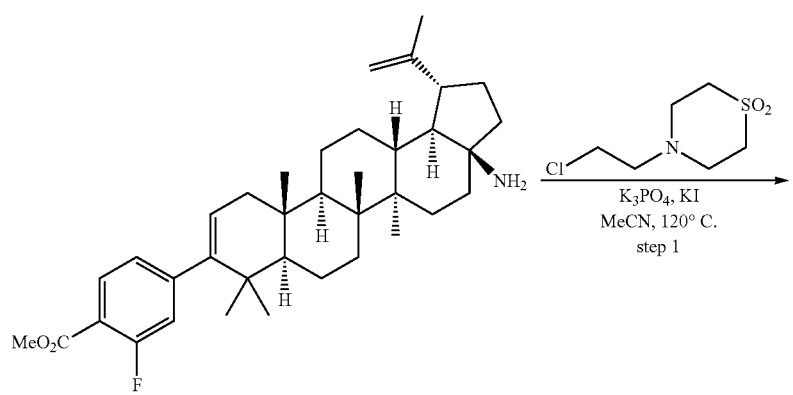

-continued

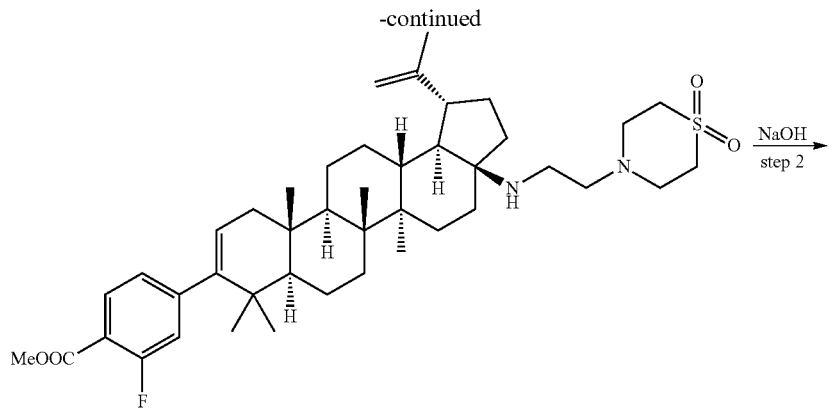

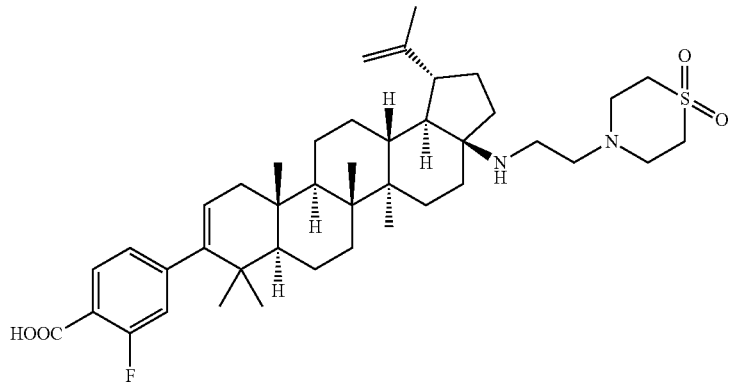

Step 1. Preparation of benzoic acid, 4-[(1R,3aS,5aR, 5bR,7aR,11aS,11bR,13aR,13bR)-3a-[[2-(1,1-di-oxido-4-thiomorpholinyl)ethyl]amino]-2,3,3a,4,5,5a, 5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]-2-fluoro-, methyl ester To a sealable flask containing methyl 4-((1R,3aS,5aR,5bR, 7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)-2-fluorobenzoate, HCl (319 mg, 0.533 mmol) was added thiomorpholine, 4-(2-chloroethyl)-1,1-dioxide, HCl (385 mg, 1.644 mmol), potassium iodide (240 mg, 1.446 mmol), and phosphoric acid, potassium salt (500 mg, 2.356 mmol). The mixture was diluted with acetonitrile (10 mL), was flushed with $N_2$, then the vial was sealed and heated to 120° C. for 115 h. The mixture was cooled to rt and was directly purified by flash chromatography using a 0-5% MeOH in DCM gradient. The fractions containing the expected product were combined and was concentrated under reduced pressure to give the title compound (0.308 g, 0.426 mmol, 80% yield) as an off white foam. LCMS: m/e 723.5 (M+H)+, 1.94 min (method 2).

Step 2. Preparation of benzoic acid, 4-[(1R,3aS,5aR, 5bR,7aR,11aS,11bR,13aR,13bR)-3a-[[2-(1,1-di-oxido-4-thiomorpholinyl)ethyl]amino]-2,3,3a,4,5,5a, 5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]-2-fluoro-, HCl To a solution of benzoic acid, 4-[(1R,3aS,5aR,5bR,7aR, 11aS,11bR,13aR,13bR)-3a-[[2-(1,1-dioxido-4-thiomorpholinyl)ethyl]amino]-2,3,3a,4,5,5a,5b,6,7,7a,8,11,11a,11b, 12,13,13a,13b-octadecahydro-5a,5b,8,8,11a-pentamethyl-1-(1-methylethenyl)-1H-cyclopenta[a]chrysen-9-yl]-2-fluoro-, methyl ester (0.308 g, 0.426 mmol) in 1,4-dioxane (5 mL) was added 1N sodium hydroxide (2.130 mL, 2.130 mmol). The mixture was heated to 70° C. for 18 h then was cooled to rt. To the mixture was added 1N HCl slowly until solids began to form. The solids were collected by filtration and were washed with water to give benzoic acid, 4-[(1R,3aS, 5aR,5bR,7aR,11aS,11bR,13aR,13bR)-3a-[[2-(1,1-dioxido-4-thiomorpholinyl)ethyl]amino]-2,3,3a,4,5,5a,5b,6,7,7a,8, 11,11a,11b,12,13,13a,13b-octadecahydro-5a,5b,8,8,11a-pentamethyl-1-(1-methylethenyl)-1H-cyclopenta[a]chrysen-9-yl]-2-fluoro-, HCl as an off-white solid (0.295 g, 0.396 mmol, 93% yield). LCMS: m/e 709.5 (M+H)+, 1.66 min (method 2). $^1$H NMR (500 MHz, Acetic acid d4) δ ppm 7.96 (1H, t, J=7.8 Hz), 7.09 (1H, dd, J=7.9, 1.5 Hz), 7.03 (1H, d, J=11.9 Hz), 5.43 (1H, d, J=4.6 Hz), 4.84 (1H, s), 4.74 (1H, s), 3.43-3.49 (1H, m), 3.02-3.36 (11H, m), 2.91-3.00 (1H, m), 1.77 (3H, s), 1.30 (3H, s), 1.15 (3H, s), 1.10 (3H, s), 1.04 (3H, s), 1.01 (3H, s), 0.98-2.34 (22H, m).

Example A3

Preparation of 2-fluoro-4-((1R,3aS,5aR,5bR,7aR,11aS,11bR,13aR,13bR)-5a,5b,8,8,11a-pentamethyl-3a-(2-morpholinoethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

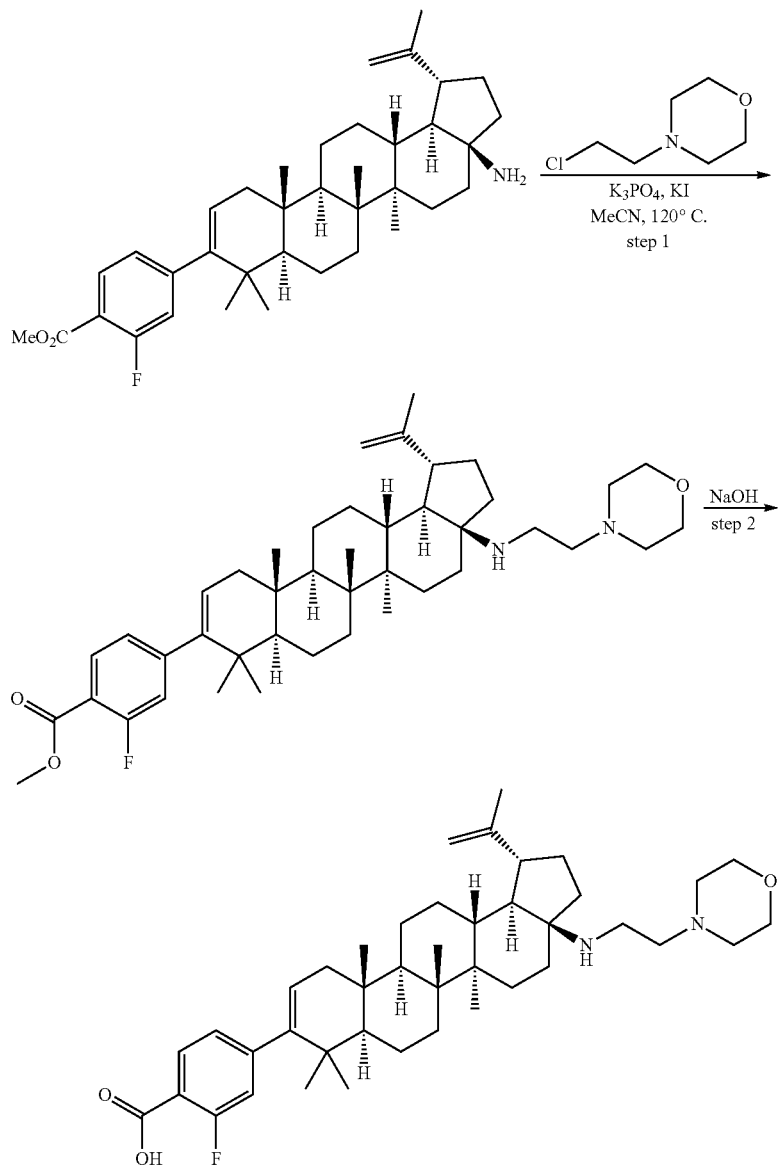

Step 1. Preparation of methyl 2-fluoro-4-((1R,3aS,5aR,5bR,7aR,11aS,11bR,13aR,13bR)-5a,5b,8,8,11a-pentamethyl-3a-(2-morpholinoethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To a sealable flask containing methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-fluorobenzoate, HCl (0.1 g, 0.167 mmol) was added 4-(2-chloroethyl)morpholine, HCl (0.093 g, 0.501 mmol), phosphoric acid, potassium salt (0.156 g, 0.735 mmol) and potassium iodide (0.075 g, 0.451 mmol). The mixture was diluted with acetonitrile (3 mL), was flushed with $N_2$, and the vial was sealed and heated to 120° C. After heating the mixture for 16 h, the it was cooled to rt. The crude product was adsorbed to silica gel then was purified by flash chromatography using a Thomson 12 g silica gel column and a 0-5% MeOH in DCM gradient. The fractions containing the expected product were combined and concentrated under reduced pressure to give methyl 2-fluoro-4-((1R,3aS,5aR, 5bR,7aR,11aS,11bR,13aR,13bR)-5a,5b,8,8,11a-pentamethyl-3a-(2-morpholinoethylamino)-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoate (77 mg, 0.114 mmol, 68.3% yield) as an off-white foam. LCMS: m/e 675.5 (M+H)+, 1.91 min (method 2).

Step 2. Preparation of 2-fluoro-4-((1R,3aS,5aR,5bR, 7aR,11aS,11bR,13aR,13bR)-5a,5b,8,8,11a-pentamethyl-3a-(2-morpholinoethylamino)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid To a solution of methyl 2-fluoro-4-((1R,3aS,5aR,5bR,7aR, 11aS,11bR,13aR,13bR)-5a,5b,8,8,11a-pentamethyl-3a-(2-morpholinoethylamino)-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)benzoate (0.075 g, 0.111 mmol) in 1,4-dioxane (1 mL) was added NaOH (1M) (0.5 mL, 0.500 mmol). The mixture was heated to 75° C. for 15 h then was cooled to rt. The mixture was purified by prep HPLC. The fractions containing the expected product were combined and concentrated under reduced pressure to give 2-fluoro-4-((1R, 3aS,5aR,5bR,7aR,11aS,11bR,13aR,13bR)-5a,5b,8,8,11a-pentamethyl-3a-(2-morpholinoethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (30 mg, 0.043 mmol, 38.8% yield) as a white solid. LCMS: m/e 661.5 (M+H)+, 1.66 min (method 2). 1H NMR (500 MHz, Acetic Acid d4) δ ppm 7.96 (1H, t, J=7.9 Hz), 7.09 (1H, dd, J=8.2, 1.2 Hz), 7.03 (1H, d, J=11.6 Hz), 5.42 (1H, d, J=4.6 Hz), 4.86 (1H, s), 4.74 (1H, s), 3.89-3.99 (4H, m), 3.53-3.69 (4H, m), 3.29 (4H, br. s.), 2.81-2.90 (1H, m), 1.77 (3H, s), 1.23 (3H, s), 1.13 (3H, s), 1.08 (3H, s), 1.04 (3H, s), 1.01 (3H, s), 0.85-2.26 (22H, m).

Example A4

Preparation of 2-fluoro-4-((1R,3aS,5aR,5bR,7aR, 11aS,11bR,13aR,13bR)-5a,5b,8,8,11a-pentamethyl-3a-(2-(2-oxopyrrolidin-1-yl)ethylamino)-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

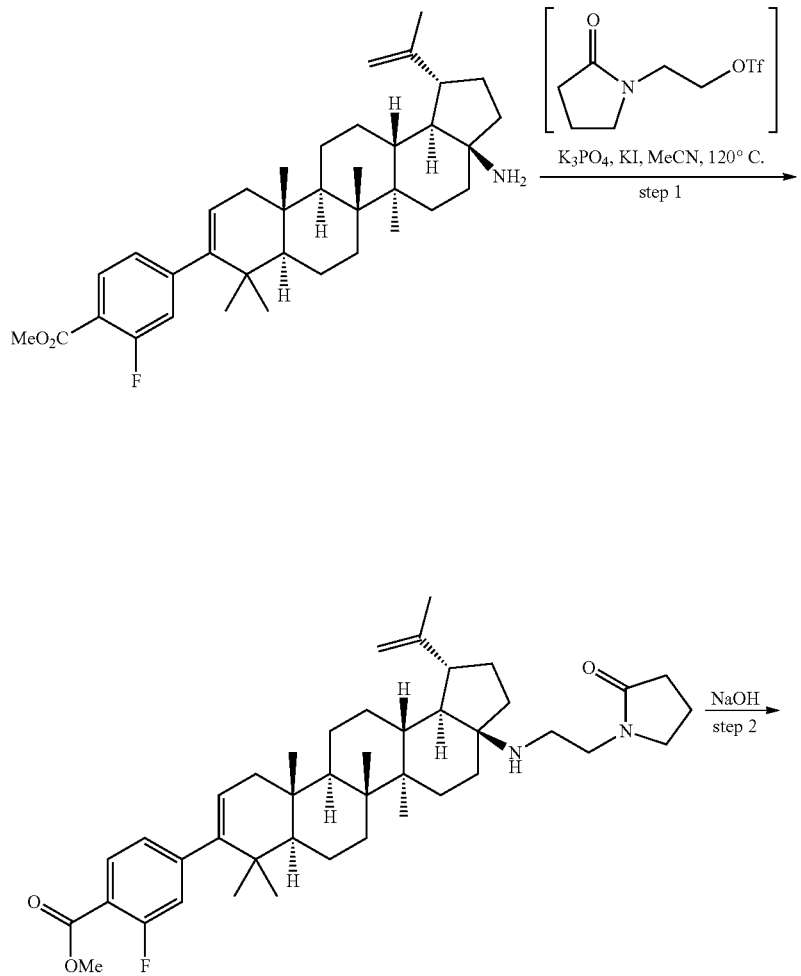

-continued

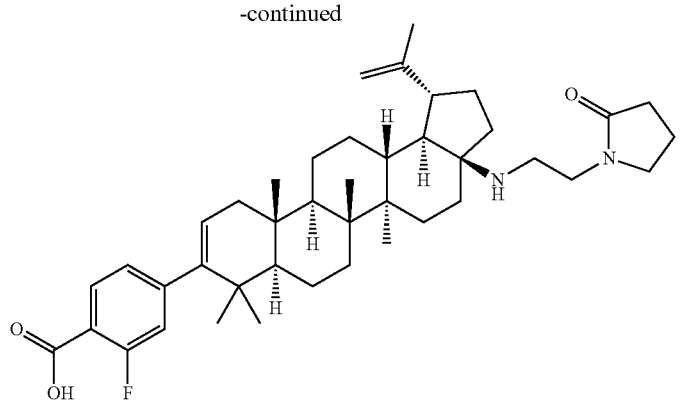

Step 1. Preparation of methyl 2-fluoro-4-((1R,3aS, 5aR,5bR,7aR,11aS,11bR,13aR,13bR)-5a,5b,8,8,11a-pentamethyl-3a-(2-(2-oxopyaolidin-1-yl)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To a vial containing N-(2-hydroxyethyl)-2-pyrrolidone (0.5 mL, 4.42 mmol) was added DMAP (0.054 g, 0.442 mmol) and TEA (0.925 mL, 6.64 mmol). The mixture was diluted with d-chloroform (10 mL) and was cooled to 0° C. then triflic anhydride (0.822 mL, 4.87 mmol) was added slowly. The mixture turned a dark red color as the anhydride was added. The mixture was warmed to rt and stirred for 45 minutes. The 0.442 M solution was used directly as the alkylating agent for the following reaction.

To a sealable flask containing methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-fluorobenzoate (50 mg, 0.089 mmol) was added potassium iodide (39.9 mg, 0.240 mmol) and phosphoric acid, potassium salt (83 mg, 0.392 mmol). The mixture was diluted with acetonitrile (1 mL) and the crude alkylating solution described above (1.007 mL, 0.445 mmol) was added. The mixture was flushed with N₂ and the vial was sealed and heated to 120° C. After 15.5 h of heating, the mixture was cooled to rt. An additional 0.5 mL of the crude alkylating solution was added and the mixture was again heated to 120° C. After 70.25 h, the mixture was cooled to rt. The mixture was adsorbed to silica gel and was purified by flash chromatography using a 0-5% MeOH in DCM gradient and a Thomson 12 g silica gel column. The fractions containing the expected product were combined and were concentrated under reduced pressure to give methyl 2-fluoro-4-((1R,3aS,5aR,5bR,7aR,11aS,11bR,13aR,13bR)-5a,5b,8,8,11a-pentamethyl-3a-(2-(2-oxopyrrolidin-1-yl)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (25 mg, 0.037 mmol, 41.7% yield) as a yellow film. LCMS: m/e 673.5 (M+H)⁺, 2.03 min (method 2).

Step 2. Preparation of 2-fluoro-4-((1R,3aS,5aR,5bR,7aR,11aS,11bR,13aR,13bR)-5a,5b,8,8,11a-pentamethyl-3a-(2-(2-oxopyrrolidin-1-yl)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

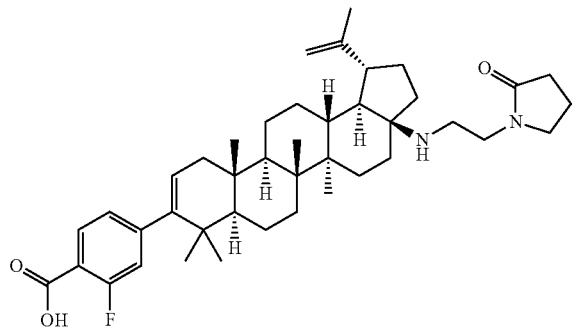

To a solution of methyl 2-fluoro-4-((1R,3aS,5aR,5bR,7aR,11aS,11bR,13aR,13bR)-5a,5b,8,8,11a-pentamethyl-3a-(2-(2-oxopyrrolidin-1-yl)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.025 g, 0.037 mmol) in 1,4-dioxane (1 mL) was added NaOH (1N) (0.5 mL, 0.500 mmol). The mixture was warmed to 60° C. for 15. 5 h then was cooled to rt and purified by prep HPLC. The fractions containing the expected product were combined and concentrated under reduced pressure to give 2-fluoro-4-((1R,3aS,5aR,5bR,7aR,11aS,11bR,13aR,13bR)-5a,5b,8,8,11a-pentamethyl-3a-(2-(2-oxopyrrolidin-1-yl)ethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (11 mg, 0.016 mmol, 42.2% yield) as a white solid. LCMS: m/e 659.5 (M+H)⁺, 1.77 min (method 2). ¹H NMR (500 MHz, CHLOROFORM-d) δ 7.82 (t, J=6.9 Hz, 1H), 6.91 (d, J=6.1 Hz, 1H), 6.86 (d, J=11.9 Hz, 1H), 5.27 (d, J=4.6 Hz, 1H), 4.71 (s, 1H), 4.58 (s, 1H), 3.54-3.43 (m, 3H), 3.39-3.31 (m, 1H), 1.68 (s, 3H), 1.06 (s, 3H), 0.96 (s, 3H), 0.93 (s, 3H), 0.90 (s, 3H), 0.90 (s, 3H), 2.75-0.66 (m, 29H).

Example A5

Preparation of 2-fluoro-4-((1R,3aS,5aR,5bR,7aR, 11aS,11bR,13aR,13bR)-5a,5b,8,8,11a-pentamethyl-3a-(3-(2-oxopyrrolidin-1-yl)propylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

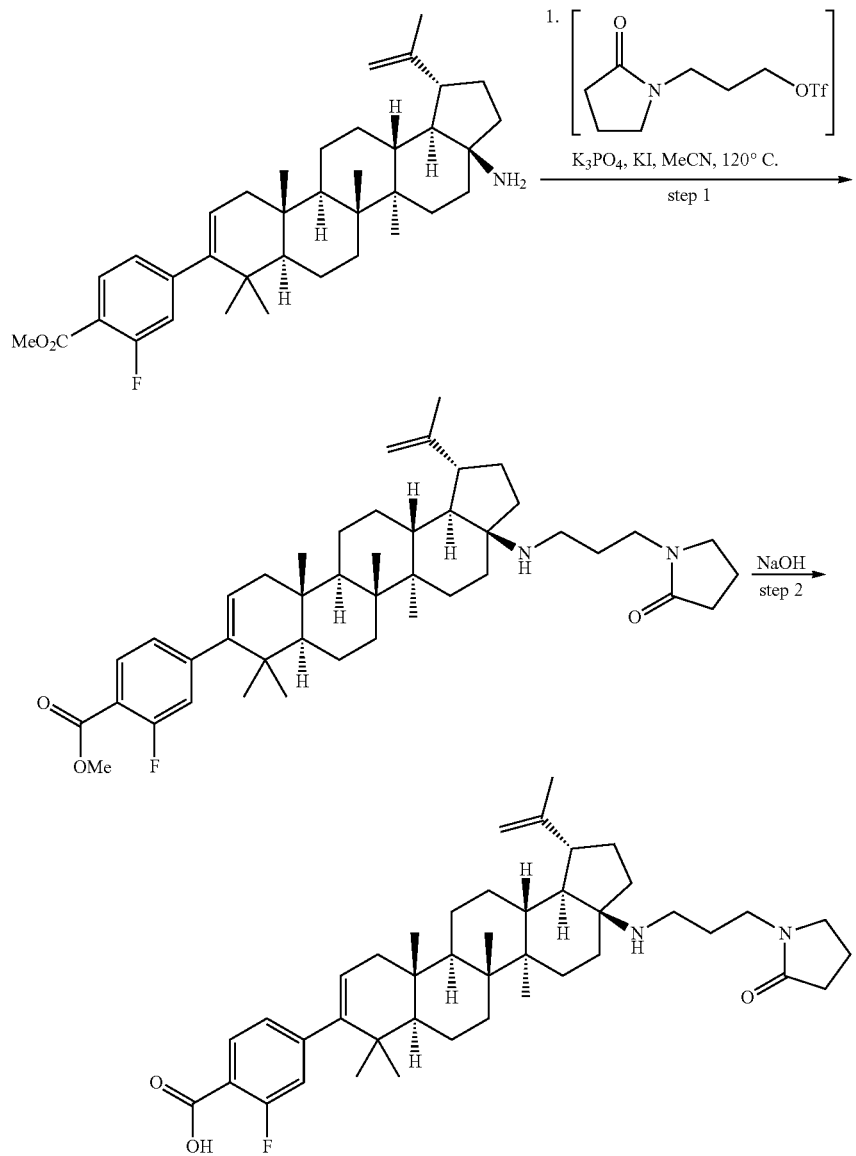

Step 1. Preparation of methyl 2-fluoro-4-((1R,3aS, 5aR,5bR,7aR,11aS,11bR,13aR,13bR)-5a,5b,8,8,11a-pentamethyl-3a-(3-(2-oxopyrrolidin-1-yl)propylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To a vial containing 1-(3-hydroxypropyl)-2-pyrrolidone (0.5 mL, 3.84 mmol) was added DMAP (0.047 g, 0.384 mmol) and TEA (0.803 mL, 5.76 mmol). The mixture was diluted with d-chloroform (10 mL) and was cooled to 0° C. To the cooled solution was added trifluoromethanesulfonic anhydride (0.714 mL, 4.23 mmol) slowly. The mixture turned dark red as the anhydride was added. The mixture was slowly warmed to rt as the ice bath melted. After 1 h of stirring at rt, $^1$HNMR showed no starting material remained. The crude reaction mixture was used directly in the following reaction with no purification.

To a sealable flask containing methyl 4-((1R,3aS,5aR,5bR, 7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]

chrysen-9-yl)-2-fluorobenzoate (50 mg, 0.089 mmol) was added potassium iodide (39.9 mg, 0.240 mmol) and phosphoric acid, potassium salt (83 mg, 0.392 mmol). The mixture was diluted with acetonitrile (1 mL) and 3-(2-oxopyrrolidin-1-yl)propyl trifluoromethanesulfonate (the crude solution prepared above) (1.0 mL, 0.384 mmol) was added. The mixture was flushed with $N_2$, then the vial was sealed and heated to 120° C. After 15.5 h of heating, the mixture was cooled to rt. An additional 0.5 mL of the above crude solution containing the triflate was added and the mixture was again heated to 120° C. After heating the mixture for an additional 70.25 h, the mixture was cooled to rt. The mixture was adsorbed to silica gel and was purified by flash chromatography using a 0-5% MeOH in DCM gradient and a Thomson 12 g silica gel column. The fractions containing the expected product were combined and concentrated under reduced pressure to give methyl 2-fluoro-4-((1R,3aS,5aR,5bR,7aR,11aS,11bR,13aR,13bR)-5a,5b,8,8,11a-pentamethyl-3a-(3-(2-oxopyrrolidin-1-yl)propylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (16 mg, 0.023 mmol, 26.2% yield) as a yellow film. LCMS: m/e 687.5 (M+H)$^+$, 2.04 min (method 2).

Step 2. Preparation of 2-fluoro-4-((1R,3aS,5aR,5bR,7aR,11aS,11bR,13aR,13bR)-5a,5b,8,8,11a-pentamethyl-3a-(3-(2-oxopyrrolidin-1-yl)propylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid To a solution of methyl 2-fluoro-4-((1R,3aS,5aR,5bR,7aR,11aS,11bR,13aR,13bR)-5a,5b,8,8,11a-pentamethyl-3a-(3-(2-oxopyrrolidin-1-yl)propylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (16 mg, 0.023 mmol) in 1,4-dioxane (1 mL) was added NaOH (1N) (0.25 mL, 0.250 mmol). The mixture was heated to 60° C. overnight for 15.25 h then was cooled to rt. The mixture was directly loaded onto the prep HPLC for purification. The fractions containing the expected product were combined and concentrated under reduced pressure to give 2-fluoro-4-((1R,3aS,5aR,5bR,7aR,11aS,11bR,13aR,13bR)-5a,5b,8,8,11a-pentamethyl-3a-(3-(2-oxopyrrolidin-1-yl)propylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (6 mg, 8.02 mmol, 34.5% yield) as a clear, colorless film. LCMS: m/e 673.5 (M+H)$^+$, 1.75 min (method 2). $^1$H NMR (500 MHz, Acetic acid $d_4$) δ 7.96 (t, J=7.9 Hz, 1H), 7.09 (dd, J=7.9, 1.2 Hz, 1H), 7.03 (d, J=11.9 Hz, 1H), 5.42 (d, J=4.6 Hz, 1H), 4.86 (s, 1H), 4.74 (s, 1H), 3.58-3.40 (m, 4H), 3.26-3.16 (m, 2H), 2.94-2.85 (m, 1H), 2.56-2.48 (m, 2H), 1.76 (s, 3H), 1.22 (s, 3H), 1.13 (s, 3H), 1.08 (s, 3H), 1.04 (s, 3H), 1.01 (s, 3H), 2.29-0.85 (m, 26H).

Example A6

Preparation of benzoic acid, 4-[(1R,3aS,5aR,5bR,7aR,11aS,11bR,13aR,13bR)-3a-[[3-(1,1-dioxido-4-thiomorpholinyl)propyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]-2-fluoro

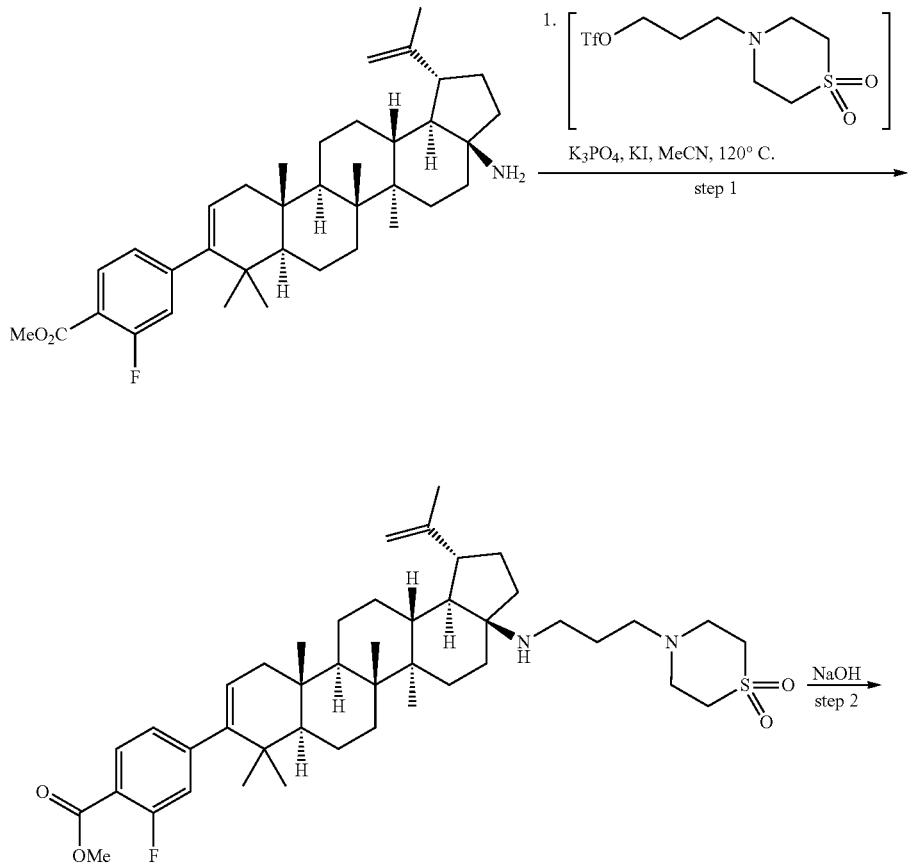

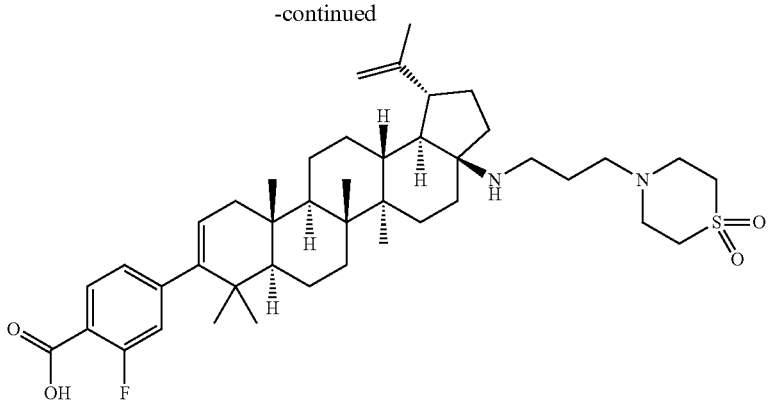

Step 1. Preparation of benzoic acid, 4-[(1R,3aS,5aR, 5bR,7aR,11aS,11bR,13aR,13bR)-3a-[[3-(1,1-di-oxido-4-thiomorpholinyl)propyl]amino]-2,3,3a,4,5, 5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]-2-fluoro-, methyl ester To a vial containing N-(3-hydroxypropyl)thiomorpholine-1,1-dioxide (0.15 g, 0.776 mmol) was added DMAP (9.48 mg, 0.078 mmol) and TEA (0.162 mL, 1.164 mmol). The mixture was diluted with d-chloroform (2 mL) and was cooled to 0° C. To the cooled solution was added trifluoromethanesulfonic anhydride (0.144 mL, 0.854 mmol) slowly. The mixture turned orange as the anhydride was added and became a thick gel which did not stir well. After 2 h the mixture was diluted with an additional 1 mL of d-chloroform and was used directly in the following reaction as the crude reaction mixture.

To a sealable flask containing methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-fluorobenzoate (50 mg, 0.089 mmol) was added potassium iodide (39.9 mg, 0.240 mmol) and phosphoric acid, potassium salt (83 mg, 0.392 mmol). The mixture was diluted with acetonitrile (1 mL) and a solution of the crude mixture from the reaction above (1.718 mL, 0.445 mmol) was added. The mixture was flushed with $N_2$ and the vial was sealed and heated to 120° C. After stirring the mixture for 66 h it was cooled to rt. The mixture was adsorbed to silica gel and was purified by flash chromatography using a 12 g Thomson silica gel column and a 0-5% MeOH in DCM gradient. The fractions containing the expected product were combined and concentrated under reduced pressure to give benzoic acid, 4-[(1R,3aS,5aR,5bR,7aR,11aS,11bR,13aR,13bR)-3a-[[3-(1,1-dioxido-4-thiomorpholinyl)propyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]-2-fluoro-, methyl ester (43 mg, 0.058 mmol, 65.6% yield) as a yellow film. LCMS: m/e 737.5 (M+H)$^+$, 1.88 min (method 2).

Step 2. Preparation of benzoic acid, 4-[(1R,3aS,5aR, 5bR,7aR,11aS,11bR,13aR,13bR)-3a-[[3-(1,1-di-oxido-4-thiomorpholinyl)propyl]amino]-2,3,3a,4,5, 5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]-2-fluoro- To a solution of benzoic acid, 4-[(1R,3aS,5aR,5bR,7aR,11aS,11bR,13aR,13bR)-3a-[[3-(1,1-dioxido-4-thiomorpholinyl)propyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]-2-fluoro-, methyl ester (0.043 g, 0.058 mmol) in 1,4-dioxane (1 mL) was added NaOH (1M) (0.5 ml, 0.500 mmol). The mixture was heated to 60° C. for 15.25 h and was cooled to rt. The mixture was directly loaded onto the prep HPLC for purification. The fractions containing the expected product were combined and concentrated under reduced pressure to give benzoic acid, 4-[(1R,3aS,5aR,5bR,7aR,11aS,11bR,13aR,13bR)-3a-[[3-(1,1-dioxido-4-thiomorpholinyl)propyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]-2-fluoro- (13.2 mg, 0.017 mmol, 29.4% yield) as a white solid. LCMS: m/e 723.5 (M+H)$^+$, 1.62 min (method 2). $^1$H NMR (400 MHz, Acetic acid d4) δ 7.92 (t, J=7.9 Hz, 1H), 7.04 (d, J=8.0 Hz, 1H), 6.98 (d, J=11.8 Hz, 1H), 5.38 (d, J=4.8 Hz, 1H), 4.82 (s, 1H), 4.70 (s, 1H), 3.71 (br. s., 4H), 3.48 (br. s., 4H), 3.25 (t, J=7.5 Hz, 4H), 2.82 (br. s., 1H), 2.46-2.30 (m, 2H), 1.72 (s, 3H), 1.16 (s, 3H), 1.08 (s, 3H), 1.03 (s, 3H), 0.99 (s, 3H), 0.97 (s, 3H), 2.24-0.82 (m, 22H).

Example A7

Preparation of 2-fluoro-4-((1R,3aS,5aR,5bR,7aR,11aS,11bR,13aR,13bR)-5a,5b,8,8,11a-pentamethyl-3a-(2-morpholinoethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

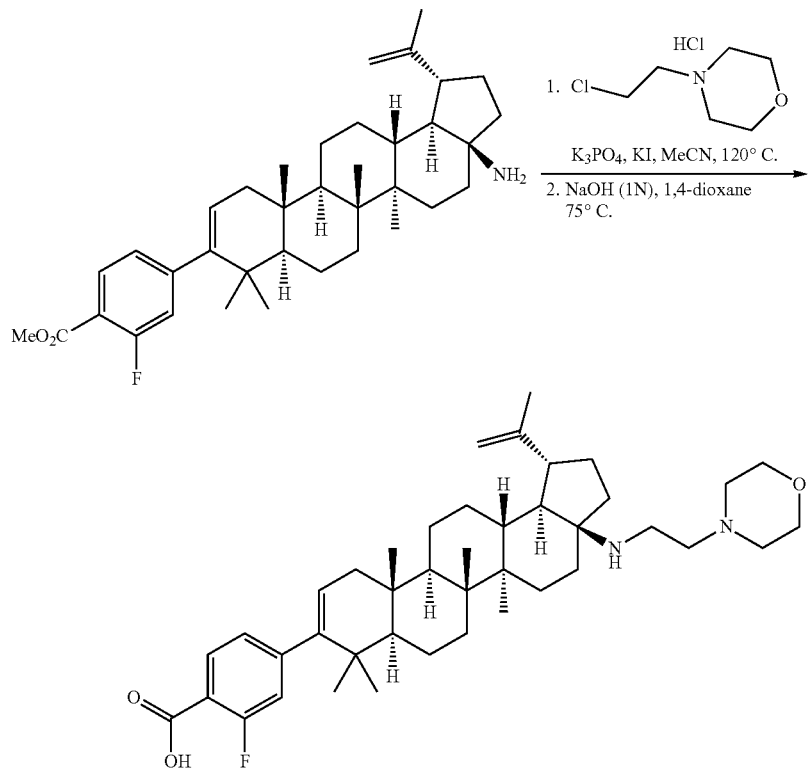

Step 1. Preparation of methyl 2-fluoro-4-((1R,3aS,5aR,5bR,7aR,11aS,11bR,13aR,13bR)-5a,5b,8,8,11a-pentamethyl-3a-(2-morpholinoethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To a sealable flask containing methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-fluorobenzoate hydrochloride (0.1 g, 0.167 mmol) was added 4-(2-chloroethyl)morpholine hydrochloride (0.093 g, 0.501 mmol), phosphoric acid, potassium salt (0.156 g, 0.735 mmol) and potassium iodide (0.075 g, 0.451 mmol). The mixture was diluted with acetonitrile (3 mL), was flushed with nitrogen, then the vial was sealed and heated to 120° C. After heating the mixture for 16 h, the mixture was cooled to rt. The crude product was adsorbed to silica gel then was purified by flash chromatography using a Thomson 12 g silica gel column and a 0-5% methanol in dichloromethane gradient. The fractions containing the expected product were combined and concentrated under reduced pressure to give methyl 2-fluoro-4-((1R,3aS,5aR,5bR,7aR,11aS,11bR,13aR,13bR)-5a,5b,8,8,11a-pentamethyl-3a-(2-morpholinoethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (77 mg, 0.114 mmol, 68.3% yield) as an off-white foam. LCMS: m/e 675.5 (M+H)$^+$, 1.91 min (method 2).

Step 2. To a solution of methyl 2-fluoro-4-((1R,3aS,5aR,5bR,7aR,11aS,11bR,13aR,13bR)-5a,5b,8,8,11a-pentamethyl-3a-(2-morpholinoethylamino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.075 g, 0.111 mmol) in 1,4-Dioxane (1 mL) was added NaOH (1M) (0.5 mL, 0.500 mmol). The mixture was heated to 75° C. for 15 h then was cooled to rt. The mixture was acidified with 1N HCl (3 mL) and was concentrated under reduced pressure. The residue was diluted with 15 mL of water and the solids that remained were collected by filtration and were washed with water then with ether. The compound was dissolved in DMF and methanol and was purified by prep HPLC. Fractions containing the expected product were combined and concentrated under reduced pressure to give 2-fluoro-4-((1R,3aS,5aR,5bR,7aR,11aS,11bR,13aR,13bR)-5a,5b,8,8,11a-pentamethyl-3a-(2-morpholinoethylamino)-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid (30 mg, 0.043 mmol, 38.8% yield) as a white solid. LCMS: m/e 661.5 (M+H)$^+$, 1.67 min (method 2). $^1$H NMR (500 MHz, Acetic acid d$_4$) ppm 7.96 (1H, t, J=7.9 Hz), 7.09 (1H, dd, J=8.2, 1.2 Hz), 7.03 (1H, d, J=11.6 Hz), 5.42 (1H, d, J=4.6 Hz), 4.86 (1H, s), 4.74 (1H, s), 3.89-3.99 (4H, m), 3.53-3.69 (4H, m), 3.29 (4H, br. s.), 2.81-2.90 (1H, m), 1.77 (3H, s), 1.23 (3H, s), 1.13 (3H, s), 1.08 (3H, s), 1.04 (3H, s), 1.01 (3H, s), 0.85-2.26 (22H, m).

Example A8

Preparation of 2-fluoro-4-((1R,3aS,5aR,5bR,7aR,11aS,11bR,13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

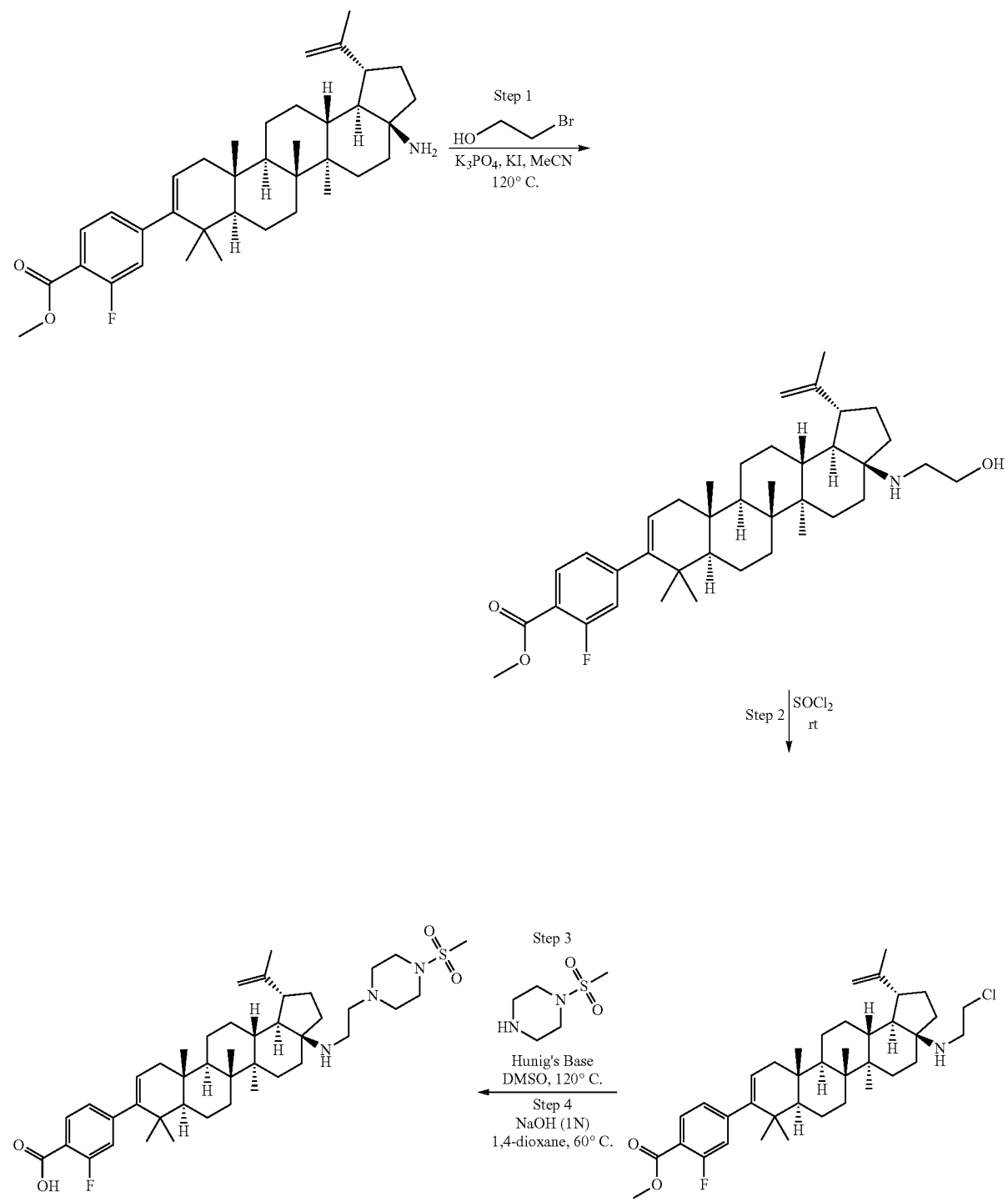

Step 1. Preparation of methyl 2-fluoro-4-((1R,3aS, 5aR,5bR,7aR,11aS,11bR,13aR,13bR)-3a-((2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To a sealable flask containing methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-fluorobenzoate, HCl (1.0 g, 1.671 mmol) was added potassium iodide (0.694 g, 4.18 mmol), phosphoric acid, potassium salt (1.774 g, 8.36 mmol) and 2-bromoethanol (0.475 mL, 6.69 mmol). The mixture was diluted with acetonitrile (15 mL) and the vial was sealed and heated to 120° C. for 21 h then was cooled to rt and was diluted with water (50 mL). The solids were collected by filtration then were washed with water. The solids were purified by flash chromatography in silica gel using a 0-5% methanol in dichloromethane gradient with 0.1% ammonium hydroxide added to the mixture The fractions containing the expected product were combined and were concentrated under reduced pressure. The product was repurified a second time using a 0-20% EtOAc in hexanes gradient with 0.1% TEA added to the mixture. The fractions containing the product combined and were concentrated under reduced pressure to give methyl 2-fluoro-4-((1R,3aS,5aR,5bR,7aR,11aS,11bR,13aR,13bR)-3a-((2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.135 g, 0.223 mmol, 13% yield) as an off-white solid. LCMS: m/e 606.7 (M+H)+, 2.02 min (method 2).

Step 2. Preparation of methyl 4-((1R,3aS,5aR,5bR,7aR,11aS,11bR,13aR,13bR)-3a-((2-chloroethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-fluorobenzoate, HCl To a flask containing methyl 2-fluoro-4-((1R,3aS,5aR,5bR,7aR,11aS,11bR,13aR,13bR)-3a-((2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.135 g, 0.223 mmol) was added thionyl chloride (2.5 ml, 34.3 mmol). The clear, colorless solution was stirred at rt for 2.5 h the reaction was carefully quenched with water (20 mL) and the solids that formed were collected by filtration and were washed with water. The expected product, methyl 4-((1R,3aS,5aR,5bR,7aR,11aS,11bR,13aR,13bR)-3a-((2-chloroethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-fluorobenzoate, HCl (0.173 g, 0.262 mmol, 117% yield) was isolated as an off-white solid which was directly used in the next step with no additional purification. LCMS: m/e 624.6 (M+H)+, 2.42 min (method 11).

Step 3. Preparation of methyl 2-fluoro-4-((1R,3aS, 5aR,5bR,7aR,11aS,11bR,13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To a suspension of methyl 4-((1R,3aS,5aR,5bR,7aR,11aS,11bR,13aR,13bR)-3a-((2-chloroethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-fluorobenzoate, HCl (0.147 g, 0.223 mmol) in DMSO (2 mL) was added 1-methanesulfonyl-piperazine (0.073 g, 0.446 mmol) and Hunig's Base (0.195 mL, 1.115 mmol). Upon addition of the base, the solids dissolved. The solution was heated to 120° C. for 2 h then was cooled to rt, was diluted with water (20 mL) and was extracted with ethyl acetate (3×20 mL). The combined organic layers were washed with water (2×30 mL) then with brine (20 mL), then were dried over magnesium sulfate. The drying agent was removed by filtration and the filtrate was concentrated under reduced pressure. The residue was purified by flash chromatography in silica gel using a 0-50% ethyl acetate in hexanes gradient with 0.1% triethyl amine added to the mixture. The fractions containing the expected product were combined and were concentrated under reduced pressure to give methyl 2-fluoro-4-((1R,3aS,5aR,5bR,7aR,11aS,11bR,13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.056 g, 0.074 mmol, 33.4% yield) as an off-white solid. LCMS: m/e 752.7 (M+H)+, 1.95 min (method 2).

Step 4. To a solution of methyl 2-fluoro-4-((1R,3aS,5aR,5bR,7aR,11aS,11bR,13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.056 g, 0.074 mmol) in 1,4-dioxane (2 mL) was added NaOH (1N) (0.372 mL, 0.372 mmol). The mixture was heated to 60° C. for 6.5 h then was cooled to rt. The mixture was diluted with methanol and 1,4-dioxane, was filtered through a plug of glass wool and was purified by prep HPLC. The fractions containing the expected product were combined and were concentrated under reduced pressure to give 2-fluoro-4-((1R,3aS,5aR,5bR,7aR,11aS,11bR,13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (30.1 mg, 0.039 mmol, 52.0% yield) as a white solid. LCMS: m/e 738.6 (M+H)+, 1.66 min (method 2). $^1$H NMR (400 MHz, Acetic acid d$_4$) 67.92 (t, J=7.9 Hz, 1H), 7.04 (dd, J=8.0, 1.5 Hz, 1H), 7.01-6.96 (m, 1H), 5.38 (d, J=5.0 Hz, 1H), 4.81 (s, 1H), 4.70 (s, 1H), 3.59-3.25 (m, 8H), 3.15 (br. s., 4H), 2.90 (s, 3H), 2.94-2.81 (m, 1H), 1.72 (s, 3H), 1.21 (s, 3H), 1.09 (s, 3H), 1.04 (s, 3H), 0.99 (s, 3H), 0.97 (s, 3H), 2.23-0.83 (m, 22H).

Section B. Amines

Continued

Example B1

Preparation of 5-((1R,3aS,5aR,5bR,7aR,11aS,11bR, 13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)thiophene-2-carboxylic acid

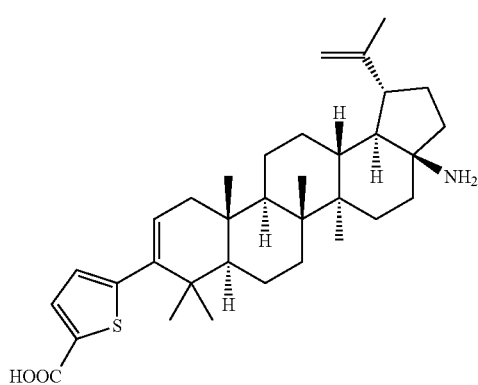

The title compound was prepared following the method described above for the synthesis of 4-((1R,3aS,5aR,5bR, 7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)-2-fluorobenzoic acid using 5-(methoxycarbonyl)thiophen-2-ylboronic acid as the coupling reagent in Step 1. The product was isolated as a white solid (2.7 mg, 44%). LCMS: m/e 536.30 (M+H)$^+$, 2.25 min (method 10). $^1$H NMR (500 MHz, Acetic) δ 7.77 (d, J=4.0 Hz, 1H), 6.98 (d, J=3.7 Hz, 1H), 5.87 (d, J=4.3 Hz, 1H), 4.88 (s, 1H), 4.75 (s, 1H), 2.79 (td, J=10.5, 6.7 Hz, 1H), 2.35-2.13 (m, 4H), 1.98-1.85 (m, 4H), 1.83-1.07 (m, 14H), 1.77 (s, 3H), 1.19 (s, 3H), 1.14 (s, 3H), 1.14 (s, 3H), 1.10 (s, 3H), 1.02 (s, 3H).

Example B2

Preparation of 4-((1S,3aS,5aR,5bR,7aS,9S,11aS, 11bR,13aR,13bR)-3a-((2-(1,1-dioxidothiomorpholino)ethyl)amino)-1-isopropyl-5a,5b,8,8,11a-pentamethylicosahydro-1H-cyclopenta[a]chrysen-9-yl)benzoic acid

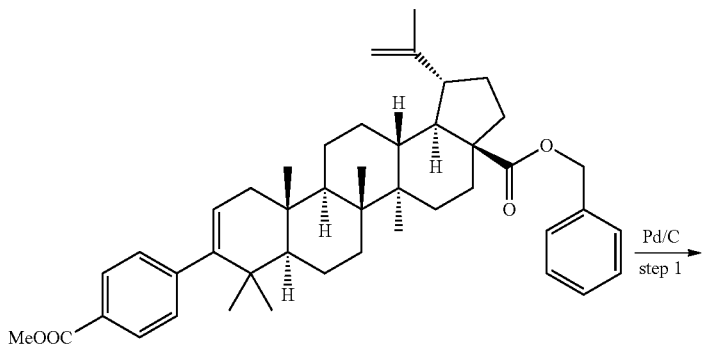

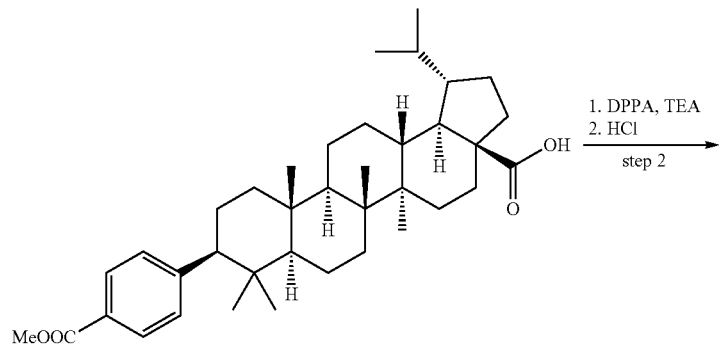

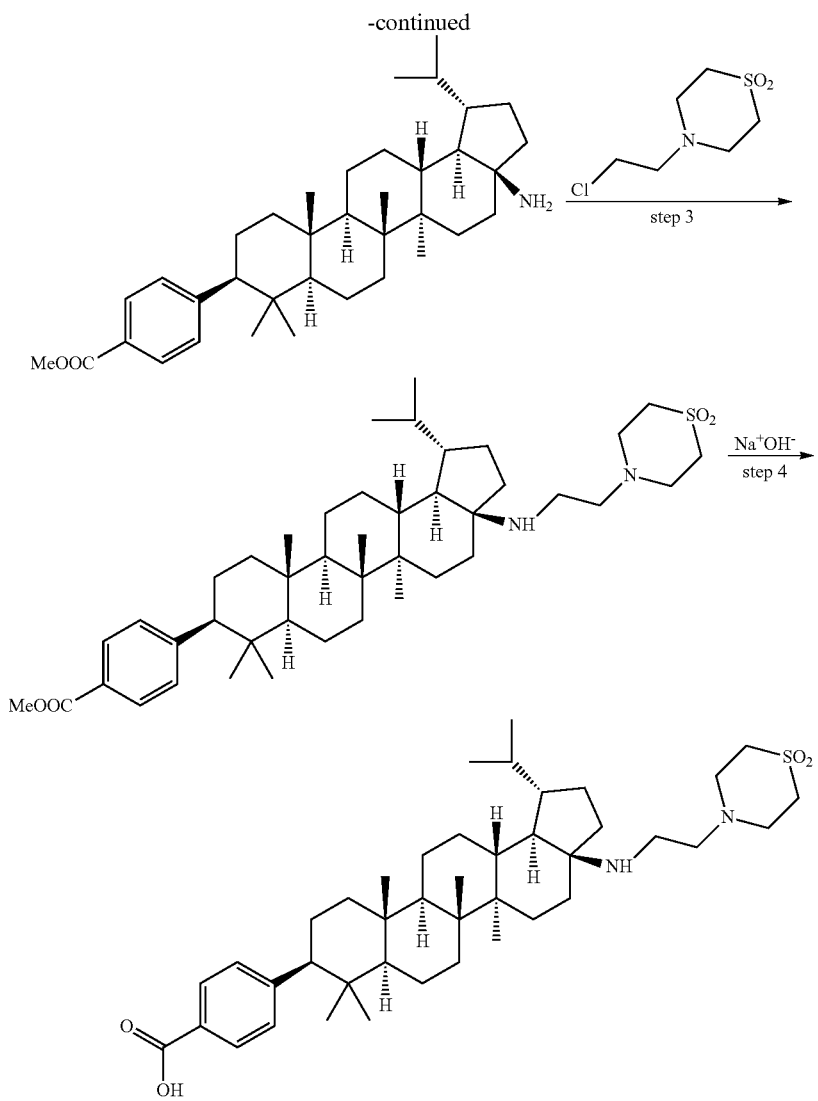

Step 1. Preparation of (1S,3aS,5aR,5bR,7aS,9S,11aS,11bR,13aR,13bR)-1-isopropyl-9-(4-(methoxycarbonyl)phenyl)-5a,5b,8,8,11a-pentamethylicosahydro-1H-cyclopenta[a]chrysene-3a-carboxylic acid A mixture of palladium on carbon (67.4 mg, 0.063 mmol) and (1R,3aS,5aR,5bR,7aR,11aS,11bR,13aR,13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (140 mg, 0.211 mmol) in methanol (2 mL) was stirred at 20° C. under hydrogen at 1 atmosphere of pressure for 20 hours. The reaction mixture was filtered through a celite pad to remove Pd/C. The filtrates were concentrated under reduced pressure to provide the title compound as a white solid (100 mg, 82%). LCMS: m/e 577.33 (M+H)+, 3.22 min (method 10).

Step 2. Preparation of methyl 4-((1S,3aS,5aR,5bR,7aS,9S,11aS,11bR,13aR,13bR)-3a-amino-1-isopropyl-5a,5b,8,8,11a-pentamethylicosahydro-1H-cyclopenta[a]chrysen-9-yl)benzoate A mixture of (1S,3aS,5aR,5bR,7aS,9S,11aS,11bR,13aR,13bR)-1-isopropyl-9-(4-(methoxycarbonyl)phenyl)-5a,5b,8,8,11a-pentamethylicosahydro-1H-cyclopenta[a]chrysene-3a-carboxylic acid (100 mg, 0.173 mmol), diphenyl phosphorazidate (0.056 mL, 0.260 mmol) and triethylamine (0.072 mL, 0.520 mmol) in toluene (4 mL) was refluxed for 18 hours. TLC indicated the consumption of starting material and the formation of desired product. The mixture was cooled to room temperature, filtered through a silica gel pad and the filtrates were concentrated under reduced pressure to produce the desired intermediate as colorless oil. To this intermediate (70 mg, 0.122 mmol) in THF (4 mL) was added HCl (0.037 mL, 1.220 mmol). The reaction mixture was stirred for 18 hours at room temperature. The reaction mixture was purified by chromatography in silica gel with 20-70% ethyl acetate/hexanes to provide the title compound as white solid (50 mg, 50%). LCMS: m/e 548.49 (M+H)+, 2.58 min (method 11).

Step 3. Preparation of methyl 4-((1S,3aS,5aR,5bR,7aS,9S,11aS,11bR,13aR,13bR)-3a-((2-(1,1-dioxidothiomorpholino)ethyl)amino)-1-isopropyl-5a,5b,8,8,11a-pentamethylicosahydro-1H-cyclopenta[a]chrysen-9-yl)benzoate A mixture of methyl 4-((1S,3aS,5aR,5bR,7aS,9S,11aS,11bR,13aR,13bR)-3a-amino-1-isopropyl-5a,5b,8,8,11a- pentamethylicosahydro-1H-cyclopenta[a]chrysen-9-yl)benzoate (50 mg, 0.091 mmol), 4-(2-chloroethyl)thiomorpholine 1,1-dioxide (54.1 mg, 0.274 mmol), potassium phosphate (77 mg, 0.365 mmol) and potassium iodide (36.4 mg, 0.219 mmol) in acetonitrile (2 mL) was heated up at 120° C. for 20 hours. The reaction mixture was quenched with distilled water (5 mL), extracted with dichloromethane (3×5 mL), the organic phases were combined, dried over sodium sulfate, filtered and concentrated under reduced pressure to provide the crude product as a yellow solid (40 mg, 62%). LCMS: m/e 709.53 (M+H)$^+$, 2.46 min (method 11).

Step 4. Preparation of 4-((1S,3aS,5aR,5bR,7aS,9S,11aS,11bR,13aR,13bR)-3a-((2-(1,1-dioxidothiomorpholino)ethyl)amino)-1-isopropyl-5a,5b,8,8,11a-pentamethylicosahydro-1H-cyclopenta[a]chrysen-9-yl)benzoic acid A mixture of methyl 4-((1S,3aS,5aR,5bR,7aS,9S,11aS,11bR,13aR,13bR)-3a-((2-(1,1-dioxidothiomorpholino)ethyl)amino)-1-isopropyl-5a,5b,8,8,11a-pentamethylicosahydro-1H-cyclopenta[a]chrysen-9-yl)benzoate (40 mg, 0.056 mmol) and sodium hydroxide (0.564 mL, 0.564 mmol) in dioxane (1 mL) was heated up at 80° C. for 3 hours. The reaction mixture was filtered and purified by HPLC to provide the title compound as white solid (30 mg, 73%). LCMS: m/e 695.46 (M+H)$^+$, 2.55 min (method 10). $^1$H NMR (500 MHz, Acetic) δ 8.02 (d, J=8.5 Hz, 2H), 7.36 (d, J=8.5 Hz, 2H), 3.44-3.36 (m, 1H), 3.35-3.21 (m, 6H), 3.19-2.99 (m, 5H), 2.50 (dd, J=13.0, 2.9 Hz, 1H), 2.34-1.01 (m, 26H), 1.28 (s, 3H), 1.13 (s, 3H), 1.10 (s, 3H), 0.93 (d, J=6.7 Hz, 3H), 0.85 (d, J=6.7 Hz, 3H), 0.84 (s, 3H), 0.80 (s, 3H).

Example B3

Preparation of 4-((1S,3aS,5aR,5bR,7aS,9S,11aS,11bR,13aR,13bR)-3a-amino-1-isopropyl-5a,5b,8,8,11a-pentamethylicosahydro-1H-cyclopenta[a]chrysen-9-yl)benzoic acid

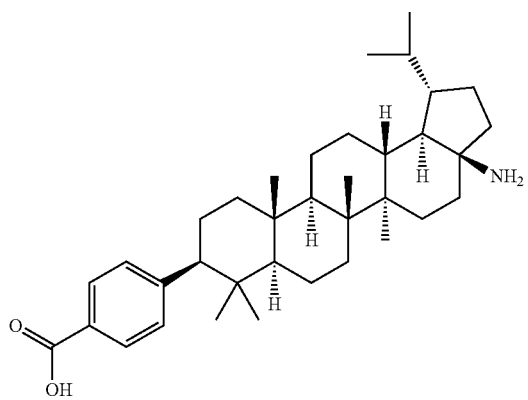

The title compound was prepared following the method described above for the synthesis of 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-fluorobenzoic acid using methyl 4-((1S,3aS,5aR,5bR,7aS,9S,11aS,11bR,13aR,13bR)-3a-amino-1-isopropyl-5a,5b,8,8,11a-pentamethylicosahydro-1H-cyclopenta[a]chrysen-9-yl)benzoate as the starting material in Step 5. The product was isolated as a white solid (12 mg, 47%). LCMS: m/e 532.43 (M–H)$^-$, 2.37 min (method 10). $^1$H NMR (500 MHz, METHANOL-d$_4$) δ 7.84 (d, J=8.2 Hz, 2H), 7.19 (d, J=8.2 Hz, 2H), 2.42 (dd, J=13.0, 2.9 Hz, 1H), 2.18 (qd, J=13.3, 3.1 Hz, 1H), 2.07-1.24 (m, 25H), 1.16 (s, 3H), 1.07 (s, 3H), 1.03 (s, 3H), 0.93 (d, J=6.7 Hz, 3H), 0.83 (d, J=6.7 Hz, 3H), 0.79 (s, 3H), 0.74 (s, 3H).

Example B4

Preparation of 4-((1S,3aS,5aR,5bR,7aS,9S,11aS,11bR,13aR,13bR)-1-isopropyl-5a,5b,8,8,11a-pentamethyl-3a-((2-morpholinoethyl)amino)icosahydro-1H-cyclopenta[a]chrysen-9-yl)benzoic acid

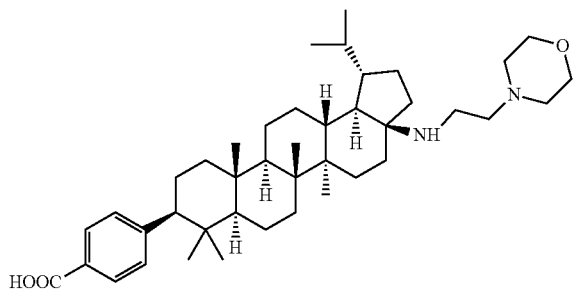

The title compound was prepared following the method described above for the synthesis of 4-((1S,3aS,5aR,5bR,7aS,9S,11aS,11bR,13aR,13bR)-3a-((2-(1,1-dioxidothiomorpholino)ethyl)amino)-1-isopropyl-5a,5b,8,8,11a-pentamethylicosahydro-1H-cyclopenta[a]chrysen-9-yl)benzoic acid using 4-(2-chloroethyl)morpholine as the alkylating reagent in Step 3. The product was isolated as a colorless oil (4 mg, 39%). LCMS: m/e 647.58 (M+H)$^+$, 2.35 min (method 11). $^1$H NMR (500 MHz, Acetic) δ 8.02 (d, J=8.2 Hz, 2H), 7.36 (d, J=8.2 Hz, 2H), 3.94 (d, J=3.7 Hz, 4H), 3.73-3.44 (m, 4H), 3.27 (br. s., 4H), 2.50 (d, J=10.4 Hz, 1H), 2.32-1.01 (m, 26H), 1.21 (s, 3H), 1.12 (s, 3H), 1.08 (s, 3H), 0.93 (d, J=6.7 Hz, 3H), 0.86 (d, J=6.7 Hz, 3H), 0.83 (s, 3H), 0.79 (s, 3H).

Example B5

Preparation of 4-((1S,3aS,5aR,5bR,7aS,9S,11aS,11bR,13aR,13bR)-3a-((2-(dimethylamino)ethyl)amino)-1-isopropyl-5a,5b,8,8,11a-pentamethylicosahydro-1H-cyclopenta[a]chrysen-9-yl)benzoic acid

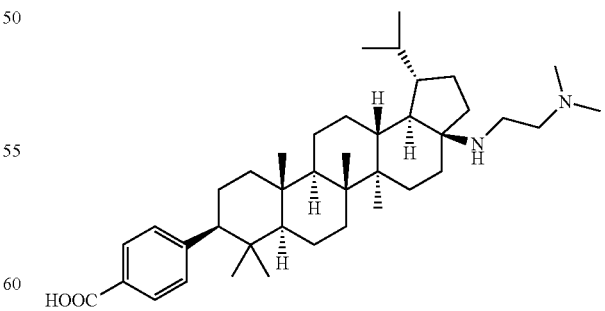

The title compound was prepared following the method described above for the synthesis of 4-((1S,3aS,5aR,5bR,7aS,9S,11aS,11bR,13aR,13bR)-3a-((2-(1,1-dioxidothiomorpholino)ethyl)amino)-1-isopropyl-5a,5b,8,8,11a-pentamethylicosahydro-1H-cyclopenta[a]chrysen-9-yl)benzoic acid using 2-chloro-N,N-dimethylethanamine as the alkylating reagent in Step 3. The product was isolated as a colorless oil (0.9 mg, 37%). LCMS: m/e 605.56 (M+H)+, 2.35 min (method 11). $^1$H NMR (500 MHz, Acetic) δ 8.02 (d, J=8.2 Hz, 2H), 7.36 (d, J=8.2 Hz, 2H), 3.89-3.72 (m, 2H), 3.70-3.55 (m, 1H), 3.07-2.91 (m, 1H), 3.00 (s, 6H), 2.60-2.40 (m, 1H), 2.34-1.04 (m, 26H), 1.18 (s, 3H), 1.12 (s, 3H), 1.07 (s, 3H), 0.93 (d, J=6.7 Hz, 3H), 0.86 (d, J=6.7 Hz, 3H), 0.83 (s, 3H), 0.79 (s, 3H).

Example B6

Preparation of 4-((1S,3aS,5aR,5bR,7aS,9S,11aS, 11bR,13aR,13bR)-3a-(bis(2-(dimethylamino)ethyl) amino)-1-isopropyl-5a,5b,8,8,11a-pentamethylicosahydro-1H-cyclopenta[a]chrysen-9-yl)benzoic acid

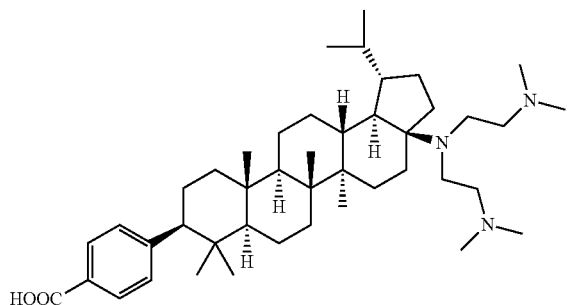

The title compound was obtained as a side product in the preparation 4-((1S,3aS,5aR,5bR,7aS,9S,11aS,11bR,13aR, 13bR)-3a-((2-(dimethylamino)ethyl)amino)-1-isopropyl-5a, 5b,8,8,11a-pentamethylicosahydro-1H-cyclopenta[a]chrysen-9-yl)benzoic acid. The product was isolated as a colorless oil (0.7 mg, 26%). LCMS: m/e 676.63 (M+H)+, 2.33 min (method 11). $^1$H NMR (500 MHz, Acetic) δ 8.02 (d, J=8.2 Hz, 2H), 7.35 (d, J=8.2 Hz, 2H), 4.33-4.09 (m, 4H), 3.85 (br. s., 3H), 3.73 (br. s., 1H), 3.40 (s, 6H), 3.01 (s, 6H), 2.50 (d, J=14.0 Hz, 1H), 2.37-1.04 (m, 26H), 1.17 (s, 3H), 1.12 (s, 3H), 1.07 (s, 3H), 0.93 (d, J=6.7 Hz, 3H), 0.87 (d, J=6.7 Hz, 3H), 0.8 s (s, 3H), 0.79 (s, 3H).

Example B7A and B7B

Preparation of (2S,3S,4S,5R,6R)-6-((4-((1R,3aS, 5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoyl)oxy)-3,4,5-trihydroxytetrahydro-2H-pyran-2-carboxylic acid

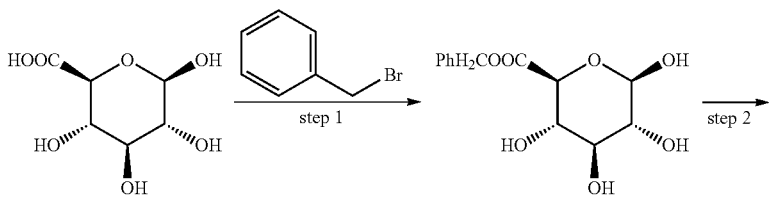

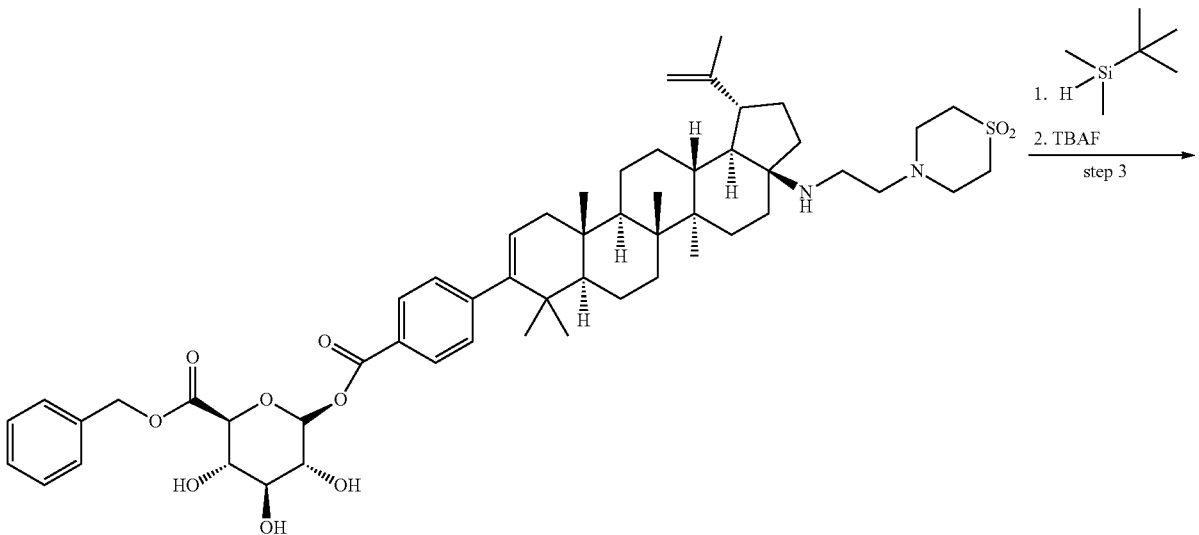

Example B7A

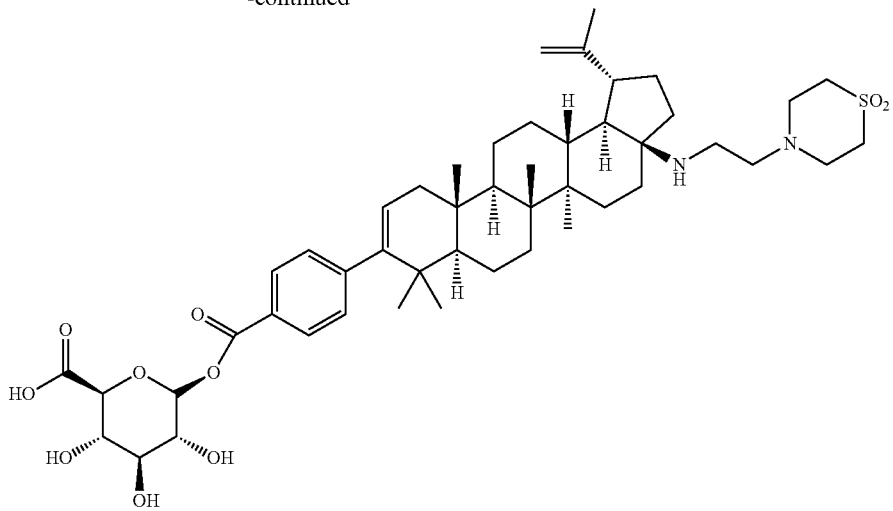

Example B7B

Step 1. Preparation of (2S,3S,4S,5R,6R)-benzyl 3,4,5,6-tetrahydroxytetrahydro-2H-pyran-2-carboxylate

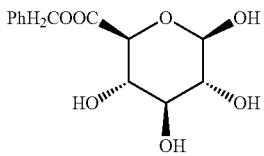

To a solution of (2S,3S,4S,5R,6R)-3,4,5,6-tetrahydroxytetrahydro-2H-pyran-2-carboxylic acid (1 g, 5.15 mmol) and TBAF in THF (6.18 mL, 6.18 mmol) in DMF (7 mL) was slowly added (bromomethyl)benzene (0.925 g, 5.41 mmol) at 0° C. The clear solution was warmed up to room temperature slowly and let it stir for 17 hours. TLC indicated the reaction was completed (20% iPrOH/CH$_2$Cl$_2$). The solvent was removed and the reaction residue was purified by silica gel chromatography with 10-20% iPrOH/CH$_2$Cl$_2$ to provide the desired product as a colorless oil (950 mg, 65%). LCMS: m/e 283.31 (M−H)$^-$, 2.55 min (method 10).

Step 2. Preparation of (2S,3S,4S,5R,6R)-benzyl 6-((4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoyl)oxy)-3,4,5-trihydroxytetrahydro-2H-pyran-2-carboxylate

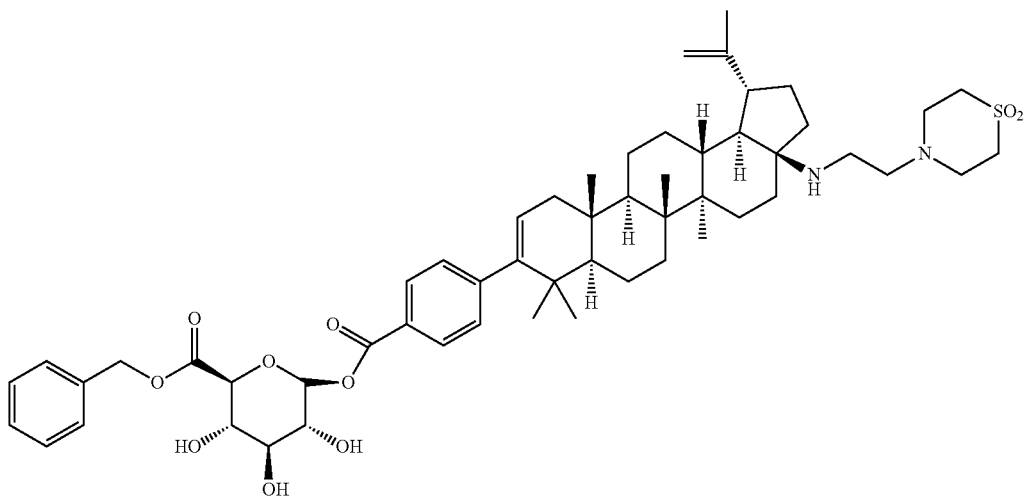

A mixture of (2S,3S,4S,5R)-benzyl 3,4,5,6-tetrahydroxytetrahydro-2H-pyran-2-carboxylate (61.7 mg, 0.217 mmol), 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (100 mg, 0.145 mmol), HATU (88 mg, 0.232 mmol) and N-methylmorpholine (0.048 mL, 0.434 mmol) in dioxane (3 mL) was stirred overnight at room temperature. The reaction mixture was filtered, the clear solution was purified by prep HPLC with acetonitrile/water/ammonium acetate to provide the desired product as white solid (20 mg, 14%). LCMS: m/e 957.7 (M+H)$^+$, 2.36 min (method 6). $^1$H NMR (500 MHz, Acetic) δ 8.05 (d, J=8.2 Hz, 2H), 7.58-7.14 (m, 7H), 5.95 (d, J=7.6 Hz, 1H), 5.38 (d, J=4.6 Hz, 1H), 5.26 (s, 2H), 4.84 (s, 1H), 4.74 (s, 1H), 4.30 (d, J=9.5 Hz, 1H), 4.05-3.78 (m, 3H), 3.46 (d, J=11.9 Hz, 1H), 3.38-3.22 (m, 6H), 3.20-3.11 (m, 3H), 3.07 (br. s., 2H), 2.95 (dt, J=10.8, 5.5 Hz, 1H), 2.42-1.01 (m, 22H), 1.77 (s, 3H), 1.30 (s, 3H), 1.15 (s, 3H), 1.12 (s, 3H), 1.03 (s, 3H), 1.00 (s, 3H).

Step 3. Preparation of (2S,3S,4S,5R,6R)-6-((4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoyl)oxy)-3,4,5-trihydroxytetrahydro-2H-pyran-2-carboxylic acid

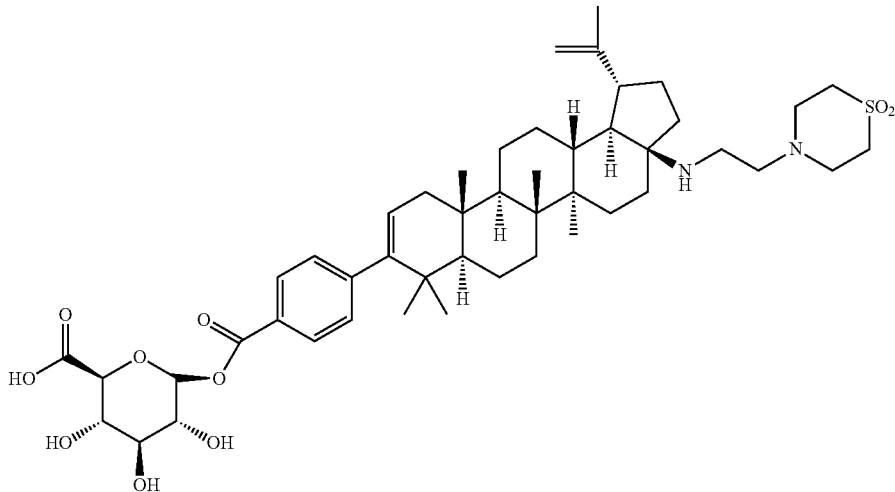

A mixture of (2S,3S,4S,5R,6R)-benzyl 6-((4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoyl)oxy)-3,4,5-trihydroxytetrahydro-2H-pyran-2-carboxylate (8 mg, 8.36 mmol), tert-butyldimethylsilane (1.943 mg, 0.017 mmol), palladium acetate (3.75 mg, 0.017 mmol) and triethylamine (5.82 µl, 0.042 mmol) in dichloroethane (1 mL) was heated up at 60° C. for 2 hours. The reaction mixture was cooled to room temperature, filtered and the filtrates were concentrated to provide the residue. To this residue in THF (1.0 mL) was added TBAF (10.93 mg, 0.042 mmol), the reaction mixture was stirred for 1 hours. The reaction mixture was then purified by prep. HPLC to provide the desired product as a colorless oil (4 mg, 52%). LCMS: m/e 867.69 (M+H)$^+$, 2.42 min (method 10). $^1$H NMR (500 MHz, Acetic) δ 8.06 (d, J=8.2 Hz, 2H), 7.31 (d, J=8.2 Hz, 2H), 5.96 (d, J=7.9 Hz, 1H), 5.37 (d, J=4.4 Hz, 1H), 4.84 (s, 1H), 4.74 (s, 1H), 4.40-4.16 (m, 1H), 4.02-3.76 (m, 3H), 3.46 (d, J=12.3 Hz, 1H), 3.37-3.22 (m, 6H), 3.20-3.11 (m, 3H), 3.07 (br. s., 2H), 3.00-2.82 (m, 1H), 2.37-1.03 (m, 22H), 1.76 (s, 3H), 1.29 (s, 3H), 1.14 (s, 3H), 1.10 (s, 3H), 1.02 (s, 3H), 0.99 (s, 3H).

Example B8

Preparation of 4-((1R,3aS,5aR,5bR,7aR,11aS,11bR,13aR,13bR)-3a-((2-((1,1-dioxidotetrahydrothiophen-3-yl)amino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

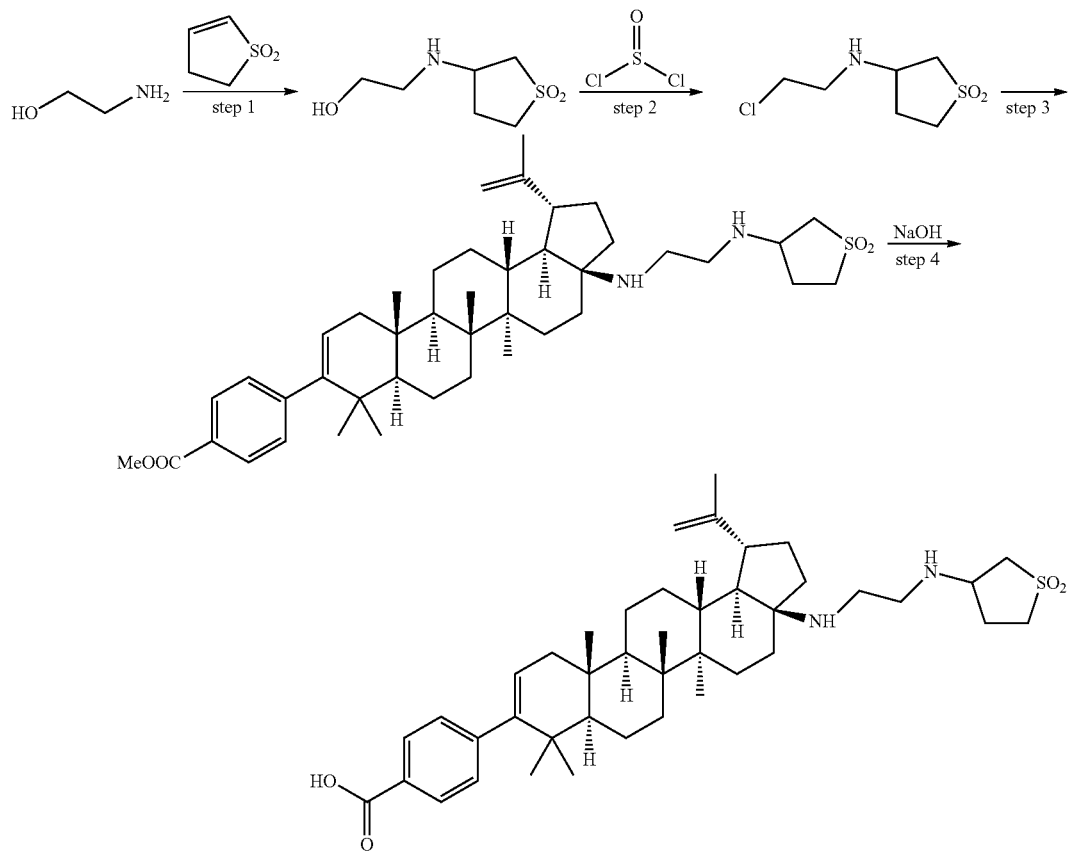

Step 1. Preparation of 3-((2-hydroxyethyl)amino)tetrahydrothiophene 1,1-dioxide

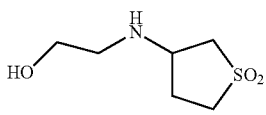

A mixture of 2-aminoethanol (310 mg, 5.08 mmol), triethylamine (514 mg, 5.08 mmol) and 2,3-dihydrothiophene 1,1-dioxide (200 mg, 1.693 mmol) in ethanol (3 mL) was heated up at 78° C. for 16 hours. TLC indicated the starting material was consumed and desired product was formed (30% methanol/ethyl acetate). The reaction mixture was concentrated under reduced pressure, the residue was purified by silica gel chromatography with 0-35% methanol/ethyl acetate to provide the title compound as a colorless oil (260 mg, 86%). $^1$H NMR (400 MHz, CHLOROFORM-d) δ 3.78-3.56 (m, 3H), 3.38-3.21 (m, 2H), 3.14-3.00 (m, 1H), 2.94 (dd, J=13.3, 6.0 Hz, 1H), 2.85-2.68 (m, 2H), 2.53-2.34 (m, 1H), 2.22-2.03 (m, 1H).

Step 2. Preparation of 3-((2-chloroethyl)amino)tetrahydrothiophene 1,1-dioxide

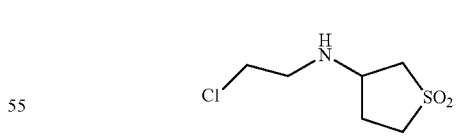

A mixture of 3-((2-hydroxyethyl)amino)tetrahydrothiophene 1,1-dioxide (260 mg, 1.451 mmol) and sulfurous dichloride (863 mg, 7.25 mmol) in dichloroethane (3 mL) was heated up at 78° C. for 3 hours. The mixture was cooled to room temperature and concentrated under reduced pressure to provide the black oil. To this black oil was added THF (5 mL) and dichloromethane (5 mL), grey-white solid was observed. The solid was filtered and collected to provide the desired product as a grey solid (230 mg, 80%). LCMS: m/e 198.1 (M+H)$^+$, 0.60 min (method 6).

Step 3. Preparation of 4-((1R,3aS,5aR,5bR,7aR, 11aS,11bR,13aR,13bR)-3a-((2-((1,1-dioxidotetrahydrothiophen-3-yl)amino)ethyl)amino)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoic acid

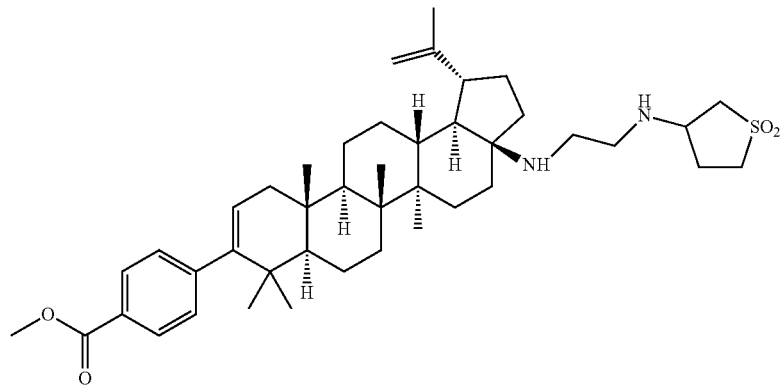

A mixture of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (50 mg, 0.092 mmol), 3-((2-chloroethyl)amino) tetrahydrothiophene 1,1-dioxide (45.4 mg, 0.230 mmol), potassium phosphate (58.5 mg, 0.276 mmol) and potassium iodide (30.5 mg, 0.184 mmol) in acetonitrile (1 mL) was heated up at 120° C. for 18 hours. The reaction mixture was quenched with distilled water (3 mL), extracted with dichloromethane (3×3 mL), the organic phases were combined, dried over sodium sulfate, filtered and concentrated under reduced pressure to provide the crude product as a white solid (40 mg, 62%). LCMS: m/e 705.48 (M+H)$^+$, 2.44 min (method 11).

Step 4. Preparation of 4-((1R,3aS,5aR,5bR,7aR, 11aS,11bR,13aR,13bR)-3a-((2-((1,1-dioxidotetrahydrothiophen-3-yl)amino)ethyl)amino)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoic acid

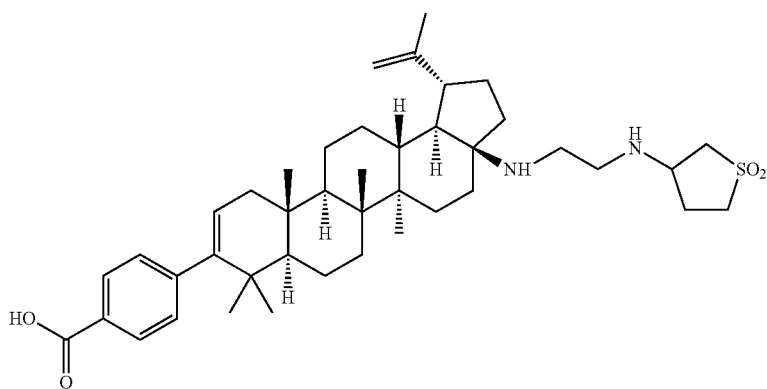

A mixture of methyl 4-((1R,3aS,5aR,5bR,7aR,11aS,11bR,13aR,13bR)-3a-((2-((1,1-dioxidotetrahydrothiophen-3-yl)amino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (40 mg, 0.057 mmol) and sodium hydroxide (0.567 mL, 0.567 mmol) in dioxane (1 mL) was heated up at 78° C. for 3 hours. The reaction mixture was cooled to room temperature, filtered and the clear solution was purified by HPLC to provide the title compound as a white solid (26 mg, 63%). LCMS: m/e 691.46 (M+H)$^+$, 2.24 min (method 11). $^1$H NMR (500 MHz, Acetic) δ 8.04 (d, J=8.2 Hz, 2H), 7.30 (d, J=8.2 Hz, 2H), 5.37 (d, J=4.9 Hz, 1H), 4.87 (s, 1H), 4.75 (s, 1H), 4.06 (quin, J=7.7 Hz, 1H), 3.67-3.45 (m, 4H), 3.44-3.34 (m, 1H), 3.33-3.11 (m, 2H), 2.92-2.80 (m, 1H), 2.77-2.59 (m, 1H), 2.42-2.29 (m, 1H), 2.26-1.02 (m, 23H), 1.77 (s, 3H), 1.22 (s, 3H), 1.13 (s, 3H), 1.10 (s, 3H), 1.02 (s, 3H), 1.00 (s, 3H).

Example B9

Preparation of 4-((1R,3aS,5aR,5bR,7aR,11aS,11bR,13aR,13bR)-3a-((2-((1,1-dioxidotetrahydrothiophen-3-yl)amino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

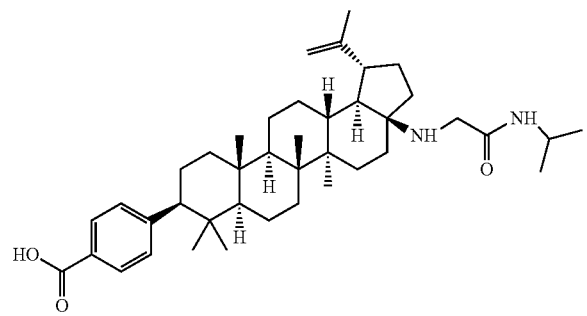

A mixture of 4-((1R,3aS,5aR,5bR,7aR,11aS,11bR,13aR,13bR)-3a-((2-(isopropylamino)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (15 mg, 0.024 mmol) and Pd/C (7.61 mg, 7.16 mmol) in methanol (1 mL) and ethyl acetate (1.000 mL) was stirred for 12 hours at room temperature under hydrogen at 1 atmosphere of pressure. The reaction mixture was filtered and the solution was purified by HPLC to provide the title compound as a white solid (6 mg, 38%). LCMS: m/e 633.48 (M+H)$^+$, 2.62 min (method 10). $^1$H NMR (500 MHz, Acetic) δ 8.02 (d, J=8.2 Hz, 2H), 7.36 (d, J=8.5 Hz, 2H), 4.17 (d, J=15.6 Hz, 1H), 4.09 (quin, J=6.6 Hz, 1H), 3.82 (d, J=15.3 Hz, 1H), 2.50 (dd, J=13.1, 2.7 Hz, 1H), 2.34-1.05 (m, 26H), 1.27 (s, 3H), 1.19 (s, 3H), 1.18 (s, 3H), 1.13 (s, 3H), 1.08 (s, 3H), 0.94 (d, J=6.7 Hz, 3H), 0.86 (d, J=6.7 Hz, 3H), 0.84 (s, 3H), 0.80 (s, 3H).

Example B10

Preparation of 4-((1S,3aS,5aR,5bR,7aS,9S,11aS,11bR,13aR,13bR)-1-isopropyl-5a,5b,8,8,11a-pentamethyl-3a-((2-(methylamino)-2-oxoethyl)amino)icosahydro-1H-cyclopenta[a]chrysen-9-yl)benzoic acid

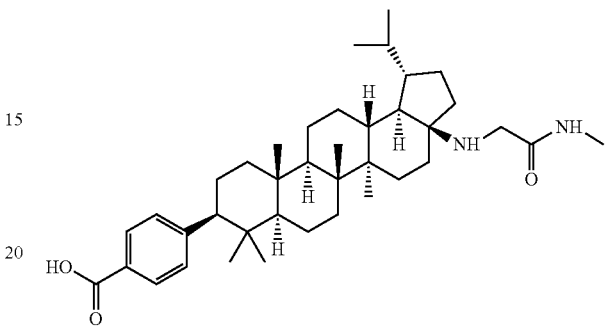

The title compound was prepared following the method described above for the synthesis 4-((1R,3aS,5aR,5bR,7aR,11aS,11bR,13aR,13bR)-3a-((2-((1,1-dioxidotetrahydrothiophen-3-yl)amino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 4-((1R,3aS,5aR,5bR,7aR,11aS,11bR,13aR,13bR)-5a,5b,8,8,11a-pentamethyl-3a-((2-(methylamino)-2-oxoethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid as the starting material. The product was isolated as a white solid (3 mg, 28%). LCMS: m/e 605.45 (M+H)$^+$, 2.58 min (method 10). $^1$H NMR (500 MHz, Acetic) δ 8.02 (d, J=8.2 Hz, 2H), 7.36 (d, J=8.2 Hz, 2H), 4.22 (d, J=15.6 Hz, 1H), 3.85 (d, J=15.6 Hz, 1H), 2.87 (s, 3H), 2.50 (dd, J=13.1, 2.4 Hz, 1H), 2.35-1.02 (m, 26H), 1.28 (s, 3H), 1.13 (s, 3H), 1.08 (s, 3H), 0.95 (d, J=6.7 Hz, 3H), 0.87 (d, J=6.7 Hz, 3H), 0.84 (s, 3H), 0.80 (s, 3H).

Example B11

Preparation of 4-((1S,3aS,5aR,5bR,7aR,11aS,11bR,13aR,13bR)-1-isopropyl-5a,5b,8,8,11a-pentamethyl-3a-((3-morpholinopropyl)amino)-2,3,3a,4,5,5a,5b,6,7,7a,8,11,11a,11b,12,13,13a,13b-octadecahydro-1H-cyclopenta[a]chrysen-9-yl)benzoic acid

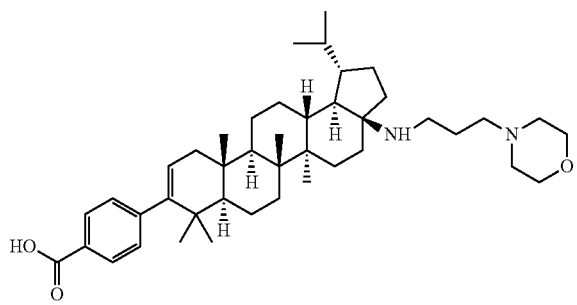

The title compound was prepared following the method described above for the synthesis 4-((1R,3aS,5aR,5bR,7aR,11aS,11bR,13aR,13bR)-3a-((2-((1,1-dioxidotetrahydrothiophen-3-yl)amino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 4-((1R,3aS,5aR,5bR,7aR,11aS,11bR,13aR,13bR)-5a,5b,8,8,11a-pentamethyl-3a-((3-morpholinopropyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid as the starting material. The product was isolated as a white solid (5 mg, 40%). LCMS: m/e 659.55 (M+H)$^+$, 2.86 min (method 10). $^1$H NMR (500 MHz, Acetic) δ 8.04 (d, J=8.5 Hz, 2H), 7.30 (d, J=8.2 Hz, 2H), 5.38 (d, J=4.6 Hz, 1H), 3.98 (br. s., 4H), 3.47-3.14 (m, 6H), 2.58-2.34 (m, 1H), 2.30-1.04 (m, 27H), 1.21 (s, 3H), 1.11 (s, 3H), 1.11 (s, 3H), 1.02 (s, 3H), 1.00 (s, 3H), 0.93 (d, J=6.7 Hz, 4H), 0.86 (d, J=6.7 Hz, 3H).

Example B12

Preparation of 4-((1R,3aS,5aR,5bR,7aR,11aS,11bR,13aR,13bR)-3a-((2-carboxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

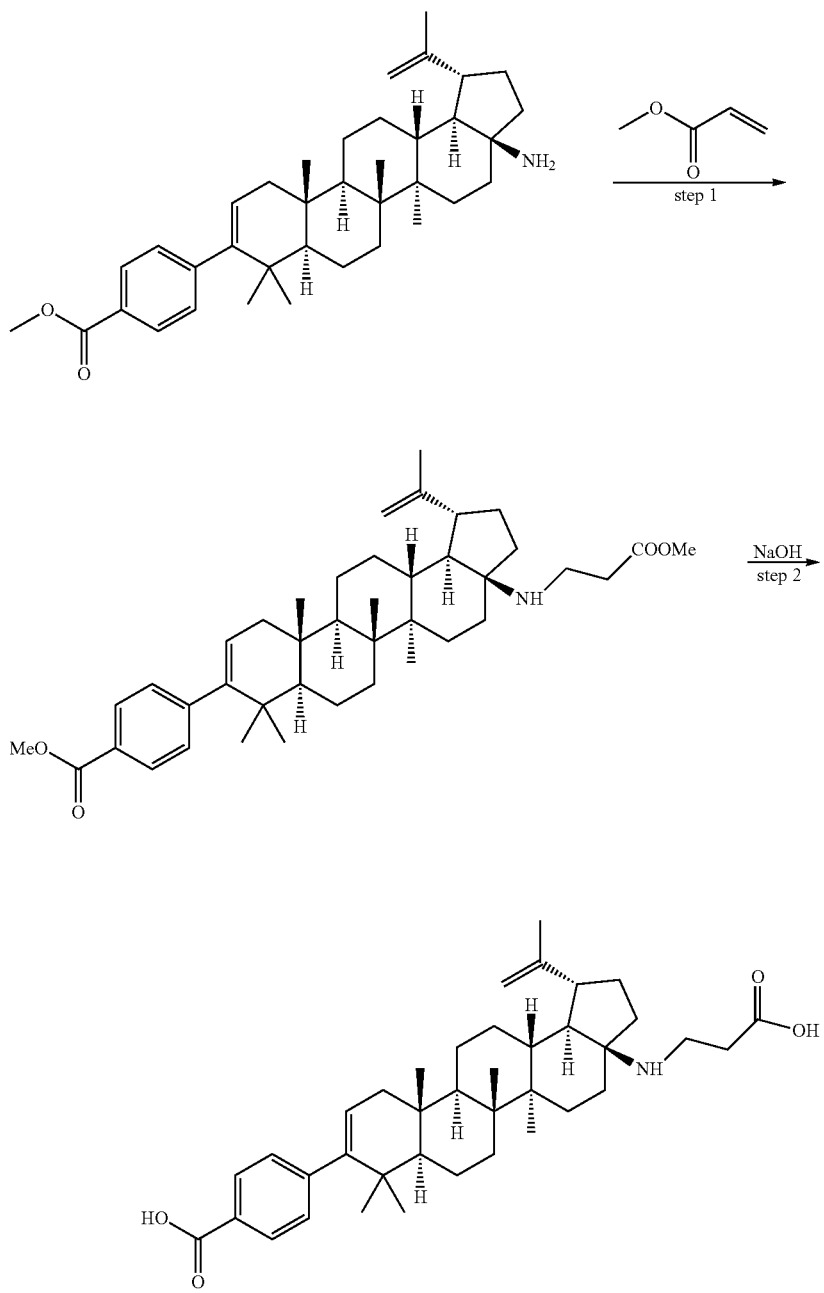

Step 1. Preparation of methyl 4-((1R,3aS,5aR,5bR,7aR,11aS,11bR,13aR,13bR)-3a-((3-methoxy-3-oxopropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate A mixture of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (20 mg, 0.037 mmol), methyl acrylate (0.013 mL, 0.147 mmol) and triethylamine (0.026 mL, 0.184 mmol) in ethanol (1 mL) was refluxed for 5 hours. The reaction mixture was cooled to room temperature and then concentrated under reduced pressure to provide the desired product as a yellow oil (15 mg 65%). LCMS: m/e 630.43 (M+H)$^+$, 3.81 min (method 10).

Step 2. Preparation of 4-((1R,3aS,5aR,5bR,7aR,11aS,11bR,13aR,13bR)-3a-((2-carboxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid A mixture of methyl 4-((1R,3aS,5aR,5bR,7aR,11aS,11bR,13aR,13bR)-3a-((3-methoxy-3-oxopropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (15 mg, 0.024 mmol) and sodium hydroxide (0.238 mL, 0.238 mmol) in dioxane (1 mL) was heated up at 80° C. for 3 hours. The reaction mixture was cooled to room temperature and then filtered, the clear solution was purified by HPLC to provide the title compound as a white solid (5 mg, 33%). LCMS: m/e 602.43 (M+H)$^+$, 2.25 min (method 10). $^1$H NMR (500 MHz, Acetic) δ 8.04 (d, J=8.2 Hz, 2H), 7.30 (d, J=8.2 Hz, 2H), 5.37 (d, J=4.9 Hz, 1H), 4.86 (s, 1H), 4.74 (s, 1H), 3.39 (t, J=4.4 Hz, 2H), 3.17-3.02 (m, 1H), 2.98-2.80 (m, 2H), 2.31-1.02 (m, 22H), 1.77 (s, 3H), 1.24 (s, 3H), 1.14 (s, 3H), 1.09 (s, 3H), 1.02 (s, 3H), 1.00 (s, 3H).

Example B13

Preparation of 4-((1R,3aS,5aR,5bR,7aR,11aS,11bR,13aR,13bR)-3a-((2-(4-(tert-butoxycarbonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

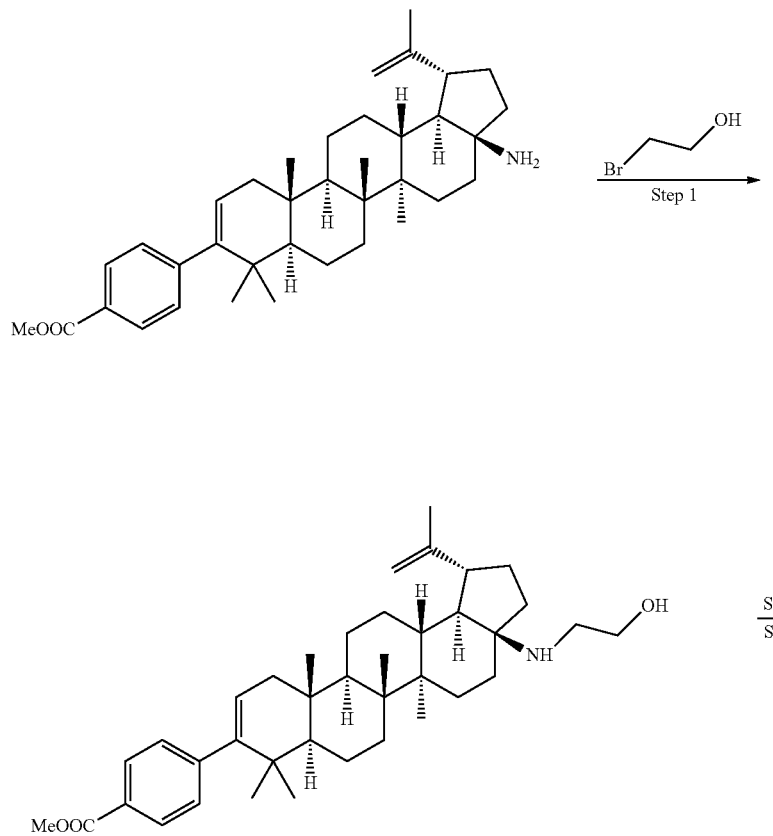

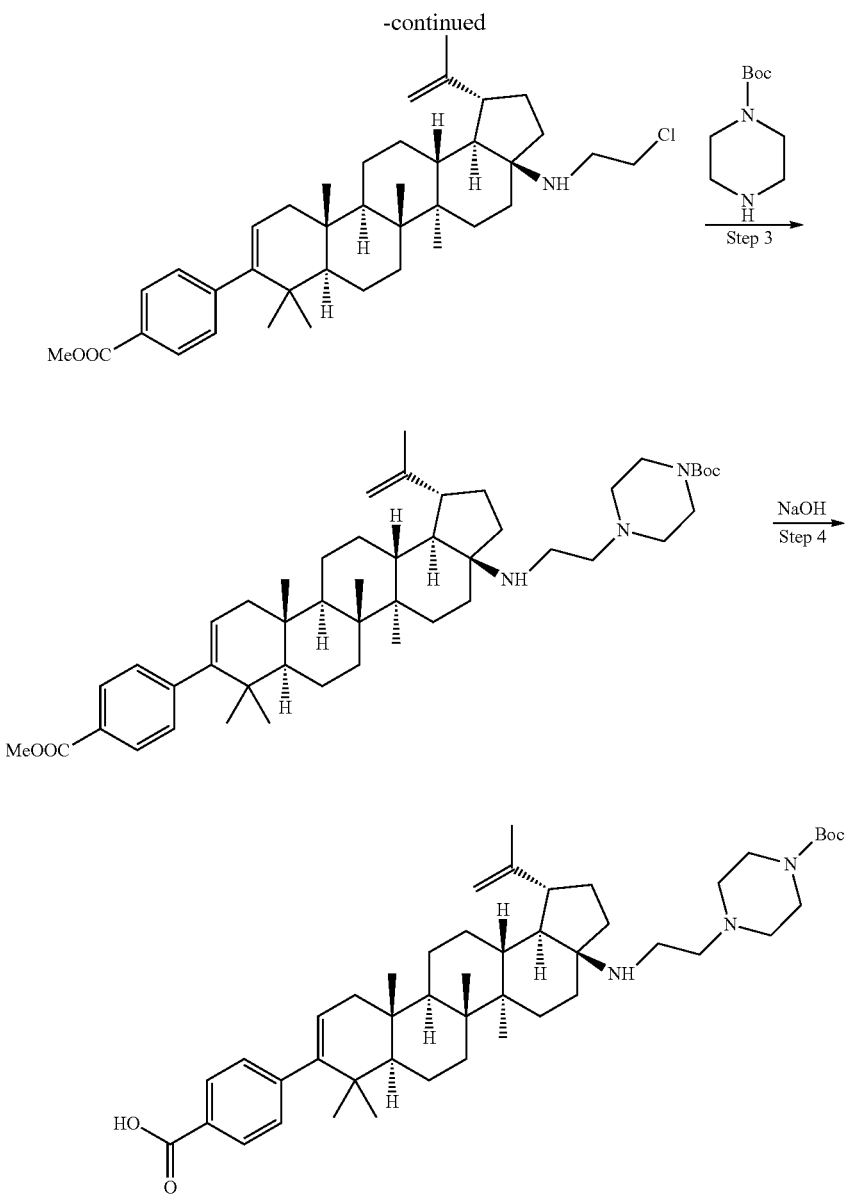

Step 1. Preparation of methyl 4-((1R,3aS,5aR,5bR, 7aR,11aS,11bR,13aR,13bR)-3a-((2-hydroxyethyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate A mixture of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (1500 mg, 2.76 mmol), 2-bromoethanol (1034 mg, 8.27 mmol), potassium phosphate (1756 mg, 8.27 mmol) and potassium iodide (916 mg, 5.52 mmol) in acetonitrile (10 mL) was heated up at 120° C. for 15 hours. The reaction mixture was poured into distilled water (40 mL). The white precipitate was filtered and washed with distilled water (100 mL). The white solid was dried under vacuum to provide the desired product (1.4 g, 86%). LCMS: m/e 588.5 (M+H)$^+$, 2.40 min (method 11).

Step 2. Preparation of methyl 4-((1R,3aS,5aR,5bR, 7aR,11aS,11bR,13aR,13bR)-3a-((2-chloroethyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate A mixture of methyl 4-((1R,3aS,5aR,5bR,7aR,11aS, 11bR,13aR,13bR)-3a-((2-hydroxyethyl)amino)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate (1400 mg, 2.381 mmol) and thionyl chloride (1.738 mL, 23.81 mmol) in dichloroethane (15 mL) was heated up at 60° C. for 2 hours. The reaction mixture was concentrated under reduced pressure to provide the desired product as brown solid (1.3 g, 90%). LCMS: m/e 606.48 (M+H)$^+$, 2.46 min (method 11).

Step 3. Preparation of tert-butyl 4-(2-(((1R,3aS,5aR, 5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)piperazine-1-carboxylate A mixture of methyl 4-((1R,3aS,5aR,5bR,7aR,11aS,11bR,13aR,13bR)-3a-((2-chloroethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (230 mg, 0.379 mmol), Hunig's Base (0.331 mL, 1.895 mmol) and tert-butyl piperazine-1-carboxylate (141 mg, 0.759 mmol) in DMSO (3 mL) was heated up at 120° C. for 1 hour. The reaction mixture was quenched with water (10 mL), extracted with ethyl acetate (3×8 mL), the extracts were combined, dried over sodium sulfate, filtered and concentrated under reduced pressure to provide the crude, the crude was purified by silica gel chromatography with 0-30% ethyl acetate/hexanes to provide the desired product as a white solid (150 mg, 52%). LCMS: m/e 756.66 (M+H)$^+$, 2.50 min (method 11).

Step 4. Preparation of 4-((1R,3aS,5aR,5bR,7aR,11aS,11bR,13aR,13bR)-3a-((2-(4-(tert-butoxycarbonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid A mixture of tert-butyl 4-(2-(((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)piperazine-1-carboxylate (4 mg, 5.29 μmol) and sodium hydroxide (0.053 mL, 0.053 mmol) in dioxane (1 mL) was heated up at 80° C. for 3 hours. The reaction mixture was filtered and the clear solution was purified by HPLC to provide the desired product as white solid (1.6 mg, 39%). LCMS: m/e 742.65 (M−H)$^-$, 2.68 min (method 10). $^1$H NMR (500 MHz, Acetic) δ 8.03 (d, J=8.2 Hz, 2H), 7.30 (d, J=8.2 Hz, 2H), 5.37 (d, J=4.6 Hz, 1H), 4.86 (s, 1H), 4.75 (s, 1H), 3.73 (br. s., 4H), 3.66-3.45 (m, 4H), 3.21 (br. s., 4H), 2.98-2.75 (m, 1H), 2.31-1.00 (m, 22H), 1.77 (s, 3H), 1.50 (s, 9H), 1.23 (s, 3H), 1.13 (s, 3H), 1.09 (s, 3H), 1.02 (s, 3H), 1.00 (s, 3H).

Example B14

Preparation of 4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

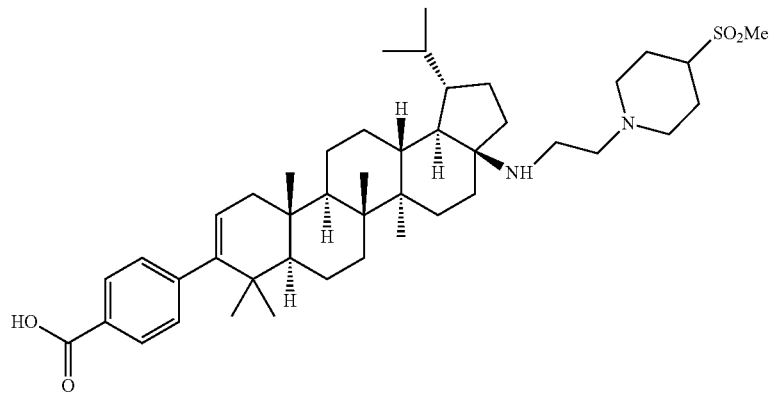

The title compound was prepared following the method described above for the synthesis of 4-((1R,3aS,5aR,5bR,7aR,11aS,11bR,13aR,13bR)-3a-((2-(4-(tert-butoxycarbonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 4-(methylsulfonyl)piperidine as the alkylating reagent in Step 3. The product was isolated as a white solid (200 mg, 84%). LCMS: m/e 719.58 (M+H)$^+$, 2.31 min (method 11). $^1$H NMR (500 MHz, Acetic) δ 8.04 (d, J=8.5 Hz, 2H), 7.30 (d, J=8.2 Hz, 2H), 5.37 (d, J=4.6 Hz, 1H), 4.87 (s, 1H), 4.75 (s, 1H), 3.76-3.70 (m, 2H), 3.68-3.54 (m, 4H), 3.48-3.29 (m, 1H), 3.18-3.03 (m, 2H), 3.02 (s, 3H), 2.84 (td, J=11.8, 4.7 Hz, 1H), 2.46-1.03 (m, 26H), 1.77 (s, 3H), 1.22 (s, 3H), 1.14 (s, 3H), 1.10 (s, 3H), 1.02 (s, 3H), 1.00 (s, 3H).

Example B15

Preparation of 4-((1R,3aS,5aR,5bR,7aR,11aS,11bR,13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

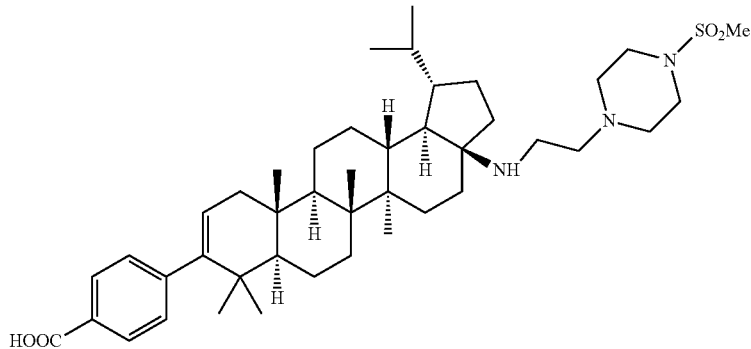

The title compound was prepared following the method described above for the synthesis of 4-((1R,3aS,5aR,5bR,7aR,11aS,11bR,13aR,13bR)-3a-((2-(4-(tert-butoxycarbonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 1-(methylsulfonyl)piperazine as the alkylating reagent in Step 3. The product was isolated as a white solid (220 mg, 89%). LCMS: m/e 720.58 (M+H)$^+$, 2.25 min (method 11). $^1$H NMR (500 MHz, Acetic) δ 8.04 (d, J=8.2 Hz, 2H), 7.30 (d, J=8.2 Hz, 2H), 5.37 (d, J=4.6 Hz, 1H), 4.86 (s, 1H), 4.74 (s, 1H), 3.74-3.38 (m, 7H), 3.37-3.25 (m, 1H), 3.17 (br. s., 4H), 2.94 (s, 3H), 2.91-2.80 (m, 1H), 2.35-1.01 (m, 22H), 1.77 (s, 3H), 1.26 (s, 3H), 1.14 (s, 3H), 1.10 (s, 3H), 1.02 (s, 3H), 1.00 (s, 3H).

Example B16

Preparation of 4-((1S,3aS,5aR,5bR,7aS,9S,11aS,11bR,13aR,13bR)-1-isopropyl-5a,5b,8,8,11a-pentamethyl-3a-((2-(4-(methylsulfonyl)piperazin-1-yl)ethyl)amino)icosahydro-1H-cyclopenta[a]chrysen-9-yl)benzoic acid

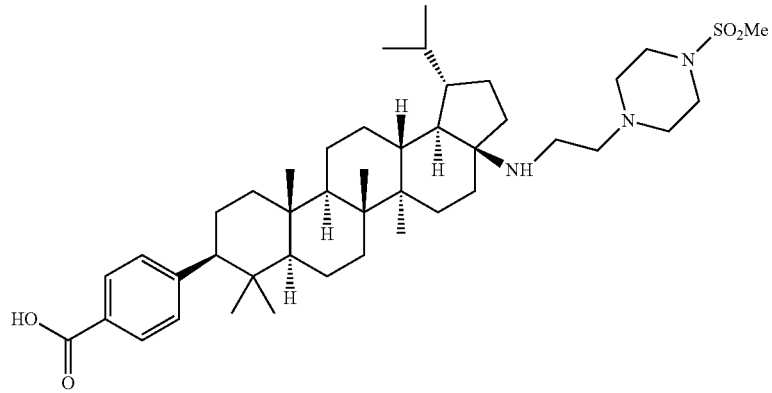

The title compound was prepared following the method described in Example B2 for the synthesis of 4-((1S,3aS,5aR,5bR,7aS,9S,11aS,11bR,13aR,13bR)-3a-((2-(1,1-dioxidothiomorpholino)ethyl)amino)-1-isopropyl-5a,5b,8,8,11a-pentamethylicosahydro-1H-cyclopenta[a]chrysen-9-yl)benzoic acid using 1-(2-chloroethyl)-4-(methylsulfonyl)piperazine (prepared as described below) as the alkylating reagent in Step 3. The product was isolated as a white solid (11 mg, 56%). LCMS: m/e 724.6 (M+H)$^+$, 2.44 min (method 10). $^1$H NMR (500 MHz, Acetic) δ 8.02 (d, J=8.2 Hz, 2H), 7.36 (d, J=8.2 Hz, 2H), 3.63-3.29 (m, 7H), 3.25-3.14 (m, 1H), 3.13-2.99 (m, 4H), 2.93 (s, 3H), 2.50 (dd, J=13.0, 2.6 Hz, 1H), 2.32-0.98 (m, 26H), 1.25 (s, 3H), 1.12 (s, 3H), 1.08 (s, 3H), 0.93 (d, J=6.7 Hz, 3H), 0.86 (d, J=6.7 Hz, 3H), 0.83 (s, 3H), 0.79 (s, 3H).

Preparation of 1-(2-chloroethyl)-4-(methylsulfonyl)piperazine

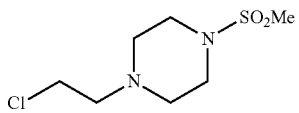 [SMILES: CS(=O)(=O)N1CCN(CCCl)CC1]

A mixture of 1-(methylsulfonyl)piperazine (250 mg, 1.522 mmol), potassium carbonate (1262 mg, 9.13 mmol) and 1-bromo-2-chloroethane (1092 mg, 7.61 mmol) in acetonitrile (5 mL) was stirred for 6 hours at room temperature. LCMS indicated the formation of desired product. The reaction mixture was filtered to remove the white precipitate, then quenched with distilled water (10 mL), extracted with ethyl acetate (3×8 mL), the extracts were combined, dried over sodium sulfate, filtered and concentrated under reduced pressure to provide the clean desired product as white solid (100 mg, 29%). LCMS: m/e 227.15 (M+H)$^+$, 1.21 min (method 10).

Example B17

Preparation of 4-((1R,3aS,5aR,5bR,7aR,11aS,11bR, 13aR,13bR)-3a-((2-(2-oxa-6-azaspiro[3.3]heptan-6-yl)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)benzoic acid

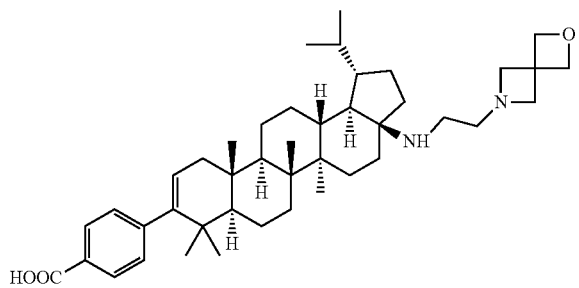

The title compound was prepared following the method described above for the synthesis of 4-((1R,3aS,5aR,5bR, 7aR,11aS,11bR,13aR,13bR)-3a-((2-((1,1-dioxidotetrahydrothiophen-3-yl)amino)ethyl)amino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)benzoic acid using 6-(2-chloroethyl)-2-oxa-6-azaspiro[3.3]heptane (prepared as described below) as the alkylating reagent in Step 3. The product was isolated as a white solid (1.1 mg, 18%). LCMS: m/e 655.53 (M+H)$^+$, 2.29 min (method 11). $^1$H NMR (500 MHz, Acetic) δ 8.04 (d, J=8.2 Hz, 2H), 7.30 (d, J=8.5 Hz, 2H), 5.37 (d, J=4.9 Hz, 1H), 4.93 (s., 4H), 4.86 (s, 1H), 4.75 (br. s., 1H), 4.71-4.32 (m, 4H), 4.05-3.86 (m, 2H), 3.70-3.40 (m, 2H), 3.00-2.66 (m, 1H), 2.25-1.05 (m, 22H), 1.76 (s, 3H), 1.18 (s, 3H), 1.13 (s, 3H), 1.08 (s, 3H), 1.02 (s, 3H), 1.00 (s, 3H).

Preparation of 6-(2-chloroethyl)-2-oxa-6-azaspiro[3.3]heptane

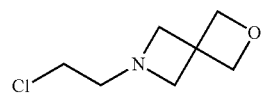

The title compound was prepared following the method described above for the synthesis of 1-(2-chloroethyl)-4-(methylsulfonyl)piperazine using 2-oxa-6-azaspiro[3.3]heptane as the starting reagent. The product was isolated as colorless oil (10 mg, 12%). LCMS: m/e 162.15 (M+H)$^+$, 0.87 min (method 10).

Example B18

Preparation of 4-((1S,3aS,5aR,5bR,7aS,9S,11aS, 11bR,13aR,13bR)-1-isopropyl-5a,5b,8,8,11a-pentamethyl-3a-((2-(4-(methylsulfonyl)piperidin-1-yl)ethyl)amino)icosahydro-1H-cyclopenta[a]chrysen-9-yl)benzoic acid

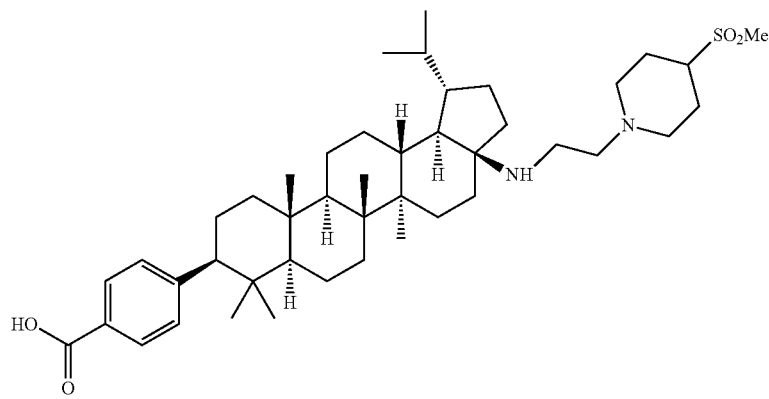

The title compound was prepared following the method described in above for the synthesis of 4-((1S,3aS,5aR,5bR,7aS,9S,11aS,11bR,13aR,13bR)-3a-((2-(1,1-dioxidothiomorpholino)ethyl)amino)-1-isopropyl-5a,5b,8,8,11a-pentamethylicosahydro-1H-cyclopenta[a]chrysen-9-yl)benzoic acid using 1-(2-chloroethyl)-4-(methylsulfonyl)piperidine (prepared as described below) as the alkylating reagent in Step 3. The product was isolated as a white solid (24 mg, 36%). LCMS: m/e 723.56 (M+H)$^+$, 2.28 min (method 11). $^1$H NMR (500 MHz, Acetic) δ 8.02 (d, J=8.2 Hz, 2H), 7.36 (d, J=8.2 Hz, 2H), 3.77-3.63 (m, 2H), 3.62-3.54 (m, 3H), 3.50 (d, J=5.5 Hz, 1H), 3.35 (td, J=11.4, 3.7 Hz, 1H), 3.08-2.89 (m, 2H), 3.02 (s, 3H), 2.50 (d, J=13.1 Hz, 1H), 2.42-2.29 (m, 2H), 2.28-1.03 (m, 28H), 1.21 (s, 3H), 1.12 (s, 3H), 1.08 (s, 3H), 1.01 (d, J=11.3 Hz, 1H), 0.93 (d, J=6.7 Hz, 4H), 0.86 (d, J=6.7 Hz, 4H), 0.83 (s, 3H), 0.79 (s, 3H).

Preparation of 1-(2-chloroethyl)-4-(methylsulfonyl)piperidine

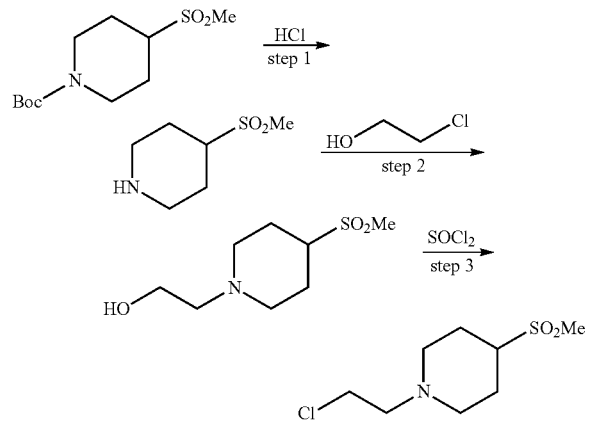

Step 1. Preparation of 4-(methylsulfonyl)piperidine

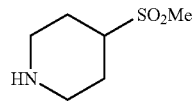

A mixture of tert-butyl 4-(methylsulfonyl)piperidine-1-carboxylate (1.5 g, 5.70 mmol) and hydrogen chloride (7.12 mL, 28.5 mmol) in THF (20 mL) was stirred at 20° C. for 15 hours. TLC indicated the formation of desired product, the reaction mixture was filtered and the pale yellow solid was collected to provide desired product (1 g, 88%). LCMS: m/e 163.96 (M+H)$^+$, 0.25 min (method 10).

Step 2. Preparation of 2-(4-(methylsulfonyl)piperidin-1-yl)ethanol

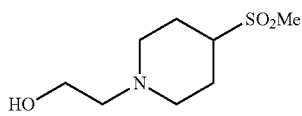 [SMILES: CS(=O)(=O)C1CCN(CCO)CC1]

A mixture of 4-(methylsulfonyl)piperidine hydrochloride (900 mg, 4.51 mmol), 2-bromoethanol (1126 mg, 9.01 mmol) and potassium carbonate (1869 mg, 13.52 mmol) in acetonitrile (4 mL) was heated up at 60° C. for 13 hours. The reaction mixture was cooled to room temperature and concentrated under reduced pressure to provide the crude, the crude was purified by 0-35% ethyl acetate/methanol to provide the desired product as colorless oil (620 mg, 66%). LCMS: m/e 208.1 (M+H)$^+$, 0.27 min (method 6).

Step 3. Preparation of 1-(2-chloroethyl)-4-(methylsulfonyl)piperidine

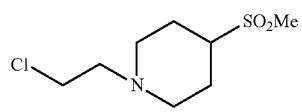 [SMILES: CS(=O)(=O)C1CCN(CCCl)CC1]

A mixture of 2-(4-(methylsulfonyl)piperidin-1-yl)ethanol (620 mg, 2.99 mmol) and thionyl chloride (1.092 mL, 14.95 mmol) in dichloroethane (5 mL) was heated up at 74° C. for 4 hours. The reaction mixture was concentrated under reduced pressure to provide the crude, to the crude was added THF (10 mL), the grey precipitate was observed and collected. The solid was dried under vacuum for 20 hour to provide the desired product as grey solid (400 mg, 59%). LCMS: m/e 226.1 (M+H)$^+$, 1.00 min (method 6).

Example B19

Preparation of 4-((1R,3aS,5aR,5bR,7aR,11aS,11bR,13aR,13bR)-3a-((2-(4-(ethylsulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

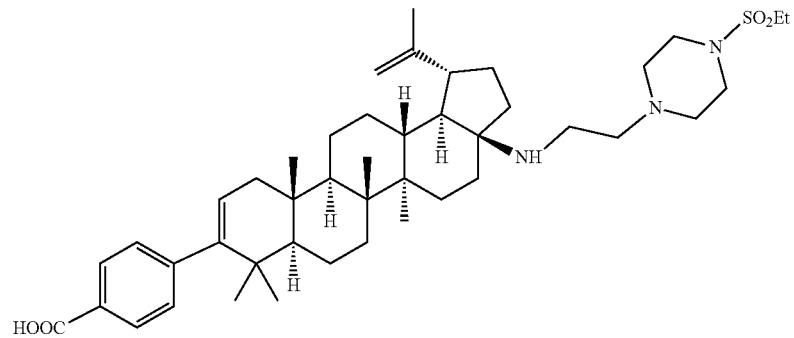

The title compound was prepared following the method described in above for the synthesis of 4-((1R,3aS,5aR,5bR,7aR,11aS,11bR,13aR,13bR)-3a-((2-(4-(tert-butoxycarbonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 1-(ethylsulfonyl)piperazine as the alkylating reagent in Step 3. The product was isolated as a white solid (11 mg, 53%). LCMS: m/e 734.56 (M+H)$^+$, 2.28 min (method 11). $^1$H NMR (400 MHz, Acetic) δ 7.99 (d, J=8.5 Hz, 2H), 7.26 (d, J=8.3 Hz, 2H), 5.34 (d, J=4.5 Hz, 1H), 4.81 (s, 1H), 4.70 (s, 1H), 3.63-3.28 (m, 7H), 3.26-3.16 (m, 1H), 3.14-2.98 (m, 6H), 2.95-2.75 (m, 1H), 2.33-1.06 (m, 22H), 1.73 (s, 3H), 1.32 (t, J=7.4 Hz, 3H), 1.23 (s, 3H), 1.10 (s, 3H), 1.06 (s, 3H), 0.98 (s, 3H), 0.97 (s, 3H).

Example B20

Preparation of 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

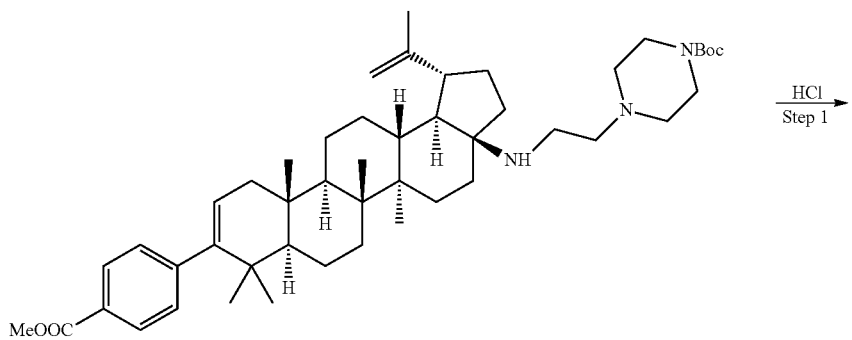

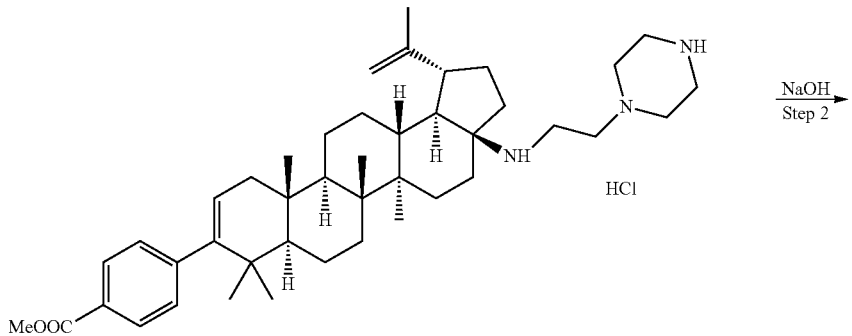

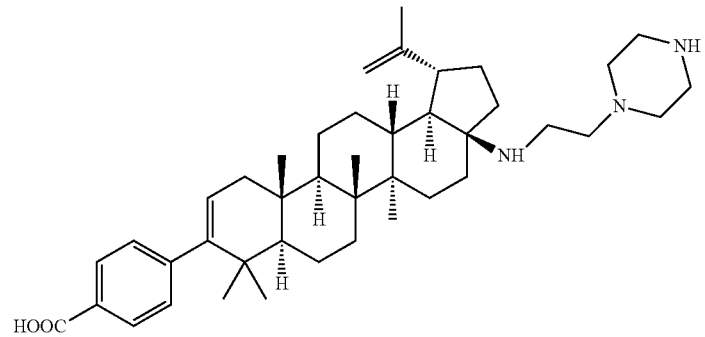

Step 1. Preparation of methyl 4-((1R,3aS,5aR,5bR, 7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoate hydrochloride A mixture of tert-butyl 4-(2-(((1R,3aS,5aR,5bR,7aR, 11aS,11bR,13aR,13bR)-9-(4-(methoxycarbonyl)phenyl)-5a,5b,8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-3a-yl)amino)ethyl)piperazine-1-carboxylate (150 mg, 0.198 mmol) and HCl (0.248 mL, 0.992 mmol) in THF (4 mL) was stirred at 20° C. for 18 hours. The reaction mixture was concentrated under reduced pressure to provide the desired product as brown solid (120 mg, 87%). LCMS: m/e 656.7 (M+H)+, 1.62 min (method 11).

Step 2. Preparation of 4-((1R,3aS,5aR,5bR,7aR, 11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoic acid A mixture of methyl 4-((1R,3aS,5aR,5bR,7aR,11aS, 11bR,13aR,13bR)-5a,5b,8,8,11a-pentamethyl-3a-((2-(piperazin-1-yl)ethyl)amino)-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)benzoate (7.5 mg, 0.011 mmol) and sodium hydroxide (0.057 mL, 0.057 mmol) in dioxane (1 mL) was heated up at 80° C. for 3 hours. The reaction mixture was filtered and the clear solution was purified by HPLC to provide the desired product as white solid (2.3 mg, 31%). LCMS: m/e 642.62 (M+H)+, 2.29 min (method 11). 1H NMR (400 MHz, Acetic) δ 8.00 (d, J=8.5 Hz, 2H), 7.26 (d, J=8.5 Hz, 2H), 5.34 (d, J=4.8 Hz, 1H), 4.80 (s, 1H), 4.70 (s, 1H), 3.59-3.28 (m, 6H), 3.25-3.11 (m, 1H), 3.09-2.73 (m, 6H), 2.31-1.15 (m, 22H), 1.73 (s, 3H), 1.26 (s, 3H), 1.11 (s, 3H), 1.08 (s, 3H), 0.99 (s, 3H), 0.97 (s, 3H).

Example B21

Preparation of 4-((1R,3aS,5aR,5bR,7aR,11aS,11bR, 13aR,13bR)-5a,5b,8,8,11a-pentamethyl-3a-((2-(methylsulfonamido)ethyl)amino)-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoic acid

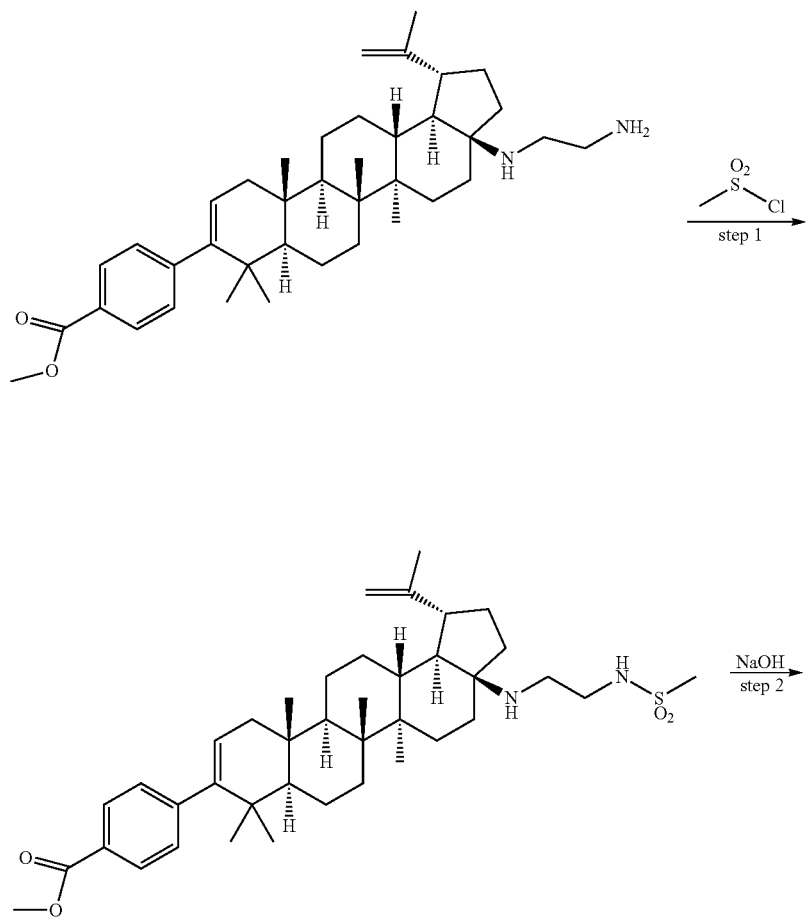

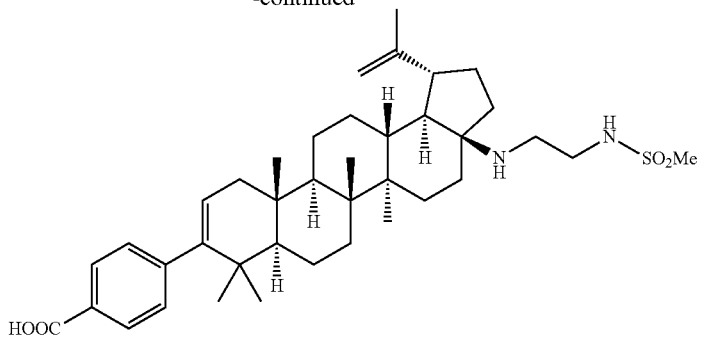

Step 1. Preparation of methyl 4-((1R,3aS,5aR,5bR, 7aR,11aS,11bR,13aR,13bR)-5a,5b,8,8,11a-pentamethyl-3a-((2-(methylsulfonamido)ethyl)amino)-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate To a solution of methyl 4-((1R,3aS,5aR,5bR,7aR,11aS,11bR,13aR,13bR)-3a-((2-aminoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (15 mg, 0.026 mmol) and Hunig's Base (0.013 mL, 0.077 mmol) in dichloromethane (1 mL) was added methanesulfonyl chloride (3.81 mg, 0.033 mmol) in dichloromethane (1 mL). The reaction mixture was stirred at 20° C. for 2 hours. The reaction mixture was diluted with distilled water (3 mL), extracted with dichloromethane (3×3 mL), the extracts were combined, dried over sodium sulfate, filtered and concentrated under reduced pressure to provide the desired product as a yellow solid (15 mg, 88%). LCMS: m/e 665.55 (M+H)$^+$, 2.44 min (method 11).

Step 2. Preparation of 4-((1R,3aS,5aR,5bR,7aR, 11aS,11bR,13aR,13bR)-5a,5b,8,8,11a-pentamethyl-3a-((2-(methylsulfonamido)ethyl)amino)-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid A mixture of methyl 4-((1R,3aS,5aR,5bR,7aR,11aS,11bR,13aR,13bR)-5a,5b,8,8,11a-pentamethyl-3a-((2-(methylsulfonamido)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (15 mg, 0.023 mmol) and sodium hydroxide (0.113 mL, 0.113 mmol) in dioxane (1 mL) was heated up at 80° C. for 3 hours. The reaction mixture was filtered and the clear solution was purified by HPLC to provide the title compound as a white solid (7 mg, 45%). LCMS: m/e 651.52 (M+H)$^+$, 2.28 min (method 11). $^1$H NMR (400 MHz, Acetic) δ 7.99 (d, J=8.3 Hz, 2H), 7.26 (d, J=8.3 Hz, 2H), 5.33 (d, J=4.5 Hz, 1H), 4.81 (s, 1H), 4.71 (s, 1H), 3.53 (br. s., 2H), 3.36-3.26 (m, 2H), 3.07 (s, 3H), 2.96-2.75 (m, 1H), 2.30-2.11 (m, 3H), 1.84-1.06 (m, 19H), 1.74 (s, 3H), 1.22 (s, 3H), 1.10 (s, 3H), 1.06 (s, 3H), 0.98 (s, 3H), 0.96 (s, 3H).

Example B22

Preparation of 4-((1R,3aS,5aR,5bR,7aR,11aS,11bR, 13aR,13bR)-3a-((2-(4-(cyclopropylsulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoic acid

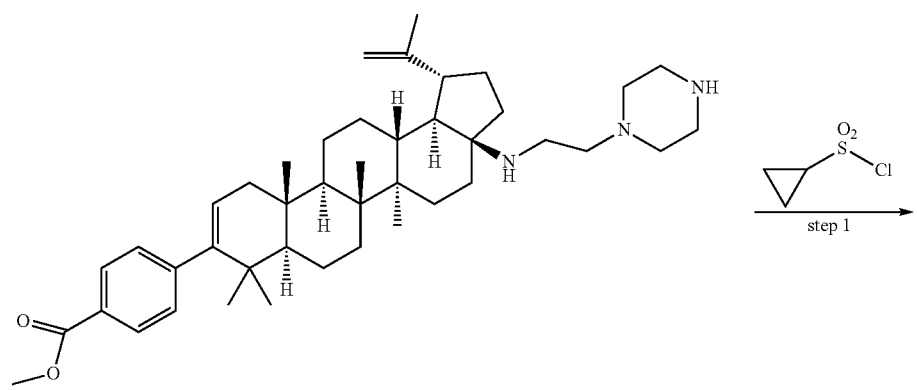

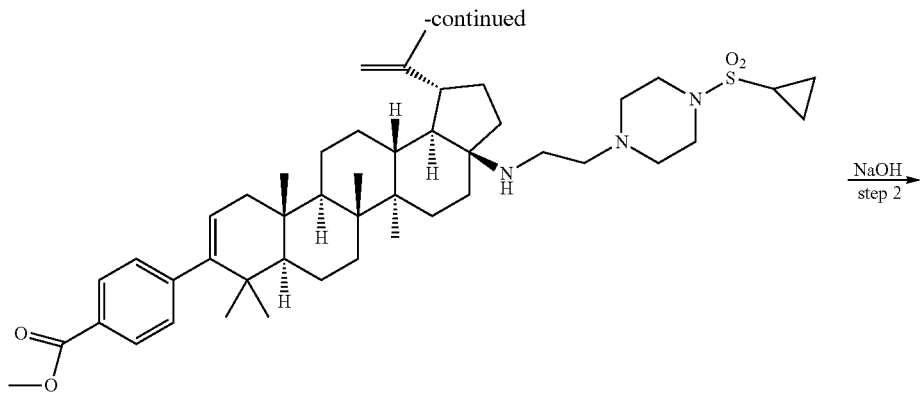

-continued

NaOH
step 2

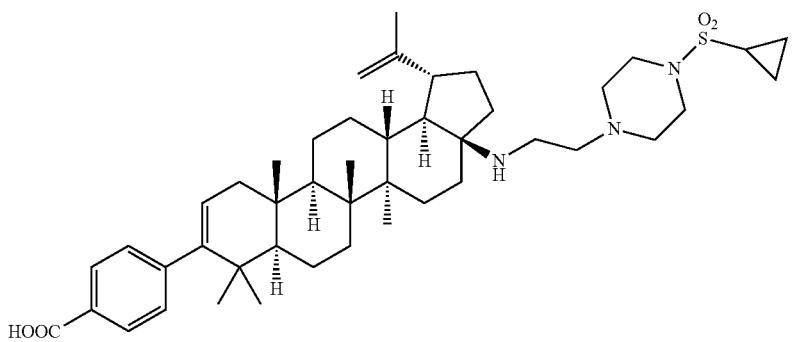

Step 1. Preparation of methyl 4-((1R,3aS,5aR,5bR,7aR,11aS,11bR,13aR,13bR)-3a-((2-(4-(cyclopropylsulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To a solution of methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (26 mg, 0.040 mmol) and Hunig's Base (0.035 mL, 0.198 mmol) in dichloromethane (1 mL) was added a solution of cyclopropanesulfonyl chloride (11.14 mg, 0.079 mmol) in dichloromethane (1 mL) at room temperature. The reaction mixture was stirred for 2 hours at 20° C. or LCMS indicated the formation of desired product and consumption of starting material. The reaction mixture was diluted with distilled water (4 mL), extracted with dichloromethane (3×4 mL), the extracts were combined, dried over sodium sulfate, filtered and concentrated under reduced pressure to provide the desired product as a yellow solid (30 mg, 100%). LCMS: m/e 760.61 (M+H)$^+$, 2.40 min (method 11).

Step 2. Preparation of 4-((1R,3aS,5aR,5bR,7aR,11aS,11bR,13aR,13bR)-3a-((2-(4-(cyclopropylsulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid A mixture of methyl 4-((1R,3aS,5aR,5bR,7aR,11aS,11bR,13aR,13bR)-3a-((2-(4-(cyclopropylsulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (30 mg, 0.039 mmol) and sodium hydroxide (0.395 mL, 0.395 mmol) in dioxane (0.5 mL) was heated up at 80° C. for 3 hours. The reaction mixture was filtered and the clear solution was purified by HPLC to provide the title compound as a white solid (13 mg, 42%). LCMS: m/e 746.58 (M+H)$^+$, 2.27 min (method 11). $^1$H NMR (400 MHz, Acetic) δ 7.99 (d, J=8.3 Hz, 2H), 7.26 (d, J=8.3 Hz, 2H), 5.34 (d, J=4.8 Hz, 1H), 4.81 (s, 1H), 4.70 (s, 1H), 3.63-3.44 (m, 5H), 3.43-3.26 (m, 2H), 3.24-3.13 (m, 1H), 3.05 (d, J=4.3 Hz, 4H), 2.86 (br. s., 1H), 2.58-2.40 (m, 1H), 2.27-1.02 (m, 22H), 1.73 (s, 3H) 1.24 (s, 3H), 1.13 (d, J=4.5 Hz, 2H), 1.10 (s, 3H), 1.06 (s, 3H), 1.02 (d, J=4.5 Hz, 2H), 0.97 (s, 3H), 0.96 (s, 3H).

Example B23

Preparation of 4-((1R,3aS,5aR,5bR,7aR,11aS,11bR,13aR,13bR)-5a,5b,8,8,11a-pentamethyl-1-(prop-1-en-2-yl)-3a-((2-(4-(propylsulfonyl)piperazin-1-yl)ethyl)amino)-2,3,3a,4,5,5a,5b,6,7,7a,8,11,11a,11b,12,13,13a,13b-octadecahydro-1H-cyclopenta[a]chrysen-9-yl)benzoic acid

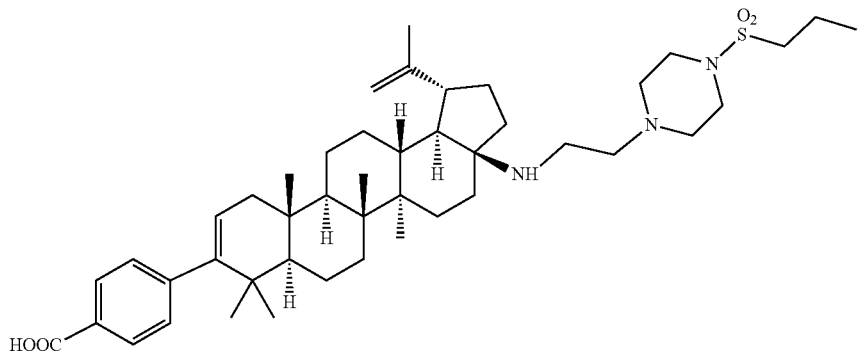

The title compound was prepared following the method described in above for the synthesis of 4-((1R,3aS,5aR,5bR,7aR,11aS,11bR,13aR,13bR)-3a-((2-(4-(cyclopropylsulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using propane-1-sulfonyl chloride as the reagent in Step 1. The product was isolated as a white solid (8 mg, 48%). LCMS: m/e 748.6 (M+H)+, 2.30 min (method 11). $^1$H NMR (400 MHz, Acetic) δ 7.99 (d, J=8.3 Hz, 2H), 7.26 (d, J=8.5 Hz, 2H), 5.34 (d, J=4.5 Hz, 1H), 4.81 (s, 1H), 4.70 (s, 1H), 3.59-3.26 (m, 7H), 3.23-3.11 (m, 1H), 3.09-2.95 (m, 6H), 2.93-2.80 (m, 1H), 2.27-1.02 (m, 24H), 1.73 (s, 3H), 1.24 (s, 3H), 1.10 (s, 3H), 1.07 (s, 3H), 1.05 (t, J=8.3 Hz, 3H), 0.98 (s, 3H), 0.97 (s, 3H).

Example B24

Preparation of 4-((1R,3aS,5aR,5bR,7aR,11aS,11bR,13aR,13bR)-3a-((2-(4-acetylpiperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

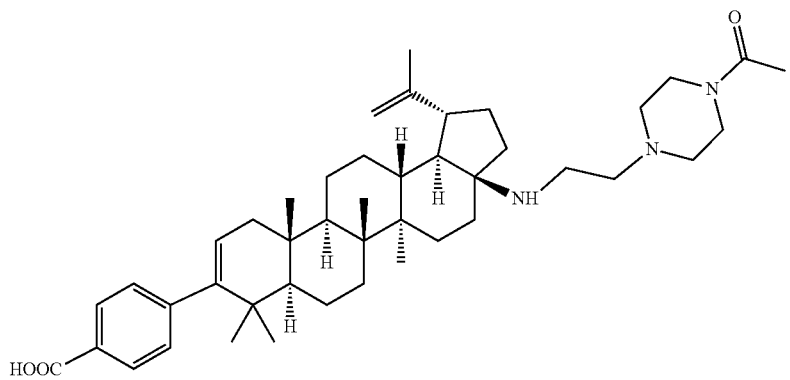

The title compound was prepared following the method described above for the synthesis of 4-((1R,3aS,5aR,5bR,7aR,11aS,11bR,13aR,13bR)-3a-((2-(4-(cyclopropylsulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using acetyl chloride as the reagent in Step 1. The product was isolated as a white solid (5.4 mg, 35%). LCMS: m/e 684.67 (M+H)+, 2.27 min (method 11). $^1$H NMR (400 MHz, Acetic) δ 7.99 (d, J=8.3 Hz, 2H), 7.26 (d, J=8.5 Hz, 2H), 5.33 (d, J=4.8 Hz, 1H), 4.82 (s, 1H), 4.72 (s, 1H), 4.09-3.89 (m, 1H), 3.85 (br. s., 3H), 3.68 (br. s., 4H), 3.53-3.14 (m, 4H), 2.92-2.66 (m, 1H), 2.28-1.01 (m, 22H), 2.17 (s, 3H), 1.73 (s, 3H), 1.18 (s, 3H), 1.10 (s, 3H), 1.05 (s, 3H), 0.98 (s, 3H), 0.96 (s, 3H).

Example B25

Preparation of 4-((1R,3aS,5aR,5bR,7aR,11aS,11bR,13aR,13bR)-3a-((2-(4-(2-(dimethylamino)-2-oxoacetyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

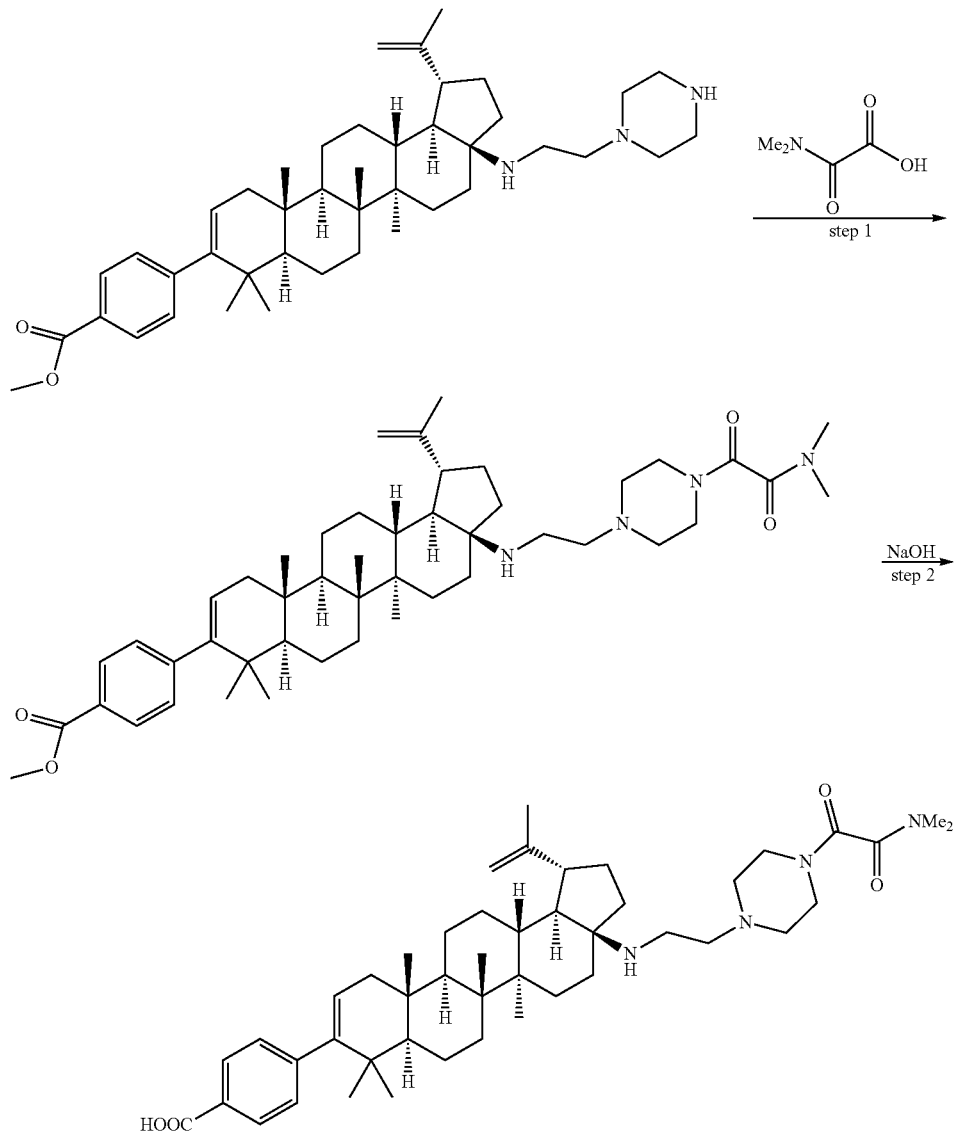

Step 1. Preparation of methyl 4-((1R,3aS,5aR,5bR,7aR,11aS,11bR,13aR,13bR)-3a-((2-(4-(2-(dimethylamino)-2-oxoacetyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoate A mixture of methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (50 mg, 0.076 mmol), 2-(1H-benzo[d][1,2,3]triazol-1-yl)-1,1,3,3-tetramethylisouronium tetrafluoroborate (29.4 mg, 0.091 mmol), N-ethyl-N-isopropylpropan-2-amine (11.82 mg, 0.091 mmol) and 2-(dimethylamino)-2-oxoacetic acid (26.8 mg, 0.229 mmol) in dichloromethane (2 mL) was stirred at 20° C. for 2 hours. The reaction mixture was diluted with distilled water (5 mL), extracted with ethyl acetate (3×4 mL), the extracts were combined, dried over sodium sulfate, filtered and concentrated under reduced pressure to provide the desired product as a Step 2. Preparation of 4-((1R,3aS,5aR,5bR,7aR, 11aS,11bR,13aR,13bR)-3a-((2-(4-(2-(dimethylamino)-2-oxoacetyl)piperazin-1-yl)ethyl)amino)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid A mixture of methyl 4-((1R,3aS,5aR,5bR,7aR,11aS, 11bR,13aR,13bR)-3a-((2-(4-(2-(dimethylamino)-2-oxoacetyl)piperazin-1-yl)ethyl)amino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate (40 mg, 0.053 mmol) and sodium hydroxide (0.530 mL, 0.530 mmol) in dioxane (1 mL) was heated up at 82° C. for 3 hours. The reaction mixture was cooled to room temperature, filtered and the clear solution was purified by HPLC to provide the title compound as a white solid (17 mg, 41%). LCMS: m/e 741.65 (M+H)+, 2.29 min (method 11). ¹H NMR (400 MHz, Acetic) δ 7.99 (d, J=8.3 Hz, 2H), 7.26 (d, J=8.3 Hz, 2H), 5.33 (d, J=4.5 Hz, 1H), 4.82 (s, 1H), 4.71 (s, 1H), 4.14-3.78 (m, 2H), 3.75-3.36 (m, 6H), 3.22 (br. s., 4H), 3.03 (s, 3H), 3.00 (s, 3H), 2.92-2.75 (m, 1H), 2.29-1.05 (m, 22H), 1.73 (s, 3H), 1.20 (s, 3H), 1.10 (s, 3H), 1.05 (s, 3H), 0.98 (s, 3H), 0.96 (s, 3H).

Example B26

Preparation of 4-((1R,3aS,5aR,5bR,7aR,11aS,11bR, 13aR,13bR)-3a-((2-(4-(isopropylsulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid

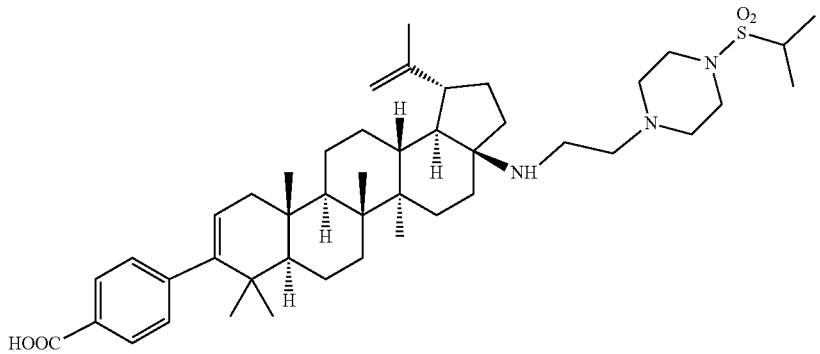

The title compound was prepared following the method described above for the synthesis of 4-((1R,3aS,5aR,5bR, 7aR,11aS,11bR,13aR,13bR)-3a-((2-(4-(cyclopropylsulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid using propane-2-sulfonyl chloride as the reagent in Step 1. The product was isolated as a colorless oil (6 mg, 36%). LCMS: m/e 748.63 (M+H)+, 2.31 min (method 11). ¹H NMR (400 MHz, Acetic) δ 7.99 (d, J=8.0 Hz, 2H), 7.26 (d, J=8.0 Hz, 2H), 5.33 (d, J=5.3 Hz, 1H), 4.82 (s, 1H), 4.71 (s, 1H), 3.80-3.55 (m, 8H), 3.49-3.25 (m, 5H), 2.92-2.68 (m, 1H), 2.32-1.04 (m, 22H), 1.73 (s, 3H), 1.32 (s, 3H), 1.30 (s, 3H), 1.17 (s, 3H), 1.10 (s, 3H), 1.05 (s, 3H), 0.98 (s, 3H), 0.96 (s, 3H).

Example B27

Preparation of 4-((1R,3aS,5aR,5bR,7aR,11aS,11bR, 13aR,13bR)-3a-((2-(4-(tert-butyl)piperazin-1-yl) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

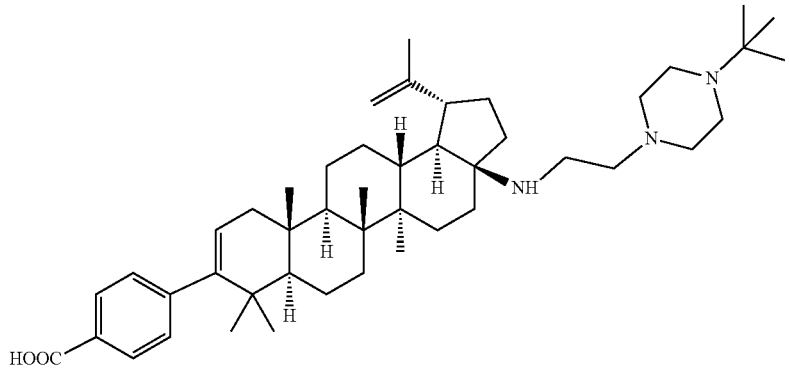

The title compound was prepared following the method described above for the synthesis of 4-((1R,3aS,5aR,5bR, 7aR,11aS,11bR,13aR,13bR)-3a-((2-(4-(tert-butoxycarbonyl)piperazin-1-yl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid using 1-(tert-butyl)piperazine as the alkylating reagent in Step 3. The product was isolated as a white solid (9 mg, 40%). LCMS: m/e 698.67 (M+H)$^+$, 2.27 min (method 11). $^1$H NMR (500 MHz, Acetic) δ 8.04 (d, J=8.0 Hz, 2H), 7.30 (d, J=8.0 Hz, 2H), 5.38 (d, J=5.2 Hz, 1H), 4.84 (s, 1H), 4.74 (s, 1H), 3.77 (br. s., 2H), 3.51-2.82 (m, 11H), 2.41-1.16 (m, 22H), 1.77 (s, 3H), 1.49 (s, 9H), 1.30 (s, 3H), 1.15 (s, 3H), 1.10 (s, 3H), 1.02 (s, 3H), 1.01 (s, 3H).

Example B28

Preparation of 4-((1R,3aS,5aR,5bR,7aR,11aS,11bR, 13aR,13bR)-5a,5b,8,8,11a-pentamethyl-3a-((2-(4-methylpiperazin-1-yl)ethyl)amino)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

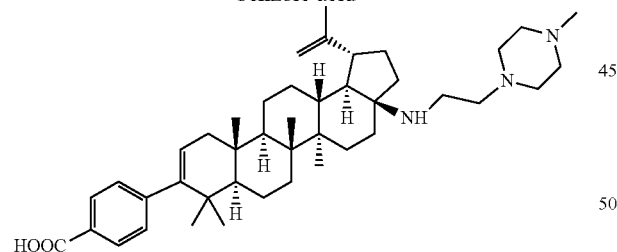

The title compound was prepared following the method described in above for the synthesis of 4-((1R,3aS,5aR,5bR, 7aR,11aS,11bR,13aR,13bR)-3a-((2-(4-(tert-butoxycarbonyl)piperazin-1-yl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid using 1-methylpiperazine as the alkylating reagent in Step 3. The product was isolated as a white solid (3 mg, 19%). LCMS: m/e 656.62 (M+H)$^+$, 2.19 min (method 11). $^1$H NMR (500 MHz, Acetic) δ 8.04 (d, J=8.0 Hz, 2H), 7.30 (d, J=8.0 Hz, 2H), 5.38 (d, J=5.7 Hz, 1H), 4.84 (s, 1H), 4.74 (s, 1H), 3.73 (br. s., 1H), 3.62-2.85 (m, 12H), 2.94 (s, 3H), 2.34-1.15 (m, 22H), 1.77 (s, 3H), 1.29 (s, 3H), 1.15 (s, 3H), 1.11 (s, 3H), 1.03 (s, 3H), 1.01 (s, 3H).

Example B29

Preparation of 4-((1R,3aS,5aR,5bR,7aR,11aS,11bR, 13aR,13bR)-5a,5b,8,8,11a-pentamethyl-3a-((2-(4-(2-oxo-2-(piperidin-1-yl)acetyl)piperazin-1-yl)ethyl) amino)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid

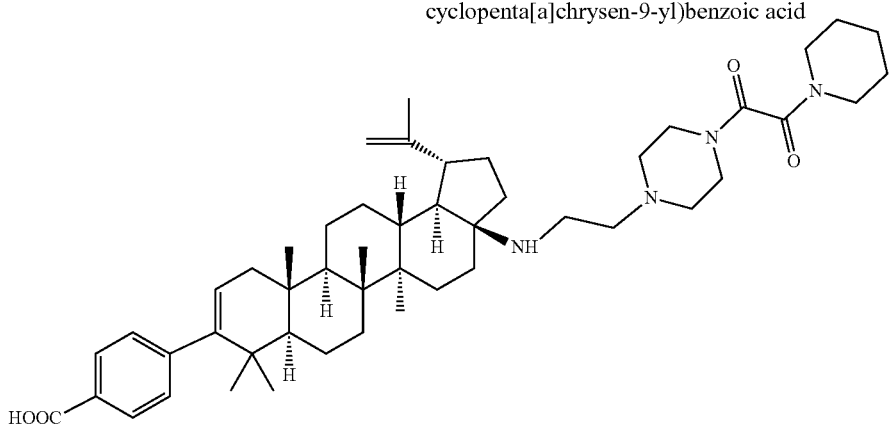

The title compound was prepared following the method described above for the synthesis of 4-((1R,3aS,5aR,5bR,7aR,11aS,11bR,13aR,13bR)-3a-((2-(4-(2-(dimethylamino)-2-oxoacetyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 2-oxo-2-(piperidin-1-yl)acetic acid as the acid in Step 1. The product was isolated as a white solid (1.1 mg, 18%). LCMS: m/e 781.7 (M+H)$^+$, 1.72 min (method 11). $^1$H NMR (500 MHz, CHLOROFORM-d) δ 7.99 (d, J=8.4 Hz, 2H), 7.24 (d, J=8.4 Hz, 2H), 5.31 (d, J=4.6 Hz, 1H), 4.77 (s, 1H), 4.65 (s, 1H), 3.84 (dd, J=7.6, 2.7 Hz, 1H), 3.68-3.56 (m, 3H), 3.49 (t, J=4.9 Hz, 2H), 3.43-3.30 (m, 2H), 2.93-2.63 (m, 9H), 2.60-1.05 (m, 28H), 1.72 (s, 3H), 1.17 (s, 3H), 1.04 (s, 3H), 1.00 (s, 3H), 0.97 (s, 3H), 0.97 (s, 3H).

3,3a,4,5,5a,5b,6,7,7a,8,11,11a,11b,12,13,13a,13b-octadecahydro-1H-cyclopenta[a]chrysen-9-yl)benzoic acid using propane-2-sulfonyl chloride as the reagent in Step 1. The product was isolated as a colorless oil (3.5 mg, 34%). LCMS: m/e 679.55 (M+H)$^+$, 2.36 min (method 11). $^1$H NMR (400 MHz, CHLOROFORM-d) δ 9.56 (br. s., 1H), 7.98 (d, J=8.5 Hz, 2H), 7.23 (d, J=8.3 Hz, 2H), 6.91 (t, J=6.3 Hz, 1H), 5.94 (br. s., 1H), 5.18 (d, J=4.5 Hz, 1H), 4.87 (s, 1H), 4.71 (s, 1H), 3.88-3.69 (m, 1H), 3.63-3.49 (m, 1H), 3.37-3.16 (m, 3H), 2.90-2.68 (m, 1H), 2.26-1.07 (m, 22H), 1.70 (s, 3H), 1.44 (dd, J=8.8, 6.8 Hz, 6H), 1.20 (s, 3H), 1.02 (s, 3H), 0.96 (s, 3H), 0.96 (s, 3H), 0.92 (s, 3H).

Example B30

Preparation of 4-((1R,3aS,5aR,5bR,7aR,11aS,11bR,13aR,13bR)-5a,5b,8,8,11a-pentamethyl-3a-((2-(1-methylethylsulfonamido)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid Example B31

Preparation of 4-((1R,3aS,5aR,5bR,7aR,11aS,11bR,13aR,13bR)-3a-((2-(cyclopropanesulfonamido)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

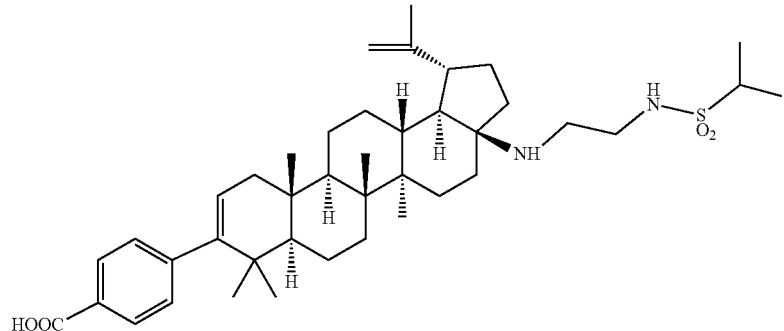

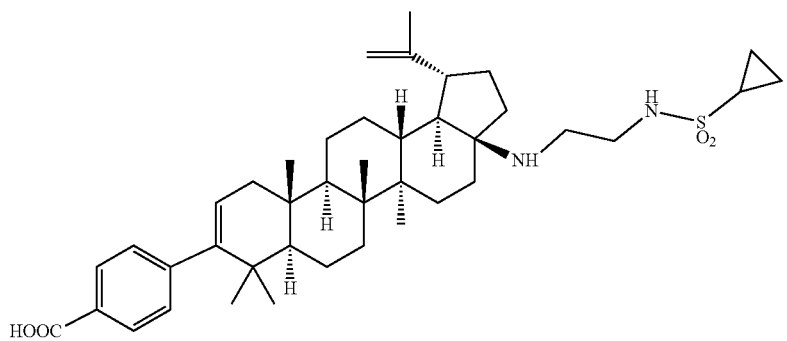

The title compound was prepared following the method described above for the synthesis of 4-((1R,3aS,5aR,5bR,7aR,11aS,11bR,13aR,13bR)-5a,5b,8,8,11a-pentamethyl-3a-((2-(methylsulfonamido)ethyl)amino)-1-(prop-1-en-2-yl)-2, The title compound was prepared following the method described above for the synthesis of 4-((1R,3aS,5aR,5bR,7aR,11aS,11bR,13aR,13bR)-5a,5b,8,8,11a-pentamethyl-3a-((2-(methylsulfonamido)ethyl)amino)-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoic acid using cyclopropanesulfonyl chloride as the reagent in Step 1. The product was isolated as a colorless oil (3.5 mg, 34%). LCMS: m/e 677.52 (M+H)+, 2.32 min (method 11). ¹H NMR (400 MHz, CHLOROFORM-d) δ 9.55 (br. s., 1H), 7.98 (d, J=8.3 Hz, 2H), 7.23 (d, J=8.3 Hz, 2H), 6.76 (br. s., 1H), 5.99 (br. s., 1H), 5.21 (d, J=5.0 Hz, 1H), 4.85 (s, 1H), 4.71 (s, 1H), 3.92-3.71 (m, 1H), 3.69-3.55 (m, 1H), 3.23 (br. s., 2H), 2.91-2.70 (m, 1H), 2.63-2.44 (m, 1H), 2.25-1.02 (m, 26H), 1.70 (s, 3H), 1.18 (s, 3H), 1.02 (s, 3H), 0.97 (s, 3H), 0.92 (s, 3H), 0.92 (s, 3H).

Example B32

Preparation of 4-((1R,3aS,5aR,5bR,7aR,11aS,11bR,13aR,13bR)-3a-((2-(1,1-dioxido-1,2-thiazinan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

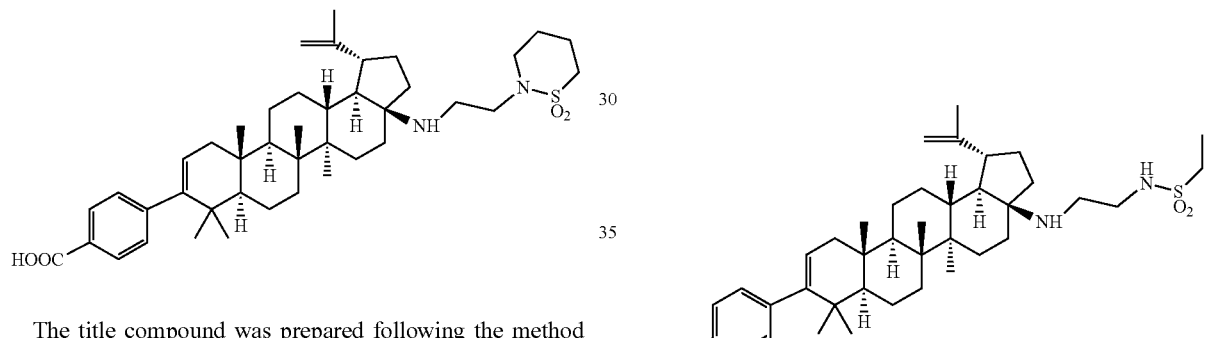

The title compound was prepared following the method described above for the synthesis of 4-((1R,3aS,5aR,5bR,7aR,11aS,11bR,13aR,13bR)-3a-((2-((1,1-dioxidotetrahydrothiophen-3-yl)amino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using 1-(2-chloroethyl)-4-(methylsulfonyl)piperazine (prepared as described below) as the alkylating reagent in Step 3. The product was isolated as a white solid (5.2 mg, 36%). LCMS: m/e 691.55 (M+H)+, 2.35 min (method 11). ¹H NMR (400 MHz, CHLOROFORM-d) δ 7.99 (d, J=8.3 Hz, 2H), 7.23 (d, J=8.5 Hz, 2H), 5.27 (d, J=4.5 Hz, 1H), 4.82 (s, 1H), 4.70 (s, 1H), 3.87-3.74 (m, 1H), 3.72-3.48 (m, 3H), 3.39 (br. s., 2H), 3.18-3.08 (m, 2H), 2.96-2.78 (m, 1H), 2.34-1.10 (m, 26H), 1.71 (s, 3H), 1.23 (s, 3H), 1.05 (s, 3H), 0.99 (s, 3H), 0.96 (s, 3H), 0.96 (s, 3H).

Preparation of
1-(2-chloroethyl)-4-(methylsulfonyl)piperazine

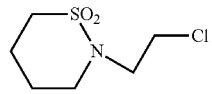 [SMILES: O=S1(=O)CCCCN1CCCl]

The title compound was prepared following the method described in previously for the synthesis of 1-(2-chloroethyl)-4-(methylsulfonyl)piperazine using 1,2-thiazinane 1,1-dioxide as the starting reagent and sodium hydride as the base. The product was isolated as colorless oil (120 mg, 41%). LCMS: m/e 198.08 (M+H)+, 1.24 min (method 11).

Example B33

Preparation of 4-((1R,3aS,5aR,5bR,7aR,11aS,11bR,13aR,13bR)-3a-((2-(ethylsulfonamido)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid The title compound was prepared following the method described above for the synthesis of 4-((1R,3aS,5aR,5bR,7aR,11aS,11bR,13aR,13bR)-5a,5b,8,8,11a-pentamethyl-3a-((2-(methylsulfonamido)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using ethanesulfonyl chloride as the reagent in Step 1. The product was isolated as a white solid (8.7 mg, 56%). LCMS: m/e 665.46 (M+H)+, 2.29 min (method 11). ¹H NMR (500 MHz, CHLOROFORM-d) δ 9.27 (br. s., 1H), 8.00 (d, J=7.1 Hz, 2H), 7.25 (d, J=7.1 Hz, 2H), 6.84 (br. s., 1H), 6.07 (br. s., 1H), 5.24 (d, J=6.3 Hz, 1H), 4.85 (s, 1H), 4.73 (s, 1H), 3.84-3.68 (m, 1H), 3.54 (d, J=14.8 Hz, 1H), 3.37-3.21 (m, 2H), 3.17 (q, J=7.4 Hz, 2H), 2.83-2.76 (m, 1H), 2.36-0.95 (m, 22H), 1.72 (s, 3H), 1.46 (t, J=7.4 Hz, 3H), 1.20 (s, 3H), 1.05 (s, 3H), 0.97 (s, 3H), 0.95 (s, 3H), 0.95 (s, 3H).

Example B34

Preparation of 4-((1R,3aS,5aR,5bR,7aR,11aS,11bR,13aR,13bR)-5a,5b,8,8,11a-pentamethyl-1-(prop-1-en-2-yl)-3a-((2-(propylsulfonamido)ethyl)amino)-2,3,3a,4,5,5a,5b,6,7,7a,8,11,11a,11b,12,13,13a,13b-octadecahydro-1H-cyclopenta[a]chrysen-9-yl)benzoic acid

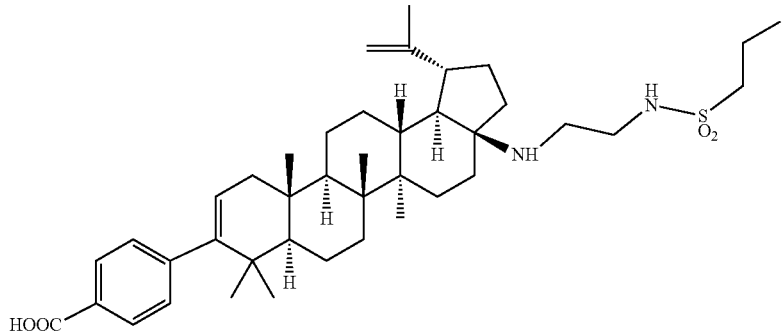

The title compound was prepared following the method described above for the synthesis of 4-((1R,3aS,5aR,5bR,7aR,11aS,11bR,13aR,13bR)-5a,5b,8,8,11a-pentamethyl-3a-((2-(methylsulfonamido)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using propane-1-sulfonyl chloride as the reagent in Step 1. The product was isolated as a white solid (9 mg, 49%). LCMS: m/e 679.48 (M+H)$^+$, 2.34 min (method 11). $^1$H NMR (500 MHz, CHLOROFORM-d) δ 9.36 (br. s., 1H), 8.00 (d, J=8.4 Hz, 2H), 7.25 (d, J=8.2 Hz, 2H), 6.81 (br. s., 1H), 6.04 (br. s., 1H), 5.31-5.19 (m, 1H), 4.86 (s, 1H), 4.73 (s, 1H), 3.85-3.67 (m, 1H), 3.54 (d, J=14.7 Hz, 1H), 3.38-3.18 (m, 2H), 3.15-3.07 (m, 2H), 2.80 (td, J=11.2, 5.9 Hz, 1H), 2.26-0.95 (m, 24H), 1.71 (s, 3H), 1.20 (s, 3H), 1.12 (t, J=7.4 Hz, 3H), 1.05 (s, 3H), 0.97 (s, 3H), 0.96 (s, 3H), 0.94 (s, 3H).

General Procedure for the Preparation of Examples B35-B-52.

To the corresponding substituted sulfonyl chloride reagent (sulfonylating agent) (0.075 mmol) was added a solution of methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (29 mg, 0.044 mmol) and DIPEA (0.039 mL, 0.221 mmols) in DCE (1 mL) at room temperature. The reaction mixture was stirred overnight at room temperature. The solvent was evaporated to provide the dry residue. To the residue in dioxane (0.8 mL) was added a solution of lithium hydroxide monohydrate (14.7 mg, 0.35 mmol) in water (0.2 mL). The reaction mixture was agitated at 350 rpm on an Innova platform shaker at 70° C. overnight. The solvent was removed and DMF (1.5 mL) was added. The mixture was filtered and the clear solution was purified by HPLC to provide the desired products with yield ranged from 6-50% over two steps.

Example B35

Preparation of 4-((1R,3aS,5aR,5bR,7aR,11aS,11bR,13aR,13bR)-3a-((2-(4-(isobutylsulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

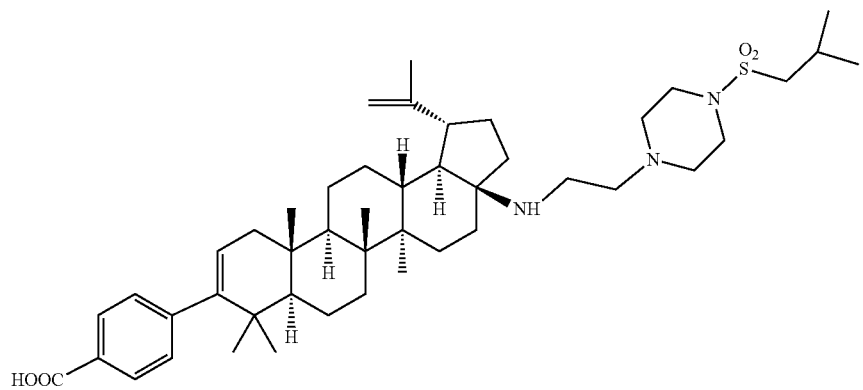

The title compound was prepared to provide 11.9 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using isobutanesulfonyl chloride as the sulfonylating agent. LCMS: m/e 762.8 (M+H)$^+$, 3.65 min (method 14). $^1$H NMR (500 MHz, DMSO-d$_6$) δ 7.87 (d, J=8.2 Hz, 2H), 7.22 (d, J=8.2 Hz, 2H), 5.25 (d, J=4.9 Hz, 1H), 4.70 (s, 1H), 4.57 (s, 1H), 3.17 (br. s., 4H), 3.00-2.82 (m, 2H), 2.70-2.53 (m, 5H), 2.48-2.30 (m, 4H), 2.24-2.03 (m, 2H), 2.00-1.83 (m, 2H), 1.80-1.01 (m, 19H), 1.67 (s, 3H), 1.11 (s, 3H), 1.06 (s, 3H), 1.05 (s, 3H), 0.98 (s, 3H), 0.96 (s, 3H), 0.90 (s, 3H), 0.88 (s, 3H).

Example B36

Preparation of 4-((1R,3aS,5aR,5bR,7aR,11aS,11bR,13aR,13bR)-5a,5b,8,8,11a-pentamethyl-1-(prop-1-en-2-yl)-3a-((2-(4-(pyridin-3-ylsulfonyl)piperazin-1-yl)ethyl)amino)-2,3,3a,4,5,5a,5b,6,7,7a,8,11,11a,11b,12,13,13a,13b-octadecahydro-1H-cyclopenta[a]chrysen-9-yl)benzoic acid

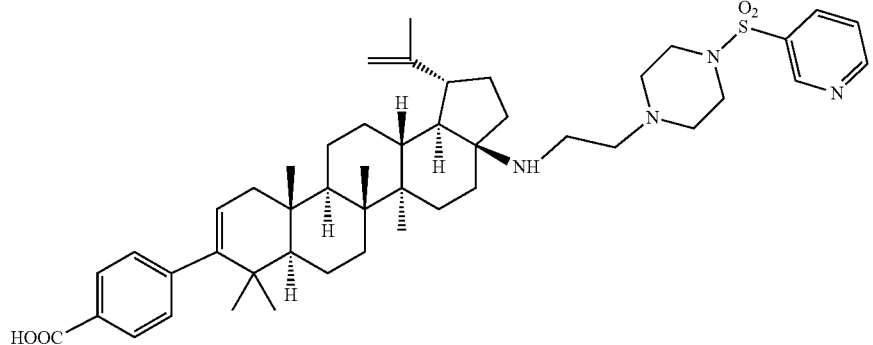

The title compound was prepared to provide 12.7 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using pyridine-3-sulfonyl chloride as the sulfonylating agent. LCMS: m/e 783.8 (M+H)$^+$, 3.42 min (method 14). $^1$H NMR (500 MHz, DMSO-d$_6$) δ 8.95 (d, J=2.1 Hz, 1H), 8.89 (dd, J=4.7, 1.4 Hz, 1H), 8.32-8.16 (m, 1H), 7.88 (d, J=8.2 Hz, 2H), 7.73 (dd, J=7.9, 4.9 Hz, 1H), 7.25 (d, J=7.9 Hz, 2H), 5.25 (d, J=4.9 Hz, 1H), 4.64 (d, J=1.8 Hz, 1H), 4.53 (s, 1H), 3.11-2.92 (m, 4H), 2.65-2.46 (m, 5H), 2.45-2.20 (m, 4H), 2.05 (dd, J=17.4, 6.4 Hz, 1H), 1.91-1.76 (m, 2H), 1.73-0.99 (m, 19H), 1.63 (s, 3H), 1.03 (s, 3H), 0.94 (s, 3H), 0.91 (s, 3H), 0.87 (s, 3H), 0.61 (s, 3H).

Example B37

Preparation of 4-((1R,3aS,5aR,5bR,7aR,11aS,11bR,13aR,13bR)-3a-((2-(4-(N,N-diethylsulfamoyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

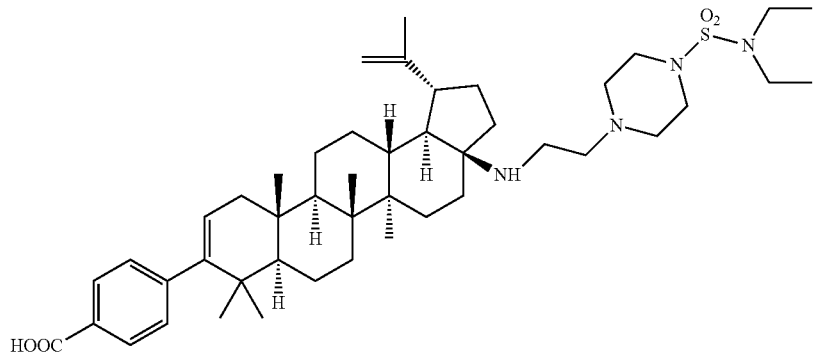

The title compound was prepared to provide 10.6 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using dimethylsulfamoyl chloride as the sulfonylating agent. LCMS: m/e 777.8 (M+H)$^+$, 3.82 min (method 14). $^1$H NMR (500 MHz, DMSO-d$_6$) δ 7.87 (d, J=7.9 Hz, 2H), 7.22 (d, J=8.2 Hz, 2H), 5.25 (d, J=4.6 Hz, 1H), 4.70 (d, J=2.1 Hz, 1H), 4.56 (s, 1H), 3.22 (q, J=7.1 Hz, 4H), 3.08 (br. s., 4H), 2.69-2.57 (m, 1H), 2.56-2.47 (m, 4H), 2.44-2.31 (m, 4H), 2.08 (dd, J=17.5, 6.3 Hz, 1H), 1.95-1.00 (m, 21H), 1.67 (s, 3H), 1.12 (t, J=7.0 Hz, 6H), 1.09 (s, 3H), 0.97 (s, 3H), 0.96 (s, 3H), 0.91 (s, 3H), 0.90 (s, 3H).

Example B38

Preparation of 4-((1R,3aS,5aR,5bR,7aR,11aS,11bR,13aR,13bR)-3a-((2-(4-((3-chloropropyl)sulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

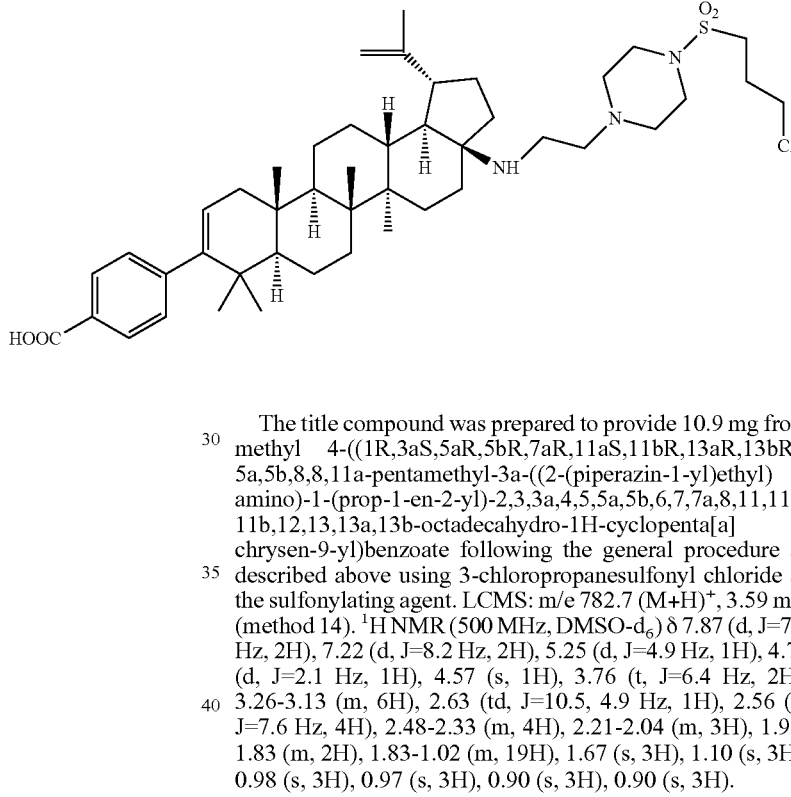

The title compound was prepared to provide 10.9 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using 3-chloropropanesulfonyl chloride as the sulfonylating agent. LCMS: m/e 782.7 (M+H)$^+$, 3.59 min (method 14). $^1$H NMR (500 MHz, DMSO-d$_6$) δ 7.87 (d, J=7.9 Hz, 2H), 7.22 (d, J=8.2 Hz, 2H), 5.25 (d, J=4.9 Hz, 1H), 4.70 (d, J=2.1 Hz, 1H), 4.57 (s, 1H), 3.76 (t, J=6.4 Hz, 2H), 3.26-3.13 (m, 6H), 2.63 (td, J=10.5, 4.9 Hz, 1H), 2.56 (d, J=7.6 Hz, 4H), 2.48-2.33 (m, 4H), 2.21-2.04 (m, 3H), 1.98-1.83 (m, 2H), 1.83-1.02 (m, 19H), 1.67 (s, 3H), 1.10 (s, 3H), 0.98 (s, 3H), 0.97 (s, 3H), 0.90 (s, 3H), 0.90 (s, 3H).

Example B39

Preparation of 4-((1R,3aS,5aR,5bR,7aR,11aS,11bR,13aR,13bR)-3a-((2-(4-(butylsulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

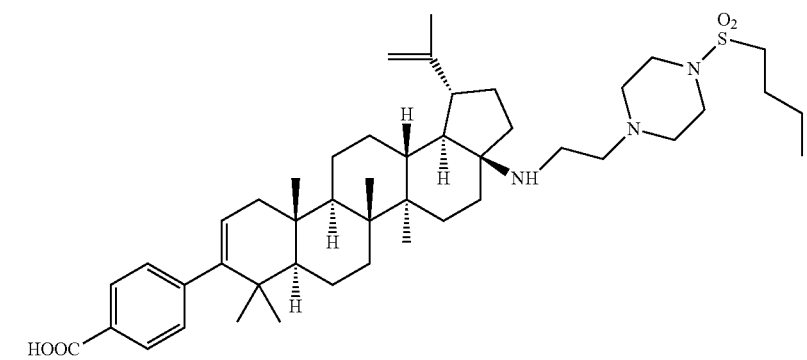

The title compound was prepared to provide 13.6 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using butane-1-sulfonyl chloride as the sulfonylating agent. LCMS: m/e 762.8 (M+H)+, 3.66 min (method 14). ¹H NMR (500 MHz, DMSO-d₆) δ 7.87 (d, J=8.2 Hz, 2H), 7.22 (d, J=8.2 Hz, 2H), 5.25 (d, J=4.6 Hz, 1H), 4.70 (d, J=2.1 Hz, 1H), 4.56 (s, 1H), 3.19 (br. s., 4H), 3.12-2.96 (m, 2H), 2.63 (td, J=10.8, 5.3 Hz, 1H), 2.55 (br. s., 4H), 2.47-2.30 (m, 4H), 2.08 (dd, J=17.2, 6.3 Hz, 1H), 1.98-1.83 (m, 2H), 1.82-1.02 (m, 23H), 1.67 (s, 3H), 1.10 (s, 3H), 0.98 (s, 3H), 0.96 (s, 3H), 0.91 (t, J=4.7 Hz, 3H), 0.90 (s, 3H), 0.89 (s, 3H).

Example B40

Preparation of 4-((1R,3aS,5aR,5bR,7aR,11aS,11bR,13aR,13bR)-3a-((2-(4-((4-ethylphenyl)sulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

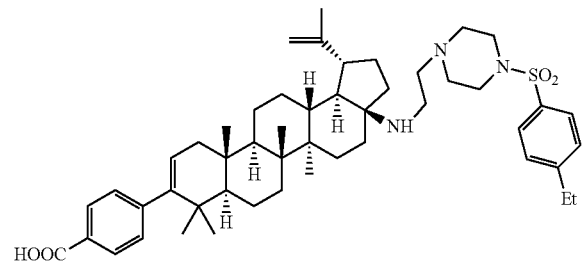

The title compound was prepared to provide 3.7 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using 4-ethyl-benzene-1-sulfonyl chloride as the sulfonylating agent. LCMS: m/e 810.9 (M+H)+, 4.12 min (method 14). ¹H NMR (500 MHz, DMSO-d₆) δ 7.89 (d, J=8.2 Hz, 2H), 7.68 (d, J=8.2 Hz, 2H), 7.49 (d, J=8.2 Hz, 2H), 7.24 (d, J=8.2 Hz, 2H), 5.26 (d, J=4.9 Hz, 1H), 4.63 (br. s., 1H), 4.55 (br. s., 1H), 3.03-2.90 (m, 4H), 2.71 (q, J=7.7 Hz, 2H), 2.52 (d, J=1.5 Hz, 5H), 2.49-2.34 (m, 4H), 2.06 (dd, J=17.7, 6.4 Hz, 1H), 1.80 (d, J=9.8 Hz, 2H), 1.75-1.01 (m, 19H), 1.63 (s, 3H), 1.21 (t, J=7.5 Hz, 3H), 0.96 (s, 3H), 0.93 (s, 3H), 0.92 (s, 3H), 0.92 (s, 3H), 0.85 (s, 3H).

Example B41

Preparation of 4-((1R,3aS,5aR,5bR,7aR,11aS,11bR,13aR,13bR)-3a-((2-(4-(benzylsulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

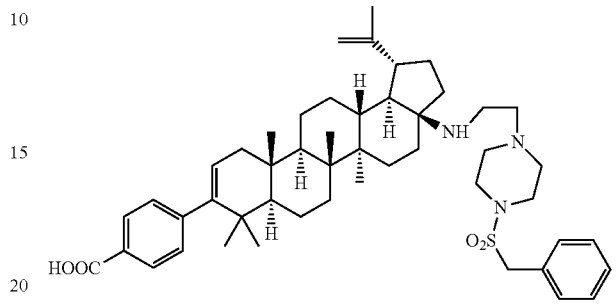

The title compound was prepared to provide 16.4 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using phenyl-methanesulfonyl chloride as the sulfonylating agent. LCMS: m/e 796.8 (M+H)+, 3.73 min (method 14). ¹H NMR (500 MHz, DMSO-d₆) δ 7.87 (d, J=8.2 Hz, 2H), 7.46-7.41 (m, 2H), 7.41-7.31 (m, 3H), 7.22 (d, J=8.2 Hz, 2H), 5.25 (d, J=4.6 Hz, 1H), 4.72 (d, J=1.5 Hz, 1H), 4.58 (s, 1H), 4.53-4.39 (m, 2H), 3.11 (br. s., 4H), 2.64-2.54 (m, 1H), 2.53-2.45 (m, 2H), 2.46-2.29 (m, 6H), 2.09 (dd, J=17.2, 6.3 Hz, 1H), 1.96-1.80 (m, 3H), 1.78-1.02 (m, 18H), 1.68 (s, 3H), 1.10 (s, 3H), 0.98 (s, 3H), 0.97 (s, 3H), 0.89 (s, 3H), 0.87 (s, 3H).

Example B42

Preparation of 4-((1R,3aS,5aR,5bR,7aR,11aS,11bR,13aR,13bR)-5a,5b,8,8,11a-pentamethyl-3a-((2-(4-(((methylsulfonyl)methyl)sulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

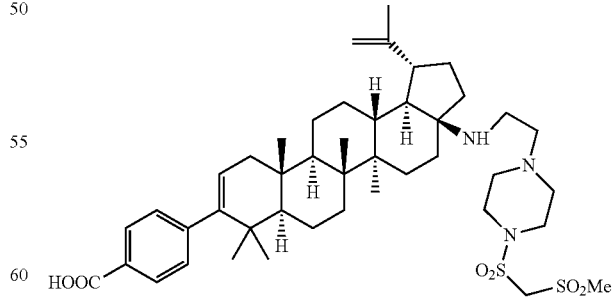

The title compound was prepared to provide 5.5 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]

chrysen-9-yl)benzoate following the general procedure as described above using methanesulfonyl-methanesulfonyl chloride as the sulfonylating agent. LCMS: m/e 798.8 (M+H)$^+$, 3.28 min (method 14). $^1$H NMR (500 MHz, DMSO-d$_6$) δ 7.87 (d, J=7.9 Hz, 2H), 7.22 (d, J=7.9 Hz, 2H), 5.29 (s, 2H), 5.25 (d, J=4.6 Hz, 1H), 4.70 (s, 1H), 4.57 (s, 1H), 3.29 (br. s., 8H), 3.19 (s, 3H), 2.64-2.55 (m, 1H), 2.48-2.34 (m, 4H), 2.08 (dd, J=17.2, 6.3 Hz, 1H), 1.97-1.80 (m, 3H), 1.79-0.99 (m, 18H), 1.67 (s, 3H), 1.09 (s, 3H), 0.97 (s, 3H), 0.97 (s, 3H), 0.90 (s, 3H), 0.90 (s, 3H).

Example B43

Preparation of 4-((1R,3aS,5aR,5bR,7aR,11aS,11bR,13aR,13bR)-5a,5b,8,8,11a-pentamethyl-3a-((2-(4-((1-methyl-1H-imidazol-4-yl)sulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

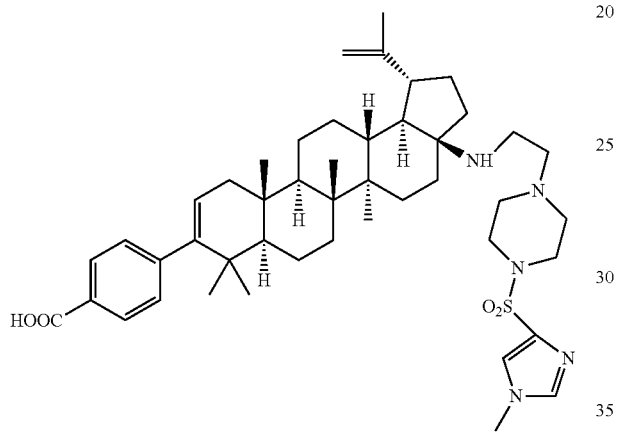

The title compound was prepared to provide 17 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using 1-methyl-1H-imidazole-4-sulfonyl chloride as the sulfonylating agent. LCMS: m/e 786.8 (M+H)$^+$, 3.08 min (method 14). $^1$H NMR (500 MHz, DMSO-d$_6$) δ 7.92-7.84 (m, 3H), 7.77 (s, 1H), 7.23 (d, J=7.9 Hz, 2H), 5.26 (d, J=4.9 Hz, 1H), 4.66 (d, J=1.8 Hz, 1H), 4.55 (s, 1H), 3.73 (s, 3H), 3.04 (br. s., 4H), 2.63-2.47 (m, 5H), 2.45-2.26 (m, 4H), 2.08 (dd, J=17.4, 6.4 Hz, 1H), 1.91-1.77 (m, 2H), 1.77-1.00 (m, 19H), 1.65 (s, 3H), 0.96 (s, 3H), 0.94 (s, 3H), 0.94 (s, 3H), 0.93 (s, 3H), 0.89 (s, 3H).

Example B44

Preparation of 4-((1R,3aS,5aR,5bR,7aR,11aS,11bR,13aR,13bR)-5a,5b,8,8,11a-pentamethyl-3a-((2-(4-(phenylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

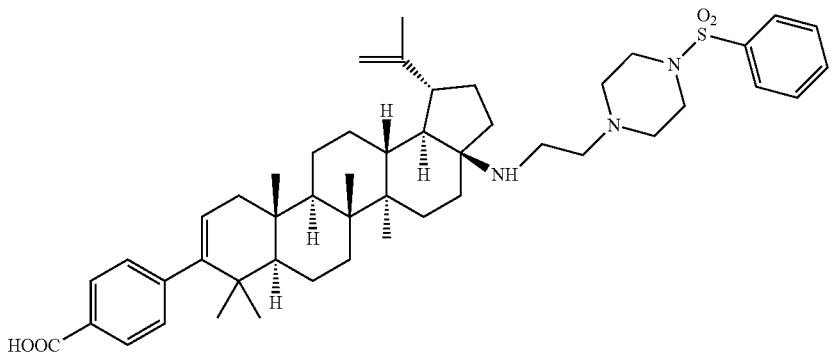

The title compound was prepared to provide 3.9 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using benzenesulfonyl chloride as the sulfonylating agent. LCMS: m/e 782.8 (M+H)$^+$, 4.98 min (method 15). $^1$H NMR (500 MHz, DMSO-d$_6$) δ 7.89 (d, J=8.2 Hz, 2H), 7.78 (d, J=7.0 Hz, 2H), 7.75-7.62 (m, 3H), 7.26 (d, J=7.9 Hz, 2H), 5.25 (d, J=4.9 Hz, 1H), 4.64 (br. s., 1H), 4.54 (br. s., 1H), 2.92 (br. s., 4H), 2.57 (br. s., 5H), 2.47-2.27 (m, 4H), 2.05 (dd, J=17.4, 6.4 Hz, 1H), 1.93-1.77 (m, 2H), 1.76-0.98 (m, 19H), 1.63 (s, 3H), 1.03 (s, 3H), 0.95 (s, 3H), 0.91 (s, 3H), 0.86 (s, 3H), 0.58 (s, 3H).

Example B45

Preparation of 4-((1R,3aS,5aR,5bR,7aR,11aS,11bR,13aR,13bR)-3a-((2-(4-((3-methoxyphenyl)sulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

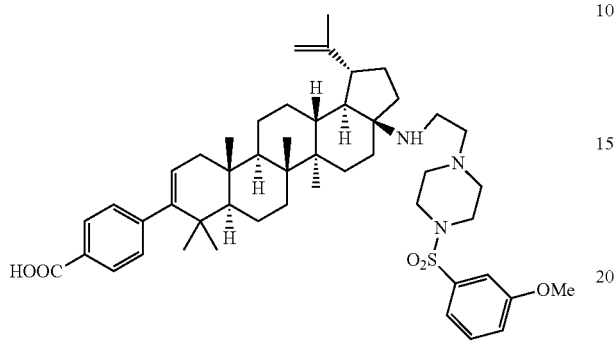

The title compound was prepared to provide 3.2 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using 3-methoxybenzenesulfonyl chloride as the sulfonylating agent. LCMS: m/e 812.8 (M+H)$^+$, 4.98 min (method 15). $^1$H NMR (500 MHz, DMSO-d$_6$) δ 7.89 (d, J=8.2 Hz, 2H), 7.64-7.51 (m, 1H), 7.34 (d, J=7.9 Hz, 1H), 7.28-7.13 (m, 4H), 5.25 (d, J=4.6 Hz, 1H), 4.64 (s, 1H), 4.53 (s, 1H), 3.85 (s, 3H), 3.03-2.87 (m, 4H), 2.64-2.51 (m, 5H), 2.46-2.22 (m, 4H), 2.05 (dd, J=17.2, 6.3 Hz, 1H), 1.93-1.76 (m, 2H), 1.75-0.98 (m, 19H), 1.63 (s, 3H), 1.02 (s, 3H), 0.94 (s, 3H), 0.91 (s, 3H), 0.87 (s, 3H), 0.63 (s, 3H).

Example B46

Preparation of 4-((1R,3aS,5aR,5bR,7aR,11aS,11bR,13aR,13bR)-3a-((2-(4-((4-chlorophenyl)sulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

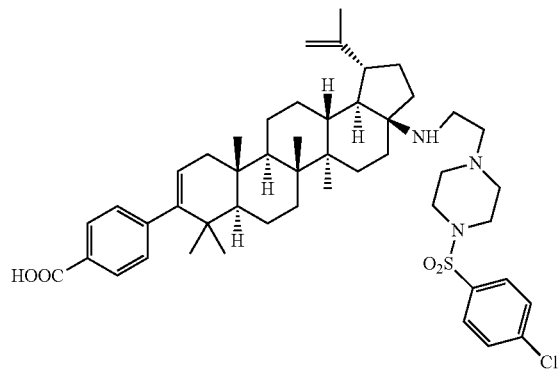

The title compound was prepared to provide 2.1 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using 4-chlorobenzene-1-sulfonyl chloride as the sulfonylating agent. LCMS: m/e 816.8 (M+H)$^+$, 3.94 min (method 14). $^1$H NMR (500 MHz, DMSO-d$_6$) δ 7.89 (d, J=8.2 Hz, 2H), 7.81 (d, J=8.5 Hz, 2H), 7.73 (d, J=8.9 Hz, 2H), 7.24 (d, J=7.9 Hz, 2H), 5.25 (d, J=4.6 Hz, 1H), 4.66 (br. s., 1H), 4.57 (br. s., 1H), 2.96 (br. s., 4H), 2.71-2.55 (m, 4H), 2.51-2.30 (m, 5H), 2.06 (dd, J=17.4, 6.4 Hz, 1H), 1.98-1.79 (m, 2H), 1.78-0.89 (m, 19H), 1.65 (s, 3H), 1.00 (s, 3H), 0.93 (s, 3H), 0.93 (s, 3H), 0.92 (s, 3H), 0.80 (s, 3H).

Example B47

Preparation of 4-((1R,3aS,5aR,5bR,7aR,11aS,11bR,13aR,13bR)-3a-((2-(4-((4-methoxyphenyl)sulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

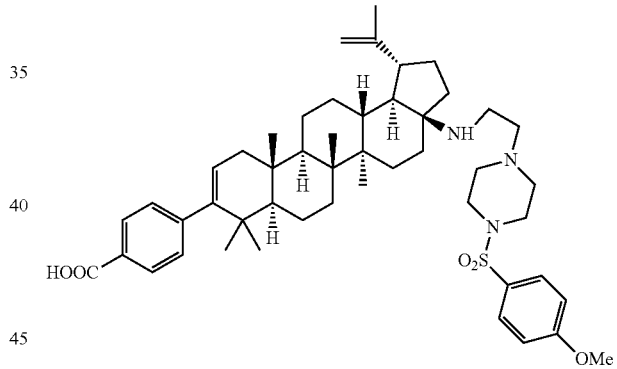

The title compound was prepared to provide 9.5 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using 4-methoxybenzene-1-sulfonyl chloride as the sulfonylating agent. LCMS: m/e 812.8 (M+H)$^+$, 3.69 min (method 14). $^1$H NMR (500 MHz, DMSO-d$_6$) δ 7.89 (d, J=8.2 Hz, 2H), 7.70 (d, J=8.9 Hz, 2H), 7.24 (d, J=8.2 Hz, 2H), 7.16 (d, J=8.9 Hz, 2H), 5.25 (d, J=4.6 Hz, 1H), 4.63 (d, J=2.1 Hz, 1H), 4.53 (s, 1H), 3.83 (s, 3H), 2.91 (s, 4H), 2.61-2.46 (m, 5H), 2.41 (br. s., 2H), 2.36-2.22 (m, 2H), 2.05 (dd, J=17.5, 6.3 Hz, 1H), 1.90-1.75 (m, 2H), 1.74-1.03 (m, 19H), 1.63 (s, 3H), 0.98 (s, 3H), 0.92 (s, 3H), 0.92 (s, 3H), 0.88 (s, 3H), 0.75 (s, 3H).

Example B48

Preparation of 4-((1R,3aS,5aR,5bR,7aR,11aS,11bR,13aR,13bR)-5a,5b,8,8,11a-pentamethyl-1-(prop-1-en-2-yl)-3a-((2-(4-tosylpiperazin-1-yl)ethyl)amino)-2,3,3a,4,5,5a,5b,6,7,7a,8,11,11a,11b,12,13,13a,13b-octadecahydro-1H-cyclopenta[a]chrysen-9-yl)benzoic acid

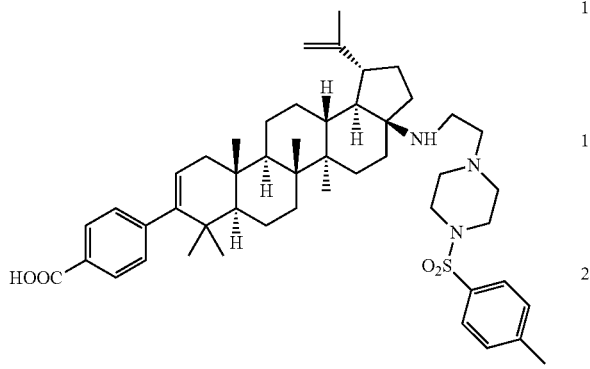

The title compound was prepared to provide 4.6 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using 4-methylbenzene-1-sulfonyl chloride as the sulfonylating agent. LCMS: m/e 796.8 (M+H)$^+$, 3.91 min (method 14). $^1$H NMR (500 MHz, DMSO-d$_6$) δ 7.88 (d, J=8.2 Hz, 2H), 7.65 (d, J=8.2 Hz, 2H), 7.46 (d, J=8.2 Hz, 2H), 7.24 (d, J=7.9 Hz, 2H), 5.25 (d, J=4.6 Hz, 1H), 4.62 (d, J=2.1 Hz, 1H), 4.53 (s, 1H), 2.91 (s, 4H), 2.59-2.45 (m, 5H), 2.41 (s, 5H), 2.36-2.25 (m, 2H), 2.06 (dd, J=17.4, 6.4 Hz, 1H), 1.88-1.74 (m, 2H), 1.73-0.99 (m, 19H), 1.63 (s, 3H), 0.97 (s, 3H), 0.92 (s, 3H), 0.92 (s, 3H), 0.91 (s, 3H), 0.81 (s, 3H).

Example B49

Preparation of 4-((1R,3aS,5aR,5bR,7aR,11aS,11bR,13aR,13bR)-5a,5b,8,8,11a-pentamethyl-3a-((2-(4-(naphthalen-1-ylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

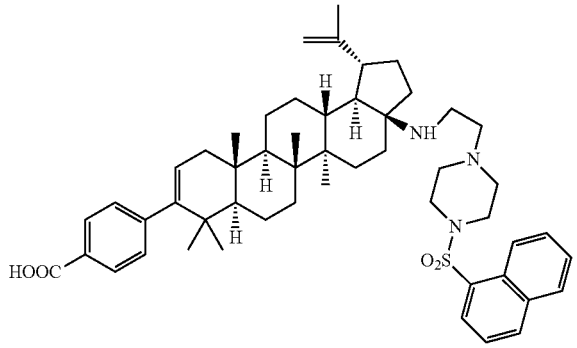

The title compound was prepared to provide 3.0 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using naphthalene-1-sulfonyl chloride as the sulfonylating agent. LCMS: m/e 832.8 (M+H)$^+$, 4.00 min (method 14). $^1$H NMR (500 MHz, DMSO-d$_6$) δ 8.75 (d, J=8.5 Hz, 1H), 8.29 (d, J=7.9 Hz, 1H), 8.17 (d, J=7.3 Hz, 1H), 8.10 (d, J=8.2 Hz, 1H), 7.90 (d, J=7.9 Hz, 2H), 7.81-7.62 (m, 3H), 7.28 (d, J=7.9 Hz, 2H), 5.24 (d, J=5.5 Hz, 1H), 4.62 (br. s., 1H), 4.52 (br. s., 1H), 3.08 (br. s., 4H), 2.52 (br. s., 5H), 2.45-2.22 (m, 4H), 2.02 (dd, J=17.7, 6.1 Hz, 1H), 1.91-1.74 (m, 2H), 1.73-1.02 (m, 19H), 1.61 (s, 3H), 1.06 (s, 3H), 0.94 (s, 3H), 0.87 (s, 3H), 0.79 (s, 3H), 0.48 (s, 3H).

Example B50

Preparation of 4-((1R,3aS,5aR,5bR,7aR,11aS,11bR,13aR,13bR)-3a-((2-(4-((4-fluorophenyl)sulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

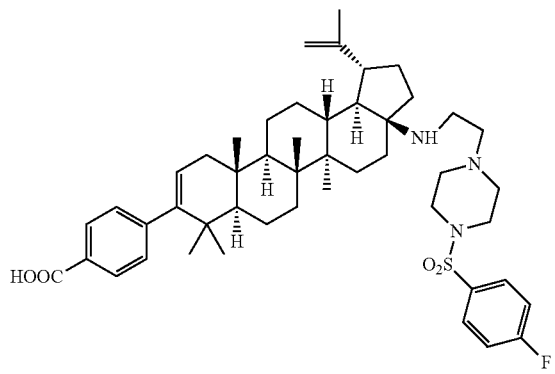

The title compound was prepared to provide 5.7 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using 4-fluorobenzene-1-sulfonyl chloride as the sulfonylating agent. LCMS: m/e 800.8 (M+H)$^+$, 4.95 min (method 15). $^1$H NMR (500 MHz, DMSO-d$_6$) δ 7.93-7.80 (m, 4H), 7.50 (t, J=8.7 Hz, 2H), 7.24 (d, J=7.9 Hz, 2H), 5.25 (d, J=4.9 Hz, 1H), 4.64 (d, J=2.1 Hz, 1H), 4.53 (s, 1H), 3.05-2.84 (m, 4H), 2.64-2.47 (m, 5H), 2.40 (br. s., 2H), 2.35-2.22 (m, 2H), 2.05 (dd, J=17.2, 6.3 Hz, 1H), 1.90-0.97 (m, 21H), 1.63 (s, 3H), 0.99 (s, 3H), 0.93 (s, 3H), 0.91 (s, 3H), 0.87 (s, 3H), 0.67 (s, 3H).

Example B51

Preparation of 4-((4-(2-(((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)piperazin-1-yl)sulfonyl)benzoic acid

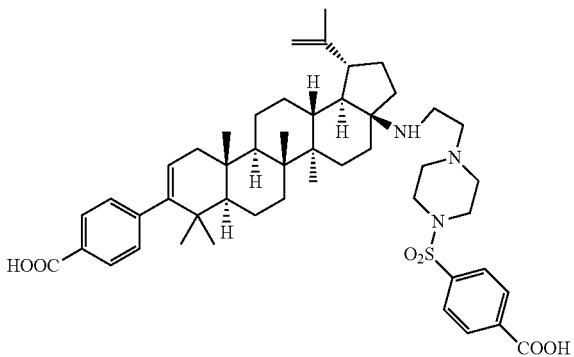

The title compound was prepared to provide 10.1 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using 4-(chlorosulfonyl)benzoic acid as the sulfonylating agent. LCMS: m/e 826.8 (M+H)$^+$, 2.75 min (method 14). $^1$H NMR (500 MHz, DMSO-d$_6$) δ 8.18 (d, J=8.2 Hz, 2H), 7.89 (dd, J=8.4, 3.8 Hz, 4H), 7.25 (d, J=8.2 Hz, 2H), 5.23 (d, J=4.9 Hz, 1H), 4.63 (s, 1H), 4.54 (s, 1H), 3.10-2.93 (m, 4H), 2.68-2.53 (m, 5H), 2.49-2.32 (m, 4H), 2.03 (dd, J=17.2, 6.0 Hz, 1H), 1.90-1.76 (m, 2H), 1.75-0.99 (m, 19H), 1.63 (s, 3H), 0.95 (s, 3H), 0.91 (s, 3H), 0.90 (s, 3H), 0.85 (s, 3H), 0.77 (s, 3H).

Example B52

Preparation of 4-((1R,3aS,5aR,5bR,7aR,11aS,11bR,13aR,13bR)-3a-((2-(4-((2,3-dihydrobenzo[b][1,4]dioxin-6-yl)sulfonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

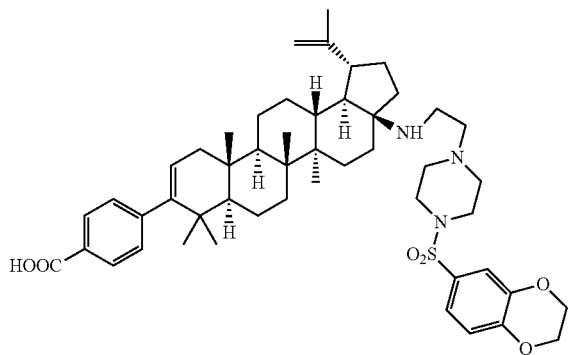

The title compound was prepared to provide 13.2 mg from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using 2,3-dihydro-1,4-benzodioxine-6-sulfonyl chloride as the sulfonylating agent. LCMS: m/e 840.8 (M+H)$^+$, 3.66 min (method 14). $^1$H NMR (500 MHz, DMSO-d$_6$) δ 7.88 (d, J=8.2 Hz, 2H), 7.31-7.18 (m, 4H), 7.08 (d, J=8.2 Hz, 1H), 5.25 (d, J=4.6 Hz, 1H), 4.64 (d, J=2.1 Hz, 1H), 4.54 (s, 1H), 4.42-4.21 (m, 4H), 2.91 (s, 4H), 2.62-2.51 (m, 5H), 2.41 (br. s., 2H), 2.36-2.26 (m, 2H), 2.06 (dd, J=17.4, 6.4 Hz, 1H), 1.90-1.76 (m, 2H), 1.75-0.88 (m, 19H), 1.64 (s, 3H), 0.98 (s, 3H), 0.93 (s, 3H), 0.92 (s, 3H), 0.91 (s, 3H), 0.78 (s, 3H).

General Procedure for the Preparation of Examples B53-B64

A solution of the corresponding substituted carboxylic acid (acylating agent) (0.039 mmol) and HATU (14.78 mg, 0.039 mmol) in DMF (0.5 mL) was stirred for 10 minutes, then a solution of methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (17 mg, 0.026 mmol) and DIPEA (0.018 mL, 0.104 mmol) in DMF (0.500 mL) was introduced. The reaction mixture was agitated at 350 rpm on an Innova platform shaker at room temperature overnight. The solvent was evaporated to provide the dry residue. To the residue in dioxane (0.8 mL) was added the lithium hydroxide monohydrate (8.70 mg, 0.207 mmol) dissolved in water (0.2 mL). The reaction mixture was stirred at 80° C. overnight. The solvent was removed and DMF (1.0 mL) was added. The mixture was filtered and the clear solution was purified by HPLC to provide the desired products with yield ranged from 2-31% over two steps.

Example B53

Preparation of 4-((1R,3aS,5aR,5bR,7aR,11aS,11bR,13aR,13bR)-3a-((2-(4-(cyclohexanecarbonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

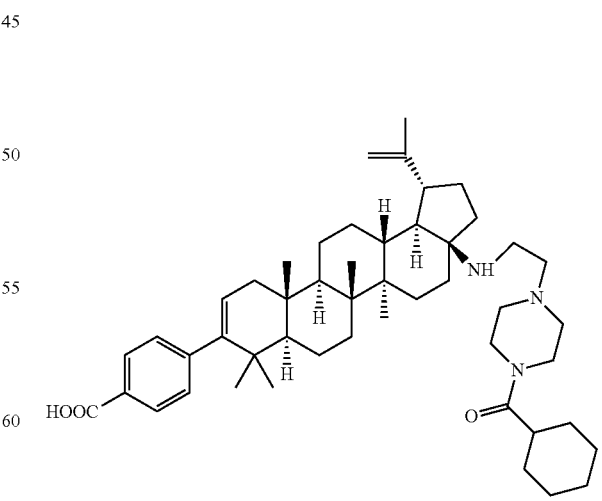

The title compound (4.9 mg) was prepared from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-

(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using cyclohexanecarboxylic acid as the acylating agent. LCMS: m/e 752.8 (M+H)+, 3.90 min (method 14). $^1$H NMR (500 MHz, DMSO-$d_6$) δ 7.85 (d, J=8.2 Hz, 2H), 7.19 (d, J=8.2 Hz, 2H), 5.24 (d, J=4.9 Hz, 1H), 4.70 (s, 1H), 4.56 (s, 1H), 3.49 (br. s., 4H), 2.70-2.53 (m, 4H), 2.48-2.31 (m, 5H), 2.31-2.18 (m, 1H), 2.08 (dd, J=17.4, 6.1 Hz, 1H), 1.99-1.79 (m, 3H), 1.78-1.00 (m, 28H), 1.67 (s, 3H), 1.08 (s., 3H), 0.97 (s, 3H), 0.96 (s, 3H), 0.90 (s, 3H), 0.90 (s, 3H).

Example B54

Preparation of 4-((1R,3aS,5aR,5bR,7aR,11aS,11bR,13aR,13bR)-3a-((2-(4-(cyclobutanecarbonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

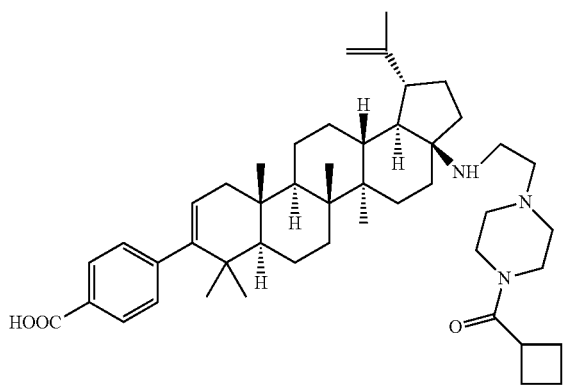

The title compound (3.1 mg) was prepared from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using cyclobutanecarboxylic acid as the acylating agent. LCMS: m/e 724.8 (M+H)+, 3.66 min (method 14). $^1$H NMR (500 MHz, METHANOL-$d_4$) δ 7.89 (d, J=8.2 Hz, 2H), 7.17 (d, J=8.2 Hz, 2H), 5.30 (d, J=4.6 Hz, 1H), 4.79 (s, 1H), 4.68 (s, 1H), 3.83-3.54 (m, 2H), 3.53-3.38 (m, 3H), 2.91 (d, J=2.1 Hz, 1H), 2.85-2.71 (m, 2H), 2.62 (d, J=10.1 Hz, 3H), 2.55-2.39 (m, 2H), 2.36-1.18 (m, 29H), 1.75 (s, 3H), 1.22 (s., 3H), 1.11 (s, 3H), 1.05 (s, 3H), 0.97 (s, 3H), 0.96 (s, 3H).

Example B55

Preparation of 4-((1R,3aS,5aR,5bR,7aR,11aS,11bR,13aR,13bR)-3a-((2-(4-(cyclopentanecarbonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

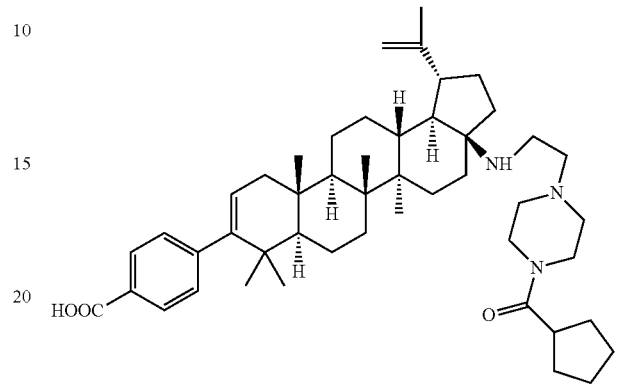

The title compound (3.1 mg) was prepared from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using cyclopentanecarboxylic acid as the acylating agent. LCMS: m/e 738.8 (M+H)+, 3.84 min (method 14). $^1$H NMR (500 MHz, METHANOL-$d_4$) δ 7.89 (d, J=8.2 Hz, 2H), 7.17 (d, J=8.2 Hz, 2H), 5.30 (d, J=4.6 Hz, 1H), 4.79 (s, 1H), 4.69 (s, 1H), 3.78-3.52 (m, 4H), 3.13-3.01 (m, 2H), 2.97-2.89 (m, 1H), 2.86-2.73 (m, 2H), 2.72-2.61 (m, 3H), 2.60-2.41 (m, 2H), 2.20-1.80 (m, 8H), 1.75 (s, 3H), 1.74-1.18 (m, 22H), 1.23 (s., 3H), 1.11 (s, 3H), 1.06 (s, 3H), 0.97 (s, 3H), 0.97 (s, 3H).

Example B56

Preparation of 4-((1R,3aS,5aR,5bR,7aR,11aS,11bR,13aR,13bR)-3a-((2-(4-(2-cyclopentylacetyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

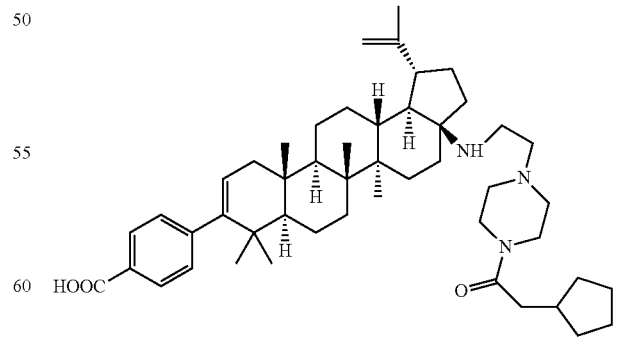

The title compound (3.1 mg) was prepared from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate following the general procedure as described above using cyclopentylacetic acid as the acylating agent. LCMS: m/e 752.9 (M+H)+, 3.93 min (method 14). ¹H NMR (500 MHz, METHANOL-d₄) δ 7.89 (d, J=8.2 Hz, 2H), 7.17 (d, J=8.2 Hz, 2H), 5.30 (d, J=4.6 Hz, 1H), 4.80 (s, 1H), 4.69 (s, 1H), 3.70 (br. s., 1H), 3.66-3.53 (m, 3H), 3.12-3.01 (m, 1H), 2.95-2.89 (m, 1H), 2.86-2.72 (m, 2H), 2.71-2.61 (m, 3H), 2.60-2.54 (m, 1H), 2.51-2.47 (m, 1H), 2.45 (d, J=7.3 Hz, 2H), 2.27-1.90 (m, 6H), 1.89-1.79 (m, 3H), 1.76 (s, 3H), 1.73-1.18 (m, 22H), 1.23 (s, 3H), 1.11 (s, 3H), 1.06 (s, 3H), 0.97 (s, 3H), 0.97 (s, 3H).

Example B57

Preparation of 4-((1R,3aS,5aR,5bR,7aR,11aS,11bR, 13aR,13bR)-3a-((2-(4-(2-cyclohexylacetyl)piperazin-1-yl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid

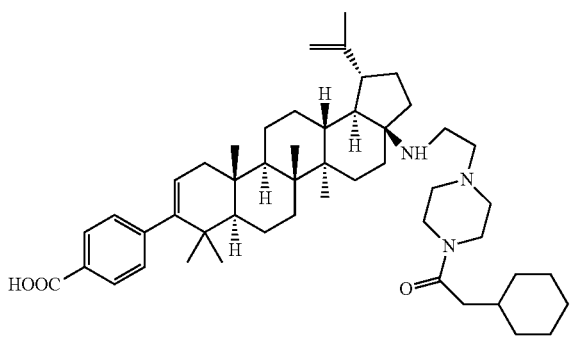

The title compound (3.4 mg) was prepared from methyl 4-((1R,3aS,5aR,5bR,7aR,11aS,11bR,13aR,13bR)-5a,5b,8, 8,11a-pentamethyl-3a-((2-(piperazin-1-yl)ethyl)amino)-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate following the general procedure as described above using cyclopentylacetic acid as the acylating agent. LCMS: m/e 766.9 (M+H)+, 4.09 min (method 14). ¹H NMR (500 MHz, METHANOL-d₄) δ 7.89 (d, J=8.2 Hz, 2H), 7.17 (d, J=8.2 Hz, 2H), 5.30 (d, J=4.9 Hz, 1H), 4.79 (s, 1H), 4.69 (s, 1H), 3.72 (dd, J=10.5, 6.0 Hz, 1H), 3.67-3.53 (m, 3H), 3.11-3.01 (m, 1H), 2.92 (d, J=10.7 Hz, 1H), 2.87-2.72 (m, 2H), 2.71-2.60 (m, 3H), 2.60-2.53 (m, 1H), 2.51-2.41 (m, 1H), 2.31 (d, J=6.4 Hz, 2H), 2.20-1.90 (m, 5H), 1.84 (td, J=12.1, 3.4 Hz, 1H), 1.75 (s, 3H), 1.75-1.02 (m, 27H), 1.23 (s, 3H), 1.11 (s, 3H), 1.06 (s, 3H), 0.97 (s, 3H), 0.97 (s, 3H).

Example B58

Preparation of 4-((1R,3aS,5aR,5bR,7aR,11aS,11bR, 13aR,13bR)-5a,5b,8,8,11a-pentamethyl-3a-((2-(4-(2-phenylpropanoyl)piperazin-1-yl)ethyl)amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid

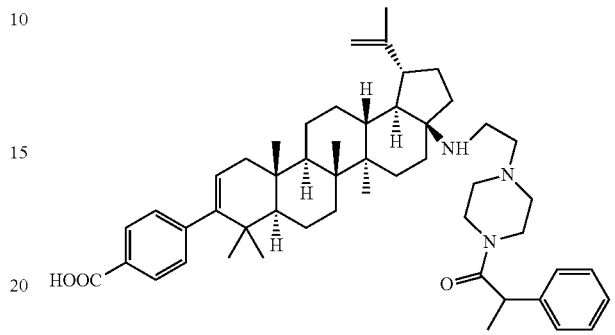

The title compound (4.1 mg) was prepared from methyl 4-((1R,3aS,5aR,5bR,7aR,11aS,11bR,13aR,13bR)-5a,5b,8, 8,11a-pentamethyl-3a-((2-(piperazin-1-yl)ethyl)amino)-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate following the general procedure as described above using 2-phenylpropionic acid as the acylating agent. LCMS: m/e 774.9 (M+H)+, 3.87 min (method 14). ¹H NMR (500 MHz, METHANOL-d₄) δ 7.89 (d, J=7.0 Hz, 2H), 7.41-7.31 (m, 2H), 7.29-7.22 (m, 3H), 7.18 (dd, J=8.2, 3.1 Hz, 2H), 5.30 (d, J=4.9 Hz, 1H), 4.77 (s, 1H), 4.67 (s, 1H), 4.11 (quin, J=6.4 Hz, 1H), 3.89-3.44 (m, 4H), 2.99-2.92 (m, 1H), 2.86-2.67 (m, 3H), 2.67-2.57 (m, 1H), 2.51 (d, J=13.7 Hz, 2H), 2.46-2.27 (m, 2H), 2.21-2.09 (m, 2H), 2.07-1.85 (m, 4H), 1.80-1.15 (m, 16H), 1.74 (s, 3H), 1.40 (d, J=6.7 Hz, 3H), 1.09 (d, J=8.5 Hz, 3H), 1.07 (d, J=13 Hz, 3H), 1.04 (s, 3H), 1.01 (s, 3H), 0.98 (s, 3H).

Example B59

Preparation of 4-((1R,3aS,5aR,5bR,7aR,11aS,11bR, 13aR,13bR)-5a,5b,8,8,11a-pentamethyl-3a-((2-(4-(3-methylbutanoyl)piperazin-1-yl)ethyl)amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid

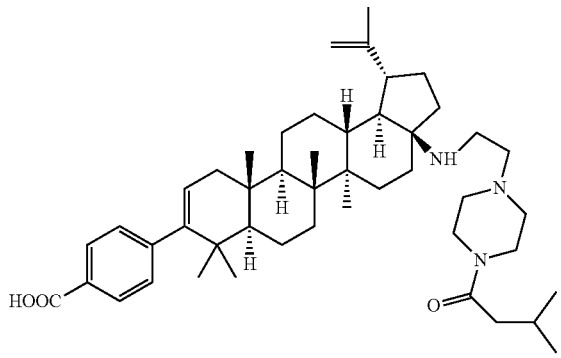

The title compound (3.3 mg) was prepared from methyl 4-((1R,3aS,5aR,5bR,7aR,11aS,11bR,13aR,13bR)-5a,5b,8, 8,11a-pentamethyl-3a-((2-(piperazin-1-yl)ethyl)amino)-1-

(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using isovaleric acid as the acylating agent. LCMS: m/e 726.8 (M+H)$^+$, 3.71 min (method 14). $^1$H NMR (500 MHz, METHANOL-d$_4$) δ 7.89 (d, J=8.2 Hz, 2H), 7.17 (d, J=8.2 Hz, 2H), 5.30 (d, J=4.9 Hz, 1H), 4.79 (s, 1H), 4.69 (s, 1H), 3.77-3.55 (m, 4H), 3.09-3.02 (m, 1H), 2.91 (br. s., 1H), 2.86-2.72 (m, 2H), 2.71-2.60 (m, 3H), 2.59-2.52 (m, 1H), 2.52-2.43 (m, 1H), 2.31 (d, J=7.3 Hz, 2H), 2.21-1.80 (m, 7H), 1.76 (s, 3H), 1.73-1.08 (m, 16H), 1.22 (s, 3H), 1.11 (s, 3H), 1.05 (s, 3H), 0.99 (d, J=6.4 Hz, 6H), 0.97 (s, 3H), 0.97 (s, 3H).

Example B60

Preparation of 4-((1R,3aS,5aR,5bR,7aR,11aS,11bR,13aR,13bR)-5a,5b,8,8,11a-pentamethyl-1-(prop-1-en-2-yl)-3a-((2-(4-propionylpiperazin-1-yl)ethyl)amino)-2,3,3a,4,5,5a,5b,6,7,7a,8,11,11a,11b,12,13,13a,13b-octadecahydro-1H-cyclopenta[a]chrysen-9-yl)benzoic acid

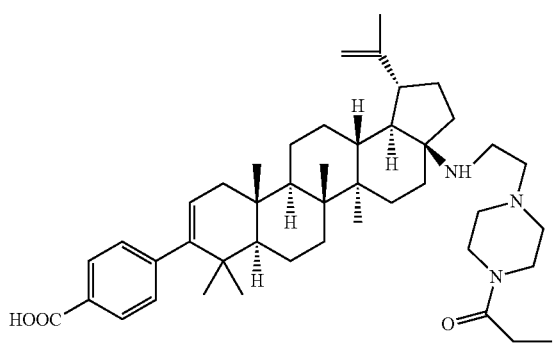

The title compound (5.5 mg) was prepared from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using propionic acid as the acylating agent. LCMS: m/e 698.8 (M+H)$^+$, 3.39 min (method 14). $^1$H NMR (500 MHz, DMSO-d$_6$) δ 7.87 (d, J=8.2 Hz, 2H), 7.22 (d, J=7.9 Hz, 2H), 5.25 (d, J=4.9 Hz, 1H), 4.70 (s, 1H), 4.56 (s, 1H), 3.52-3.43 (m, 4H), 3.11 (br. s., 2H), 2.71-2.53 (m, 2H), 2.47-2.20 (m, 7H), 2.08 (dd, J=17.2, 6.3 Hz, 1H), 1.97-1.80 (m, 3H), 1.79-1.03 (m, 18H), 1.67 (s, 3H), 1.08 (s, 3H), 0.99 (t, J=8.0 Hz, 3H), 0.97 (s, 3H), 0.96 (s, 3H), 0.90 (s, 3H), 0.90 (s, 3H).

Example B61

Preparation of 4-((1R,3aS,5aR,5bR,7aR,11aS,11bR,13aR,13bR)-3a-((2-(4-butyrylpiperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

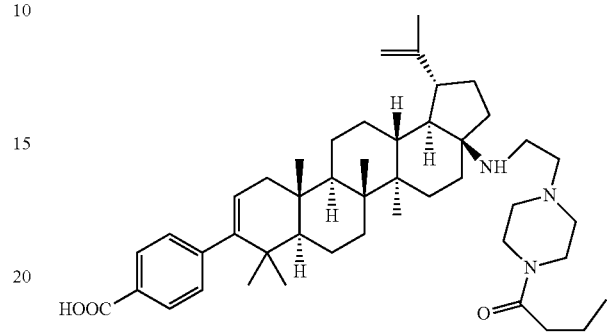

The title compound (1.2 mg) was prepared from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using butyric acid as the acylating agent. LCMS: m/e 712.8 (M+H)$^+$, 4.97 min (method 15). $^1$H NMR (500 MHz, METHANOL-d$_4$) δ 7.89 (d, J=8.2 Hz, 2H), 7.16 (d, J=8.2 Hz, 2H), 5.30 (d, J=4.6 Hz, 1H), 4.78 (s, 1H), 4.68 (s, 1H), 3.79-3.55 (m, 4H), 3.12-2.98 (m, 1H), 2.97-2.82 (m, 2H), 2.78 (td, J=10.9, 5.0 Hz, 1H), 2.71-2.61 (m, 3H), 2.60-2.54 (m, 1H), 2.52-2.44 (m, 1H), 2.40 (t, J=7.5 Hz, 2H), 2.19-1.80 (m, 6H), 1.75 (s, 3H), 1.73-1.04 (m, 18H), 1.23 (s, 3H), 1.11 (s, 3H), 1.05 (s, 3H), 0.99 (t, J=7.5 Hz, 3H), 0.97 (s, 3H), 0.97 (s, 3H).

Example B62

Preparation of 4-((1R,3aS,5aR,5bR,7aR,11aS,11bR,13aR,13bR)-3a-((2-(4-(cyclopropanecarbonyl)piperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

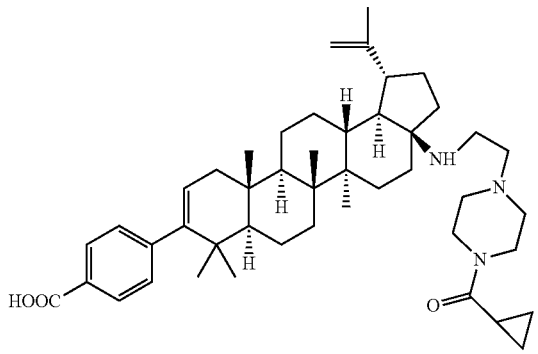

The title compound (0.9 mg) was prepared from methyl 4-((1R,3aS,5aR,5bR,7aR,11aS,11bR,13aR,13bR)-5a,5b,8, 8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using cyclopropanecarboxylic acid as the acylating agent. LCMS: m/e 710.8 (M+H)⁺, 4.41 min (method 15). ¹H NMR (500 MHz, METHANOL-d₄) δ 7.88 (d, J=7.9 Hz, 2H), 7.16 (d, J=7.9 Hz, 2H), 5.30 (d, J=4.9 Hz, 1H), 4.78 (s, 1H), 4.67 (s, 1H), 3.84 (br. s., 2H), 3.77-3.50 (m, 2H), 3.09-2.97 (m, 1H), 2.94-2.81 (m, 2H), 2.77 (td, J=10.5, 5.3 Hz, 1H), 2.73-2.57 (m, 4H), 2.48 (br. s., 1H), 2.21-1.82 (m, 8H), 1.75 (s, 3H), 1.73-1.07 (m, 15H), 1.24 (s, 3H), 1.10 (s, 3H), 1.06 (s, 3H), 0.97 (s, 3H), 0.97 (s, 3H), 0.93-0.87 (m, 2H), 0.87-0.79 (m, 2H).

Example B63

Preparation of 4-((1R,3aS,5aR,5bR,7aR,11aS,11bR,13aR,13bR)-5a,5b,8,8,11a-pentamethyl-3a-((2-(4-(1-methylcyclopropanecarbonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

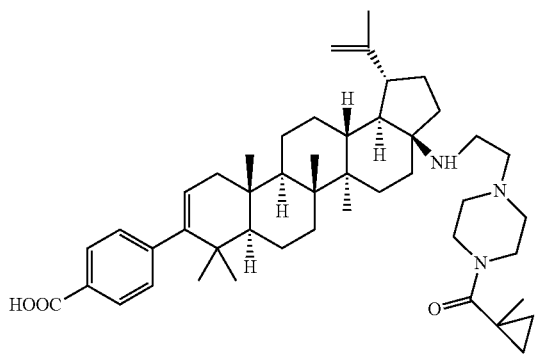

The title compound (0.9 mg) was prepared from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using 1-methylcyclopropane-1-carboxylic acid as the acylating agent. LCMS: m/e 724.8 (M+H)⁺, 4.49 min (method 15). ¹H NMR (500 MHz, METHANOL-d₄) δ 7.89 (d, J=8.2 Hz, 2H), 7.16 (d, J=8.2 Hz, 2H), 5.30 (d, J=4.6 Hz, 1H), 4.78 (s, 1H), 4.67 (s, 1H), 3.90-3.63 (m, 4H), 3.09-2.98 (m, 1H), 2.96-2.82 (m, 2H), 2.81-2.73 (m, 1H), 2.71-2.61 (m, 3H), 2.54 (br. s., 2H), 2.24-2.12 (m, 1H), 2.11-1.82 (m, 5H), 1.75 (s, 3H), 1.72-1.14 (m, 16H), 1.32 (s., 3H), 1.23 (s., 3H), 1.11 (s, 3H), 1.06 (s, 3H), 0.97 (s, 3H), 0.97 (s, 3H), 0.93-0.88 (m, 2H), 0.68-0.58 (m, 2H).

Example B64

Preparation of 4-((1R,3aS,5aR,5bR,7aR,11aS,11bR,13aR,13bR)-3a-((2-(4-isobutyrylpiperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

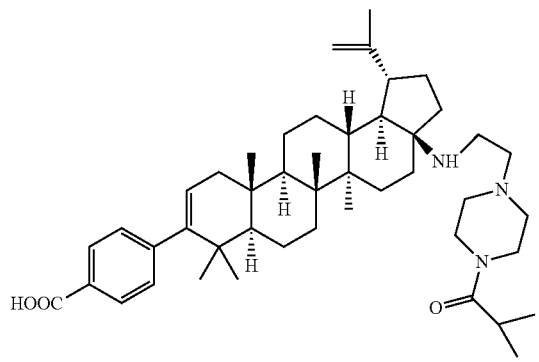

The title compound (0.4 mg) was prepared from methyl 4-((1R,3aS,5aR,5bR,7aR,11aS,11bR,13aR,13bR)-5a,5b,8,8,11a-pentamethyl-3a-((2-(piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the general procedure as described above using isobutyric acid as the acylating agent. LCMS: m/e 712.8 (M+H)⁺, 4.46 min (method 15). ¹H NMR (500 MHz, METHANOL-d₄) δ 7.88 (d, J=8.2 Hz, 2H), 7.15 (d, J=7.9 Hz, 2H), 5.30 (d, J=4.9 Hz, 1H), 4.78 (s, 1H), 4.67 (s, 1H), 3.77-3.54 (m, 4H), 2.97 (dt, J=13.4, 6.6 Hz, 2H), 2.86-2.71 (m, 3H), 2.70-2.51 (m, 4H), 2.46 (br. s., 1H), 2.15 (dd, J=17.1, 6.4 Hz, 1H), 2.08-1.82 (m, 5H), 1.75 (s, 3H), 1.73-1.18 (m, 16H), 1.22 (s, 3H), 1.11 (d, J=6.7 Hz, 6H), 1.10 (s, 3H), 1.05 (s, 3H), 0.97 (s., 3H), 0.97 (s., 3H), Example B65

Preparation of (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate

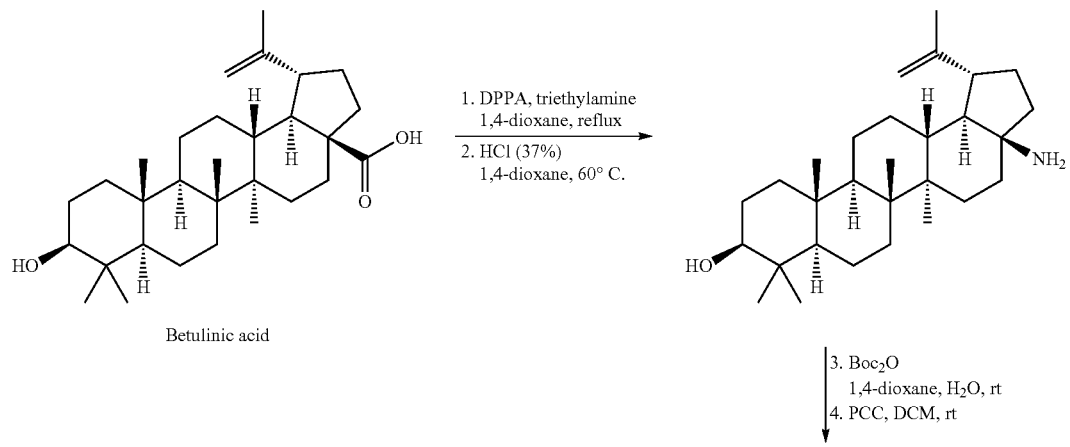

-continued

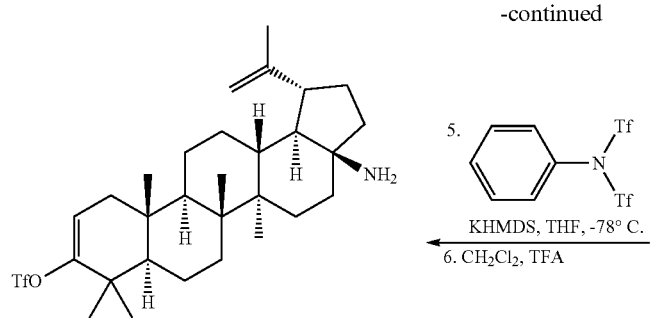

Step 1. Preparation of (1R,3aS,5aR,5bR,7aR,9S, 11aR,11bR,13aR,13bR)-3a-isocyanato-5a,5b,8,8, 11a-pentamethyl-1-(prop-1-en-2-yl)icosahydro-1H-cyclopenta[a]chrysen-9-ol

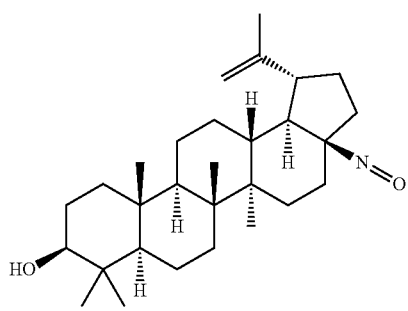

To a suspension of betulinic acid (10 g, 21.90 mmol) in 1,4-Dioxane (100 mL) was added triethylamine (9.16 mL, 65.7 mmol) and diphenyl phosphorazidate (7.08 mL, 32.8 mmol). The mixture was heated to reflux. Upon heating, all solids dissolved. After heating the mixture for 26 h, the mixture was cooled to rt and was concentrated under reduced pressure. The residue was diluted with 100 mL of water and was extracted with dichloromethane (3×100 mL). The combined organic layers were dried with sodium sulfate. The drying agent was removed by filtration and the filtrate was concentrated under reduced pressure. The residue was purified by flash chromatography in silica gel using a 0-15% EtOAc in hexanes gradient and a Thomson 240 g silica gel column. The fractions containing the expected product were combined and concentrated under reduced pressure. A second batch of less-pure product was concentrated and was repurified using a Thomson 240 g column and the same gradient The fractions containing the expected product were combined with the first batch to give (1R,3aS,5aR,5bR,7aR, 9S,11aR,11bR,13aR,13bR)-3a-isocyanato-5a,5b,8,8,11a-pentamethyl-1-(prop-1-en-2-yl)icosahydro-1H-cyclopenta[a]chrysen-9-ol (7.76 g, 17.10 mmol, 78% yield) as a white solid. $^1$H NMR (400 MHz, chloroform-d) δ=4.75 (s, 1H), 4.67-4.62 (m, 1H), 3.20 (dt, J=11.3, 5.6 Hz, 1H), 2.55 (td, J=10.9, 5.9 Hz, 1H), 2.17-2.03 (m, 1H), 1.92-1.76 (m, 5H), 1.69 (s, 3H), 1.06 (s, 3H), 0.98 (s, 3H), 0.95 (s, 3H), 0.85 (s, 3H), 0.78 (s, 3H), 1.74-0.66 (m, 19H).

Step 2. Preparation of (1R,3aS,5aR,5bR,7aR,9S, 11aR,11bR,13aR,13bR)-3a-amino-5a,5b,8,8,11a-pentamethyl-1-(prop-1-en-2-yl)icosahydro-1H-cyclopenta[a]chrysen-9-ol, HCl

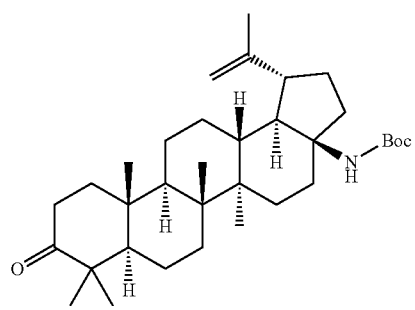

To a solution of (1R,3aS,5aR,5bR,7aR,9S,11aR,11bR, 13aR,13bR)-3a-isocyanato-5a,5b,8,8,11a-pentamethyl-1-(prop-1-en-2-yl)icosahydro-1H-cyclopenta[a]chrysen-9-ol (7.76 g, 17.10 mmol) in 1,4-dioxane (100 mL) was added HCl (37%) (21.07 mL, 257 mmol). The mixture was heated to 60° C. for 15 h of heating then was cooled to rt and was concentrated under reduced pressure. The residue was dissolved in dichloromethane and methanol and was concentrated two additional times to give (1R,3aS,5aR,5bR,7aR,9S,11aR, 11bR,13aR,13bR)-3a-amino-5a,5b,8,8,11a-pentamethyl-1-(prop-1-en-2-yl)icosahydro-1H-cyclopenta[a]chrysen-9-ol, HCl (7.75 g, 16.70 mmol, 98% yield) as an off-white foam. The crude product was used in the next step with no purification.

Step 3. Preparation of tert-butyl ((1R,3aS,5aR,5bR, 7aR,9S,11aR,11bR,13aR,13bR)-9-hydroxy-5a,5b,8, 8,11a-pentamethyl-1-(prop-1-en-2-yl)icosahydro-1H-cyclopenta[a]chrysen-3a-yl)carbamate

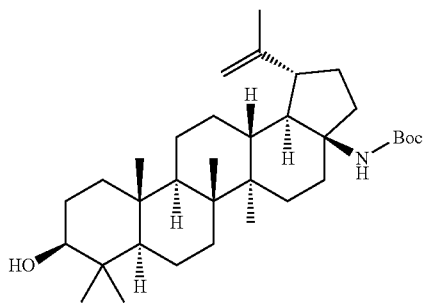

To a solution of (1R,3aS,5aR,5bR,7aR,9S,11aR,11bR, 13aR,13bR)-3a-amino-5a,5b,8,8,11a-pentamethyl-1-(prop- 1-en-2-yl)icosahydro-1H-cyclopenta[a]chrysen-9-ol, HCl (7.76 g, 16.72 mmol) in 1,4-Dioxane (100 mL) was added water (25 mL), sodium bicarbonate (4.21 g, 50.2 mmol) and Boc anhydride (5.82 mL, 25.08 mmol). The mixture was stirred at rt for 16 h then the mixture was diluted with 100 mL of water and was extracted with ethyl acetate (3×100 mL). The combined organic layers were washed with brine, dried over magnesium sulfate, filtered and concentrated under reduced pressure to give tert-butyl ((1R,3aS,5aR,5bR,7aR, 9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)carbamate as an off-white foam. ¹H NMR (500 MHz, chloroform-d) δ=4.74 (d, J=1.6 Hz, 1H), 4.64-4.62 (m, 1H), 4.34 (br. s., 1H), 3.24-3.18 (m, 1H), 2.63-2.35 (m, 3H), 2.06-1.93 (m, 1H), 1.71 (s, 3H), 1.46 (s, 9H), 1.04 (s, 3H), 0.99 (s, 3H), 0.98 (s, 3H), 0.86 (s, 3H), 0.79 (s, 3H), 1.77-0.68 (m, 22H).

Step 4. Preparation of tert-butyl ((1R,3aS,5aR,5bR, 7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate

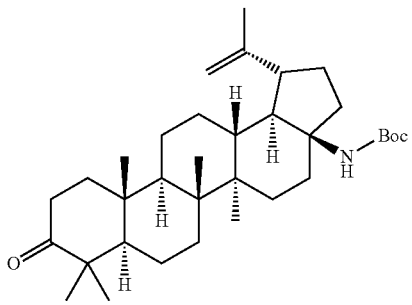

To a solution of the resulting tert-butyl ((1R,3aS,5aR,5bR, 7aR,9S,11aR,11bR,13aR,13bR)-9-hydroxy-5a,5b,8,8,11a-pentamethyl-1-(prop-1-en-2-yl)icosahydro-1H-cyclopenta [a]chrysen-3a-yl)carbamate in dichloromethane (100 mL) was added pyridinium chlorochromate (4.69 g, 21.74 mmol). The mixture was stirred at rt for 5 h then an additional 1.0 g of PCC was added and the mixture was stirred at rt for 1 h. The mixture was filtered through a plug of silica gel and celite which was washed with a solution of 25% ethyl acetate in hexanes. The filtrate was concentrated under reduced pressure to give tert-butyl ((1R,3aS,5aR,5bR,7aR,11aR,11bR, 13aR,13bR)-5a,5b,8,8,11a-pentamethyl-9-oxo-1-(prop-1-en-2-yl)icosahydro-1H-cyclopenta[a]chrysen-3a-yl) carbamate as a light-yellow foam. ¹H NMR (500 MHz, CHLOROFORM-d) δ=4.74 (d, J=1.7 Hz, 1H), 4.63 (t, J=1.7 Hz, 1H), 4.34 (br. s., 1H), 2.65-2.34 (m, 5H), 2.05-1.88 (m, 2H), 1.71 (s, 3H), 1.47 (s, 9H), 1.10 (s, 3H), 1.08 (s, 3H), 1.05 (s, 3H), 0.99 (s, 3H), 0.96 (s, 3H), 1.76-0.93 (m, 18H).

Step 5. Preparation of (1R,3aS,5aR,5bR,7aR,11aR, 11bR,13aR,13bR)-3a-((tert-butoxycarbonyl)amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl trifluoromethanesulfonate

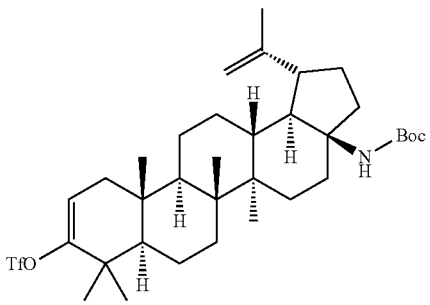

A solution of the resulting tert-butyl ((1R,3aS,5aR,5bR, 7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate in THF (100 mL) was cooled to −78° C. To the solution was added KHMDS (0.91M in THF) (40.4 mL, 36.8 mmol). The mixture was stirred for 20 minutes at −78° C. then a solution of 1,1,1-trifluoro-N-phenyl-N-(trifluoromethyl)sulfonyl methanesulfonamide (7.47 g, 20.90 mmol) in THF (100 mL) was added via canula. The mixture was stirred at −78° C. for 5 h then was quenched with 100 mL of water and was extracted with ethyl acetate (3×75 mL). The combined organic layers were dried with magnesium sulfate. The drying agent was removed by filtration and the filtrate was concentrated under reduced pressure. The residue was taken up in a small amount of DCM and methanol and the yellow solids that formed were removed by filtration. The filtrate was again concentrated and treated with methanol and the solids that formed were again removed by filtration. The filtrate was concentrated and was adsorbed to silica gel and was then purified by flash chromatography using a 0-50% ethyl acetate in hexanes gradient and a Thomson 240 g silica gel column. The fractions containing the deprotected product were combined and were concentrated under reduced pressure to give a mixture of products The expected product was repurified by flash chromatography using a 0-10% EtOAc in hexanes gradient and a 240 g Thomson silica gel column. The fractions containing the expected product were combined and were concentrated under reduced pressure to give (1R,3aS, 5aR,5bR,7aR,11aR,11bR,13aR,13bR)-3a-((tert-butoxycarbonyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (1.31 g, 1.99 mmol, 11.9% over 3 steps). ¹H NMR (500 MHz, CHLOROFORM-d) δ=5.57 (dd, J=6.7, 1.8 Hz, 1H), 4.73 (s, 1H), 4.62 (s, 1H), 4.32 (br. s., 1H), 2.64-2.31 (m, 3H), 2.16 (dd, J=17.0, 6.8 Hz, 1H), 2.04-1.94 (m, 1H), 1.70 (s, 3H), 1.45 (s, 9H), 1.13 (s, 3H), 1.06 (s, 3H), 1.03 (s, 3H), 0.97 (s, 3H), 0.93 (s, 3H), 1.82-0.86 (m, 18H).

Step 6. Preparation of (1R,3aS,5aR,5bR,7aR,11aR, 11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl trifluoromethanesulfonate

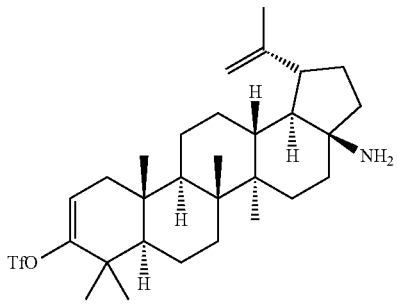

To a solution of (1R,3aS,5aR,5bR,7aR,11aR,11bR,13aR, 13bR)-3a-((tert-butoxycarbonyl)amino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl trifluoromethanesulfonate (0.2 g, 0.304 mmol) in dichloromethane (2 mL) was added trifluoroacetic acid (0.5 mL, 6.49 mmol). The mixture was stirred at rt for 1.5 h then was concentrated under reduced pressure. The residue was diluted with saturated aqueous sodium bicarbonate (20 mL) and was extracted with dichloromethane (3×20 mL). The combined organic layers were dried with $Na_2SO_4$. The drying agent was removed by filtration and the filtrate was concentrated and adsorbed to silica gel then was purified by flash chromatography using a 12-100% ethyl acetate in hexanes gradient and a 12 g Thomson silica gel column. The fractions containing the expected product were combined and were concentrated under reduced pressure to give (1R,3aS,5aR, 5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl trifluoromethanesulfonate (0.109 g, 0.195 mmol, 64.3% yield) as an off-white solid. $^1$H NMR (500 MHz, chloroform-d) δ=5.57 (dd, J=6.8, 1.9 Hz, 1H), 4.73 (d, J=1.6 Hz, 1H), 4.63-4.60 (m, 1H), 2.54 (td, J=10.9, 5.3 Hz, 1H), 2.17 (dd, J=17.1, 6.9 Hz, 1H), 2.08-1.99 (m, 1H), 1.70 (s, 3H), 1.13 (s, 3H), 1.08 (s, 3H), 1.03 (s, 3H), 0.97 (s, 3H), 0.93 (s, 3H), 1.82-0.91 (m, 20H).

Biology Data for the Examples
"μM" means micromolar;
"mL" means milliliter;
"μl" means microliter;
"mg" means milligram;
"μg" means microgram;

The materials and experimental procedures used to obtain the results reported in Tables 1-2 are described below.

HIV Cell Culture Assay

MT-2 cells and 293T cells were obtained from the NIH AIDS Research and Reference Reagent Program. MT-2 cells were propagated in RPMI 1640 media supplemented with 10% heat inactivated fetal bovine serum, 100 μg/ml penicillin G and up to 100 units/ml streptomycin. The 293T cells were propagated in DMEM media supplemented with 10% heat inactivated fetal bovine serum (FBS), 100 units/ml penicillin G and 100 μg/ml streptomycin. The proviral DNA clone of $NL_{4-3}$ was obtained from the NIH AIDS Research and Reference Reagent Program. A recombinant $NL_{4-3}$ virus, in which a section of the nef gene from NL4-3 was replaced with the *Renilla* luciferase gene, was used as a reference virus. In addition, residue Gag P373 was converted to P373S. Briefly, the recombinant virus was prepared by transfection of the altered proviral clone of $NL_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) μL of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The $EC_{50}$ data for the compounds is shown in Table 2. Table 1 is the key for the data in Table 2.

Results

TABLE 1

Biological Data Key for $EC_{50}$

| Compounds with $EC_{50}$ >0.1 μM | Compounds with $EC_{50}$ <0.1 μM |
|---|---|
| Group "B" | Group "A" |

TABLE 2

| Example # | Structure | $EC_{50}$ (μM) |
|---|---|---|
| 1 | 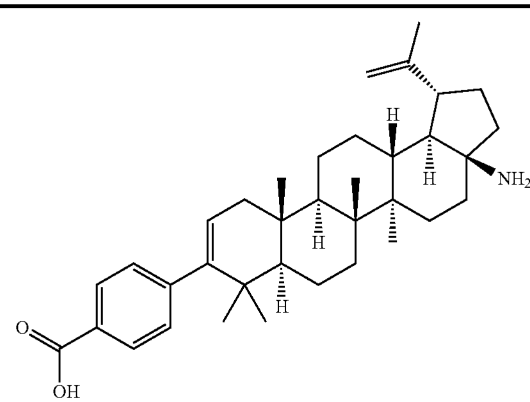 | A |

TABLE 2-continued
| Example # | Structure | EC$_{50}$ (μM) |
|---|---|---|
| 2 | 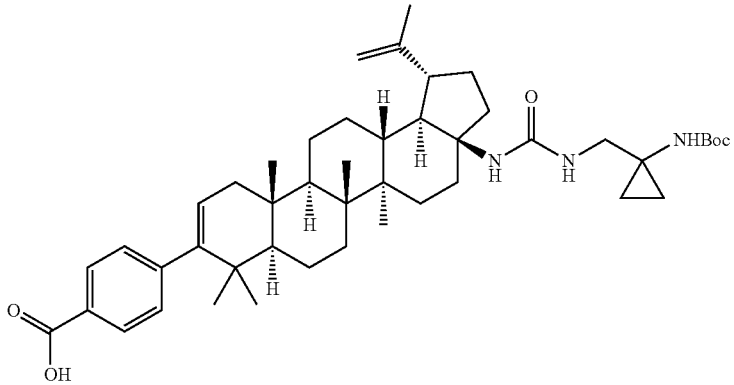 | A |
| 3 | 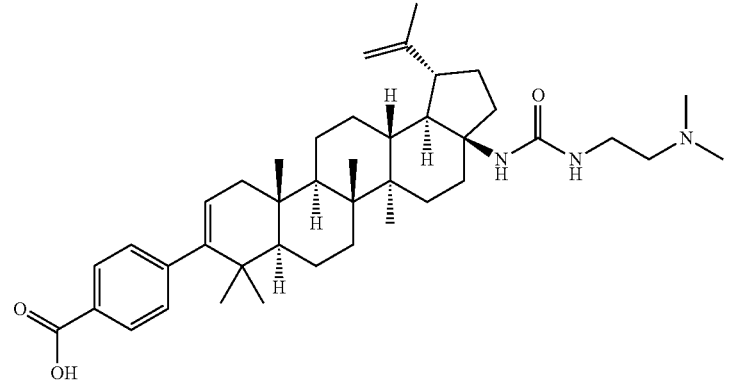 | 0.004 |
| 4 | 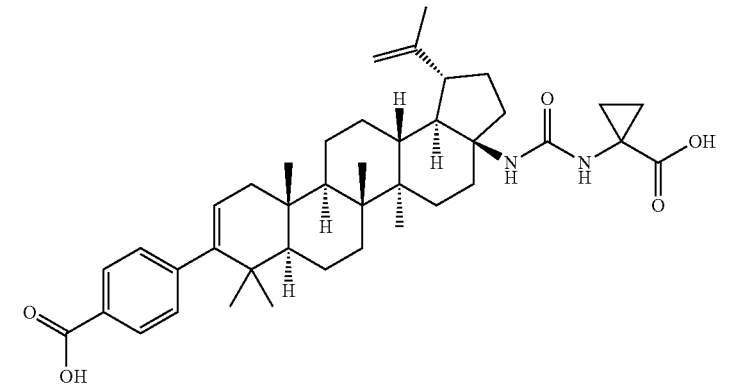 | B |
| 5 | 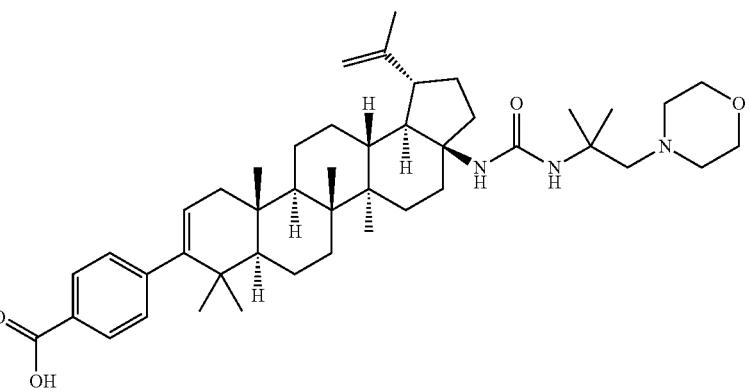 | A |

TABLE 2-continued

| Example # | Structure | EC$_{50}$ (μM) |
|---|---|---|
| 6 | 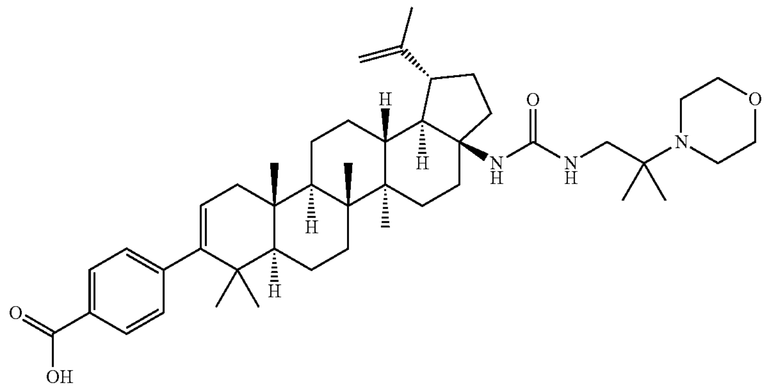 | A |
| 7 | 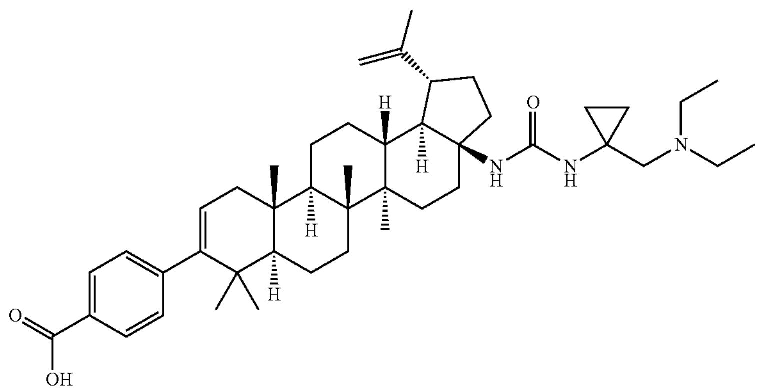 | A |
| 8 | 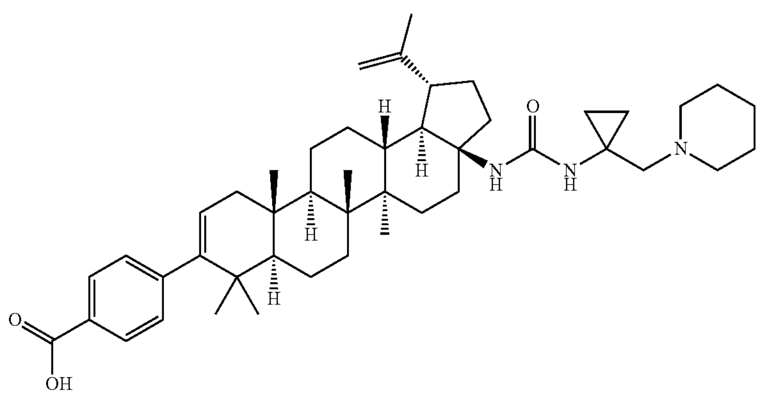 | A |
| 9 | 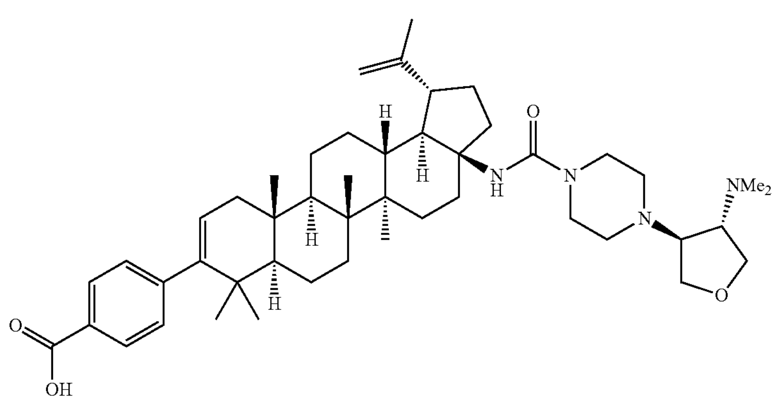 | 0.003 |

TABLE 2-continued

| Example # | Structure | EC$_{50}$ (μM) |
|---|---|---|
| 10 | 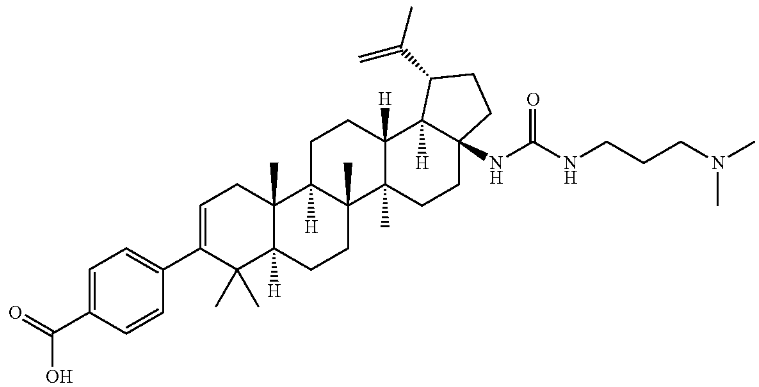 | A |
| 11 | 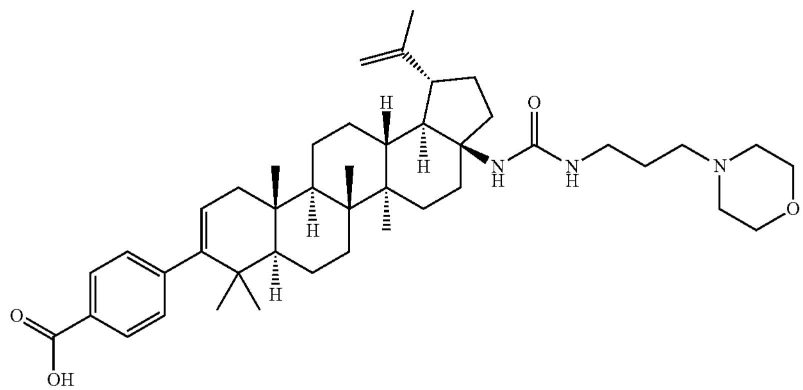 | A |
| 12 | 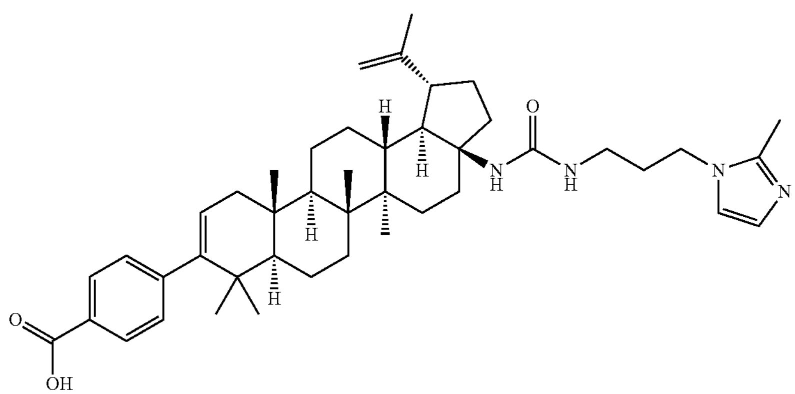 | A |
| 13 | 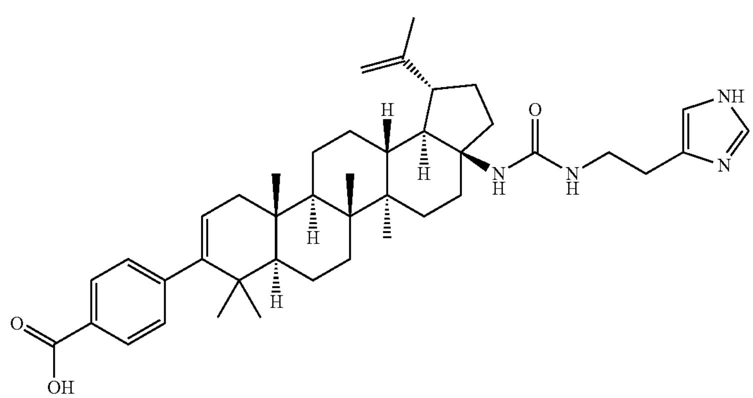 | A |

TABLE 2-continued

| Example # | Structure | EC₅₀ (µM) |
|---|---|---|
| 14 | 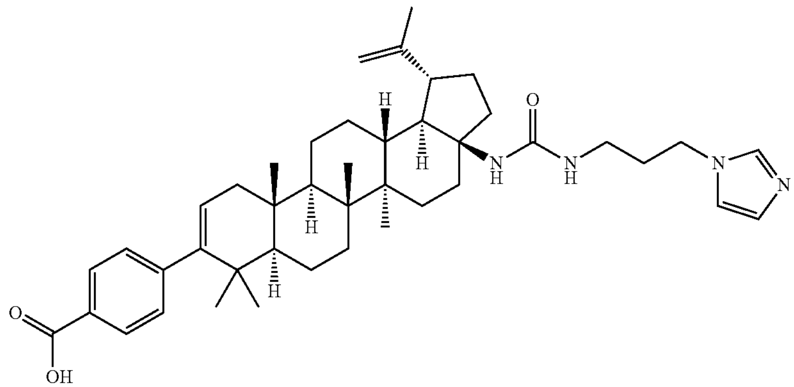 | A |
| 15 | 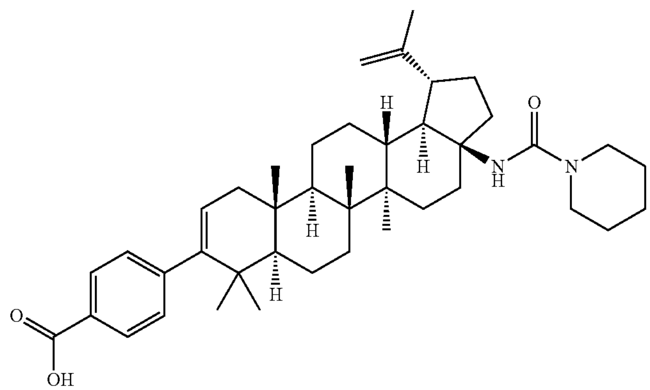 | A |
| 16 | 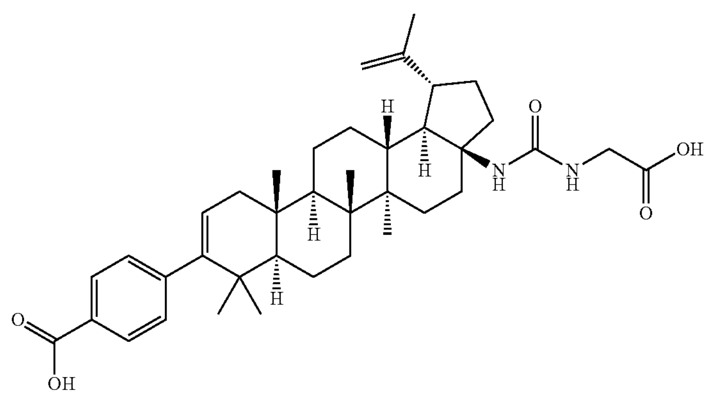 | A |
| 17 | 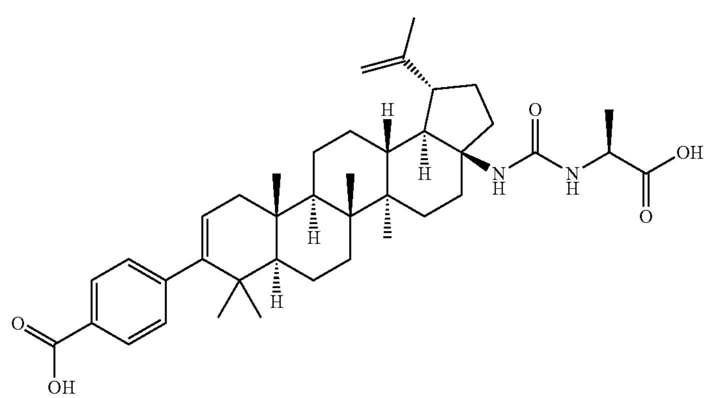 | A |

TABLE 2-continued

| Example # | Structure | EC$_{50}$ (μM) |
|---|---|---|
| 18 | 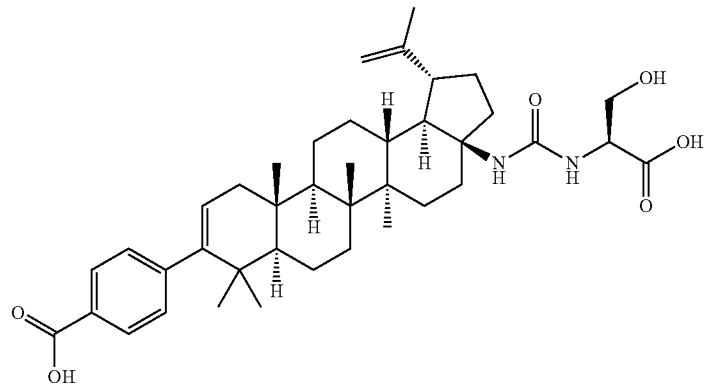 | 0.25 |
| 19 | 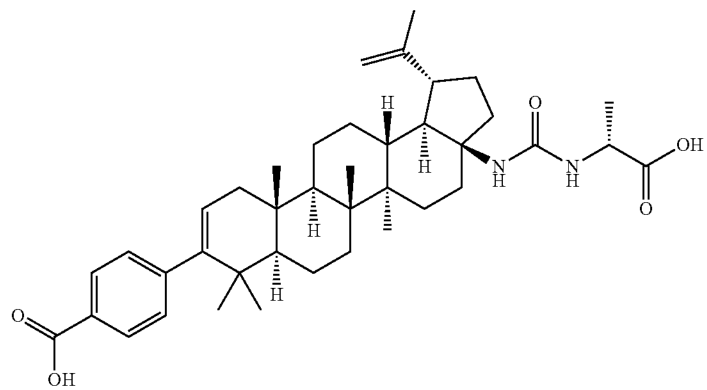 | A |
| 20 | 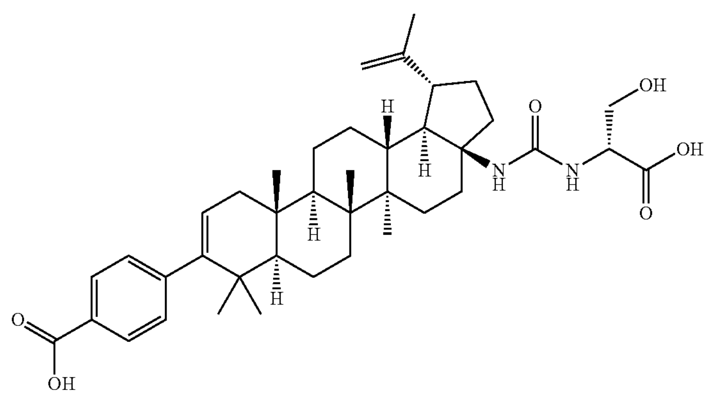 | 0.4 |
| 21 | 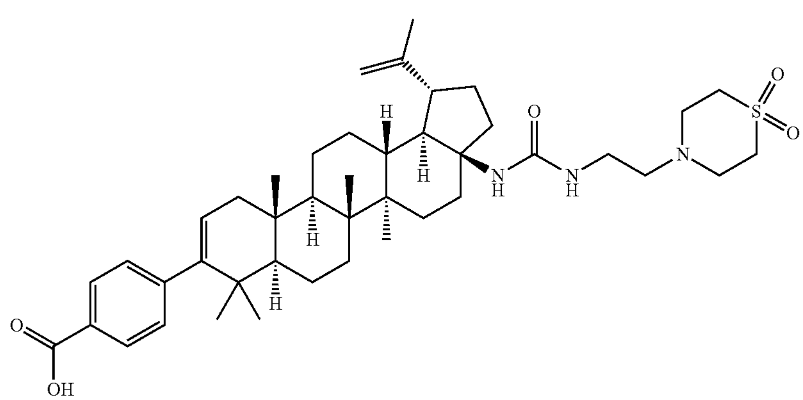 | A |

TABLE 2-continued

| Example # | Structure | EC$_{50}$ (μM) |
|---|---|---|
| 22 | 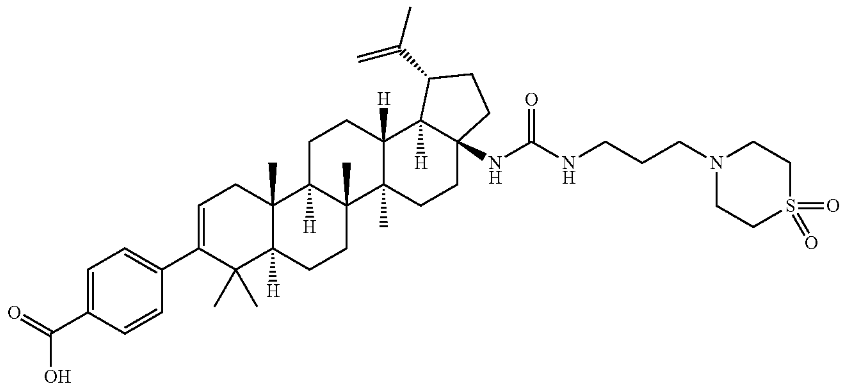 | A |
| 23 | 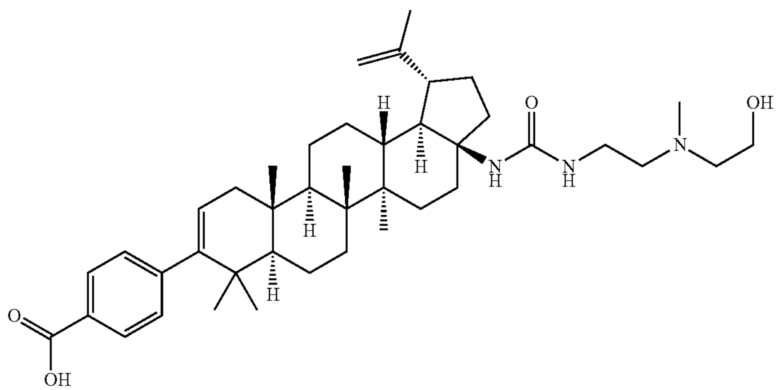 | A |
| 24 | 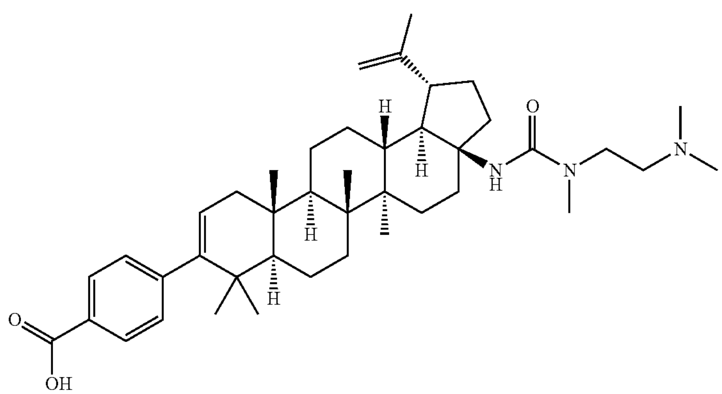 | A |
| 25 | 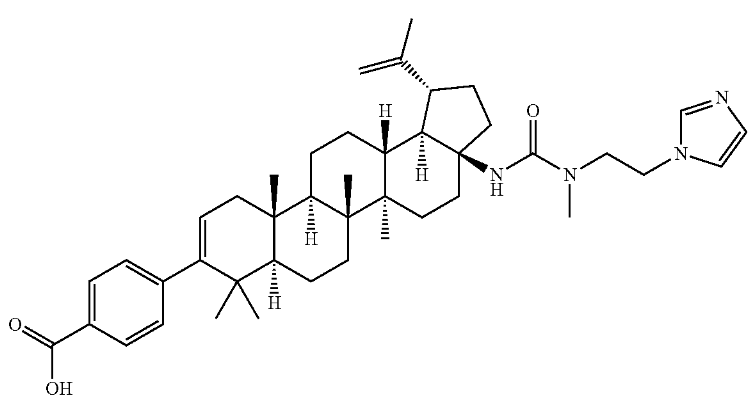 | A |

TABLE 2-continued

| Example # | Structure | EC$_{50}$ (μM) |
|---|---|---|
| 26 | 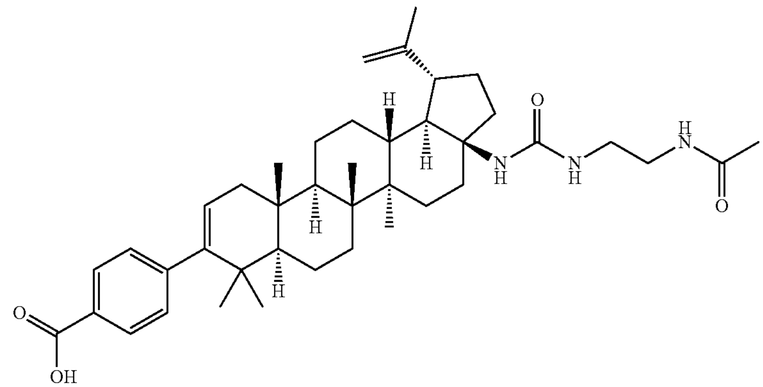 | A |
| 27 | 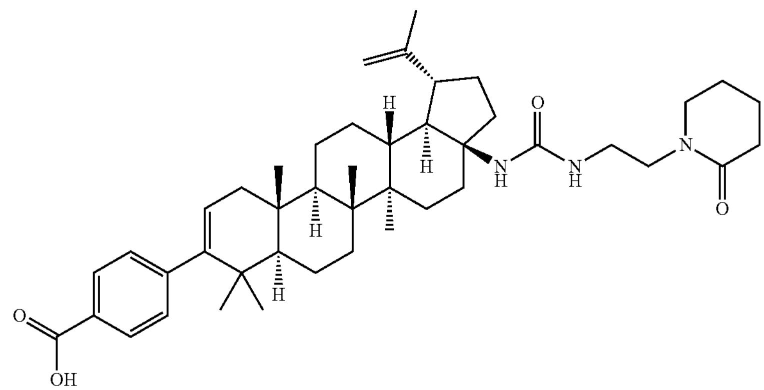 | A |
| 28 | 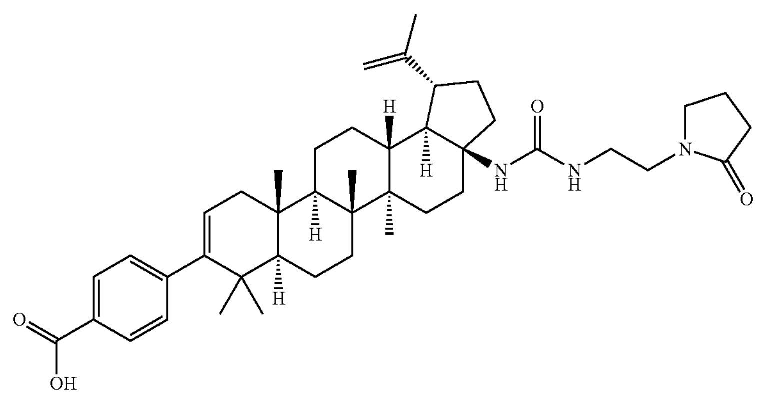 | 0.004 |
| 29 | 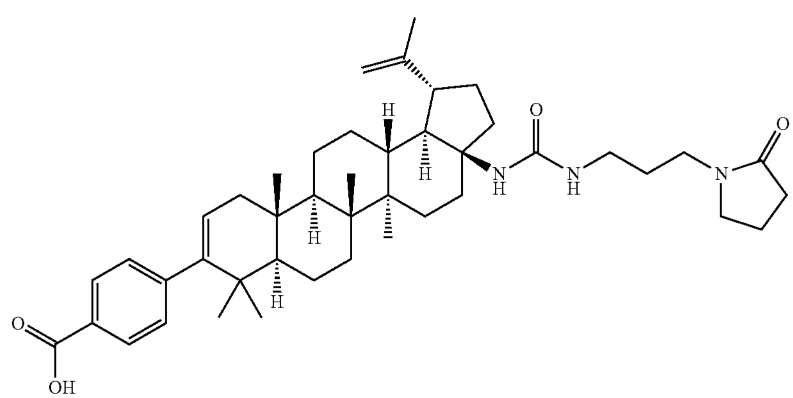 | 0.01 |

TABLE 2-continued
| Example # | Structure | EC$_{50}$ (μM) |
|---|---|---|
| 30 | 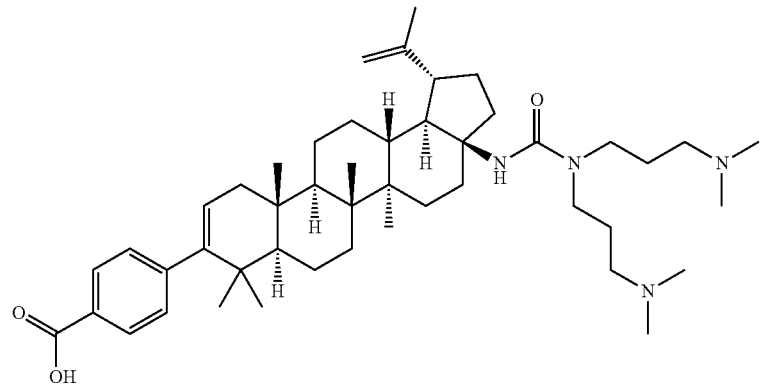 | A |
| 31 | 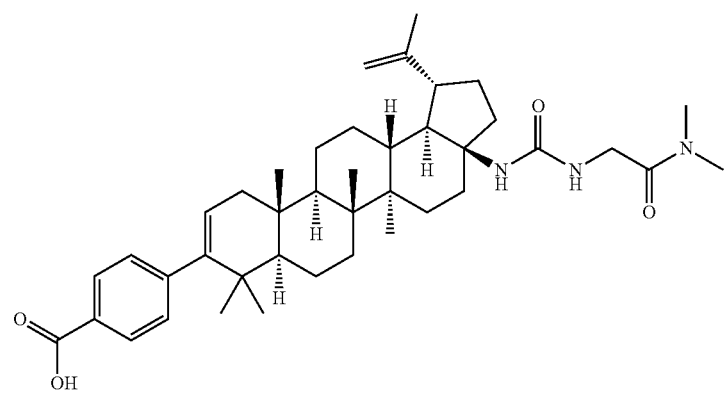 | A |
| 32 | 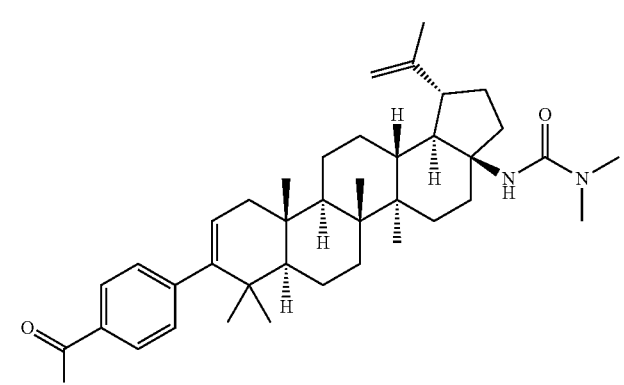 | 0.01 |
| 33 | 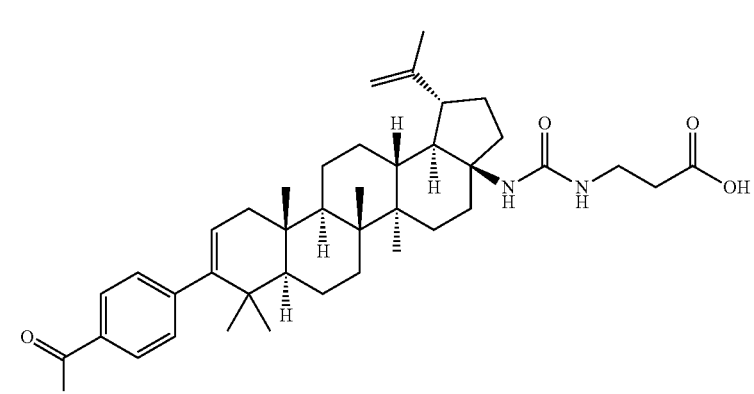 | A |

TABLE 2-continued

| Example # | Structure | EC$_{50}$ (μM) |
|---|---|---|
| 34 | 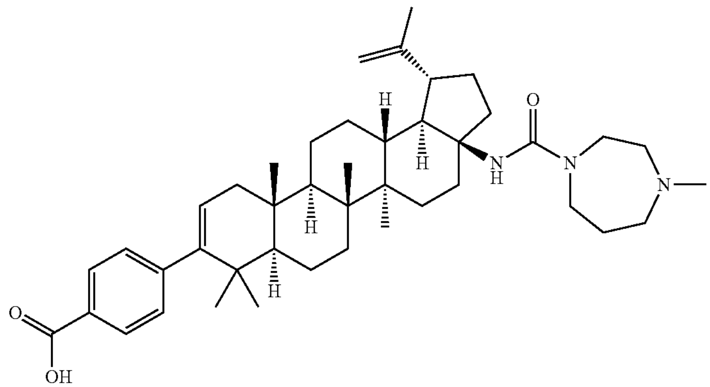 | 0.002 |
| 35 | 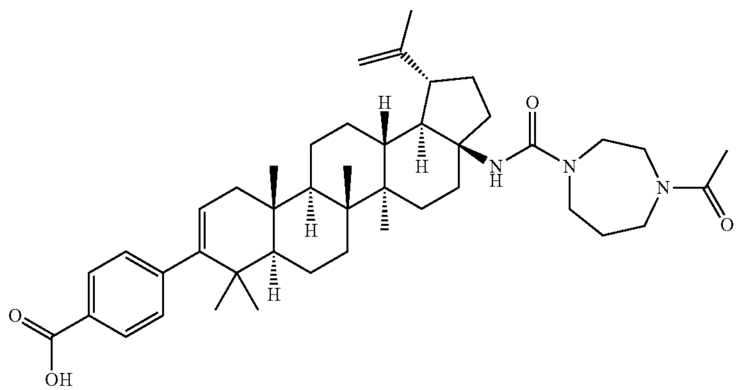 | A |
| 36 | 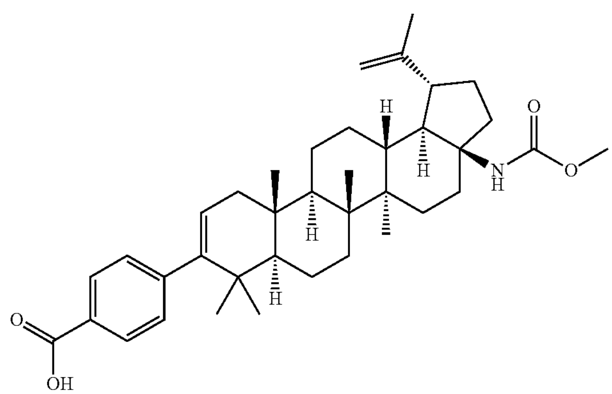 | A |
| 37 | 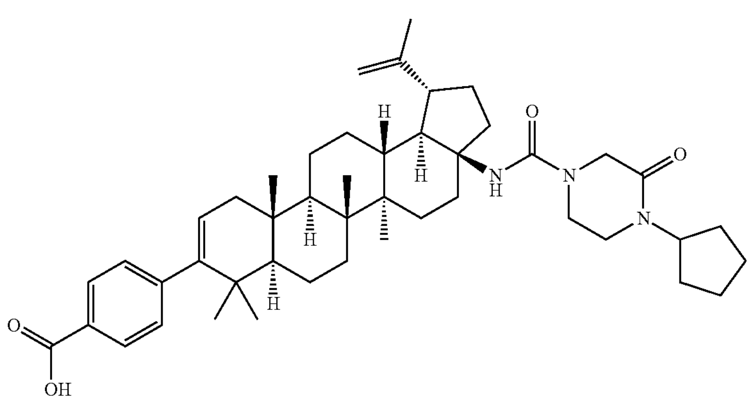 | 0.004 |

TABLE 2-continued
| Example # | Structure | EC$_{50}$ (μM) |
|---|---|---|
| 38 | 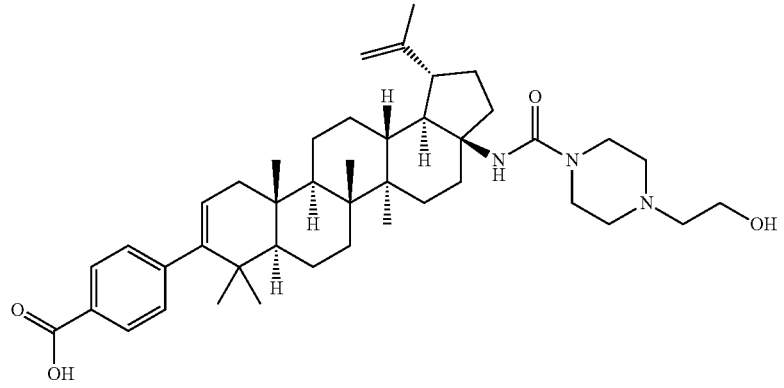 | A |
| 39 | 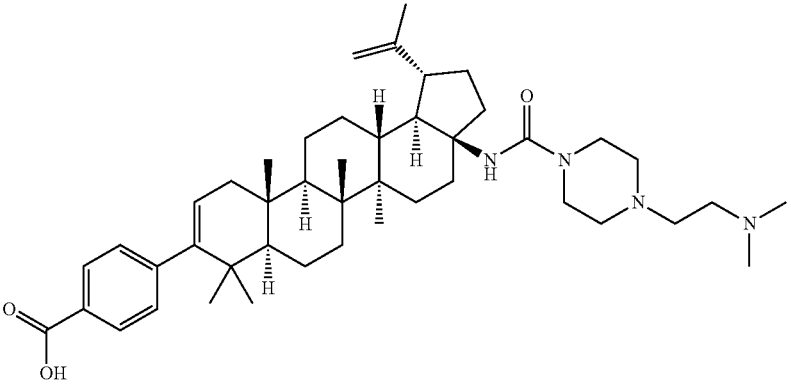 | A |
| 40 | 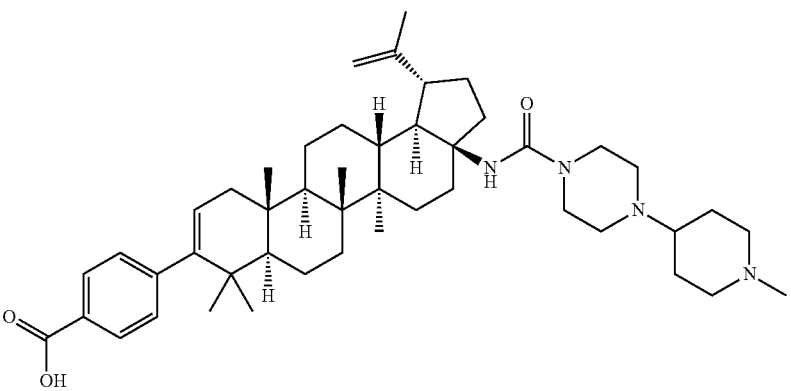 | A |
| 41 | 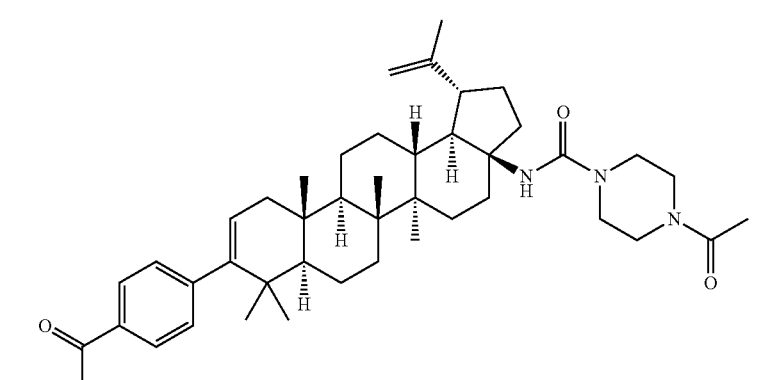 | A |

TABLE 2-continued
| Example # | Structure | EC$_{50}$ (µM) |
|---|---|---|
| 42 | 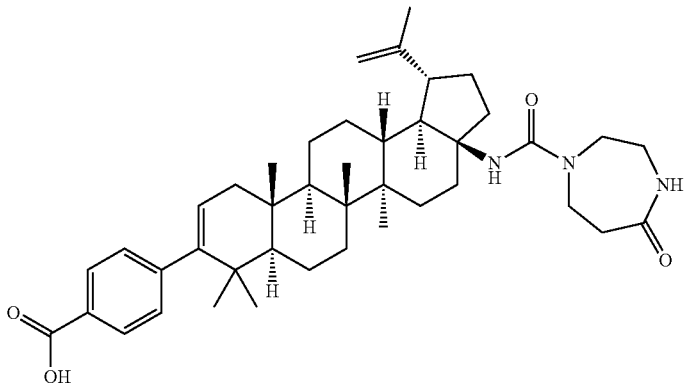 | A |
| 43 | 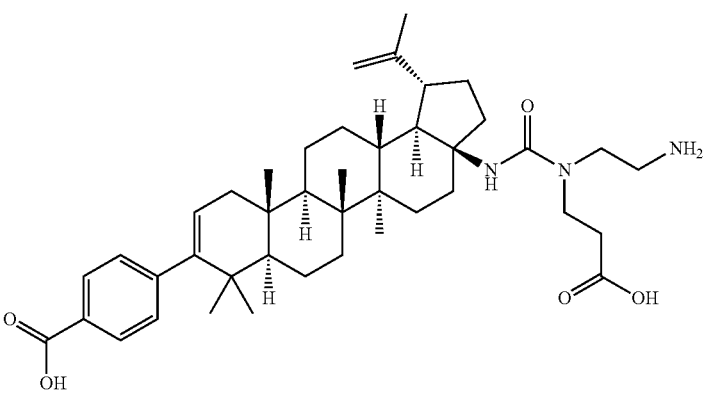 | 0.03 |
| 44 | 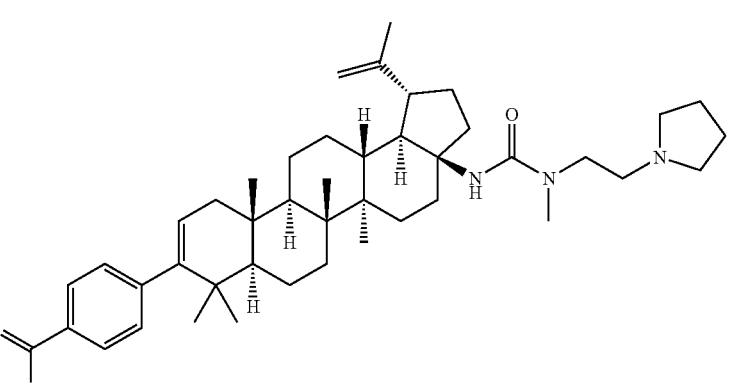 | A |
| 45 | 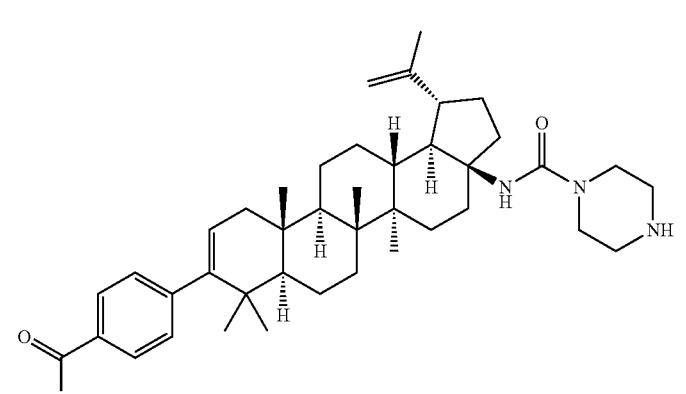 | A |

TABLE 2-continued

| Example # | Structure | EC$_{50}$ (μM) |
|---|---|---|
| 46 | 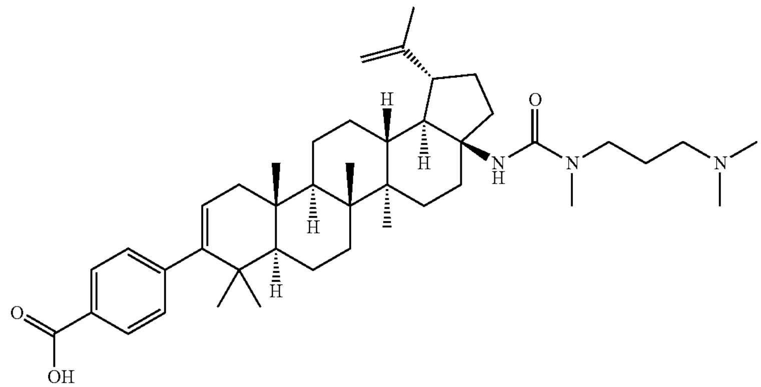 | A |
| 47 | 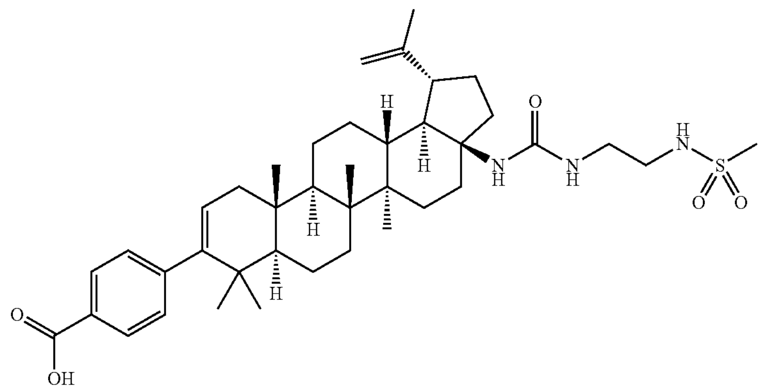 | A |
| 48 | 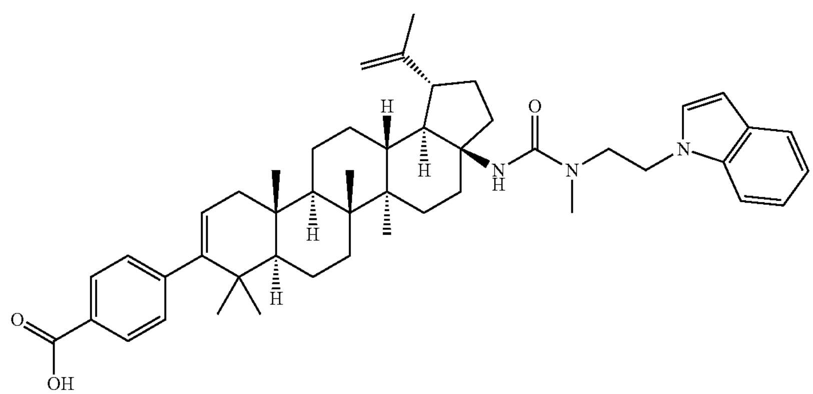 | A |
| 49 | 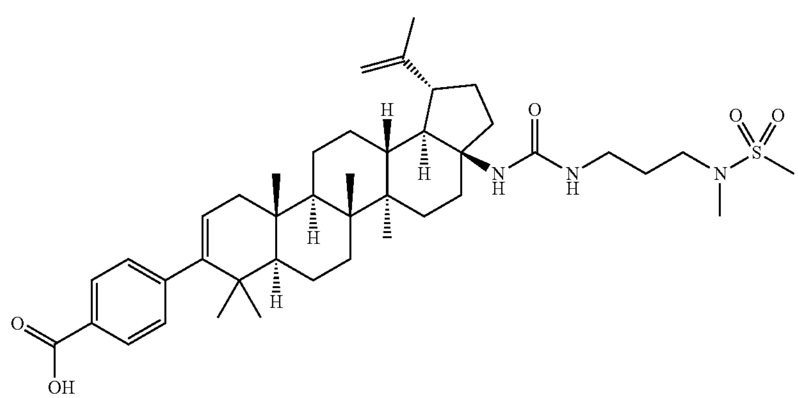 | A |

TABLE 2-continued

| Example # | Structure | EC$_{50}$ (μM) |
|---|---|---|
| 50 | 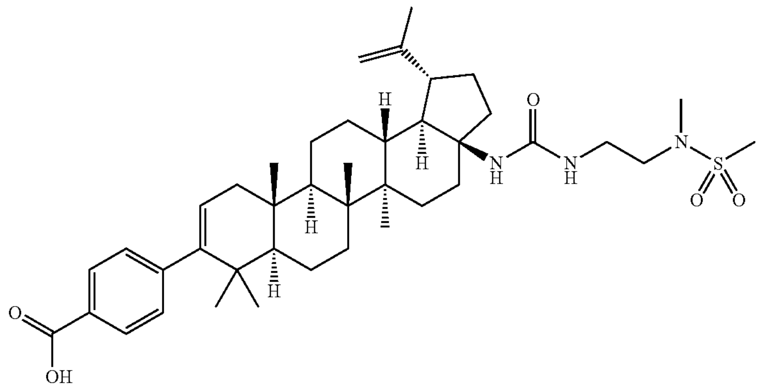 | A |
| 51 | 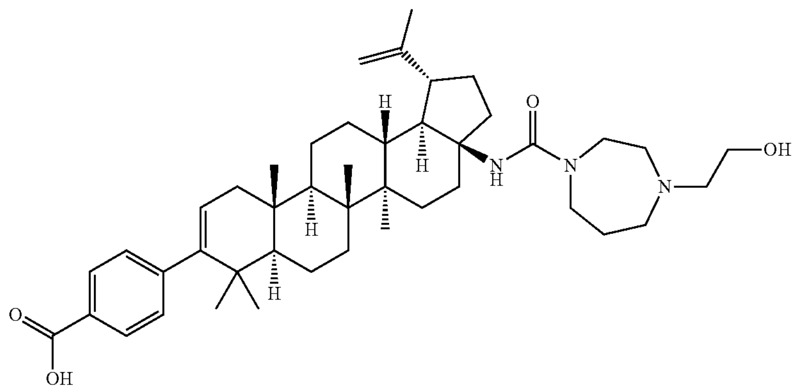 | A |
| 52 | 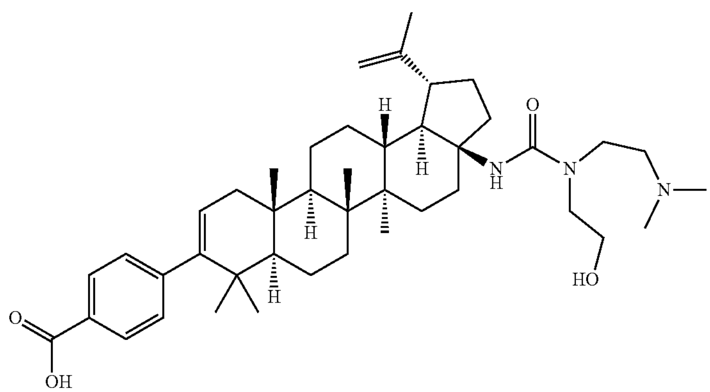 | A |
| 53 | 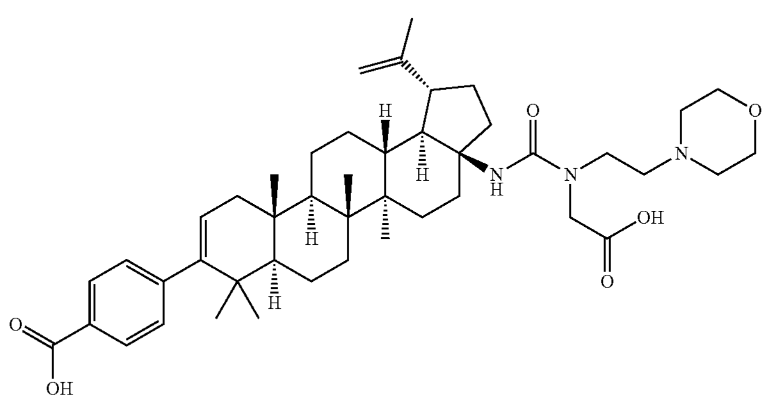 | A |

TABLE 2-continued

| Example # | Structure | EC$_{50}$ (μM) |
|---|---|---|
| 54 | 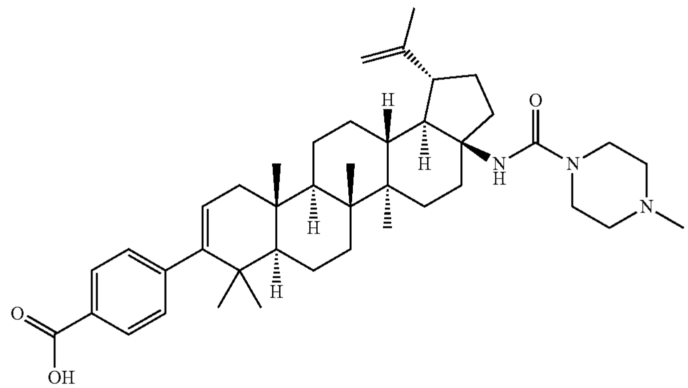 | A |
| 55 | 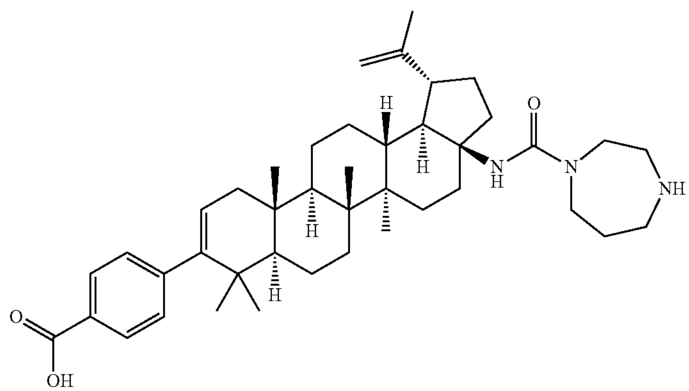 | A |
| 56 | 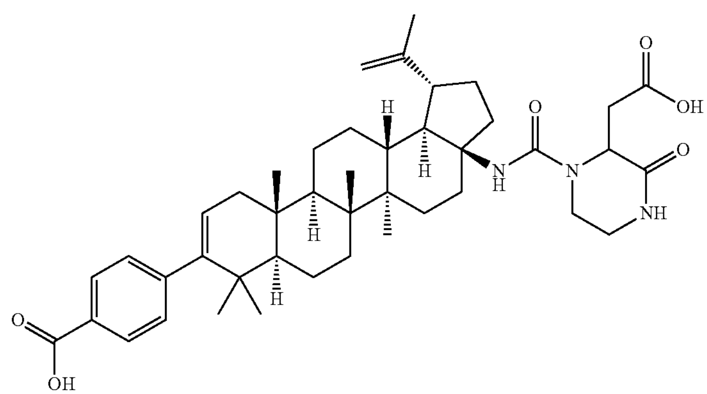 | A |
| 57 | 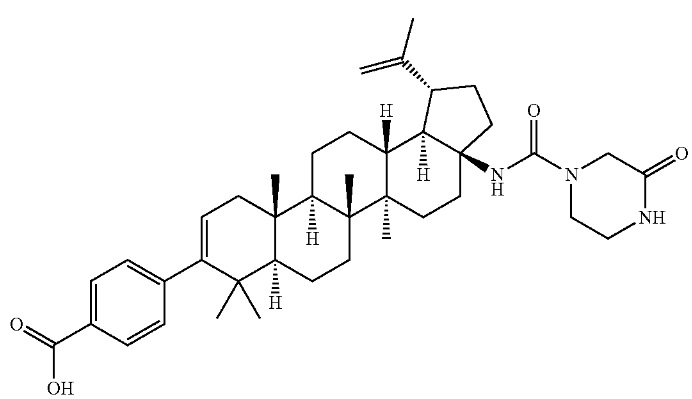 | A |

TABLE 2-continued

| Example # | Structure | EC$_{50}$ (μM) |
|---|---|---|
| 58 | 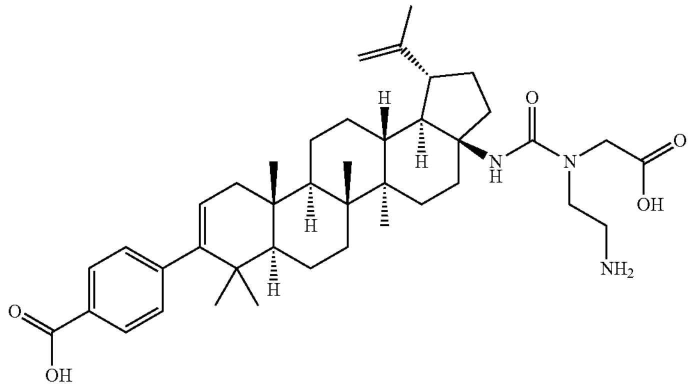 | A |
| 59 | 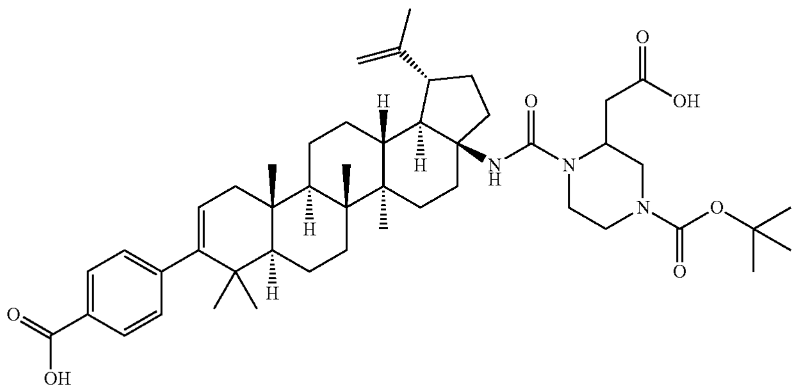 | A |
| 60 | 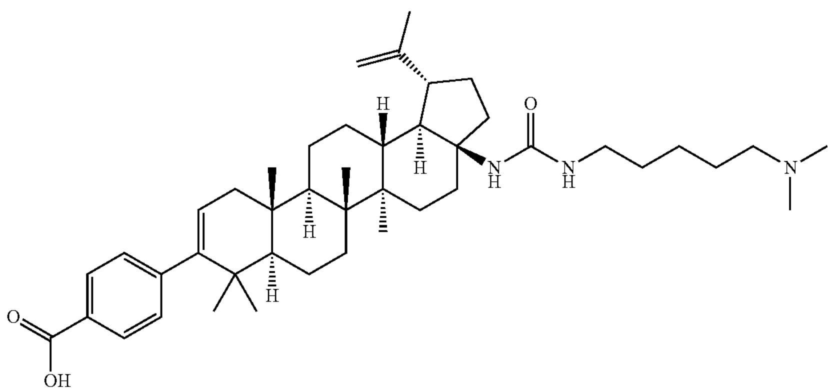 | A |
| 61 | 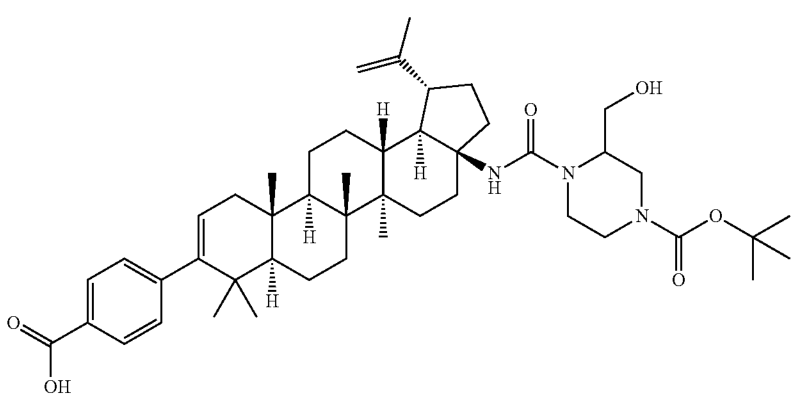 | A |

TABLE 2-continued
| Example # | Structure | EC$_{50}$ (μM) |
|---|---|---|
| 62 | | A |
| 63 | 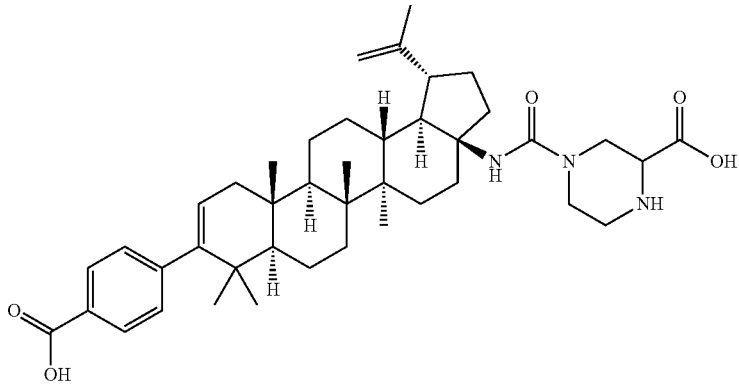 | A |
| 64 | 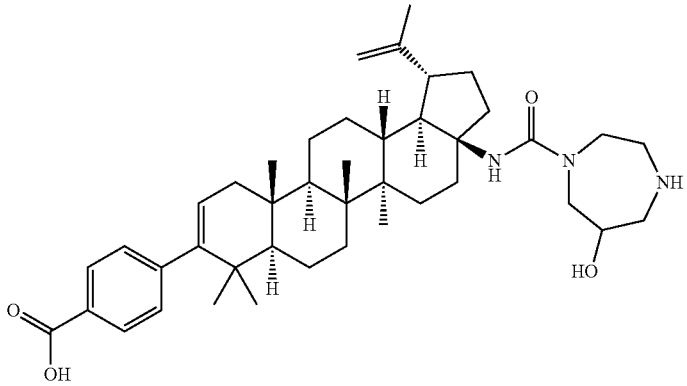 | A |
| 65 | 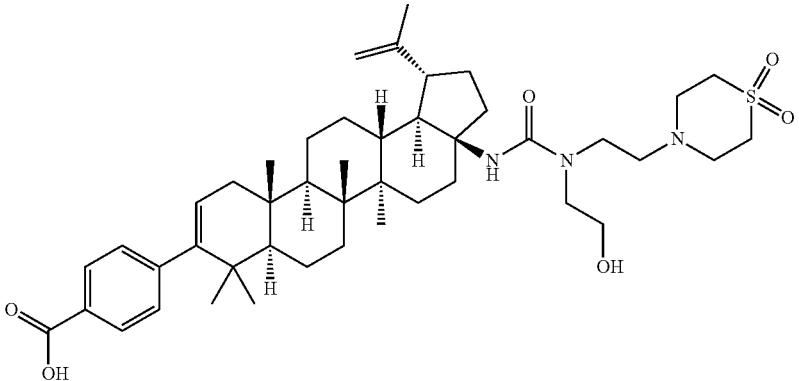 | A |

TABLE 2-continued

| Example # | Structure | EC$_{50}$ (μM) |
|---|---|---|
| 66 | 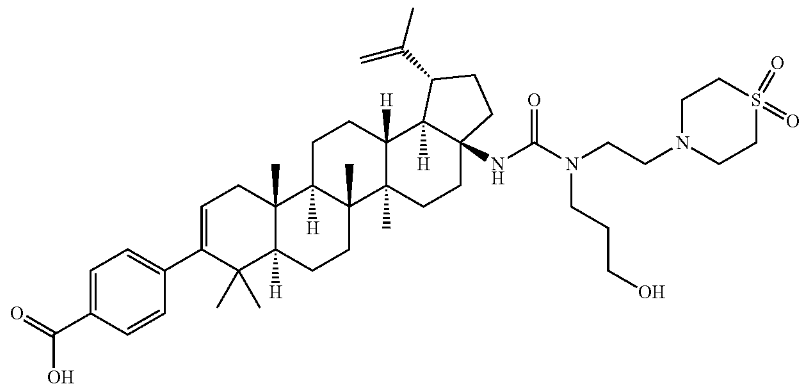 | A |
| 67 | 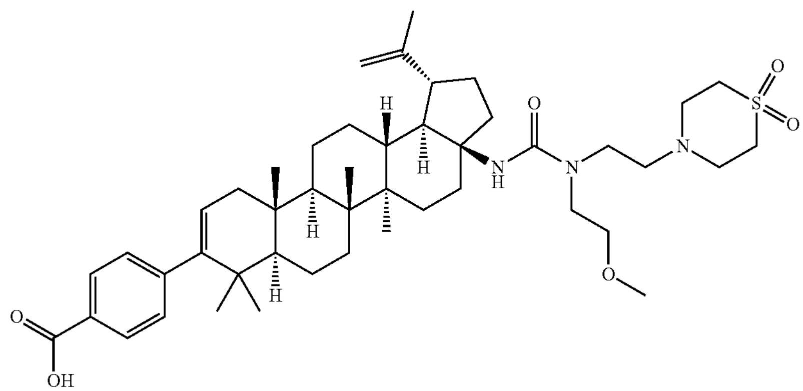 | A |
| 68 | 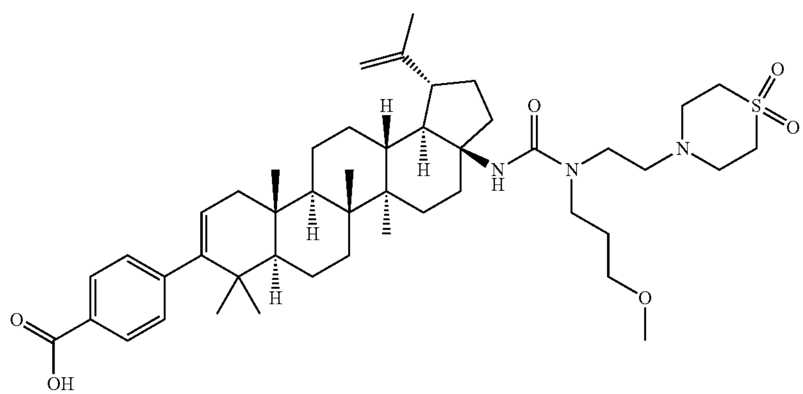 | A |
| 69 | 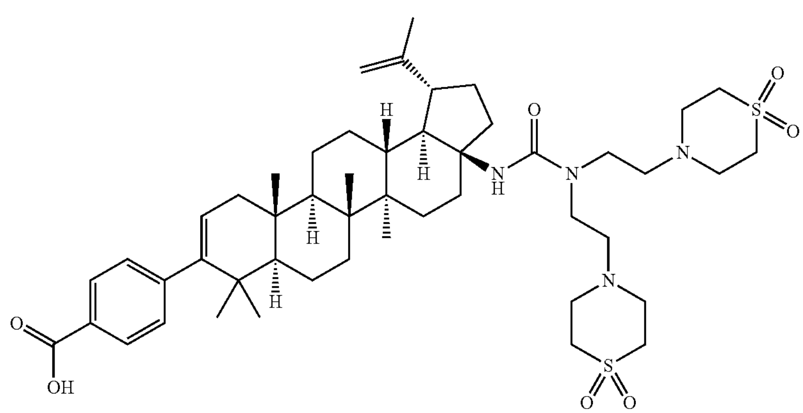 | A |

TABLE 2-continued

| Example # | Structure | EC$_{50}$ (μM) |
|---|---|---|
| 69-1 | 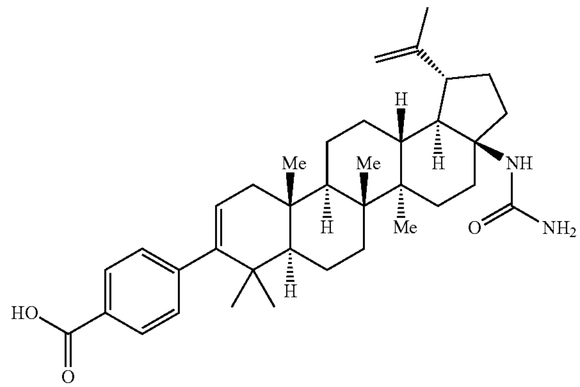 | A |
| 70 | 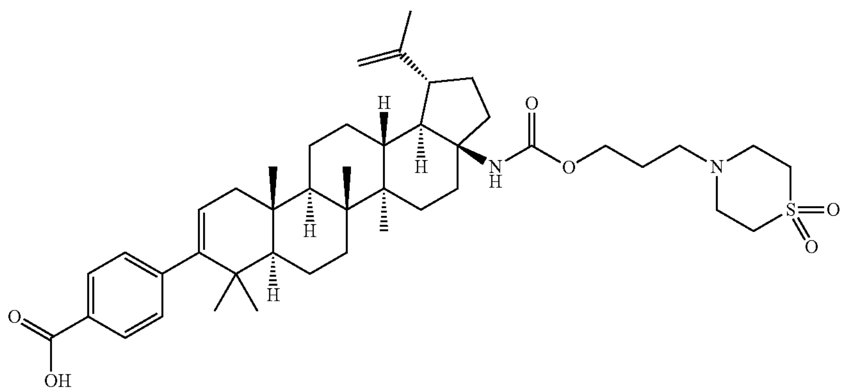 | A |
| 71 | 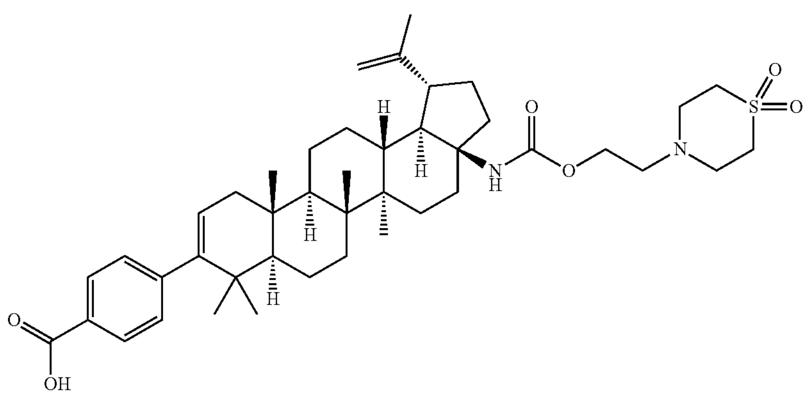 | A |
| 72 | 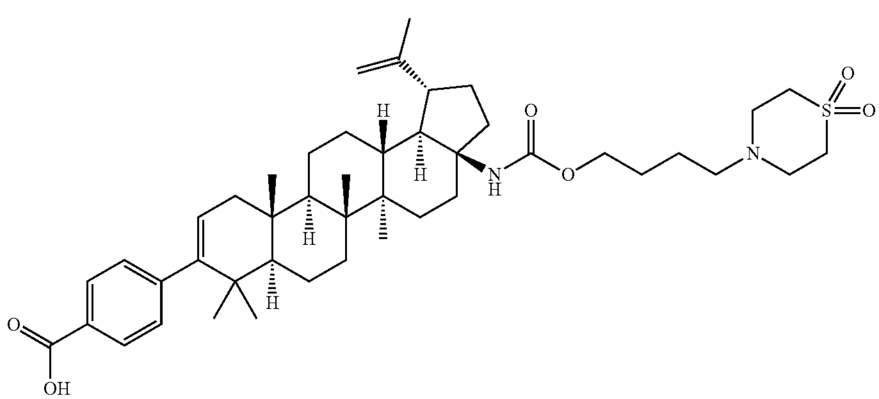 | A |

TABLE 2-continued

| Example # | Structure | EC$_{50}$ (μM) |
|---|---|---|
| 73 | 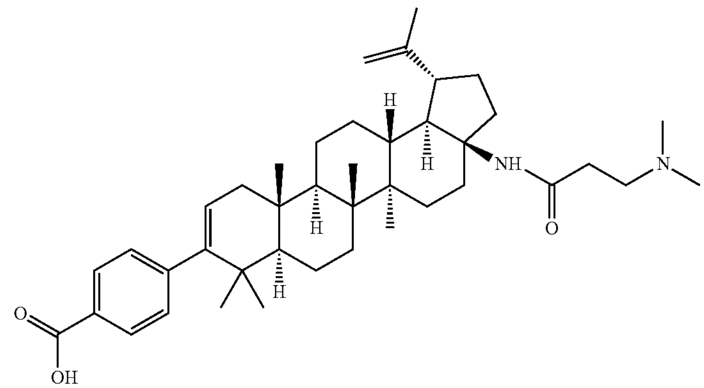 | A |
| 74 | 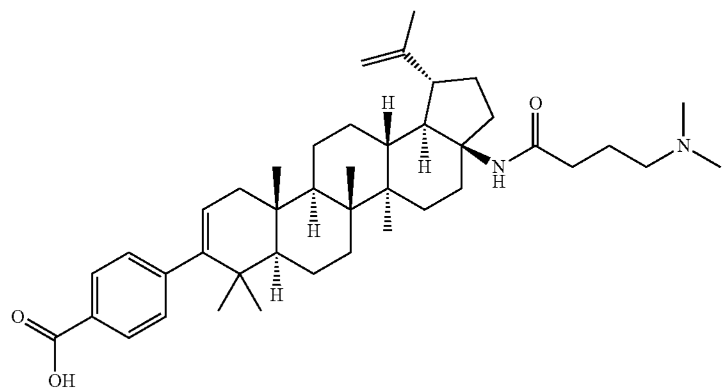 | A |
| 75 | 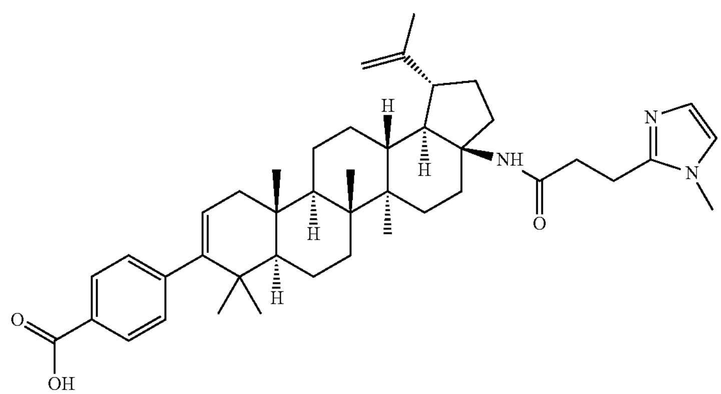 | A |
| 76 | 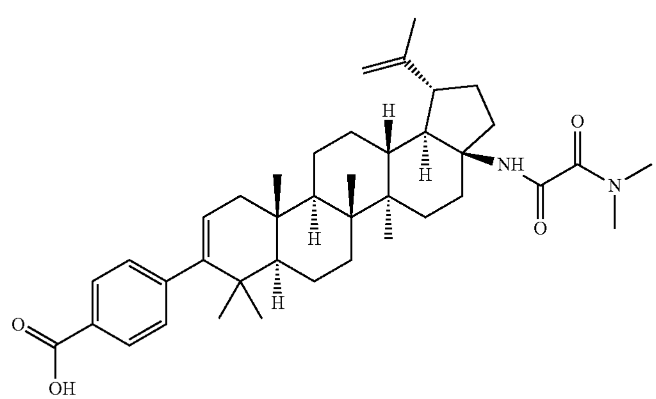 | A |

TABLE 2-continued
| Example # | Structure | EC$_{50}$ (μM) |
|---|---|---|
| 77 | 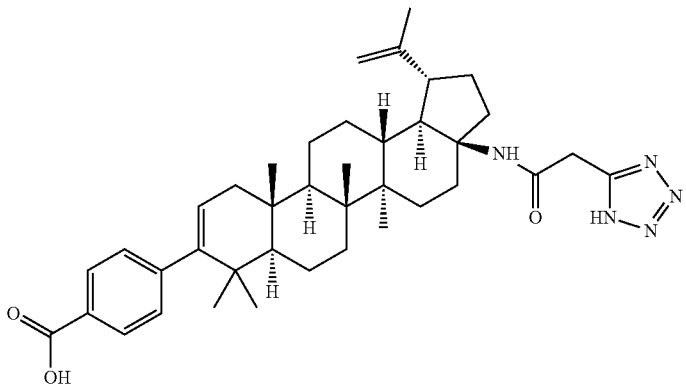 | A |
| 78 | 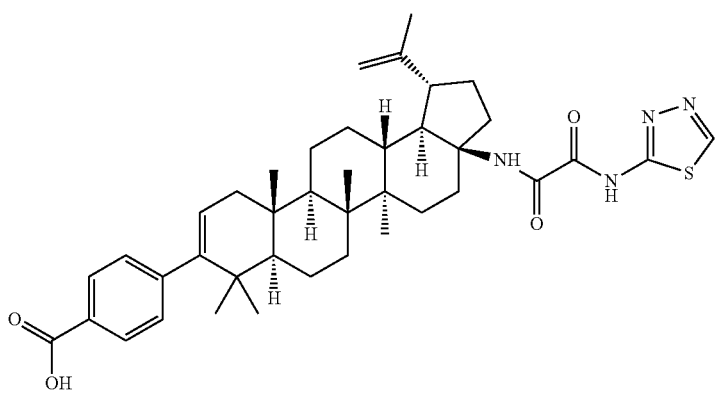 | A |
| 79 | 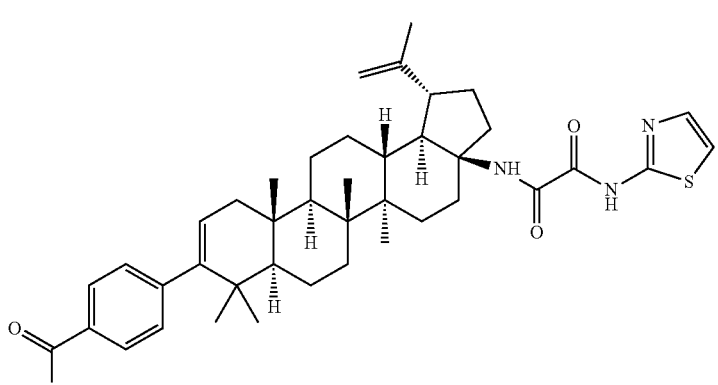 | A |
| 80 | 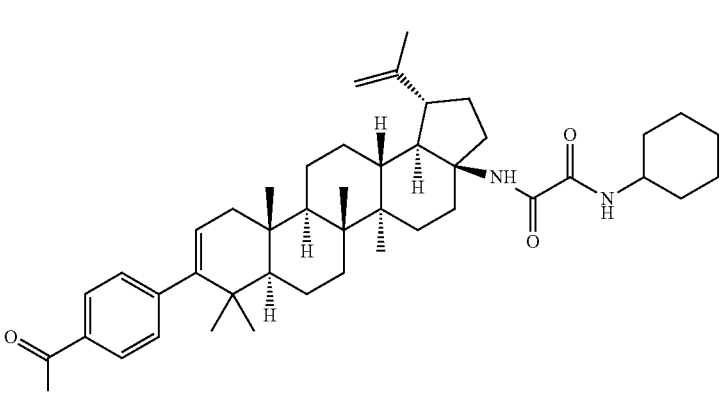 | 0.11 |

TABLE 2-continued

| Example # | Structure | EC$_{50}$ (μM) |
|---|---|---|
| 81 | 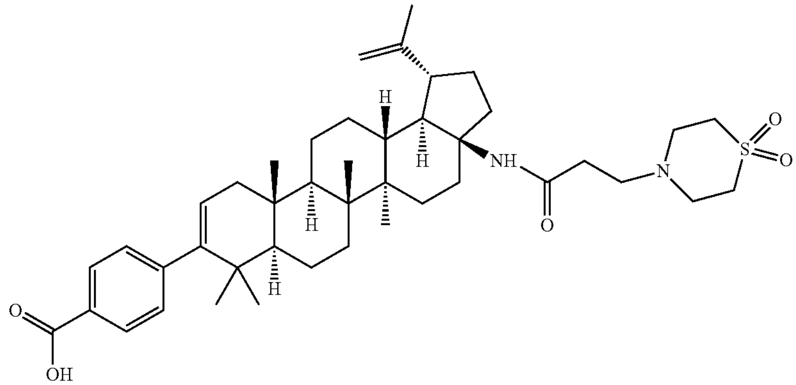 | A |
| 82 | 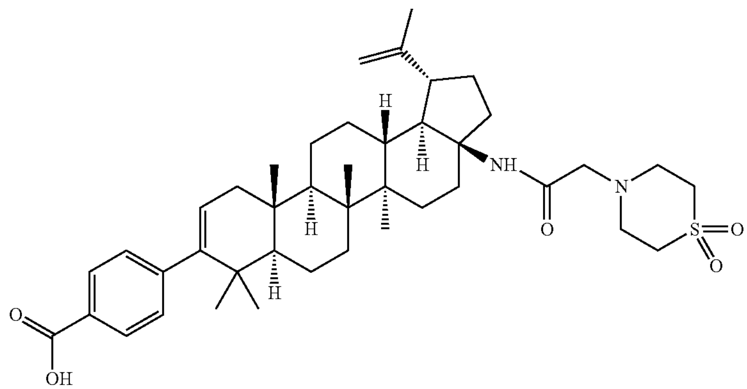 | A |
| 83 | 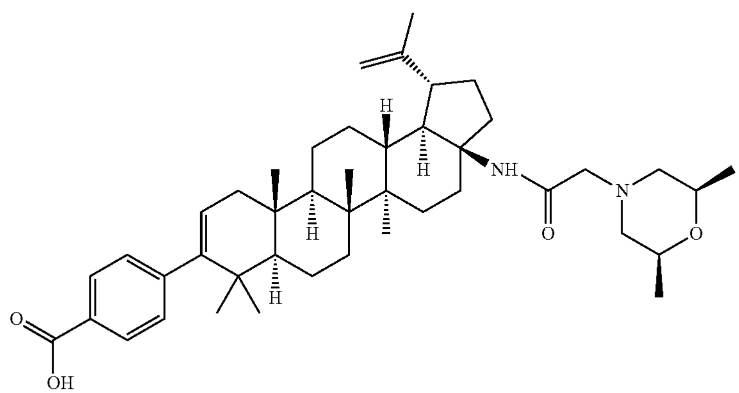 | A |
| 84 | 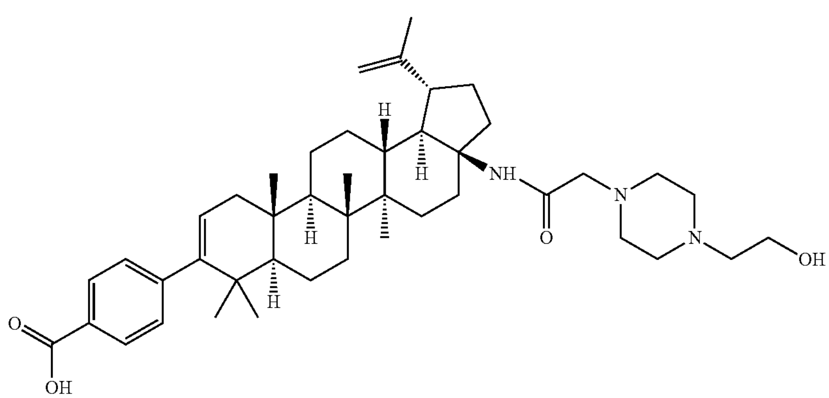 | A |

TABLE 2-continued
| Example # | Structure | EC$_{50}$ (µM) |
|---|---|---|
| 85 | 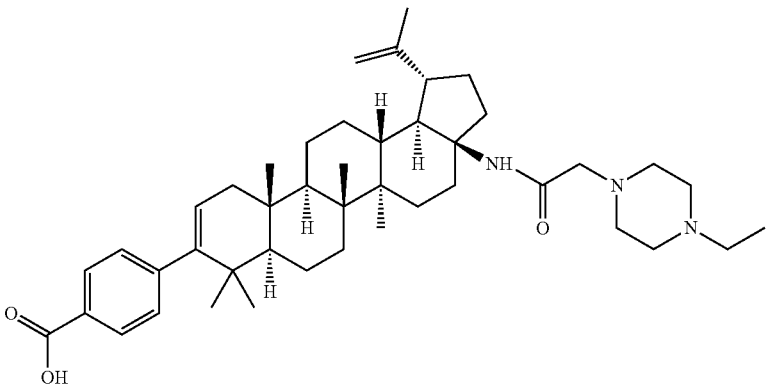 | A |
| 86 | 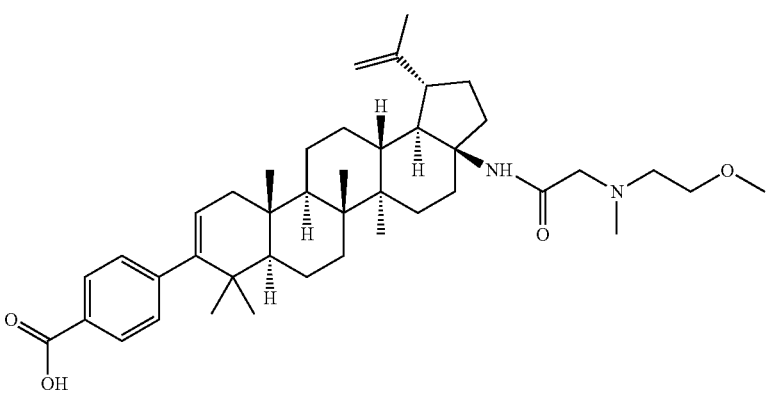 | A |
| 87 | 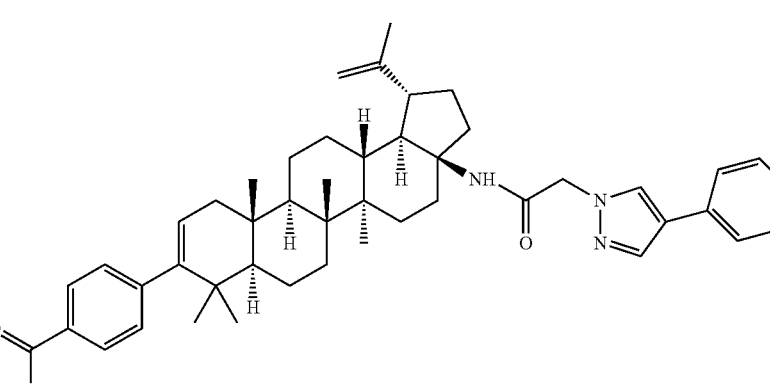 | A |
| 88 | 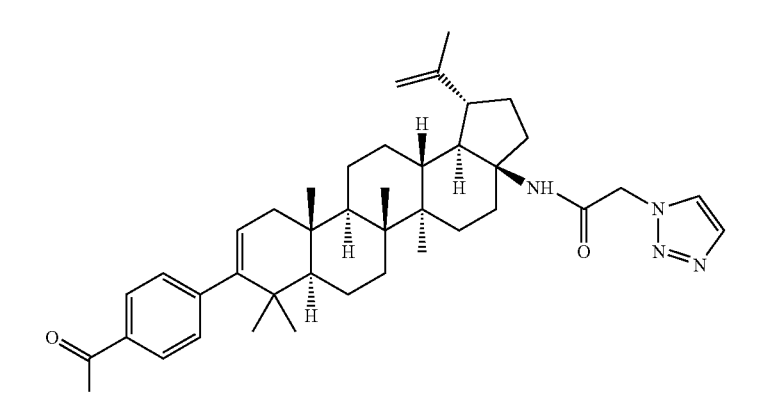 | A |

TABLE 2-continued

| Example # | Structure | EC$_{50}$ (μM) |
|---|---|---|
| 89 | 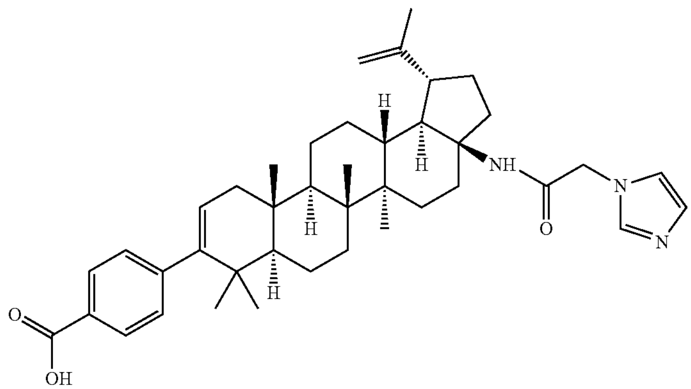 | A |
| 90 | 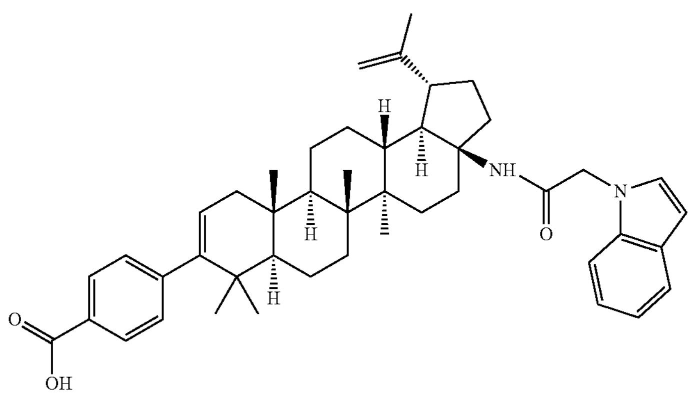 | 0.02 |
| 91 | Isomer 1 | A |

TABLE 2-continued

| Example # | Structure | EC$_{50}$ (μM) |
|---|---|---|
| 92 | Isomer 2 | A |
| 93 | 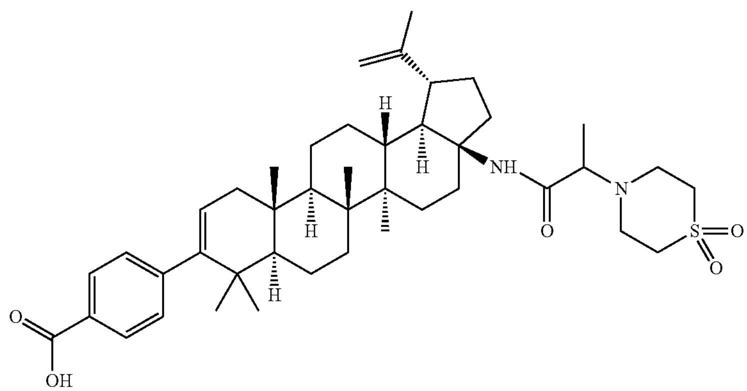 | A |
| 94 | 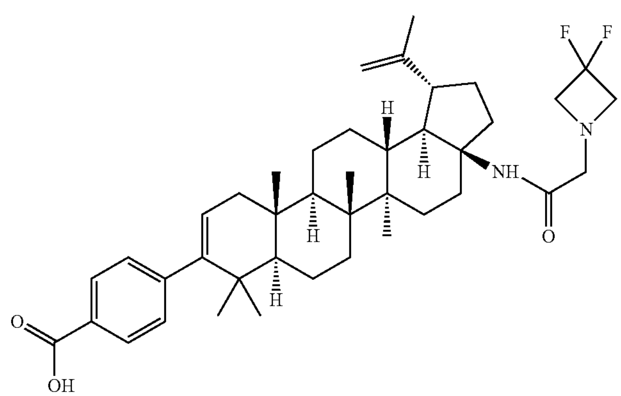 | A |
| 95 | 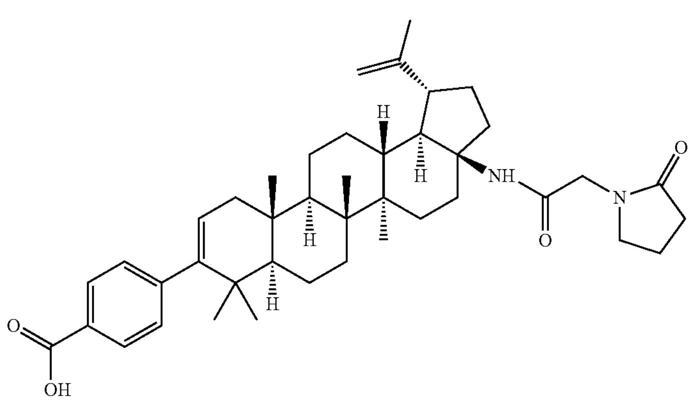 | A |

TABLE 2-continued

| Example # | Structure | EC$_{50}$ (µM) |
|---|---|---|
| 96 | 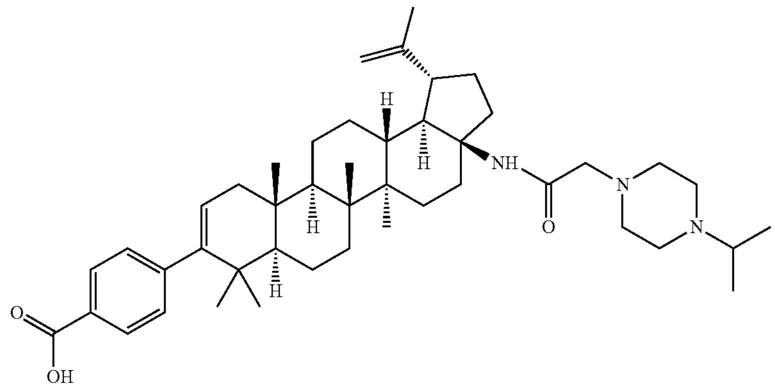 | A |
| 97 | 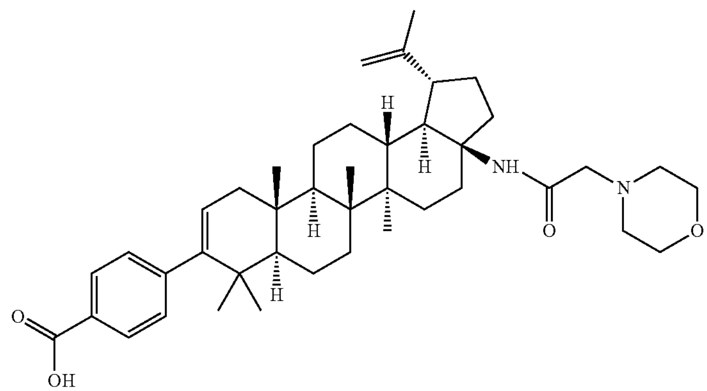 | A |
| 98 | 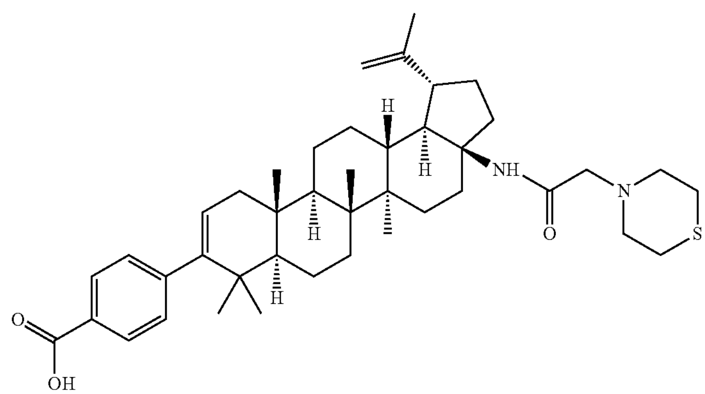 | A |
| 99 | 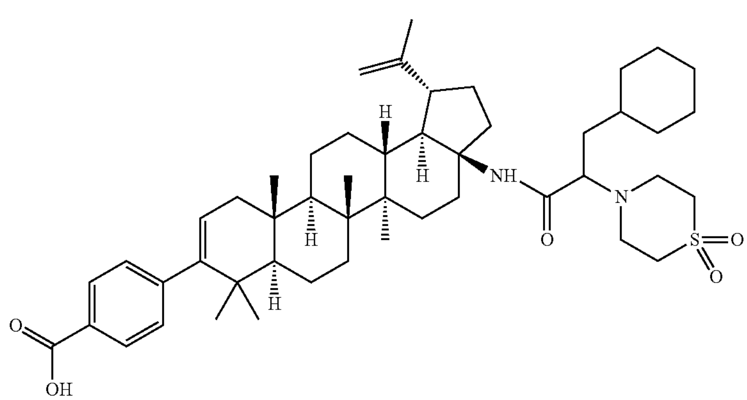 | A |

TABLE 2-continued
| Example # | Structure | EC$_{50}$ (μM) |
|---|---|---|
| 100 | 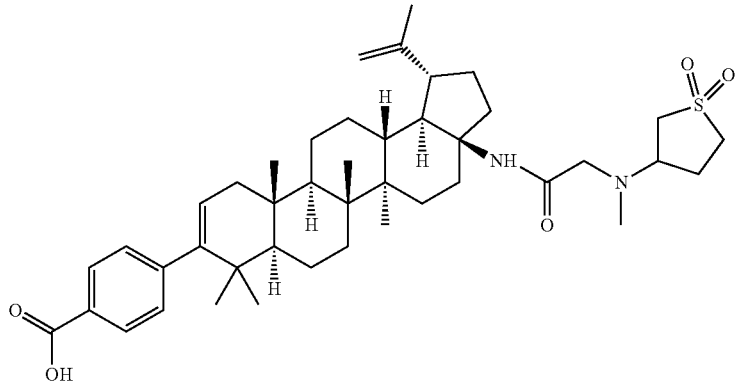 | A |
| 101 | 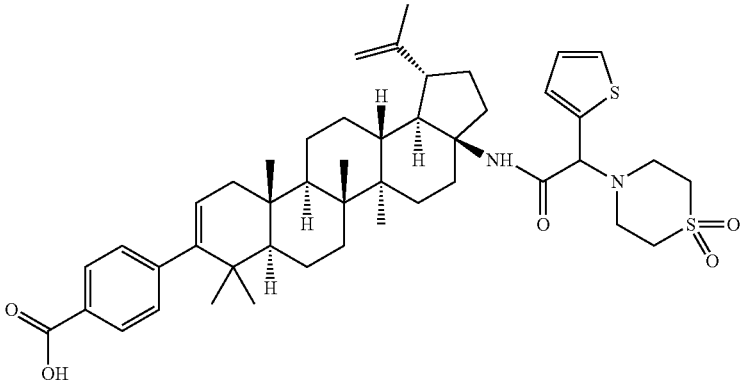 | A |
| 102 | 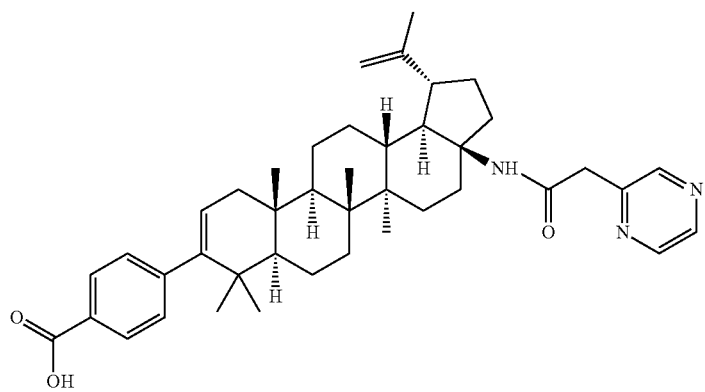 | A |
| 103 | 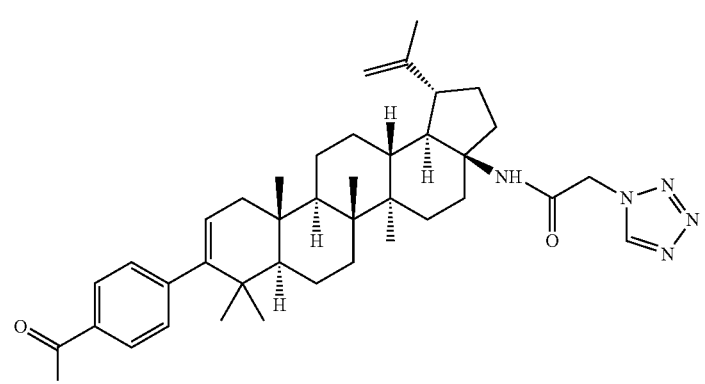 | A |

TABLE 2-continued

| Example # | Structure | EC$_{50}$ (µM) |
|---|---|---|
| 104 | 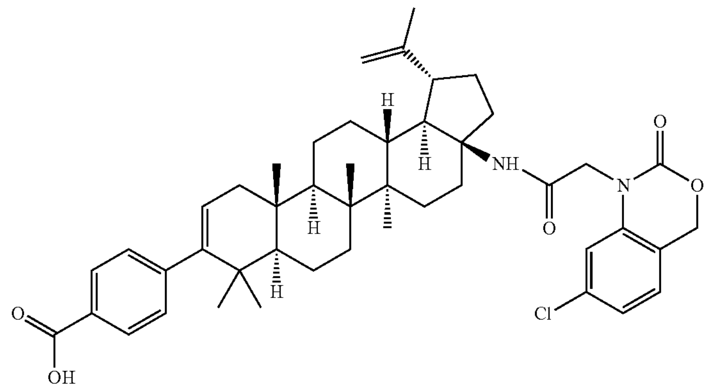 | A |
| 105 | 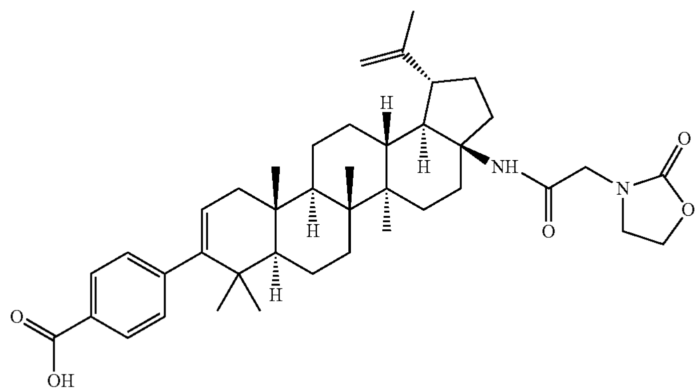 | A |
| 106 | 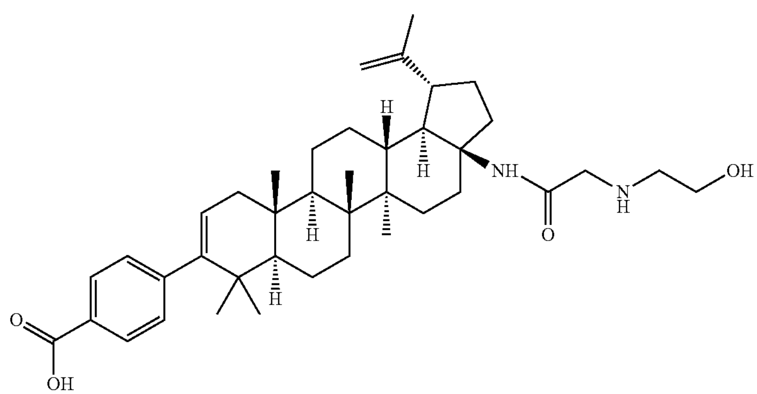 | A |
| 107 | 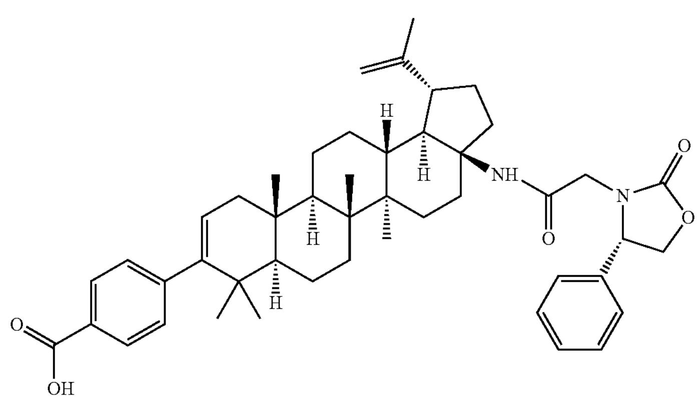 | A |

TABLE 2-continued

| Example # | Structure | EC$_{50}$ (μM) |
|---|---|---|
| 108 | 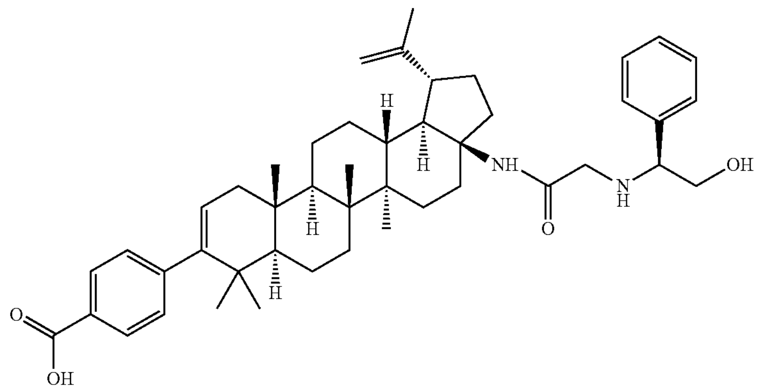 | A |
| 109 | 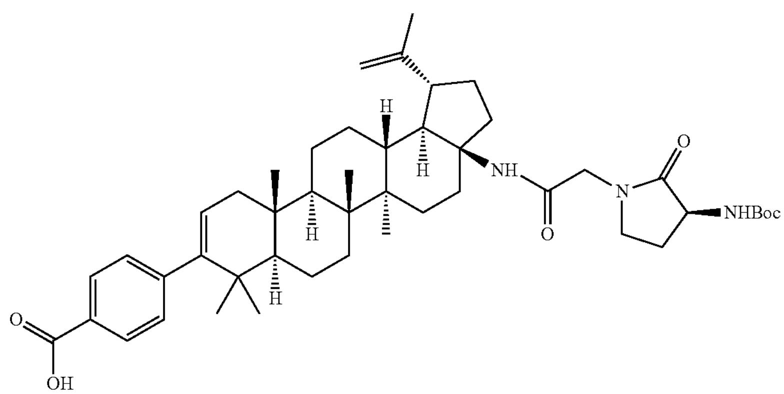 | A |
| 110 | Isomer 1 | A |

TABLE 2-continued

| Example # | Structure | EC$_{50}$ (µM) |
|---|---|---|
| 111 | Isomer 2 | A |
| 112 | 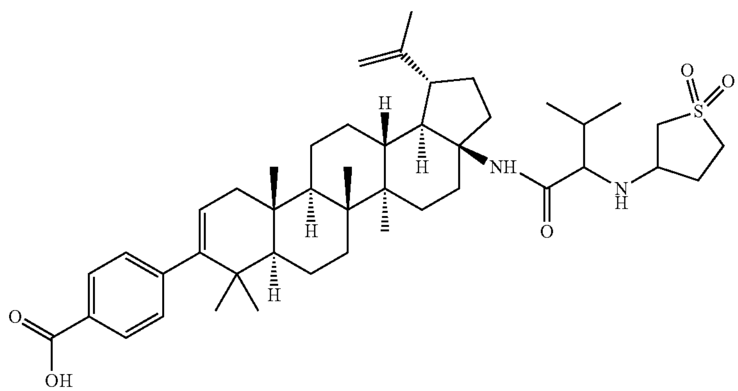 | A |
| 113 | 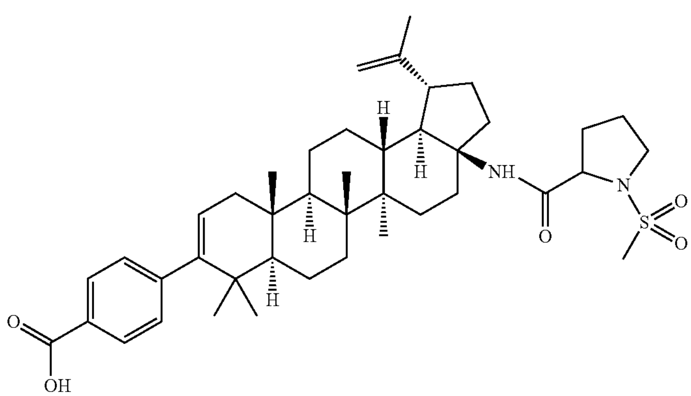 | A |
| 114 | 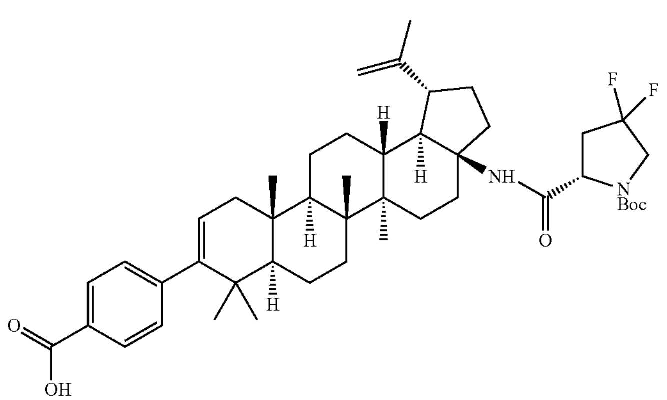 | A |

TABLE 2-continued

| Example # | Structure | EC$_{50}$ (μM) |
|---|---|---|
| 115 | 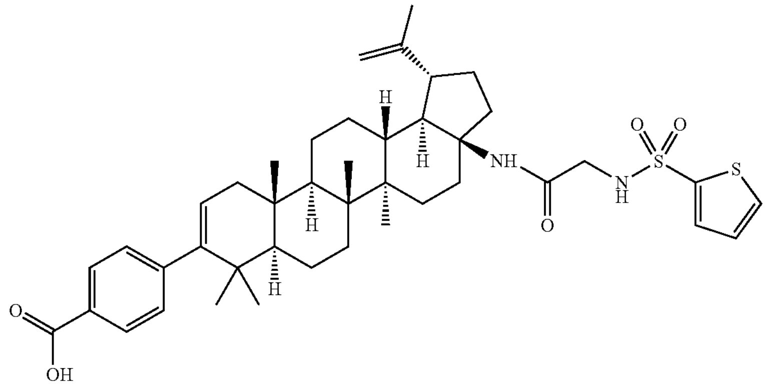 | A |
| 116 | 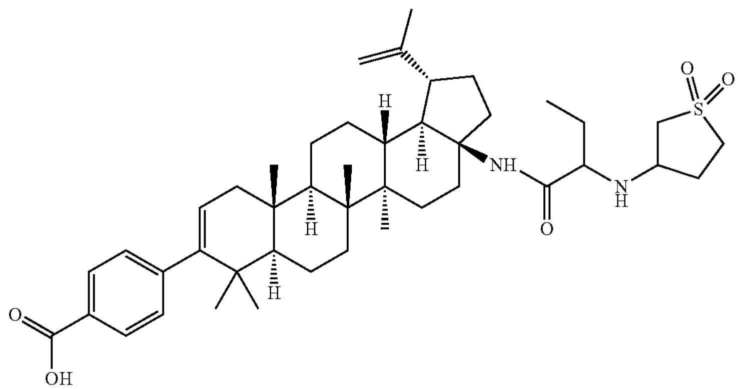 | A |
| 117 | 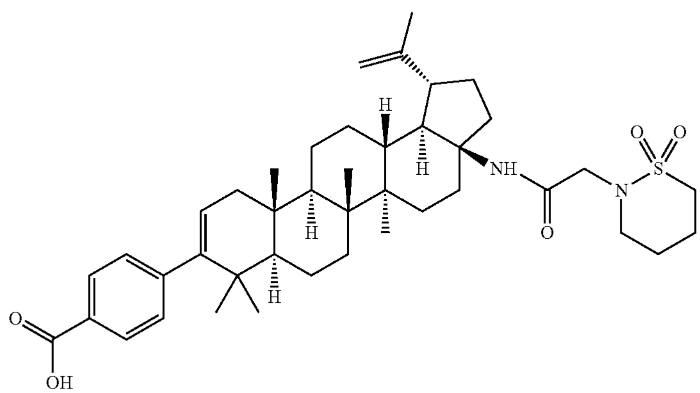 | A |
| 118 | 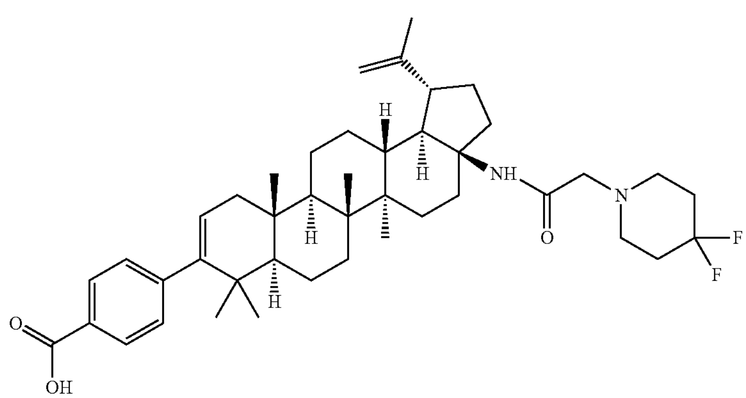 | A |

TABLE 2-continued

| Example # | Structure | EC$_{50}$ (μM) |
|---|---|---|
| 119 | 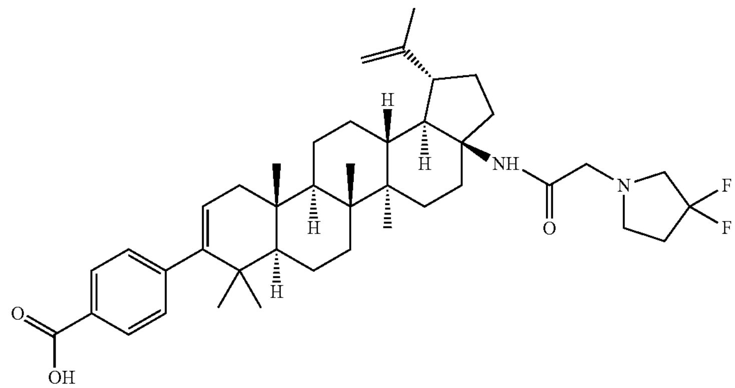 | A |
| 120 | 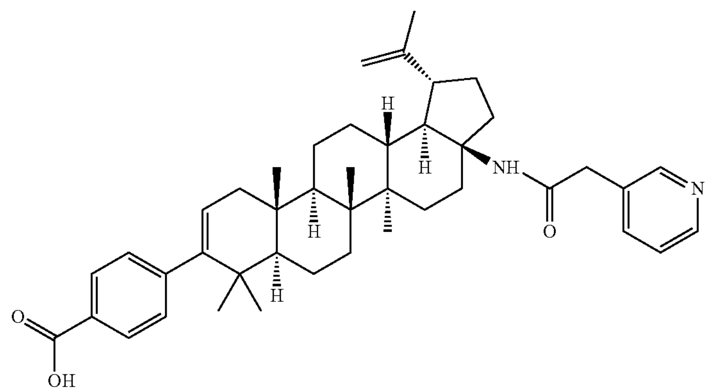 | A |
| 121 | 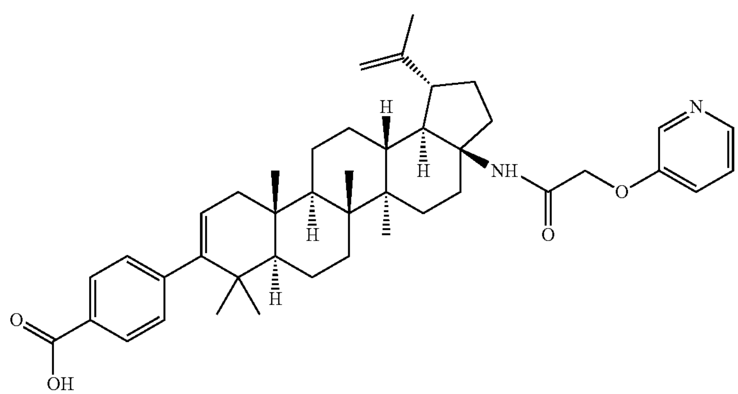 | A |
| 122 | 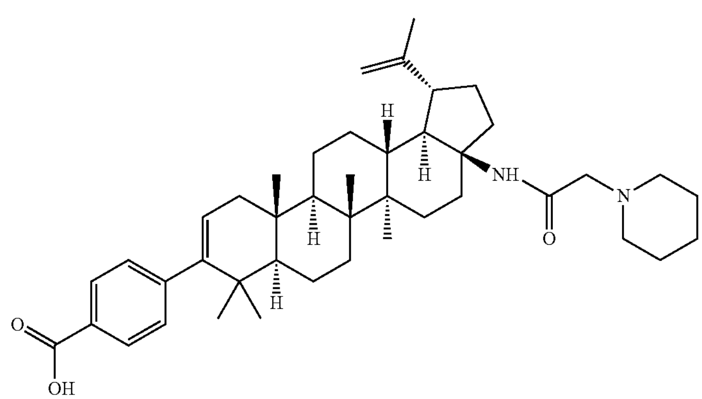 | A |

TABLE 2-continued

| Example # | Structure | EC$_{50}$ (µM) |
|---|---|---|
| 123 | 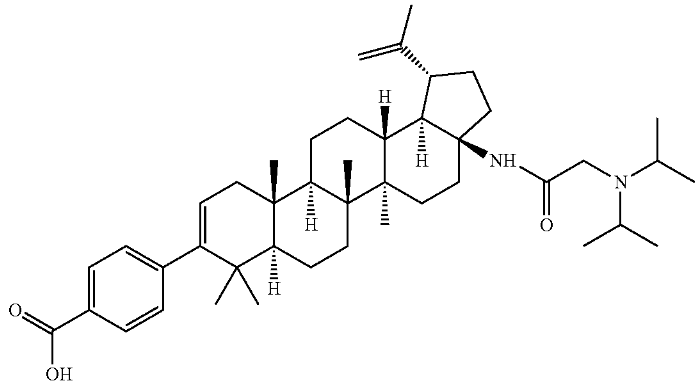 | A |
| 124 | 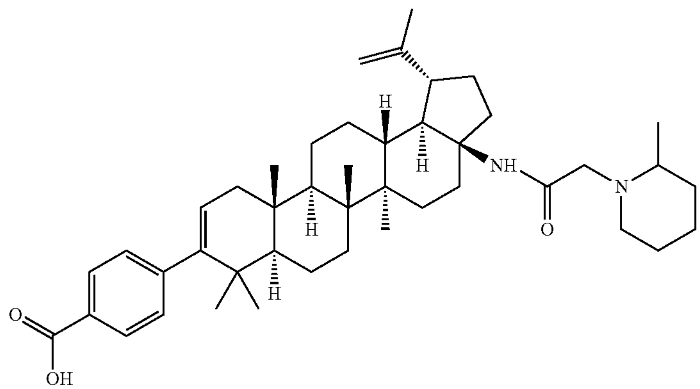 | A |
| 125 | 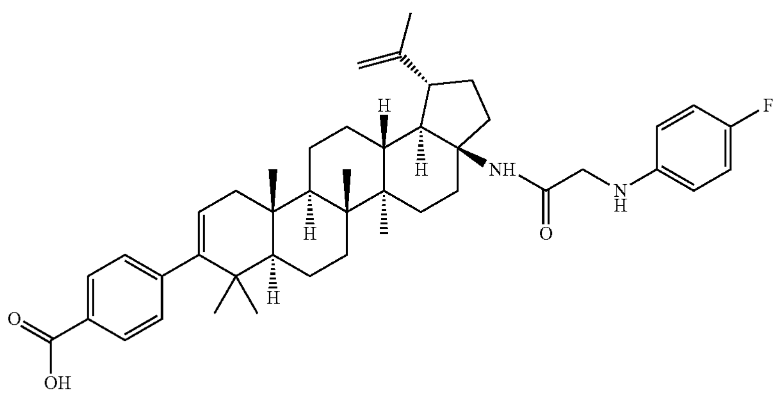 | A |
| 126 | 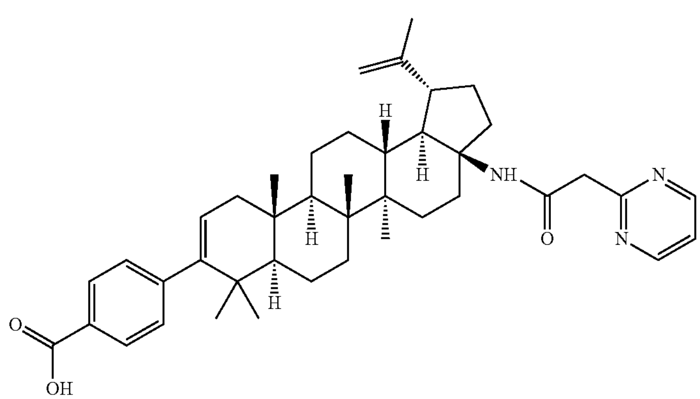 | A |

TABLE 2-continued
| Example # | Structure | EC$_{50}$ (µM) |
|---|---|---|
| 127 | 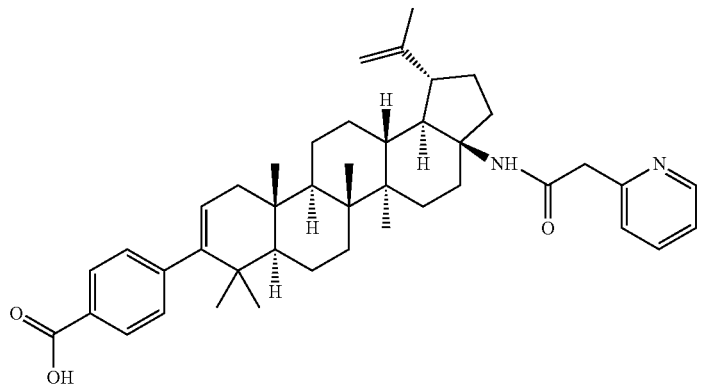 | A |
| 128 | 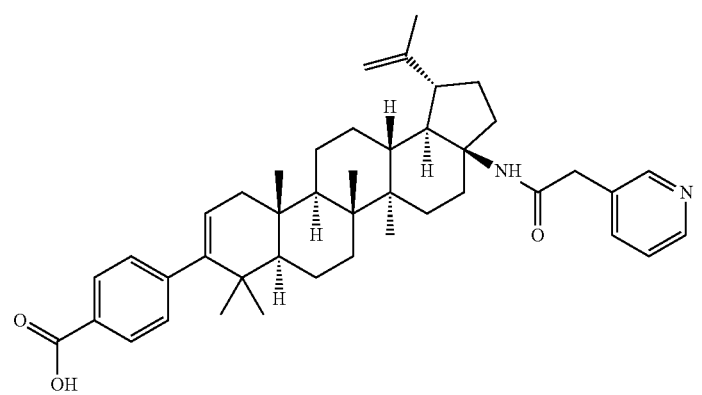 | A |
| 129 | 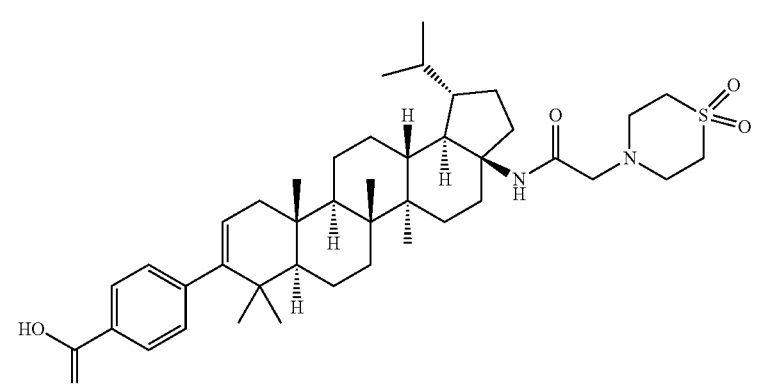 | A |
| 130 | 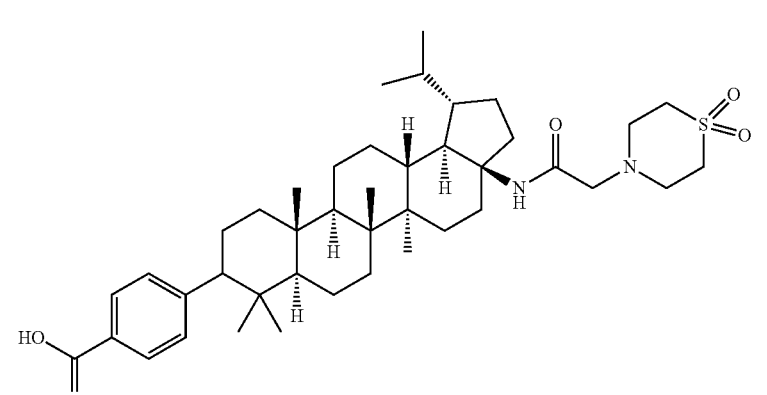 | A |

TABLE 2-continued

| Example # | Structure | EC$_{50}$ (μM) |
|---|---|---|
| 130-1 | 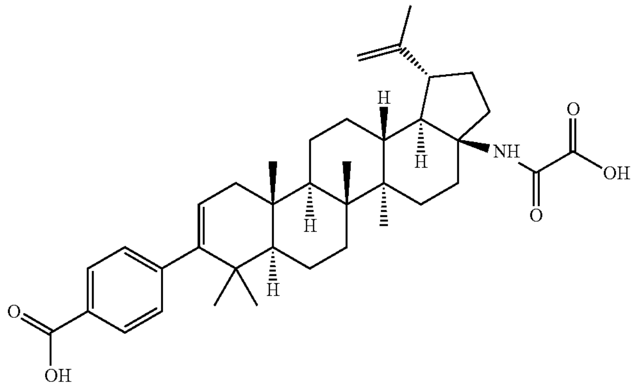 | B |
| 130-2 | 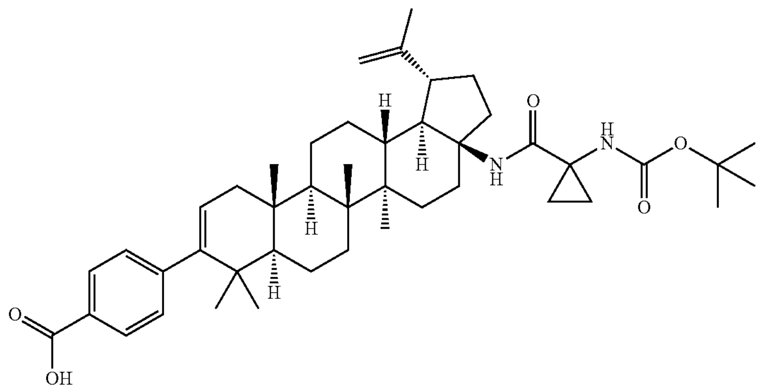 | A |
| 130-3 | 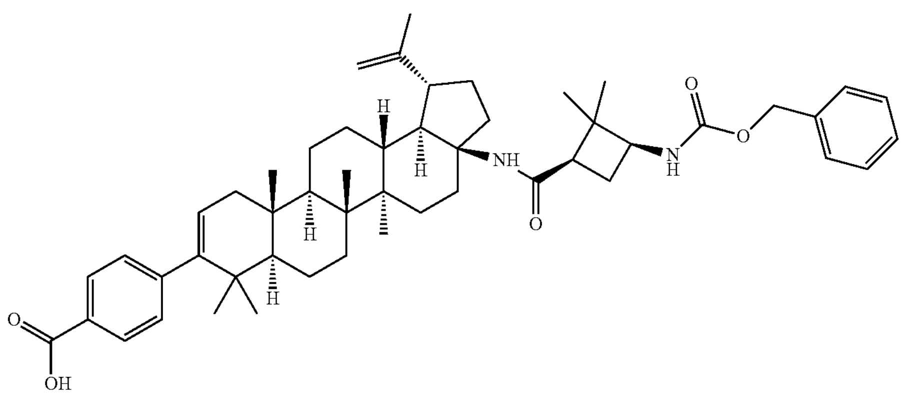 | A |
| 131 | 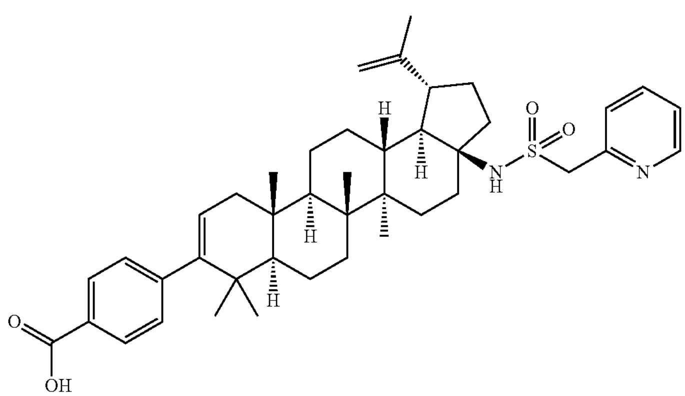 | A |

TABLE 2-continued

| Example # | Structure | EC$_{50}$ (μM) |
|---|---|---|
| 132 | 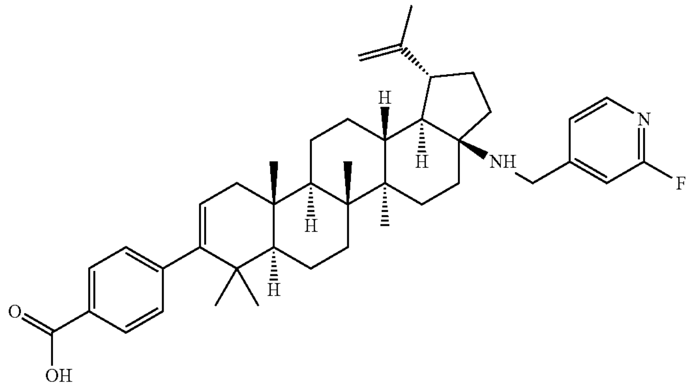 | A |
| 133 | 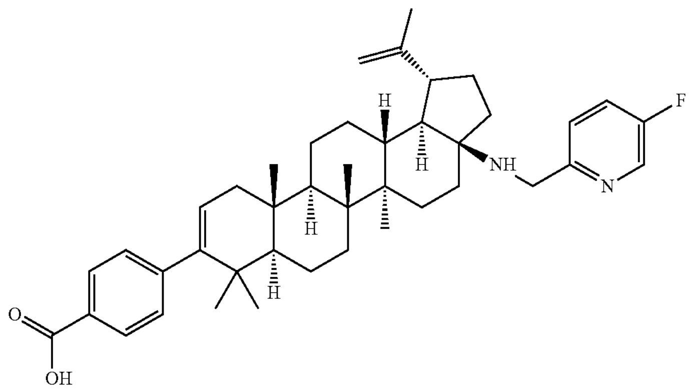 | 0.03 |
| 134 | 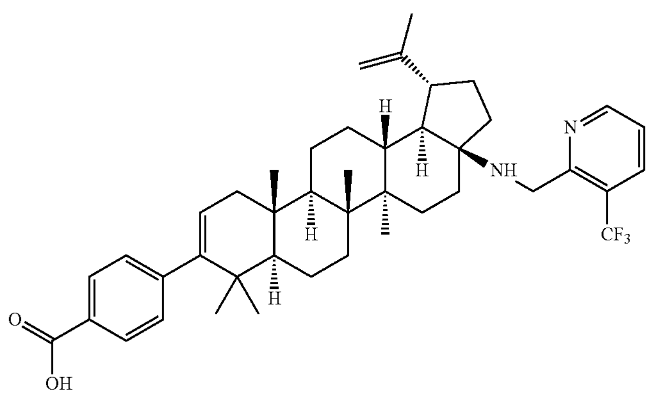 | 0.10 |
| 135 | 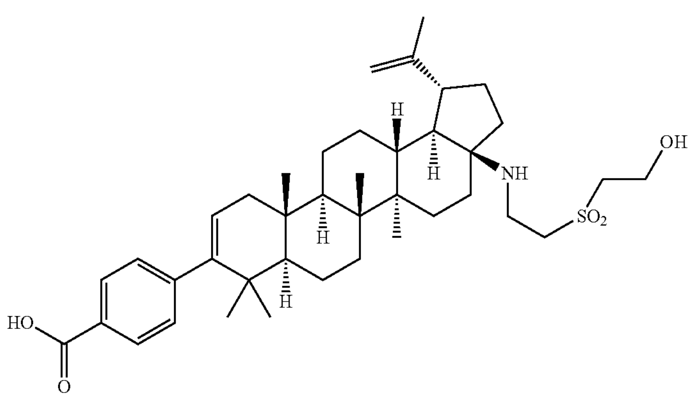 | A |

TABLE 2-continued

| Example # | Structure | EC$_{50}$ (μM) |
|---|---|---|
| 136 | 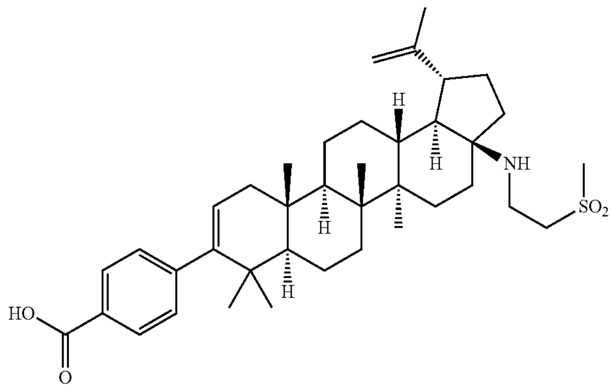 | A |
| 137 | 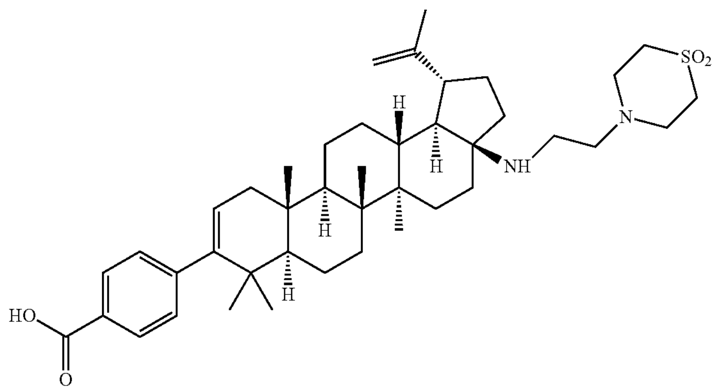 | A |
| 138 | 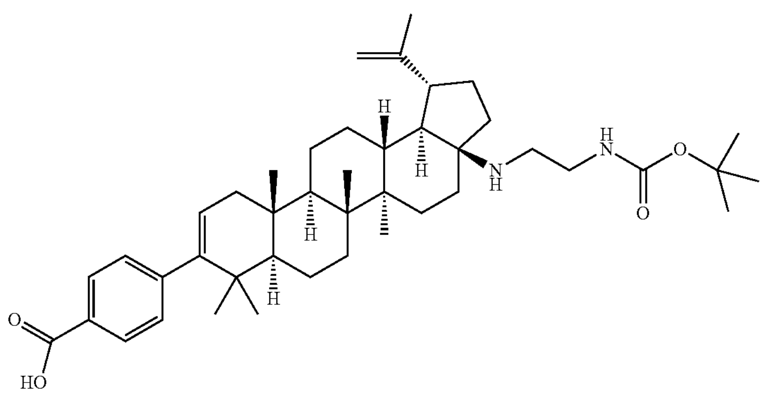 | A |
| 139 | 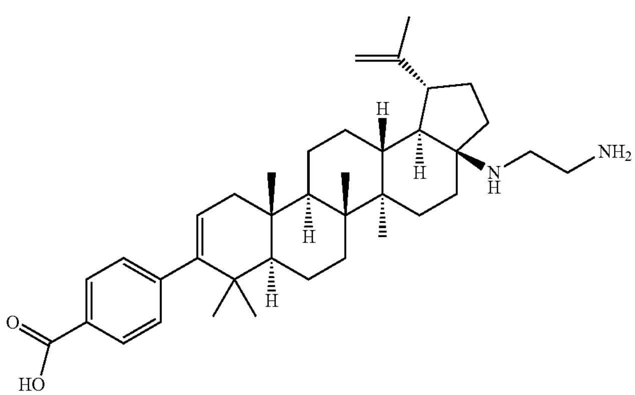 | A |

TABLE 2-continued

| Example # | Structure | EC$_{50}$ (μM) |
|---|---|---|
| 140 | 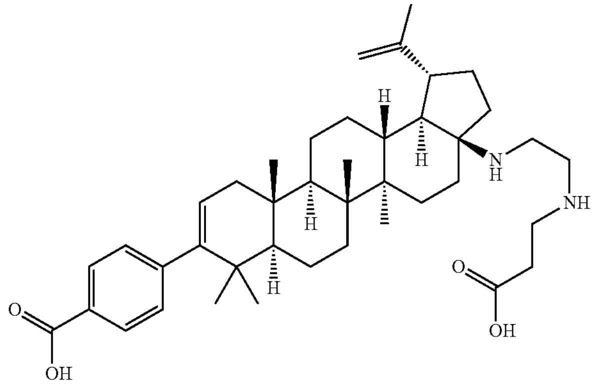 | 0.009 |
| 141 | 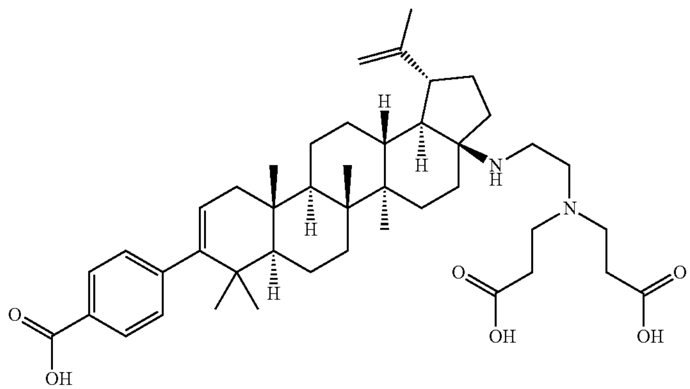 | A |
| 142 | 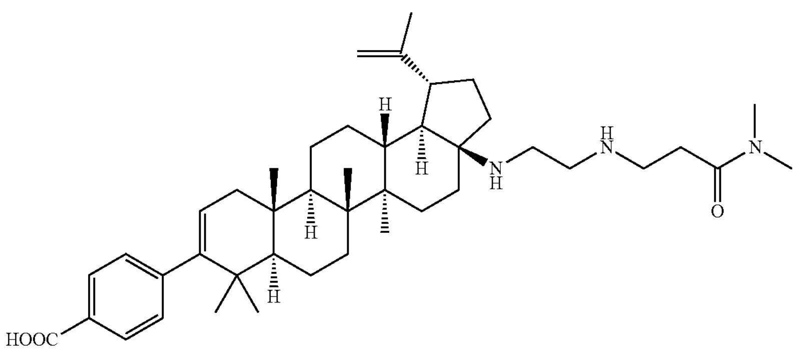 | A |
| 143 | 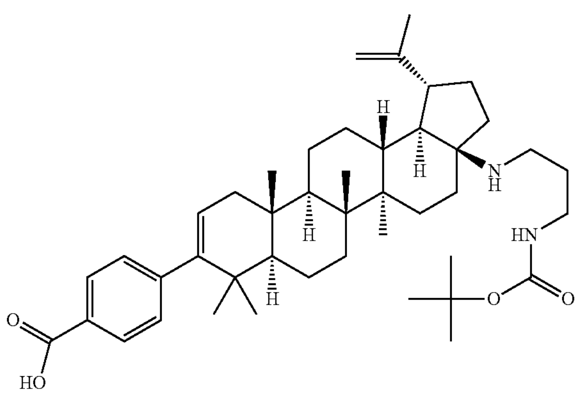 | A |

TABLE 2-continued

| Example # | Structure | EC$_{50}$ (μM) |
|---|---|---|
| 144 | 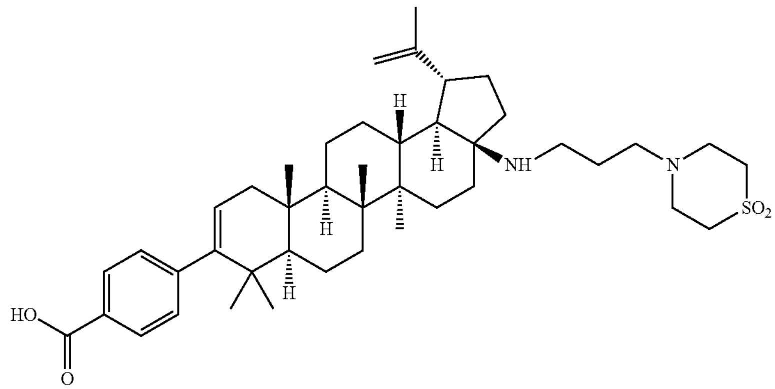 | A |
| 145 | 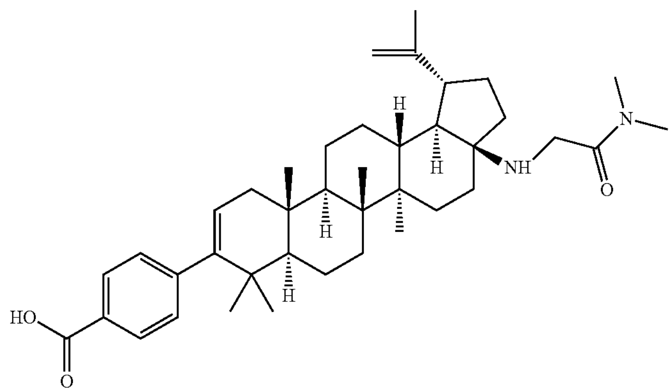 | A |
| 146 | 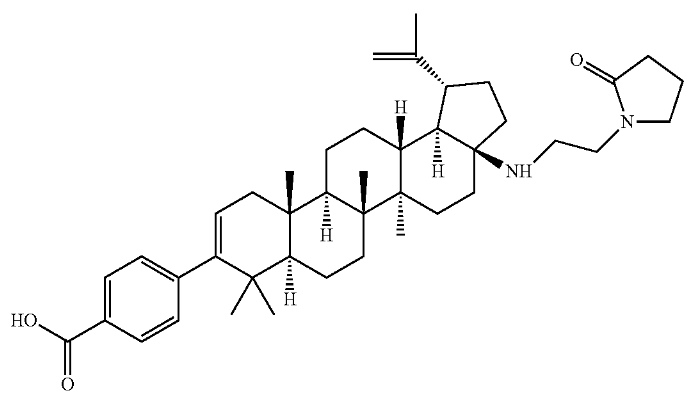 | A |
| 147 | 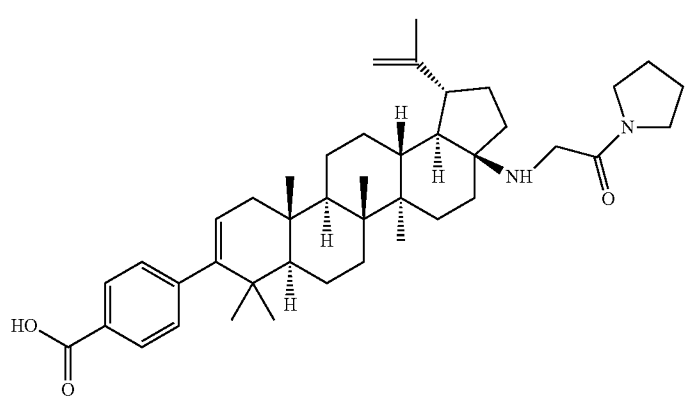 | A |

TABLE 2-continued

| Example # | Structure | EC₅₀ (μM) |
|---|---|---|
| 148 | 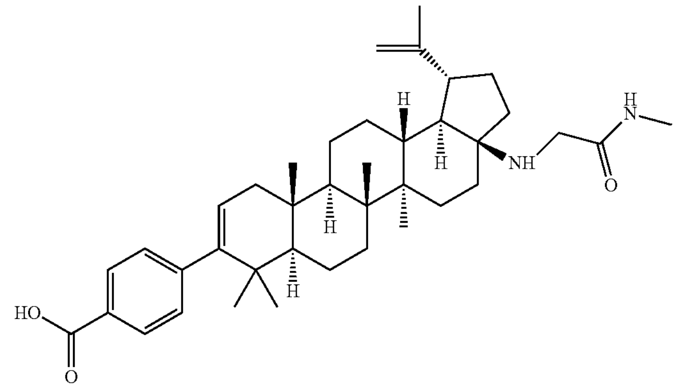 | A |
| 149 | 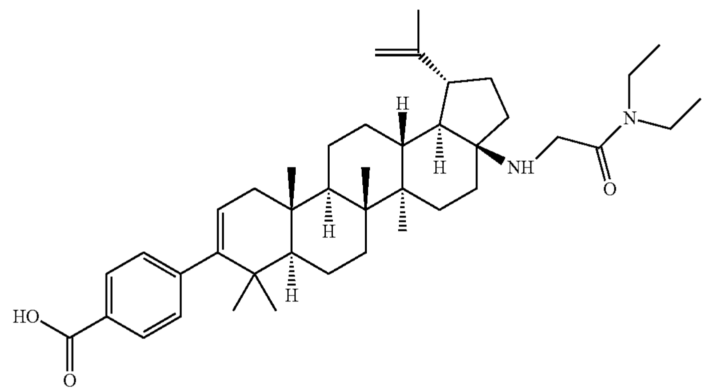 | A |
| 150 | 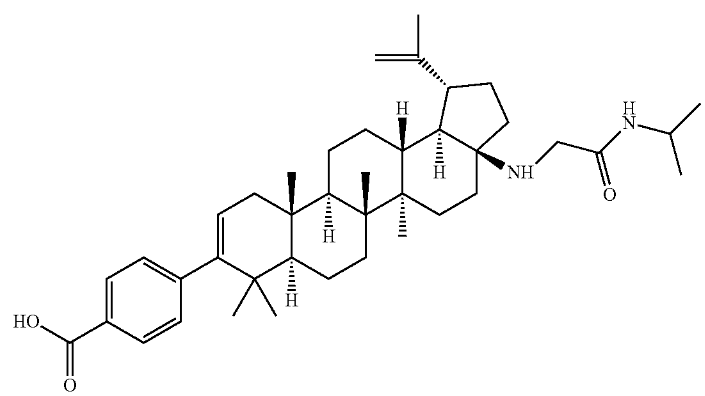 | A |
| 151 | 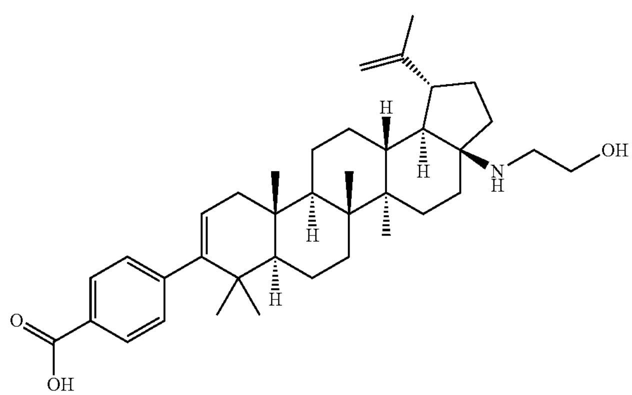 | A |

TABLE 2-continued
| Example # | Structure | EC$_{50}$ (μM) |
|---|---|---|
| 152 | 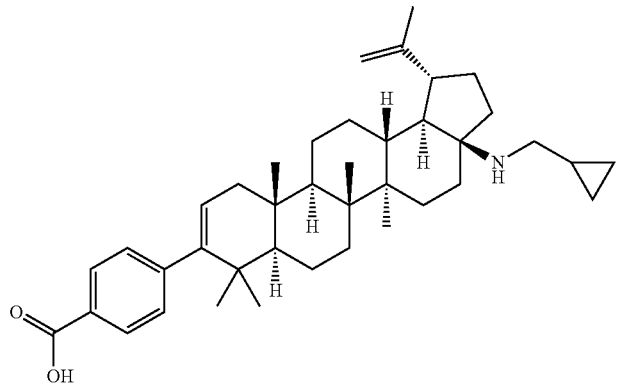 | A |
| 153 | 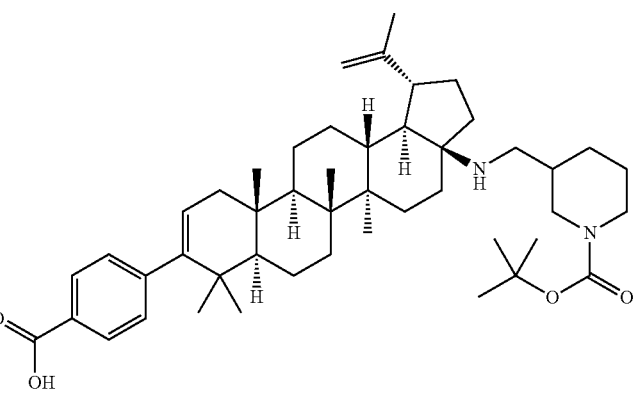 | B |
| 154 | 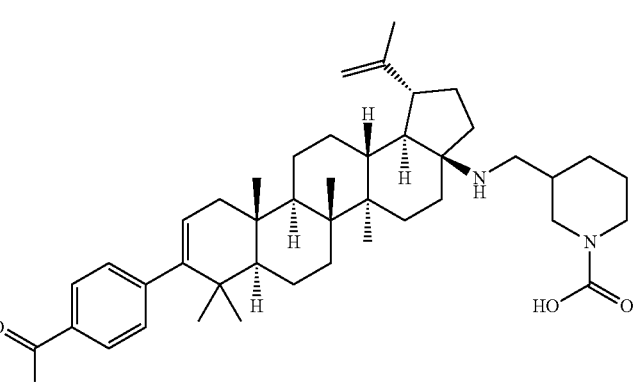 | A |
| 155 | 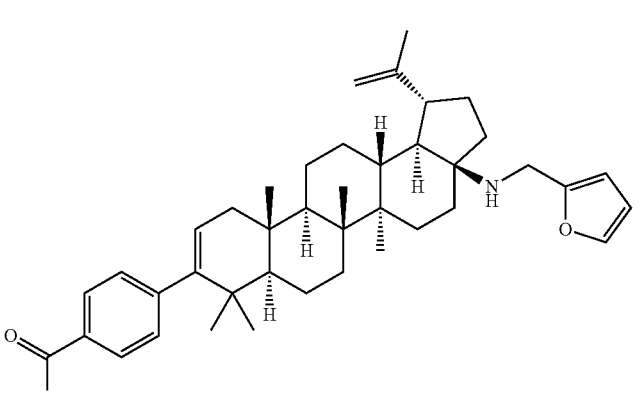 | A |

TABLE 2-continued

| Example # | Structure | EC$_{50}$ (μM) |
|---|---|---|
| 156 | 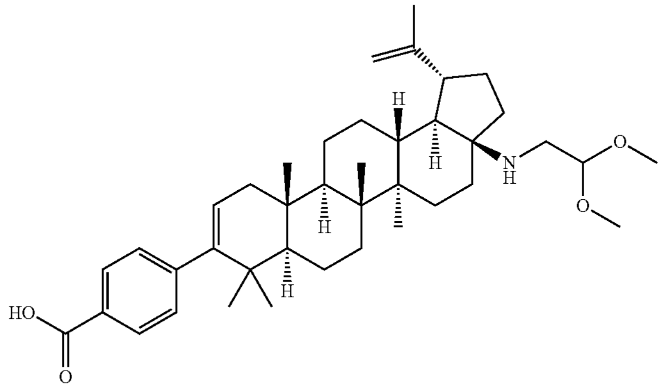 | 0.12 |
| 157 | 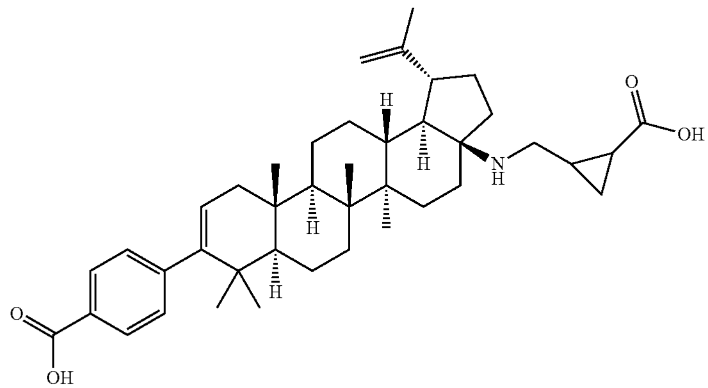 | A |
| 158 | 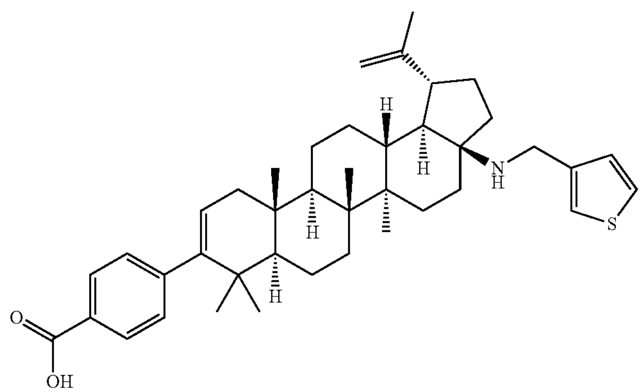 | A |
| 159 | 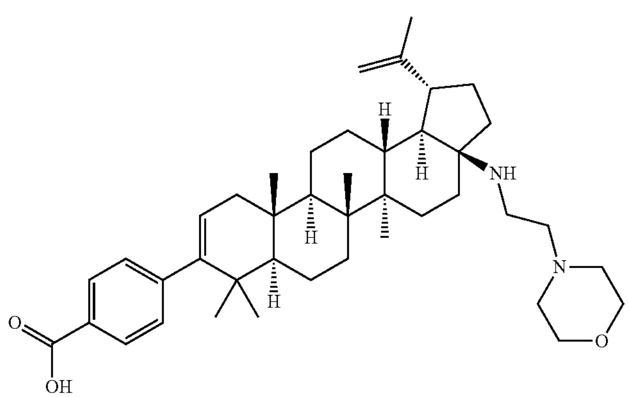 | A |

TABLE 2-continued

| Example # | Structure | EC$_{50}$ (μM) |
|---|---|---|
| 160 | 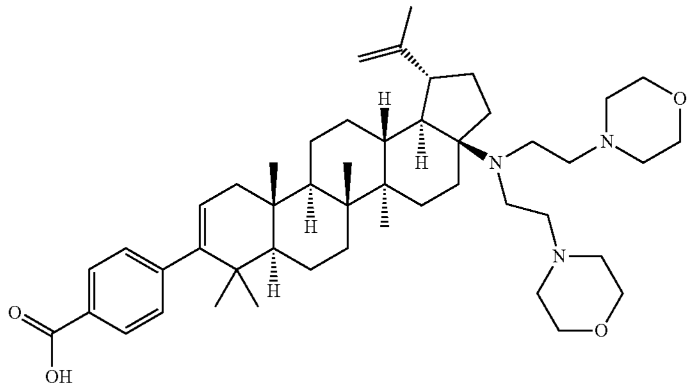 | A |
| 161 | 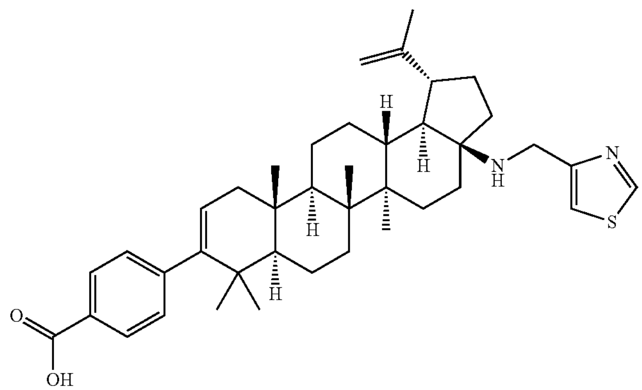 | A |
| 162 | 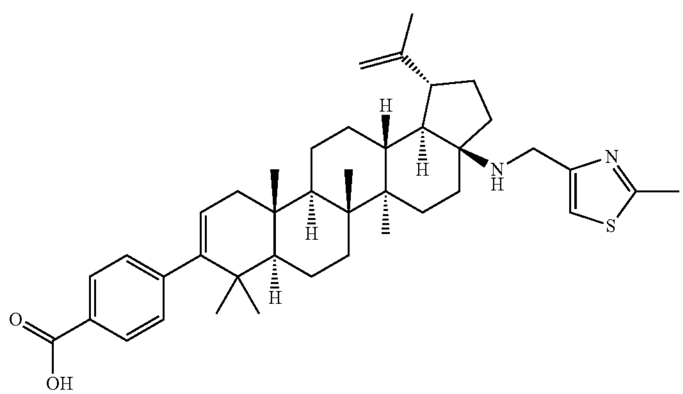 | A |
| 163 | 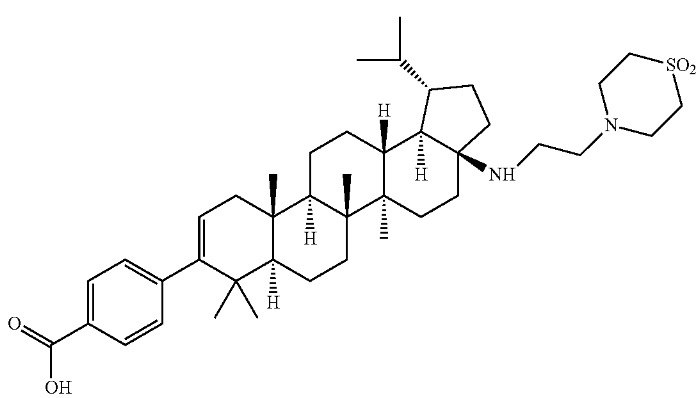 | A |

TABLE 2-continued
| Example # | Structure | EC$_{50}$ (μM) |
|---|---|---|
| 164 | 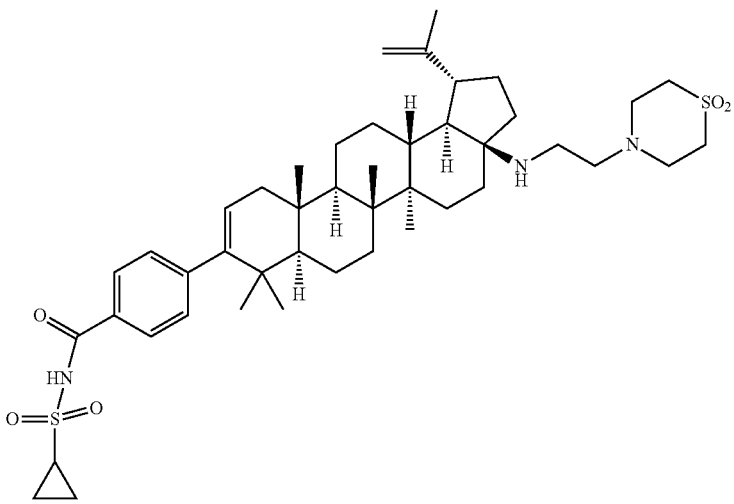 | A |
| 165 | 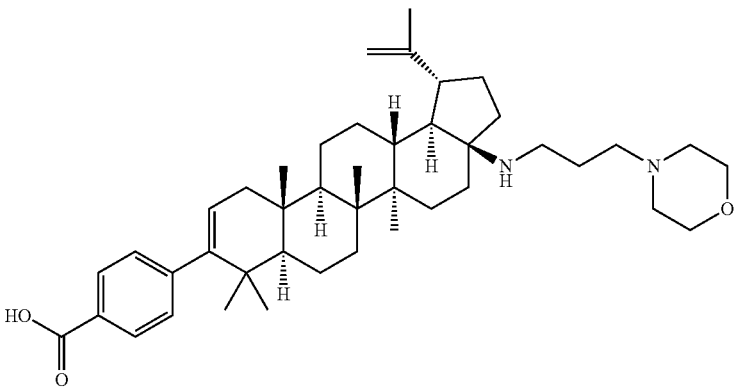 | A |
| 166 | 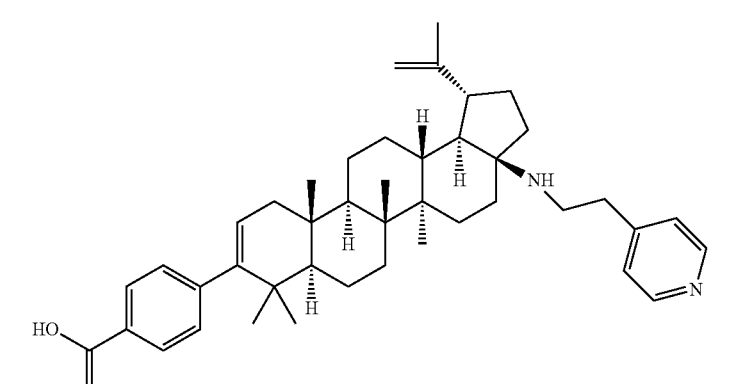 | A |

TABLE 2-continued

| Example # | Structure | EC$_{50}$ (μM) |
|---|---|---|
| 167 | 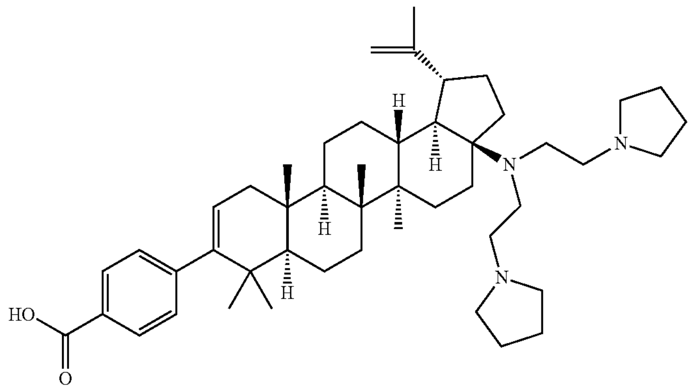 | 0.004 |
| 168 | 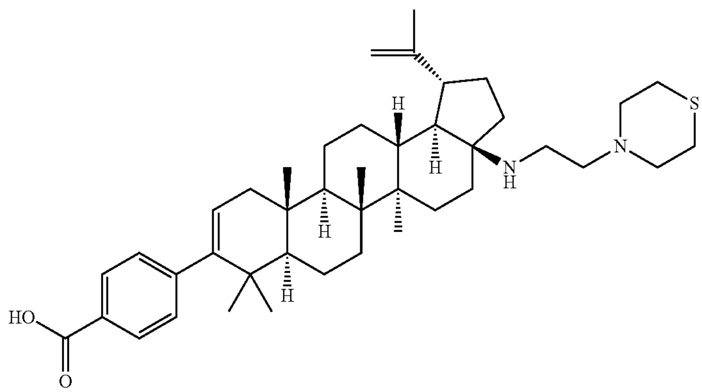 | A |
| 169 | 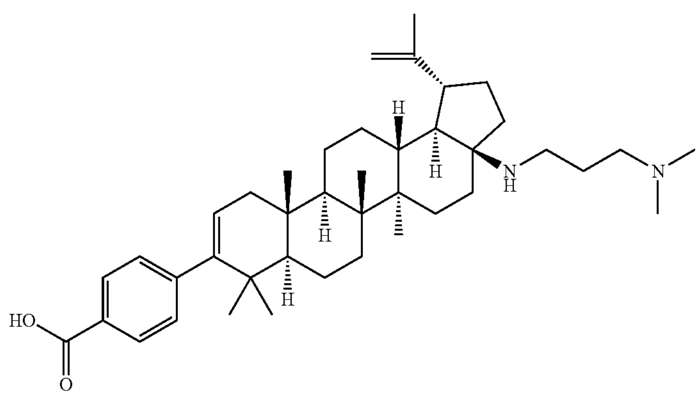 | A |
| 170 | 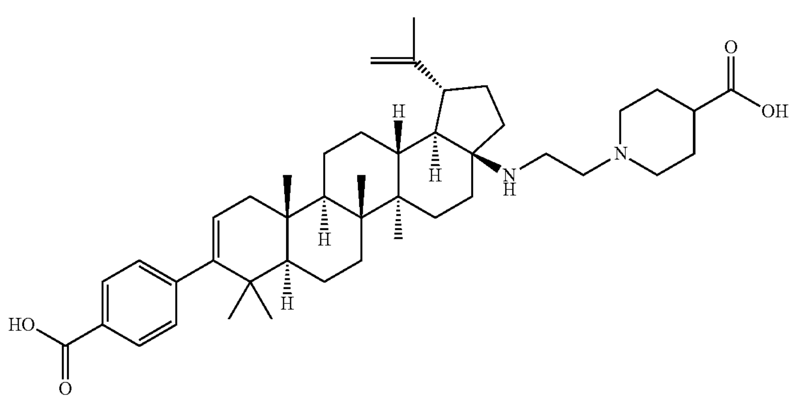 | A |

TABLE 2-continued

| Example # | Structure | EC$_{50}$ (µM) |
|---|---|---|
| 171 | 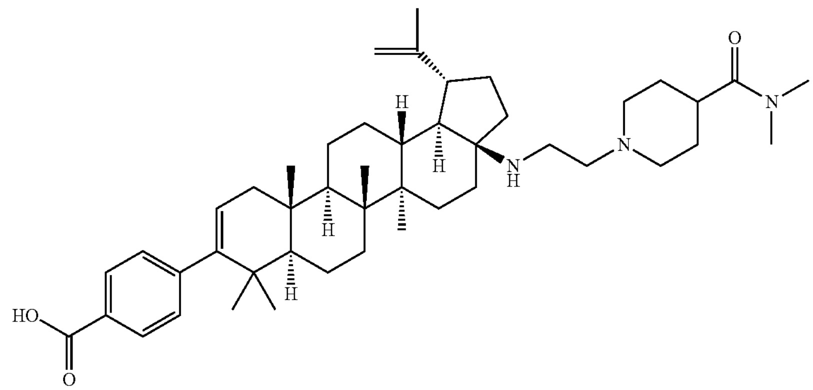 | A |
| 172 | 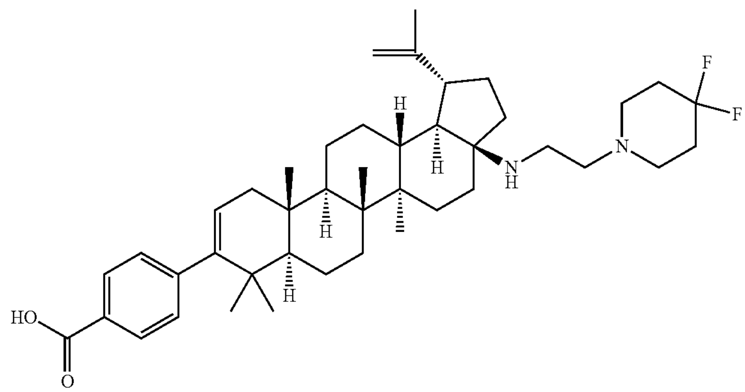 | A |
| 173 | 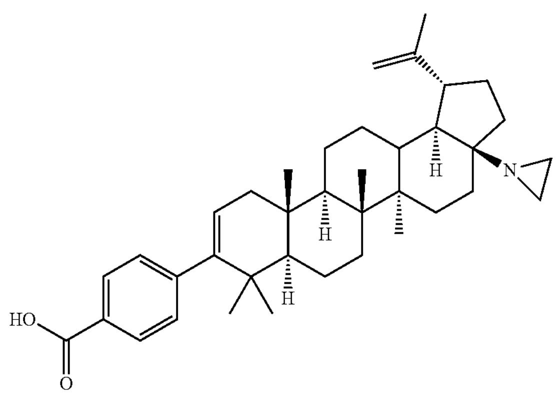 | A |
| 174 | 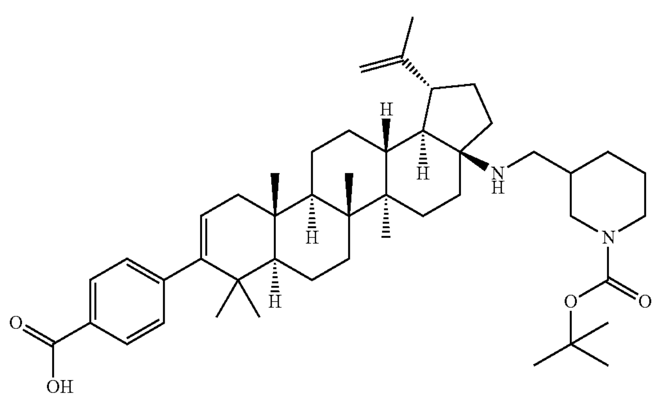 | 0.3 |

TABLE 2-continued
| Example # | Structure | EC$_{50}$ (μM) |
|---|---|---|
| 175 | 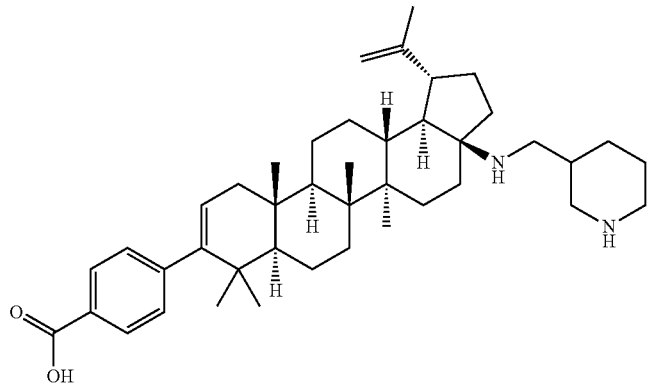 | 0.01 |
| 176 | 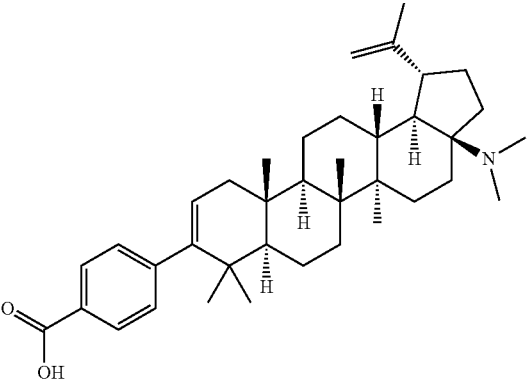 | A |
| 177 | 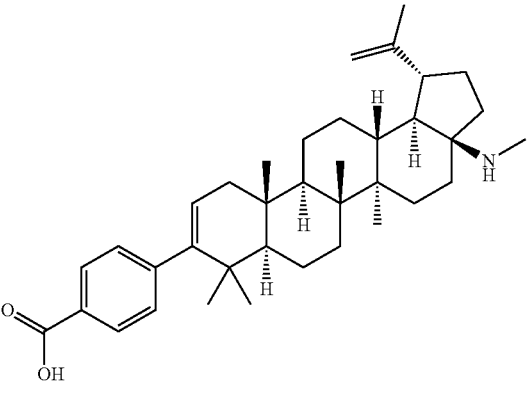 | 0.009 |
| 178 | 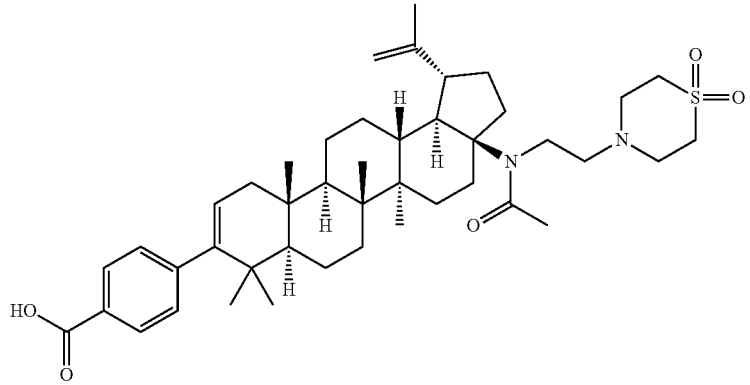 | A |

TABLE 2-continued

| Example # | Structure | EC$_{50}$ (μM) |
|---|---|---|
| 179 | 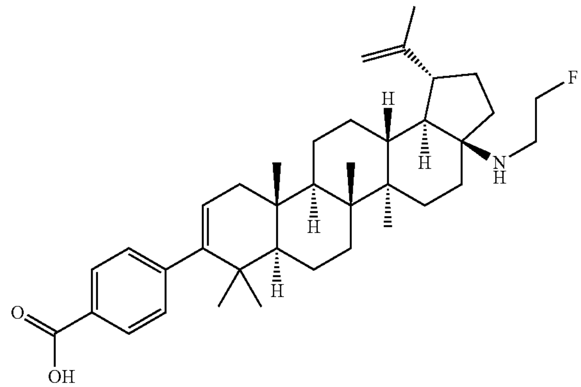 | A |
| 180 | 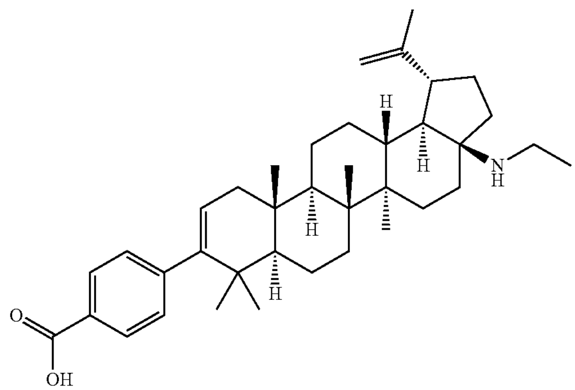 | A |
| 181 | 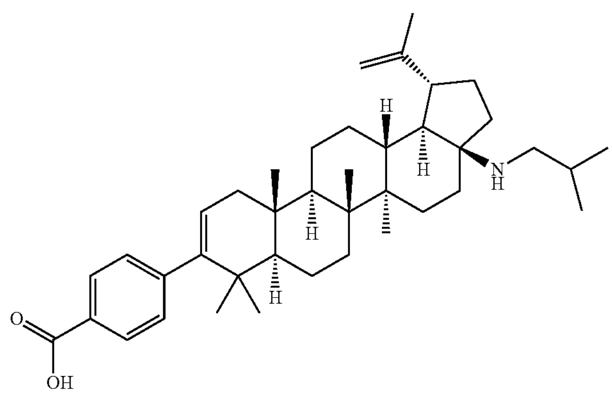 | A |
| 182 | 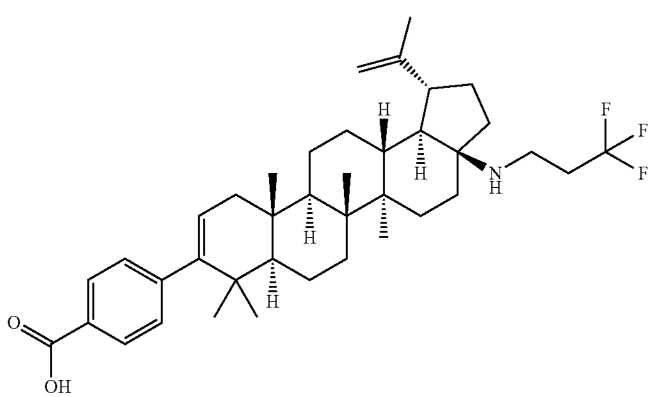 | B |

TABLE 2-continued

| Example # | Structure | EC$_{50}$ (μM) |
|---|---|---|
| 183 | 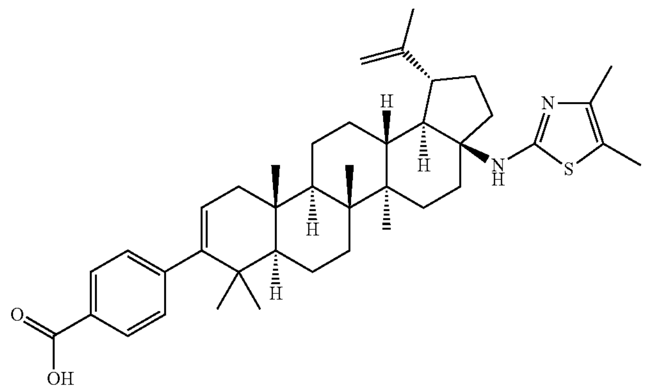 | A |
| 184A | 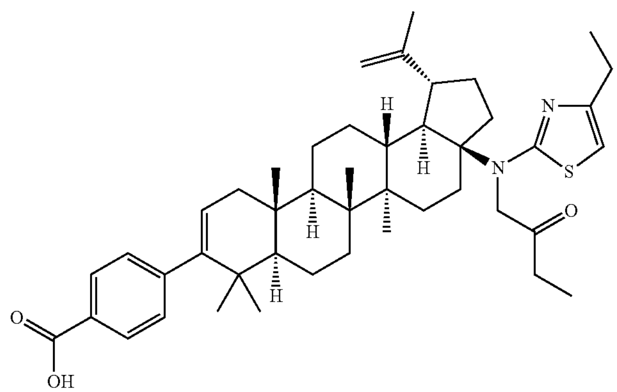 | 0.39 |
| 184B | 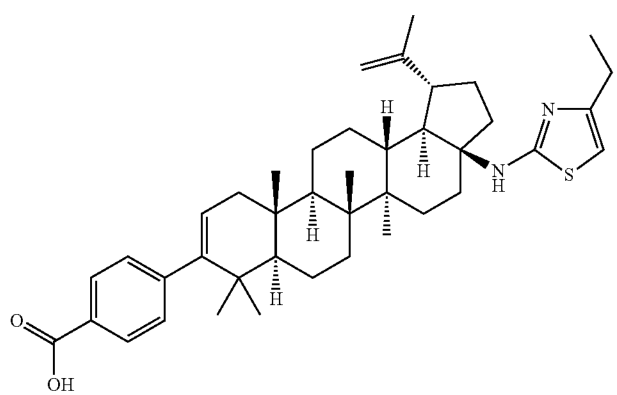 | A |
| 185 | 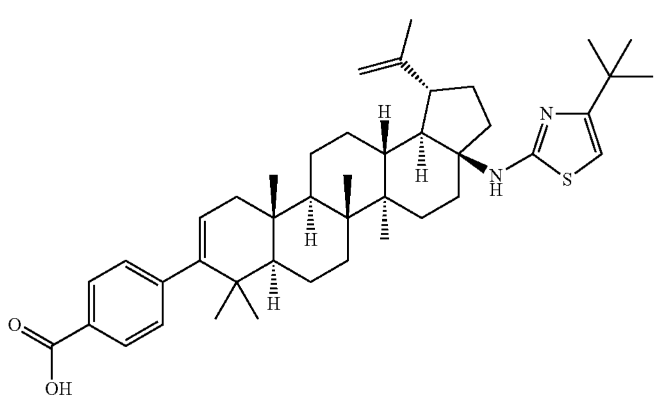 | B |

TABLE 2-continued
| Example # | Structure | EC$_{50}$ (μM) |
|---|---|---|
| 186 | 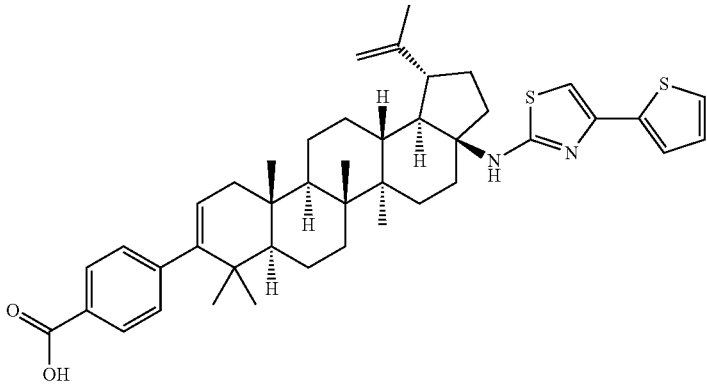 | B |
| 187 | 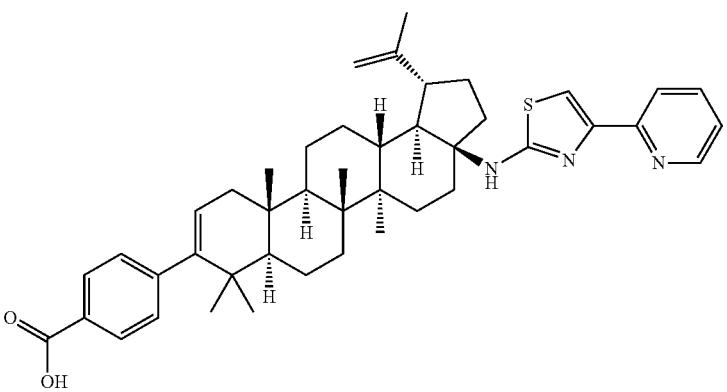 | A |
| 188 | 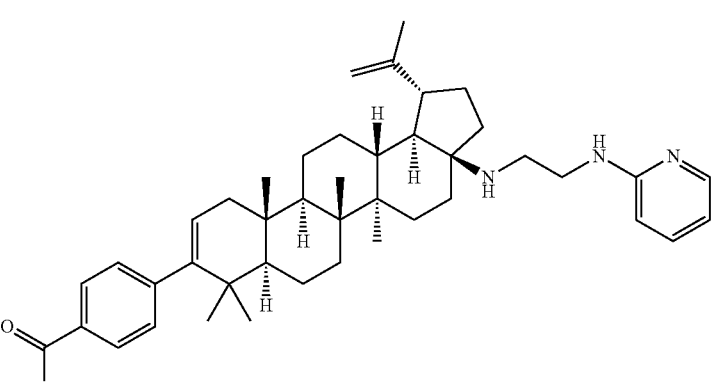 | 0.001 |
| 189 | 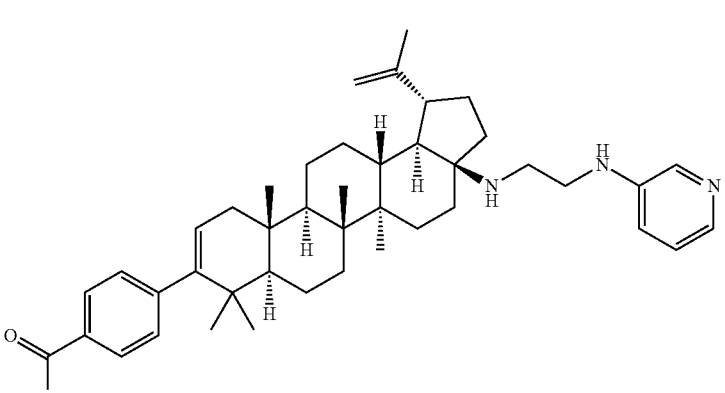 | A |

TABLE 2-continued
| Example # | Structure | EC$_{50}$ (μM) |
|---|---|---|
| 190 | 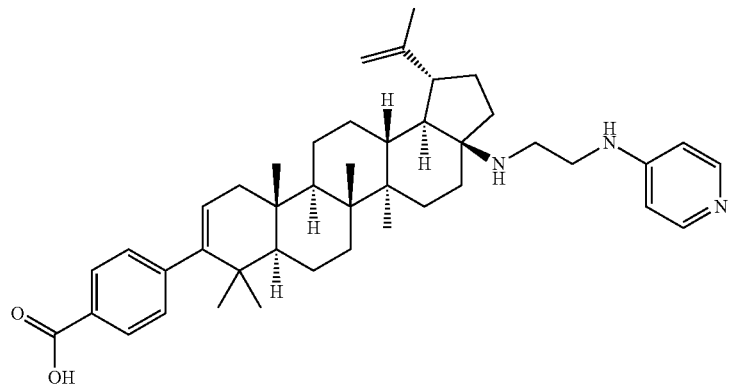 | A |
| 191 | 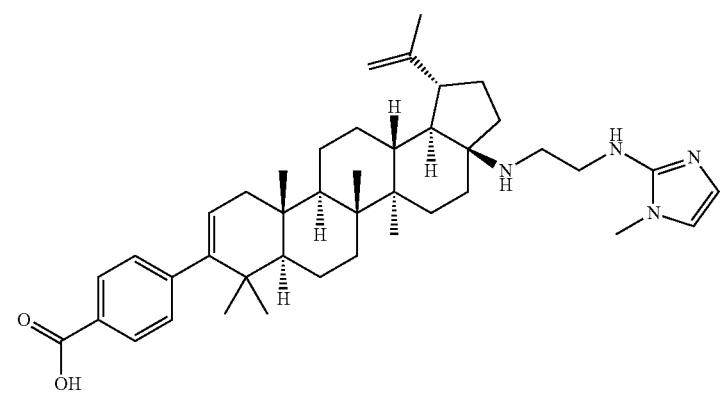 | A |
| 192 | 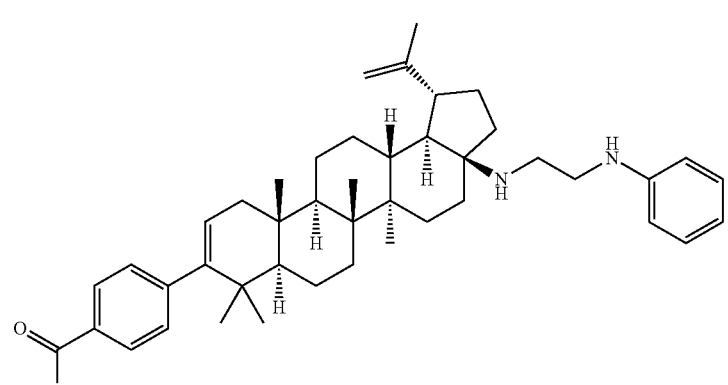 | A |
| 193 | 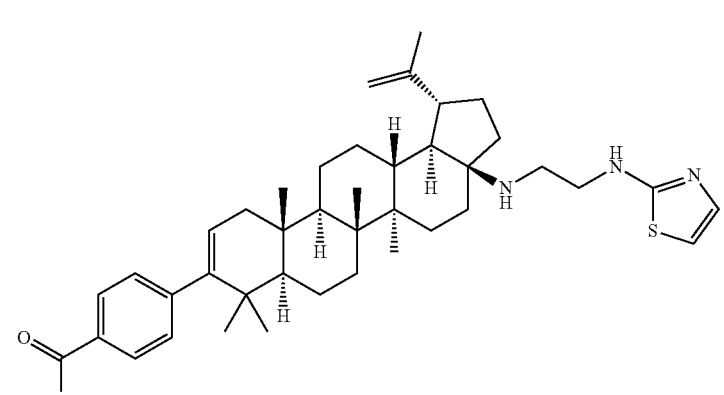 | 0.02 |

TABLE 2-continued

| Example # | Structure | EC$_{50}$ (μM) |
|---|---|---|
| 194 | 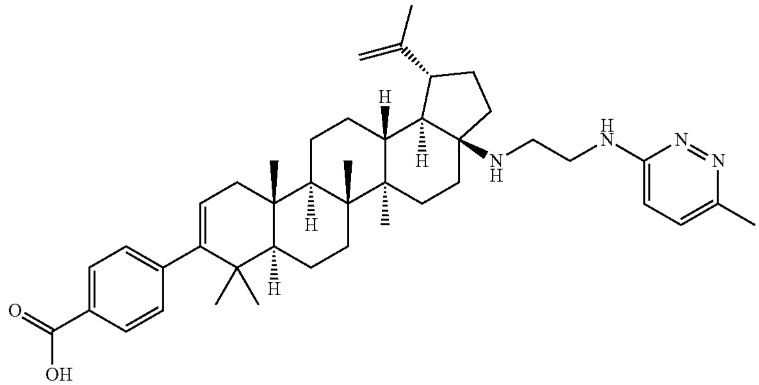 | A |
| 195 | 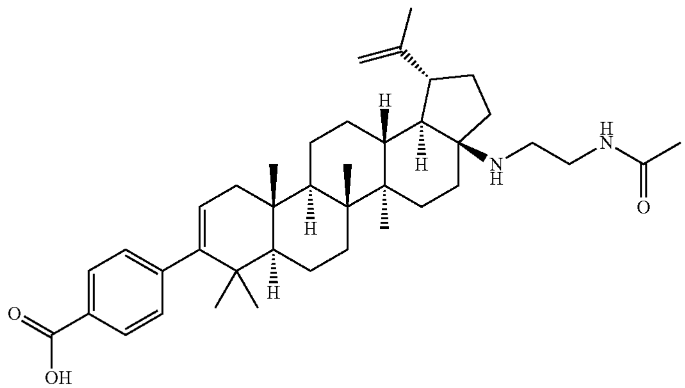 | A |
| 196 | 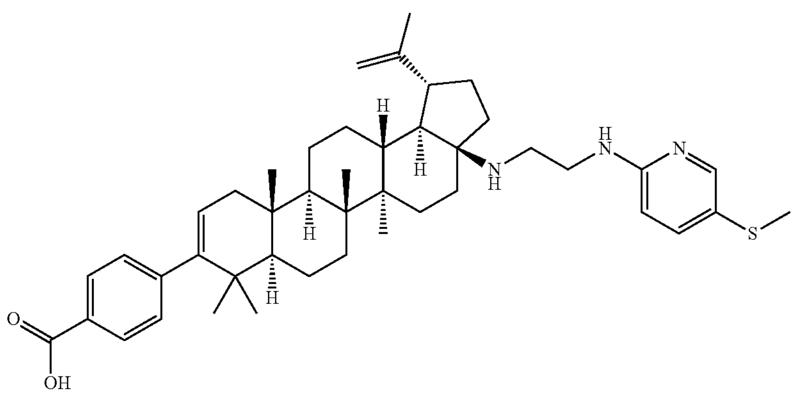 | A |
| 197 | 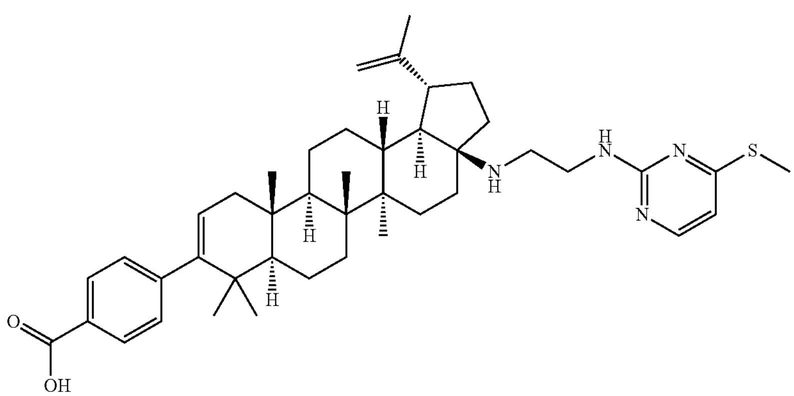 | A |

TABLE 2-continued

| Example # | Structure | EC$_{50}$ (μM) |
|---|---|---|
| 198 | 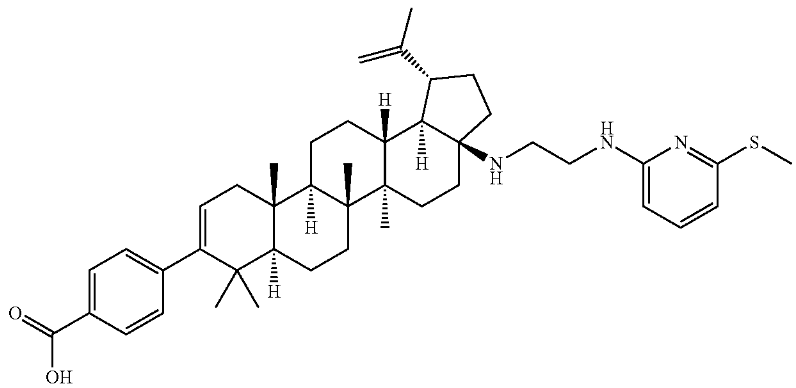 | A |
| 199 | 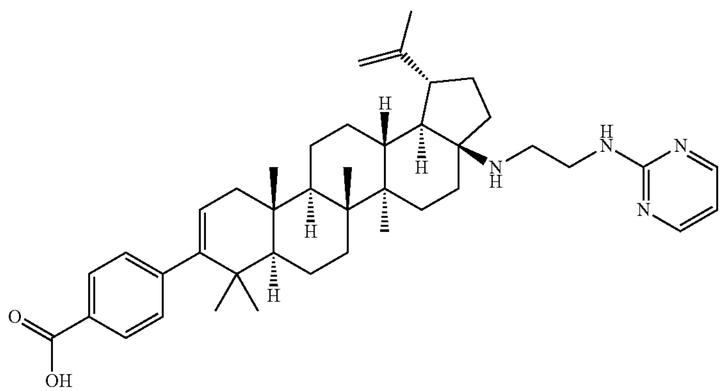 | A |
| 200 | 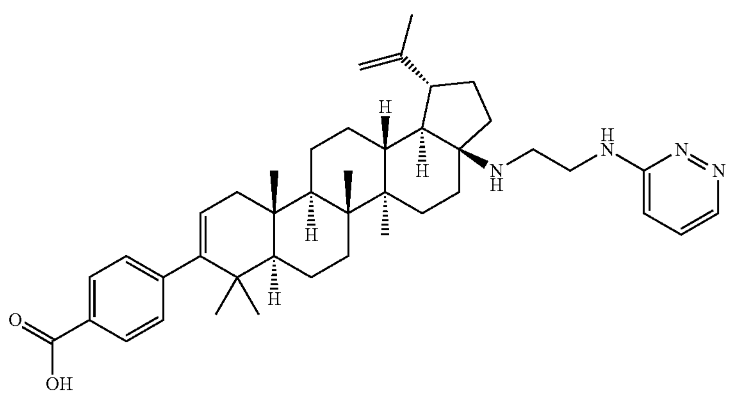 | A |
| 201 | 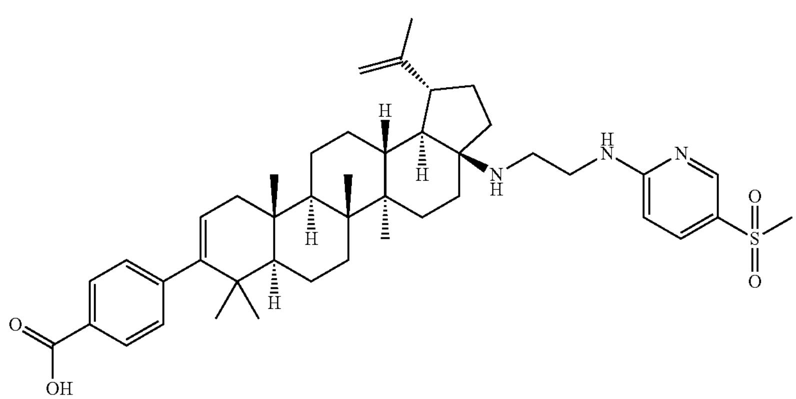 | A |

TABLE 2-continued

| Example # | Structure | EC$_{50}$ (μM) |
|---|---|---|
| A1 | 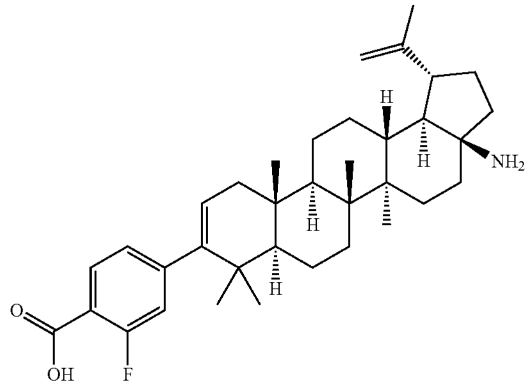 | A |
| A2 | 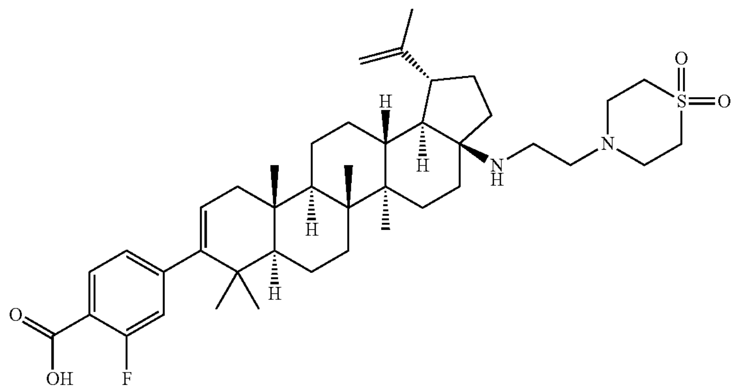 | A |
| A3 | 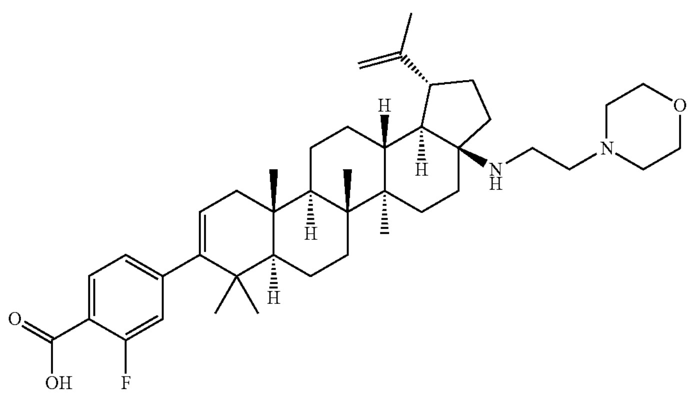 | A |
| A4 | 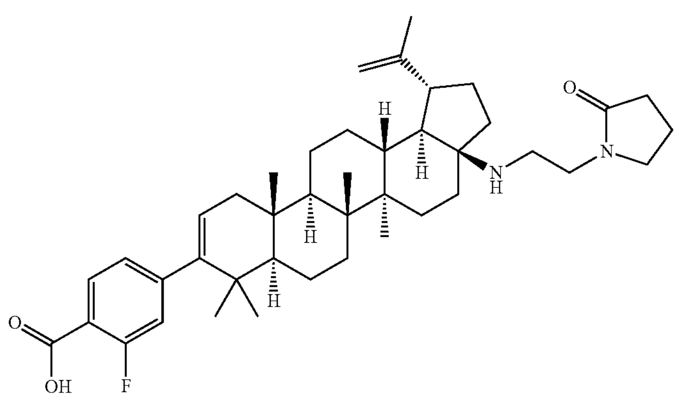 | A |

TABLE 2-continued
| Example # | Structure | EC$_{50}$ (μM) |
|---|---|---|
| A5 | 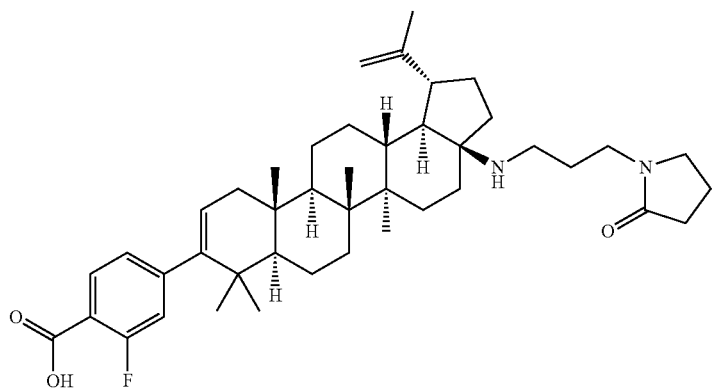 | A |
| A6 | 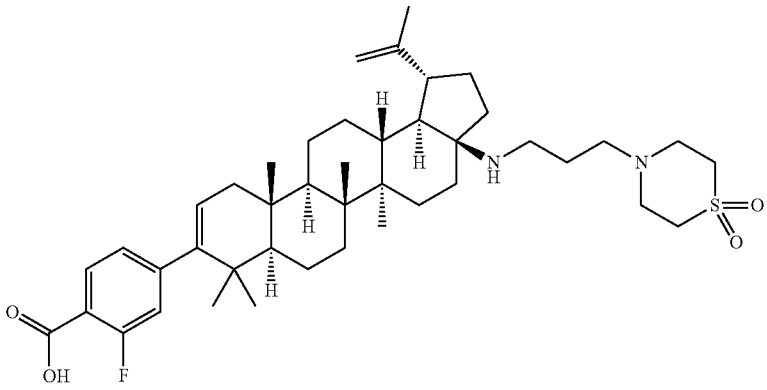 | A |
| A7 | 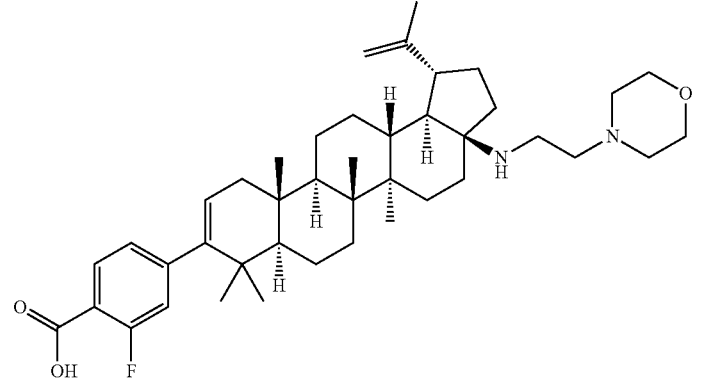 | A |
| A8 | 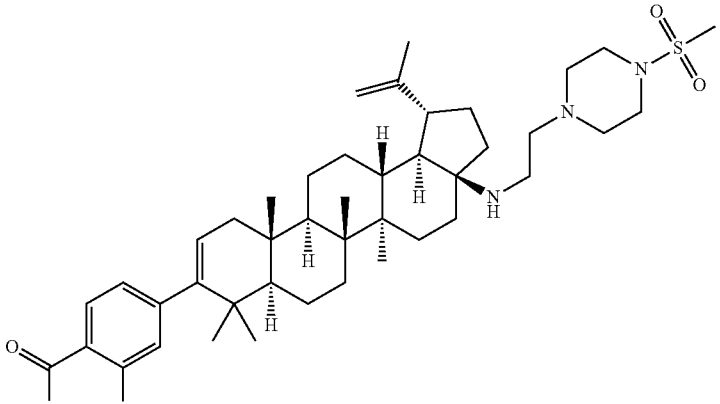 | A |

TABLE 2-continued

| Example # | Structure | EC$_{50}$ (µM) |
|---|---|---|
| B1 | 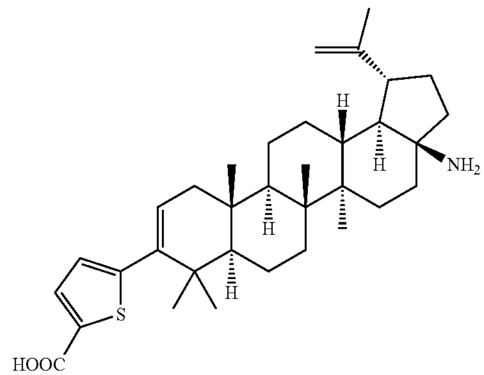 | A |
| B2 | 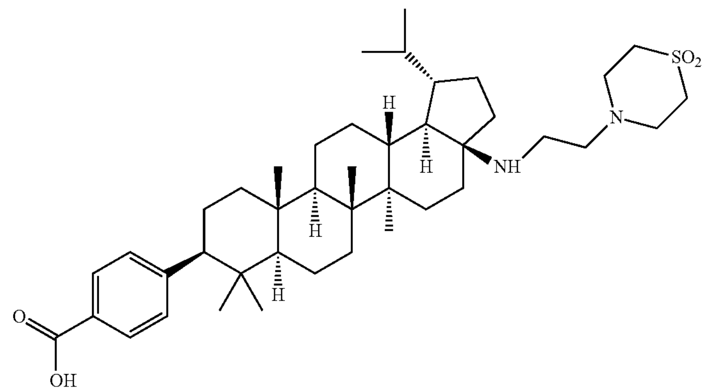 | A |
| B3 | 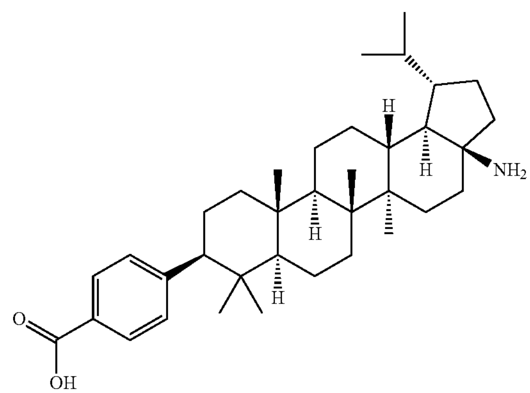 | A |
| B4 | 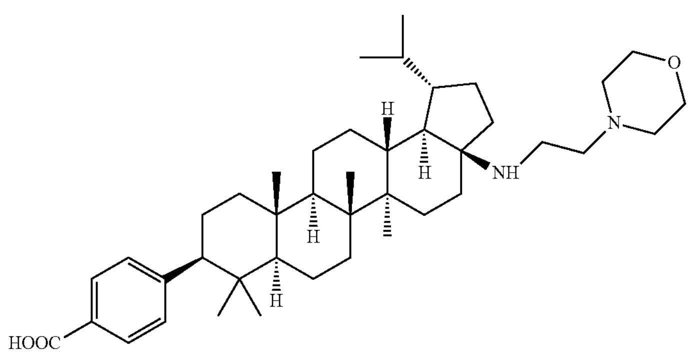 | A |

TABLE 2-continued

| Example # | Structure | EC$_{50}$ (μM) |
|---|---|---|
| B5 | 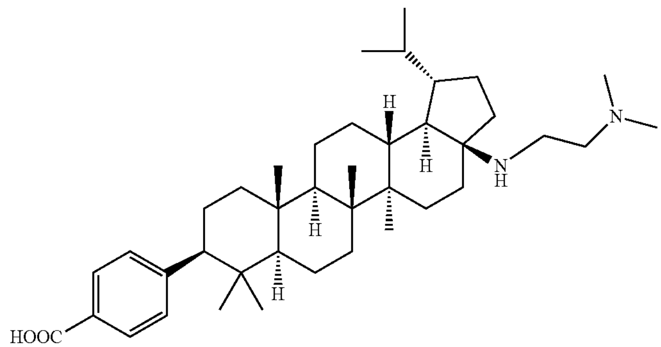 | A |
| B6 | 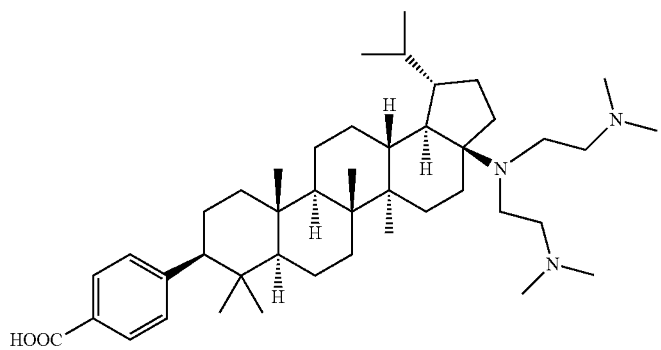 | A |
| B7A | 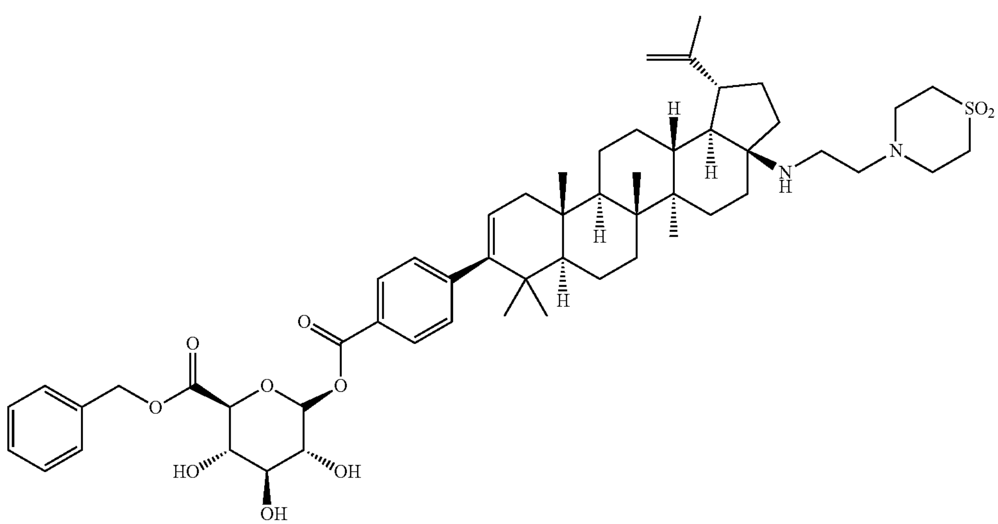 | A |

TABLE 2-continued

| Example # | Structure | EC$_{50}$ (μM) |
|---|---|---|
| B7B | 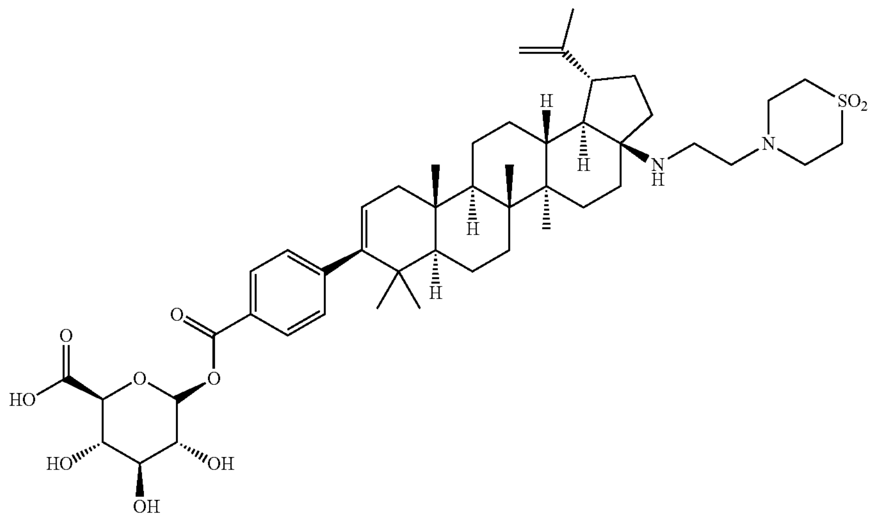 | A |
| B8 | 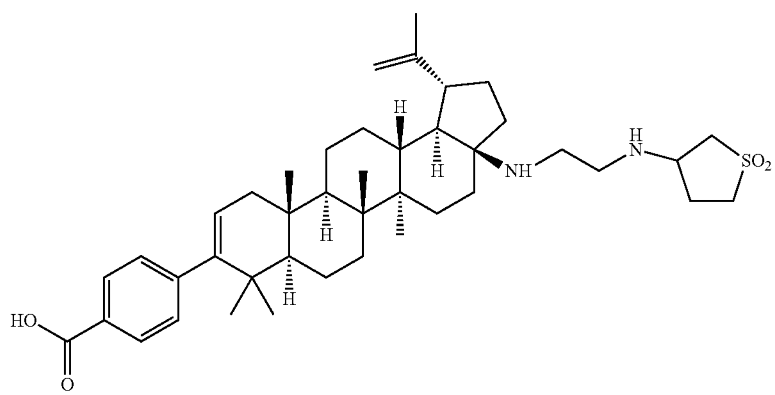 | A |
| B9 | 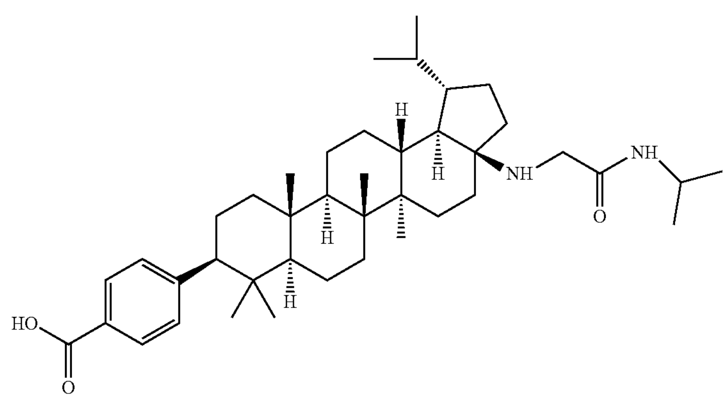 | 0.01 |

TABLE 2-continued

| Example # | Structure | EC$_{50}$ (μM) |
|---|---|---|
| B10 | 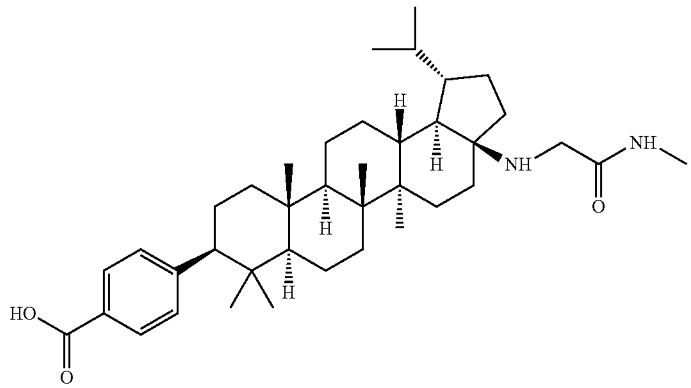 | A |
| B11 | 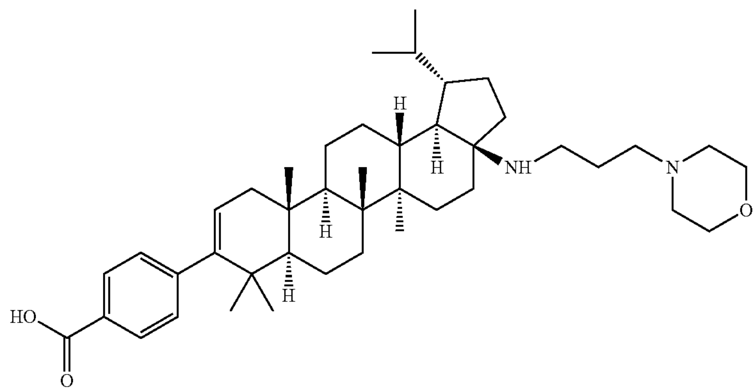 | A |
| B12 | 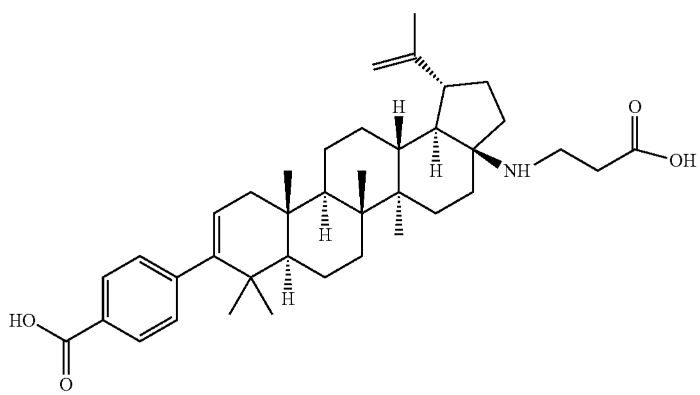 | A |
| B13 | 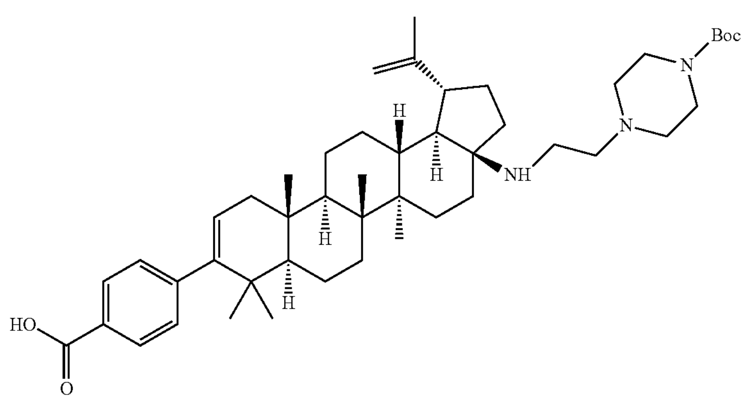 | A |

TABLE 2-continued

| Example # | Structure | EC₅₀ (μM) |
|---|---|---|
| B14 | 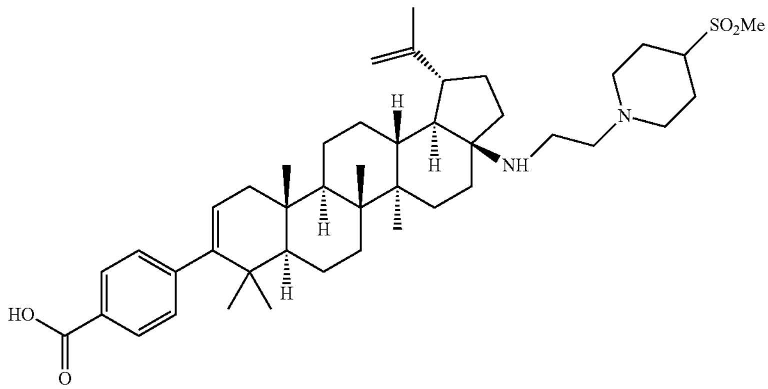 | A |
| B15 | 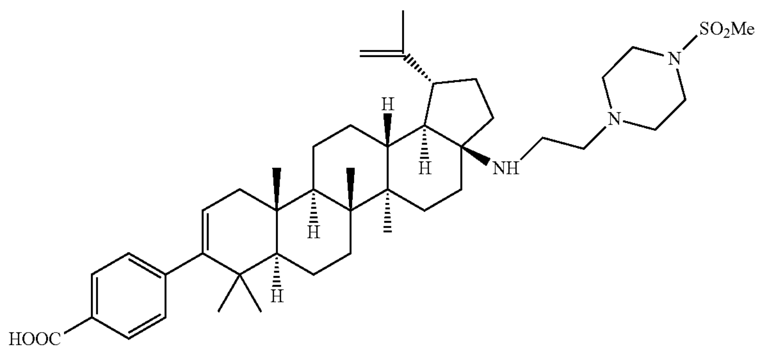 | A |
| B16 | 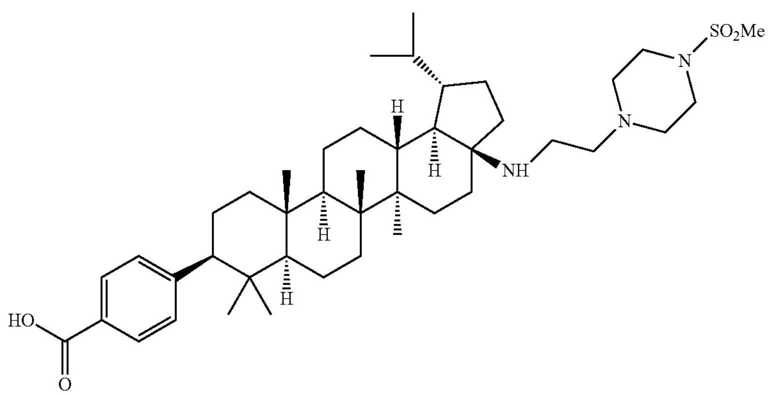 | A |
| B17 | 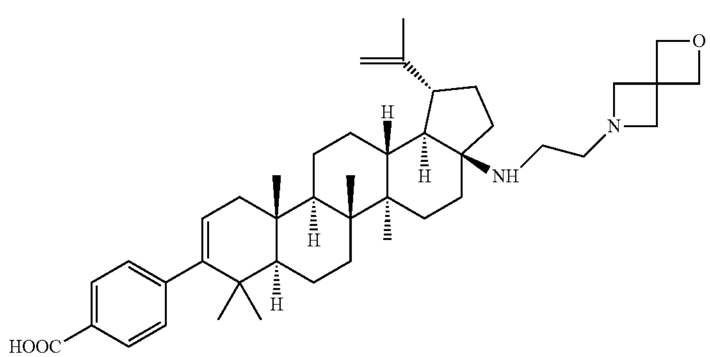 | A |

TABLE 2-continued

| Example # | Structure | EC$_{50}$ (μM) |
|---|---|---|
| B18 | 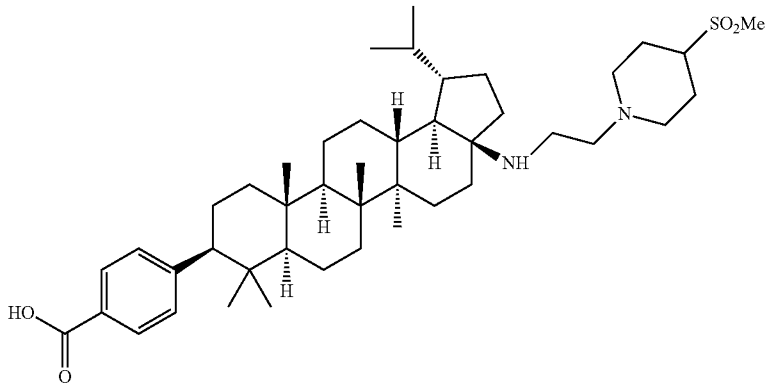 | A |
| B19 | 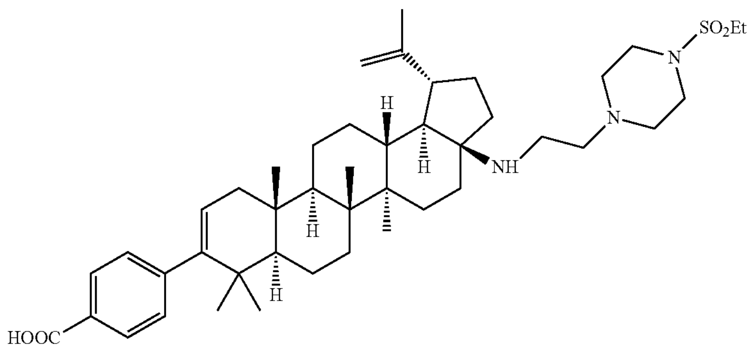 | A |
| B20 | 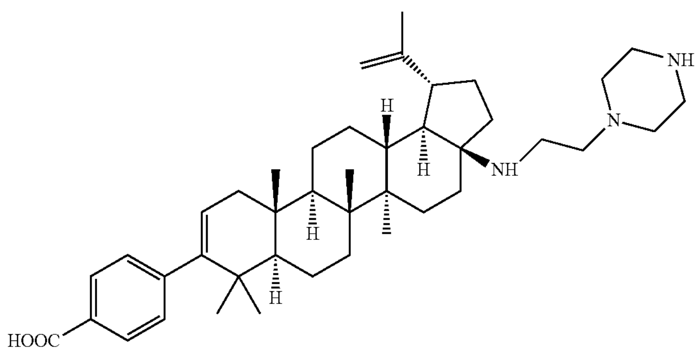 | A |
| B21 | 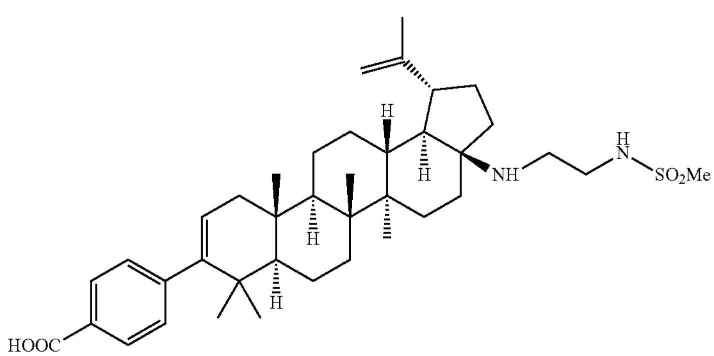 | A |

TABLE 2-continued

| Example # | Structure | EC$_{50}$ (μM) |
|---|---|---|
| B22 | 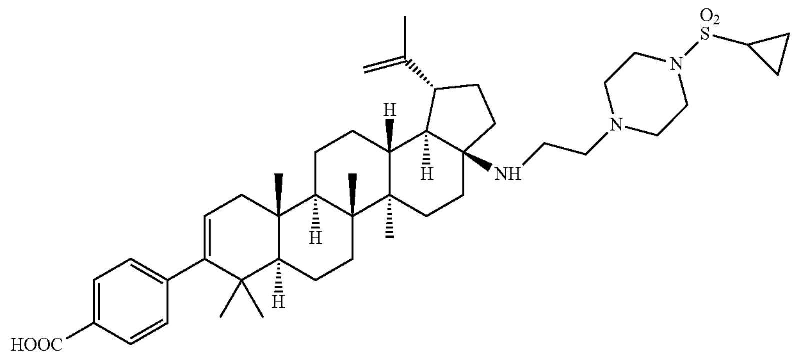 | A |
| B23 | 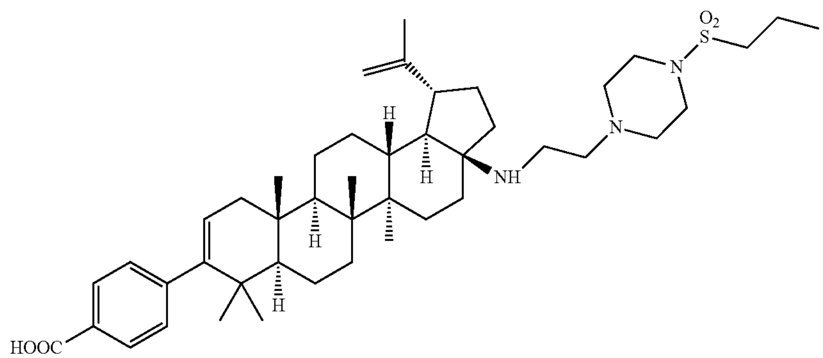 | A |
| B24 | 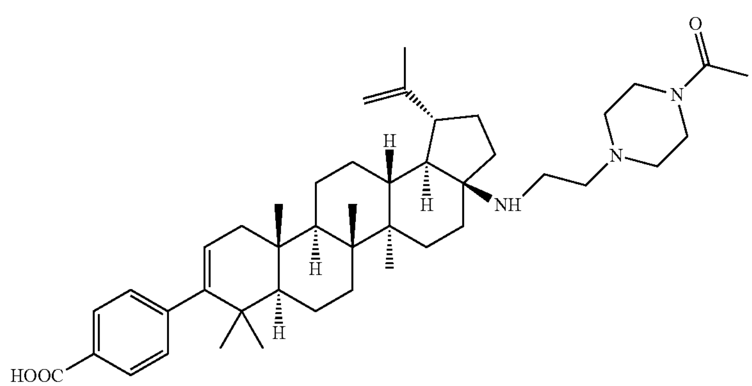 | A |
| B25 | + | A |
| B26 | 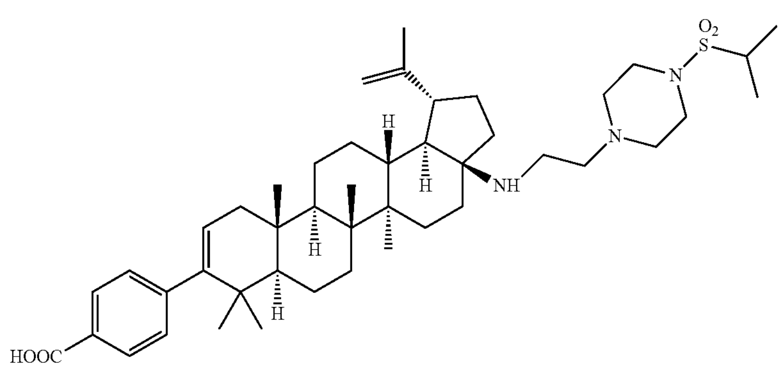 | A |

TABLE 2-continued

| Example # | Structure | EC$_{50}$ (μM) |
|---|---|---|
| B27 | 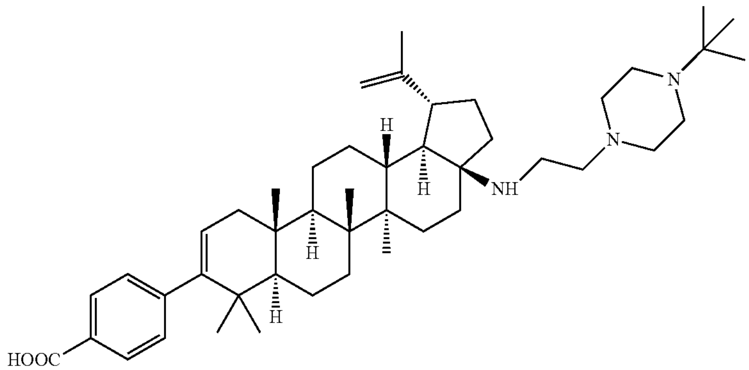 | A |
| B28 | 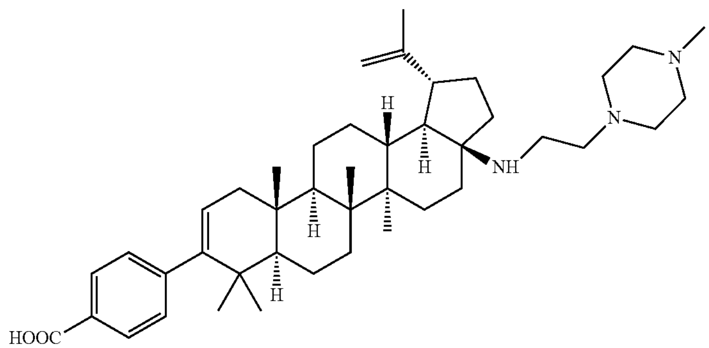 | A |
| B29 | 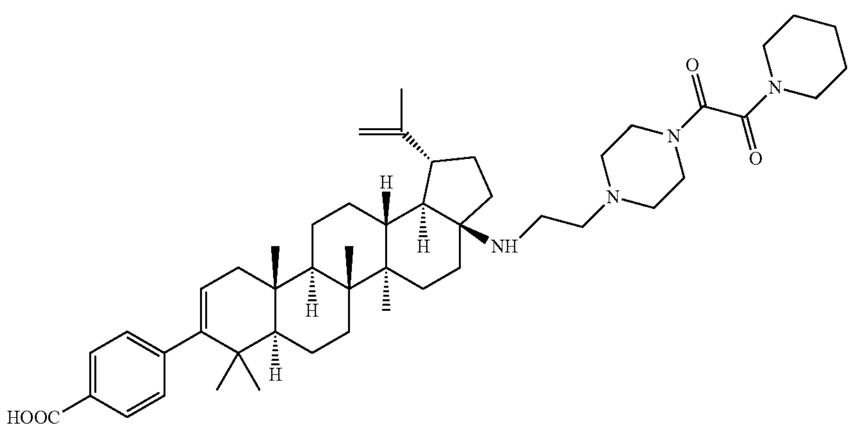 | A |
| B30 | 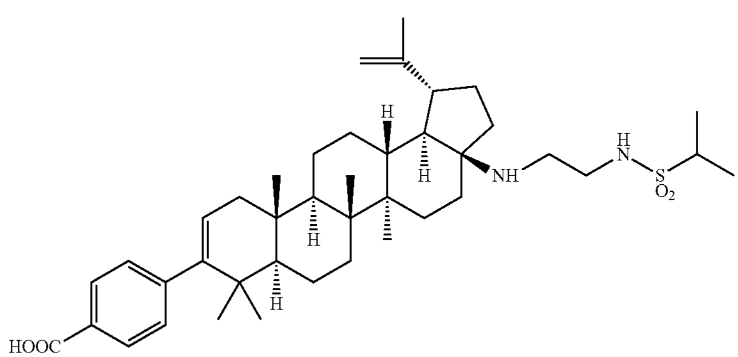 | A |

TABLE 2-continued

| Example # | Structure | EC$_{50}$ (μM) |
|---|---|---|
| B31 | 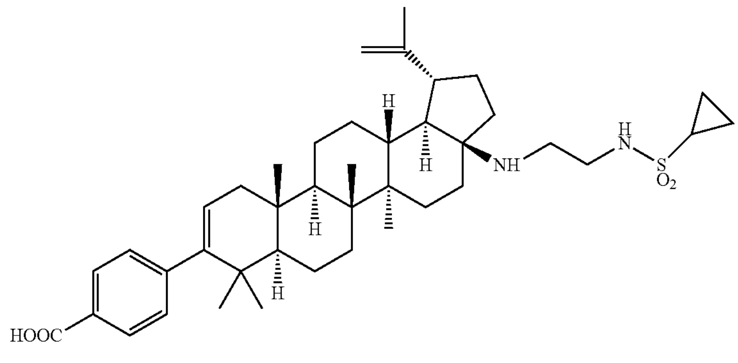 | A |
| B32 | 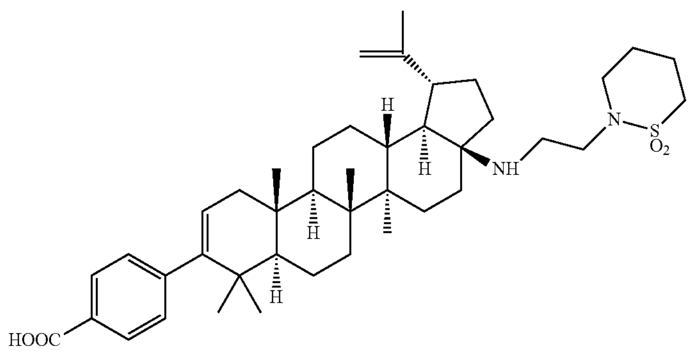 | A |
| B33 | 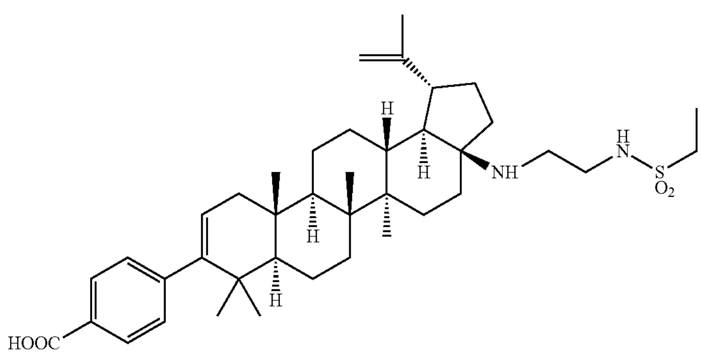 | 0.005 |
| B34 | 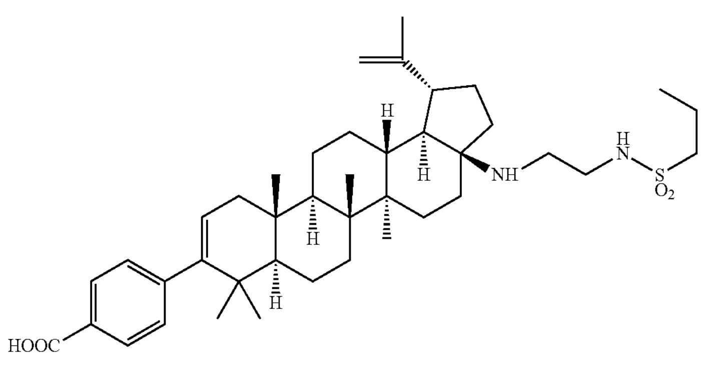 | A |

TABLE 2-continued

| Example # | Structure | EC$_{50}$ (μM) |
|---|---|---|
| B35 | 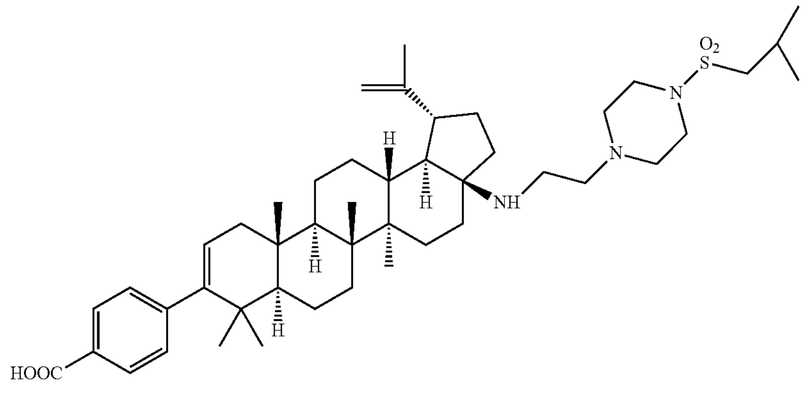 | A |
| B36 | 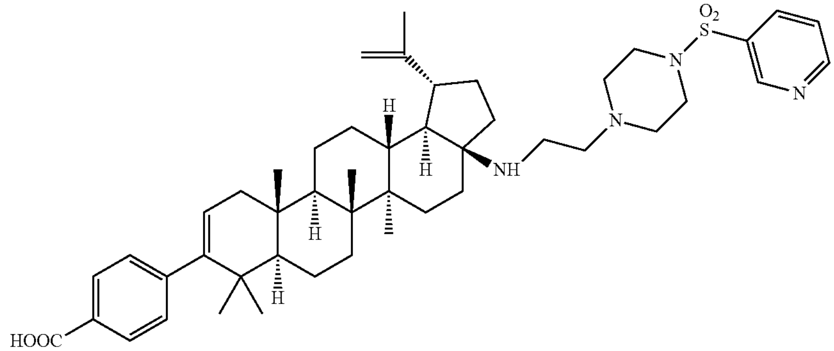 | A |
| B37 | 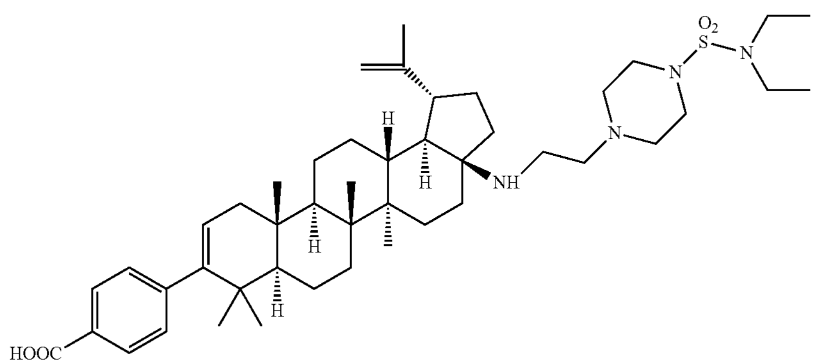 | A |
| B38 | 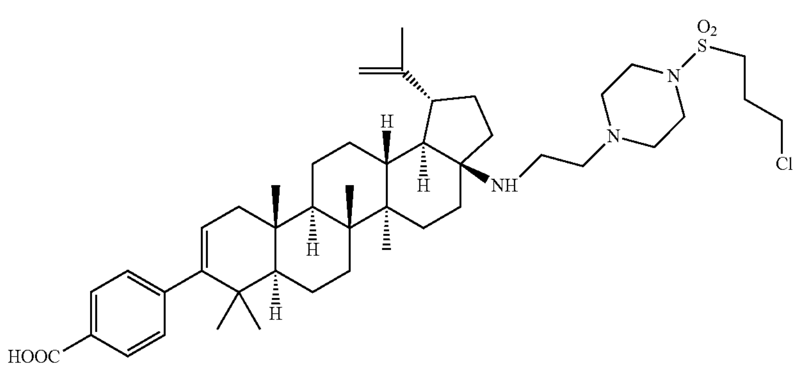 | A |

TABLE 2-continued
| Example # | Structure | EC$_{50}$ (μM) |
|---|---|---|
| B39 | 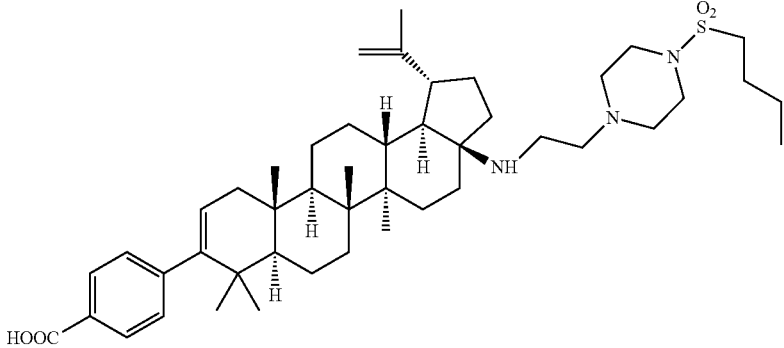 | A |
| B40 | 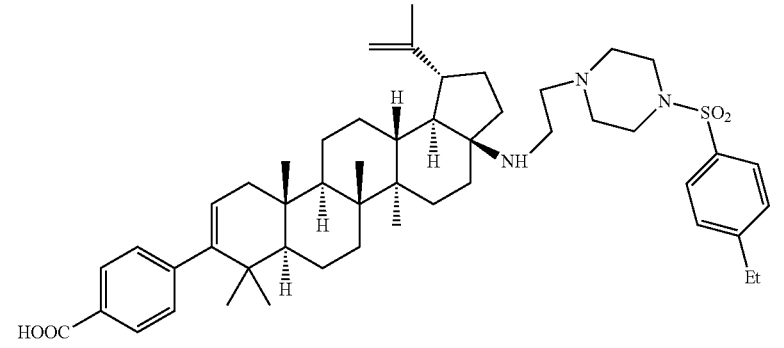 | A |
| B41 | 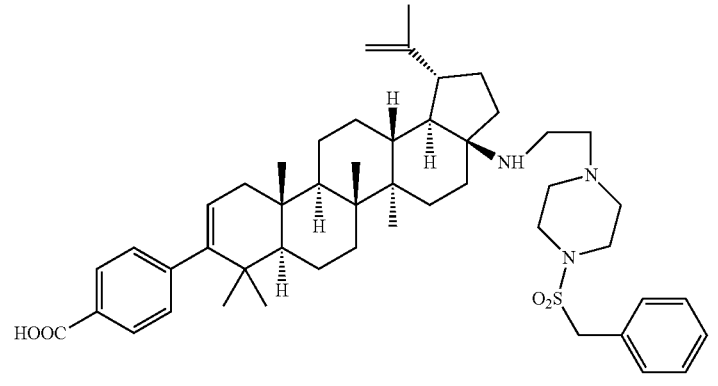 | A |
| B42 | 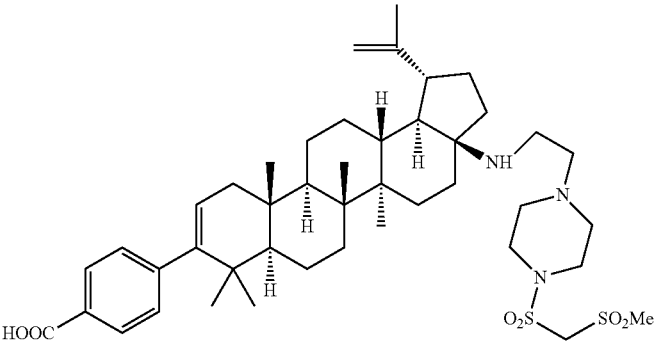 | A |

TABLE 2-continued

| Example # | Structure | EC$_{50}$ (μM) |
|---|---|---|
| B43 | 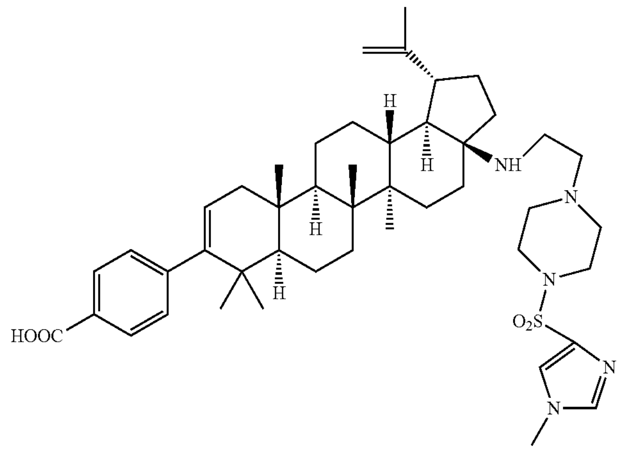 | A |
| B44 | 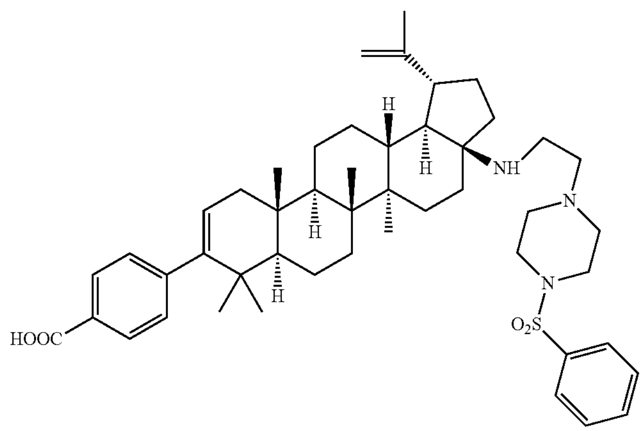 | A |
| B45 | 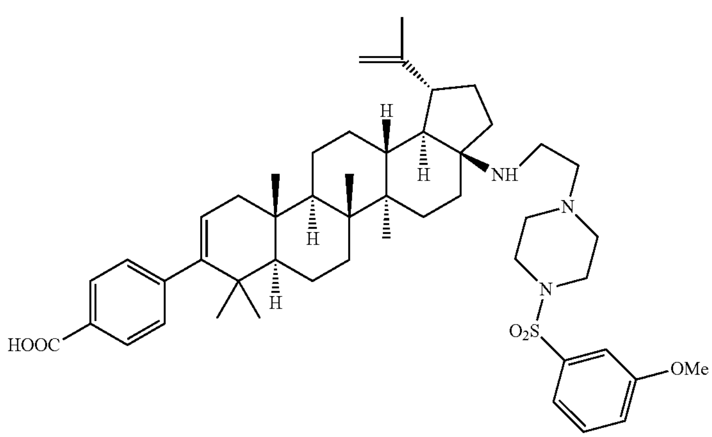 | 0.004 |

TABLE 2-continued

| Example # | Structure | EC$_{50}$ (μM) |
|---|---|---|
| B46 | 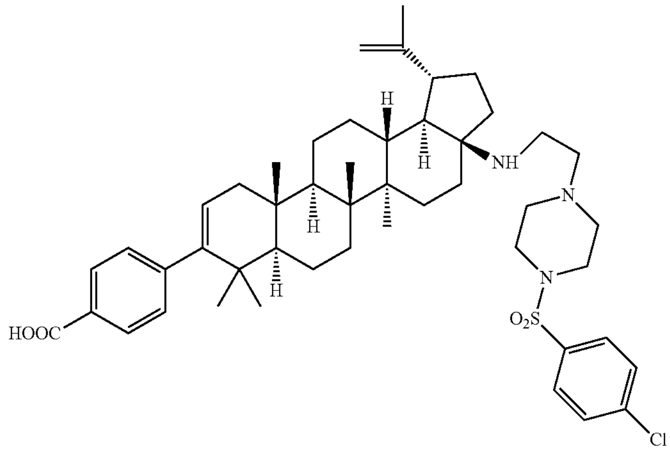 | A |
| B47 | 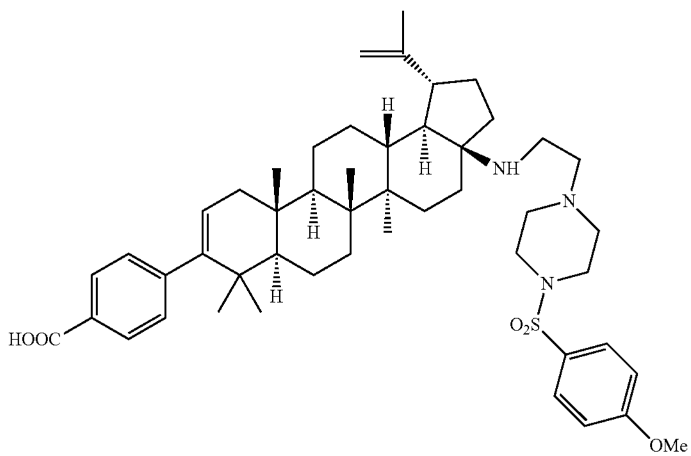 | A |
| B48 | 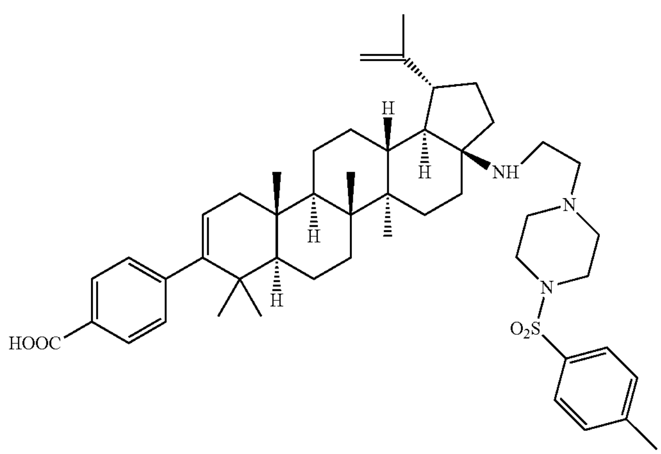 | A |

TABLE 2-continued
| Example # | Structure | EC$_{50}$ (μM) |
|---|---|---|
| B49 | 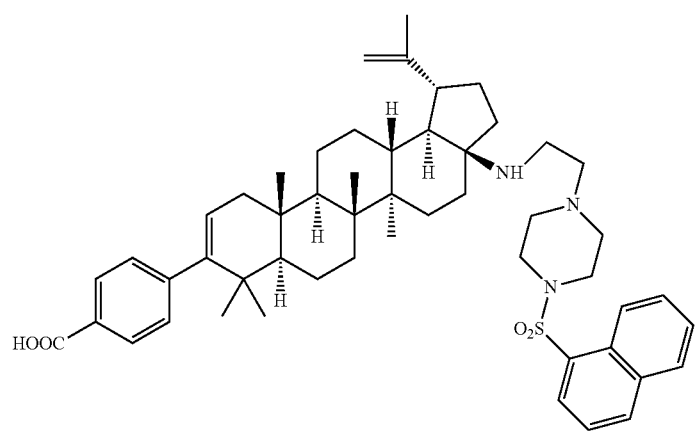 | A |
| B50 | 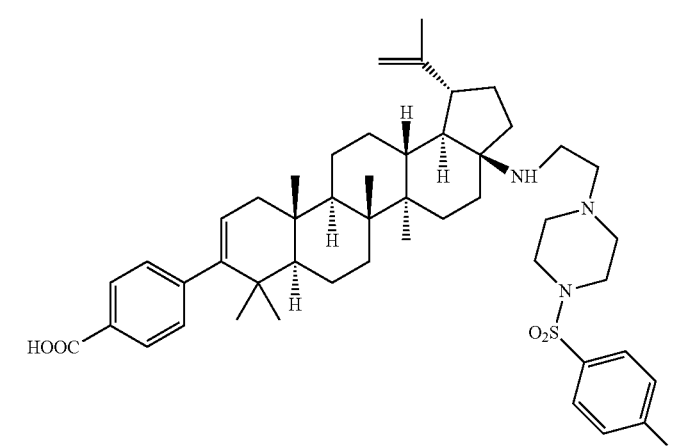 | A |
| B51 | 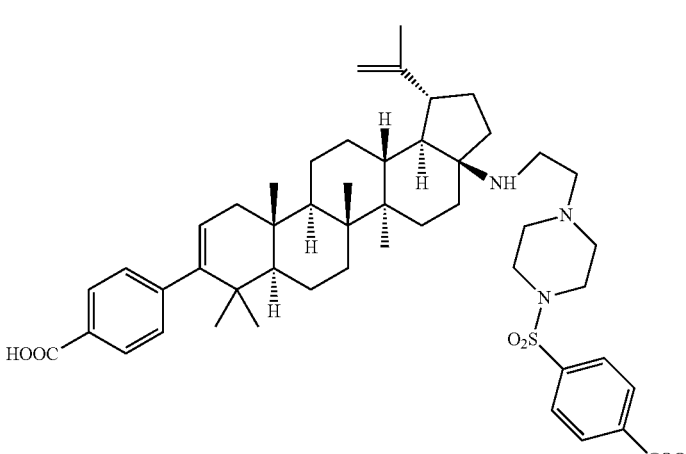 | A |

TABLE 2-continued

| Example # | Structure | EC$_{50}$ (μM) |
|---|---|---|
| B52 | 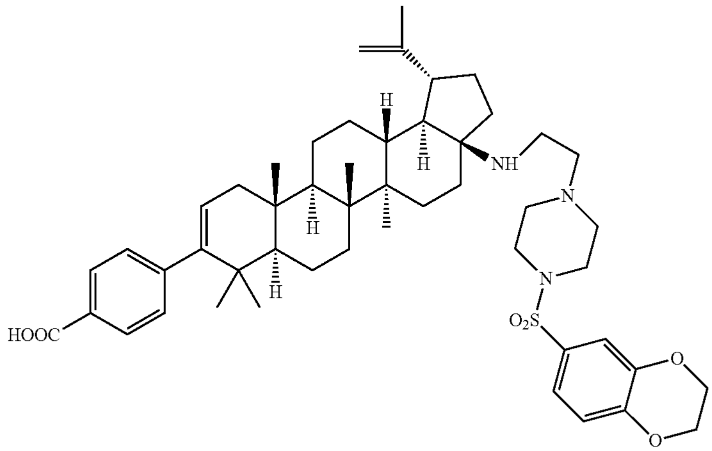 | A |
| B53 | 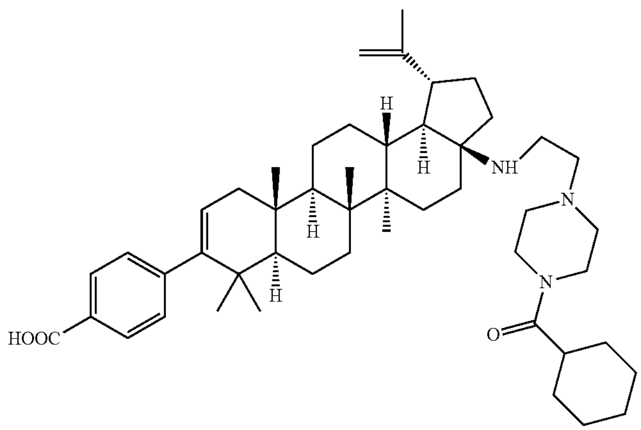 | A |
| B54 | 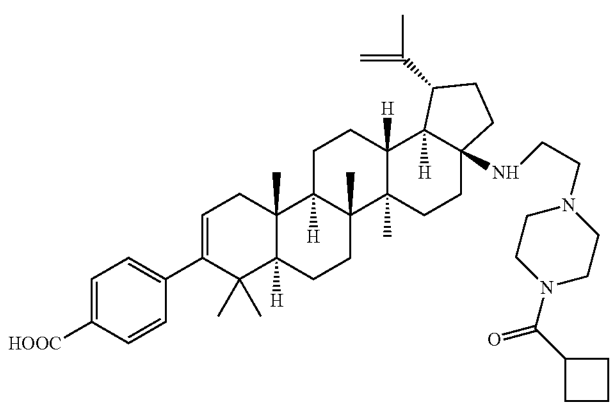 | A |

TABLE 2-continued

| Example # | Structure | EC$_{50}$ (μM) |
|---|---|---|
| B55 | 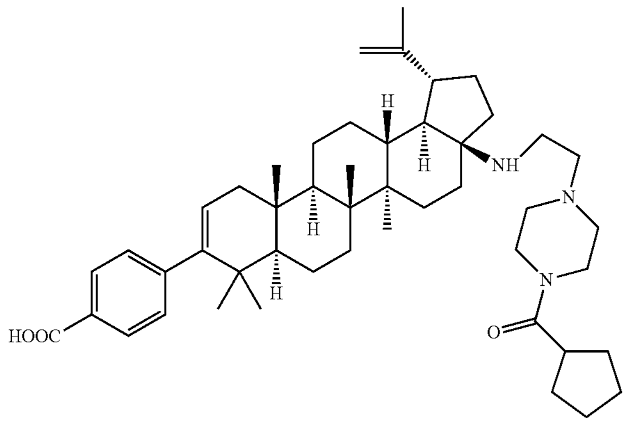 | A |
| B56 | 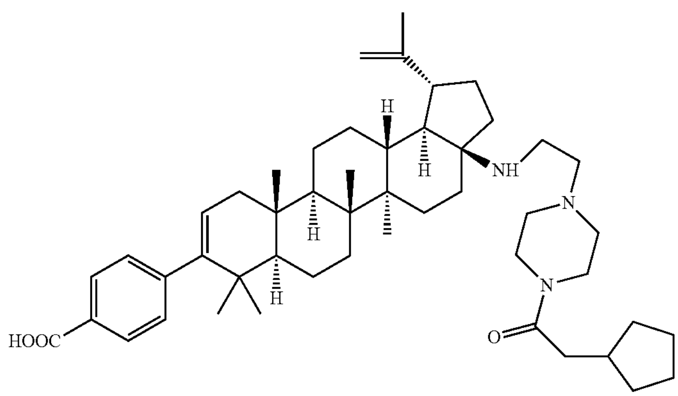 | A |
| B57 | 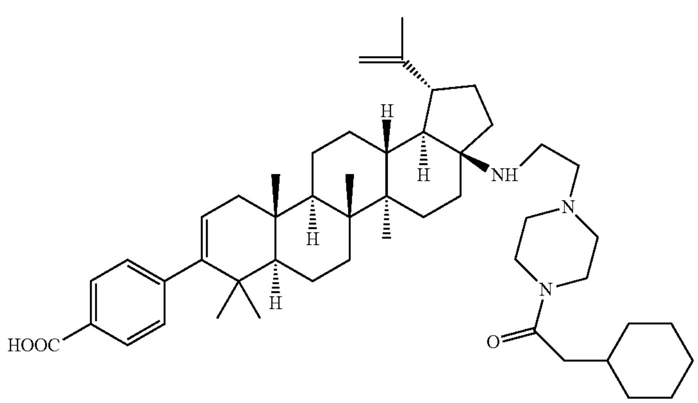 | A |

TABLE 2-continued

| Example # | Structure | EC$_{50}$ (μM) |
|---|---|---|
| B58 | 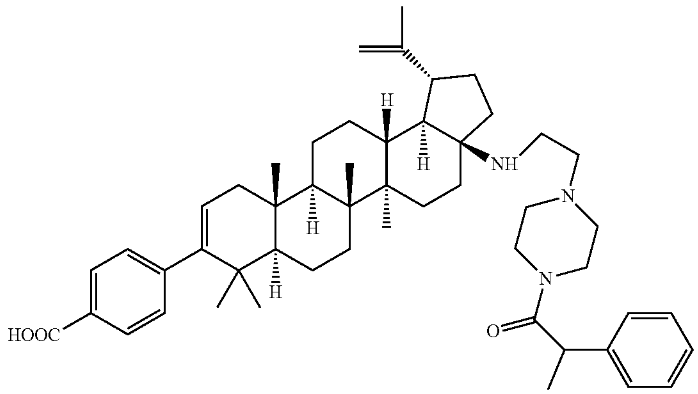 | A |
| B59 | 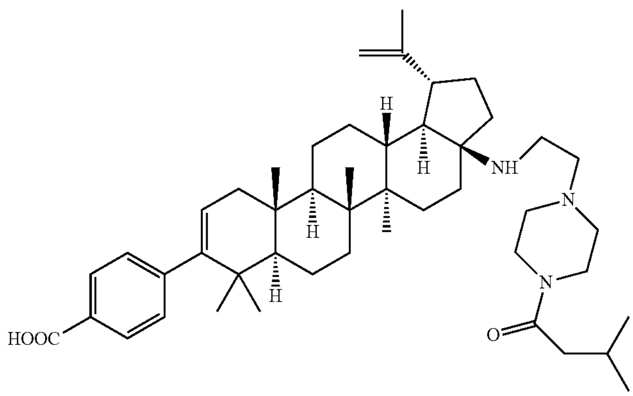 | A |
| B60 | 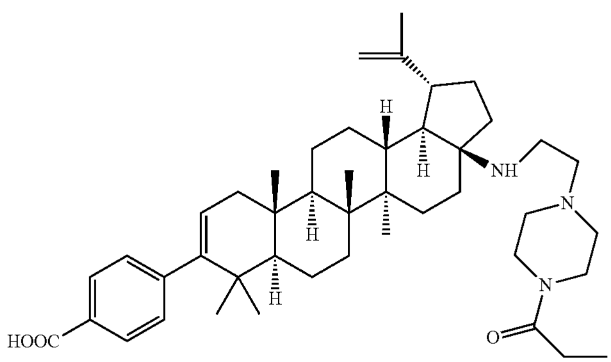 | A |
| B61 | 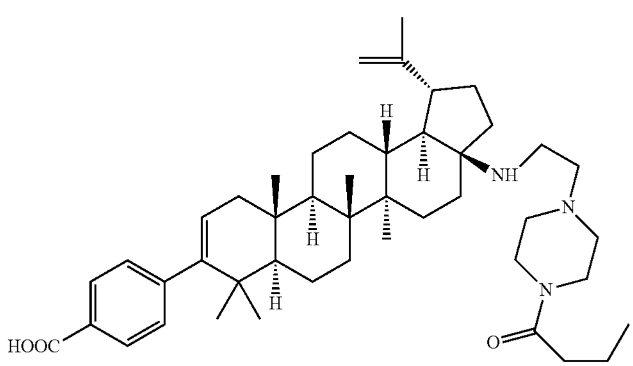 | A |

TABLE 2-continued

| Example # | Structure | EC$_{50}$ (µM) |
|---|---|---|
| B62 | 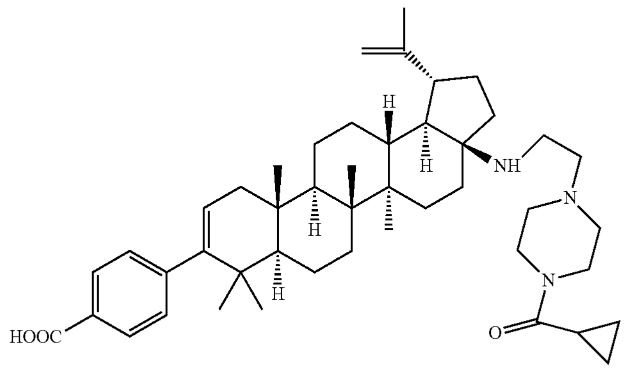 | A |
| B63 | 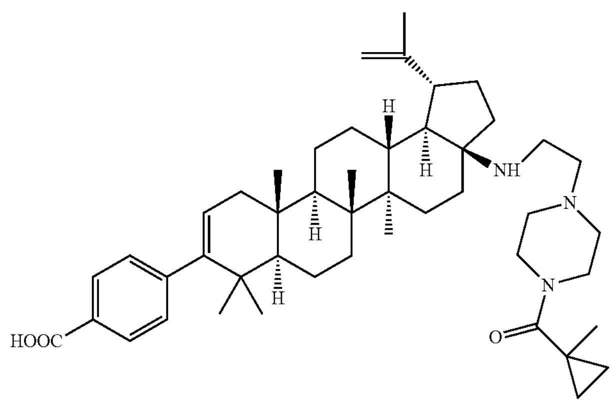 | A |
| B64 | 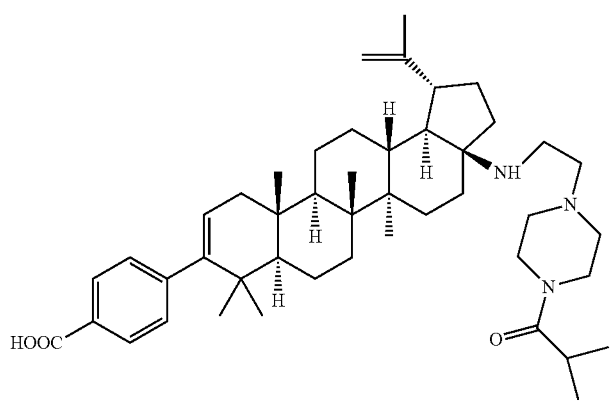 | A |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound which is selected from the group consisting of:
a compound of formula I

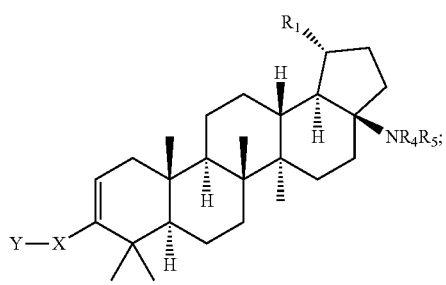

Formula I a compound of formula II

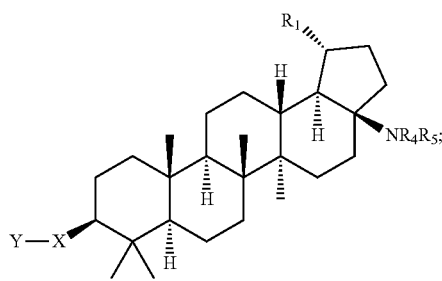

Formula II and
a compound of formula III

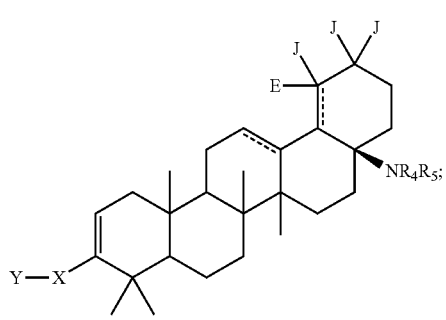

Formula III wherein $R_1$ is isopropenyl or isopropyl;
J and E are independently —H or —CH$_3$, and E is absent when the double bond is present;

X is a phenyl or heteroaryl ring substituted with A, wherein A is at least one member selected from the group of —H, -halo, -hydroxyl, —C$_{1-6}$ alkyl, —C$_{1-6}$ alkoxy, and —COOR$_2$;

$R_2$ is —H, —C$_{1-6}$ alkyl, -alkylsubstituted C$_{1-6}$ alkyl or -arylsubstituted C$_{1-6}$ alkyl;

Y is selected from the group of —COOR$_2$, —C(O)NR$_2$SO$_2$R$_3$, —C(O)NHSO$_2$NR$_2$R$_2$, —NR$_2$SO$_2$R$_2$, —SO$_2$NR$_2$R$_2$, —C$_{3-6}$ cycloalkyl-COOR$_2$, —C$_{2-6}$ alkenyl-COOR$_2$, —C$_{2-6}$ alkynyl-COOR$_2$, —C$_{1-6}$ alkyl-COOR$_2$, —NHC(O)(CH$_2$)$_n$—COOR$_2$, —SO$_2$NR$_2$C(O)R$_2$, -tetrazole, and —CONHOH, wherein n=1-6;

$R_3$ is —C$_{1-6}$ alkyl or -alkylsubstituted C$_{1-6}$ alkyl;

$R_4$ is selected from the group of —H, —C$_{1-6}$ alkyl, —C$_{1-6}$ alkyl-C(OR$_3$)$_2$—C$_{3-6}$ cycloalkyl, —C$_{1-6}$ substituted alkyl, —C$_{1-6}$ alkyl-C$_{3-6}$ cycloalkyl, —C$_{1-6}$ alkyl-Q$_1$, —C$_{1-6}$ alkyl-C$_{3-6}$ cycloalkyl-Q$_1$, aryl, heteroaryl, substituted heteroaryl, —COR$_6$, —COCOR$_6$, —SO$_2$R$_7$, —SO$_2$NR$_2$R$_2$,

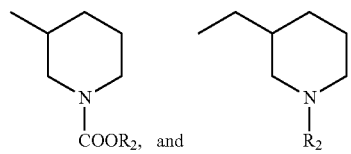

wherein Q$_1$ is selected from the group of heteroaryl, substituted heteroaryl, halogen, —CF$_3$, —OR$_2$, —COOR$_2$, —NR$_8$R$_9$, —CONR$_{10}$R$_{11}$ and —SO$_2$R$_7$;

$R_5$ is selected from the group of —H, —C$_{1-6}$ alkyl, —C$_{3-6}$ cycloalkyl, —C$_{1-6}$ alkylsubstituted alkyl, —C$_{1-6}$ alkyl-NR$_8$R$_9$, —COR$_{10}$, —COR$_6$, —COCOR$_6$, —SO$_2$R$_7$ and —SO$_2$NR$_2$R$_2$;

with the proviso that only one of R$_4$ or R$_5$ can be selected from the group of —COR$_6$, —COCOR$_6$, —SO$_2$R$_7$ and —SO$_2$NR$_2$R$_2$;

or R$_4$ and R$_5$ are taken together with the adjacent N to form

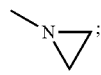

$R_6$ is selected from the group of —H, —C$_{1-6}$ alkyl, —C$_{1-6}$ alkyl-substitutedalkyl, —C$_{3-6}$ cycloalkyl, —C$_{3-6}$ substitutedcycloalkyl-Q$_2$, —C$_{1-6}$ alkyl-Q$_2$, —C$_{1-6}$ alkyl-substitutedalkyl-Q$_2$, —C$_{3-6}$ cycloalkyl-Q$_2$, aryl-Q$_2$, —NR$_{13}$R$_{14}$, and —OR$_{15}$;

wherein Q$_2$ is selected from the group of aryl, heteroaryl, substituted heteroaryl, —OR$_2$, —COOR$_2$, —NR$_8$R$_9$, SO$_2$R$_7$, —CONHSO$_2$R$_3$, and —CONHSO$_2$NR$_2$R$_2$;

$R_7$ is selected from the group of —C$_{1-6}$ alkyl, —C$_{1-6}$ substituted alkyl, —C$_{3-6}$ cycloalkyl, aryl, and heteroaryl;

$R_8$ and $R_9$ are independently selected from the group of —H, —C$_{1-6}$ alkyl, —C$_{1-6}$ substituted alkyl, aryl, heteroaryl, substituted aryl, substituted heteroaryl, —C$_{1-6}$ alkyl-Q$_2$, and —COOR$_3$, or R$_8$ and R$_9$ are independently selected from the group of

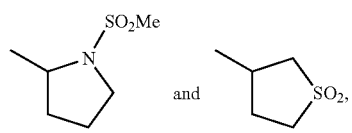

or R₈ and R₉ are taken together with the adjacent N to form a cycle selected from the group of:

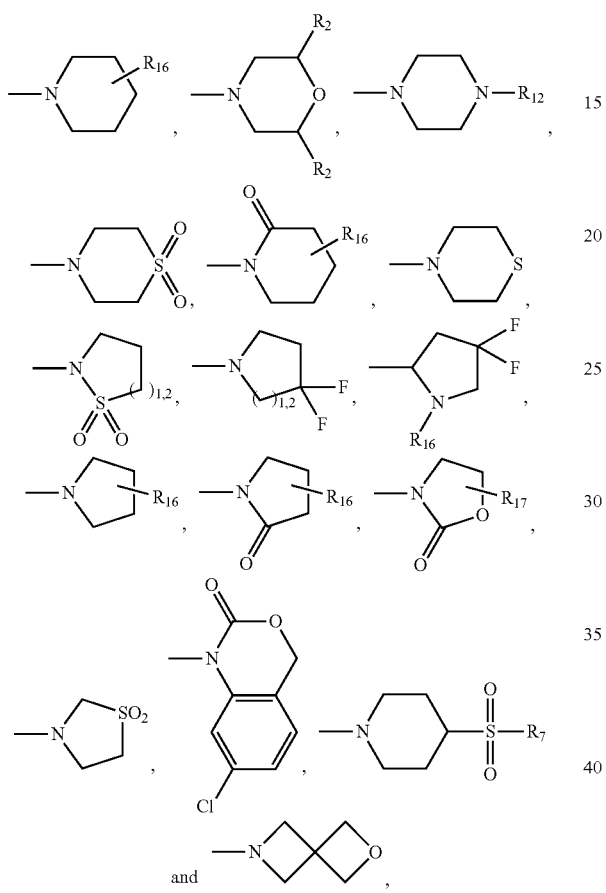

with the proviso that only one of $R_8$ or $R_9$ is $COOR_3$;

$R_{10}$ and $R_{11}$ are independently selected from the group of —H, —$C_{1-6}$ alkyl, —$C_{1-6}$ substituted alkyl and —$C_{3-6}$ cycloalkyl, or $R_{10}$ and $R_{11}$ are taken together with the adjacent N to form the cycle

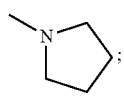

$R_{12}$ is selected from the group of —$C_{1-6}$ alkyl, —$NR_2R_2$, —$C_{1-6}$ alkyl-OH, —$C_{1-6}$ alkyl, —$C_{1-6}$ substituted alkyl, —$C_{3-6}$ cycloalkyl, —$COR_7$, —$COONR_{22}R_{23}$, —$SOR_7$, and —$SONR_{24}R_{25}$;

$R_{13}$ and $R_{14}$ are independently selected from the group of —H, —$C_{1-6}$ alkyl, —$C_{3-6}$ cycloalkyl, substituted alkyl, —$C_{1-6}$ alkyl-$Q_3$, —$C_{1-6}$ alkyl-$C_{3-6}$ cycloalkyl-$Q_3$, $C_{1-6}$ substituted alkyl-$Q_3$ and or $R_{13}$ and $R_{14}$ are taken together with the adjacent N to form a cycle selected from the group of:

$Q_3$ is selected from the group of heteroaryl, substituted heteroaryl, —$NR_{20}R_{21}$, —$CONR_2R_2$, —$COOR_2$, —$OR_2$, and —$SO_2R_3$;

$R_{15}$ is selected from the group of —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$ and —$C_{1-6}$ substituted alkyl-$Q_3$;

$R_{16}$ is selected from the group of —H, —$C_{1-6}$ alkyl, —$NR_2R_2$, and —$COOR_3$;

$R_{17}$ is selected from the group of —H, —$C_{1-6}$ alkyl, —$COOR_3$, and aryl;

$R_{18}$ is selected from the group of —$COOR_2$ and —$C_{1-6}$ alkyl-$COOR_2$;

$R_{19}$ is selected from the group of —H, —$C_{1-6}$ alkyl, —$C_{1-6}$ alkyl-$Q_4$, —$COR_3$, —$COOR_3$, wherein $Q_4$ is selected from the group of —$NR_2R_2$ and —$OR_2$;

$R_{20}$ and $R_{21}$ are independently selected from the group of —H, —$C_{1-6}$ alkyl, —$C_{1-6}$ substituted alkyl, —$C_{1-6}$ substituted alkyl-$OR_2$, and —$COR_3$, or $R_{20}$ and $R_{21}$ are taken together with the adjacent N to form a cycle selected from the group of

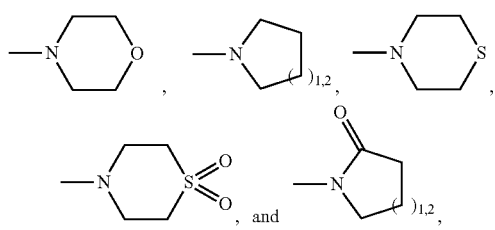

with the proviso that only one of $R_{20}$ or $R_{21}$ is —$COR_3$;
$R_{22}$ and $R_{23}$ are independently selected from the group of H, —$C_{1-6}$ alkyl, —$C_{1-6}$ substituted alkyl, and —$C_{1-6}$ cycloalkyl,
or $R_{22}$ and $R_{23}$ are taken together with the adjacent N to form a cycle selected from the group of

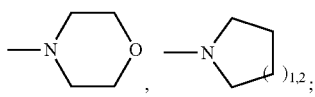

$R_{24}$ and $R_{25}$ are independently from the group of H, —$C_{1-6}$ alkyl, —$C_{1-6}$ substituted alkyl, —$C_{1-6}$ alkyl-$Q_5$, —$C_{1-6}$ cycloalkyl, aryl, substituted aryl, heteroaryl, and substituted heteroaryl,
and $Q_5$ is selected from the group of halogen and $SO_2R_3$; and pharmaceutically acceptable salts thereof.

2. The compound as claimed in claim 1, wherein said compound is a compound of Formula I.

3. The compound as claimed in claim 1, wherein said compound is a compound of Formula II.

4. The compound as claimed in claim 1, wherein said compound is a compound of Formula III.

5. The compound as claimed in claim 2, wherein $R_1$ is isopropenyl.

6. The compound as claimed in claim 5, wherein X is phenyl.

7. The compound as claimed in claim 6, wherein Y is —$COOR_2$.

8. The compound as claimed in claim 7, wherein Y is —COOH.

9. The compound as claimed in claim 6, wherein A is —H.

10. The compound as claimed in claim 6, wherein $R_4$ is selected from the group of —H, —$C_{1-6}$ alkyl, —$C_{1-6}$ alkyl-$Q_1$, and —$COR_6$.

11. The compound as claimed in claim 10, wherein $R_5$ is —H.

12. The compound as claimed in claim 10, wherein $R_4$ is —$C_{1-6}$ alkyl-$Q_1$.

13. The compound as claimed in claim 12, wherein $Q_1$ is —$NR_8R_9$.

14. The compound as claimed in claim 10, wherein $R_4$ is —$COR_6$.

15. A compound which is selected from the group consisting of:

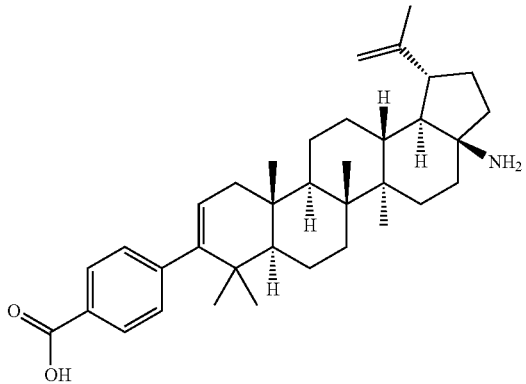

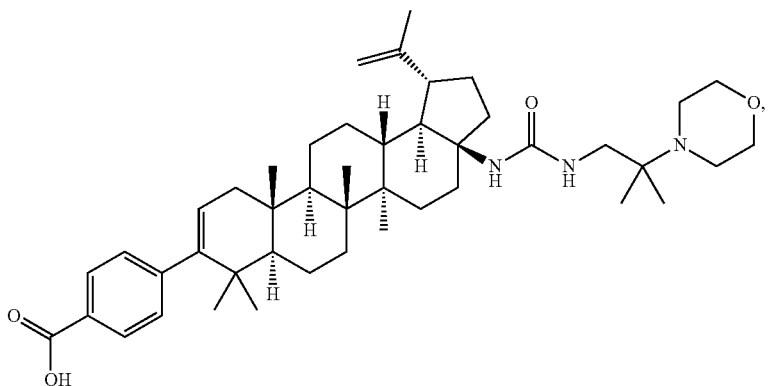

-continued
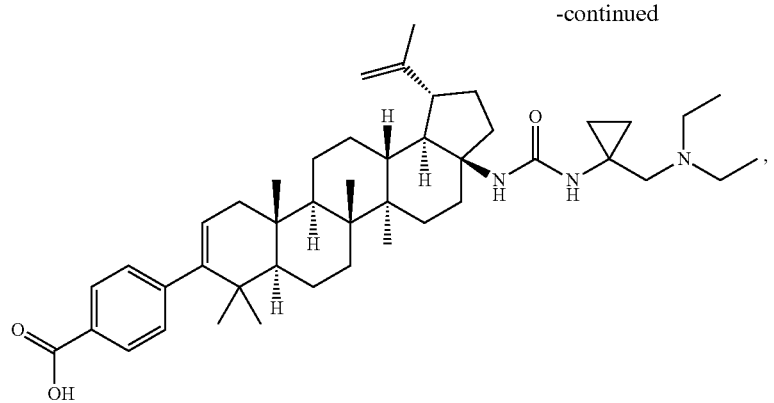
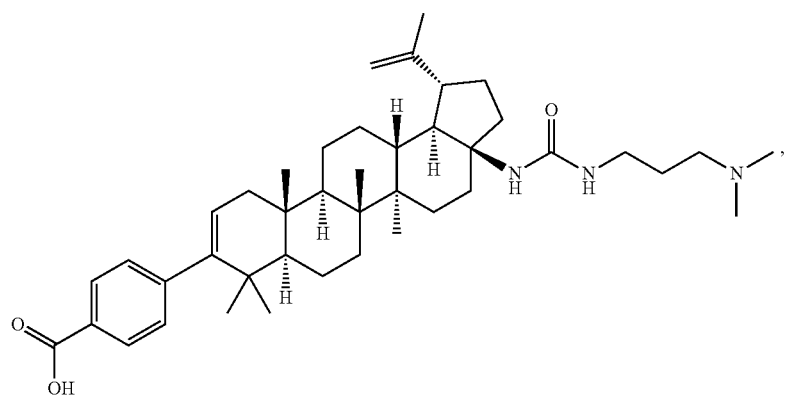
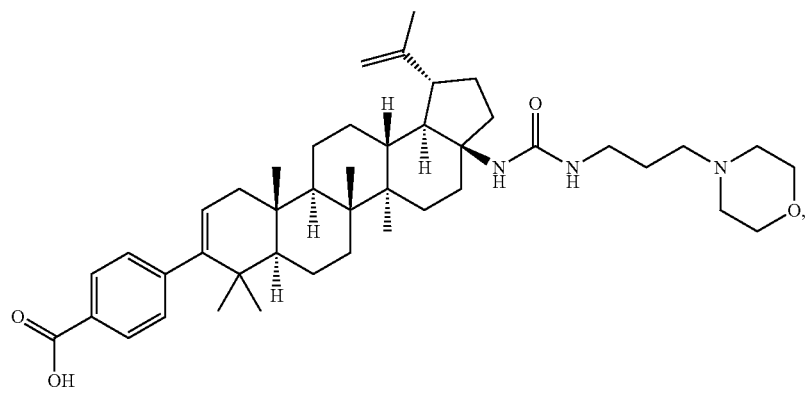
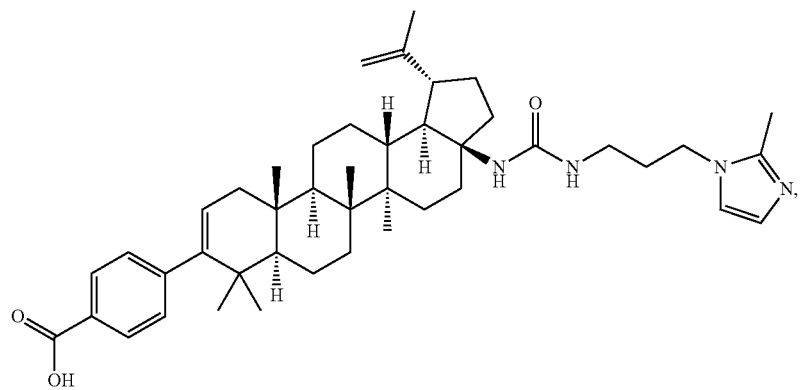

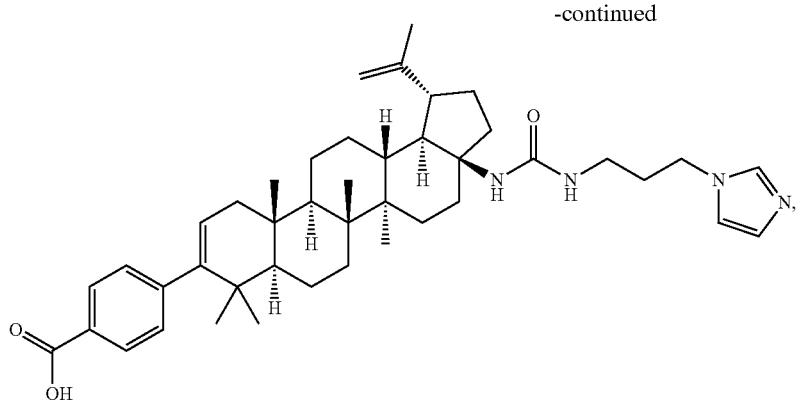
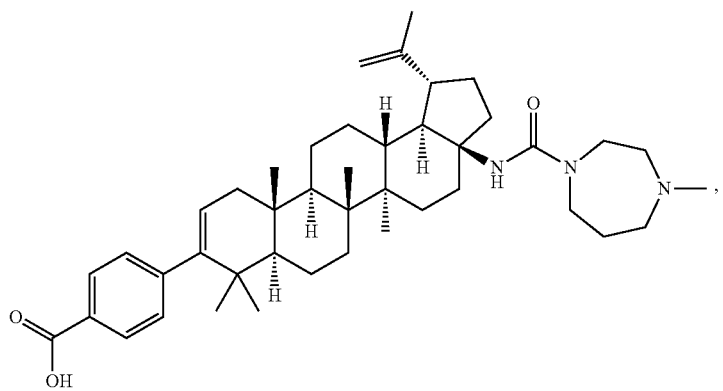
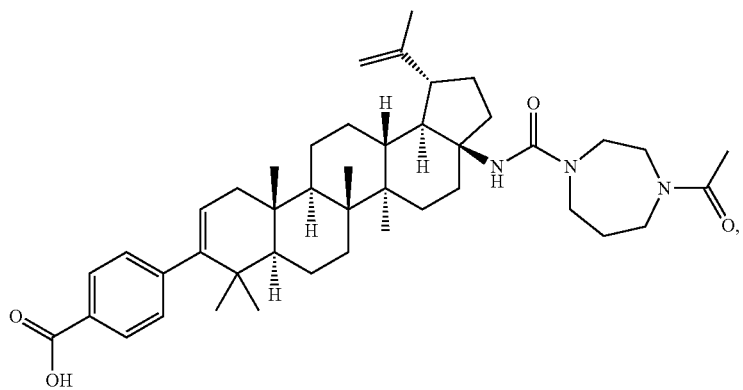
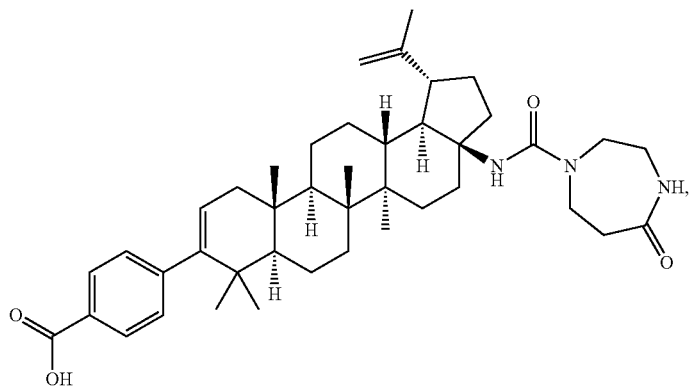

-continued
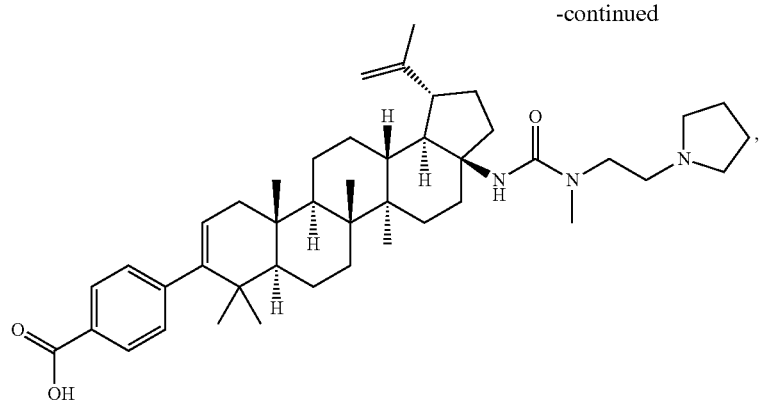
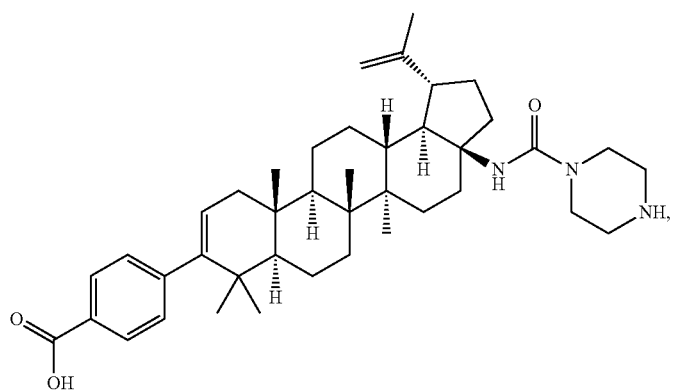
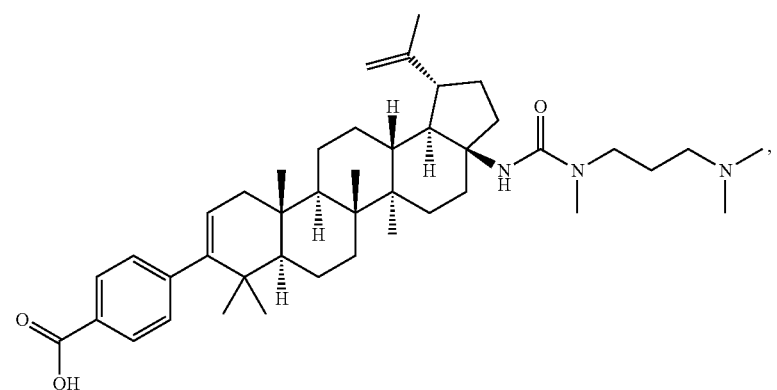
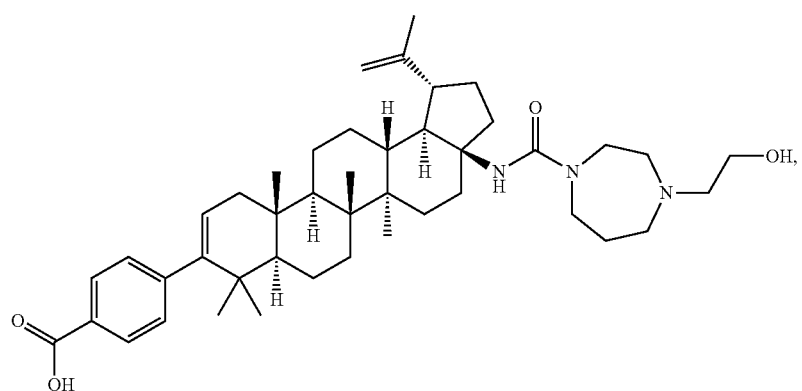

621
-continued
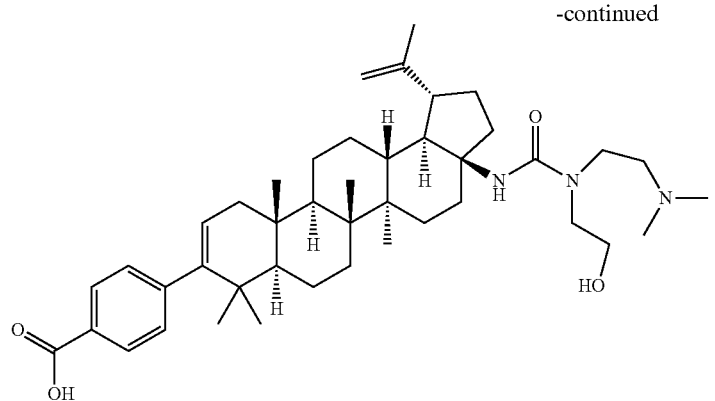
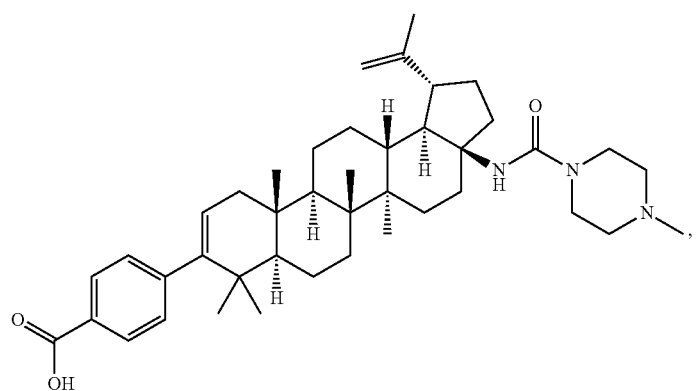
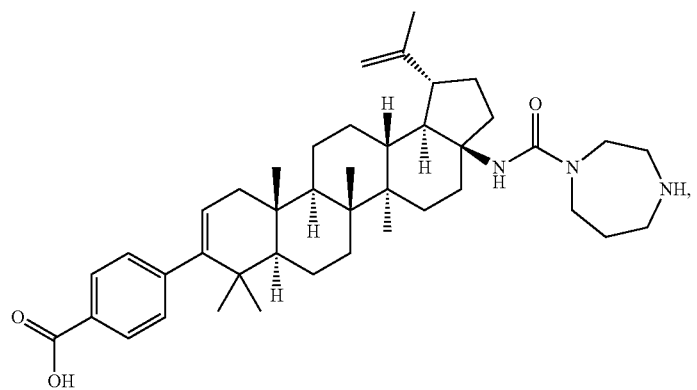
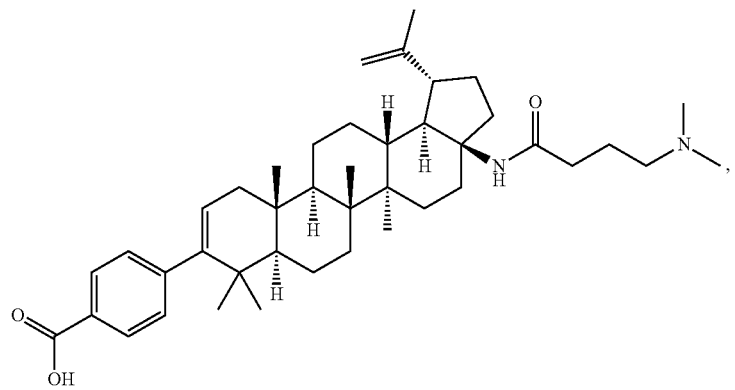
622

-continued
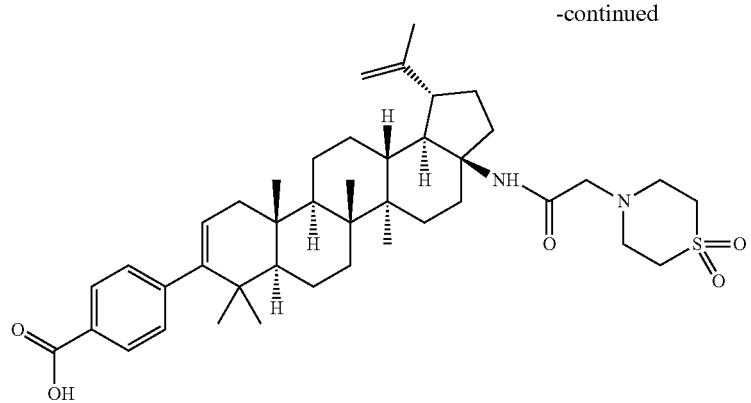
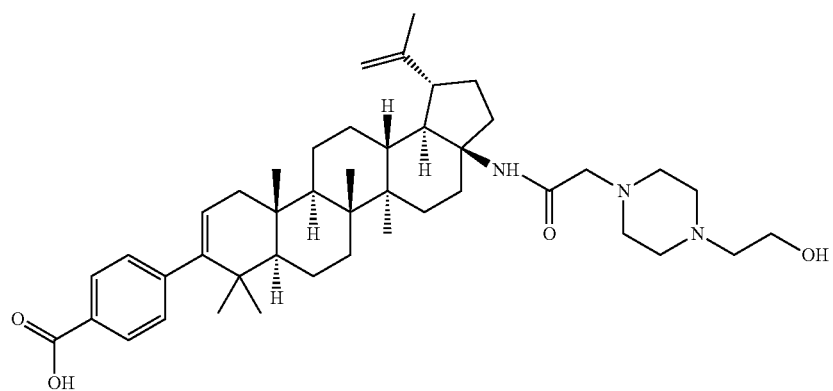
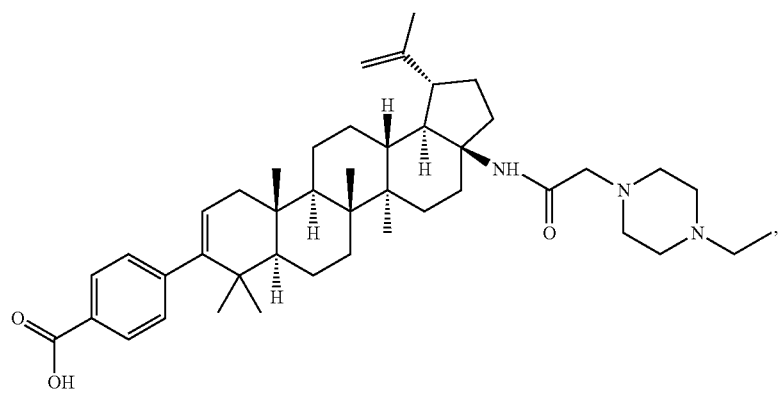
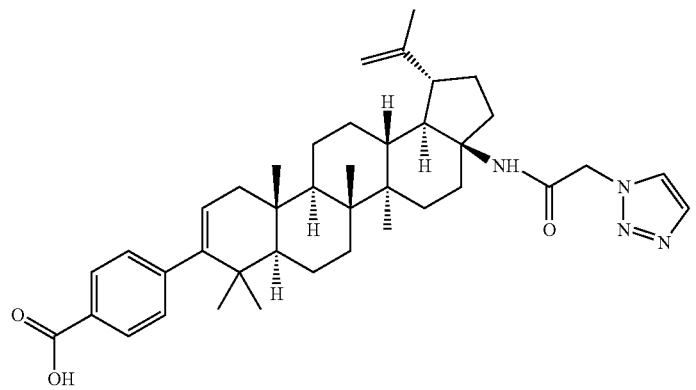

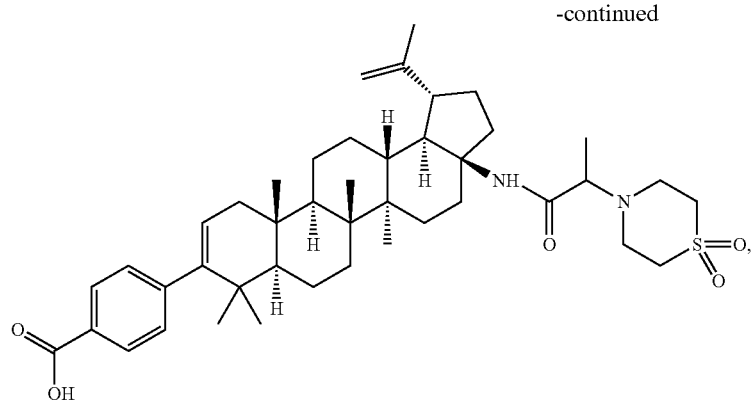
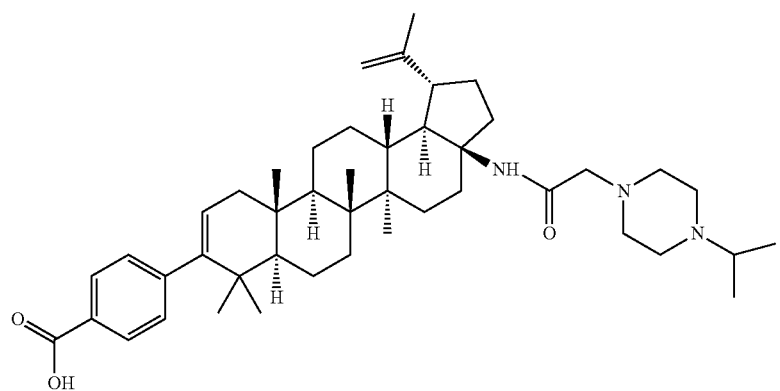
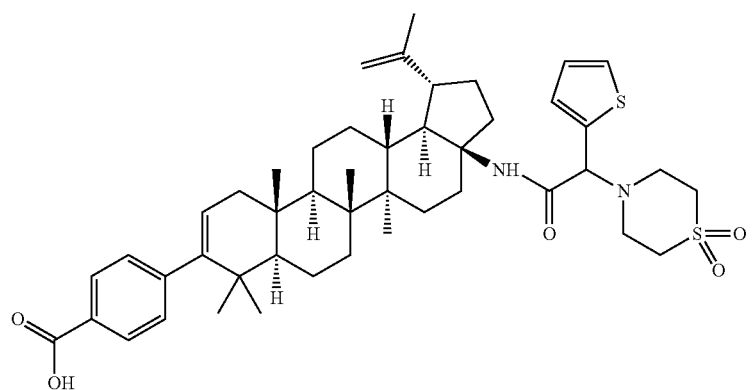
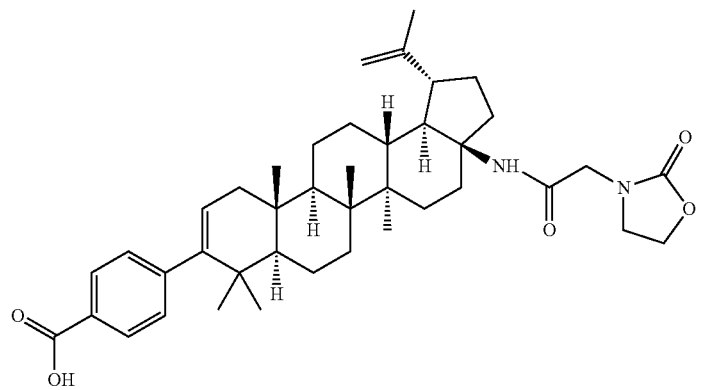

-continued
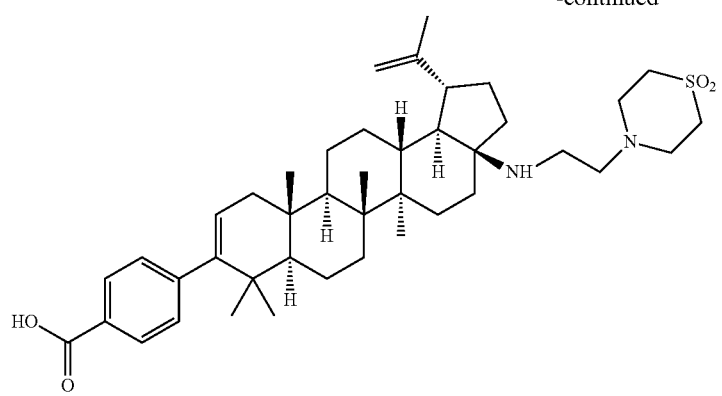
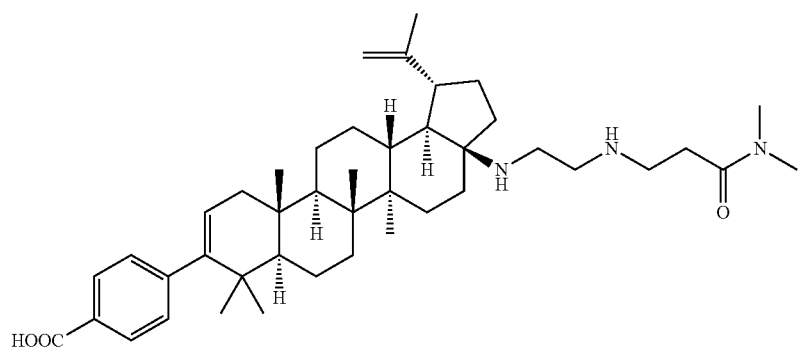
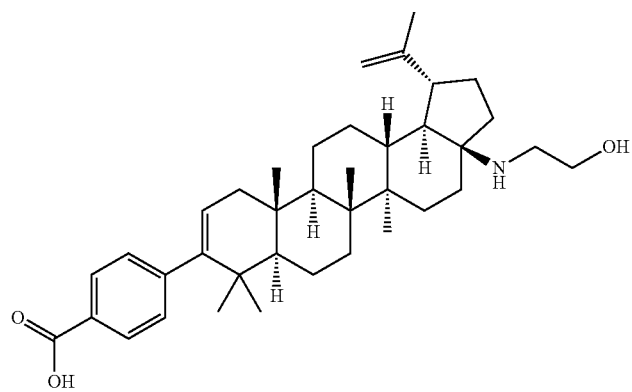
627
628
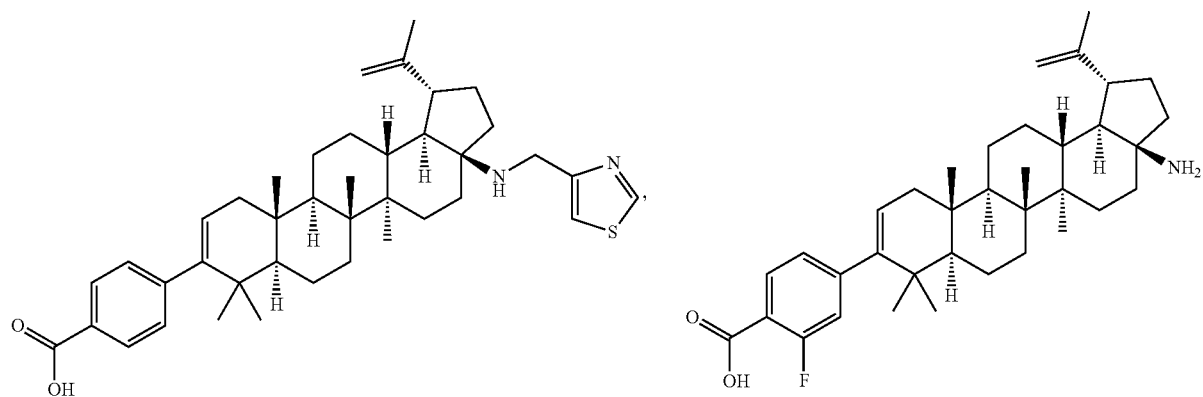

-continued
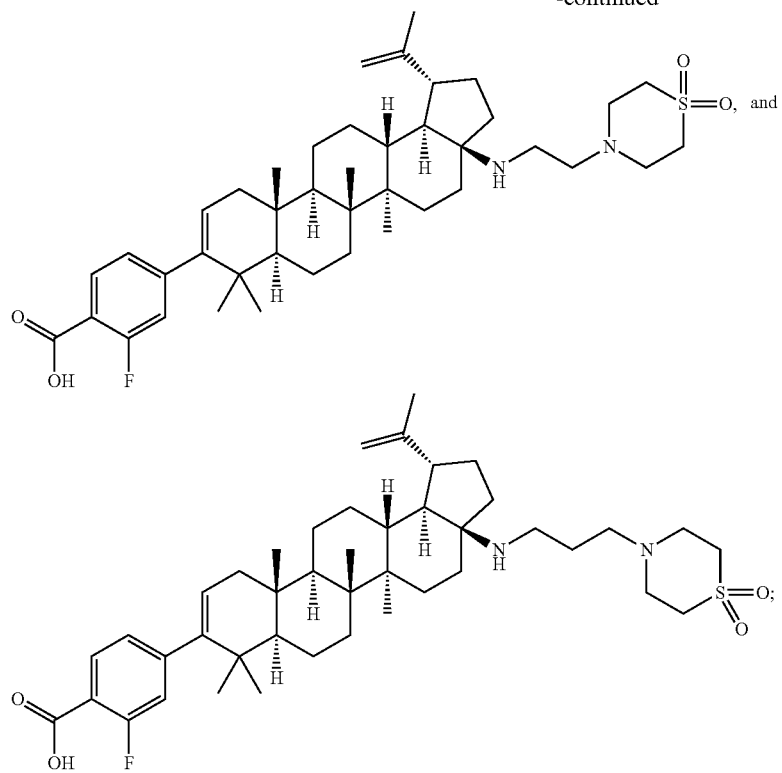
and pharmaceutically acceptable salts thereof.
16. A compound which is selected from the group consisting of:
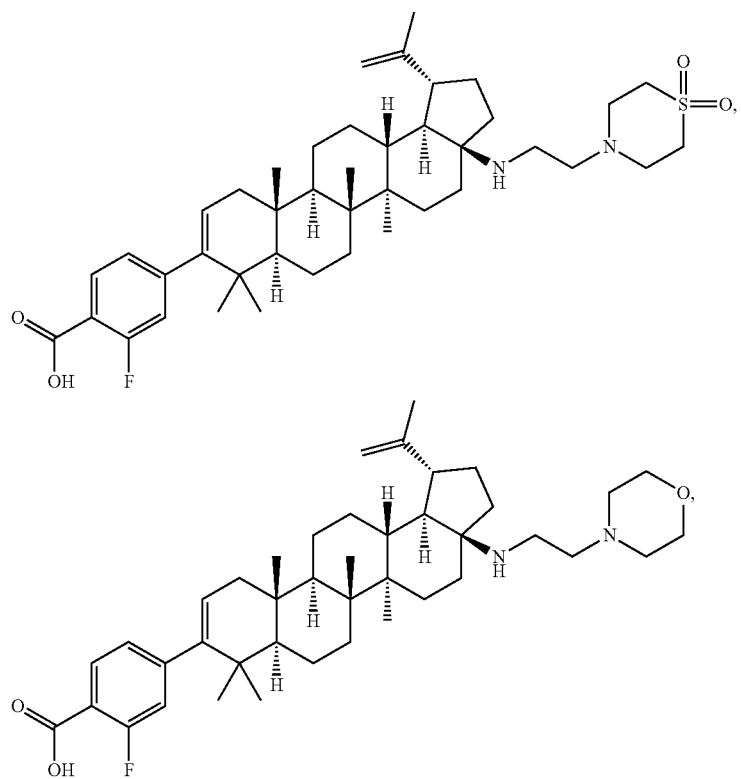

-continued
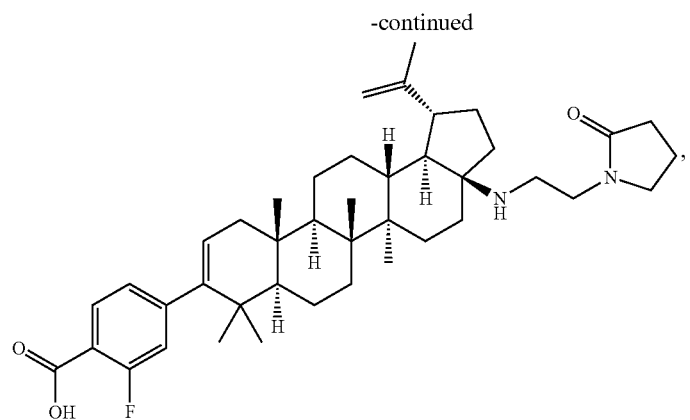
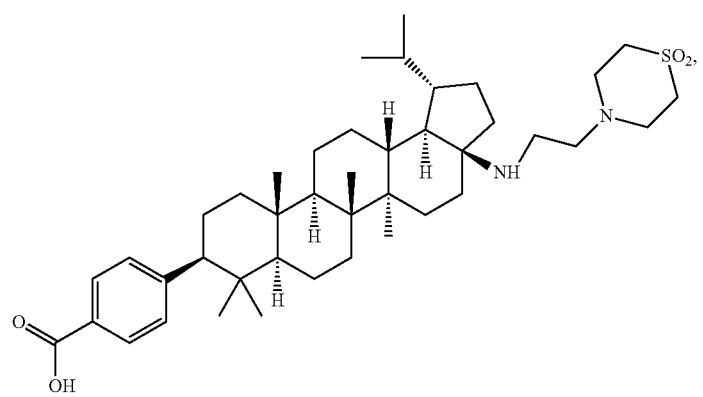
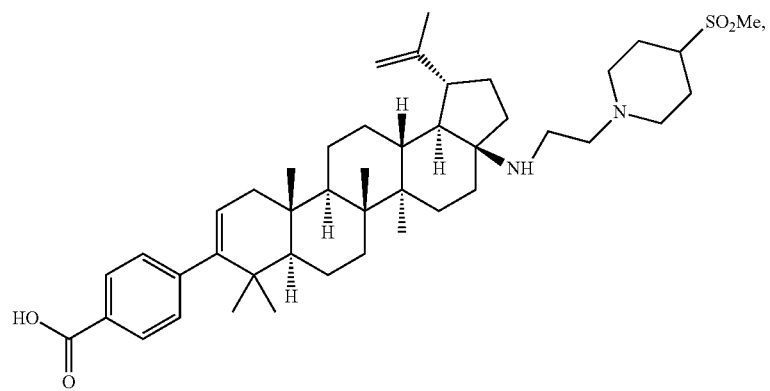
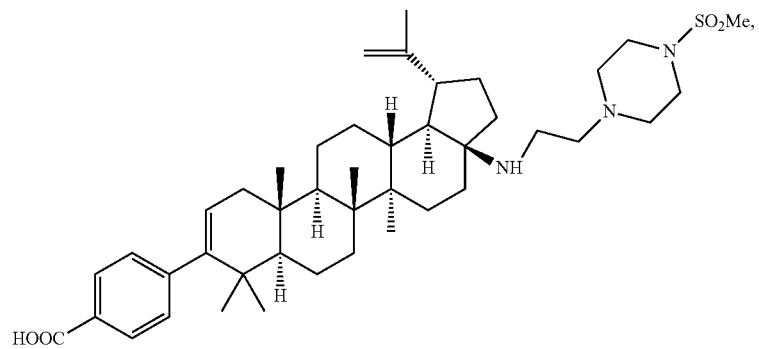

-continued
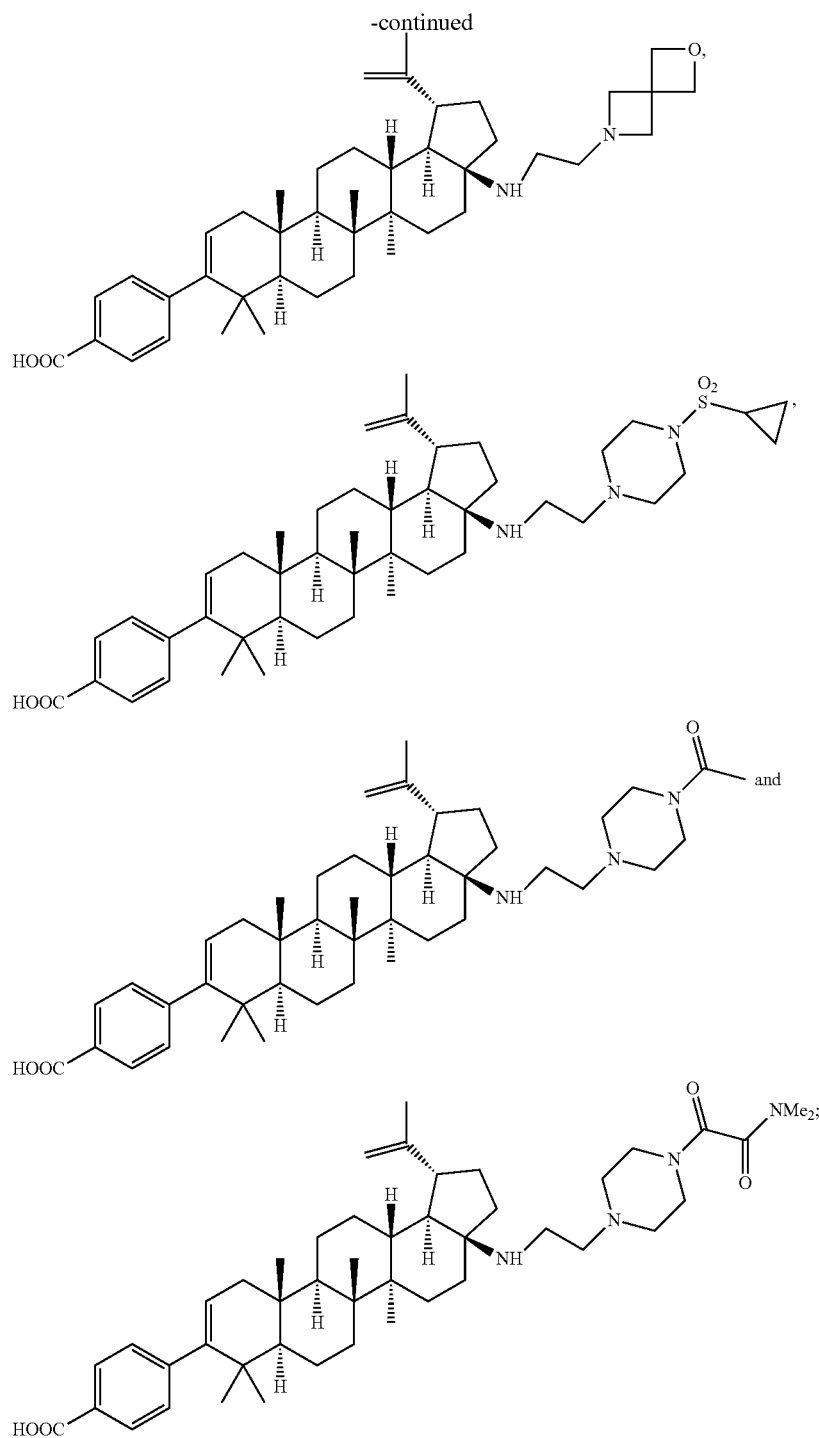
and pharmaceutically acceptable salts thereof.
* * * * *